(12) United States Patent
Yamaki et al.

(10) Patent No.: US 10,538,514 B2
(45) Date of Patent: Jan. 21, 2020

(54) COMPOUND, COMPOSITION, ORGANIC ELECTROLUMINESCENCE ELEMENT, AND ELECTRONIC DEVICE

(71) Applicant: IDEMITSU KOSAN CO., LTD., Chiyoda-ku (JP)

(72) Inventors: Taro Yamaki, Sodegaura (JP); Kiyoshi Ikeda, Sodegaura (JP); Takashi Kashiwamura, Sodegaura (JP); Hironori Kawakami, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 168 days.

(21) Appl. No.: 15/549,212

(22) PCT Filed: Feb. 12, 2016

(86) PCT No.: PCT/JP2016/054186
§ 371 (c)(1),
(2) Date: Aug. 7, 2017

(87) PCT Pub. No.: WO2016/129691
PCT Pub. Date: Aug. 18, 2016

(65) Prior Publication Data
US 2018/0037574 A1  Feb. 8, 2018

(30) Foreign Application Priority Data

Feb. 13, 2015 (JP) .................. 2015-027021

(51) Int. Cl.
*C07D 403/14* (2006.01)
*H01L 51/00* (2006.01)
(Continued)

(52) U.S. Cl.
CPC ............ *C07D 403/14* (2013.01); *C09K 11/06* (2013.01); *H01L 51/0067* (2013.01);
(Continued)

(58) Field of Classification Search
CPC .. C07D 403/14; C07D 221/00; C07D 213/04; C07D 231/00; C07D 233/00;
(Continued)

(56) References Cited

U.S. PATENT DOCUMENTS 8,993,129 B2 * 3/2015 Endo ..................... C09B 57/00
257/40
2012/0235133 A1  9/2012 Kai et al.
(Continued)

FOREIGN PATENT DOCUMENTS

CN    102648268 A    8/2012
CN    102696126 A    9/2012
(Continued)

OTHER PUBLICATIONS

Computer-Generated English-Language Translation of JP-2010-040830 A.*
(Continued)

*Primary Examiner* — Vu A Nguyen
(74) *Attorney, Agent, or Firm* — Oblon, McClelland, Maier & Neustadt, L.L.P.

(57) ABSTRACT

A compound has a first structure represented by a formula (1), a second structure represented by a formula (2), a third structure represented by a formula (3), and a fourth structure represented by a formula (4), the first structure, the second structure, the third structure and the fourth structure being mutually independently present in a molecule,
(Continued)

US 10,538,514 B2
Page 2

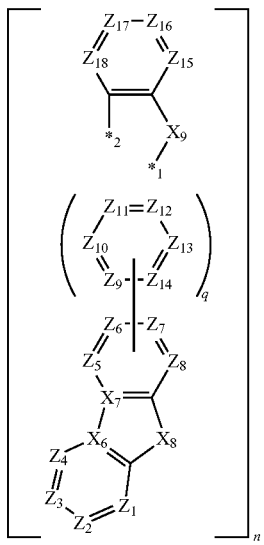

(3)

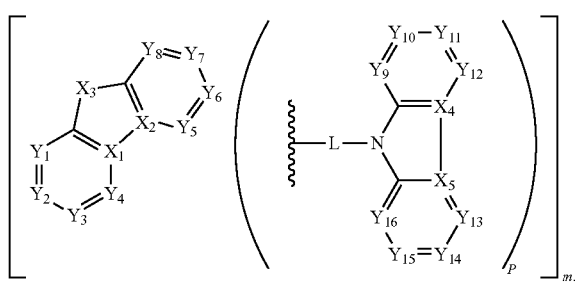

(4)

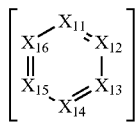

(1)

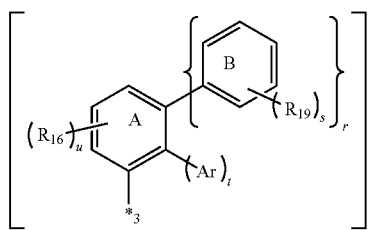

(2)

26 Claims, 1 Drawing Sheet

(51) Int. Cl.
*C09K 11/06* (2006.01)
*H01L 51/50* (2006.01)

(52) U.S. Cl.
CPC .. *H01L 51/0072* (2013.01); *C09K 2211/1007* (2013.01); *C09K 2211/1029* (2013.01); *C09K 2211/185* (2013.01); *H01L 51/0085* (2013.01); *H01L 51/5024* (2013.01); *H01L 51/5056* (2013.01); *H01L 51/5072* (2013.01)

(58) Field of Classification Search
CPC .. C07D 235/00; C07D 237/00; C07D 239/00; C07D 241/00; C07D 251/00; H01L 51/0072
See application file for complete search history.

(56) References Cited

U.S. PATENT DOCUMENTS

| | | |
|---|---|---|
| 2012/0238105 A1 | 9/2012 | Anémian et al. |
| 2013/0261708 A1 | 10/2013 | Anémian et al. |
| 2015/0041785 A1 | 2/2015 | Sannomiya et al. |
| 2015/0057445 A1 | 2/2015 | Anémian et al. |
| 2015/0166886 A1 | 6/2015 | Endo et al. |
| 2015/0214491 A1 | 7/2015 | Ikeda et al. |

FOREIGN PATENT DOCUMENTS

| | | | | |
|---|---|---|---|---|
| JP | 2010-40830 A | | 2/2010 | |
| JP | 2010040830 A | * | 2/2010 | |
| JP | 2011-198899 A | | 10/2011 | |
| JP | 2013-504884 A | | 2/2013 | |
| JP | 2013-527989 A | | 7/2013 | |
| JP | 2014-508114 A | | 4/2014 | |
| JP | 2017-521397 A | | 8/2017 | |
| JP | 6492385 B2 | | 4/2019 | |
| WO | 2011/032686 A1 | | 3/2011 | |
| WO | 2011/070963 A1 | | 6/2011 | |
| WO | 2011/080972 A1 | | 7/2011 | |
| WO | 2012/086170 A1 | | 6/2012 | |
| WO | 2012/087007 A1 | | 6/2012 | |
| WO | 2013/012298 A1 | | 1/2013 | |
| WO | WO-2013012297 A1 | * | 1/2013 | ............. C09K 11/06 |
| WO | 2013/137001 A1 | | 9/2013 | |
| WO | WO-2013137001 A1 | * | 9/2013 | ............ C07D 487/04 |
| WO | 2014/038677 A1 | | 3/2014 | |
| WO | 2015/011924 A1 | | 1/2015 | |
| WO | WO-2015011924 A1 | * | 1/2015 | ............ C07D 403/14 |
| WO | 2015/137471 A1 | | 9/2015 | |
| WO | 2015/192939 A1 | | 12/2015 | |

OTHER PUBLICATIONS

STN Structure Search (Sep. 9, 2019).*
International Search Report dated May 17, 2016 in PCT/JP2016/054186 filed Feb. 12, 2016.
Office Action dated Oct. 30, 2019, in Chinese Patent Application No. 201680009717.X, filed Feb. 12, 2016.
Office Action dated Nov. 12, 2019, Japanese Patent Application No. 2016-574872, filed Feb. 12, 2016.

* cited by examiner

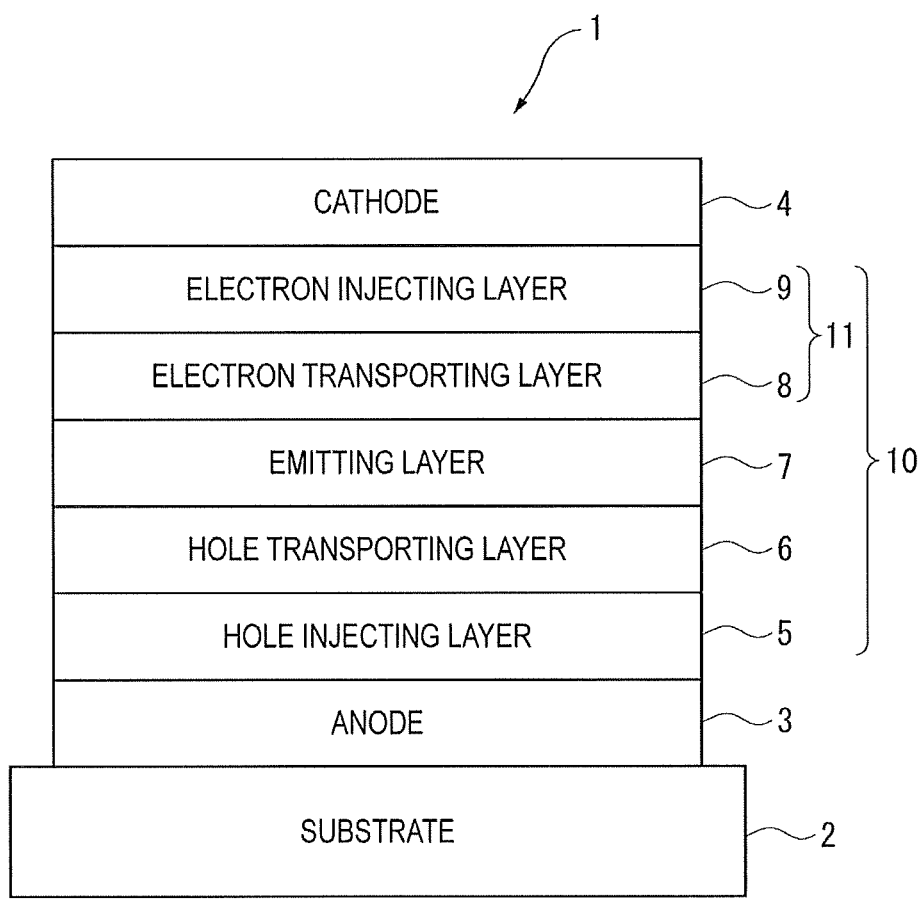

COMPOUND, COMPOSITION, ORGANIC ELECTROLUMINESCENCE ELEMENT, AND ELECTRONIC DEVICE

TECHNICAL FIELD

The present invention relates to a compound, a composition, an organic electroluminescence device and an electronic device.

BACKGROUND ART

An organic electroluminescence device (hereinafter, occasionally abbreviated as organic EL device) using an organic substance is highly expected to be used as an inexpensive solid-emitting full-color display device having a large area and has been variously developed. A typical organic EL device includes an emitting layer and a pair of opposing electrodes between which the emitting layer is interposed. When an electric field is applied on both electrodes, electrons are injected from the cathode while holes are injected from the anode. Further, the electrons are recombined with the holes in the emitting layer to generate an excited state. When the excited state is returned to a ground state, energy is emitted as light.

In recent years, various compounds used for forming an organic layer of the organic EL device have been studied in order to improve performance of the organic EL device (Patent Literatures 1 and 4).

CITATION LIST

Patent Literatures

Patent Literature 1: International Publication No. WO2011/032686
Patent Literature 2: International Publication No. WO2012/087007
Patent Literature 3: International Publication No. WO2013/012298
Patent Literature 4: International Publication No. WO2012/086170

SUMMARY OF THE INVENTION

Problems to be Solved by the Invention

The compounds used for forming the organic layer have exhibited an insufficient solubility.

An object of the invention is to provide a compound having an improvable solubility. Another object of the invention is to provide a composition containing the compound, to provide an organic electroluminescence device containing the compound, and to provide an electronic device including the organic electroluminescence device.

Means for Solving the Problems

According to an aspect of the invention, a compound has a first structure represented by a formula (1), a second structure represented by a formula (2), a third structure represented by a formula (3), and a fourth structure represented by a formula (4), the first structure, the second structure, the third structure and the fourth structure being mutually independently present in a molecule.

[Formula 1]

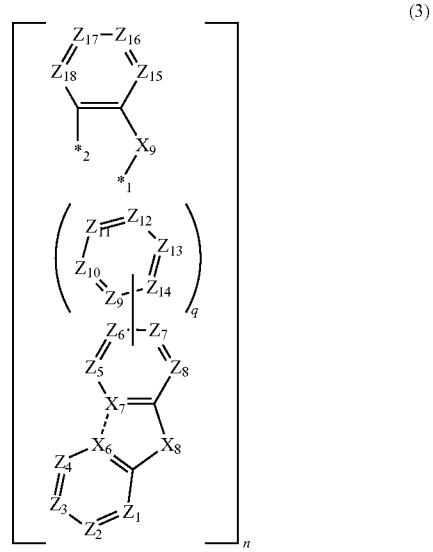

(3)

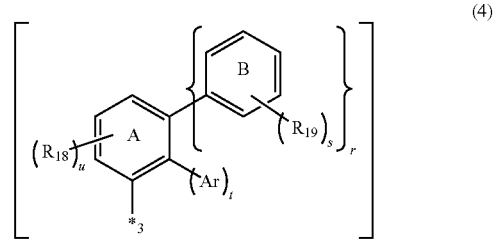

(4)

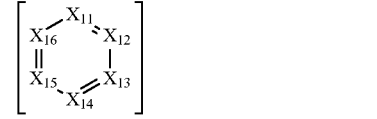

(1)

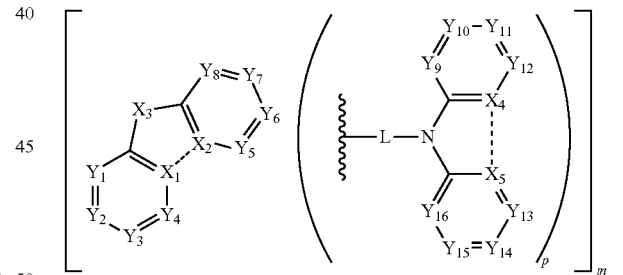

(2)

In the formula (1), $X_{11}$ to $X_{16}$ are each independently a carbon atom bonded to $R_1$, a nitrogen atom, or a carbon atom bonded to an atom contained in at least one of the second structure, the third structure and the fourth structure in a molecule; at least one of $X_{11}$ to $X_{16}$ is a nitrogen atom; $R_1$ is a hydrogen atom or a substituent; a plurality of $R_1$ are optionally mutually the same or different; and the plurality of $R_1$ are optionally bonded to each other to form a cyclic structure.

In the formula (2), $X_1$ is a carbon atom bonded to $R_2$, or a carbon atom bonded to $X_2$; $X_2$ is a carbon atom bonded to $R_3$, or a carbon atom bonded to $X_1$; $X^3$ is an oxygen atom, a sulfur atom, a nitrogen atom, or a carbon atom bonded to $R_a$ and $R_b$; $R_a$ and $R_b$ are each independently a hydrogen atom or a substituent; the nitrogen atom in $X_3$ is bonded to $R_4$, bonded to L, or bonded to an atom contained in at least one of the first structure, the third structure and the fourth structure in a molecule; $X_4$ is a carbon atom bonded to $R_5$, or a carbon atom bonded to $X_5$; and $X_5$ is a carbon atom bonded to $R_6$, or a carbon atom bonded to $X_4$. At least one of a combination of $X_1$ and $X_2$ and a combination of $X_4$ and $X_5$ is a combination of mutually bonded carbon atoms.

L is a single bond or a substituted or unsubstituted aromatic hydrocarbon group; L is bonded to one of $Y_1$ to $Y_8$, bonded to $X_3$, bonded to $R_5$ or $R_6$, bonded to an atom contained in at least one of the first structure, the third structure and the fourth structure in a molecule, or bonded to a substituent.

L as a substituted or unsubstituted aromatic hydrocarbon group may be bonded to $Y_9$ or $Y_{16}$ to form a cyclic structure.

$Y_1$ to $Y_8$ are each independently a carbon atom bonded to $R_7$, a carbon atom bonded to L, a carbon atom bonded to one of $Y_9$ to $Y_{16}$, or a carbon atom bonded to an atom contained in at least one of the first structure, the third structure and the fourth structure in a molecule.

$Y_9$ to $Y_{16}$ are each independently a carbon atom bonded to $R_8$, a carbon atom bonded to one of $Y_1$ to $Y_8$, or a carbon atom bonded to an atom contained in at least one of the first structure, the third structure and the fourth structure in a molecule.

$Y_9$ or $Y_{16}$ may be bonded to L as a substituted or unsubstituted aromatic hydrocarbon group to form a cyclic structure.

$R_2$ to $R_8$ are each independently a hydrogen atom or a substituent.

A plurality of $R_7$ may be mutually the same or different.

A plurality of $R_8$ may be mutually the same or different.

m represents the number of the second structure in a molecule and is an integer of 1 or more.

p is an integer of 1 to 3.

In the formula (3), $X_6$ is a carbon atom bonded to $R_9$, or a carbon atom bonded to $X_7$; $X_7$ is a carbon atom bonded to $R_{10}$, or a carbon atom bonded to $X_6$; $R_9$ and $R_{10}$ are each independently a hydrogen atom or a substituent.

$X_8$ is a nitrogen atom bonded to a substituted or unsubstituted aromatic hydrocarbon group, or a nitrogen atom bonded to an atom contained in at least one of the first structure, the second structure and the fourth structure in a molecule.

$Z_1$ to $Z_4$ are each independently a carbon atom bonded to $R_{11}$, a carbon atom bonded to an atom contained in at least one of the first structure, the second structure and the fourth structure in a molecule, or a carbon atom bonded at a position represented by *1 or *2.

$Z_5$ to $Z_8$ are each independently a carbon atom bonded to $R_{12}$, a carbon atom bonded to one of $Z_9$ to $Z_{14}$, a carbon atom bonded to an atom contained in at least one of the first structure, the second structure and the fourth structure in a molecule, or a carbon atom bonded at a position represented by *1 or *2.

$R_{11}$ and $R_{12}$ are each independently a hydrogen atom or a substituent.

A plurality of $R_{11}$ may be mutually the same or different.

The plurality of $R_{11}$ may be bonded to each other to form a cyclic structure.

A plurality of $R_{12}$ may be mutually the same or different.

The plurality of $R_{12}$ may be bonded to each other to form a cyclic structure.

$Z_9$ to $Z_{14}$ are each independently a carbon atom bonded to $R_{13}$, a carbon atom bonded to one of $Z_5$ to $Z_8$, a carbon atom bonded to an atom contained in at least one of the first structure, the second structure and the fourth structure in a molecule, or a carbon atom bonded at a position represented by *1 or *2. $R_{13}$ is a hydrogen atom or a substituent.

A plurality of $R_{13}$ may be mutually the same or different.

The plurality of $R_{13}$ may be bonded to each other to form a cyclic structure.

q is 0 or an integer of 1 to 4.

$X_9$ is an oxygen atom, a sulfur atom, a nitrogen atom, or a carbon atom bonded to $R_{14}$ and $R_{15}$.

$R_{14}$ and $R_{15}$ are each independently a hydrogen atom or a substituent.

The nitrogen atom in $X_9$ is bonded to $R_{16}$, or bonded to an atom contained in at least one of the first structure, the second structure and the fourth structure in a molecule.

$R_{16}$ is a hydrogen atom or a substituent.

$Z_{15}$ to $Z_{18}$ are each independently a carbon atom bonded to $R_{17}$, or a carbon atom bonded to an atom contained in at least one of the first structure, the second structure and the fourth structure in a molecule.

$R_{17}$ is a hydrogen atom or a substituent.

A plurality of $R_{17}$ may be mutually the same or different.

The plurality of $R_{17}$ may be bonded to each other to form a cyclic structure.

*1 and *2 are each independently a bonding position to a carbon atom in $Z_1$ to $Z_{14}$, or a bonding position to a substituted or unsubstituted aromatic hydrocarbon group bonded to the nitrogen atom in $X_8$.

n represents the number of the third structure in a molecule and is an integer of 1 or more In the formula (4), $R_{18}$ is a hydrogen atom or a substituent.

A plurality of $R_{18}$ may be mutually the same or different.

The plurality of $R_{18}$ may be bonded to each other to form a cyclic structure.

Ar is a substituted or unsubstituted aromatic hydrocarbon group.

$R_{19}$ is a substituent.

s is an integer of 1 to 5.

A plurality of $R_{19}$ may be mutually the same or different.

The plurality of $R_{19}$ may be bonded to each other to form a cyclic structure.

u is 3 or 4.

t is 0 or 1.

r is 0 or 1.

t+r is 1 or 2.

When r=0, t=1, u=4 and $R_{18}$ in place of a ring B is bonded to a ring A.

When t=0, r=1, u=4 and $R_{18}$ in place of Ar is bonded to the ring A.

*3 is a bonding position bonded to an atom contained in at least one of the first structure, the second structure and the third structure.

A composition according to another aspect of the invention contains: the compound according to the above aspect of the invention; and a solvent.

An organic electroluminescence device according to still another aspect of the invention includes: an anode; an organic layer; and a cathode, in which the organic layer contains the compound according to the above aspect of the invention; and a solvent.

An electronic device according to a further aspect of the invention includes the organic electroluminescence device according to the above aspect of the invention.

According to the above aspect of the invention, a compound having an improvable solubility can be provided. Moreover, a composition containing the compound, an organic electroluminescence device containing the compound, and an electronic device including the organic electroluminescence device can be provided.

BRIEF DESCRIPTION OF DRAWINGS

The FIGURE schematically shows an exemplary arrangement of an organic EL device according to an exemplary embodiment of the invention.

DESCRIPTION OF EMBODIMENT(S)

Compound

According to an exemplary embodiment of the invention, a compound has a first structure represented by a formula (1), a second structure represented by a formula (2), a third structure represented by a formula (3), and a fourth structure represented by a formula (4), the first structure, the second structure, the third structure and the fourth structure being mutually independently present in a molecule.

[Formula 2]

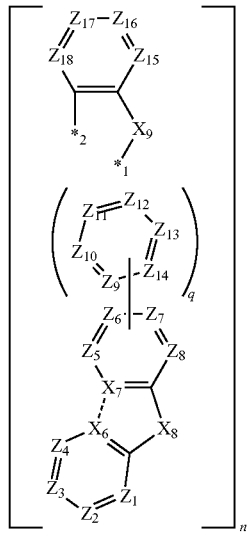

(3)

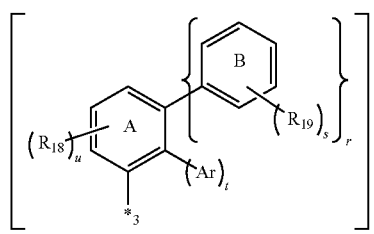

(4)

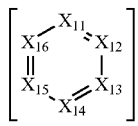

(1)

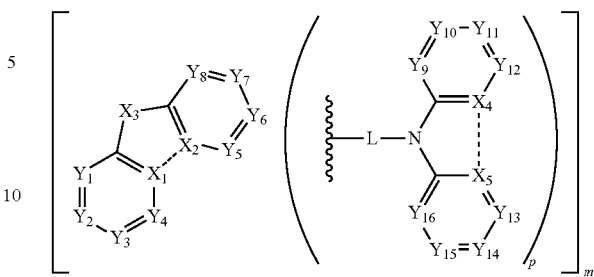

(2)

In the formula (1): $X_{11}$ to $X_{16}$ are each independently a carbon atom bonded to $R_1$, a nitrogen atom, or a carbon atom bonded to an atom contained in at least one of the second structure, the third structure and the fourth structure in a molecule.

At least one of $X_{11}$ to $X_{16}$ is a nitrogen atom.

$R_1$ is a hydrogen atom or a substituent.

A plurality of $R_1$ may be mutually the same or different.

The plurality of $R_1$ are optionally bonded to each other to form a cyclic structure.

In the formula (2): $X_1$ is a carbon atom bonded to $R_2$, or a carbon atom bonded to $X_2$; $X_2$ is a carbon atom bonded to $R_3$, or a carbon atom bonded to $X_1$; $X^3$ is an oxygen atom, a sulfur atom, a nitrogen atom, or a carbon atom bonded to $R_a$ and $R_b$; $R_a$ and $R_b$ are each independently a hydrogen atom or a substituent.

The nitrogen atom in $X_3$ is bonded to $R_4$, bonded to L, or bonded to an atom contained in at least one of the first structure, the third structure and the fourth structure in a molecule.

$X_4$ is a carbon atom bonded to $R_5$, or a carbon atom bonded to $X_5$.

$X_5$ is a carbon atom bonded to $R_6$, or a carbon atom bonded to $X_4$.

At least one of a combination of $X_1$ and $X_2$ and a combination of $X_4$ and $X_5$ is a combination of mutually bonded carbon atoms.

L is a single bond or a substituted or unsubstituted aromatic hydrocarbon group.

L is bonded to one of $Y_1$ to $Y_8$, bonded to $X_3$, bonded to $R_5$ or $R_6$, bonded to an atom contained in at least one of the first structure, the third structure and the fourth structure in a molecule, or bonded to a substituent.

L as a substituted or unsubstituted aromatic hydrocarbon group may be bonded to $Y_9$ or $Y_{16}$ to form a cyclic structure.

$Y_1$ to $Y_8$ are each independently a carbon atom bonded to $R_7$, a carbon atom bonded to L, a carbon atom bonded to one of $Y_9$ to $Y_{16}$, or a carbon atom bonded to an atom contained in at least one of the first structure, the third structure and the fourth structure in a molecule.

$Y_9$ to $Y_{16}$ are each independently a carbon atom bonded to $R_8$, a carbon atom bonded to one of $Y_1$ to $Y_8$, or a carbon atom bonded to an atom contained in at least one of the first structure, the third structure and the fourth structure in a molecule.

$Y_9$ or $Y_{16}$ may be bonded to L as a substituted or unsubstituted aromatic hydrocarbon group to form a cyclic structure.

$R_2$ to $R_8$ are each independently a hydrogen atom or a substituent.

A plurality of $R_7$ may be mutually the same or different.

A plurality of $R_8$ may be mutually the same or different.

m represents the number of the second structure in a molecule and is an integer of 1 or more.

p is an integer of 1 to 3.

When m is an integer of 2 or more, a plurality of second structures may be mutually the same or different. When m is an integer of 2 or more, the plurality of second structures are each independently bonded to one of the first structure, the third structure and the fourth structure. Each of the plurality of second structures is preferably bonded to the first structure.

In the formula (3): $X_6$ is a carbon atom bonded to $R_9$, or a carbon atom bonded to $X_7$.

$X_7$ is a carbon atom bonded to $R_{10}$, or a carbon atom bonded to $X_6$.

$R_9$ and $R_{10}$ are each independently a hydrogen atom or a substituent.

$X_8$ is a nitrogen atom bonded to a substituted or unsubstituted aromatic hydrocarbon group, or a nitrogen atom bonded to an atom contained in at least one of the first structure, the second structure and the fourth structure in a molecule.

$Z_1$ to $Z_4$ are each independently a carbon atom bonded to $R_{11}$, a carbon atom bonded to an atom contained in at least one of the first structure, the second structure and the fourth structure in a molecule, or a carbon atom bonded at a position represented by *1 or *2

$Z_5$ to $Z_8$ are each independently a carbon atom bonded to $R_{12}$, a carbon atom bonded to one of $Z_9$ to $Z_{14}$, a carbon atom bonded to an atom contained in at least one of the first structure, the second structure and the fourth structure in a molecule, or a carbon atom bonded at a position represented by *1 or *2.

$R_{11}$ and $R_{12}$ are each independently a hydrogen atom or a substituent.

A plurality of $R_{11}$ may be mutually the same or different.

The plurality of $R_{11}$ may be bonded to each other to form a cyclic structure.

A plurality of $R_{12}$ may be mutually the same or different.

The plurality of $R_{12}$ may be bonded to each other to form a cyclic structure.

$Z_9$ to $Z_{14}$ are each independently a carbon atom bonded to $R_{13}$, a carbon atom bonded to one of $Z_5$ to $Z_8$, a carbon atom bonded to an atom contained in at least one of the first structure, the second structure and the fourth structure in a molecule; or a carbon atom bonded at a position represented by *1 or *2.

$R_{13}$ is a hydrogen atom or a substituent.

A plurality of $R_{13}$ may be mutually the same or different.

The plurality of $R_{13}$ may be bonded to each other to form a cyclic structure.

q is 0 or an integer of 1 to 4.

$X_9$ is an oxygen atom, a sulfur atom, a nitrogen atom, or a carbon atom bonded to $R_{14}$ and $R_{15}$.

$R_{14}$ and $R_{15}$ are each independently a hydrogen atom or a substituent.

The nitrogen atom in $X_9$ is bonded to $R_{16}$, or bonded to an atom contained in at least one of the first structure, the second structure and the fourth structure in a molecule.

$R_{16}$ is a hydrogen atom or a substituent.

$Z_{15}$ to $Z_{18}$ are each independently a carbon atom bonded to $R_{17}$, or a carbon atom bonded to an atom contained in at least one of the first structure, the second structure and the fourth structure in a molecule.

$R_{17}$ is a hydrogen atom or a substituent.

A plurality of $R_{17}$ may be mutually the same or different.

The plurality of $R_{17}$ may be bonded to each other to form a cyclic structure.

*1 and *2 are each independently a bonding position to a carbon atom in $Z_1$ to $Z_{14}$, or a bonding position to a substituted or unsubstituted aromatic hydrocarbon group bonded to the nitrogen atom in $X_8$.

n represents the number of the third structure in a molecule and is an integer of 1 or more.

When n is an integer of 2 or more, a plurality of third structures may be mutually the same or different. When n is an integer of 2 or more, the plurality of third structures are each independently bonded to one of the first structure, the third structure and the fourth structure. Each of the plurality of third structures is preferably bonded to the first structure.

In the formula (4): $R_{18}$ is a hydrogen atom or a substituent.

A plurality of $R_{18}$ may be mutually the same or different.

The plurality of $R_{18}$ may be bonded to each other to form a cyclic structure.

Ar is a substituted or unsubstituted aromatic hydrocarbon group.

$R_{19}$ is a substituent.

s is an integer of 1 to 5.

A plurality of $R_{19}$ may be mutually the same or different.

The plurality of $R_{19}$ may be bonded to each other to form a cyclic structure.

u is 3 or 4.

t is 0 or 1.

r is 0 or 1.

t+r is 1 or 2.

When r=0, t=1, u=4 and $R_{18}$ in place of the ring B is bonded to the ring A.

When t=0, r=1, u=4 and $R_{18}$ in place of Ar is bonded to the ring A.

*3 is a bonding position bonded to an atom contained in at least one of the first structure, the second structure and the third structure.

In the compound according to the exemplary embodiment, the fourth structure is preferably represented by a formula (41).

[Formula 3]

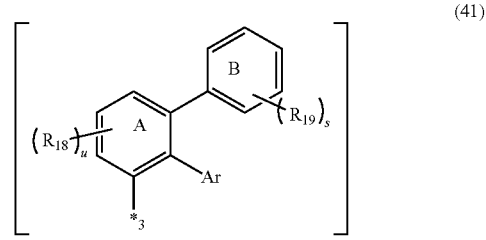

(41)

In the formula (41): $R_{18}$, $R_{19}$, Ar, s and *3 respectively represent the same as $R_{18}$, $R_{19}$, Ar, s and *3 in the formula (4); and u is 3.

In the compound according to the exemplary embodiment, the fourth structure is preferably represented by a formula (42).

[Formula 4]

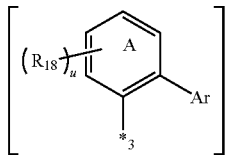

(42)

In the formula (42): $R_{18}$, Ar and *3 respectively represent the same as $R_{18}$, Ar and *3 in the formula (4); and u is 4.

In the compound according to the exemplary embodiment, the fourth structure is preferably represented by a formula (43).

[Formula 5]

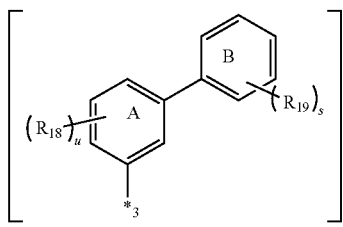

(43)

In the formula (43): $R_{18}$, $R_{19}$, s and *3 respectively represent the same as $R_{18}$, $R_{19}$, s and *3 in the formula (4); and u is 4.

In the compound according to the exemplary embodiment, the fourth structure is preferably bonded to the first structure.

In the compound according to the exemplary embodiment, *3 in the formula (4) represents a bonding position to $X_{11}$.

$X_{11}$ is preferably a carbon atom bonded to the fourth structure.

In other words, the compound according to the exemplary embodiment preferably includes a structure represented by formula (1-4) formed by bonding the first structure to the fourth structure.

[Formula 6]

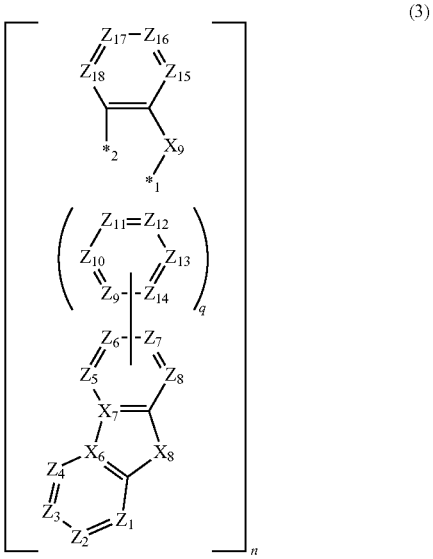

(3)

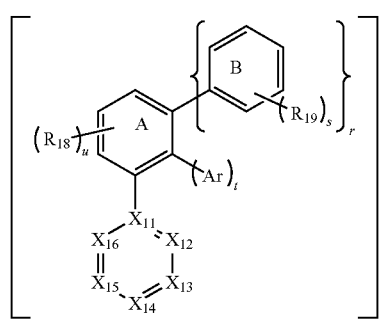

(1-4)

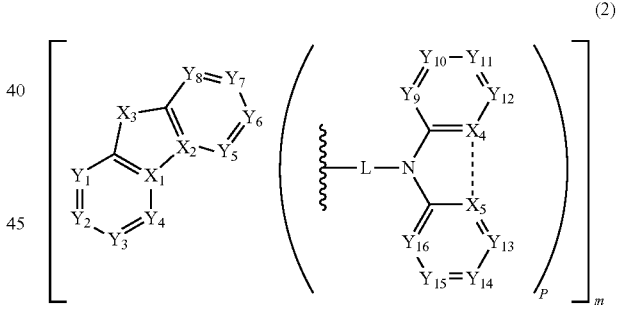

(2)

In the formula (1-4): $X_{12}$ to $X_{16}$, $R_{18}$, $R_{19}$, Ar, s, u, t and r respectively represent the same as $X_{12}$ to $X_{16}$ in the formula (1) and $R_{18}$, $R_{19}$, Ar, s, u, t and r in the formula (4). $X_{11}$ is a carbon atom bonded to the fourth structure.

In the formula (1-4), one or three of $X_{12}$ to $X_{16}$ are preferably nitrogen atoms.

In the formula (1-4), it is also preferable that $X_{12}$ and $X_{14}$ are nitrogen atoms; $X_{13}$ and $X_{15}$ are each a carbon atom bonded to the second or third structure; and $X_{16}$ is a carbon atom bonded to $R_1$.

In the formula (1-4), it is also preferable that $X_{12}$, $X_{14}$ and $X_{16}$ are nitrogen atoms; and $X_{13}$ and $X_{15}$ are each a carbon atom bonded to the second or third structure.

In the compound according to the exemplary embodiment, at least one of the second structure and the third structure is preferably bonded to $R_1$ of the first structure.

In the compound according to the exemplary embodiment, a sum (m+n) of m and n is preferably an integer of 2 to 4.

In the compound according to the exemplary embodiment, the second structure represented by the formula (2) is preferably represented by a formula (20).

[Formula 7]

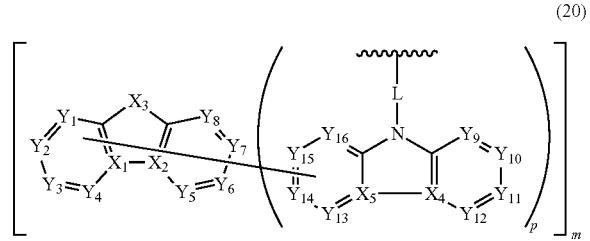

(20)

In the formula (20): $X_3$, $Y_1$ to $Y_8$, $Y_9$ to $Y_{16}$, L, m and p respectively represent the same as $X_3$, $Y_1$ to $Y_8$, $Y_9$ to $Y_{16}$, L, m and p in the formula (2); $X_1$ and $X_2$ are carbon atoms bonded to each other; and $X_4$ and $X_5$ are carbon atoms bonded to each other.

In the formula (20): it is preferable that p is 1; one of $Y_1$ to $Y_8$ is a carbon atom bonded to one of $Y_{13}$ to $Y_{16}$, and one of $Y_{13}$ to $Y_{16}$ is a carbon atom bonded to one of $Y_1$ to $Y_8$.

In the compound according to the exemplary embodiment, it is preferable that L is a substituted or unsubstituted aromatic hydrocarbon group having 6 ring carbon atoms, $Y_{16}$ is a carbon atom bonded to L, and L and $Y_{16}$ are bonded to each other to form a cyclic structure.

Specifically, the second structure represented by the formula (2) is also preferably represented by a formula (21).

[Formula 8]

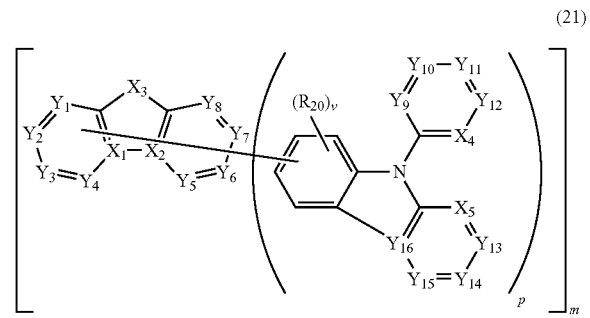

(21)

In the formula (21): $X_3$, $Y_1$ to $Y_8$, $Y_9$ to $Y_{16}$, m and p respectively represent the same as $X_3$, $Y_1$ to $Y_8$, $Y_9$ to $Y_{16}$, m and p in the formula (2); one of $Y_1$ to $Y_8$ and $X_3$ is a carbon atom or a nitrogen atom bonded to the aromatic hydrocarbon group as L; $X_1$ and $X_2$ are carbon atoms bonded to each other; $X_4$ is a carbon atom bonded to $R_5$; $X_5$ is a carbon atom bonded to $R_6$; $R_5$ to $R_6$ represent the same as $R_5$ to $R_6$ in the formula (2); $R_{20}$ is a hydrogen atom or a substituent; and v is 3. A plurality of $R_{20}$ may be mutually the same or different.

In the formula (21): p is preferably an integer of 1 to 3.

In the compound according to the exemplary embodiment, the second structure represented by the formula (2) is also preferably represented by a formula (22).

[Formula 9]

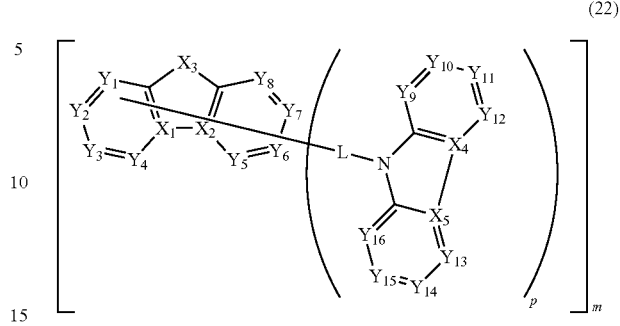

(22)

In the formula (22): $X_3$, $Y_1$ to $Y_{16}$, L, m and p respectively represent the same as $X_3$, $Y_1$ to $Y_{16}$, L, m and p in the formula (2); one of $Y_1$ to $Y_8$ and $X_3$ is a carbon atom or a nitrogen atom bonded to L; $X_1$ and $X_2$ are carbon atoms bonded to each other; and $X_4$ and $X_5$ are carbon atoms bonded to each other.

In the formula (22): p is preferably 2; $X_3$ is preferably a nitrogen atom bonded to $R_4$, or a nitrogen atom bonded to an atom contained in at least one of the first structure, the third structure and the fourth structure in a molecule.

$Y_1$ to $Y_8$ are each independently preferably a carbon atom bonded to $R_7$, a carbon atom bonded to L, or a carbon atom bonded to an atom contained in at least one of the first structure, the third structure and the fourth structure in a molecule.

$Y_9$ to $Y_{16}$ are each independently preferably a carbon atom bonded to $R_8$, or a carbon atom bonded to an atom contained in at least one of the first structure, the third structure and the fourth structure in a molecule.

In the compound according to the exemplary embodiment, the second structure represented by the formula (2) is also preferably represented by a formula (23).

[Formula 10]

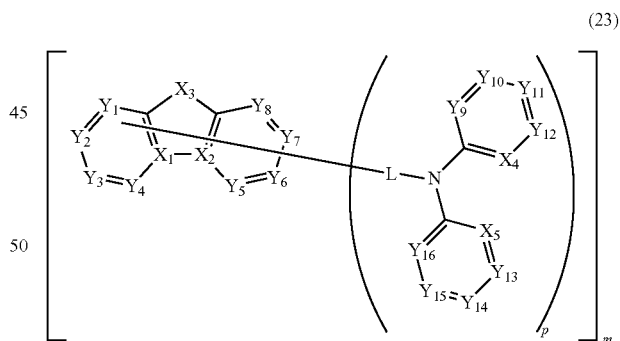

(23)

In the formula (23): $X_3$, $Y_1$ to $Y_{16}$, L, m and p respectively represent the same as $X_3$, $Y_1$ to $Y_{16}$, L, m and p in the formula (2); one of $Y_1$ to $Y_8$ and $X_3$ is a carbon atom or a nitrogen atom bonded to L; $X_1$ and $X_2$ are carbon atoms bonded to each other; and $X_4$ is a carbon atom bonded to $R_5$; and $X_5$ are carbon atoms bonded to $R_6$.

In the formula (23): $X_3$ is preferably a nitrogen atom bonded to $R_4$, or a nitrogen atom bonded to an atom contained in at least one of the first structure, the third structure and the fourth structure in a molecule.

In the compound according to the exemplary embodiment, the second structure represented by the formula (2) is also preferably represented by a formula (24).

[Formula 11]

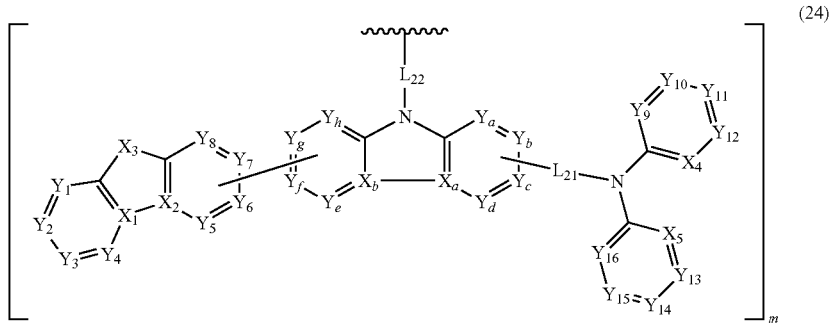

In the formula (24): $X_3$, $Y_1$ to $Y_{16}$ and m respectively represent the same as $X_3$, $Y_1$ to $Y_{16}$ and m in the formula (2); $Y_a$ to $Y_h$ respectively represent the same as $Y_9$ to $Y_{16}$ in the formula (2); $L_{21}$ and $L_{22}$ respectively represent the same as L in the formula (2); one of $Y_a$ to $Y_d$ is a carbon atom bonded to $L_{21}$; one of $Y_e$ to $Y_h$ is a carbon atom bonded to one of $Y_5$ to $Y_3$; $X_1$ and $X_2$ are carbon atoms bonded to each other; $X_4$ is a carbon atom bonded to $R_5$; $X_5$ is a carbon atom bonded to $R_6$; $X_a$ is a carbon atom bonded to $X_b$; and $X_b$ is a carbon atom bonded to $X_a$.

In the formula (24): $X_3$ is preferably a nitrogen atom bonded to $R_4$, or a nitrogen atom bonded to an atom contained in at least one of the first structure, the third structure and the fourth structure in a molecule.

$Y_a$ to $Y_d$ are each independently preferably a carbon atom bonded to $R_8$, a carbon atom bonded to $L_{21}$, or a carbon atom bonded to an atom contained in at least one of the first structure, the third structure and the fourth structure in a molecule.

$Y_e$ to $Y_h$ are each independently preferably a carbon atom bonded to $R_8$, a carbon atom bonded to one of $Y_5$ to $Y_8$, or a carbon atom bonded to an atom contained in at least one of the first structure, the third structure and the fourth structure in a molecule.

$Y_1$ to $Y_4$ are each independently preferably a carbon atom bonded to $R_7$, or a carbon atom bonded to an atom contained in at least one of the first structure, the third structure and the fourth structure in a molecule.

$Y_5$ to $Y_8$ are each independently preferably a carbon atom bonded to $R_7$, a carbon atom bonded to one of $Y_e$ to $Y_h$, or a carbon atom bonded to an atom contained in at least one of the first structure, the third structure and the fourth structure in a molecule.

In the compound according to the exemplary embodiment, the second structure is exemplified by structures below. A wavy line of each of the structures below represents a bonding position of the second structure to another structure.

[Formula 12]

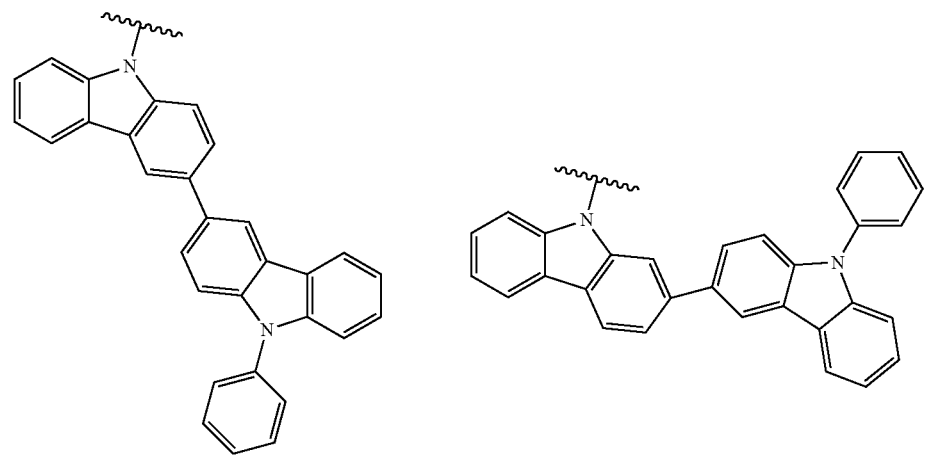

-continued
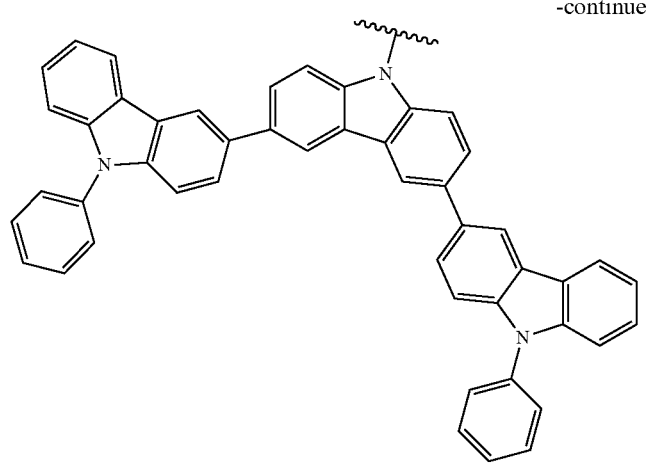
[Formula 13]
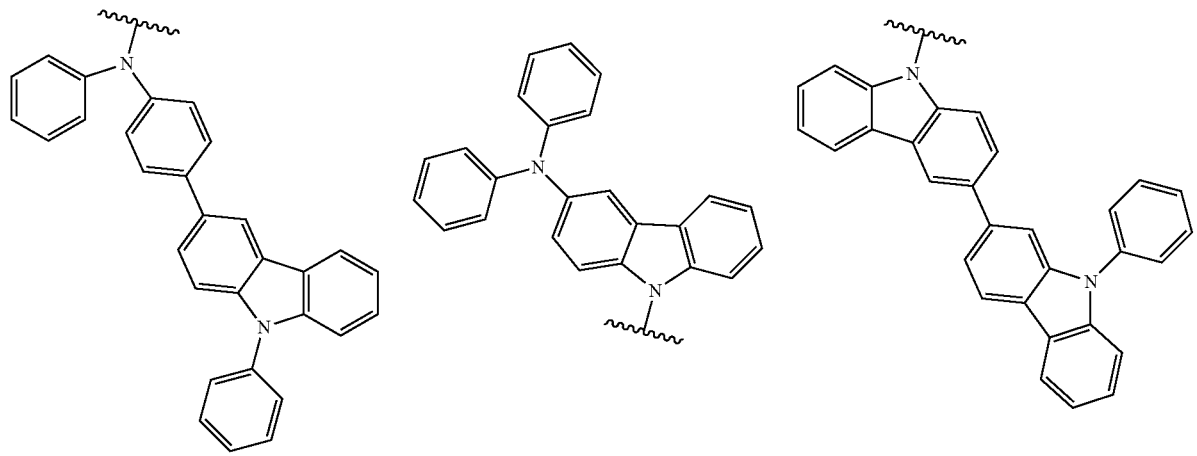
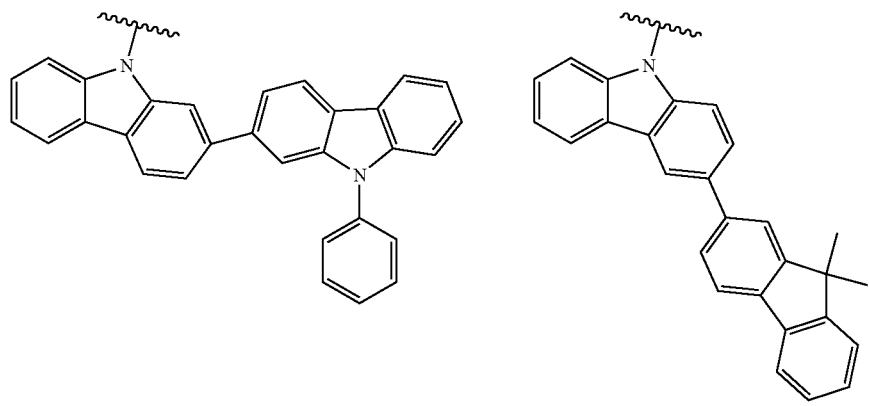

-continued
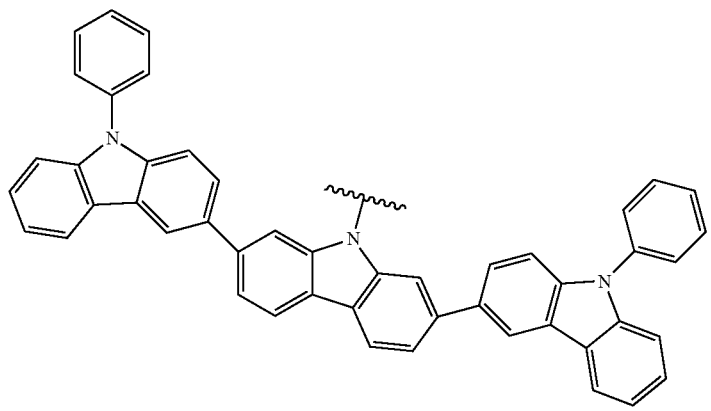
[Formula 14]
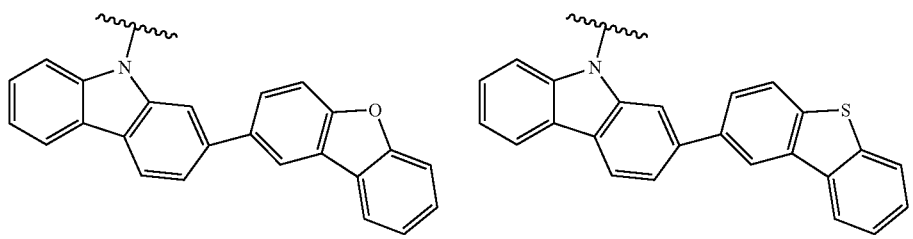
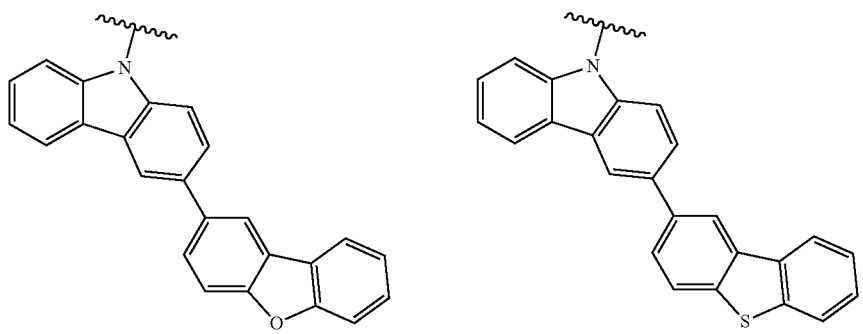
[Formula 15]
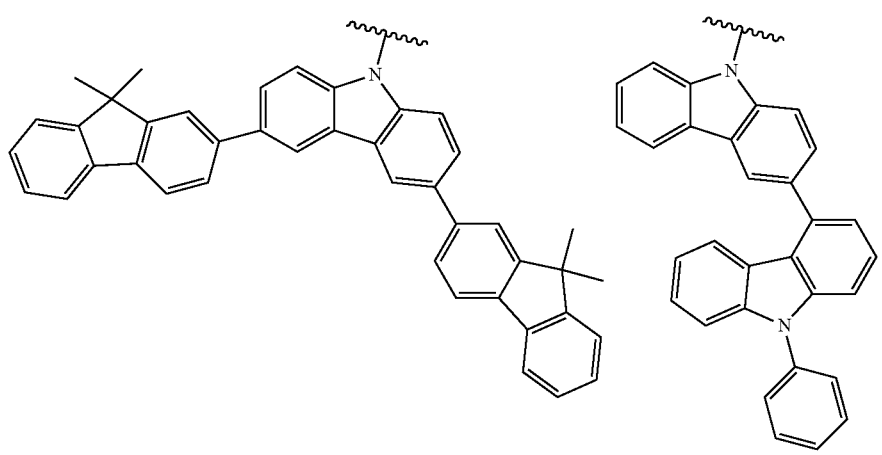

-continued
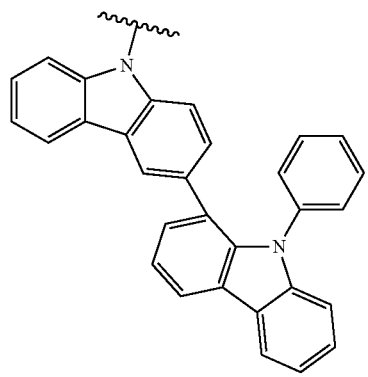
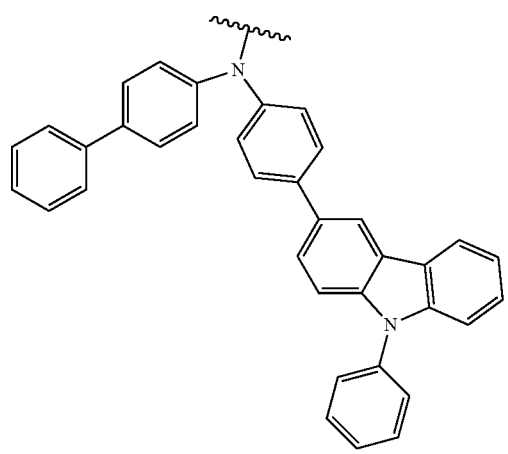
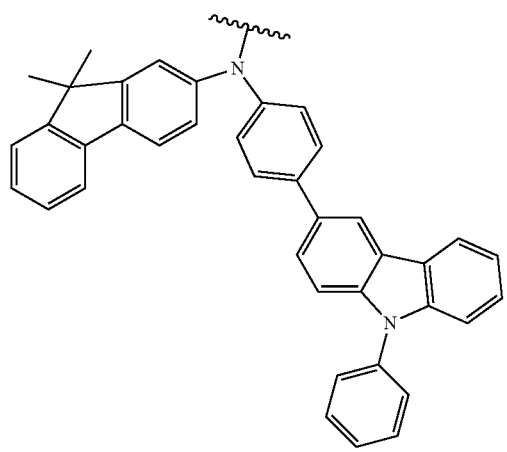
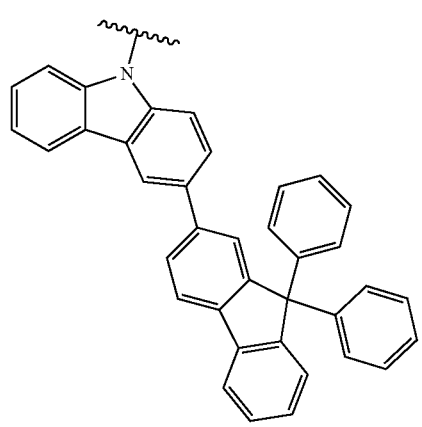
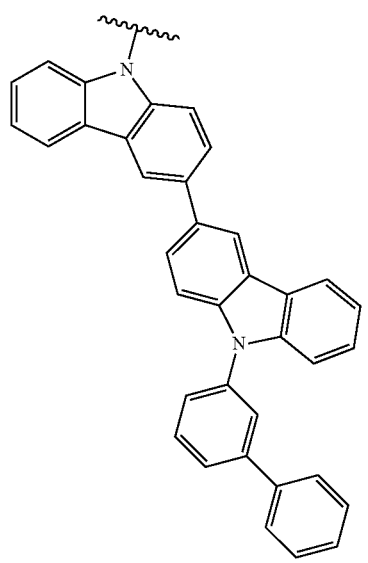
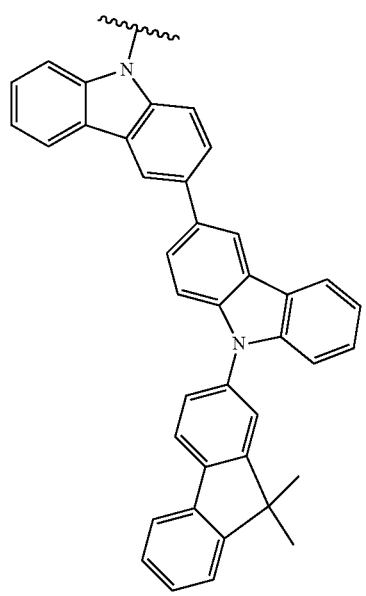
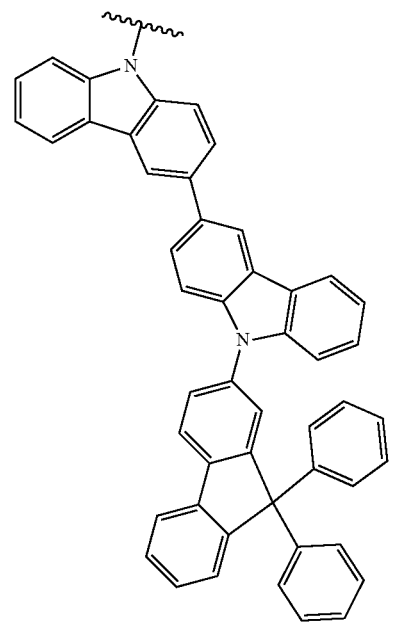

-continued
[Formula 16]
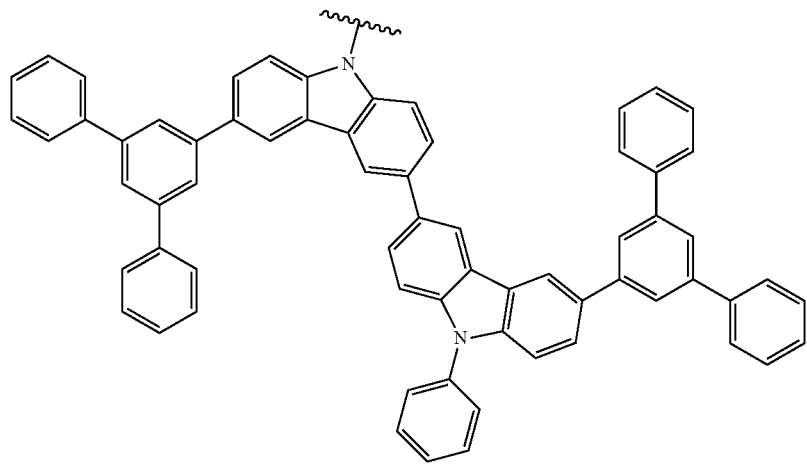
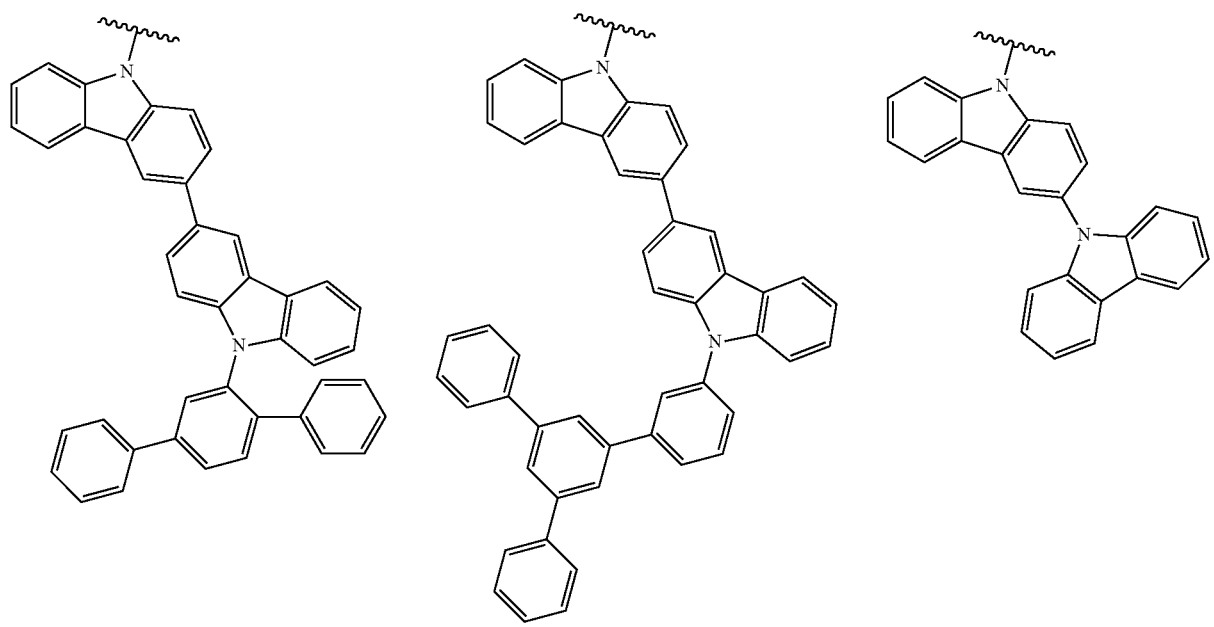
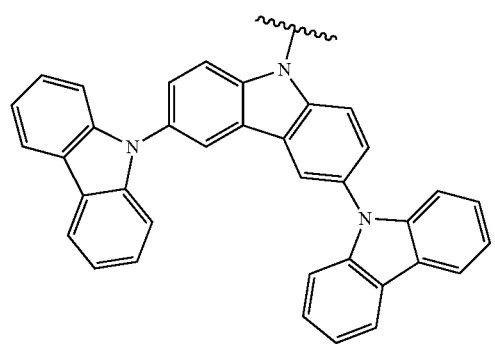

-continued

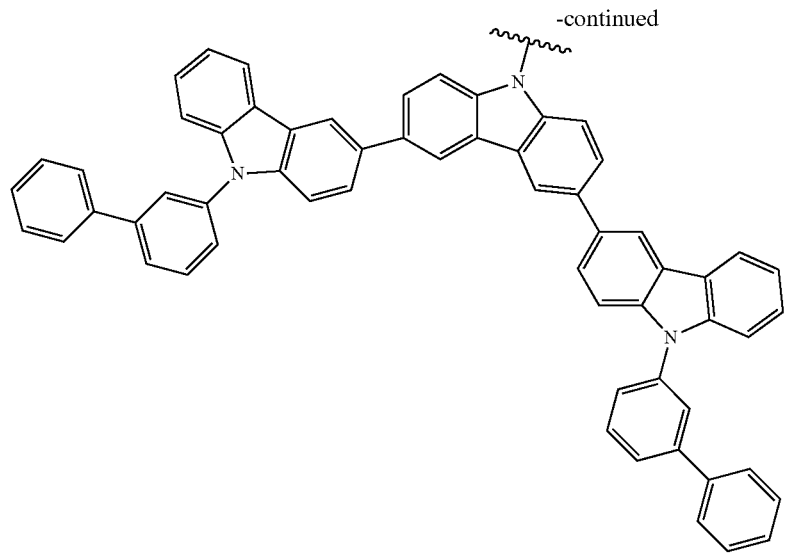

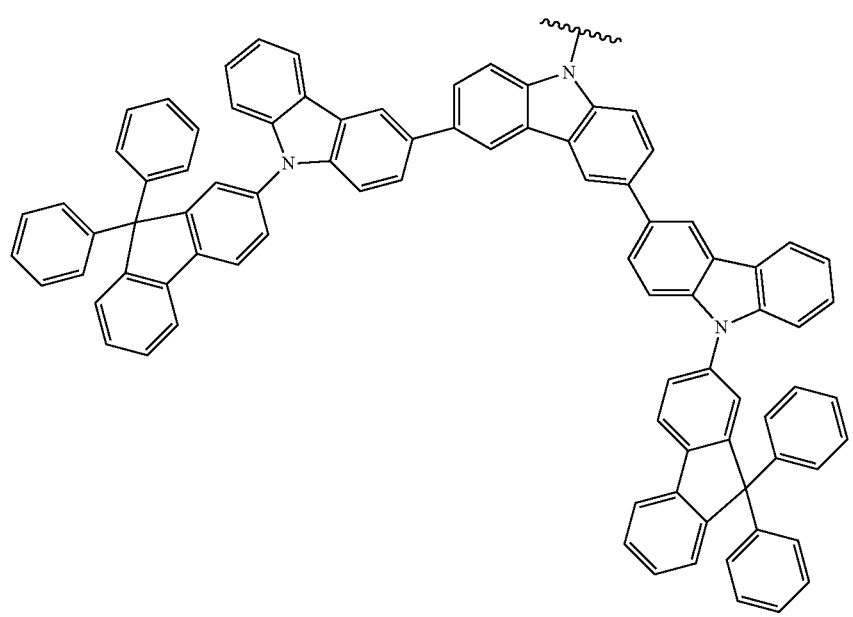 [SMILES: *n1c2ccc(-c3ccc4c(c3)c3ccccc3n4-c3ccc4c(c3)C(c3ccccc3)(c3ccccc3)c3ccccc3-4)cc2c2cc(-c3ccc4c(c3)c3ccccc3n4-c3ccc4c(c3)C(c3ccccc3)(c3ccccc3)c3ccccc3-4)ccc21]

In the compound according to the exemplary embodiment, q=0 is preferable and the third structure is more preferably represented by a formula (31).

[Formula 17]

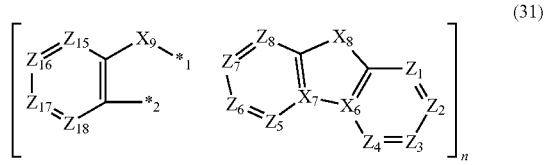

(31)

In the formula (31): $X_8$, $X_9$, $Z_1$ to $Z_4$, $Z_{15}$ to $Z_{18}$ and n respectively represent the same as $X_8$, $X_9$, $Z_1$ to $Z_4$, $Z_{15}$ to $Z_{18}$ and n in the formula (3).

$X_6$ and $X_7$ are carbon atoms bonded to each other.

*1 and *2 are each independently a bonding position to a carbon atom of $Z_1$ to $Z_8$.

$Z_5$ to $Z_8$ are each independently a carbon atom bonded to $R_{12}$, a carbon atom bonded to an atom contained in at least one of the first structure, the second structure and the fourth structure in a molecule, or a carbon atom bonded at a position represented by *1 or *2.

$R_{12}$ represents the same as $R_{12}$ in the formula (3).

At least two of $Z_1$ to $Z_8$ each are a carbon atom bonded at a position represented by *1 or *2.

In the formula (31), the third structure is preferably a structure selected from the group consisting of structures represented by formulae (31a), (31b), (31c), (31d), (31e) and (31f).

[Formula 18]

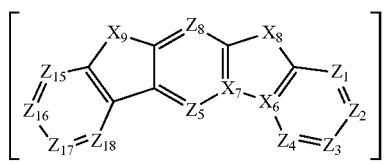
(31a)

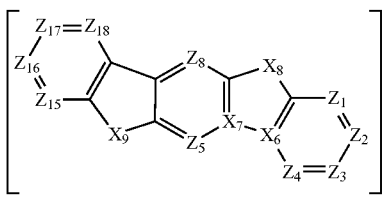
(31b)

[Formula 19]

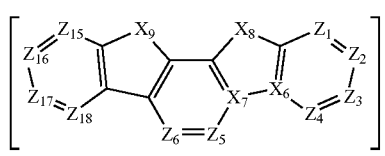
(31c)

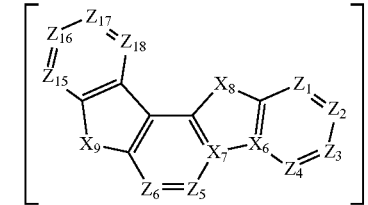
(31d)

[Formula 20]

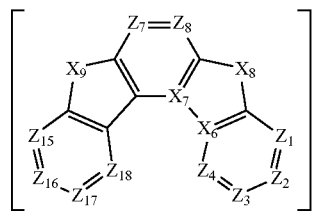
(31e)

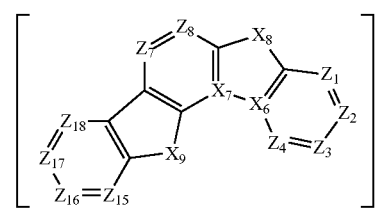
(31f)

In the formulae (31a) to (31f), $X_6$ to $X_9$, $Z_1$ to $Z_4$, and $Z_{15}$ to $Z_{18}$ respectively represent the same as $X_6$ to $X_9$, $Z_1$ to $Z_4$, and $Z_{15}$ to $Z_{18}$ in the formula (31). In the formulae (31a) to (31b), $Z_5$ and $Z_8$ respectively represent the same as $Z_5$ and $Z_8$ in the formula (31).

In the formulae (31c) to (31d), $Z_5$ and $Z_6$ respectively represent the same as $Z_5$ and $Z_6$ in the formula (31). In the formulae (31e) to (31f), $Z_7$ and $Z_8$ respectively represent the same as $Z_7$ and $Z_8$ in the formula (31).

In the compound according to the exemplary embodiment, the third structure is exemplified by structures below. A wavy line of each of the structures below represents a bonding position of the third structure to another structure.

[Formula 21]

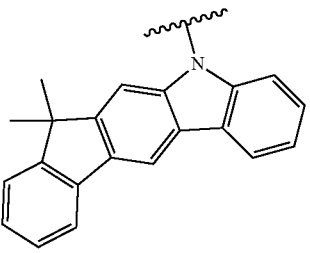

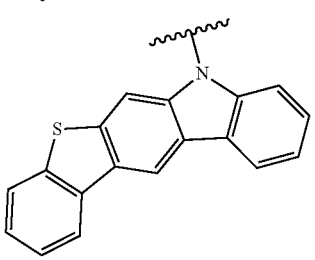

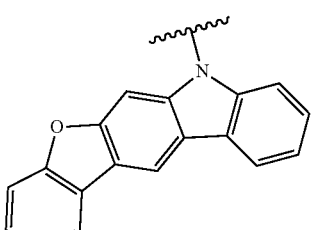

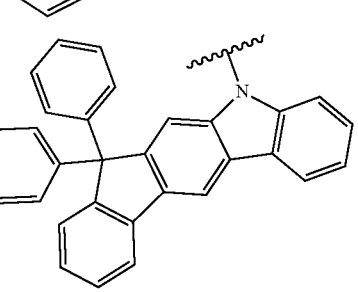

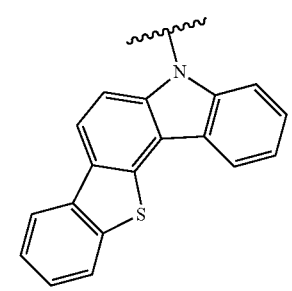

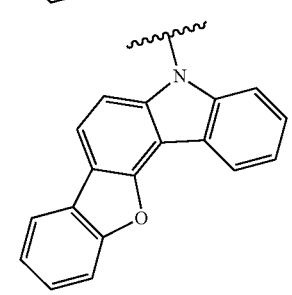

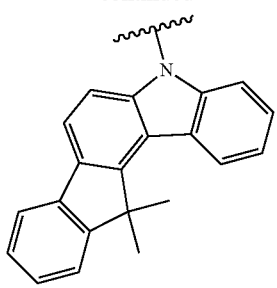

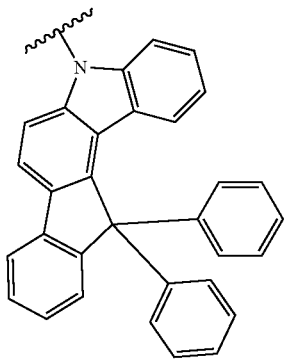

[Formula 22]

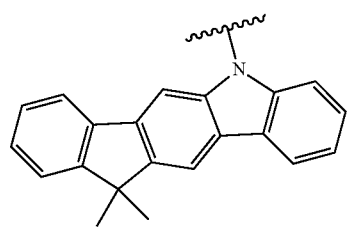

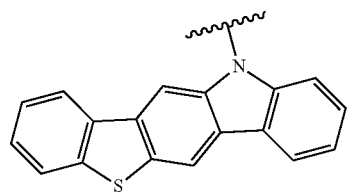

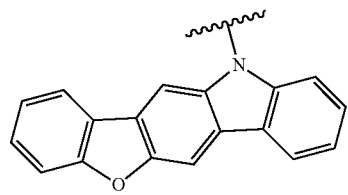

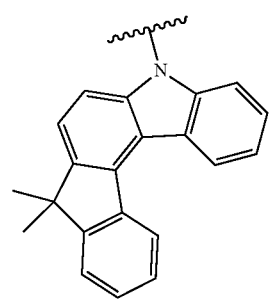

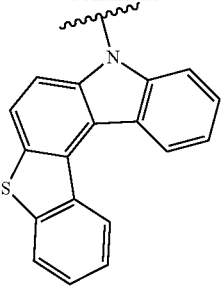

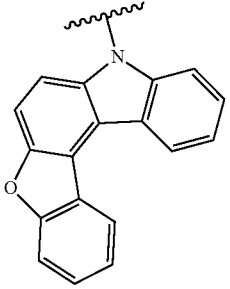 [SMILES: *n1c2ccccc2c2c3c(ccc21)oc1ccccc13]

In the compound according to the exemplary embodiment, a plurality of $R_1$ are preferably not bonded to each other to avoid formation of a cyclic structure.

In the compound according to the exemplary embodiment, a plurality of $R_1$ are preferably not bonded to each other to avoid formation of a cyclic structure.

In the compound according to the exemplary embodiment, $R_1$ to $R_{20}$, $R_a$ and $R_b$ as a substituent are each independently preferably selected from the group consisting of a substituted or unsubstituted aromatic hydrocarbon group having 6 to 30 ring carbon atoms, substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a halogen atom, a cyano group, a nitro group, and a carboxy group.

In the compound according to the exemplary embodiment, $R_4$ as a substituent is preferably a substituted or unsubstituted aromatic hydrocarbon group having 6 to 30 ring carbon atoms.

$R_{14}$, $R_{15}$, $R_a$ and $R_b$ as a substituent are each independently preferably selected from the group consisting of a substituted or unsubstituted aromatic hydrocarbon group having 6 to 30 ring carbon atoms, and a substituted or unsubstituted alkyl group having 1 to 30 carbon atoms.

A substituted or unsubstituted aromatic hydrocarbon group as a substituent for $X_8$ is preferably a substituted or unsubstituted aromatic hydrocarbon group having 6 to 30 ring carbon atoms.

In the compound according to the exemplary embodiment, it is preferable that the first structure is bonded to the second structure, the first structure is bonded to the third structure, and the first structure is bonded to the fourth structure.

The compound according to the exemplary embodiment is preferably represented by one of formulae (100) to (109).

[Formula 23]
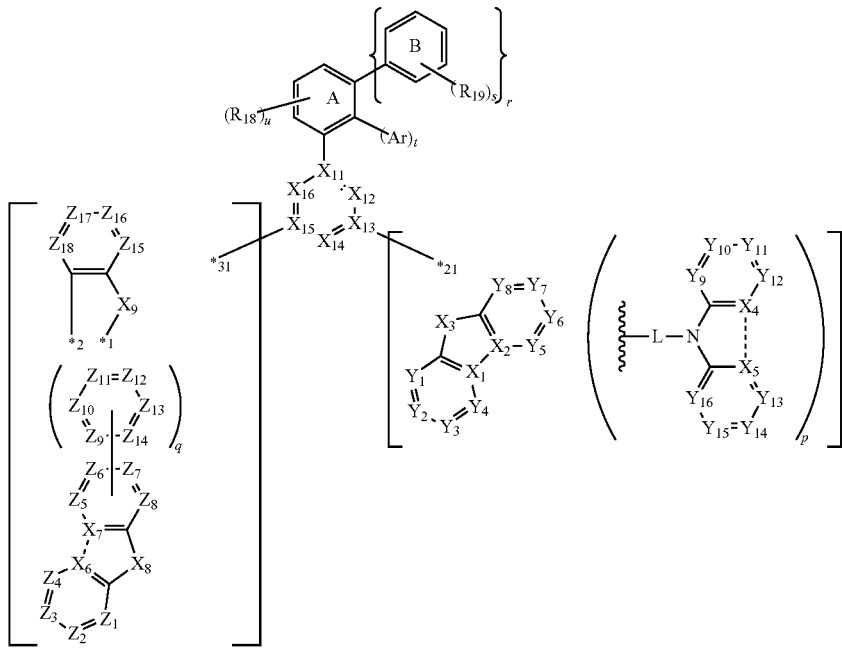
[Formula 24]
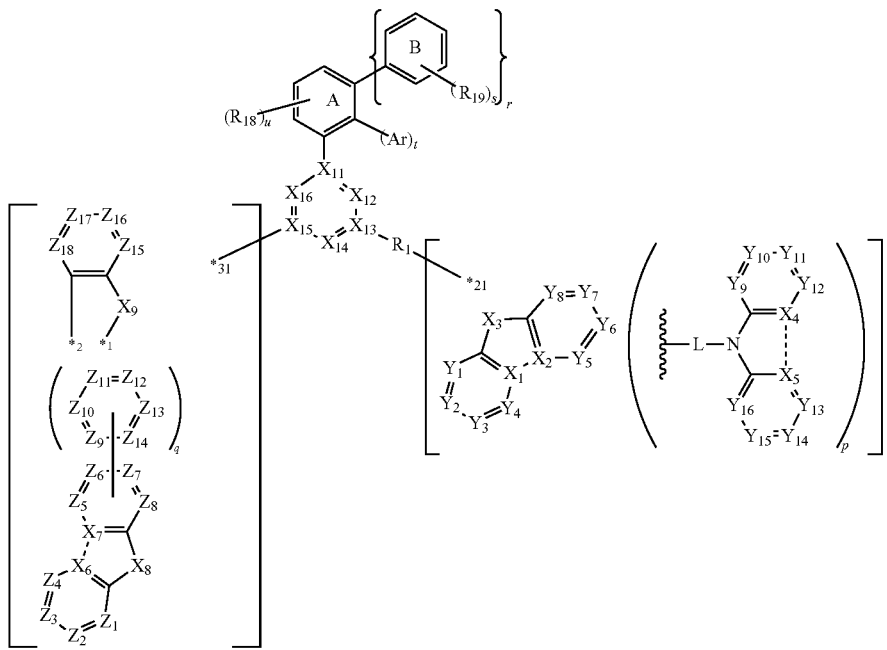

-continued
[Formula 25]
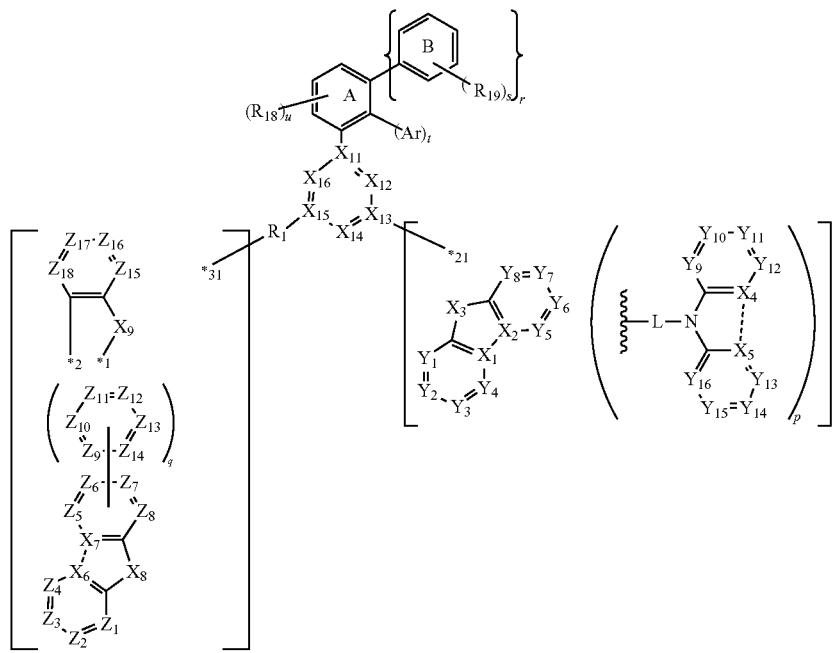
[Formula 26]
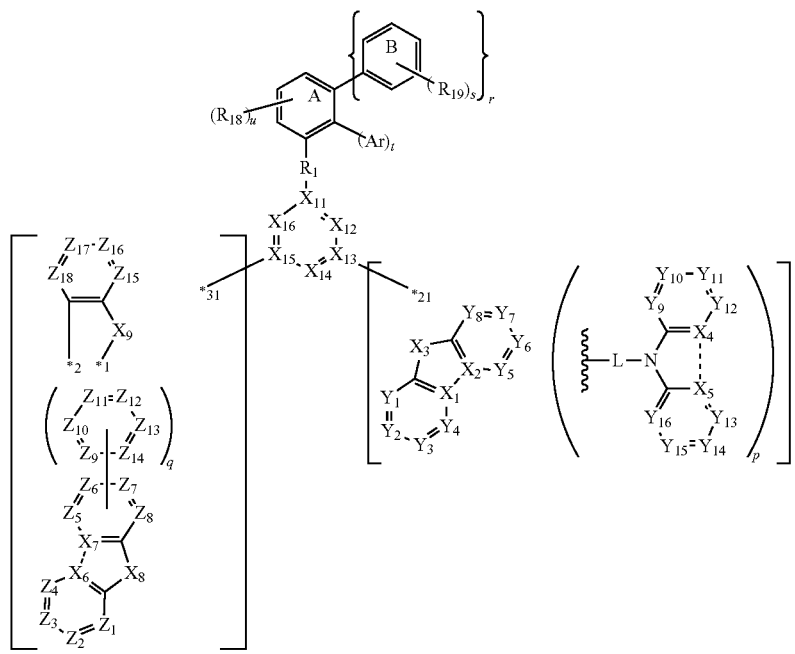

[Formula 27]
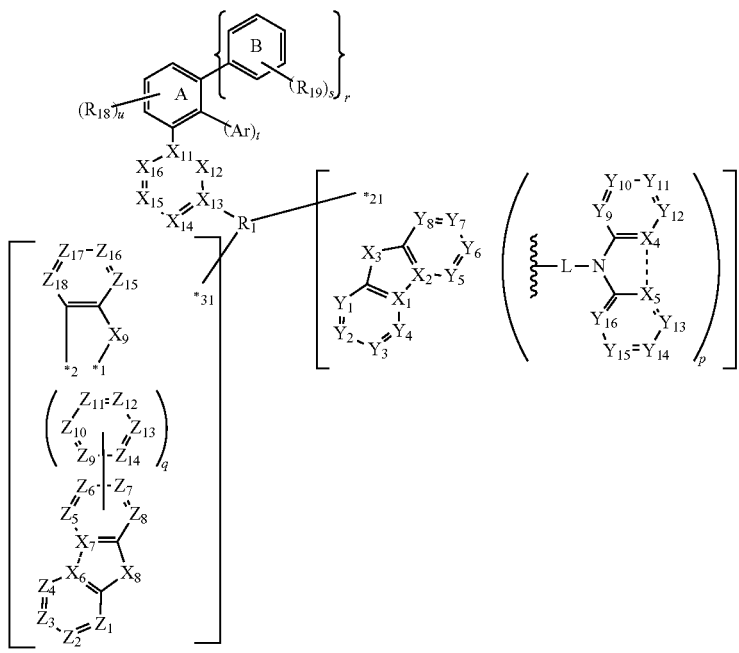
[Formula 28]
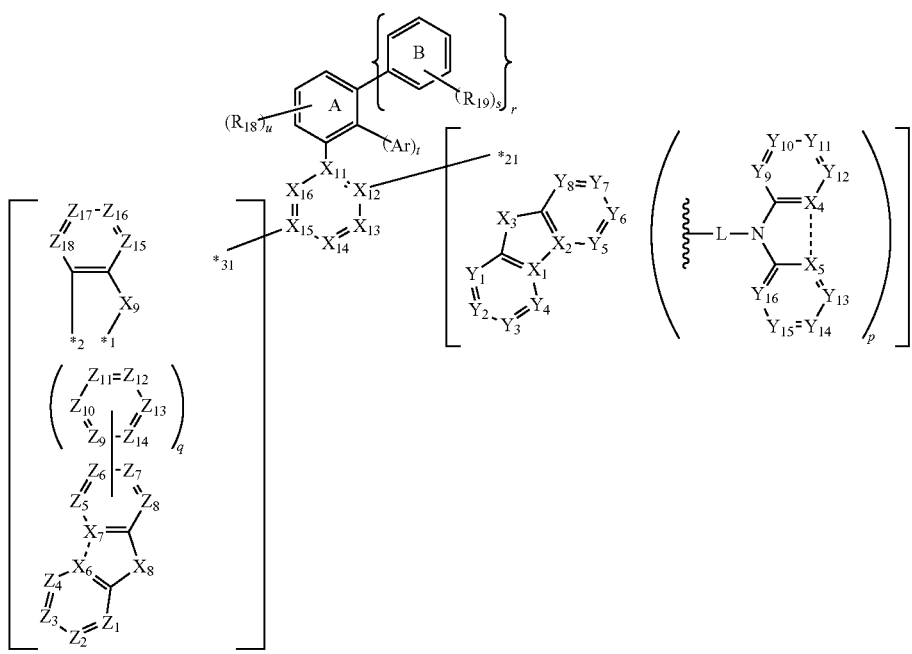

[Formula 29]
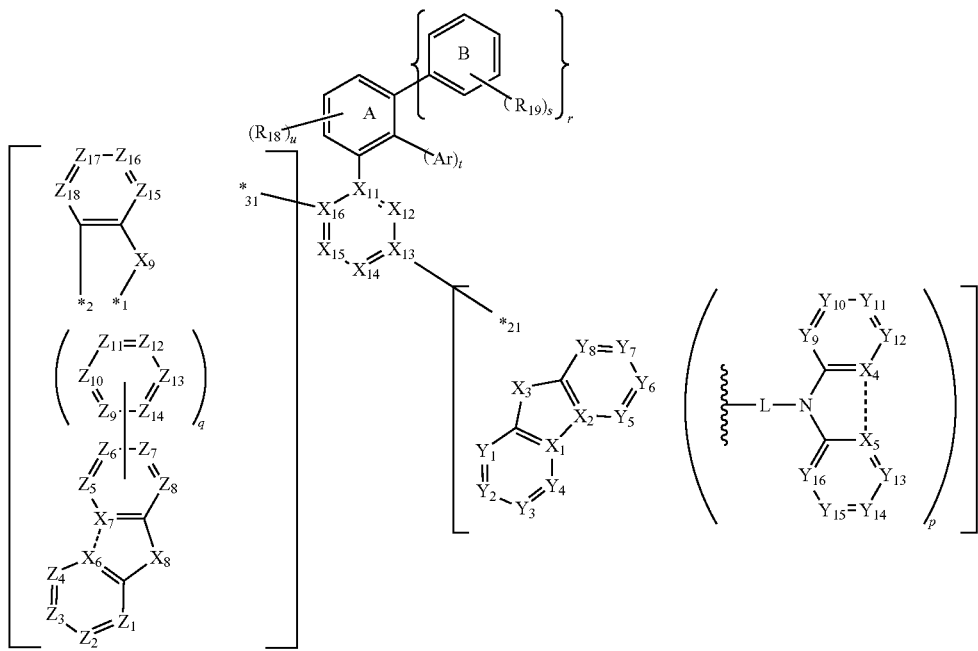
[Formula 30]
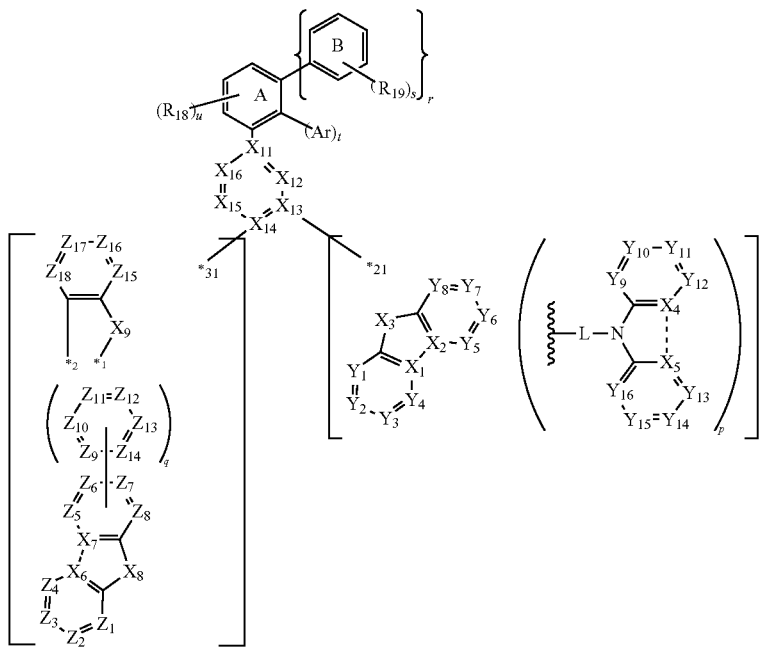

[Formula 31]

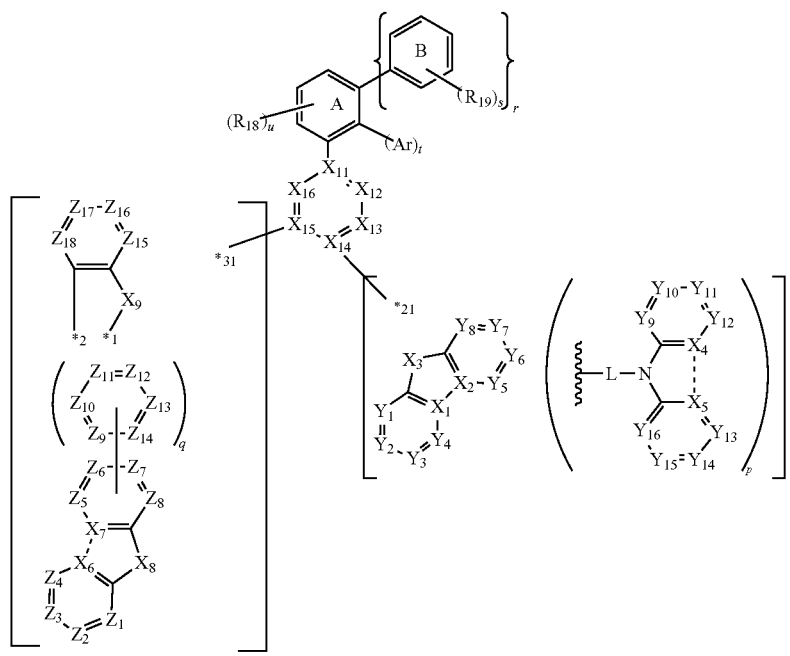

[Formula 32]

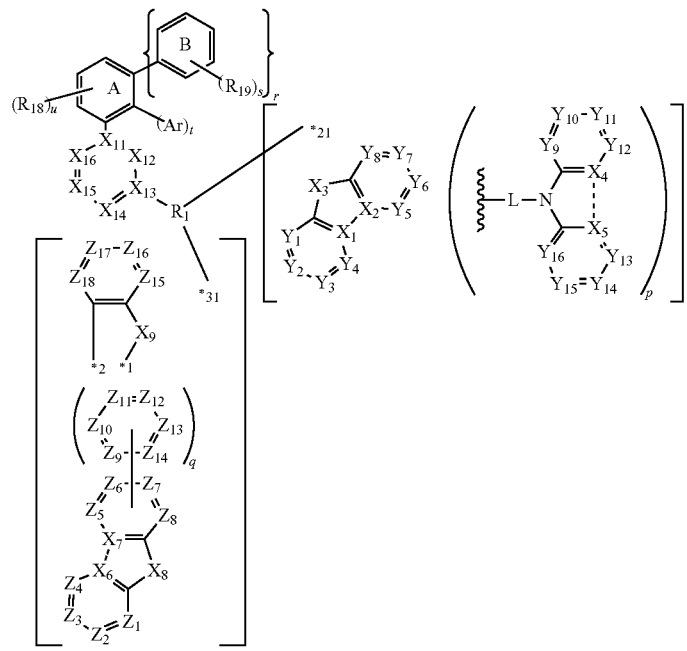

In the formulae (100) to (109): $X_{11}$ to $X_{16}$ and $R_1$ respectively represent the same as $X_{11}$ to $X_{16}$ and $R_1$ in the formula (1); $X_1$ to $X_5$, $Y_1$ to $Y_{16}$, L and p respectively represent the same as $X_1$ to $X_5$, $Y_1$ to $Y_{16}$, L and p in the formula (2); $X_6$ to $X_9$, $Z_1$ to $Z_{18}$, q, *1 and *2 respectively represent the same as $X_6$ to $X_9$, $Z_1$ to $Z_{18}$, q, *1 and *2 in the formula (3); $R_{18}$, $R_{19}$, Ar, s, u, t and r respectively represent the same as $R_{18}$, $R_{19}$, Ar, s, u, t and r in the formula (4); $*_{21}$ represents a bonding position of the second structure to the first structure; and $*_{31}$ represents a bonding position of the third structure to the first structure.

Manufacturing Method of Compound in Embodiment

The compound according to the exemplary embodiment can be manufactured by a method described in a later-described Example. The compound according to the exemplary embodiment can be manufactured by using a known alternative reaction and a material suitable for a target product according to the method described in the Example.

Examples of the compound according to the exemplary embodiment will be shown below. However, the compound of the invention is not limited to the examples.

[Formula 33]
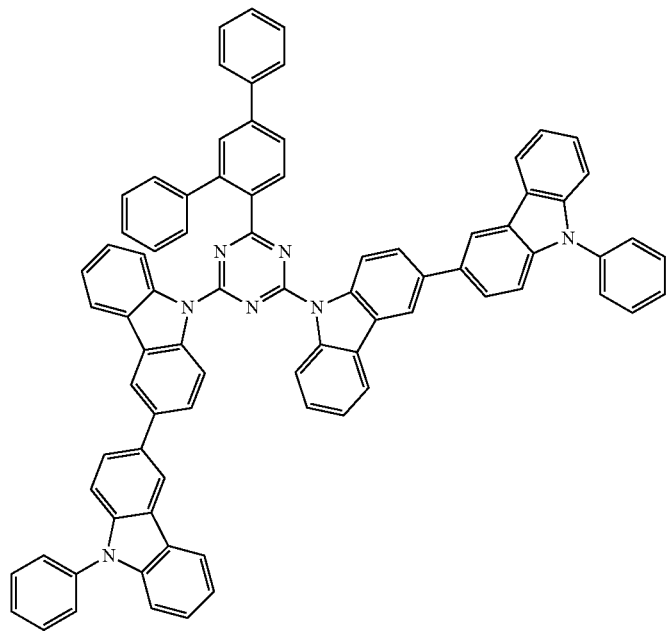
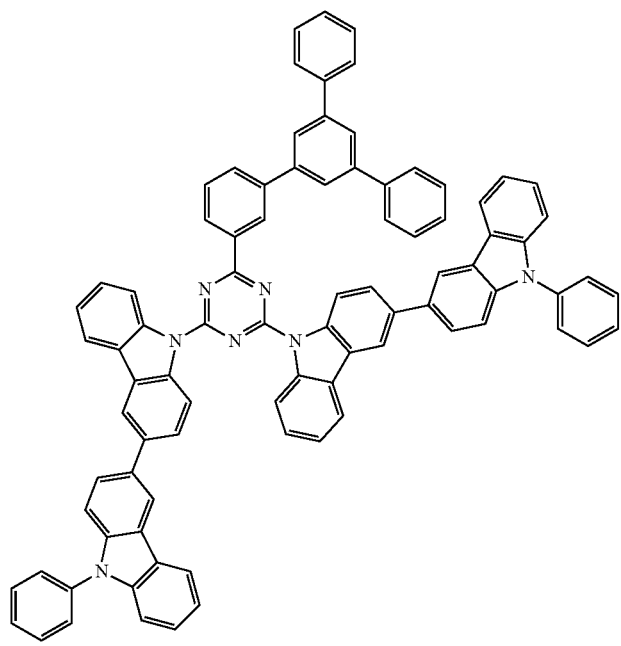

-continued
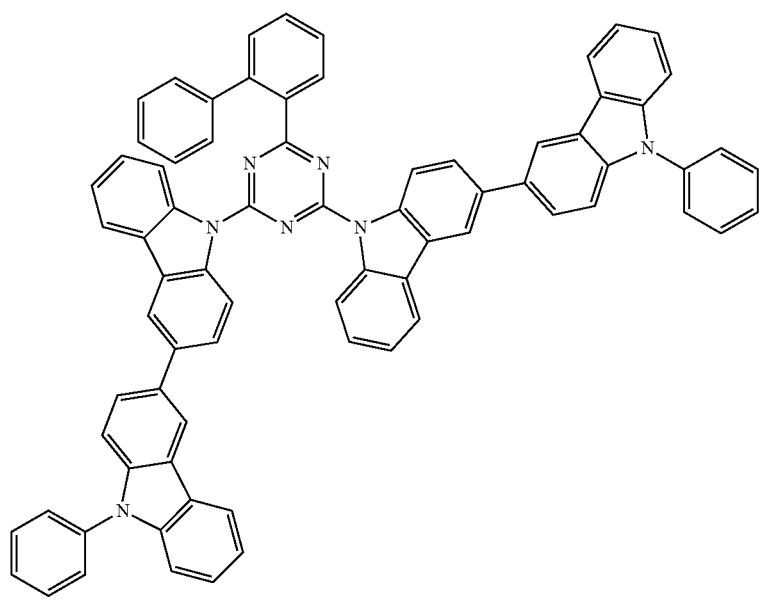
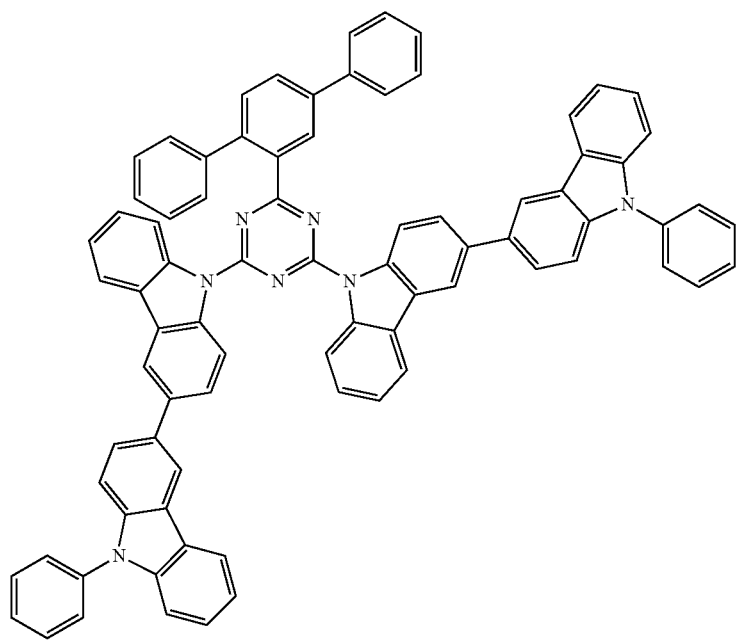

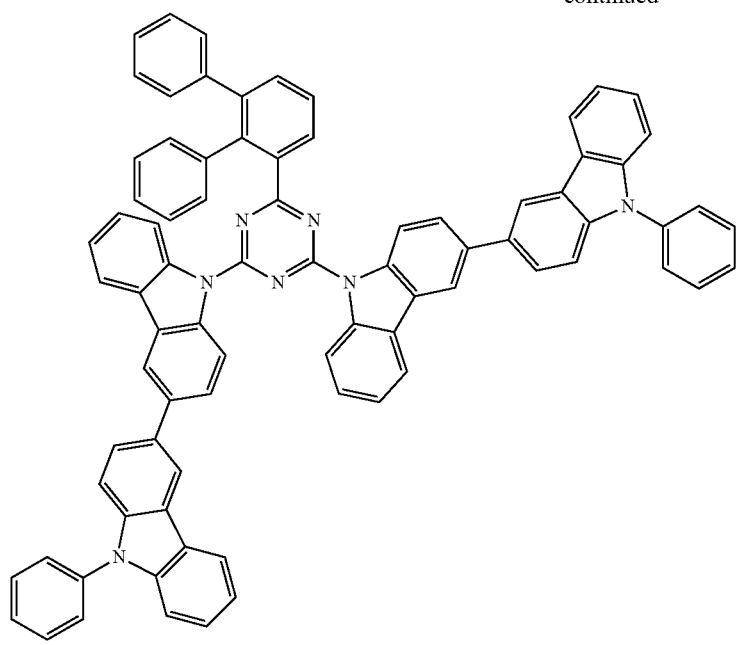
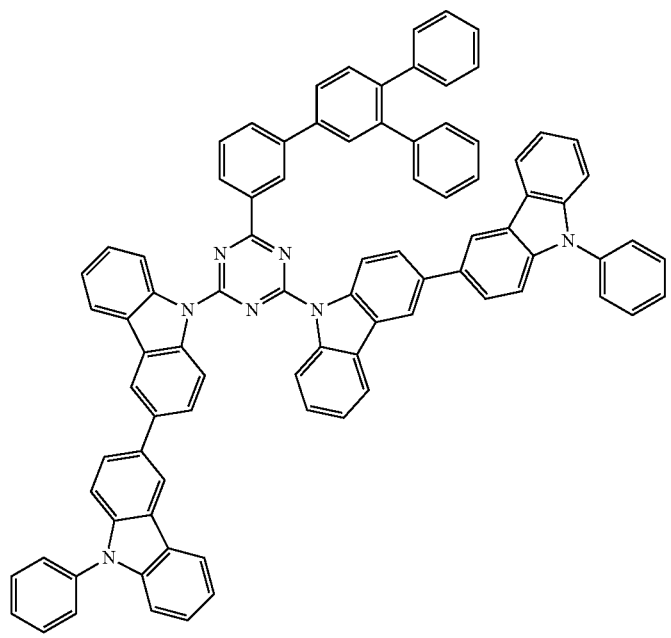

[Formula 34]
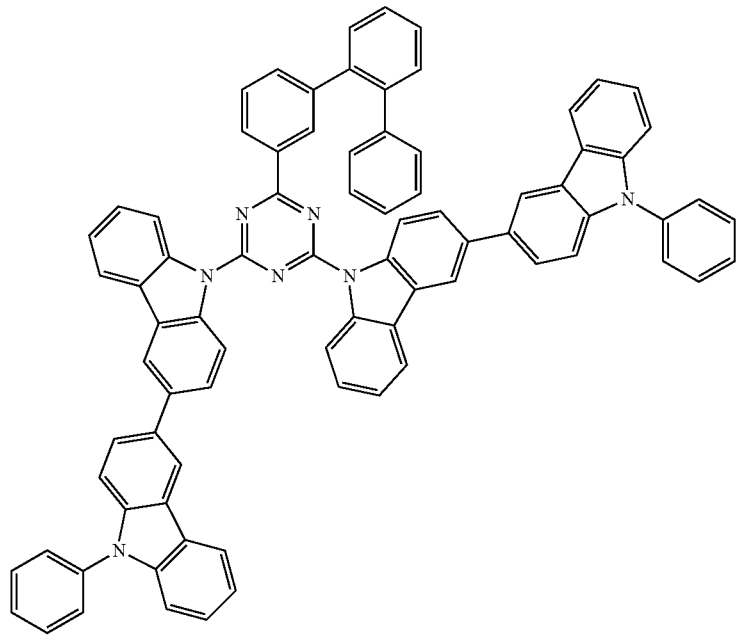
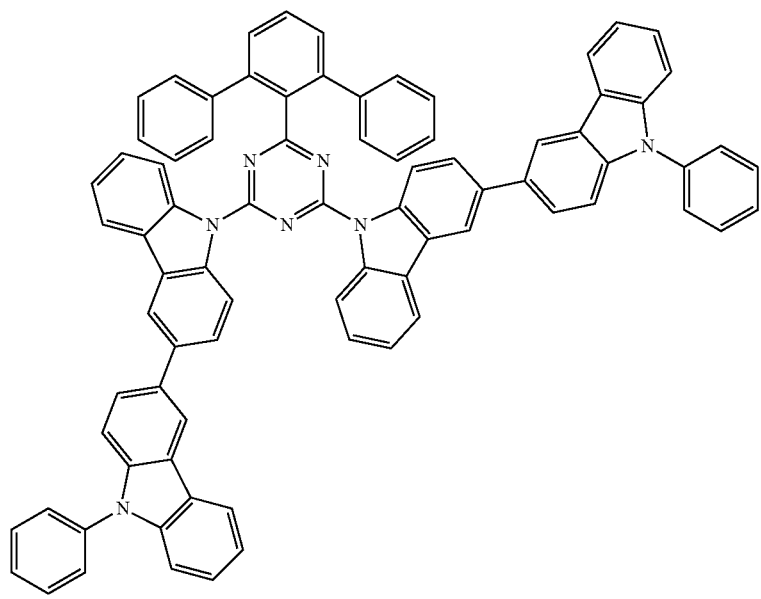

-continued
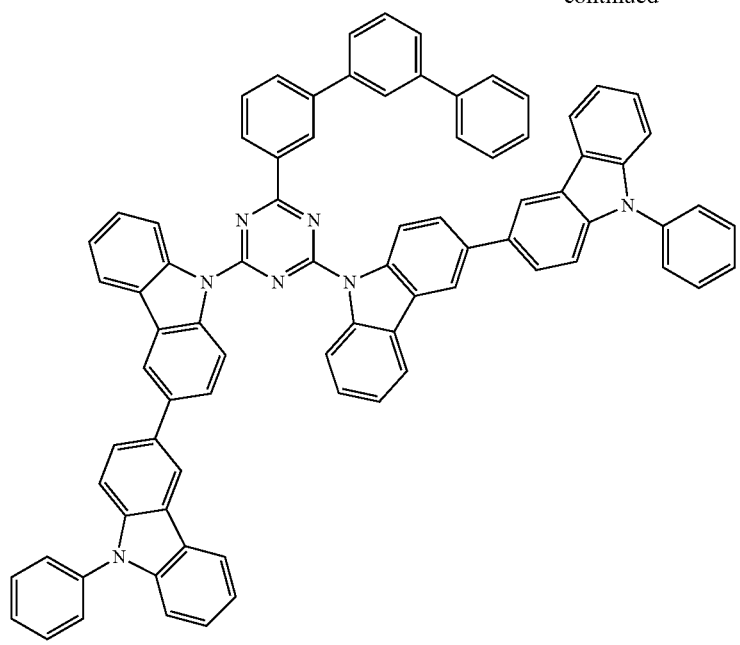
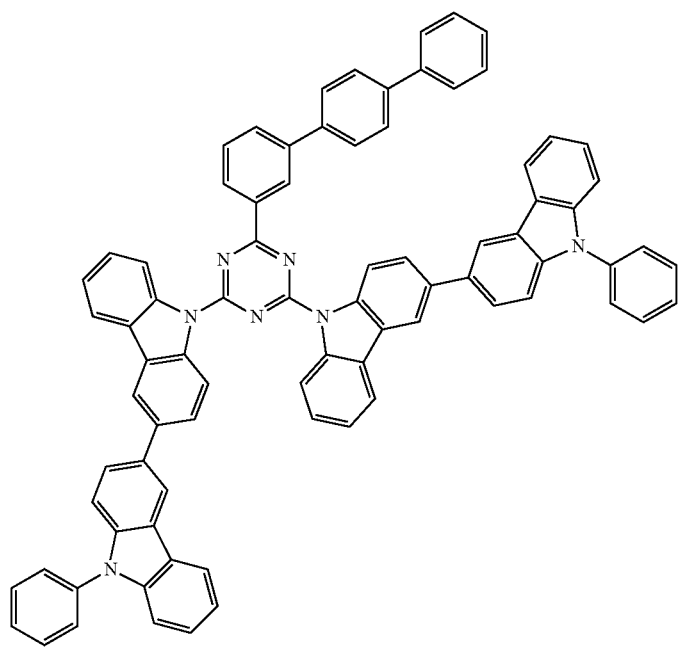

[Formula 35]
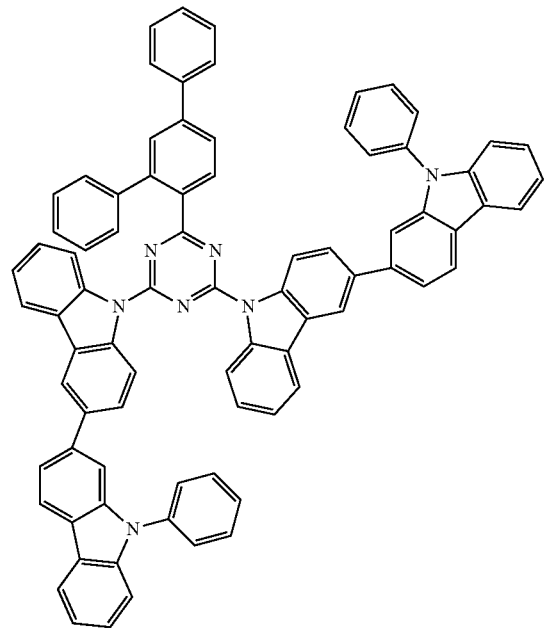 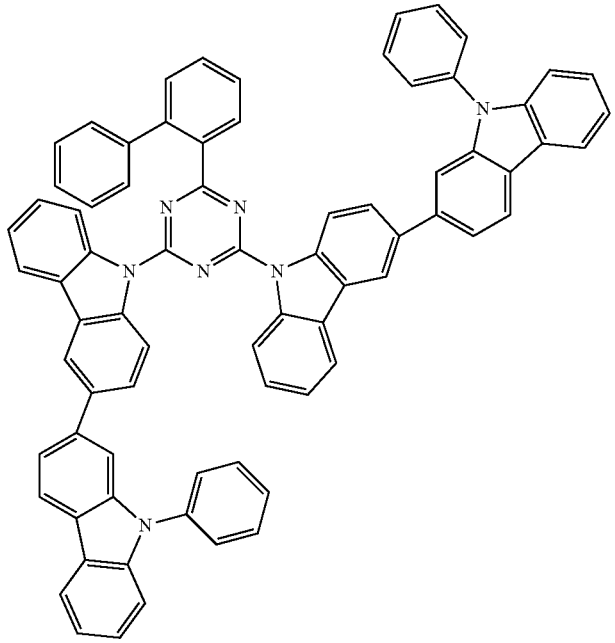
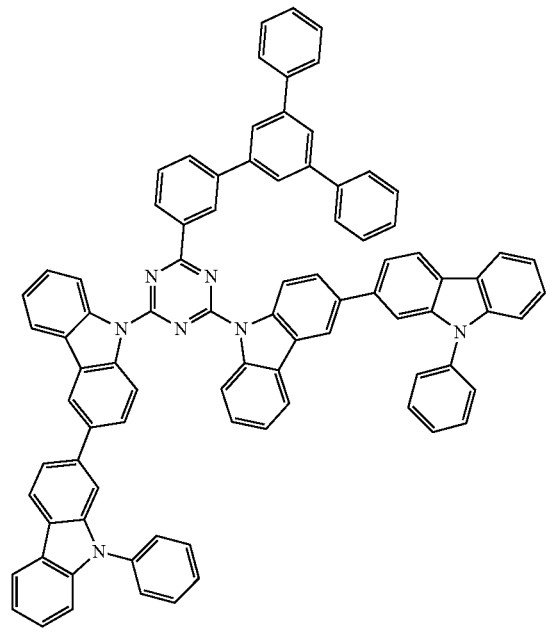 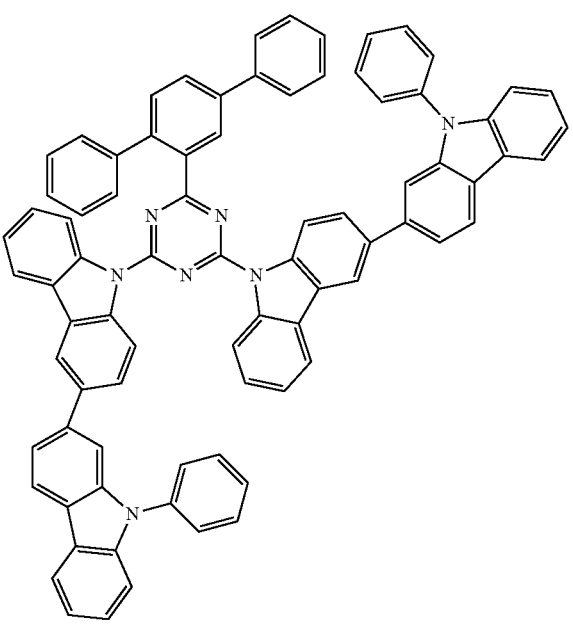

51
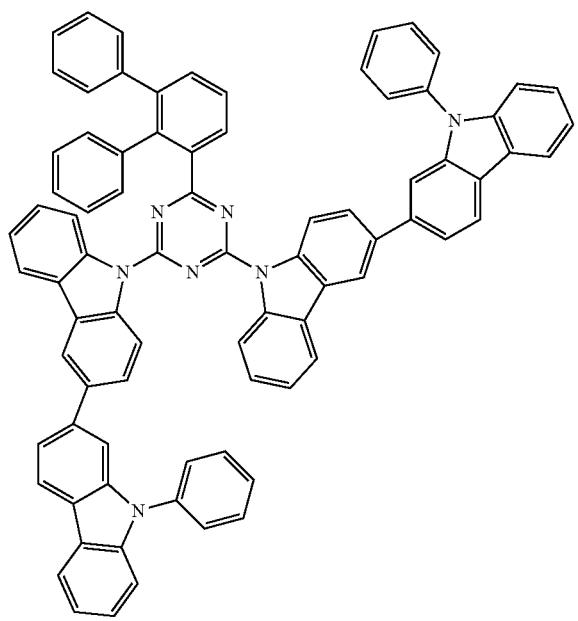
52
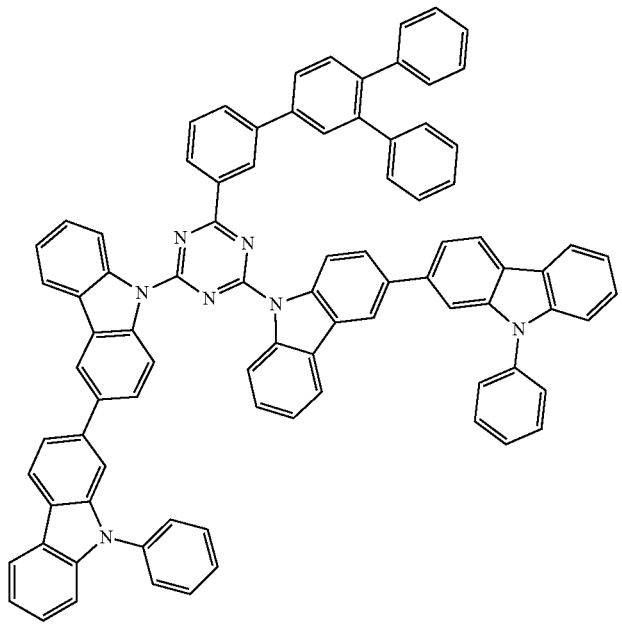
[Formula 36]
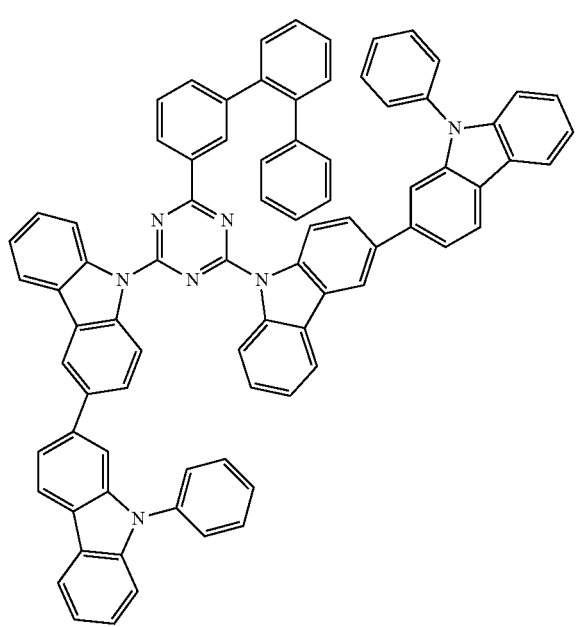
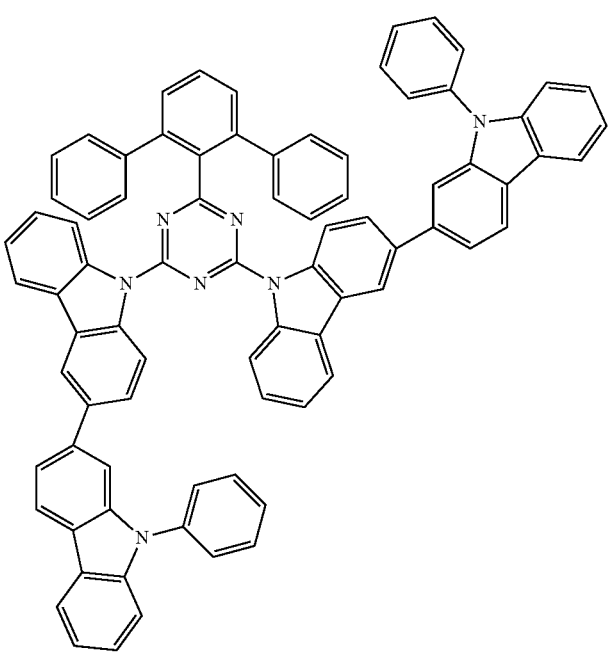

-continued
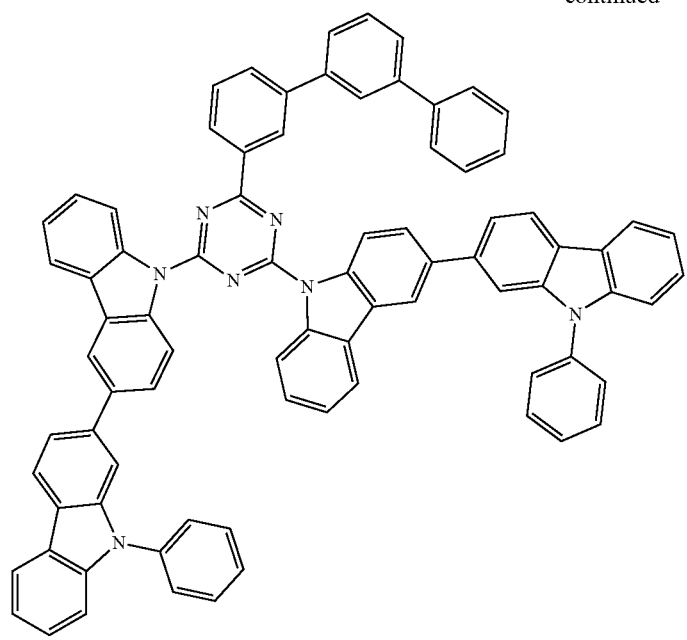
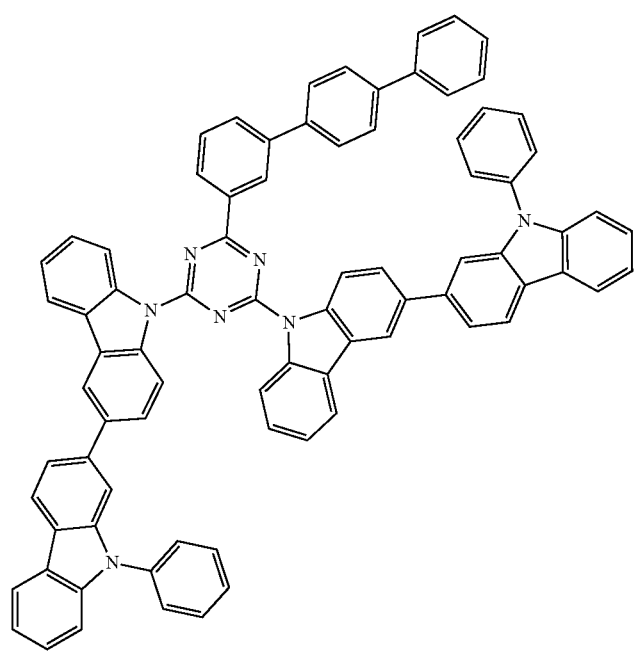

[Formula 37]
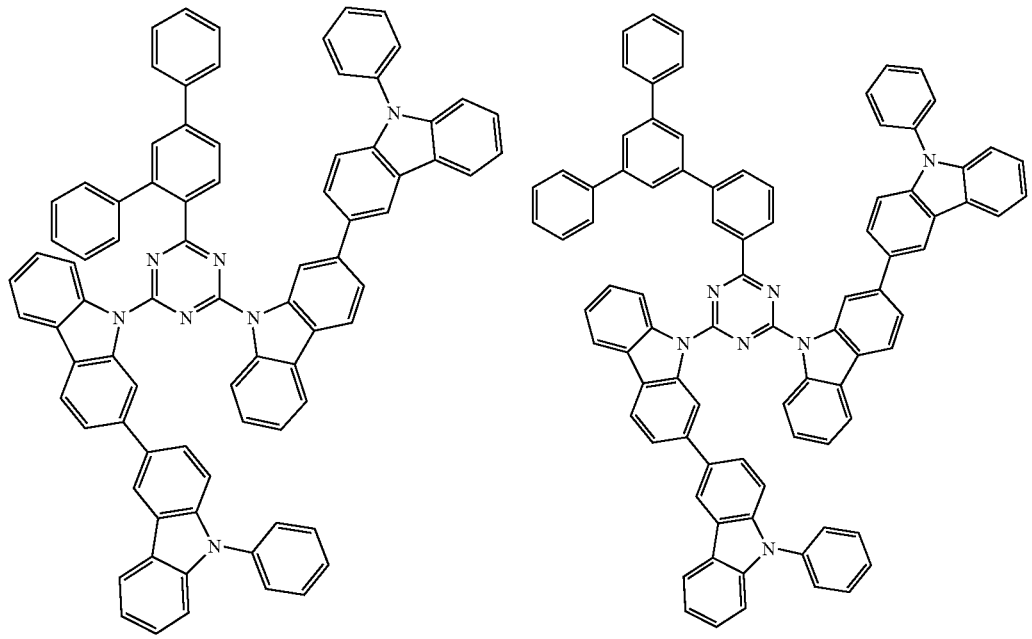
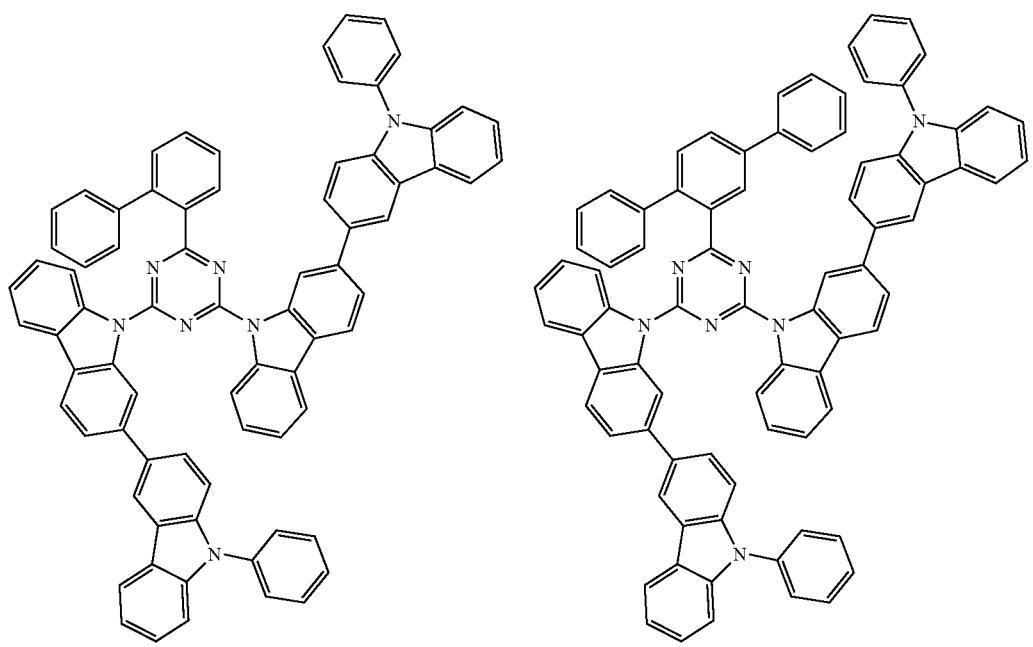

-continued
57
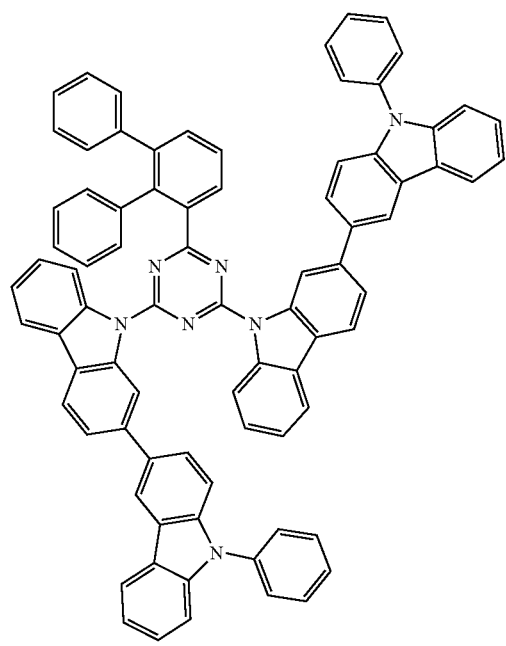
58
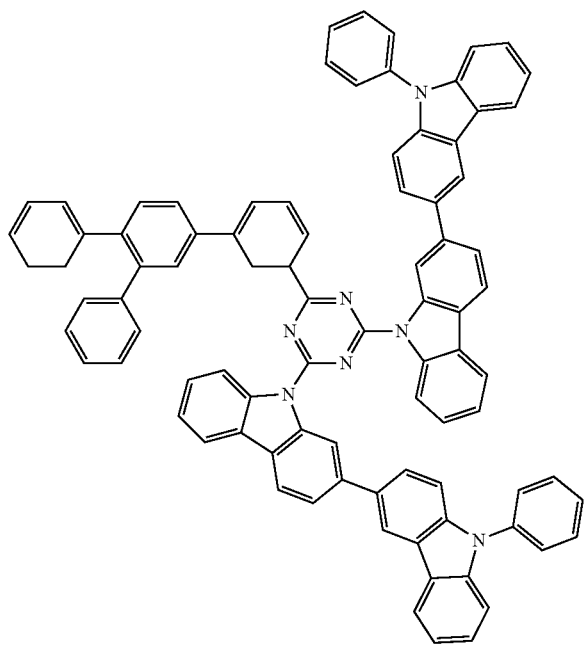
[Formula 38]
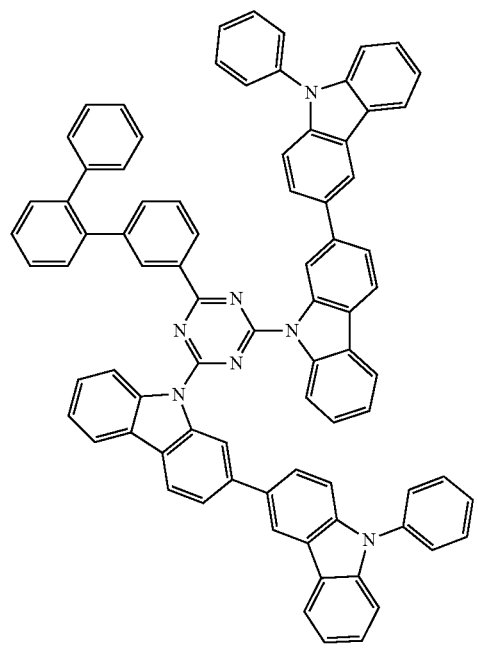 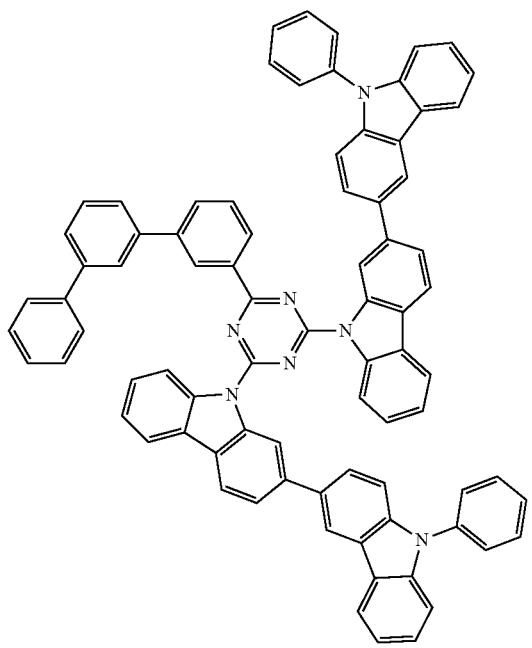

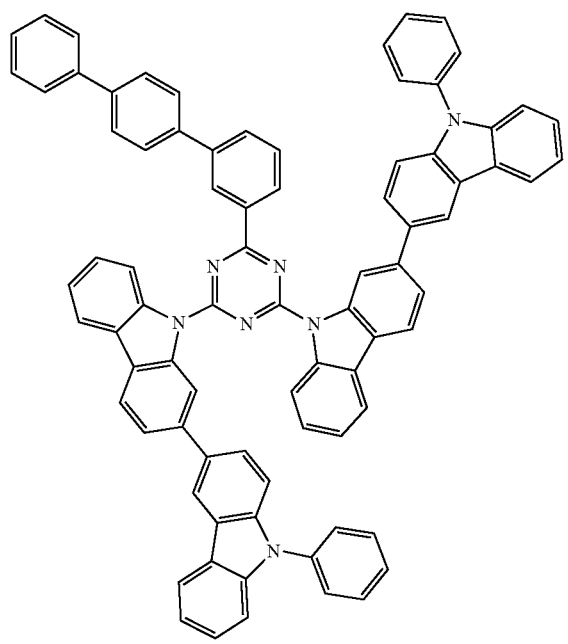
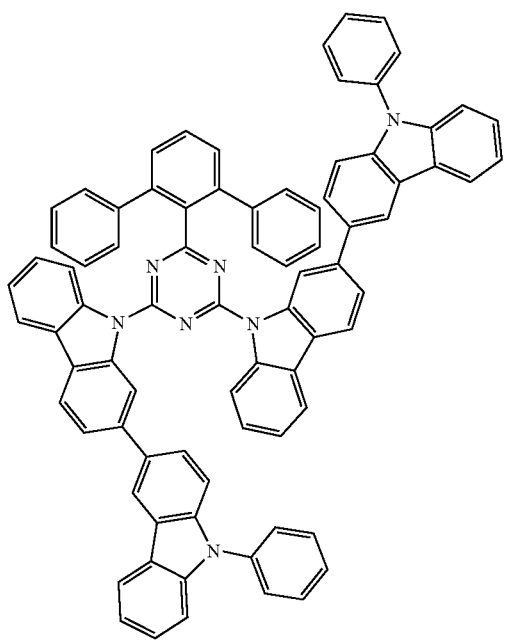
[Formula 39]
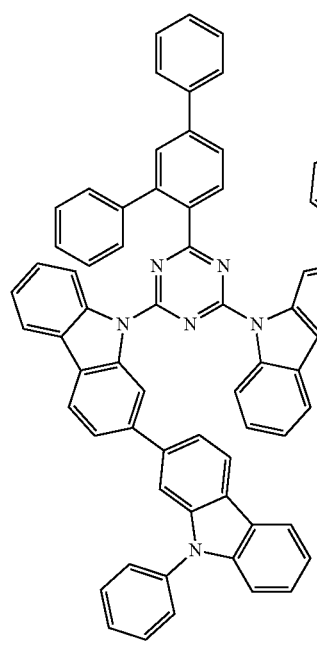
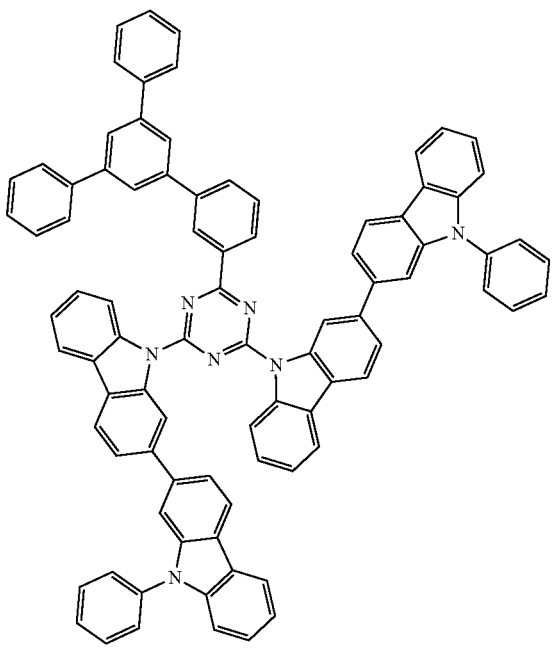

61
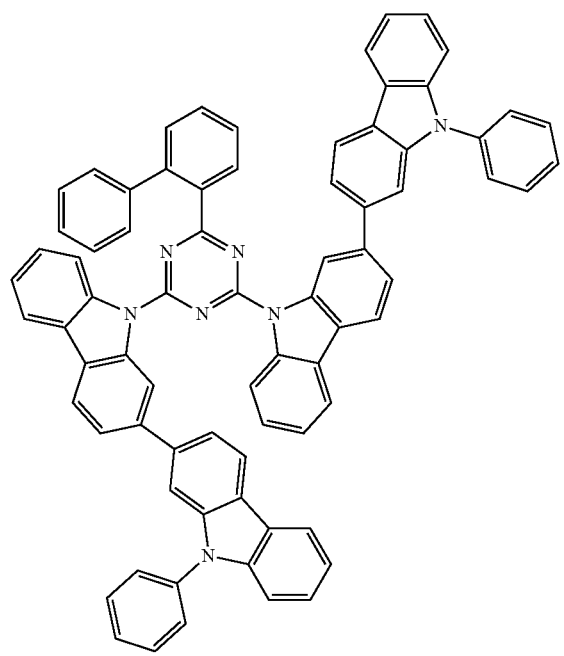
62
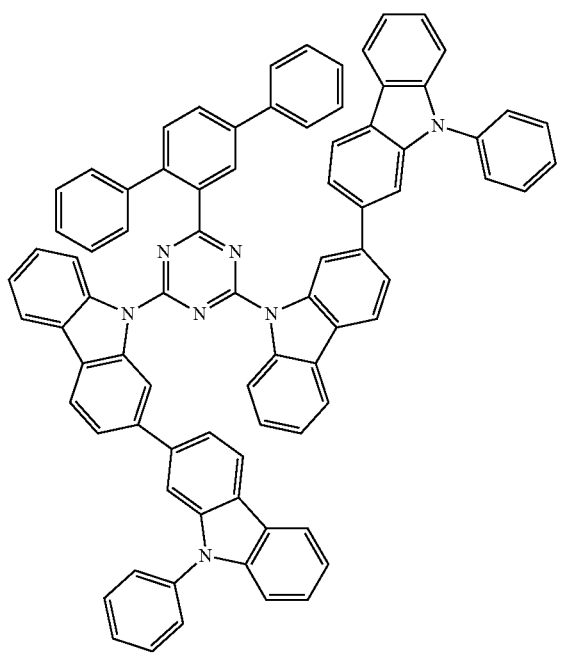
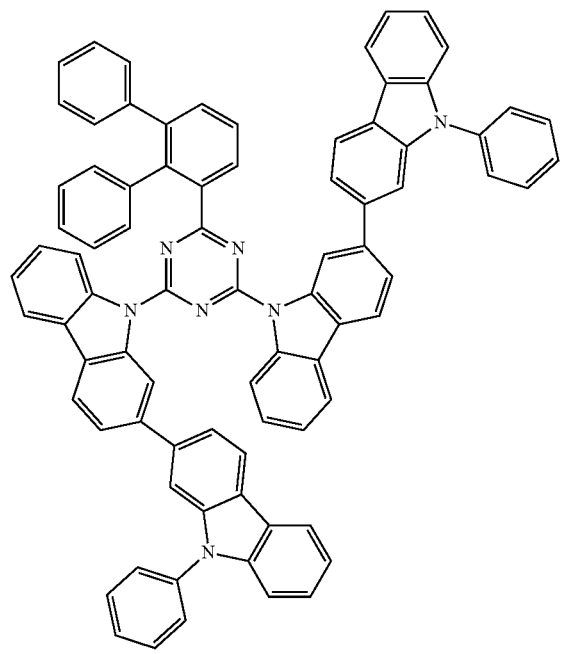
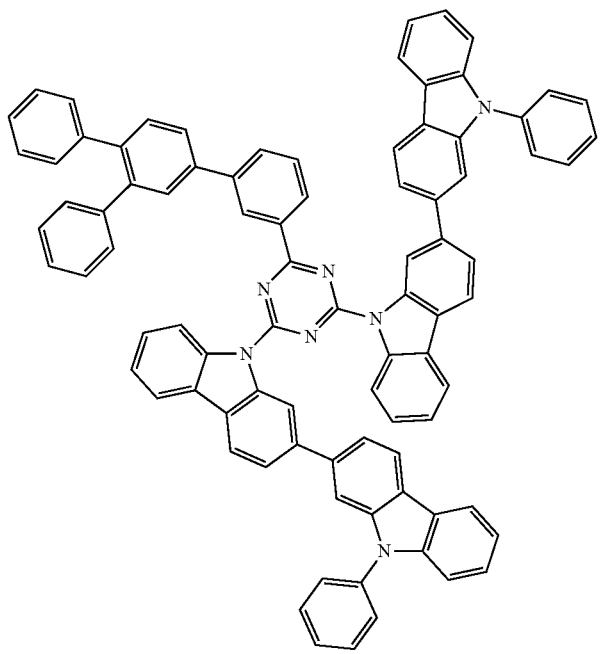

[Formula 40]
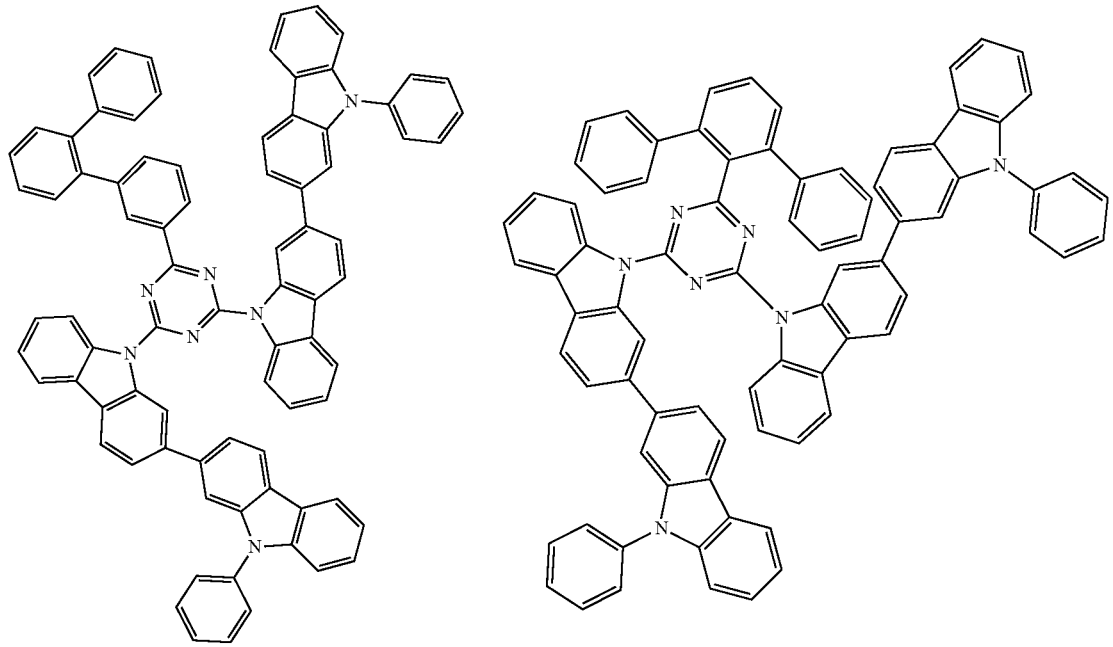
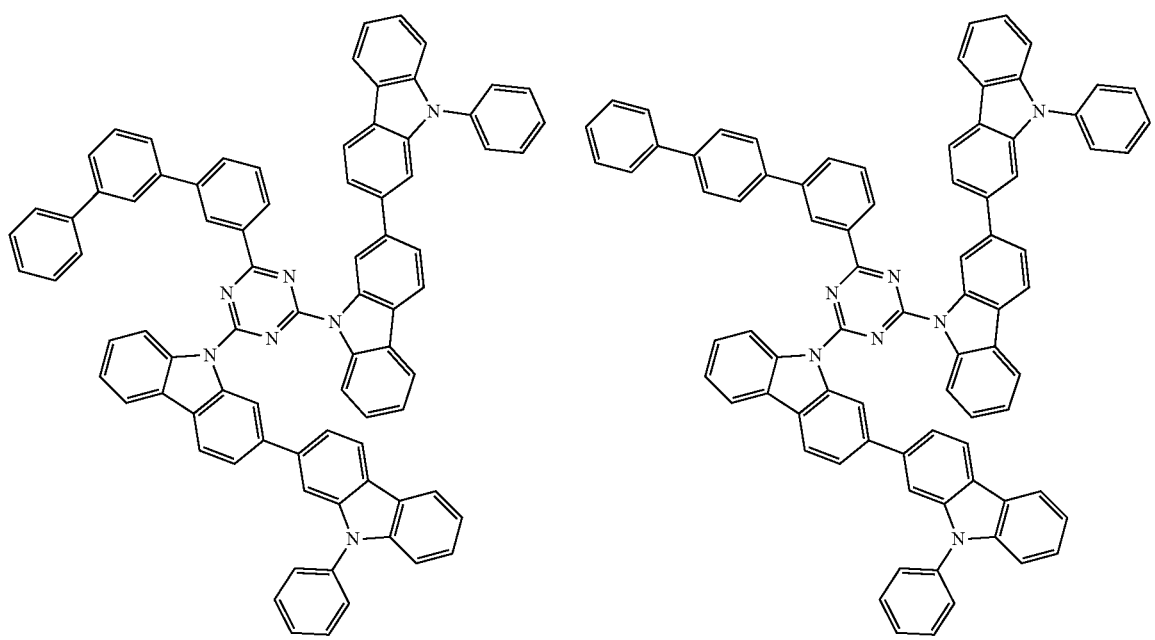

[Formula 41]
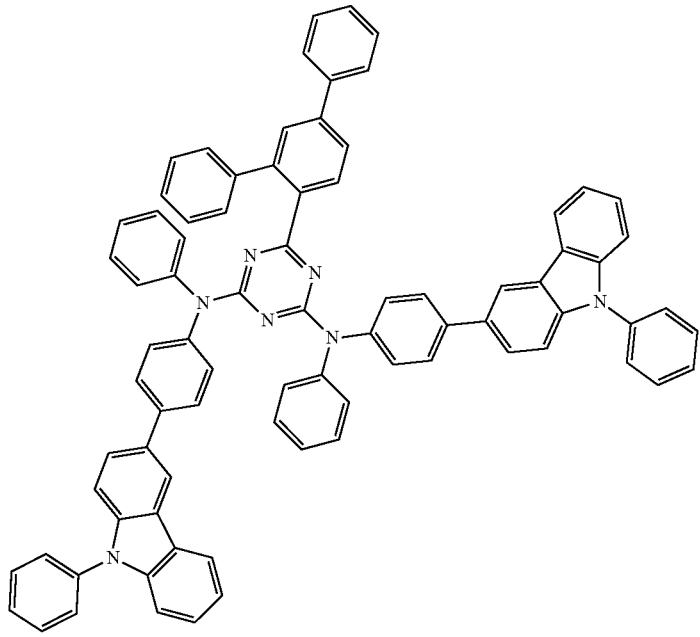
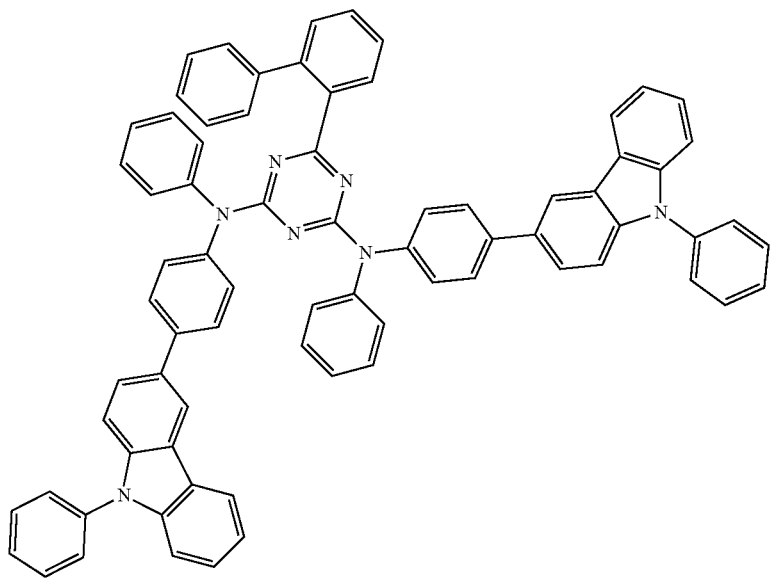

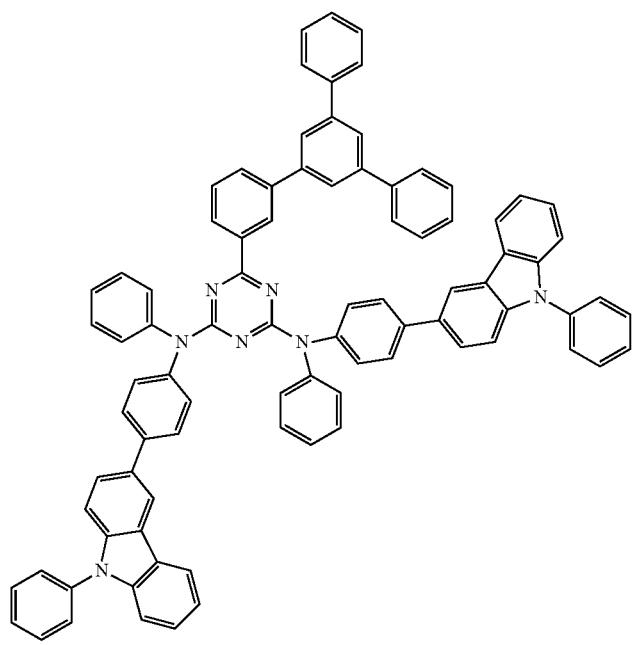
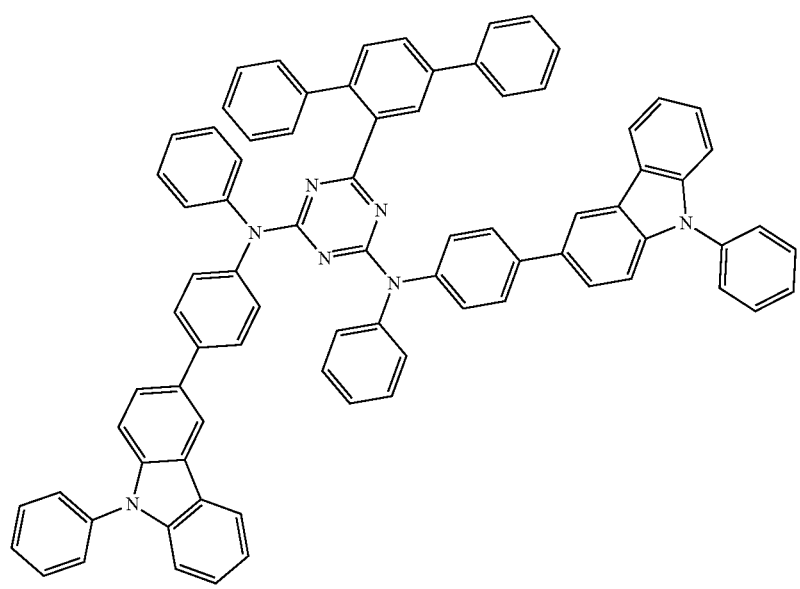

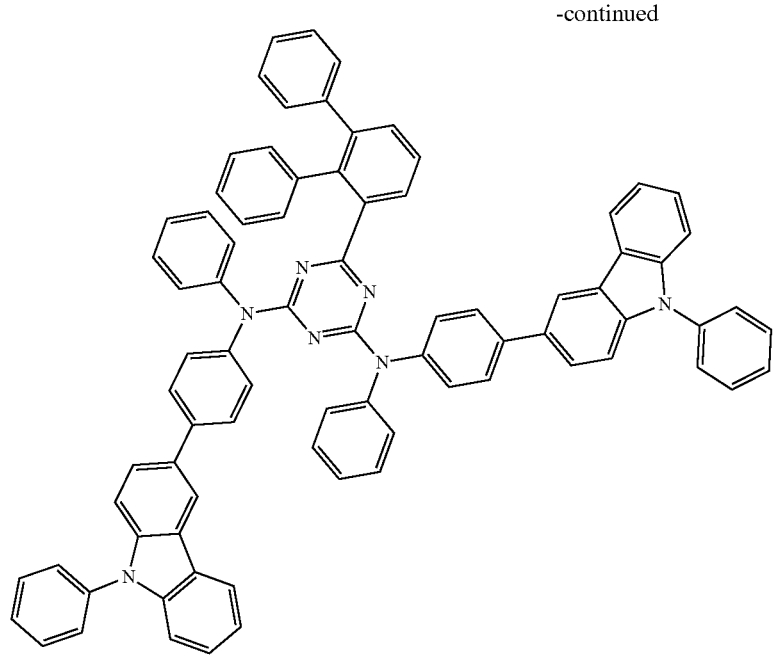
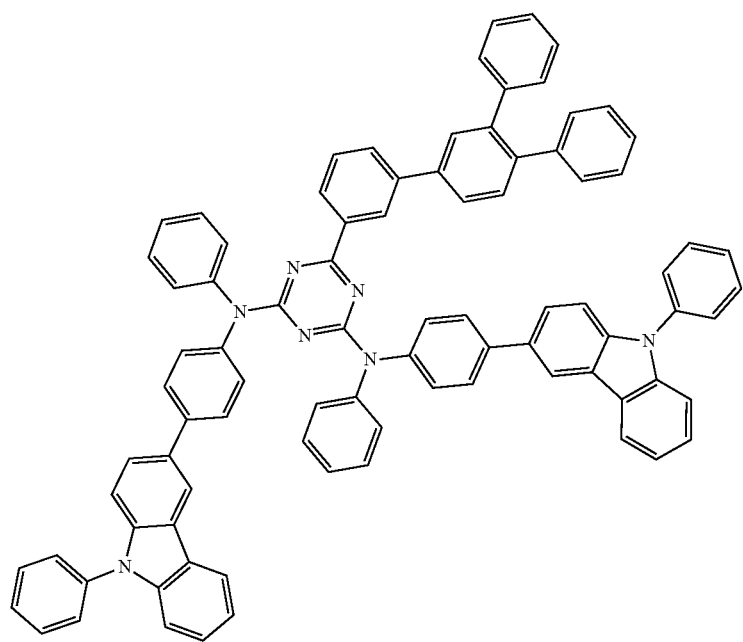

[Formula 42]
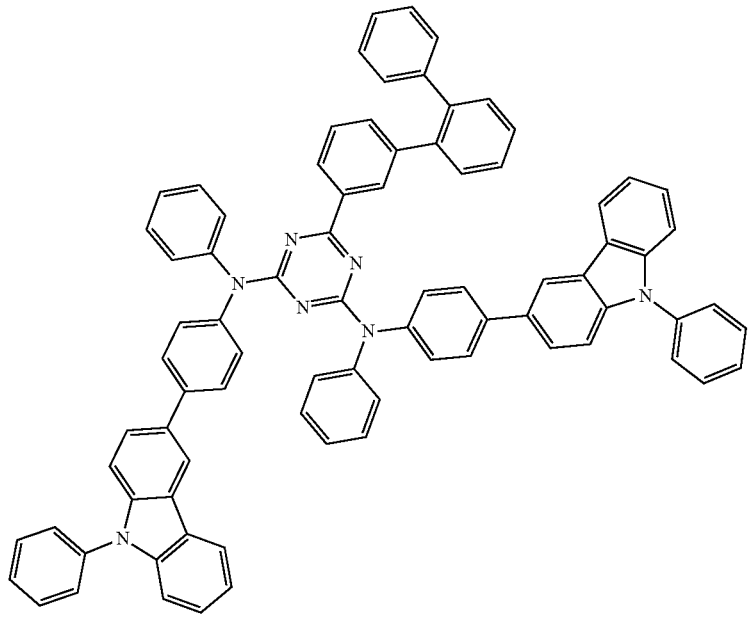
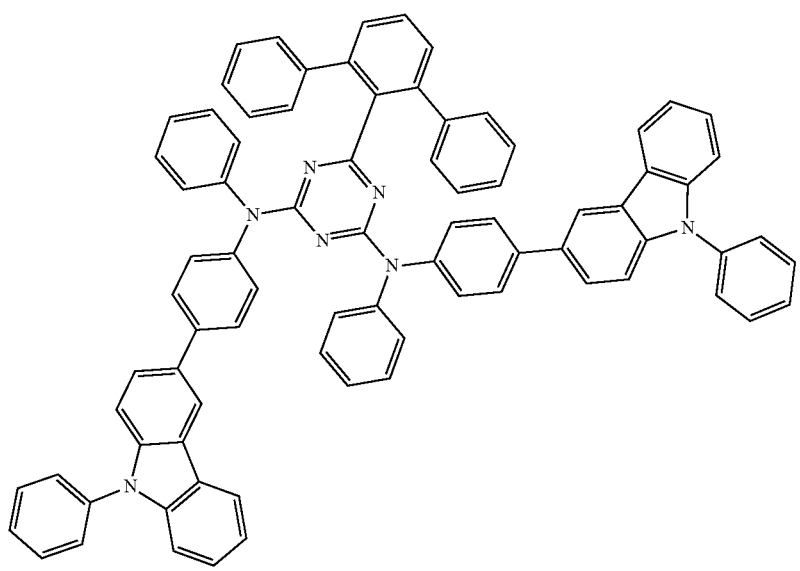

-continued
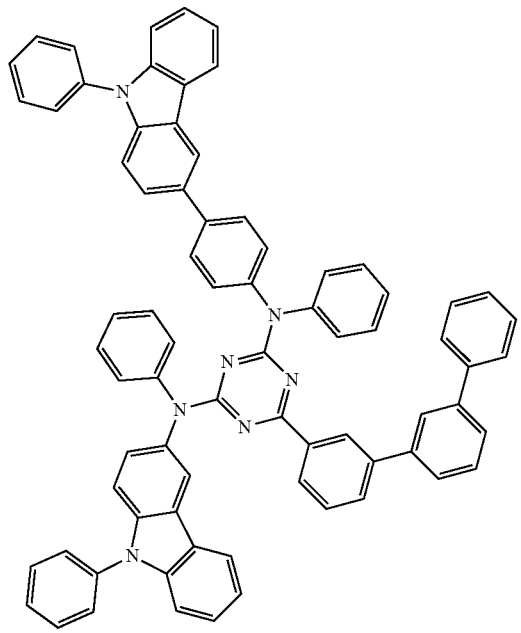
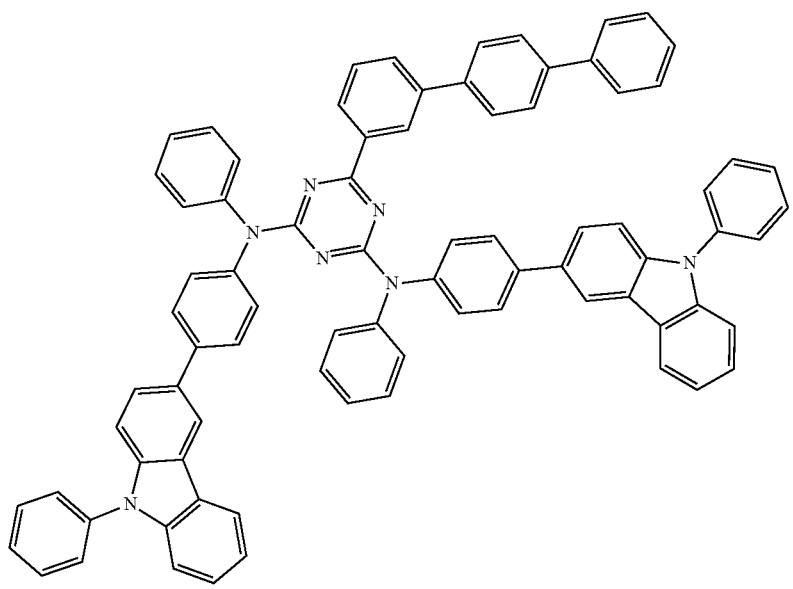

[Formula 43]
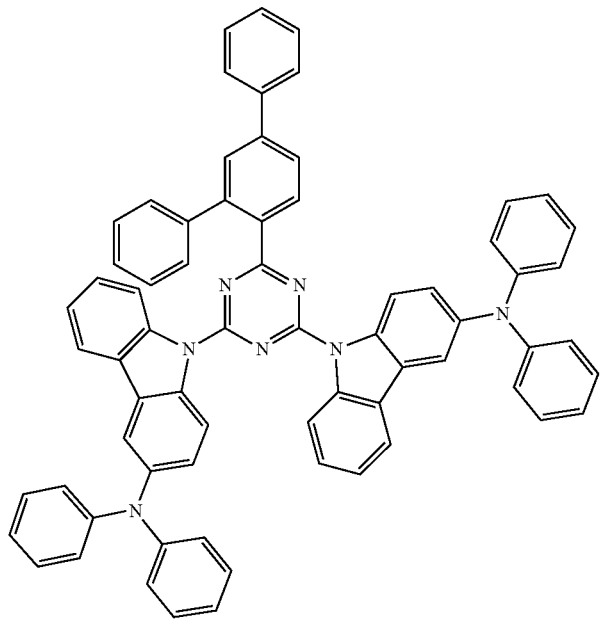
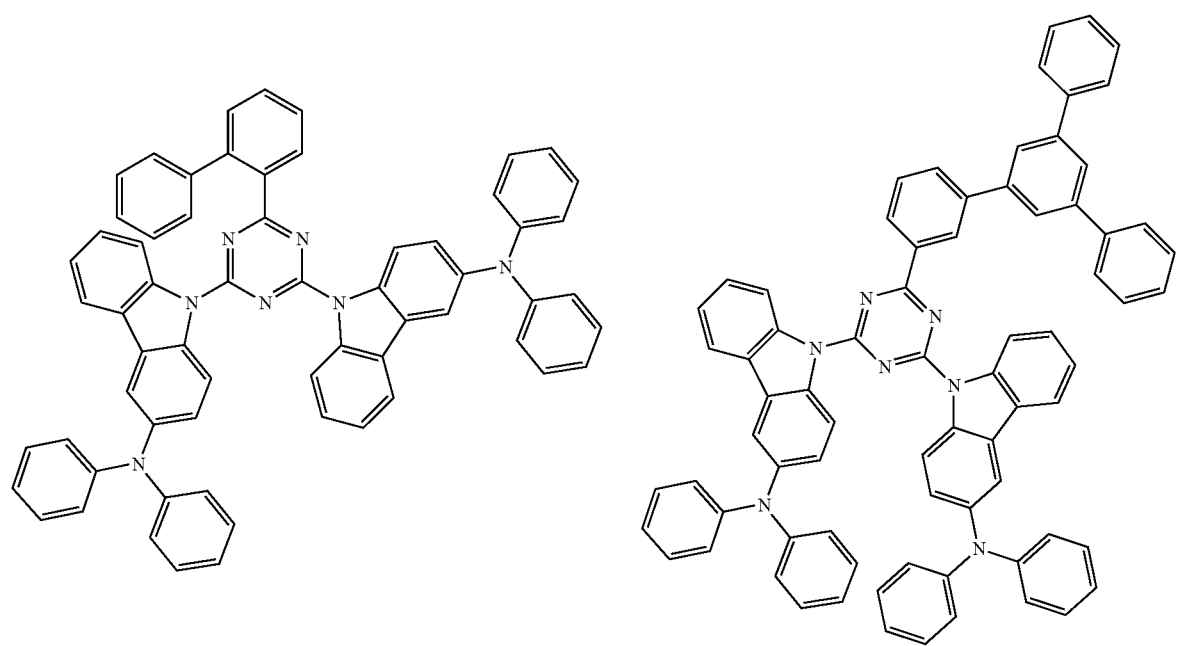

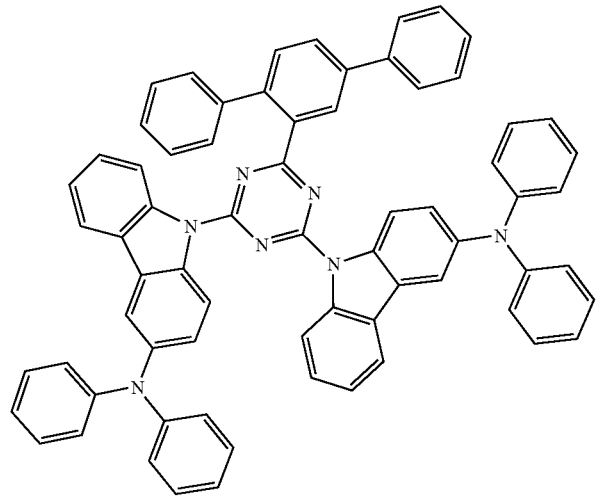
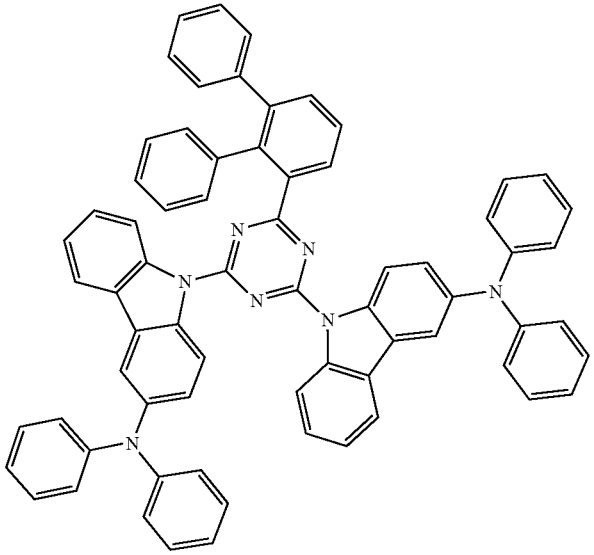
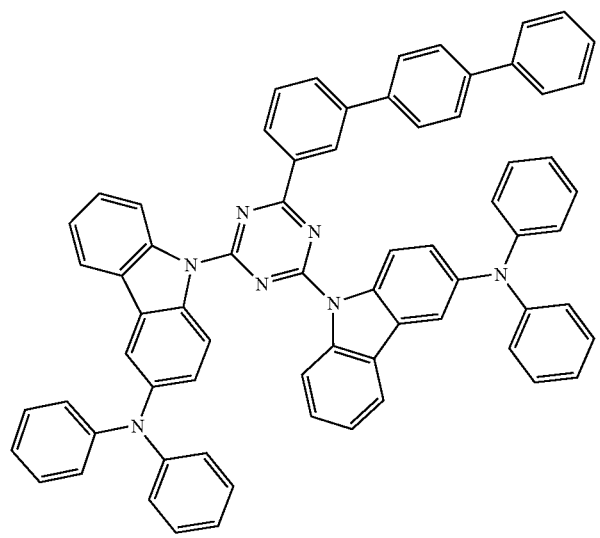
[Formula 44]
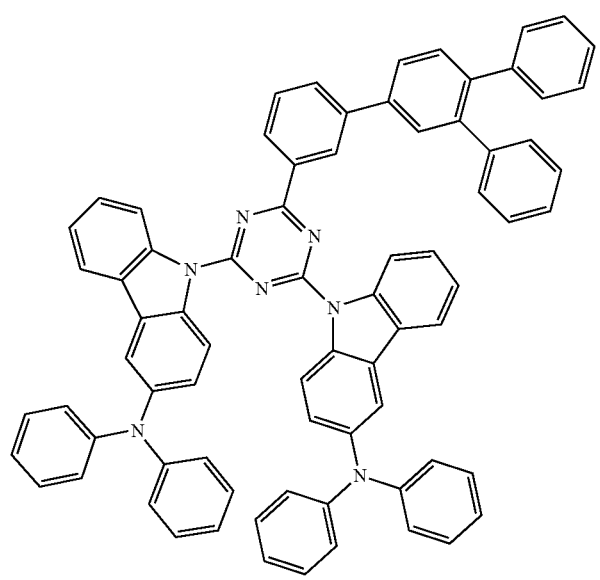
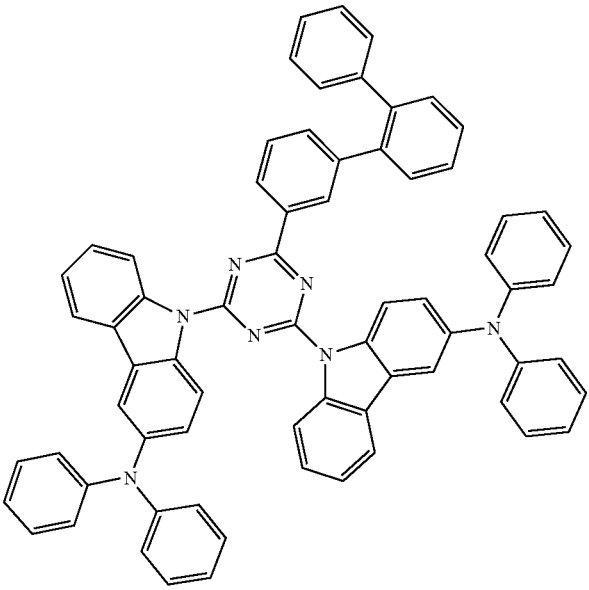

79
80
-continued
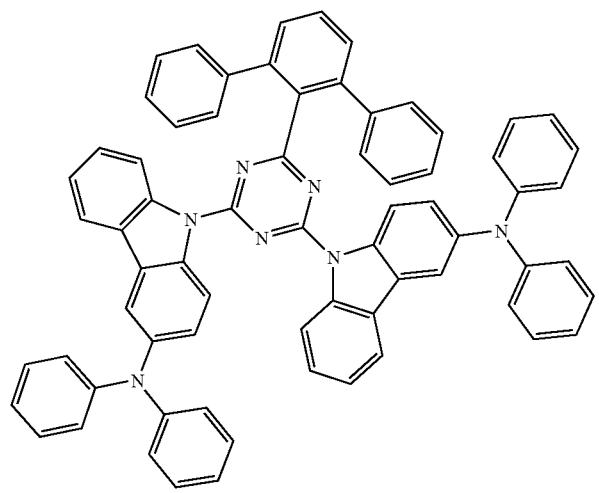
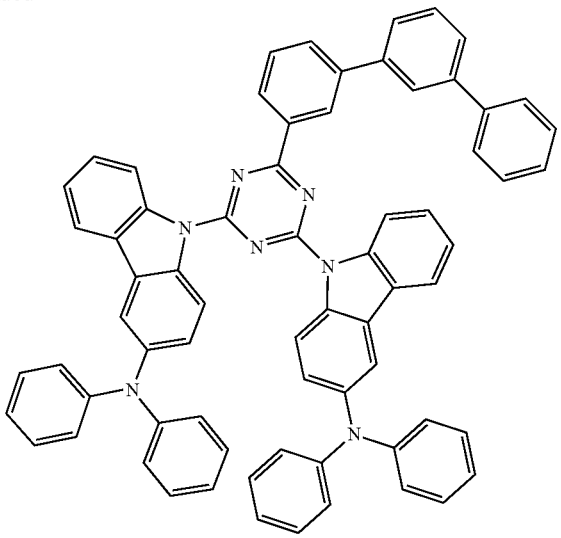
[Formula 45]
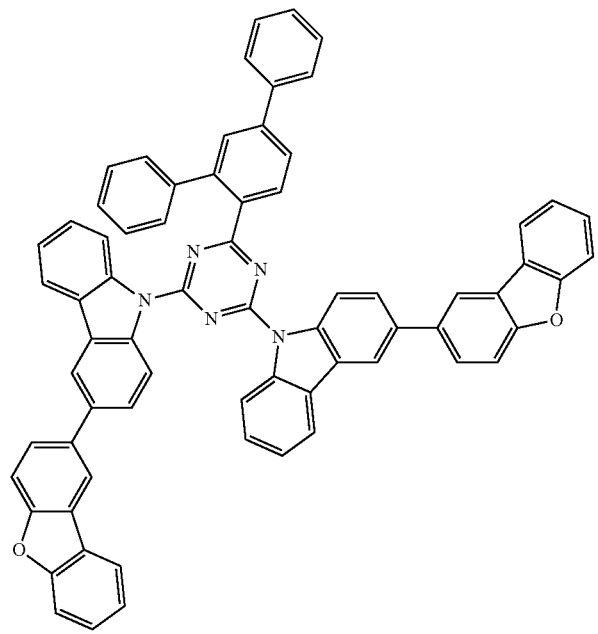

81
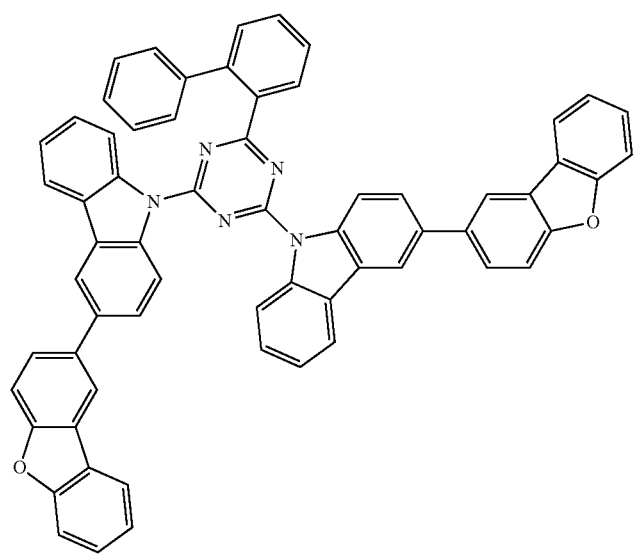
82
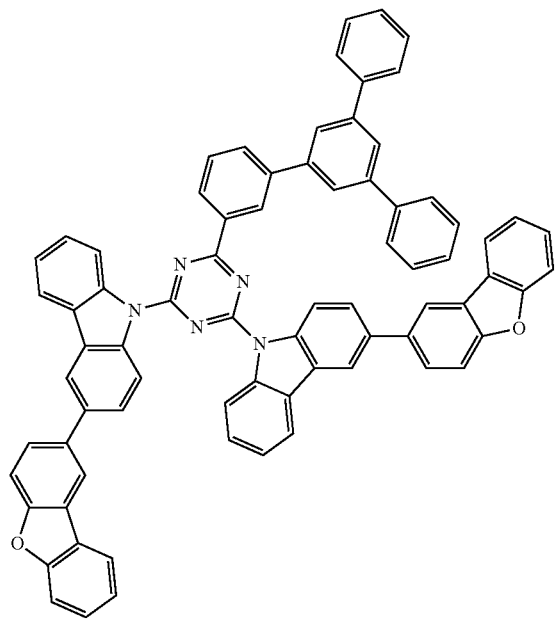
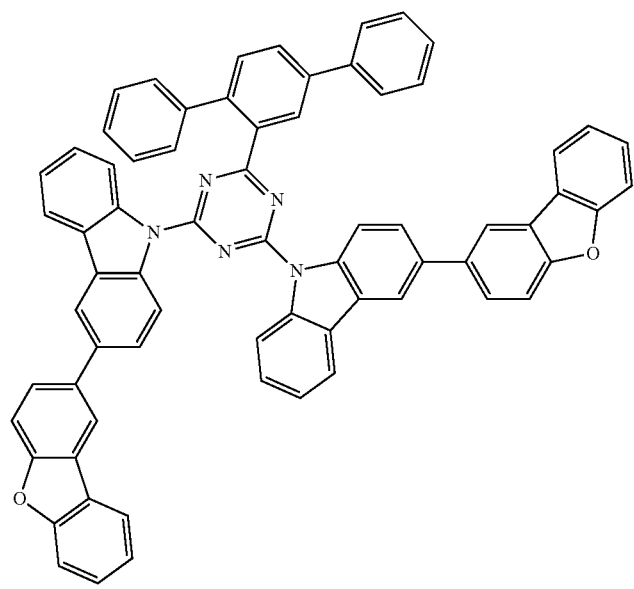

-continued
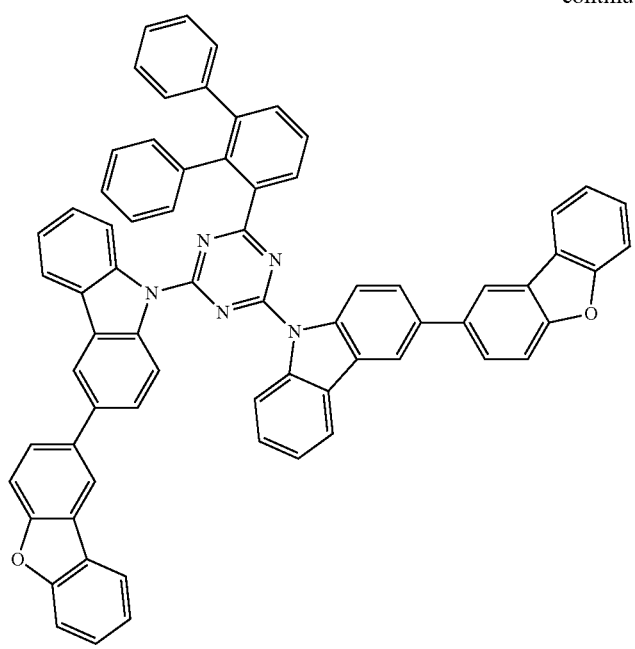
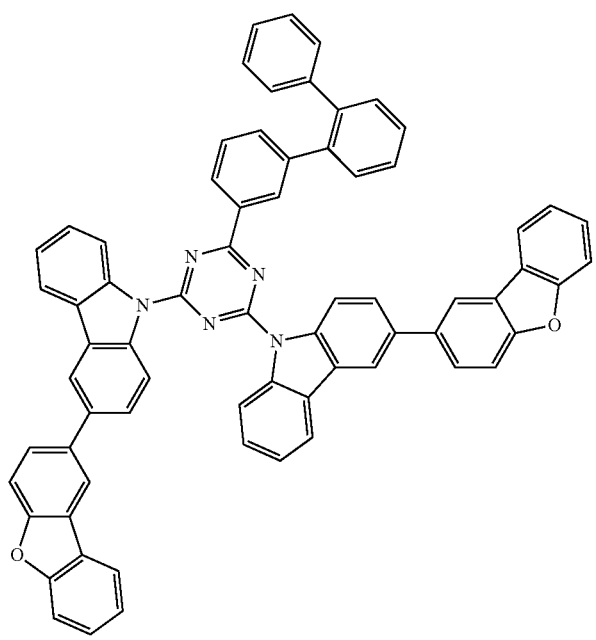

[Formula 46]
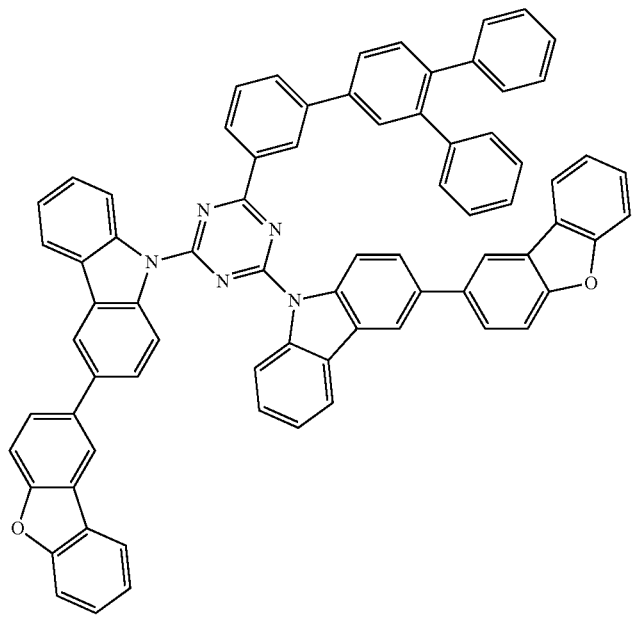
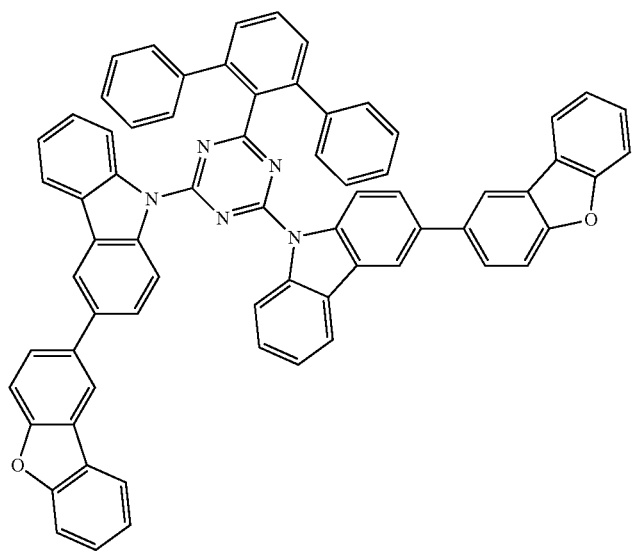

87
88
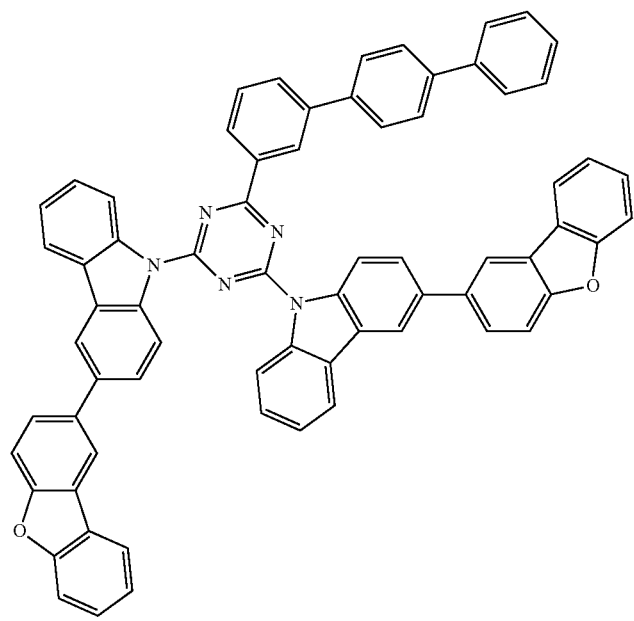
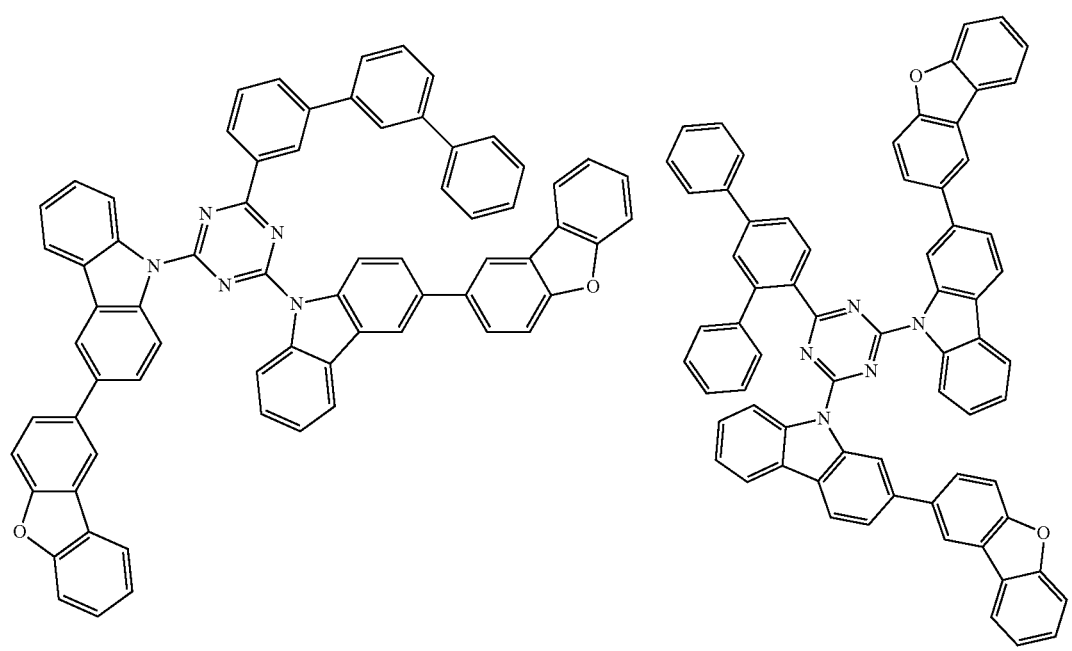

-continued
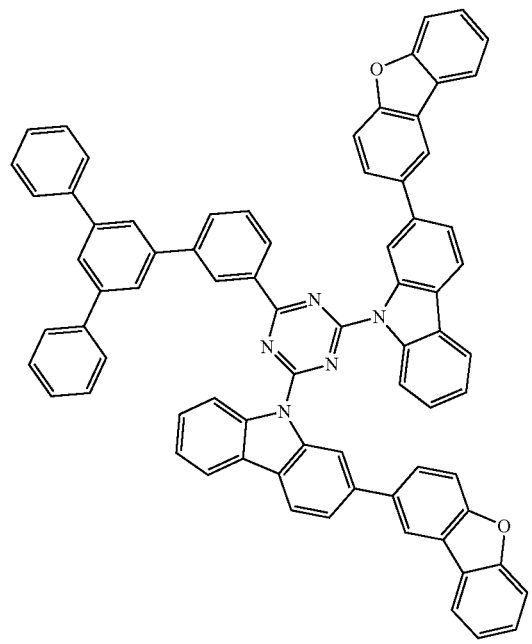
[Formula 47]
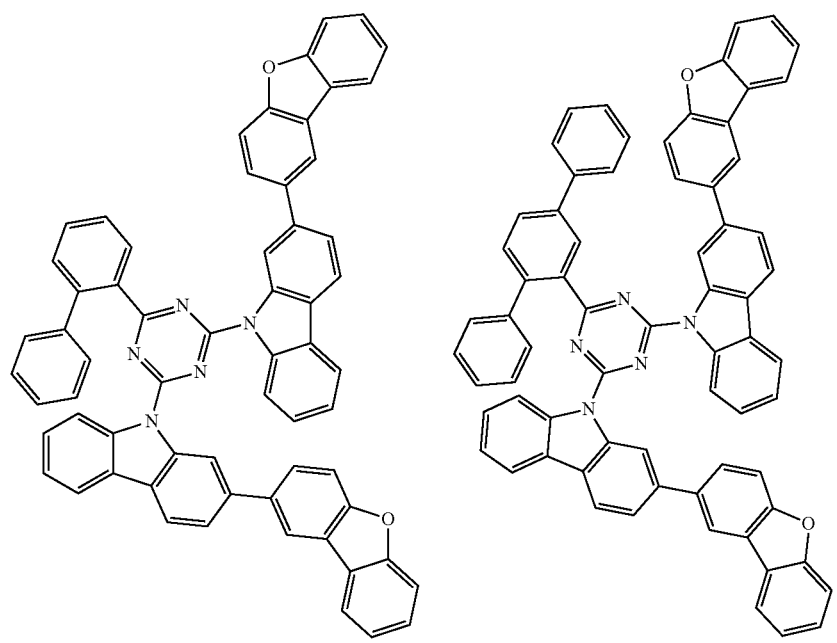

-continued
91
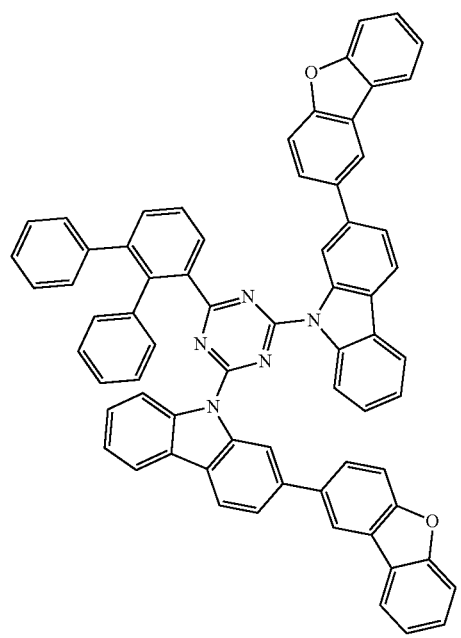
92
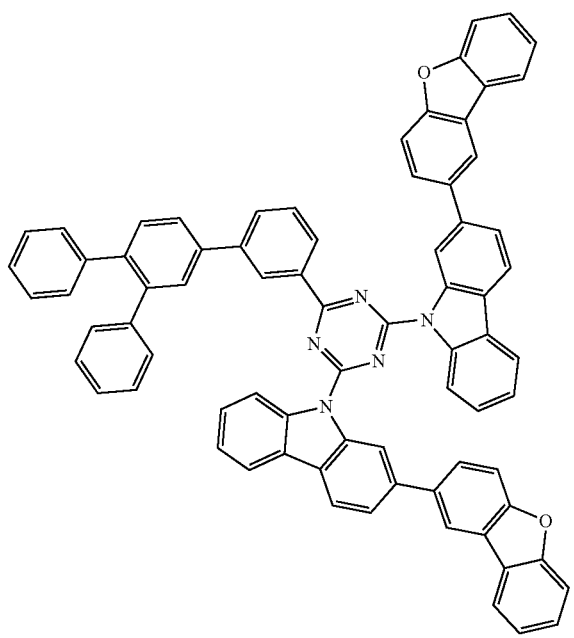
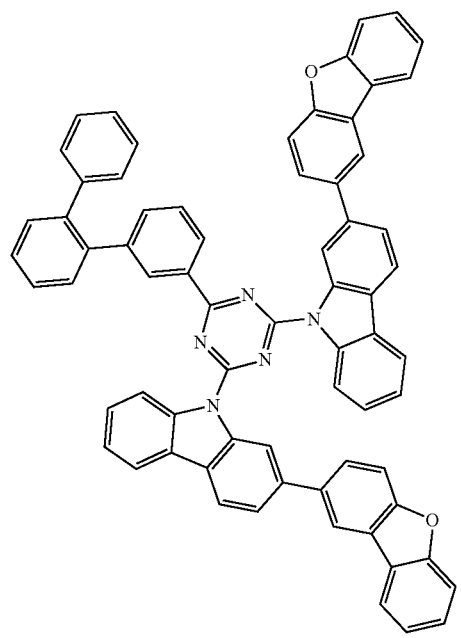
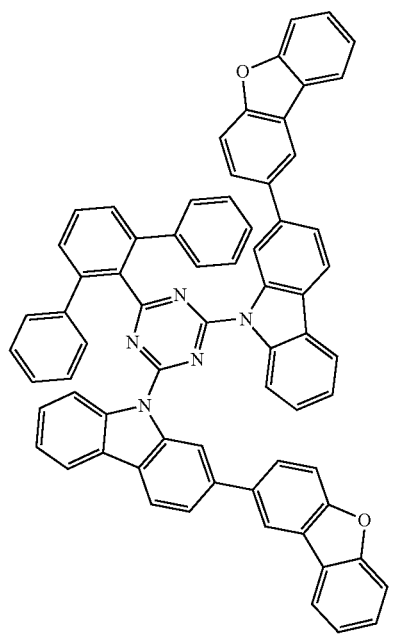

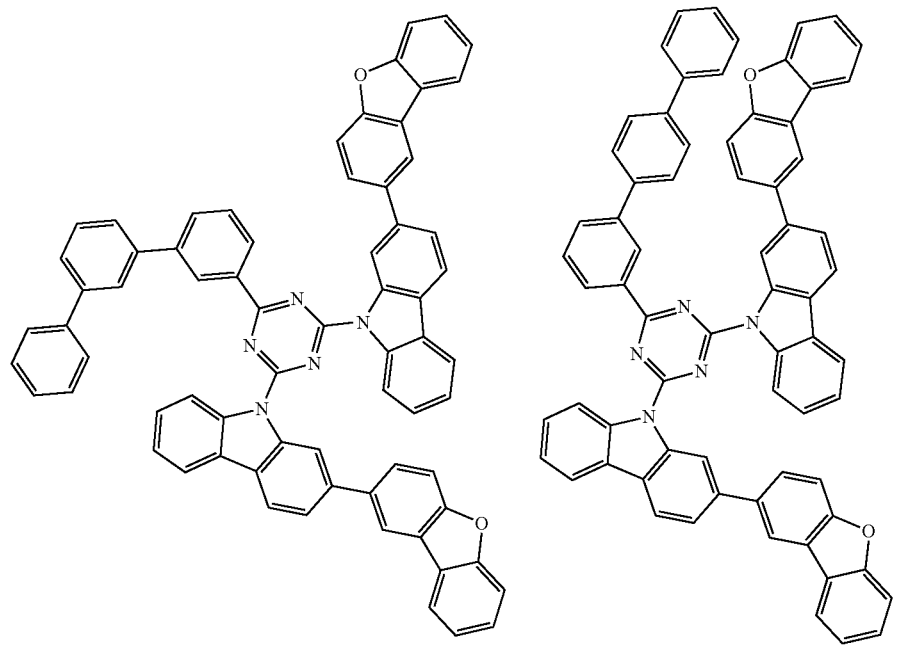
[Formula 48]
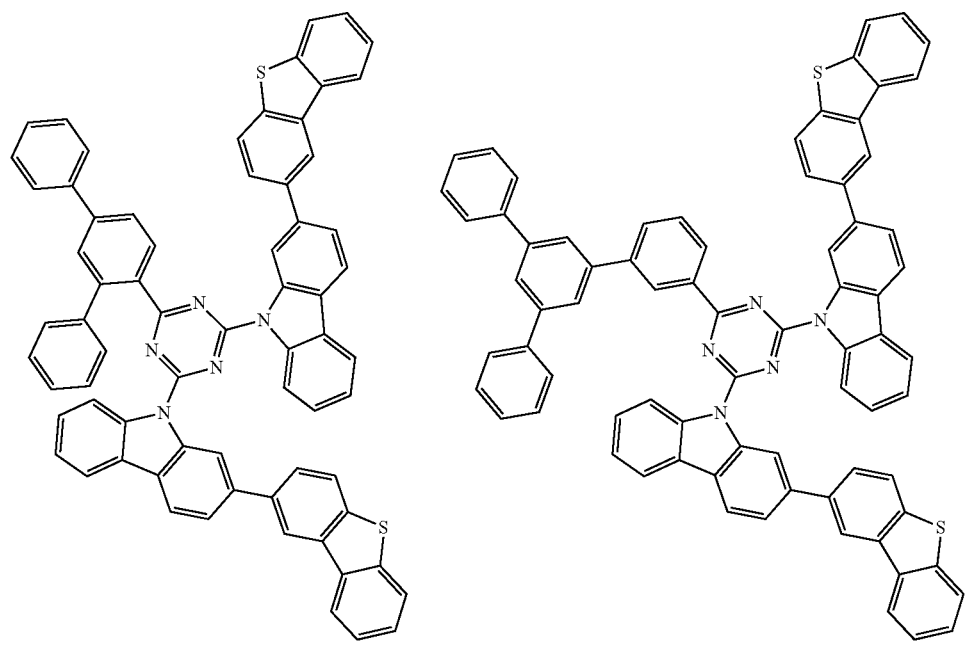

-continued
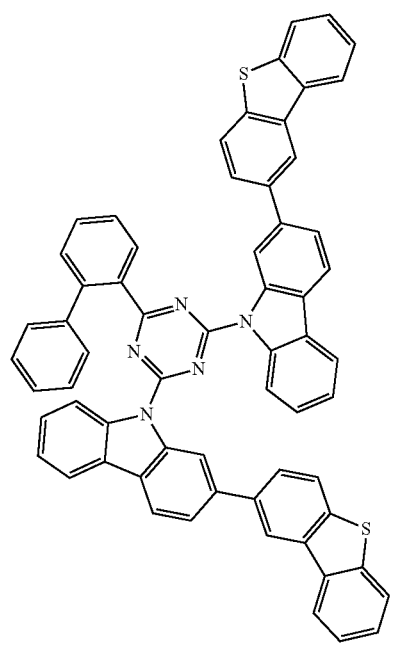
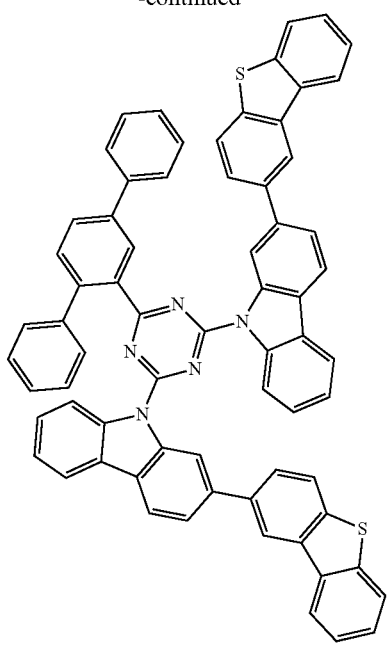
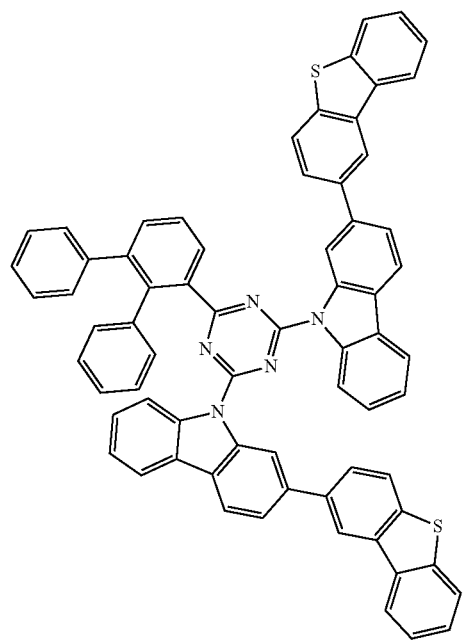
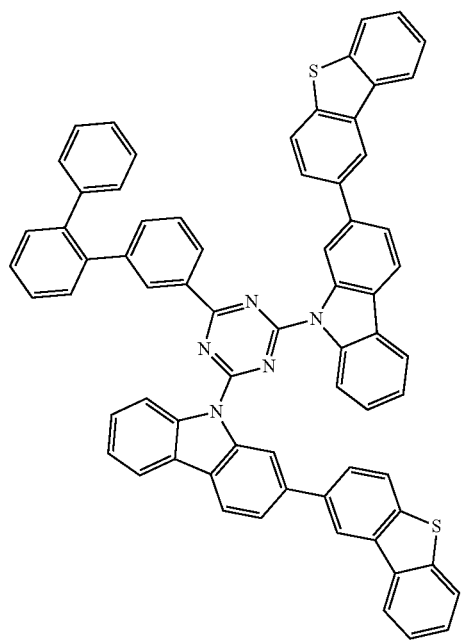

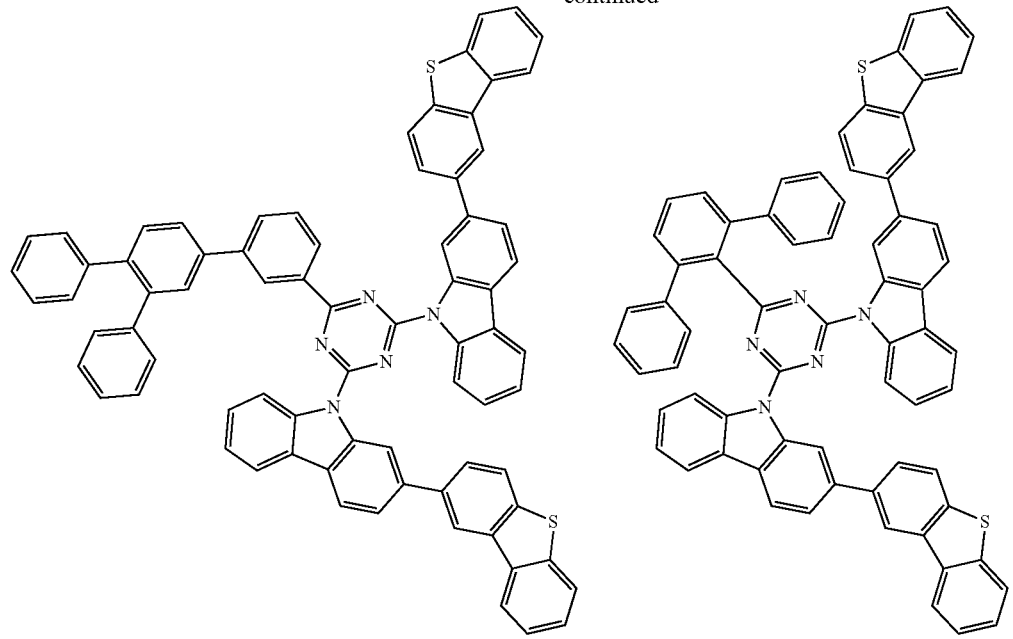
[Formula 49]
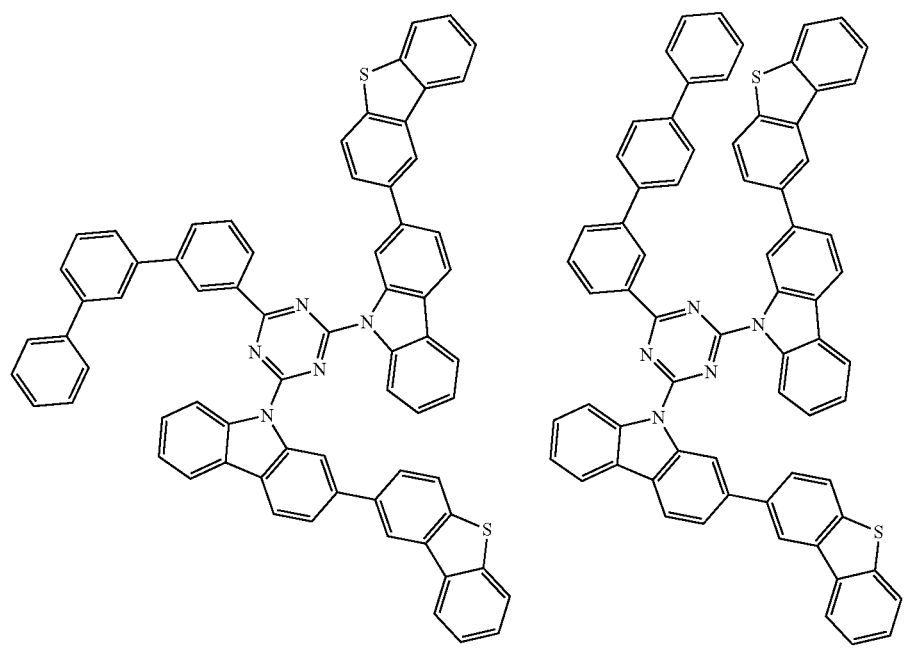

99
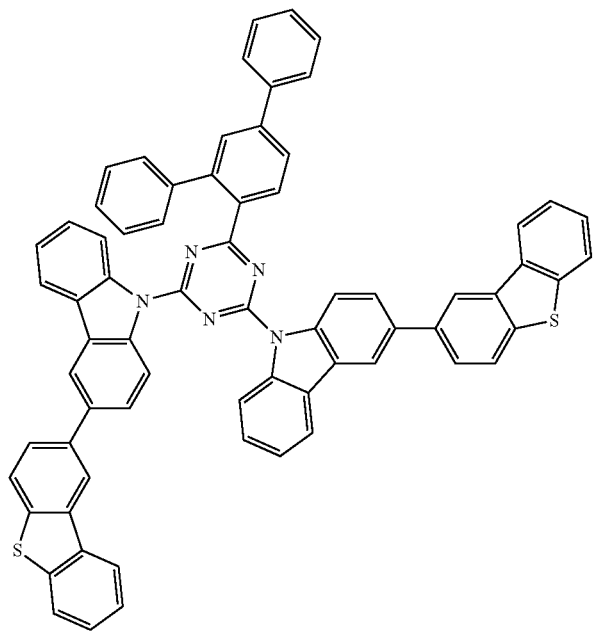
100
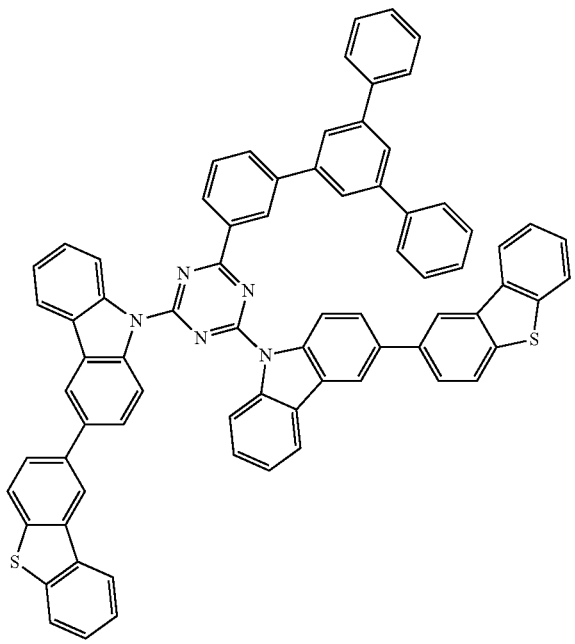
-continued
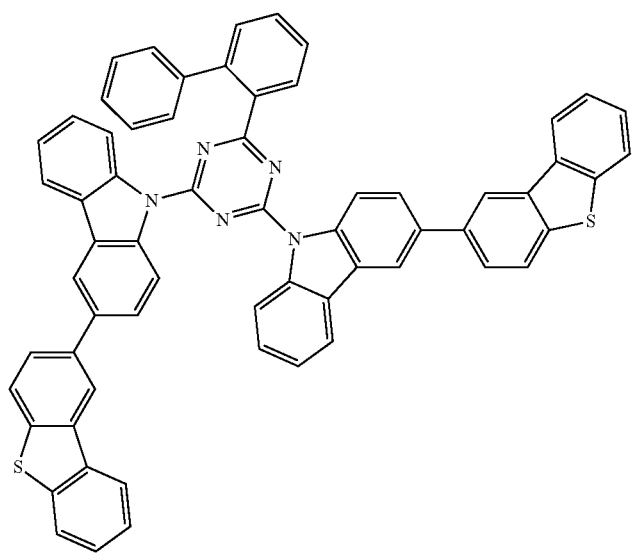

-continued
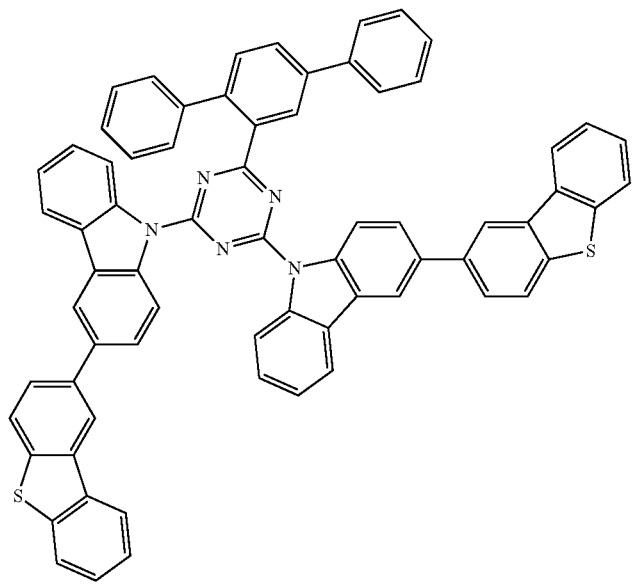
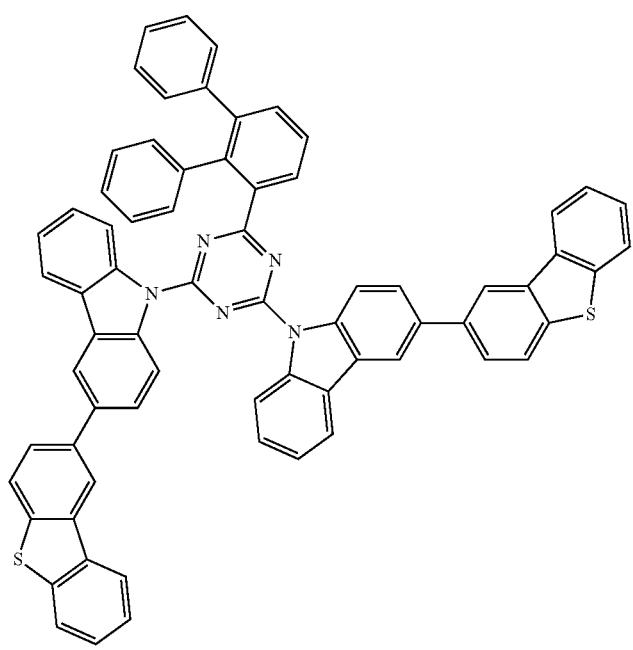

[Formula 50]
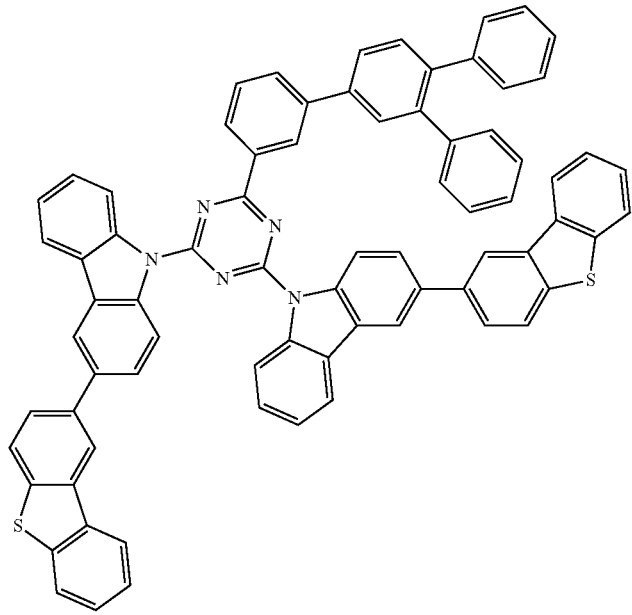
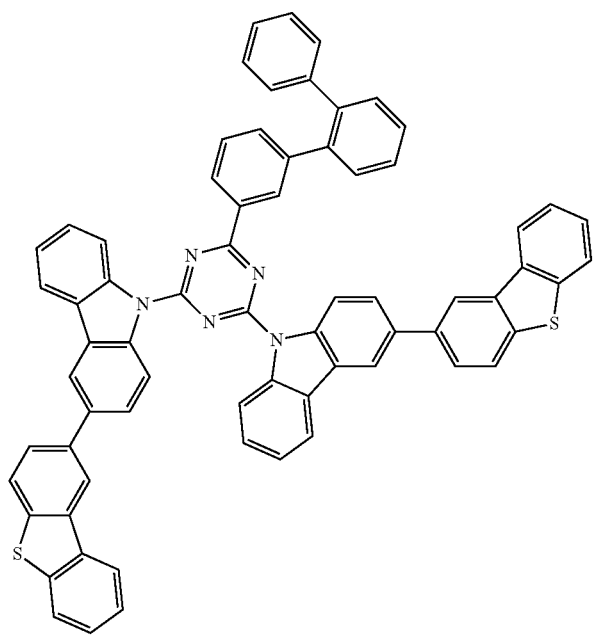

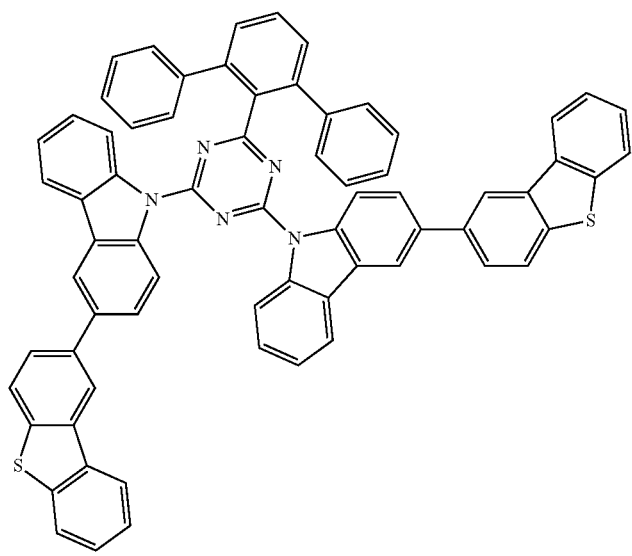
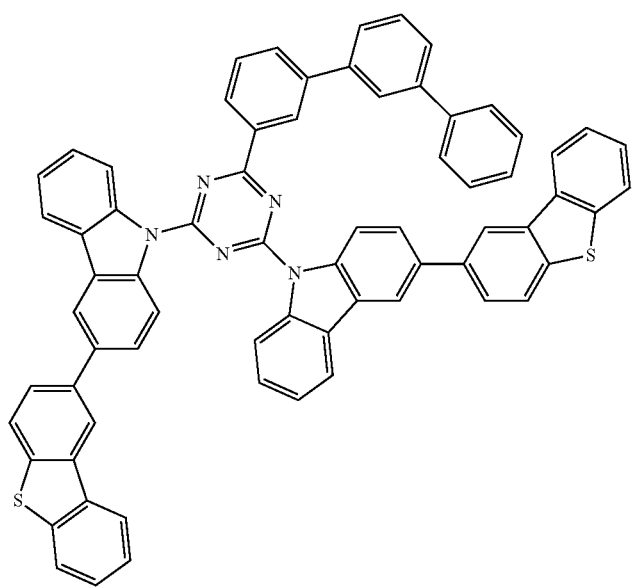

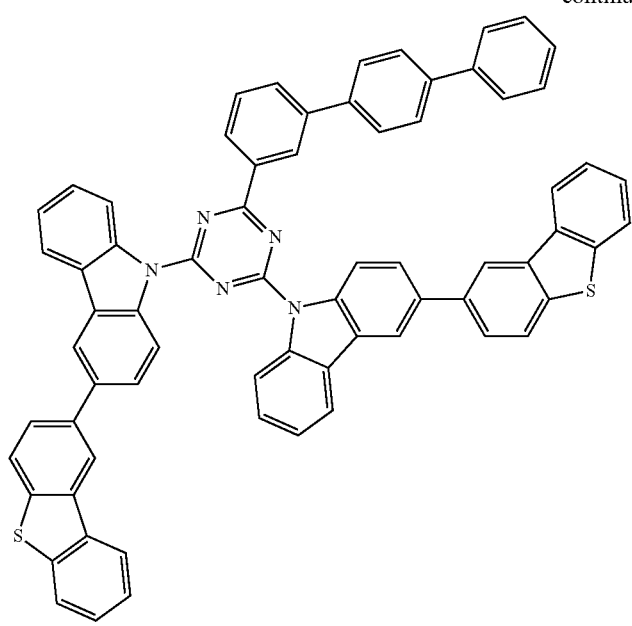
[Formula 51]
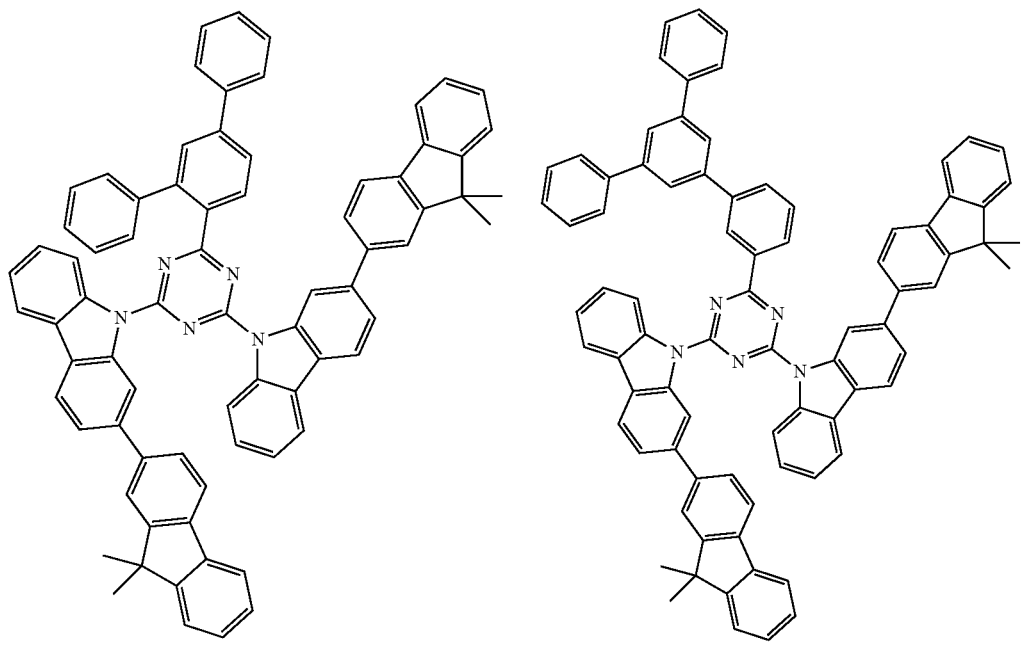

109
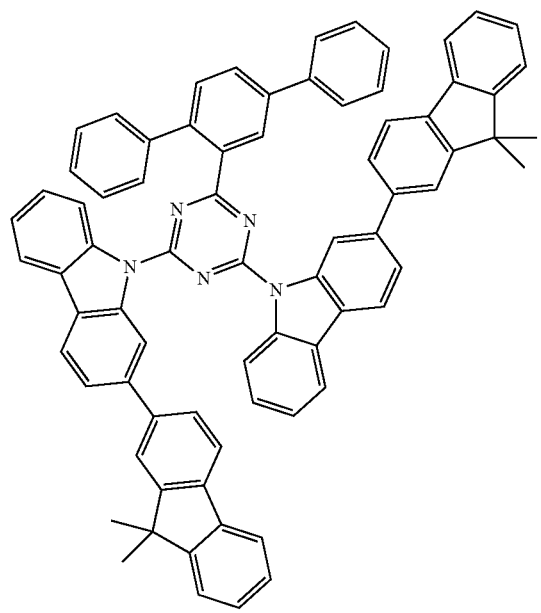
110
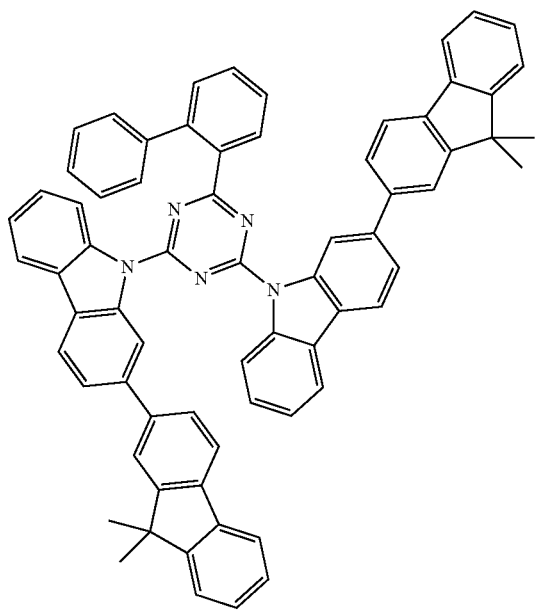
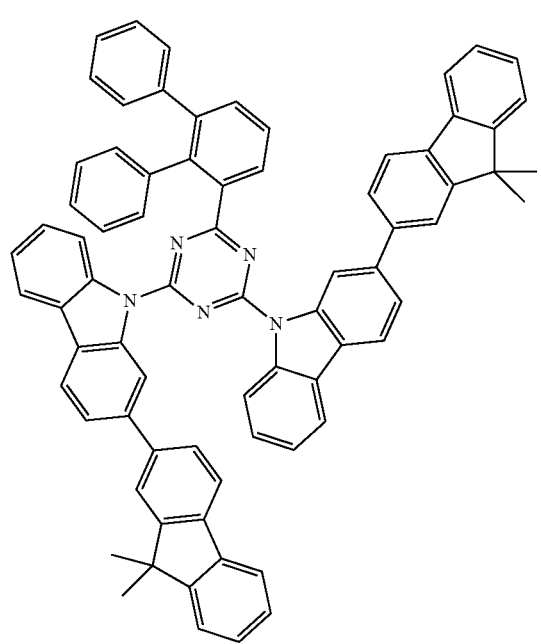
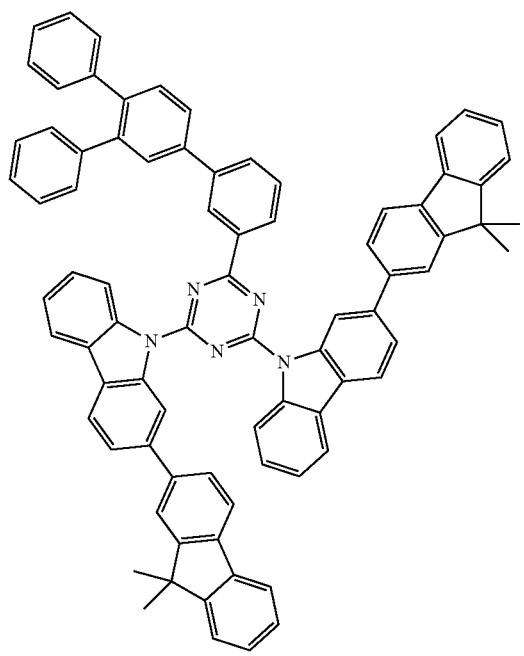

111
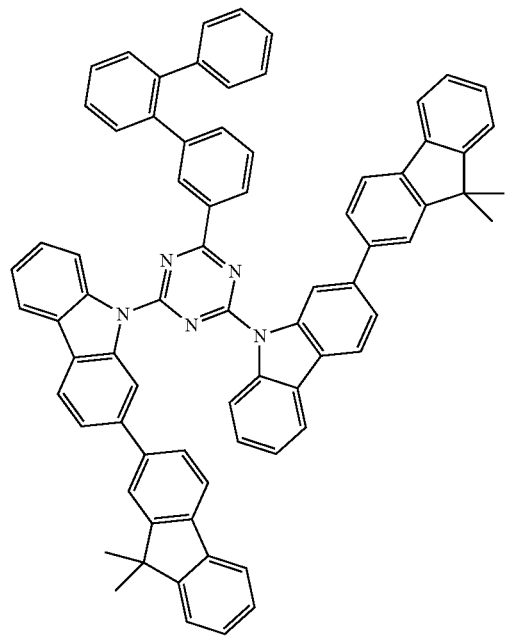
112
-continued
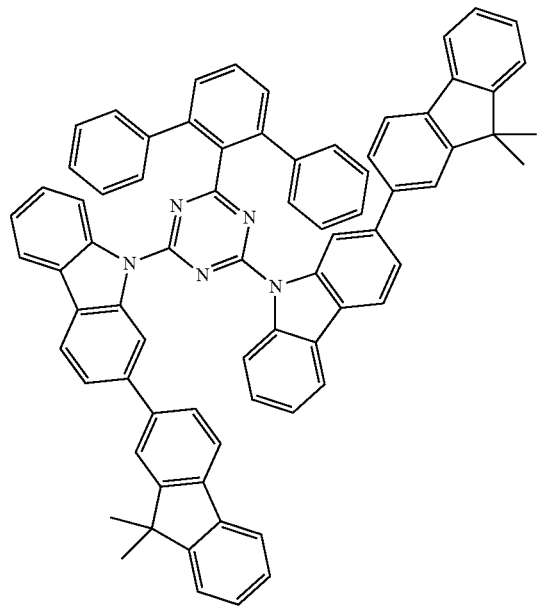
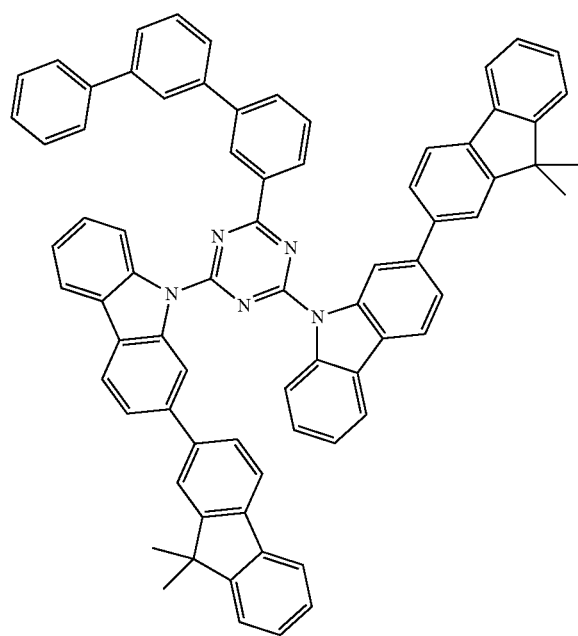
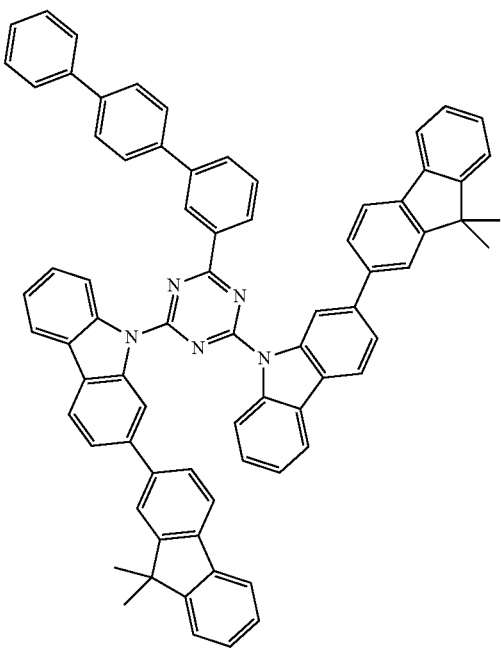

[Formula 52]
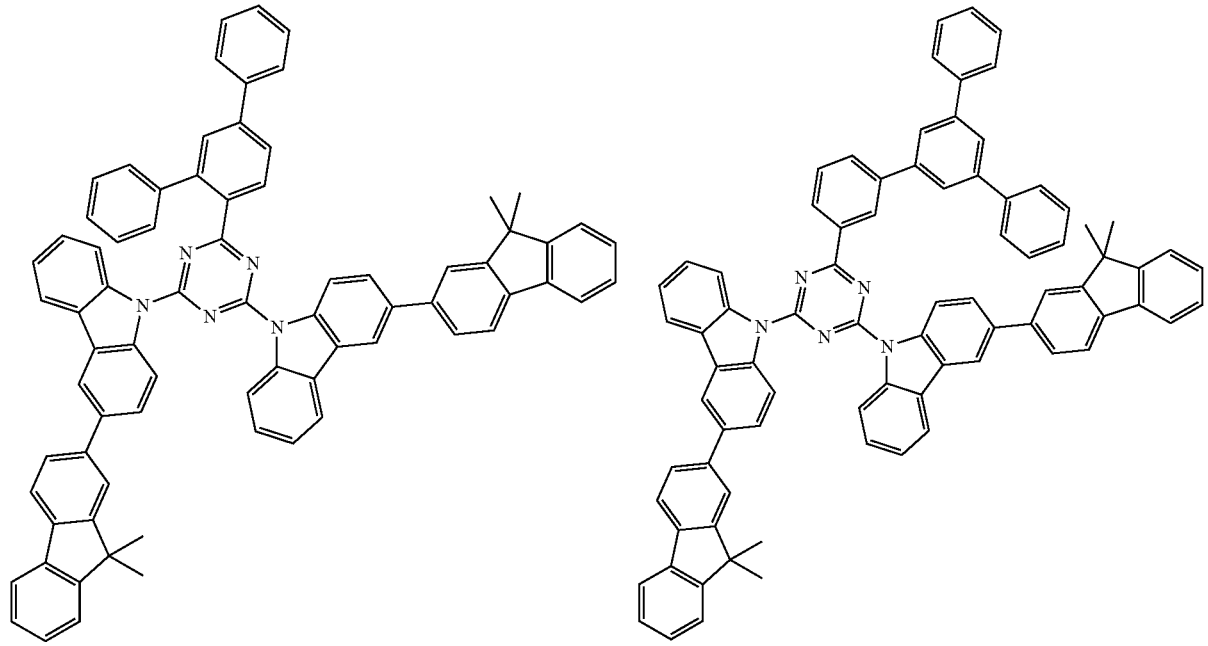
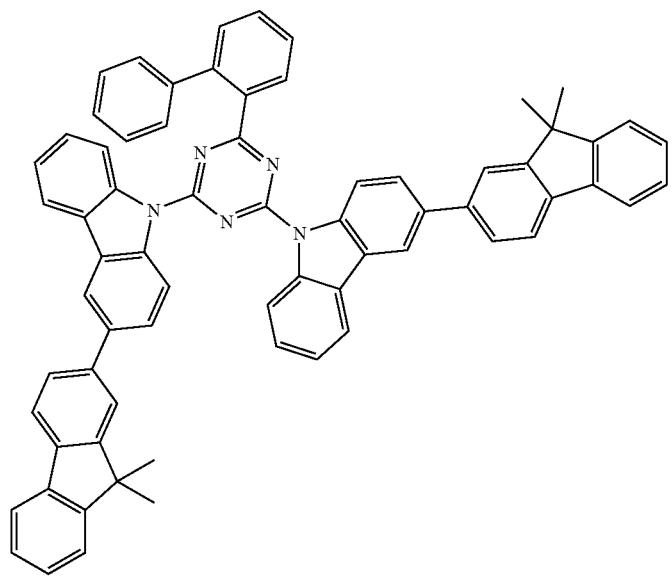

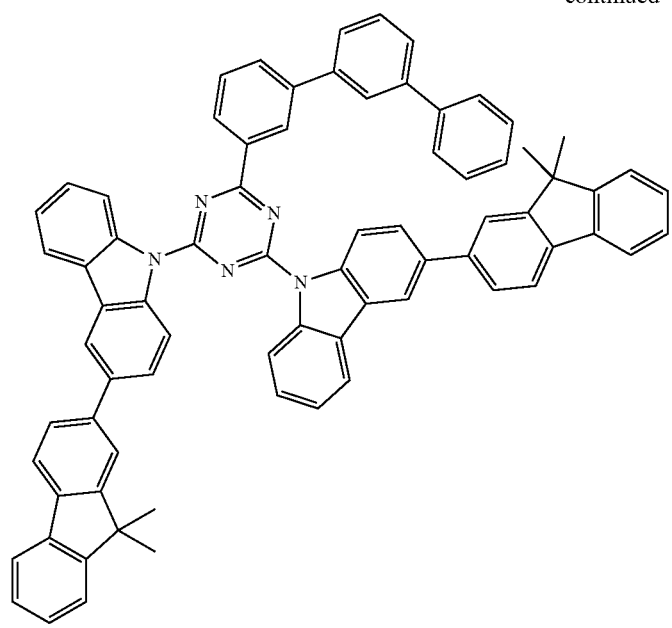
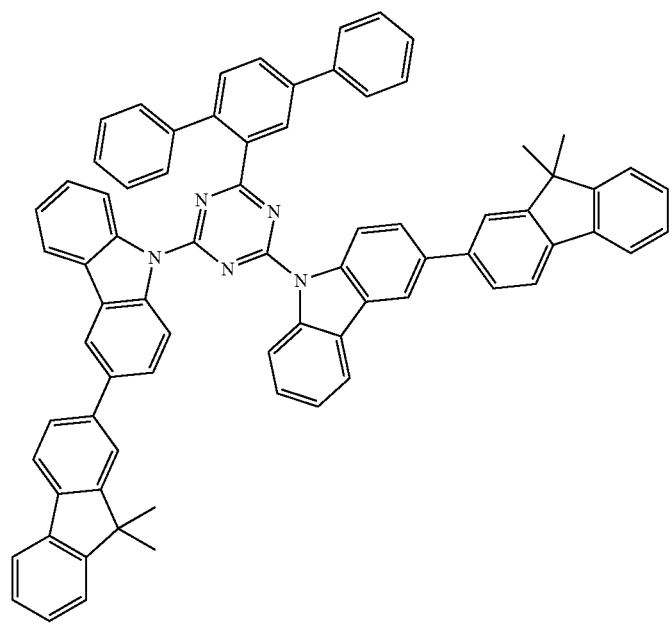

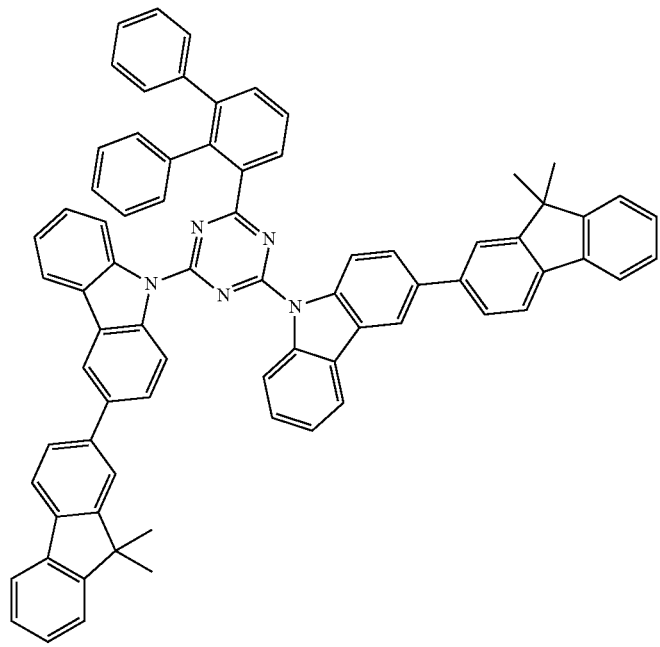
[Formula 53]
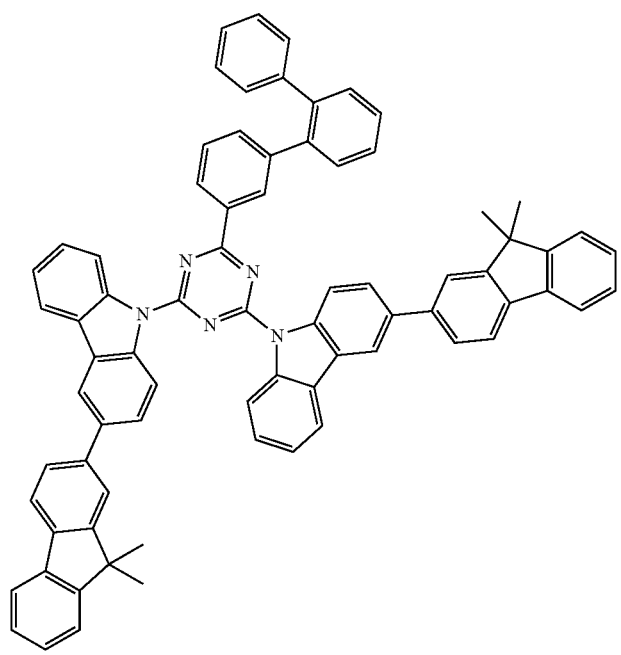

-continued
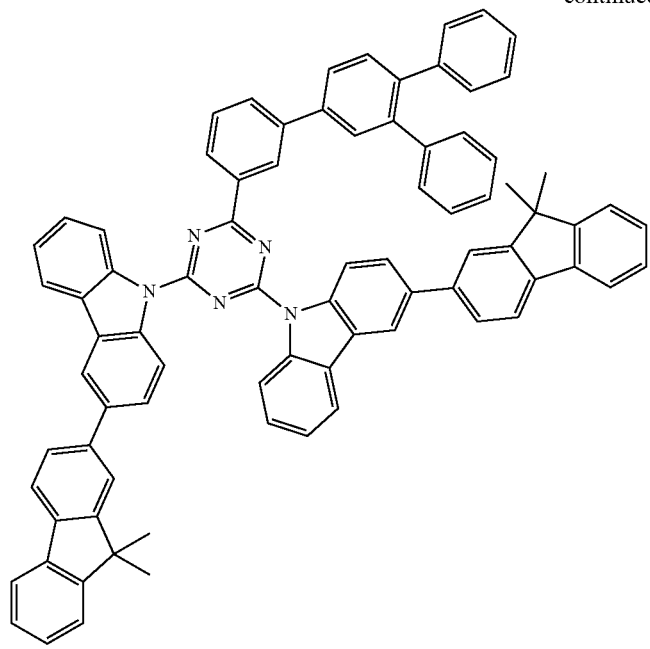
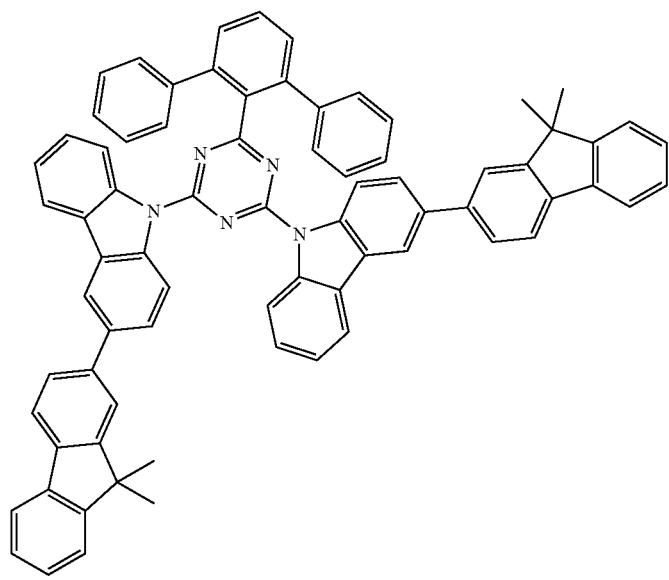

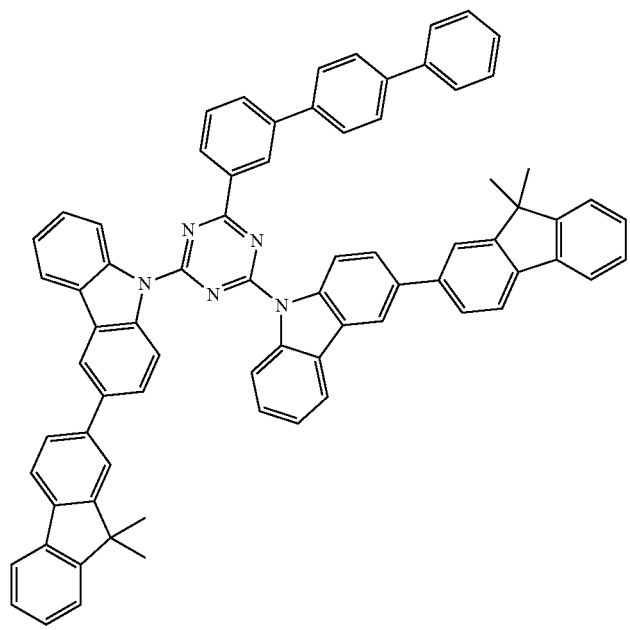
[Formula 54]
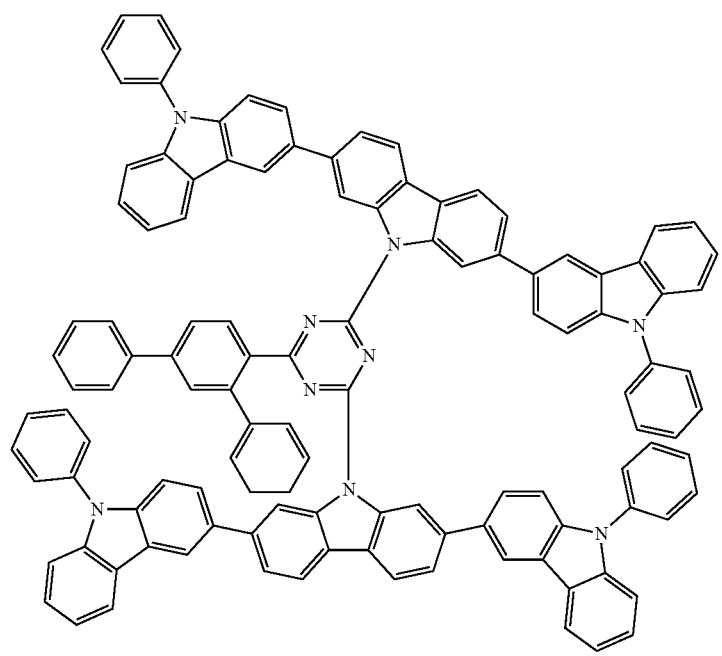

-continued
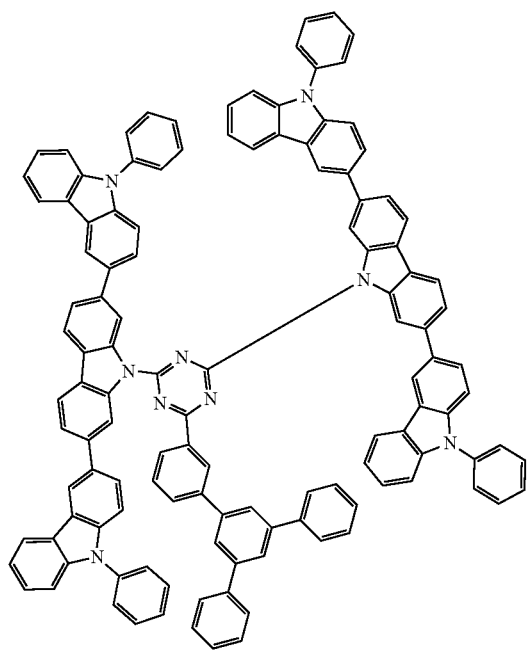
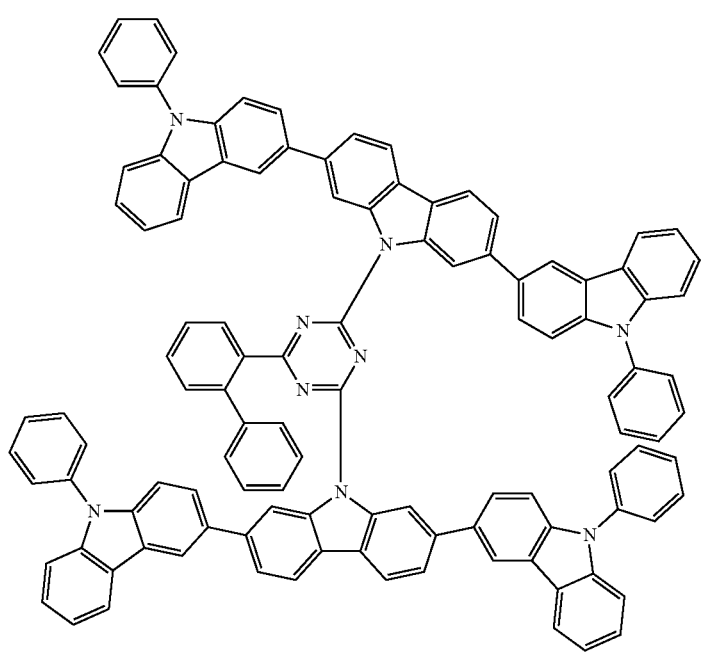

-continued
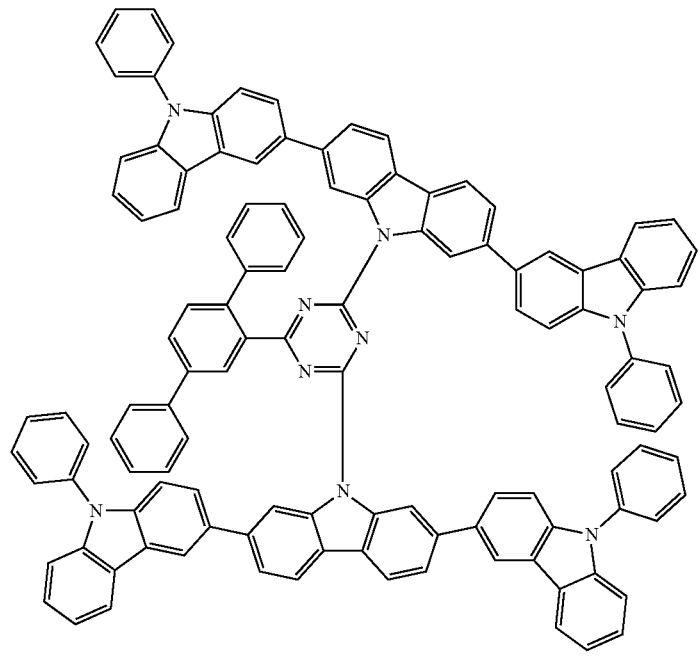
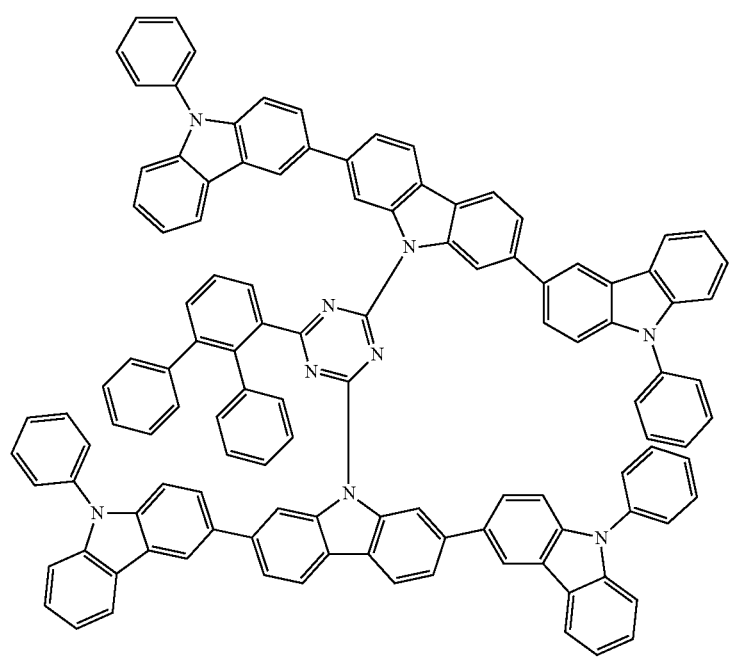

127 128
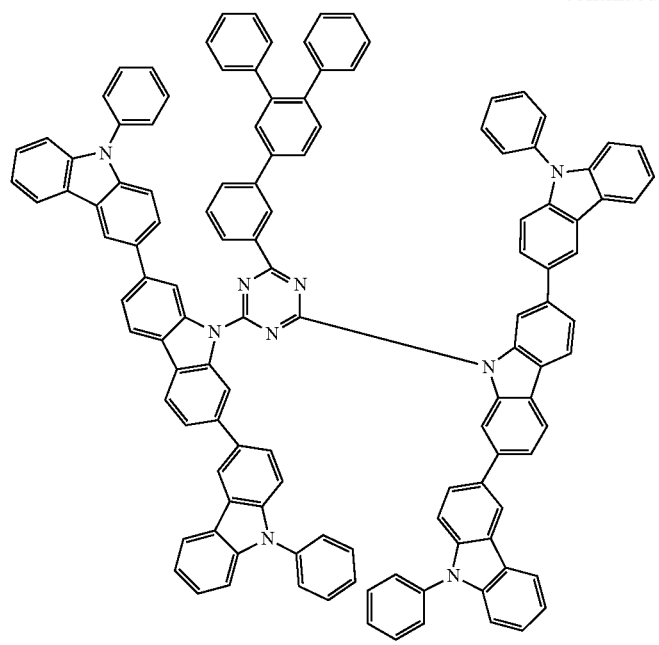
[Formula 55]
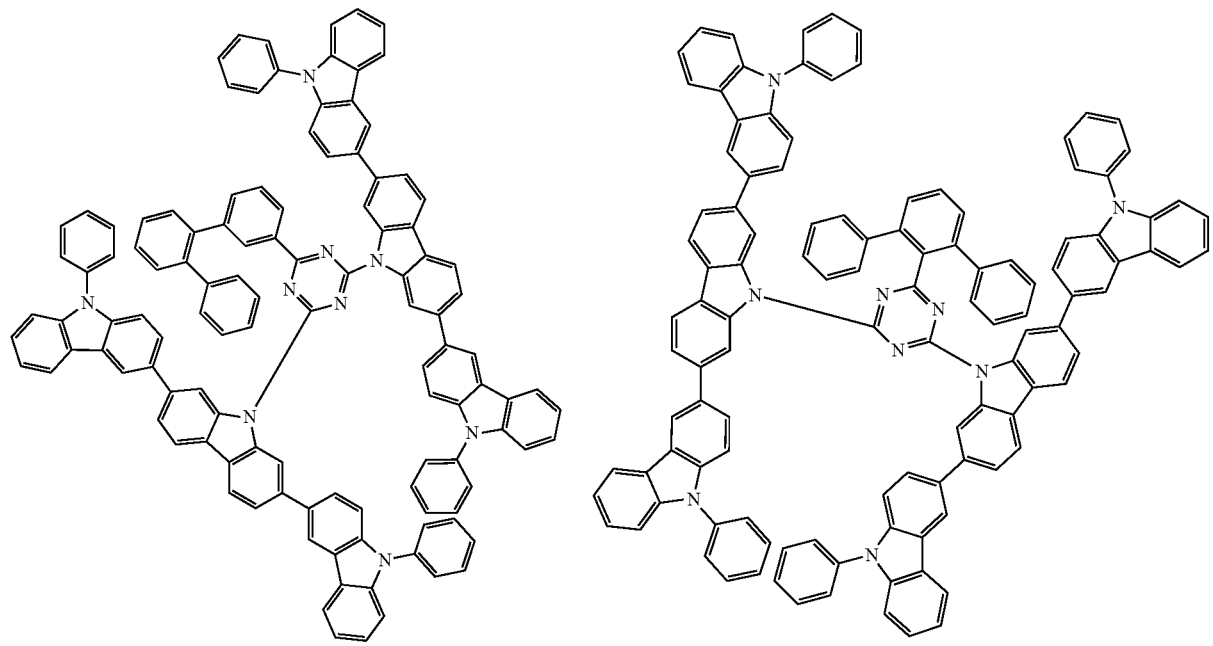

129
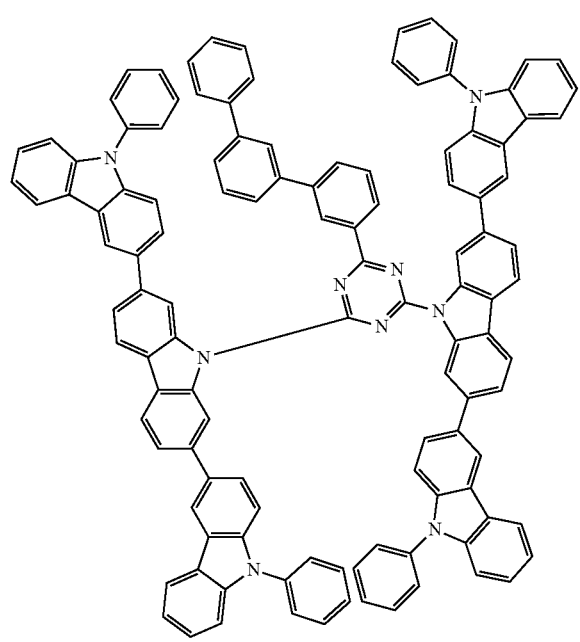
130
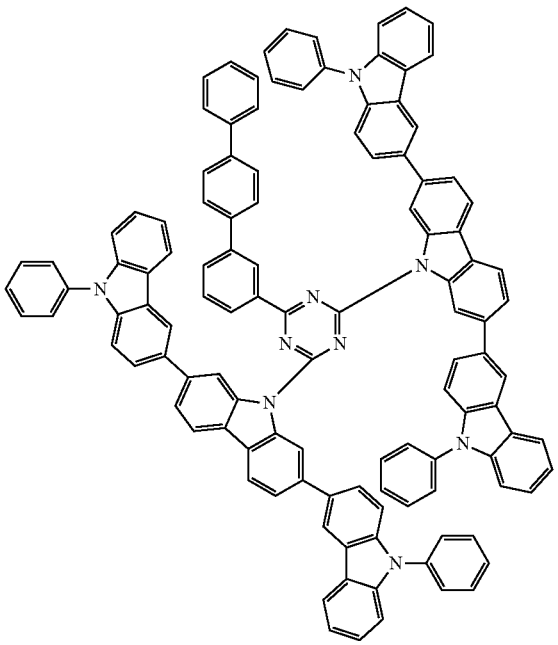
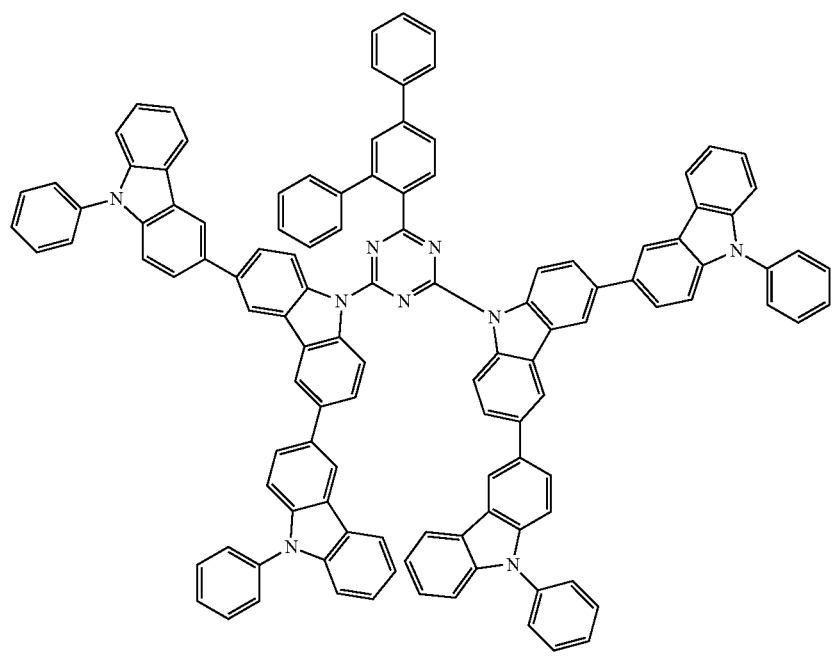

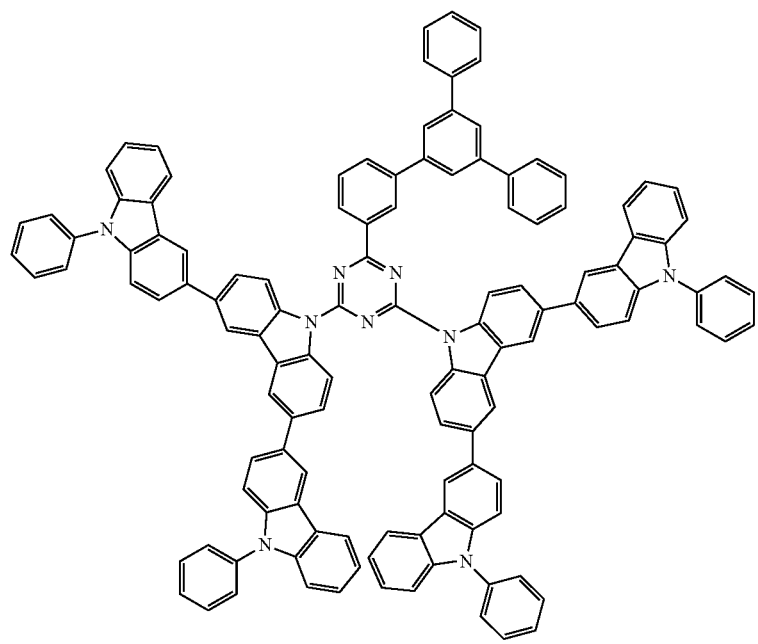
[Formula 56]
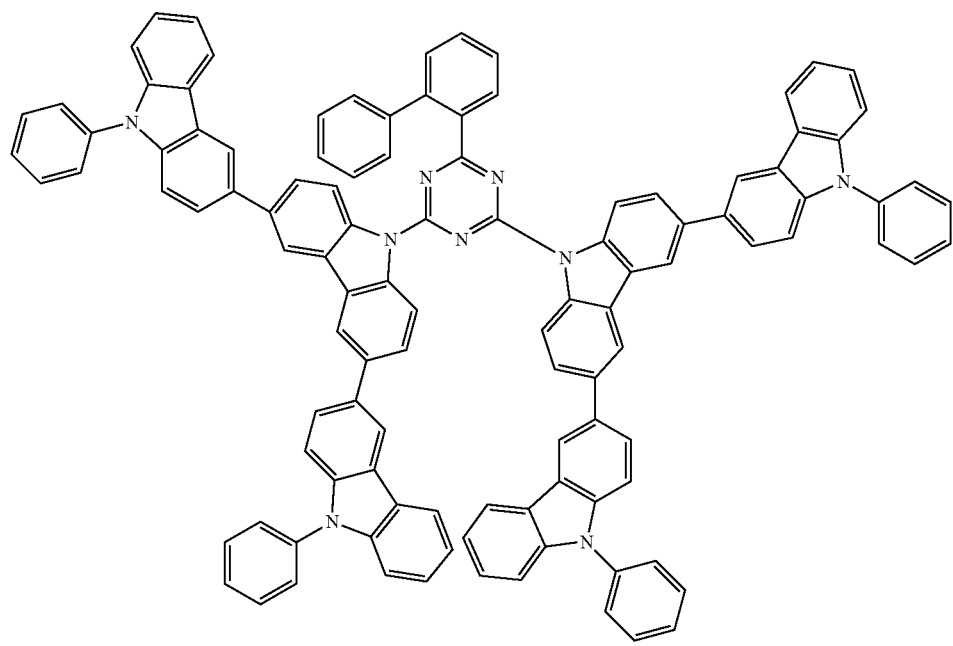

-continued
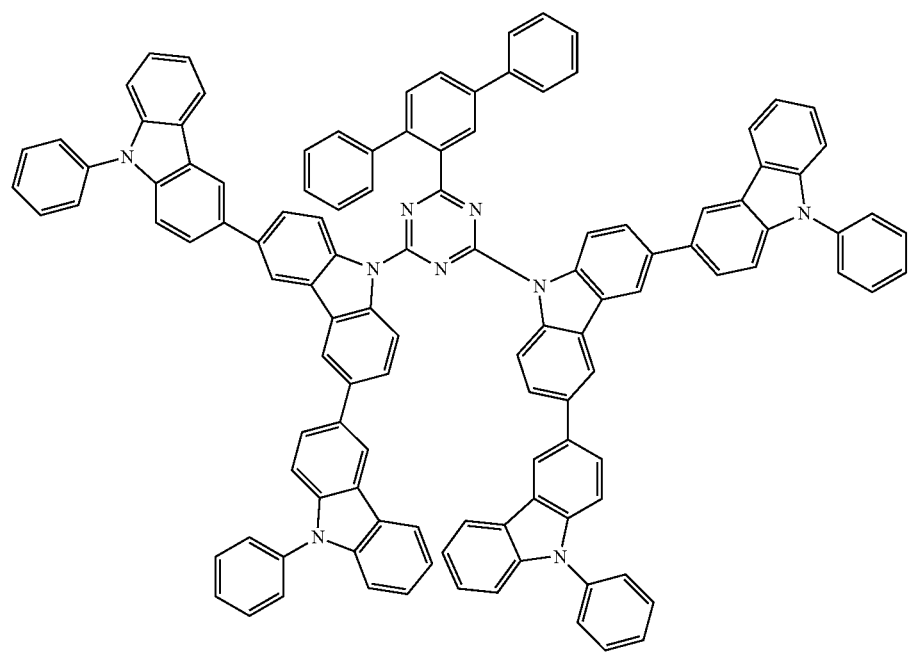
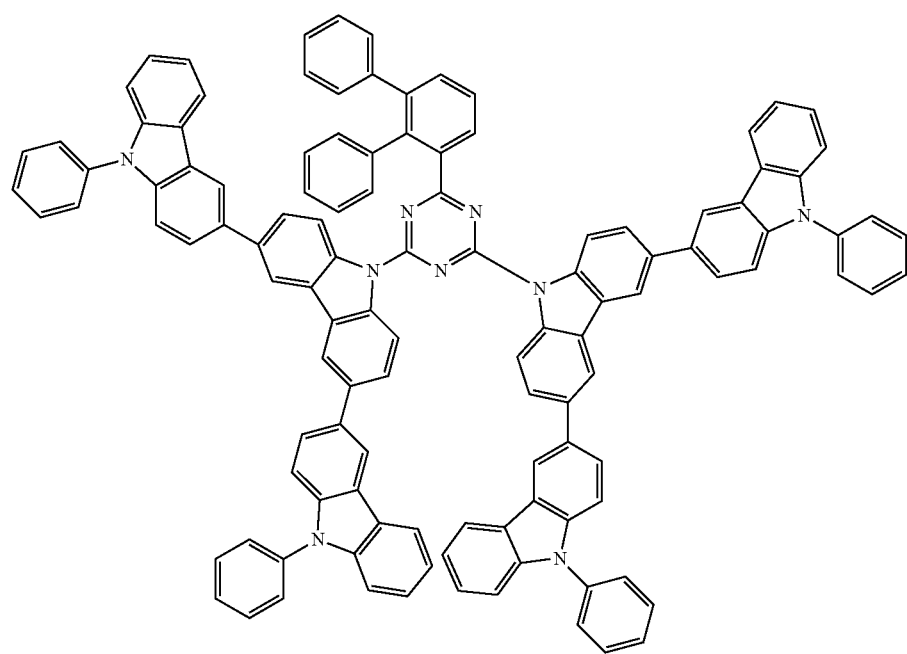

-continued
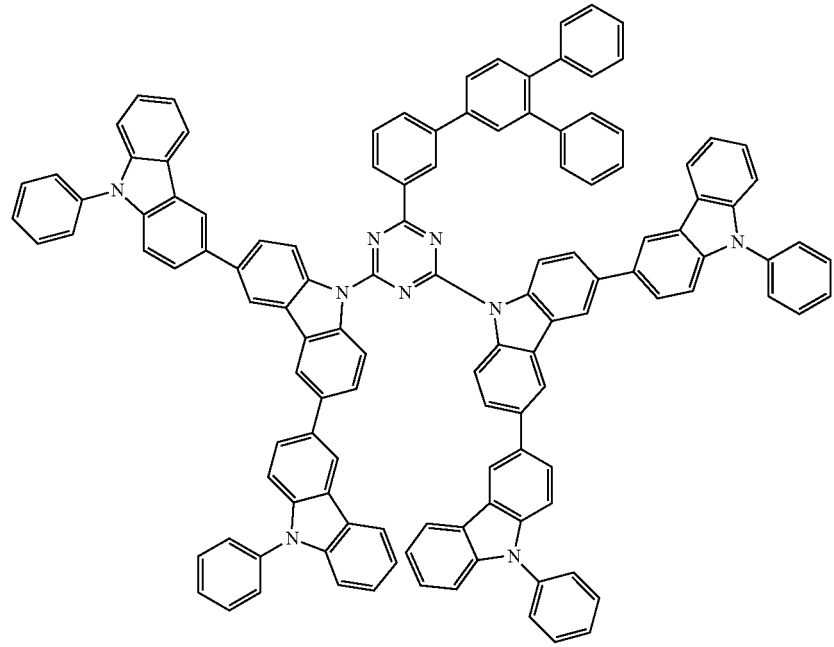
[Formula 57]
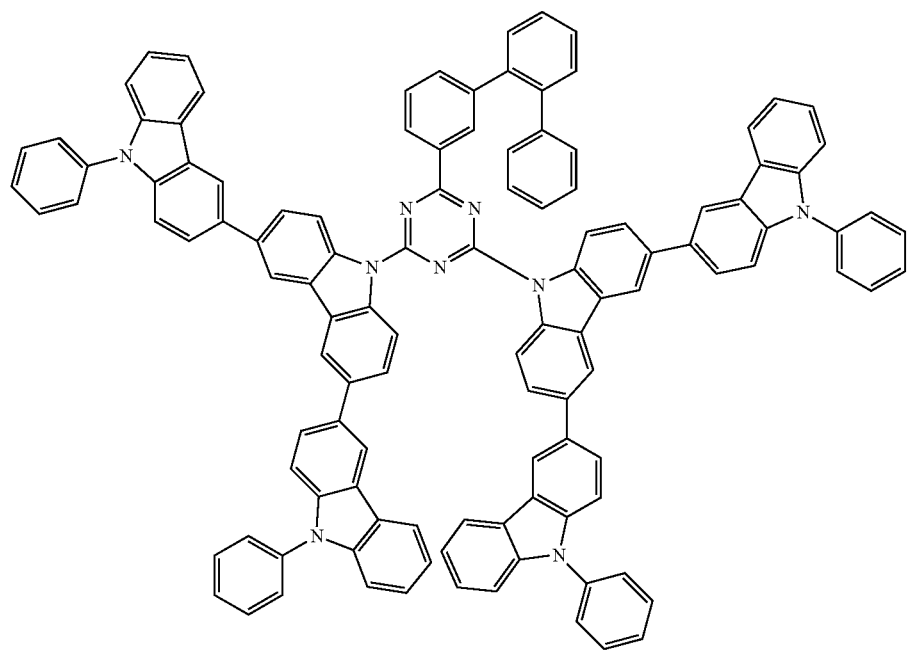

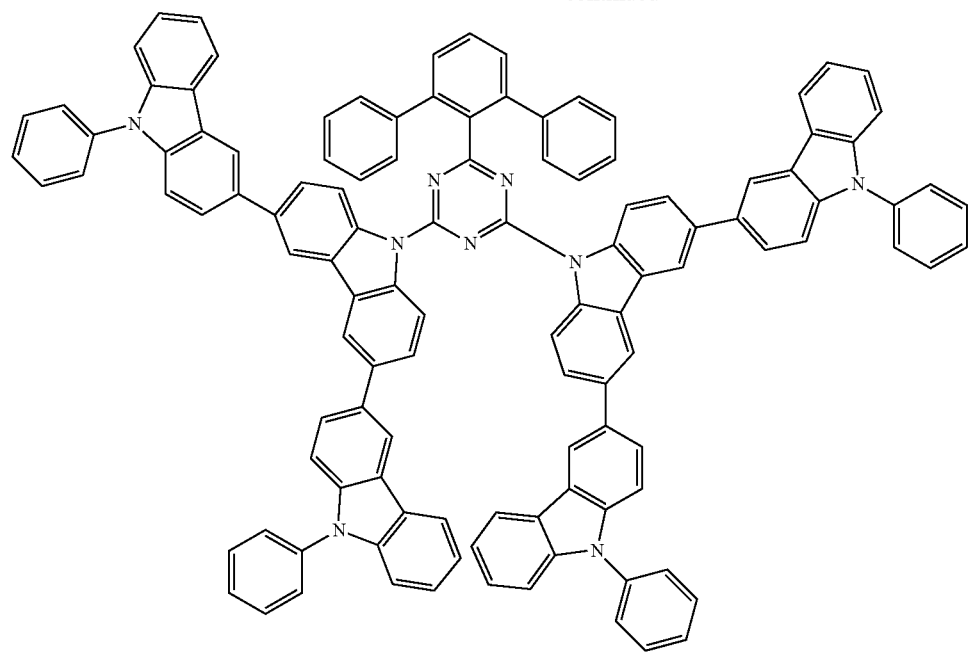
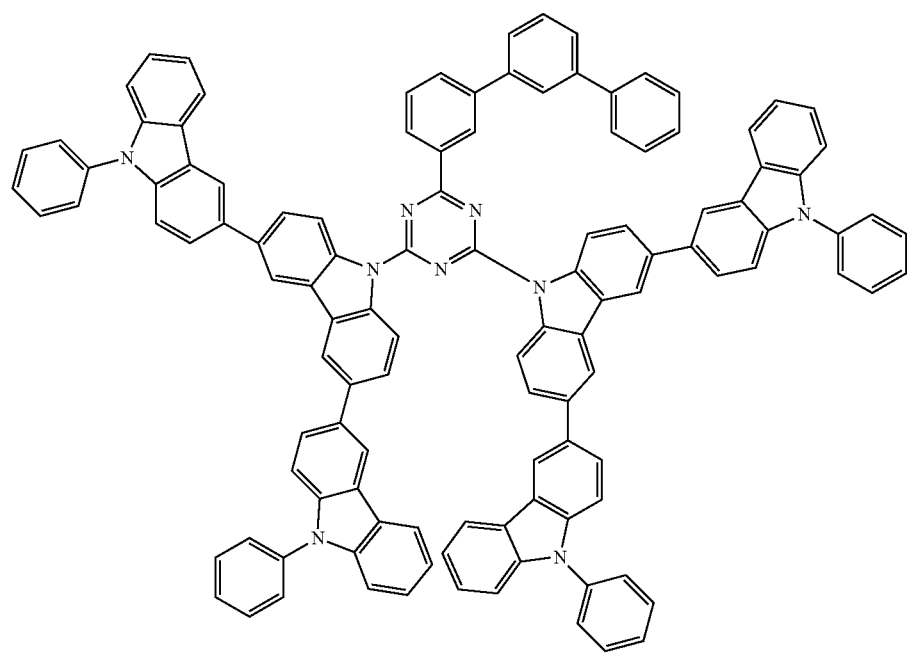

-continued
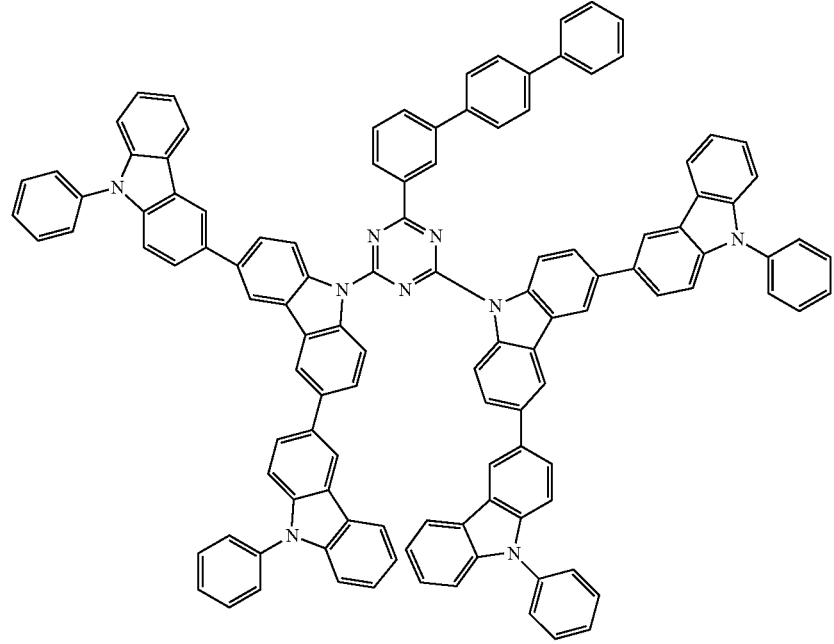
[Formula 58]
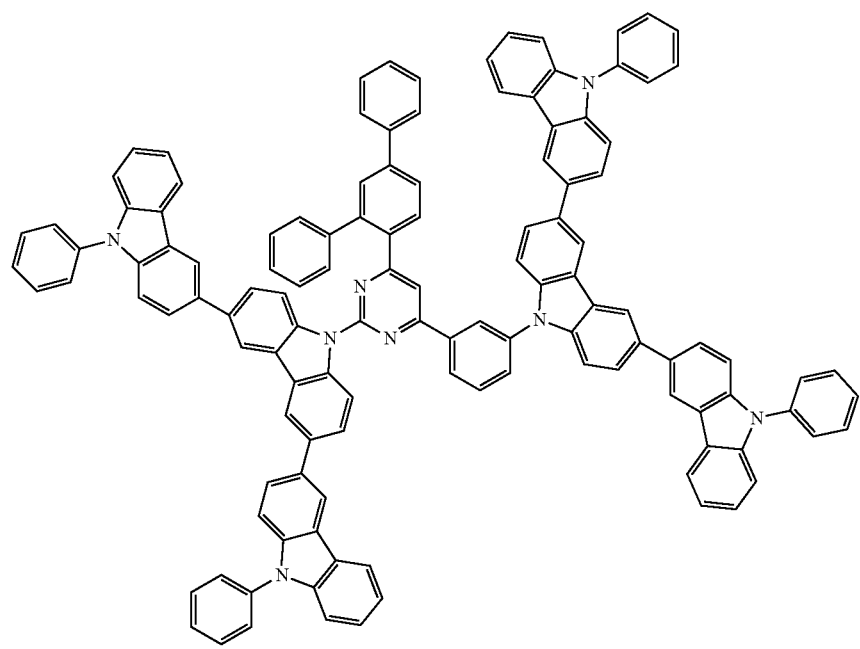

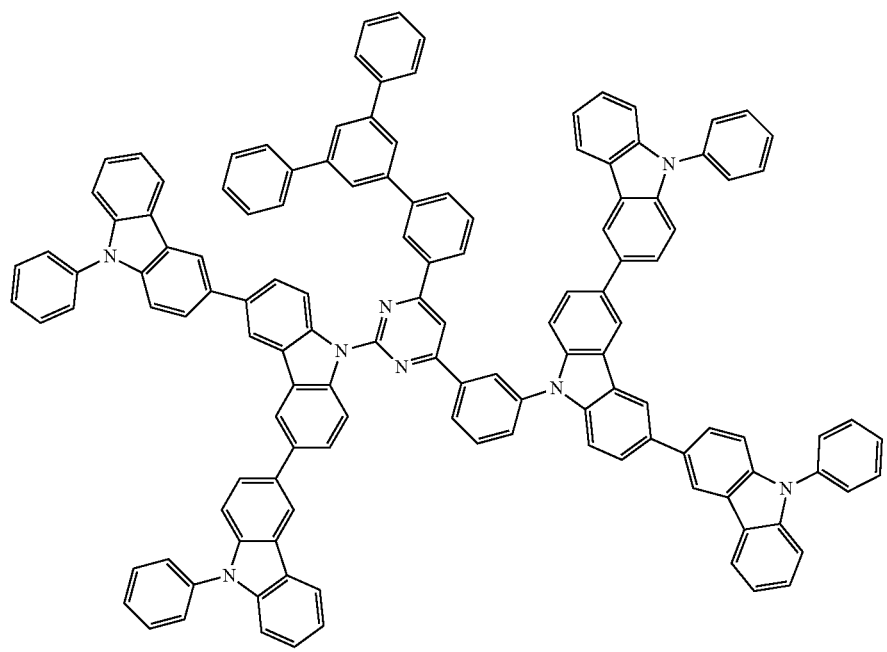
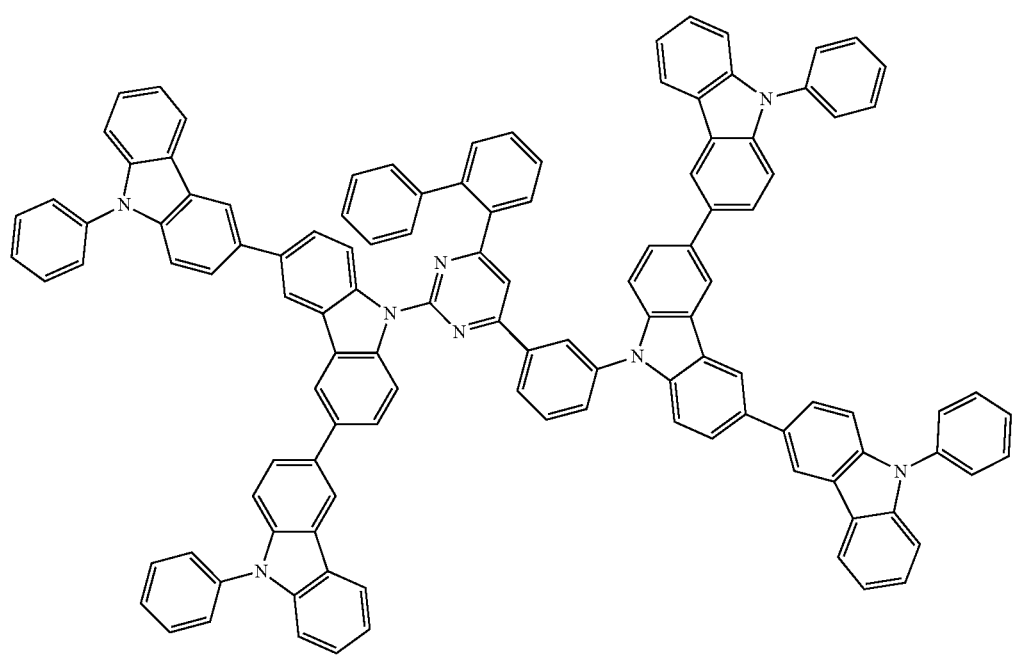

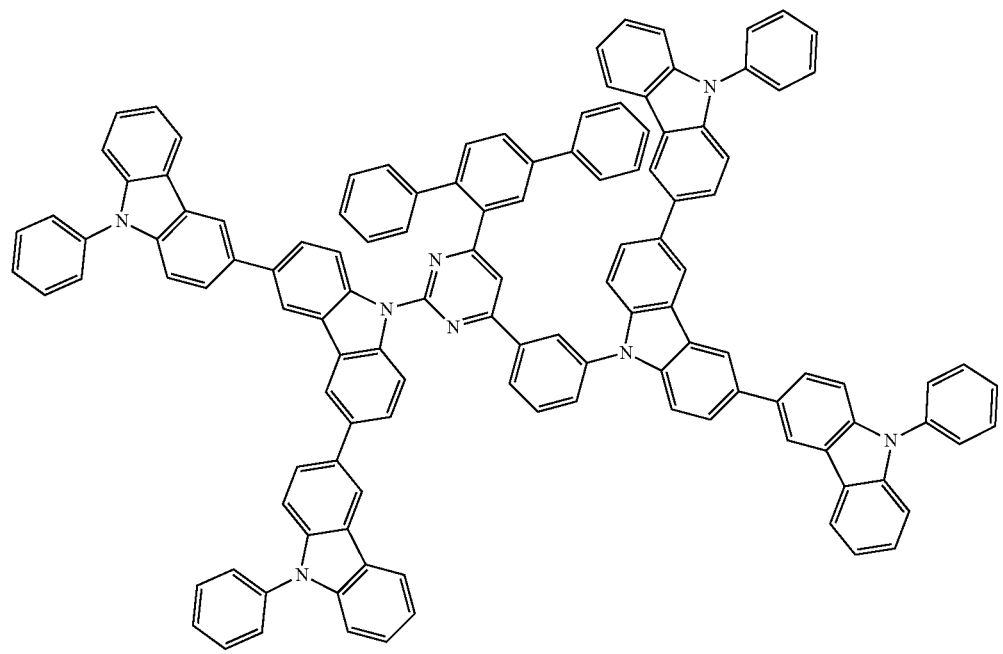
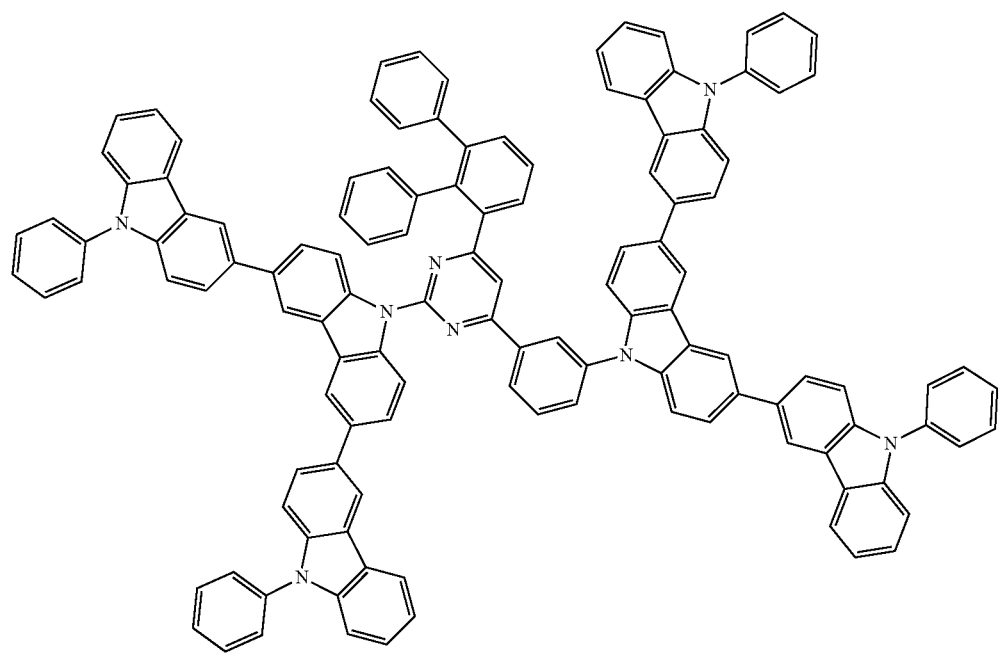

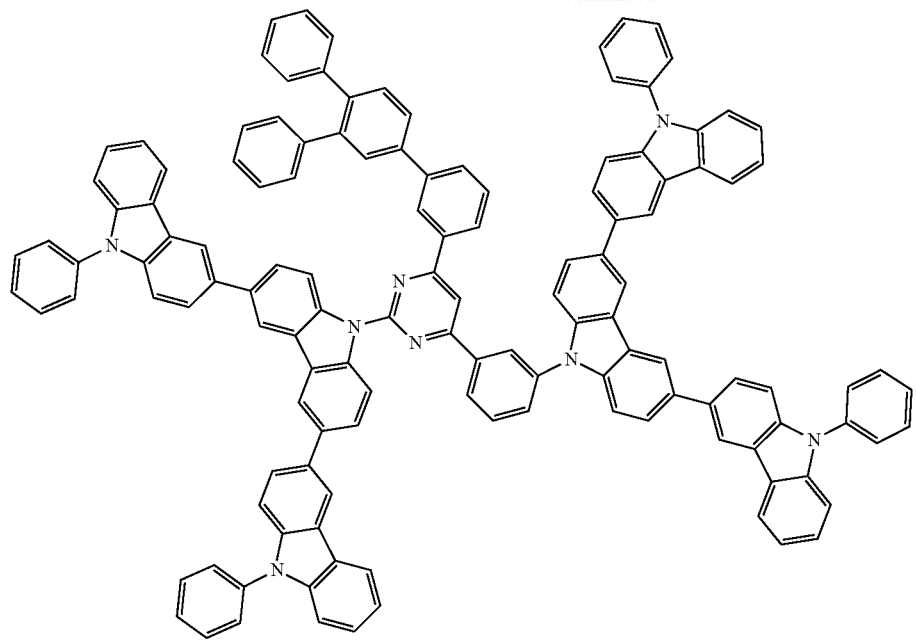
[Formula 59]
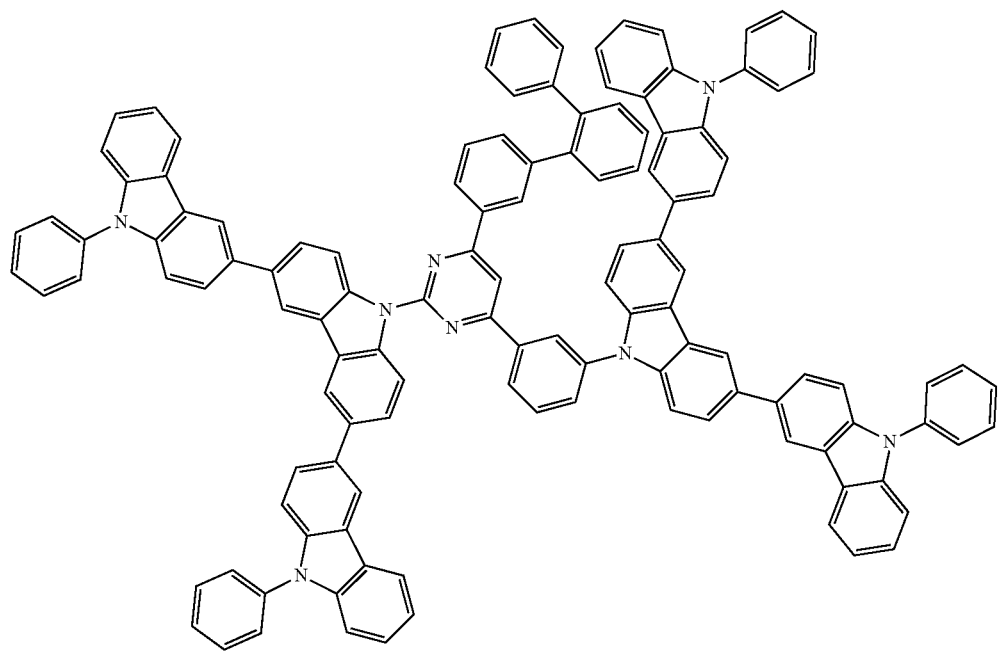

-continued
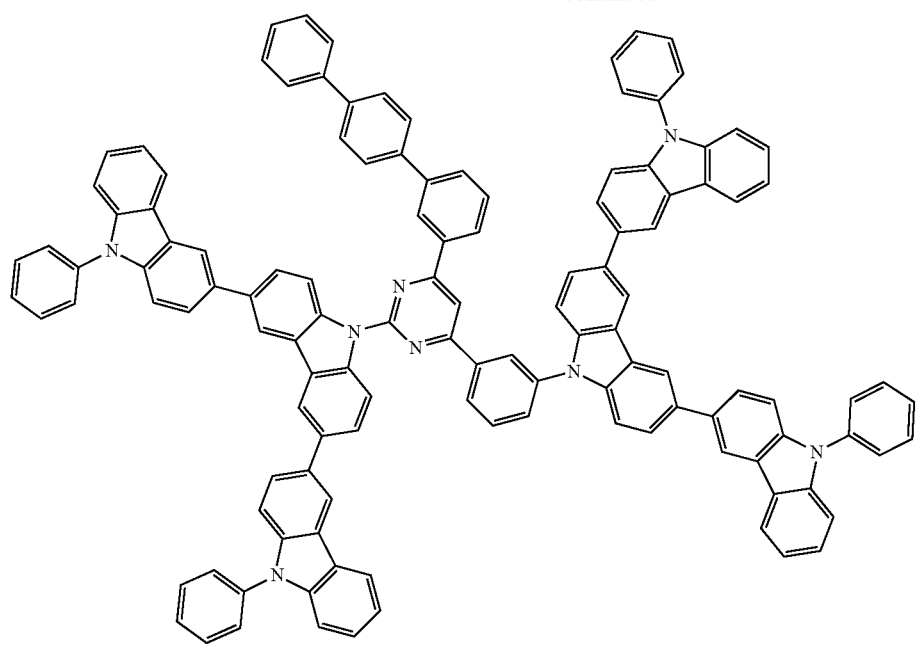
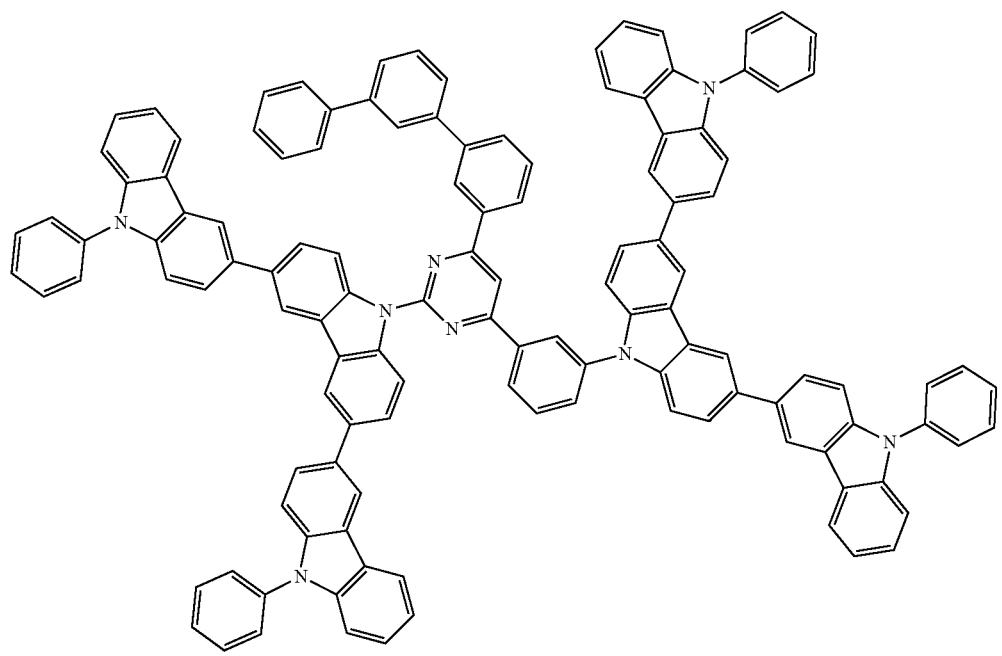

-continued
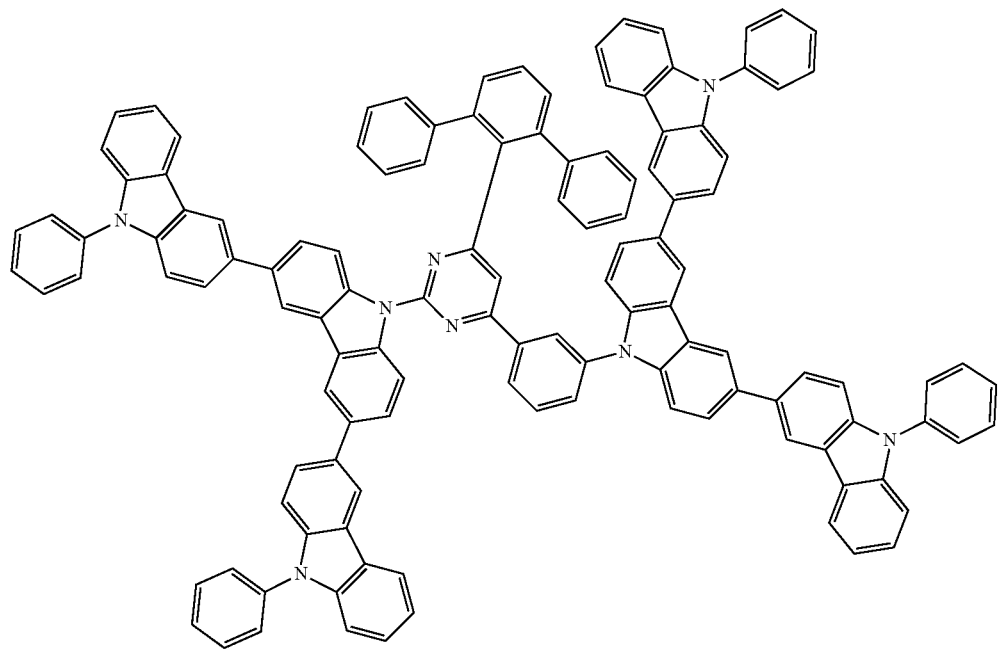
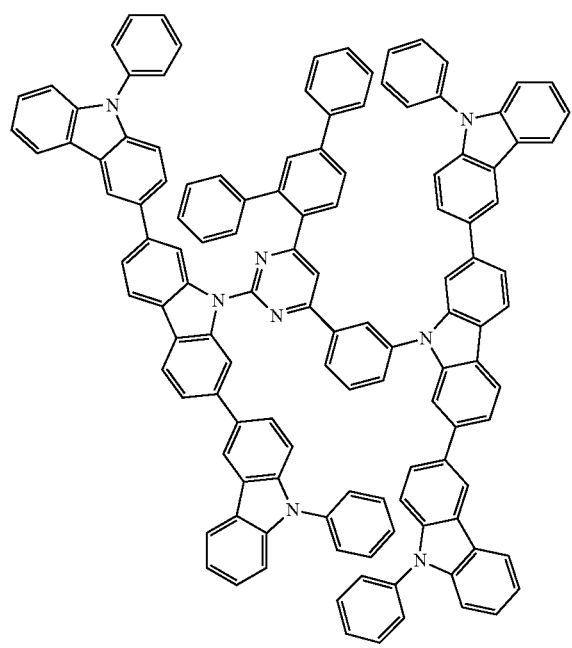

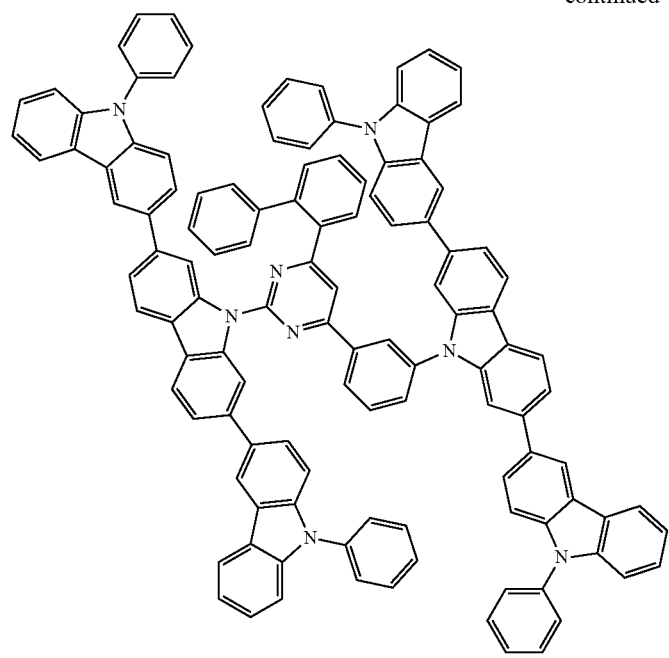
[Formula 60]
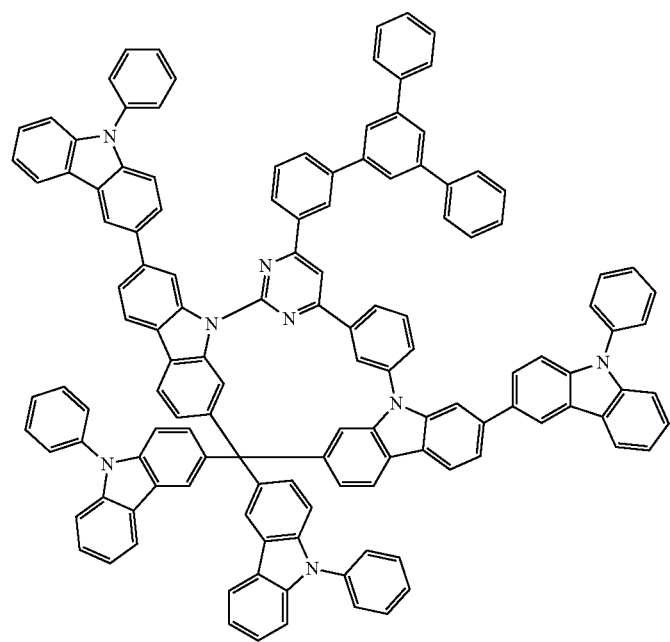

-continued
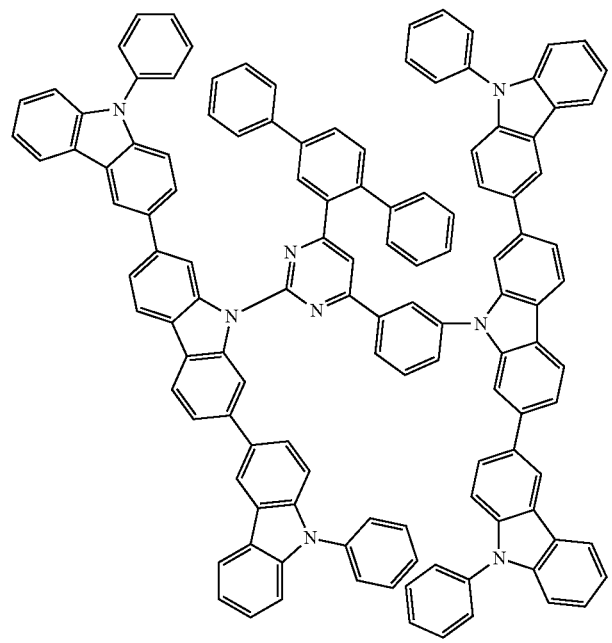
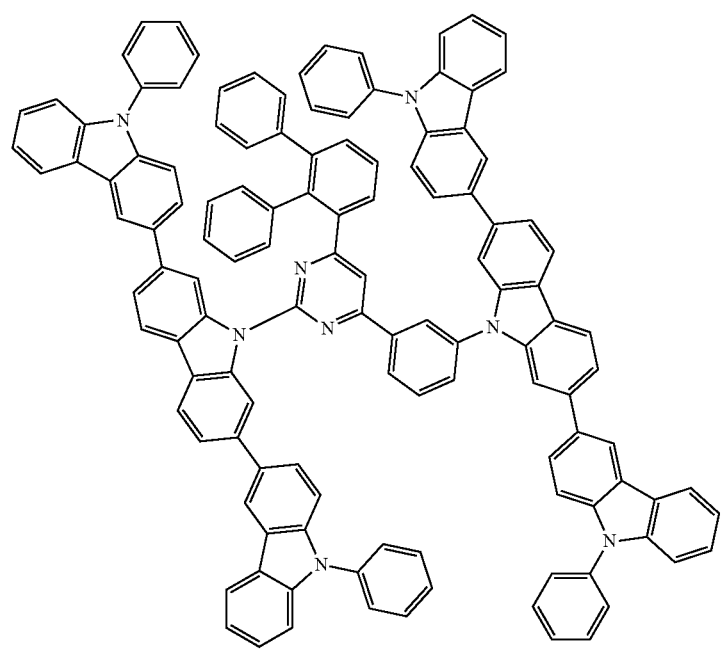

-continued
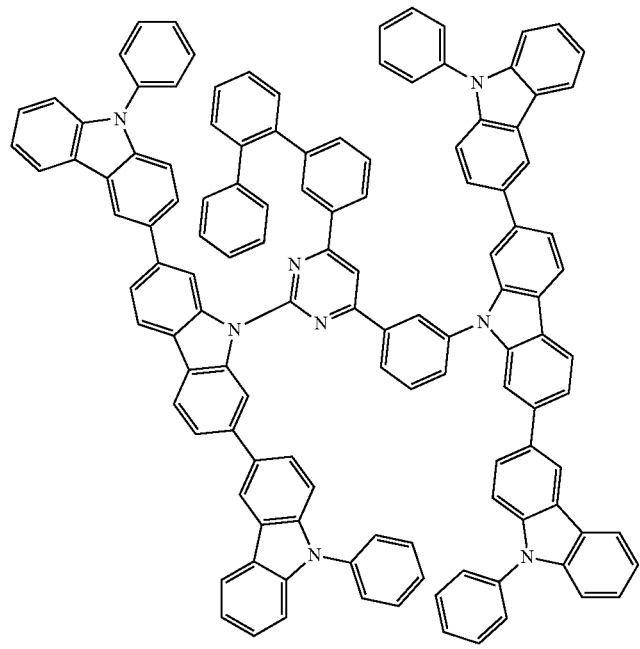
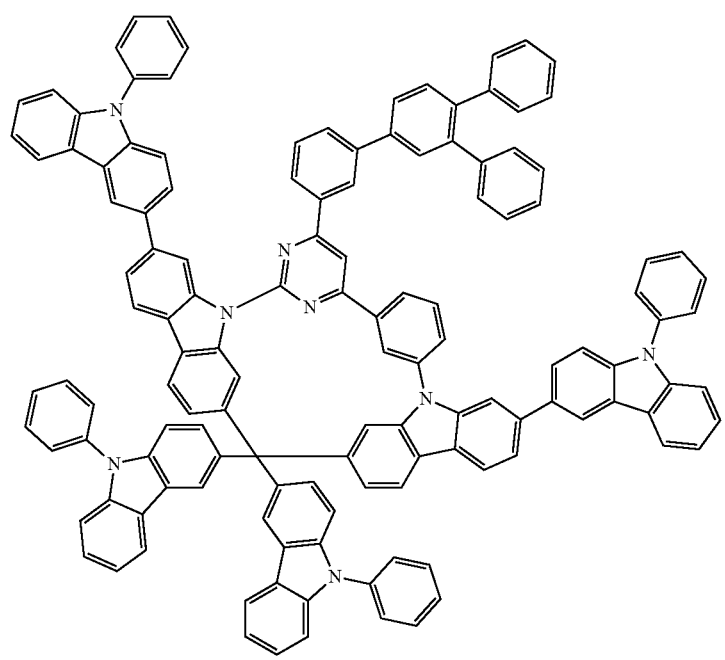

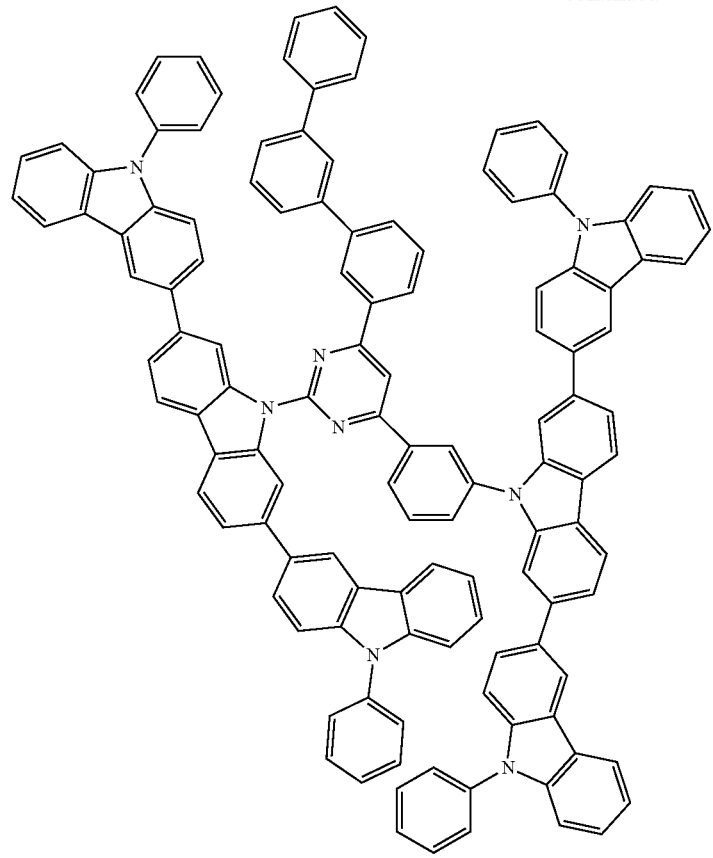
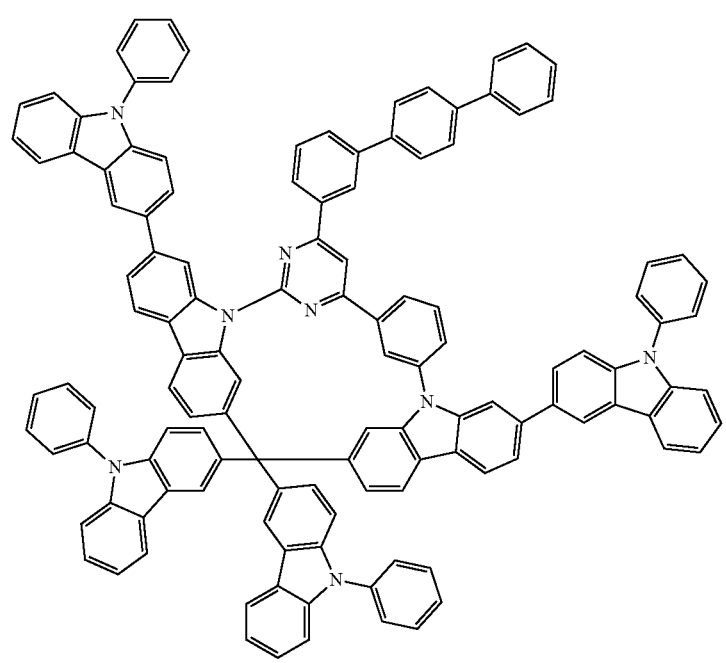

159 160
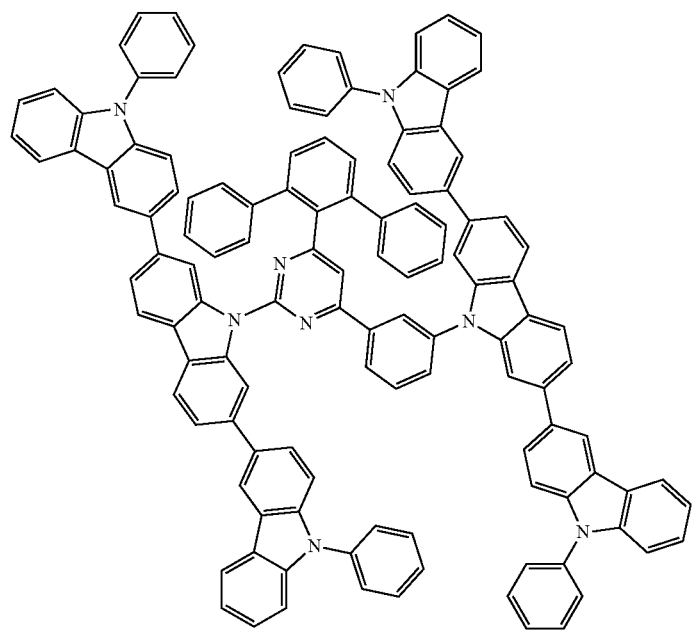
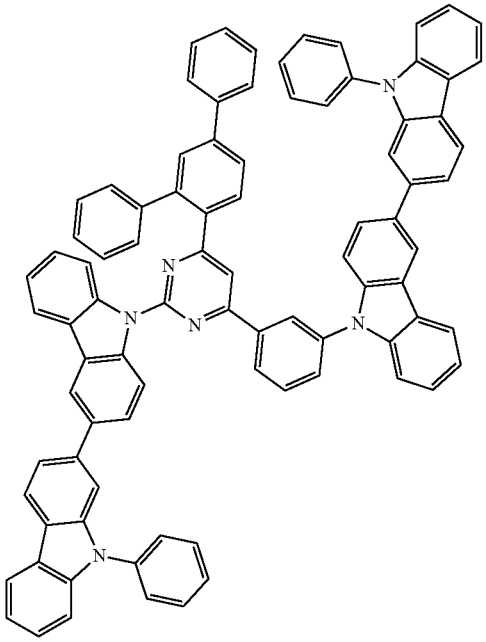
[Formula 61]
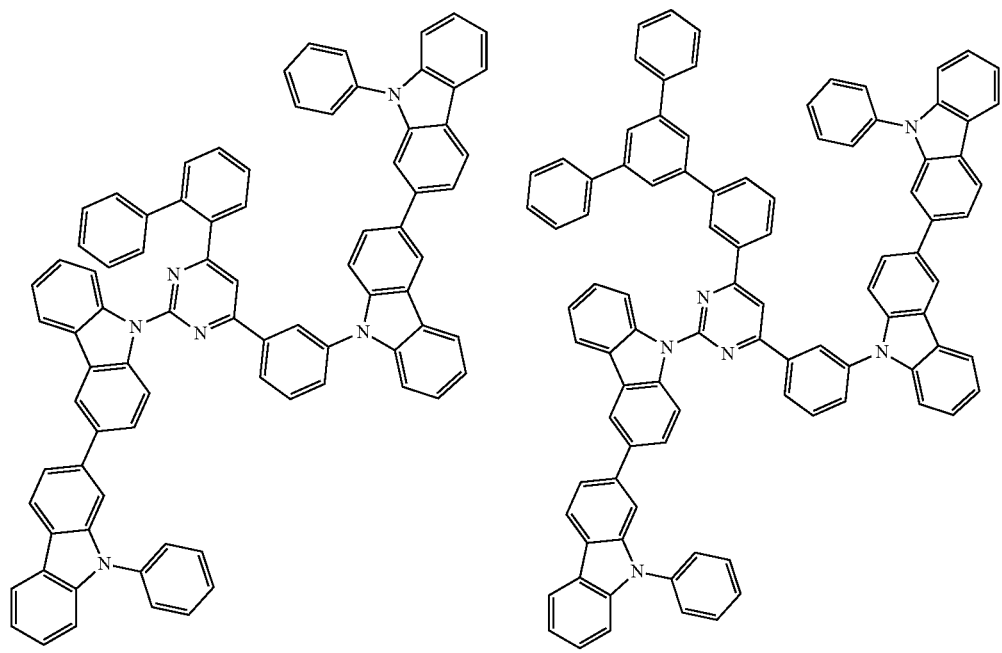

161
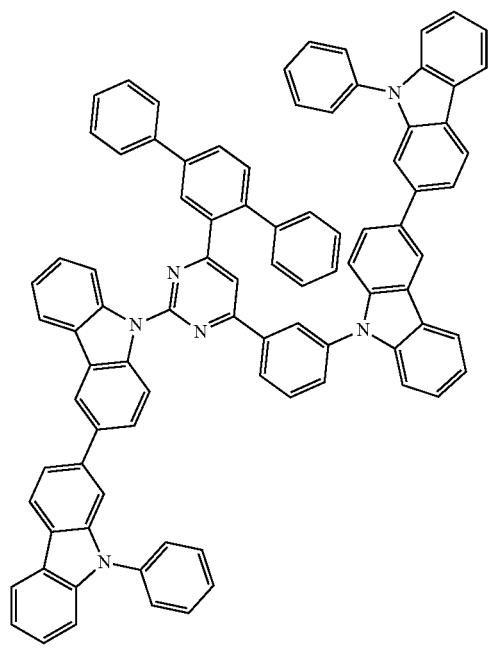
162
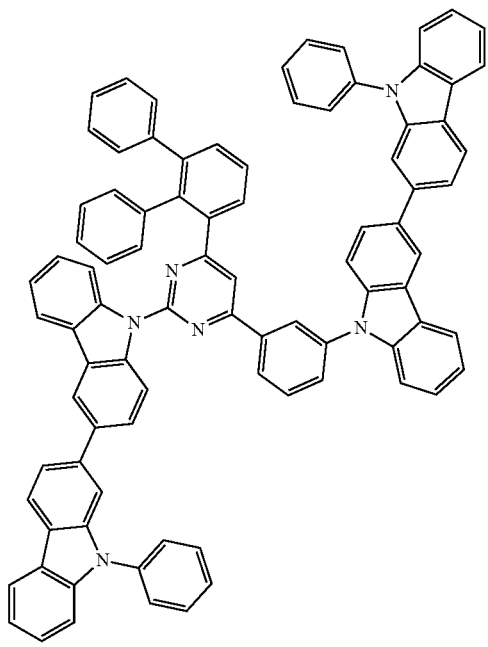
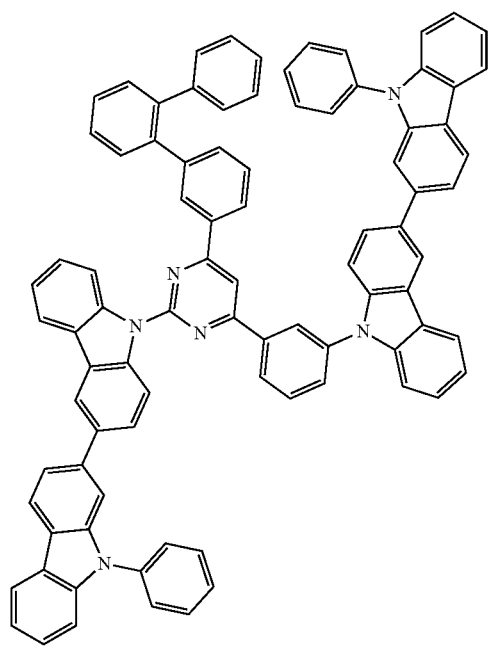
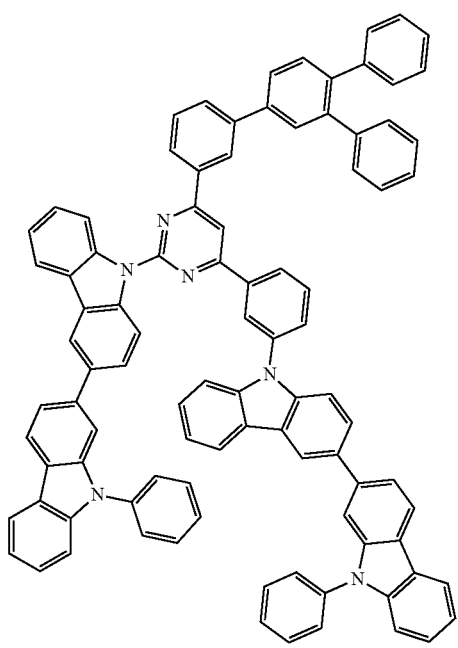

-continued
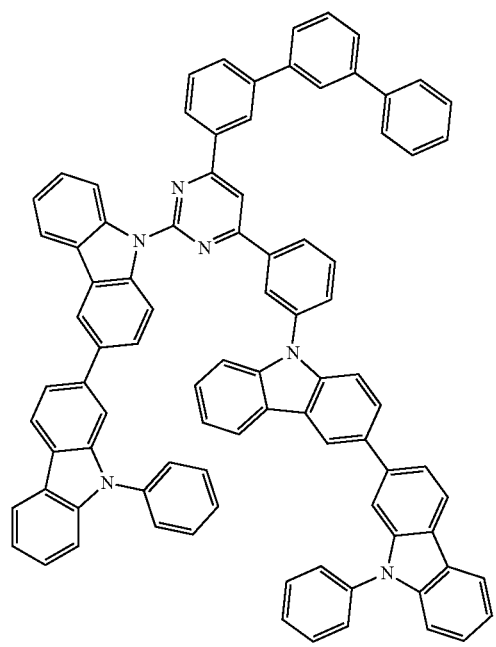
[Formula 62]
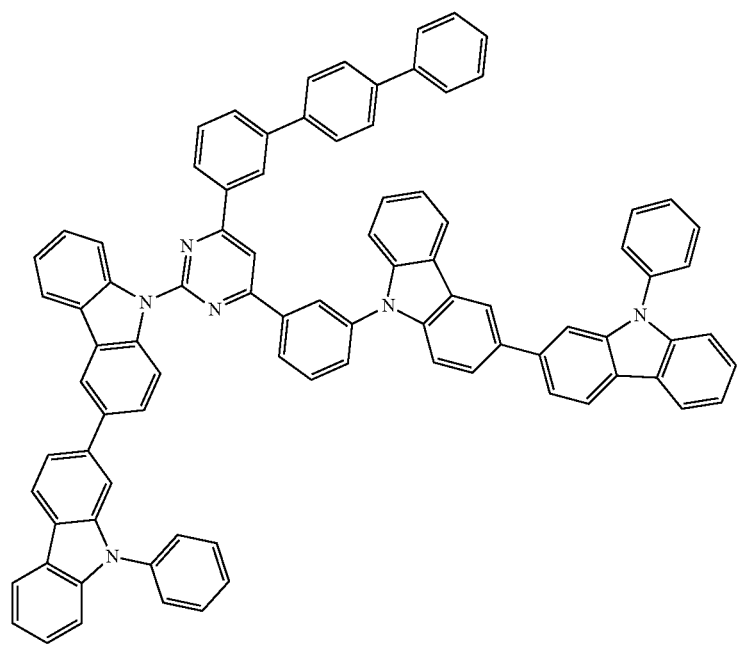

165
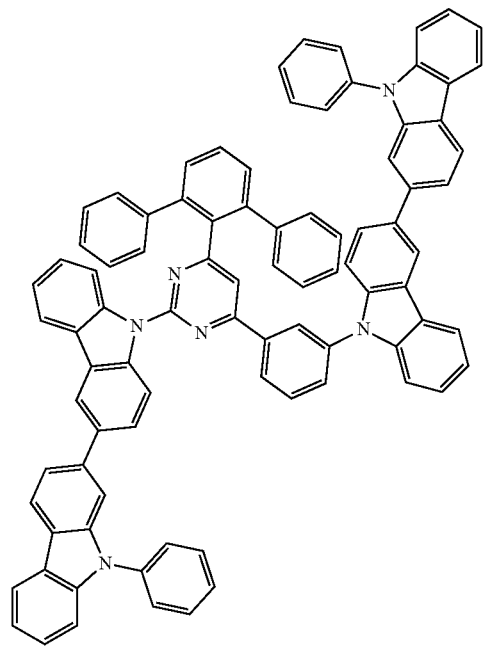
166
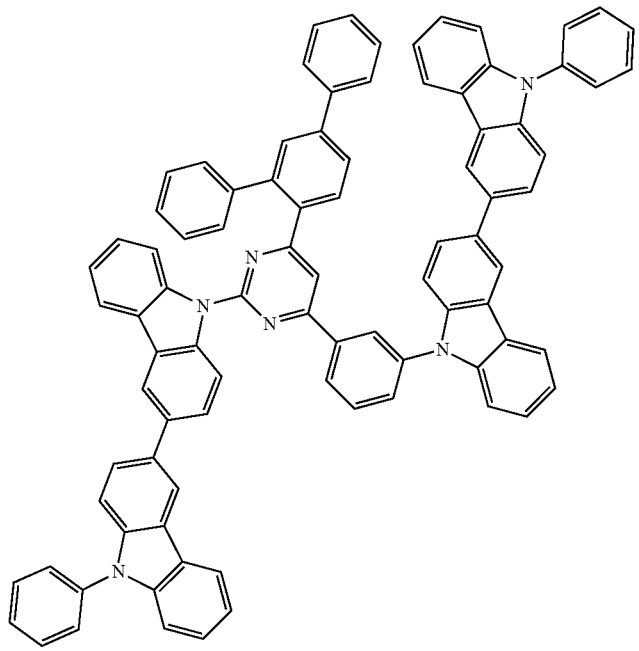
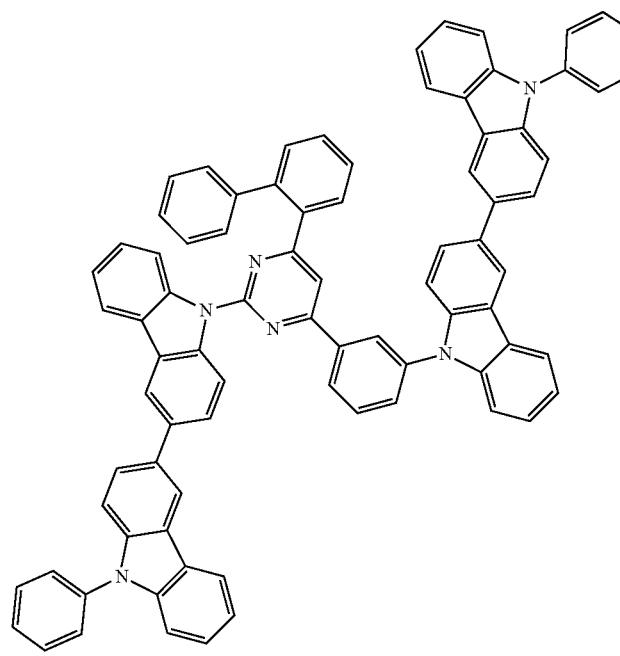
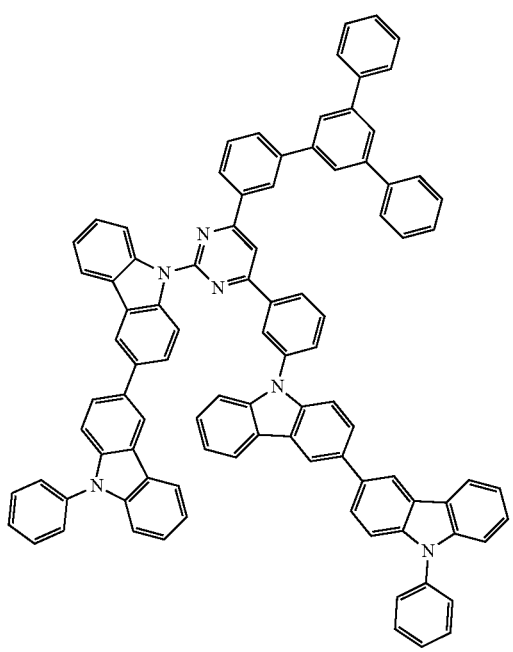

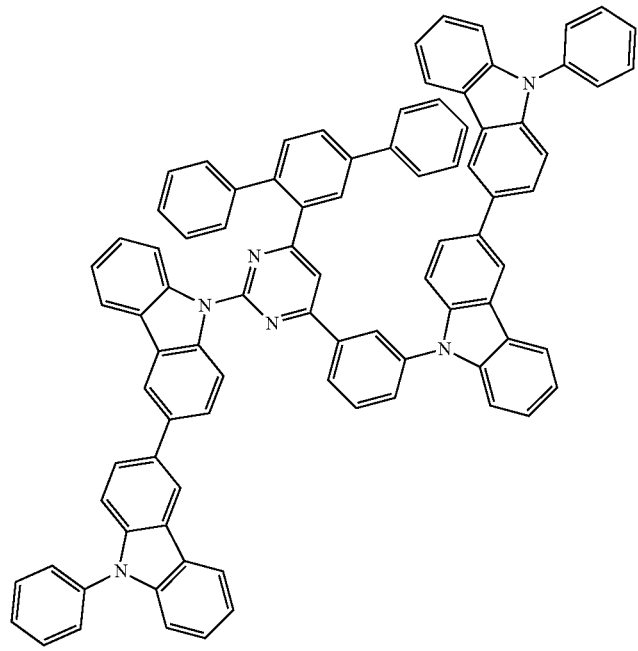
[Formula 63]
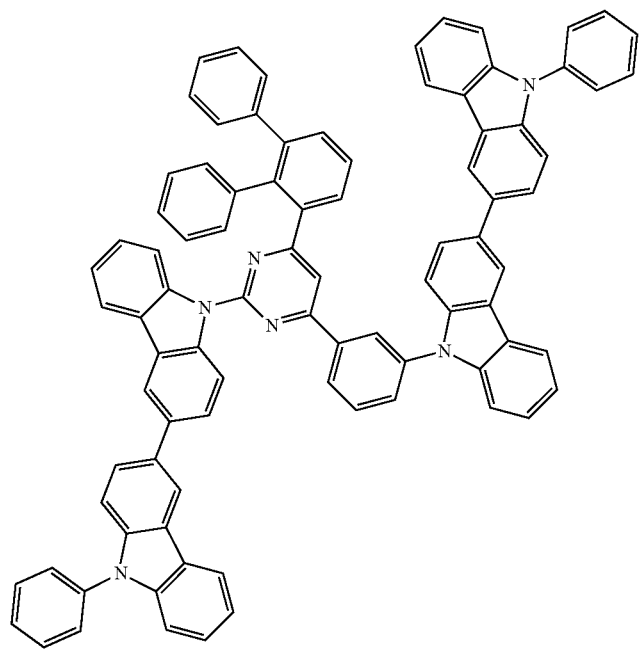

-continued
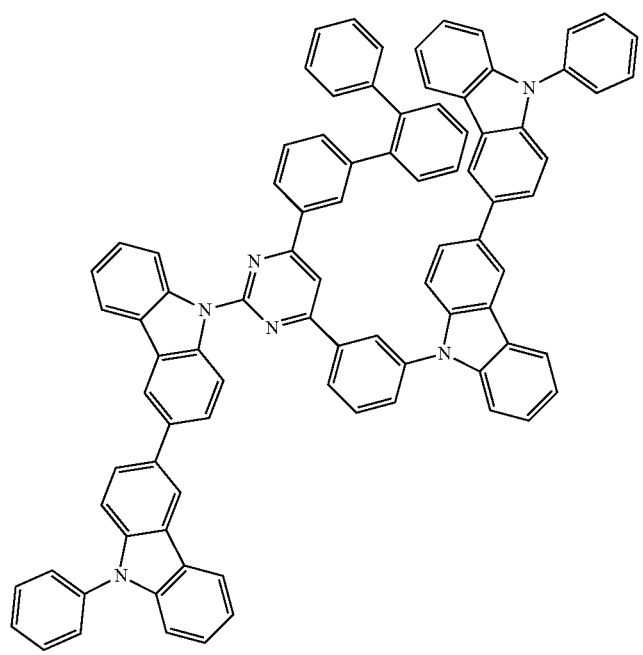
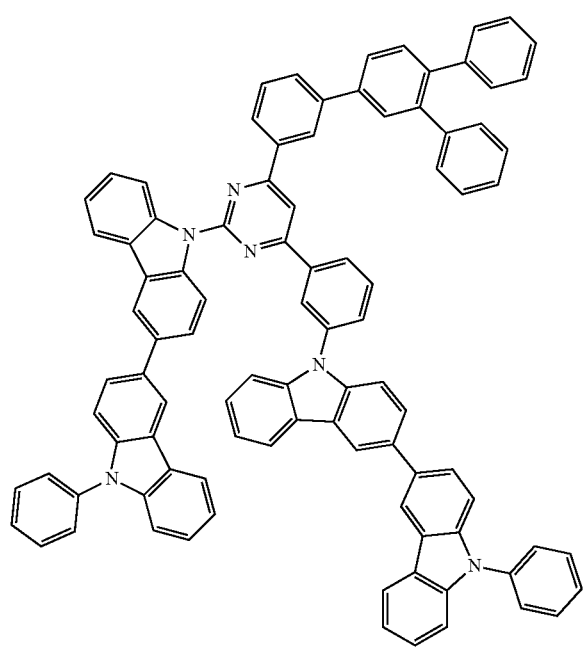

-continued
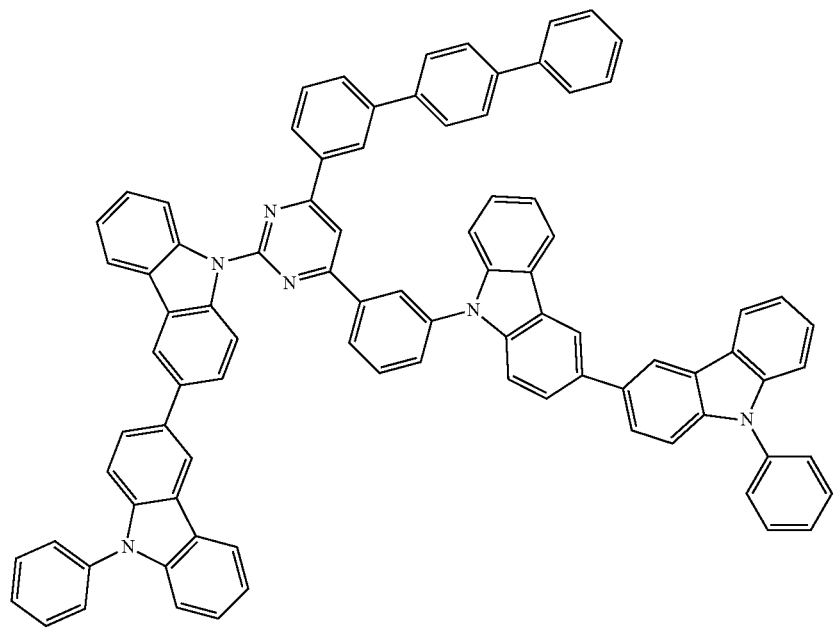
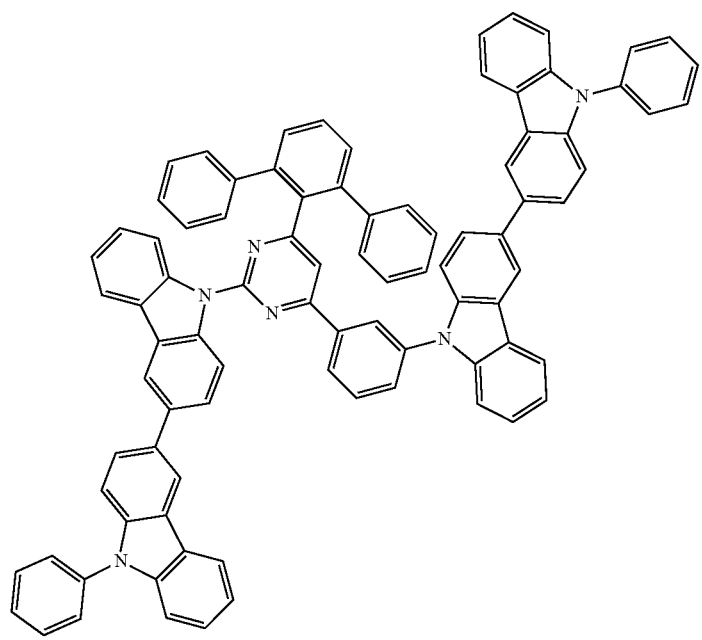

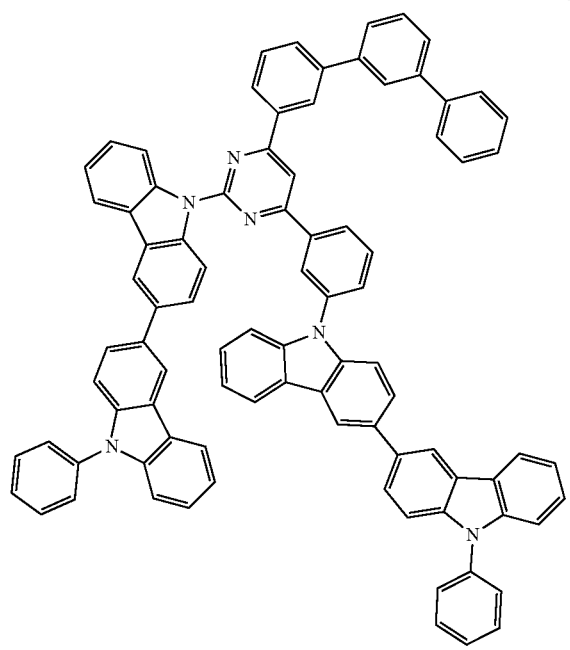
[Formula 64]
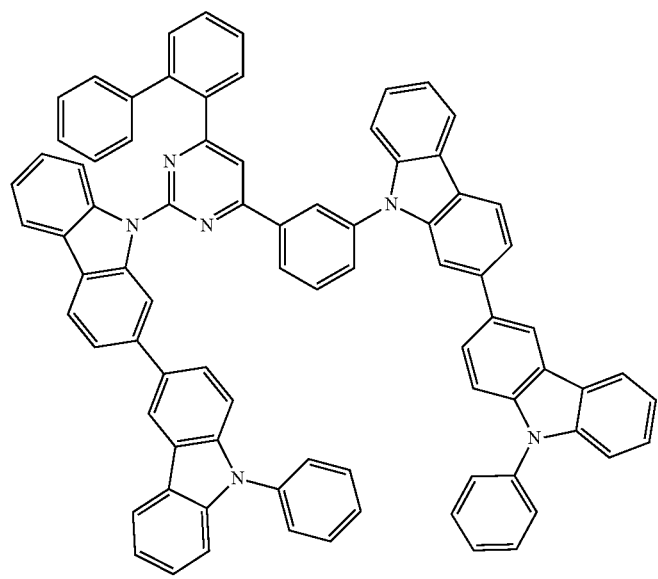

-continued
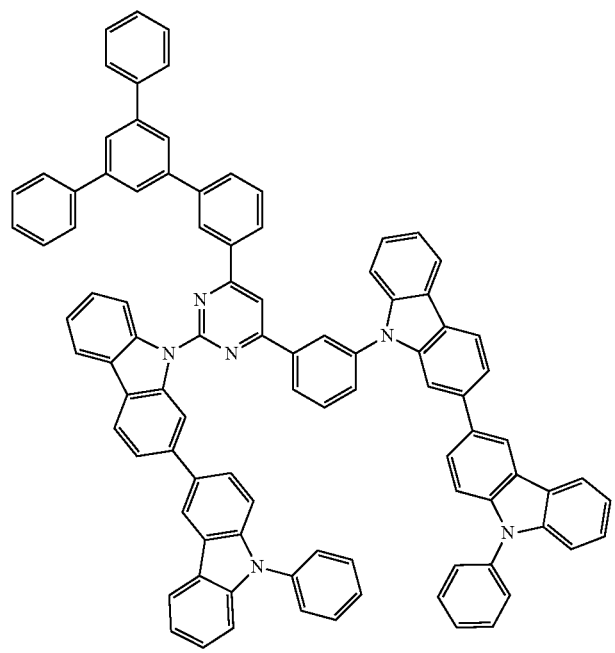
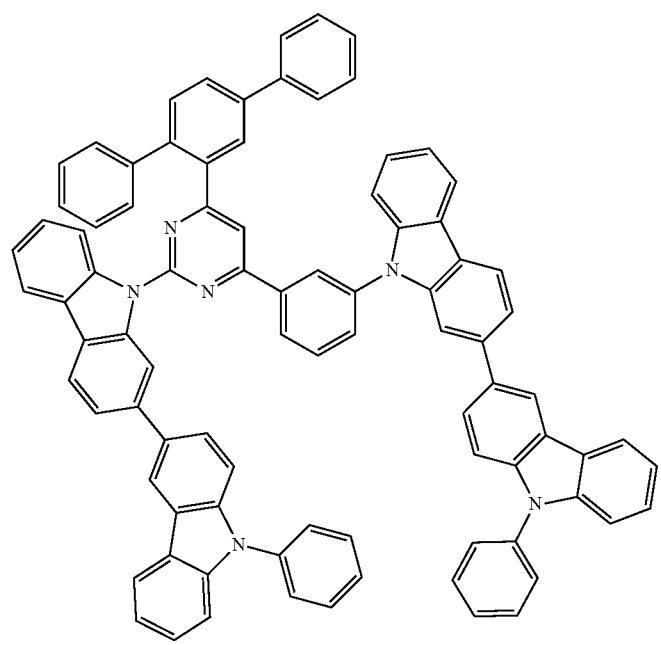

-continued
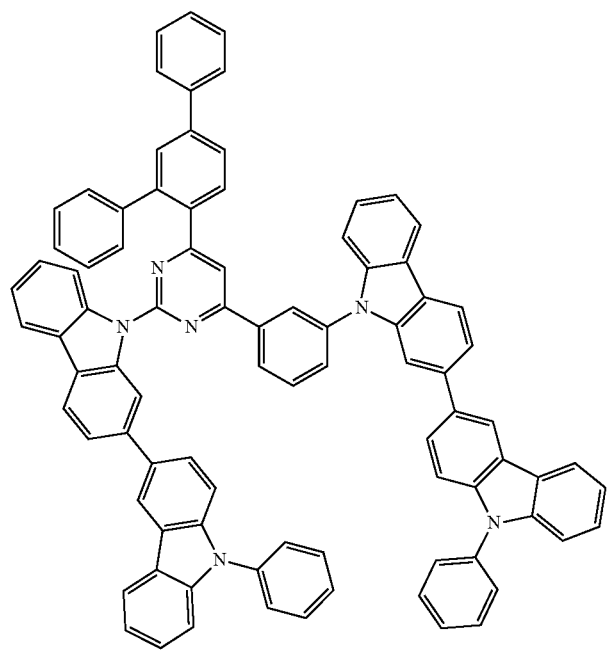
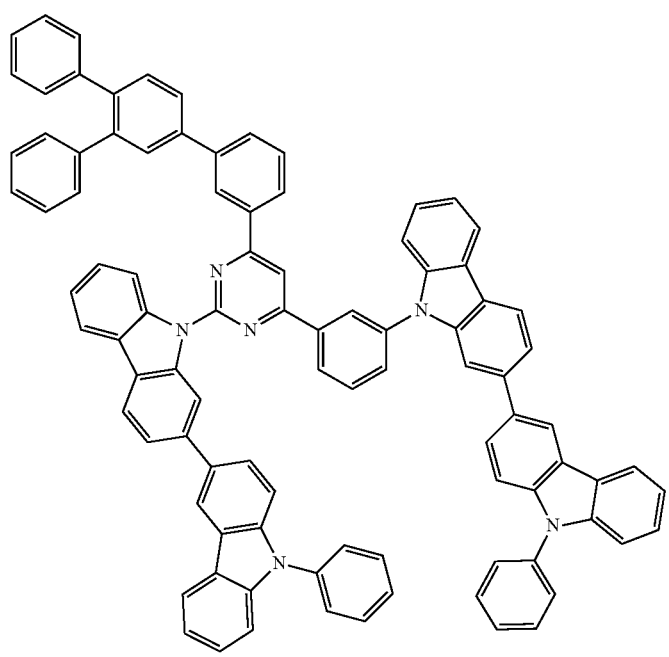

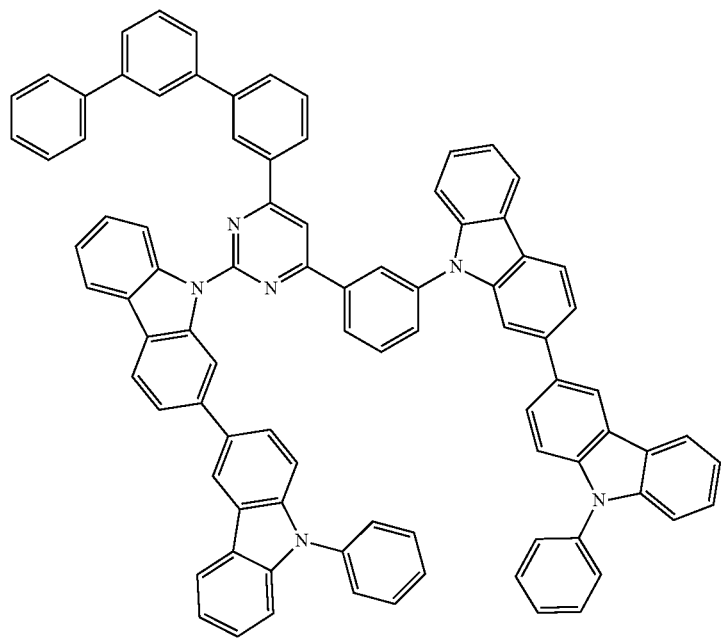
[Formula 65]
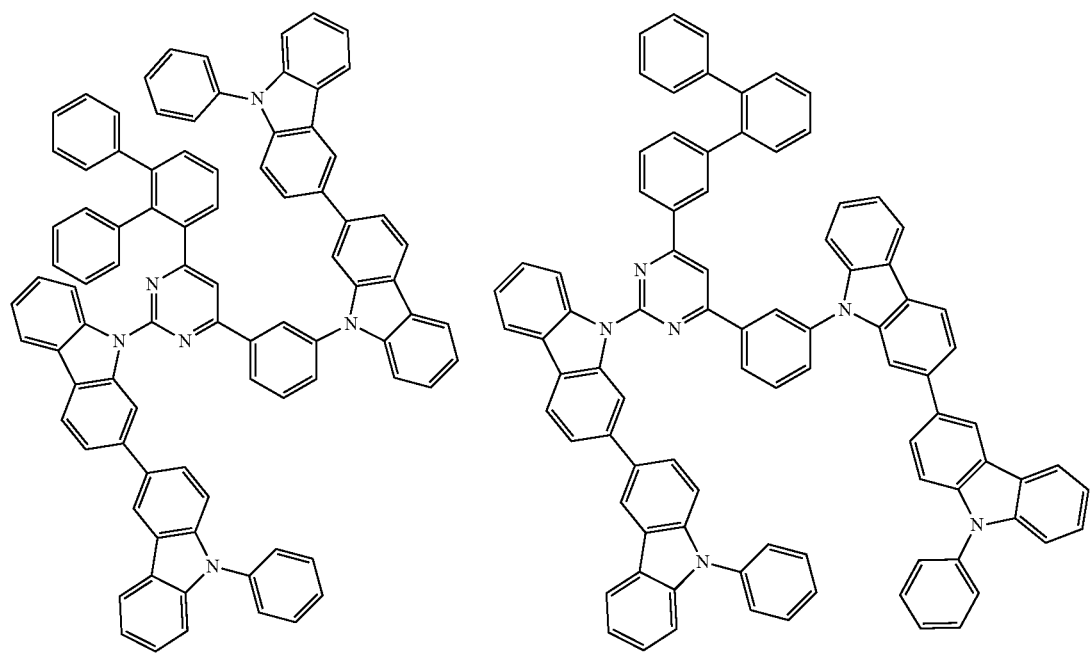

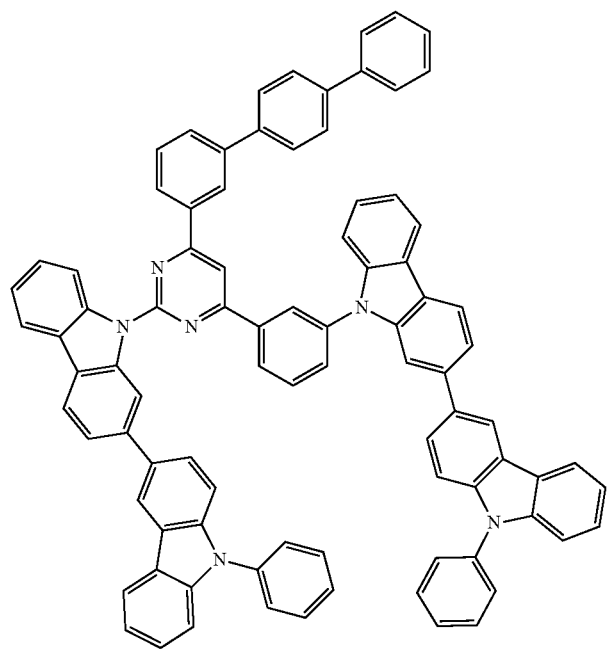
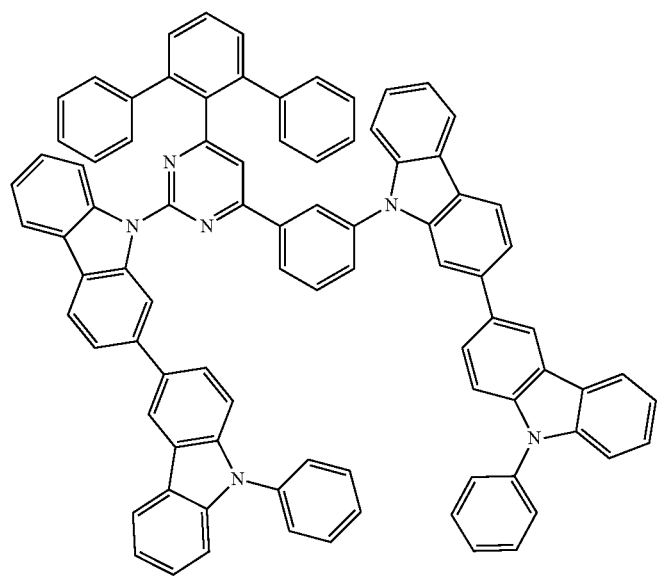

[Formula 66]
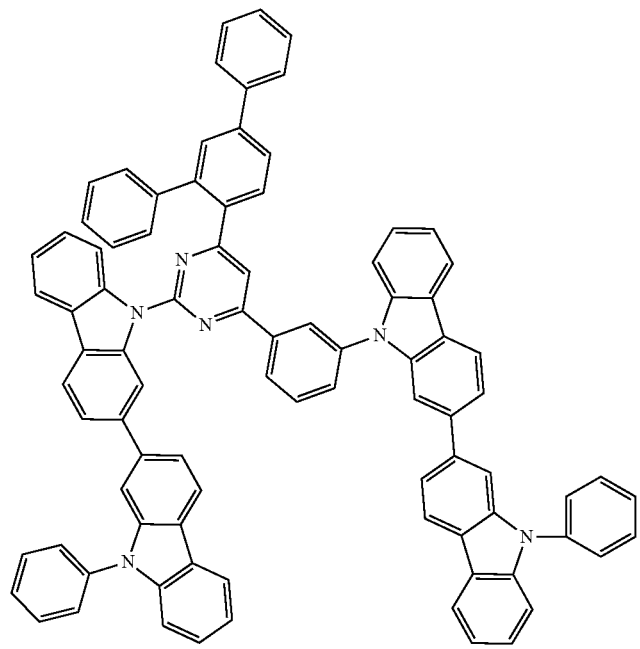
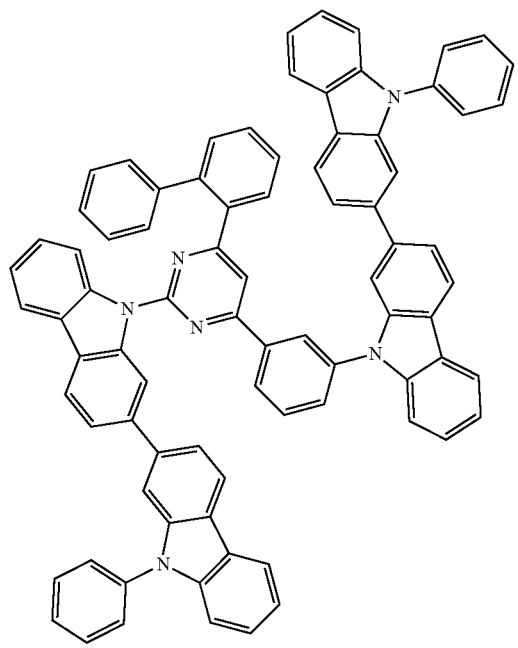
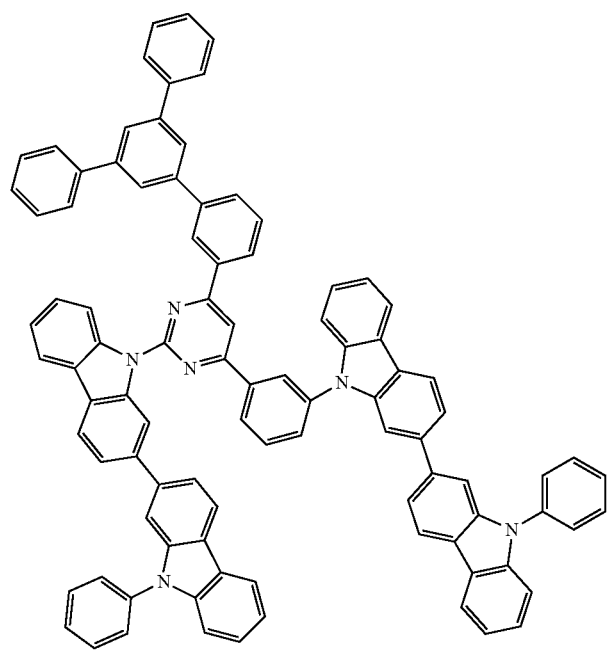

185
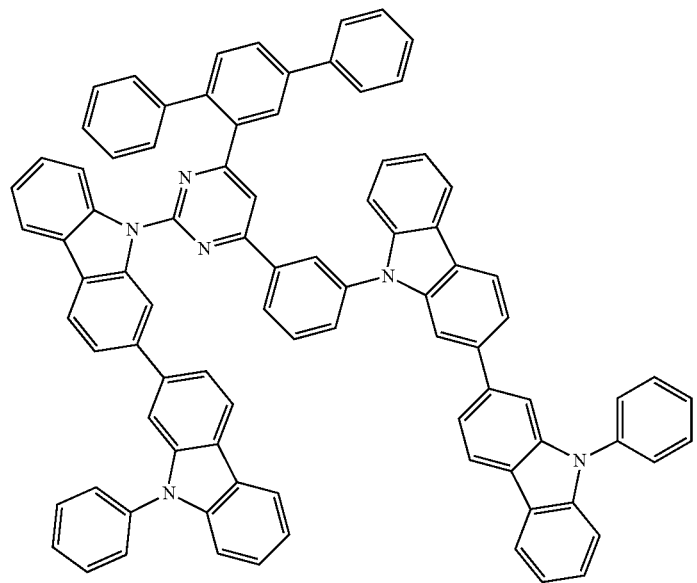
186
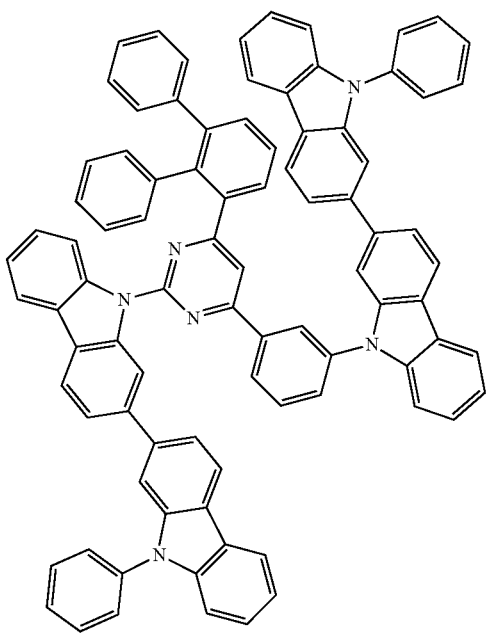
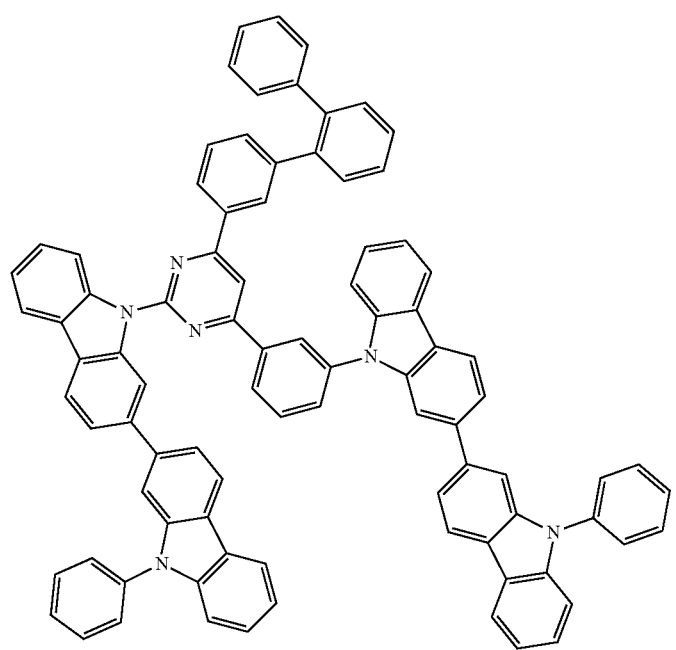

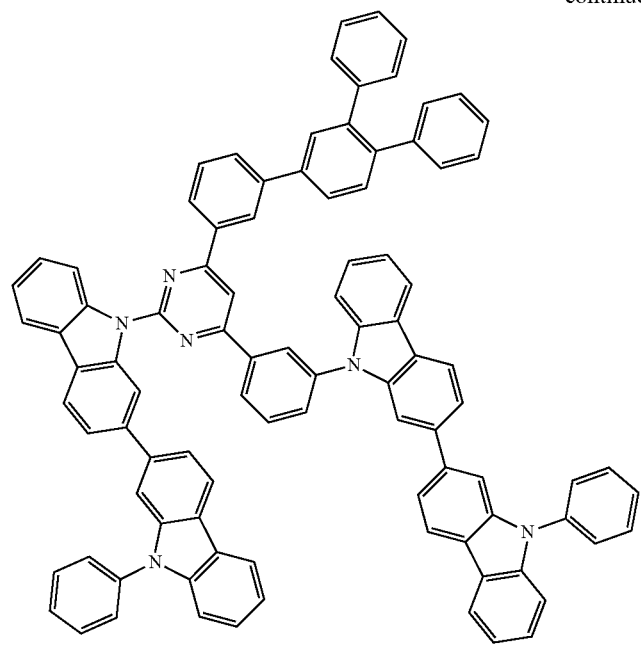
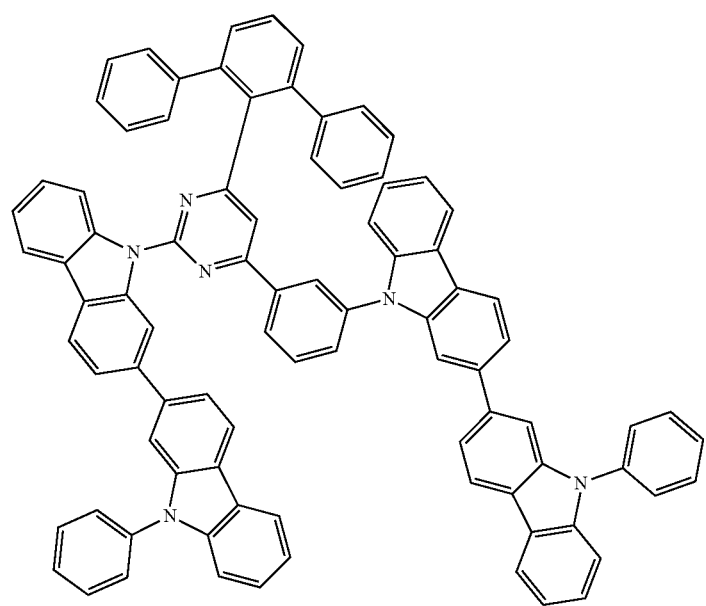

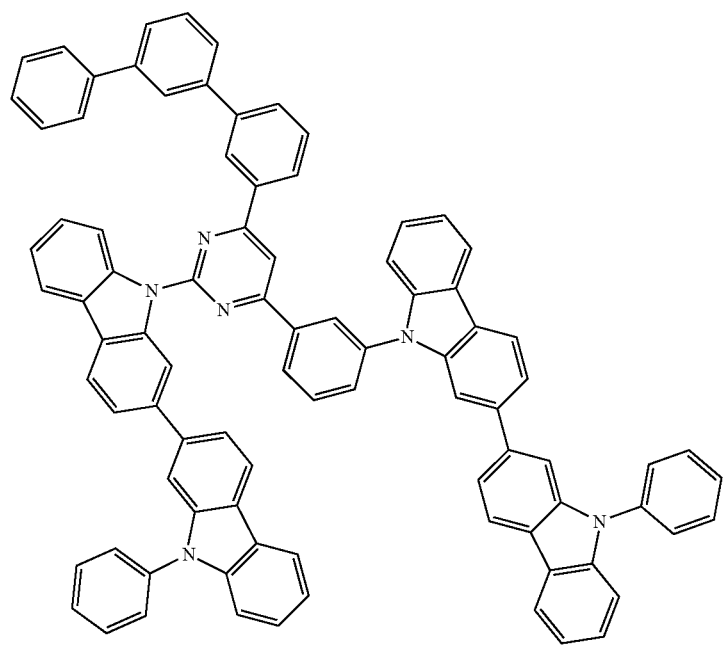
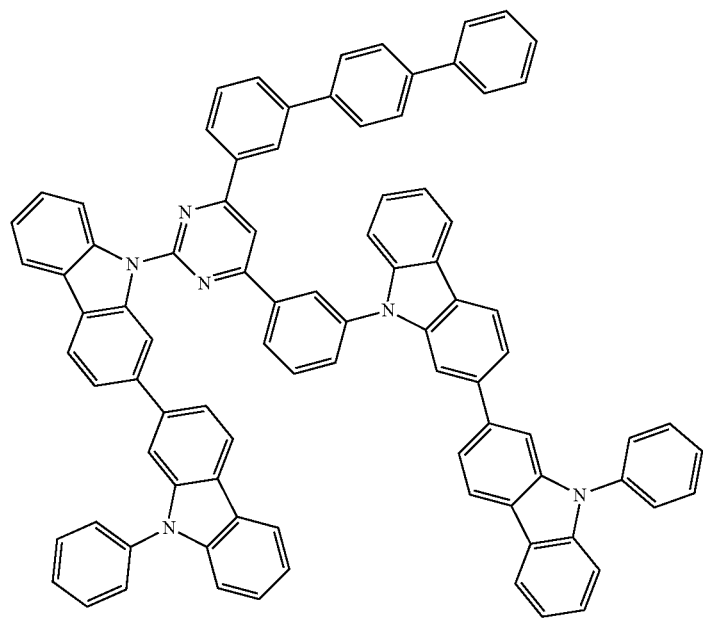

[Formula 67]
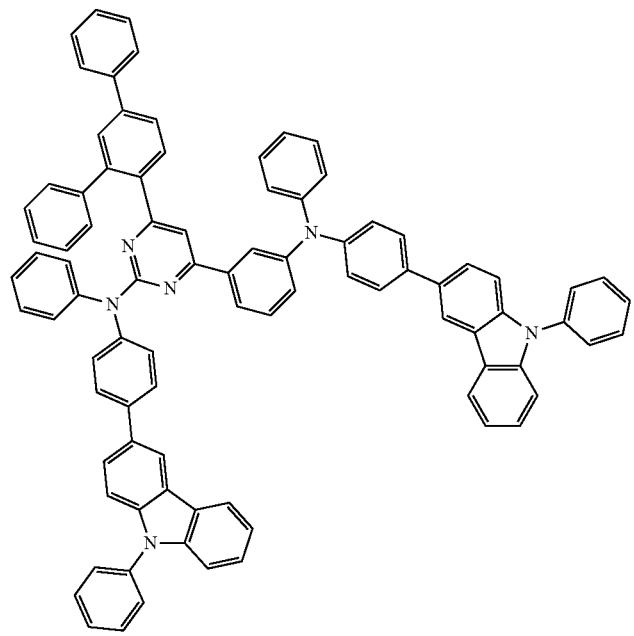
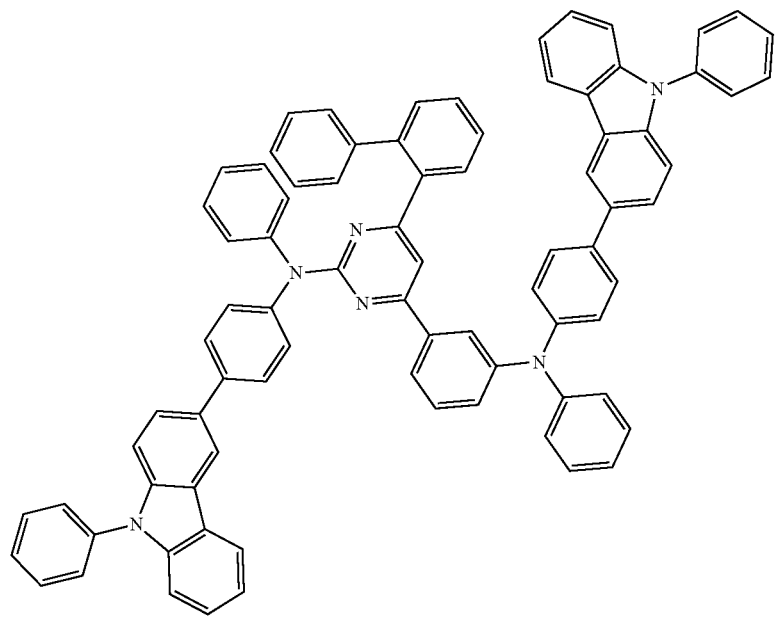

-continued
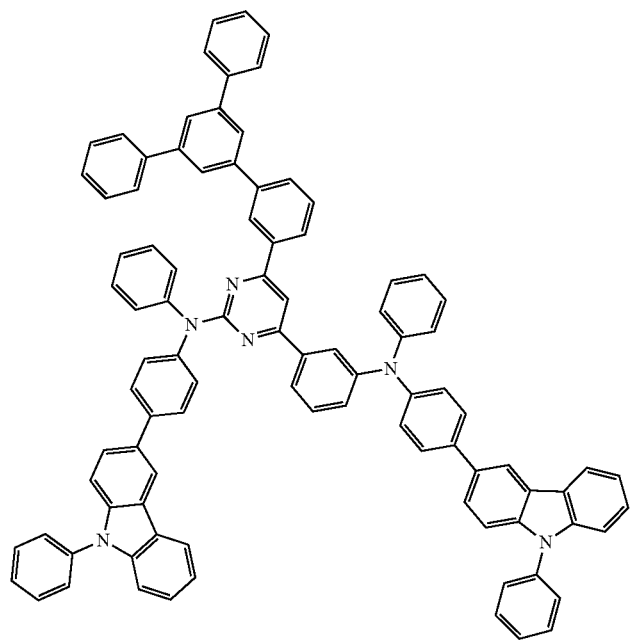
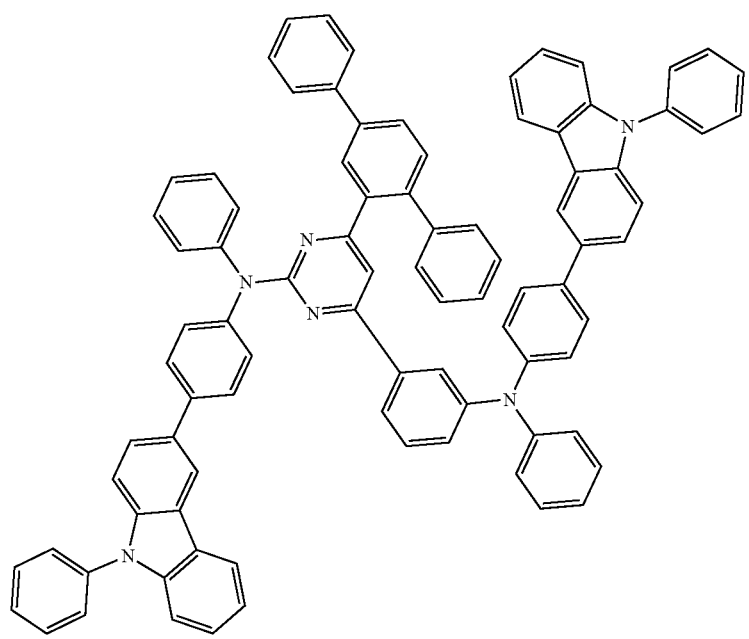

-continued
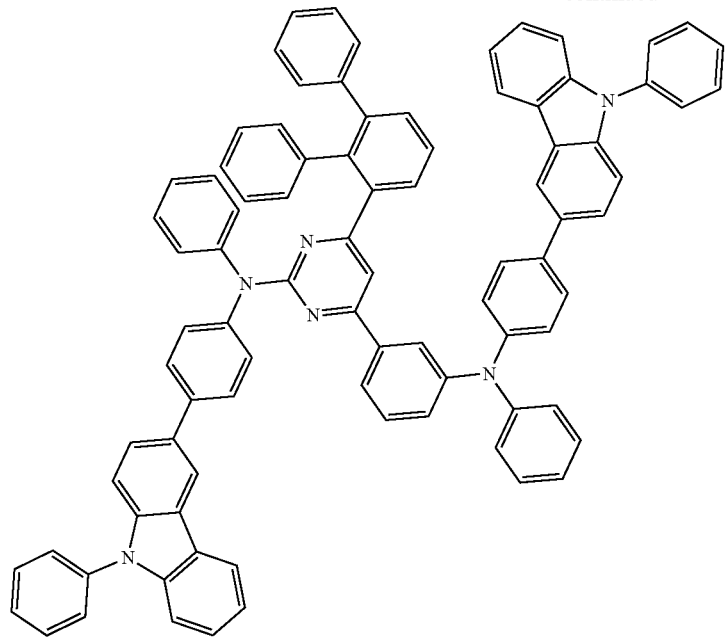
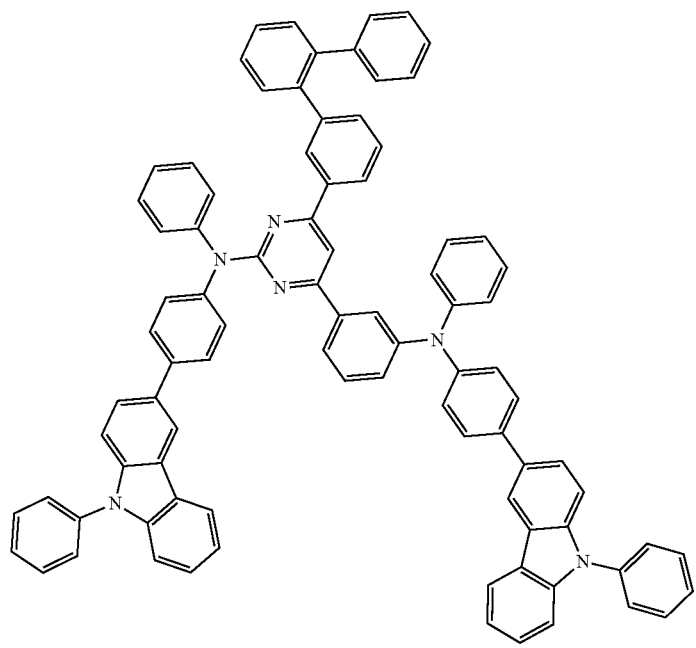

[Formula 68]
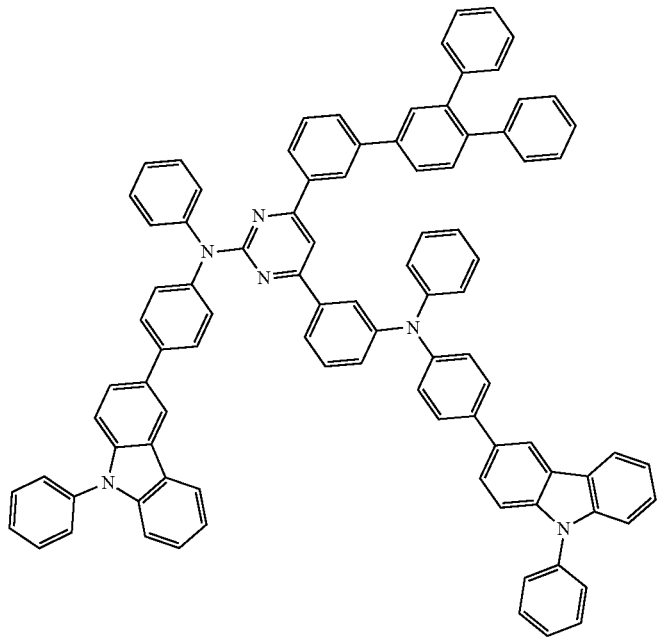
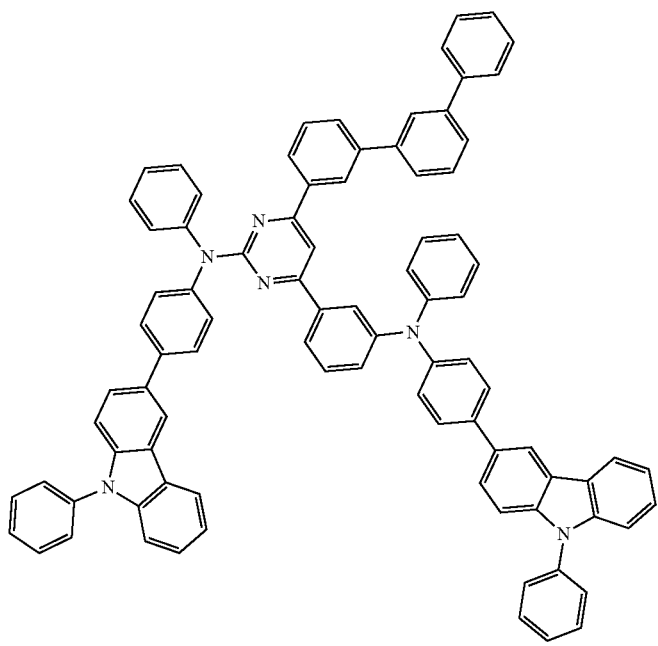

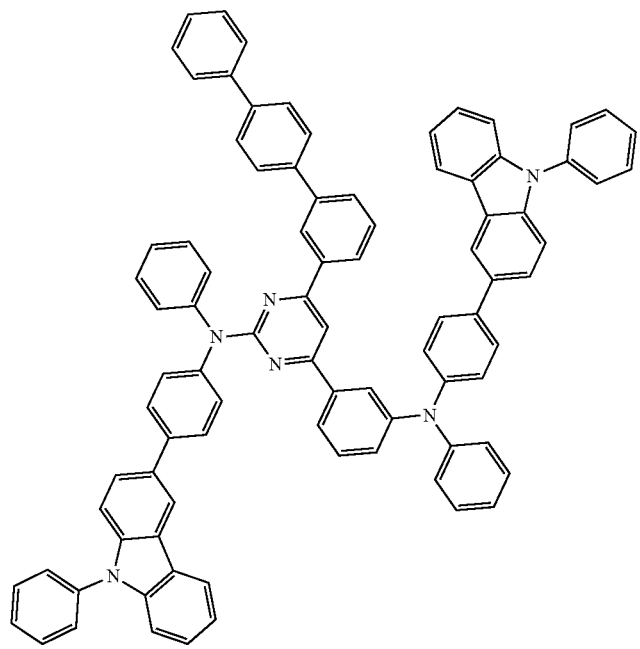
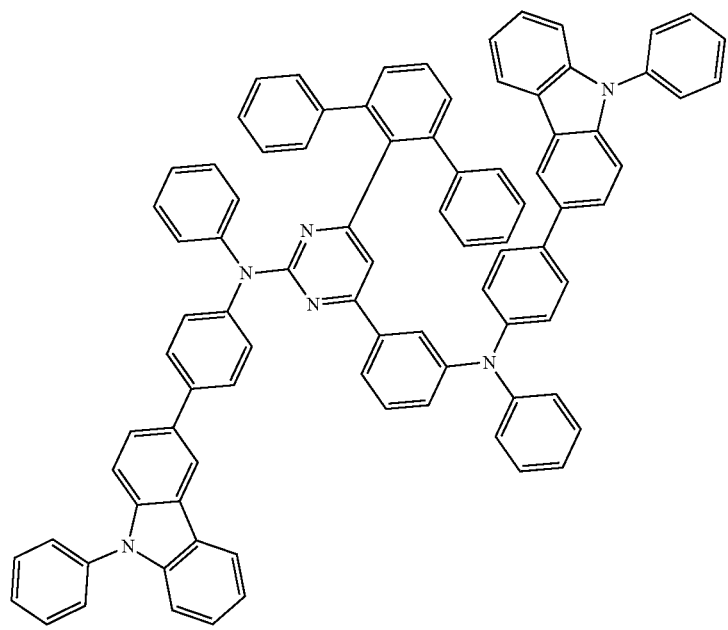

-continued
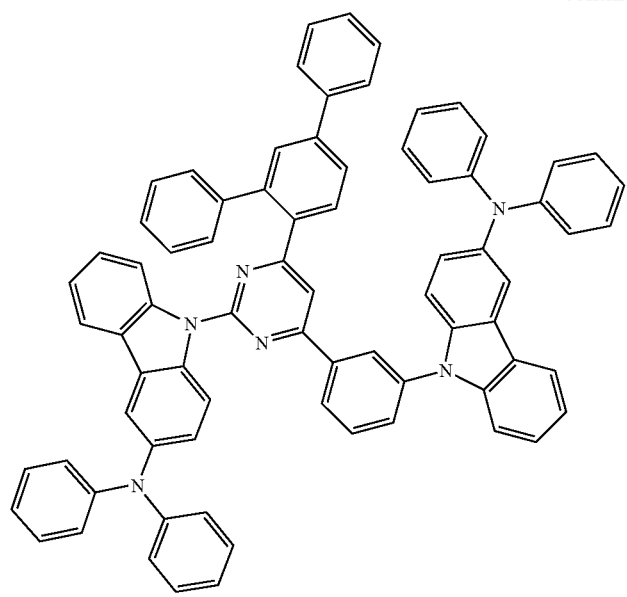
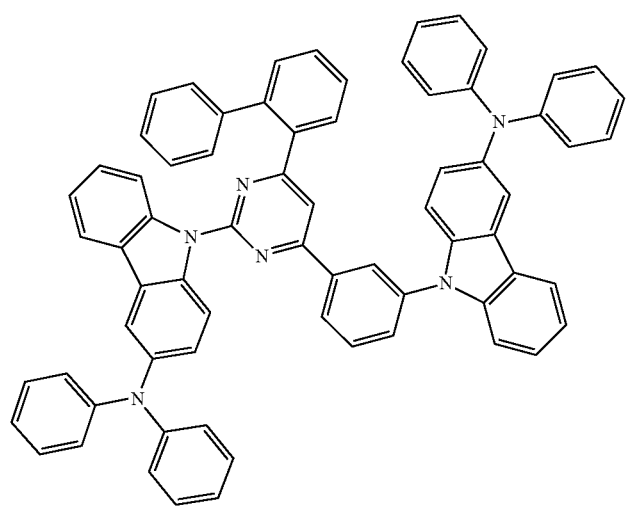

[Formula 69]
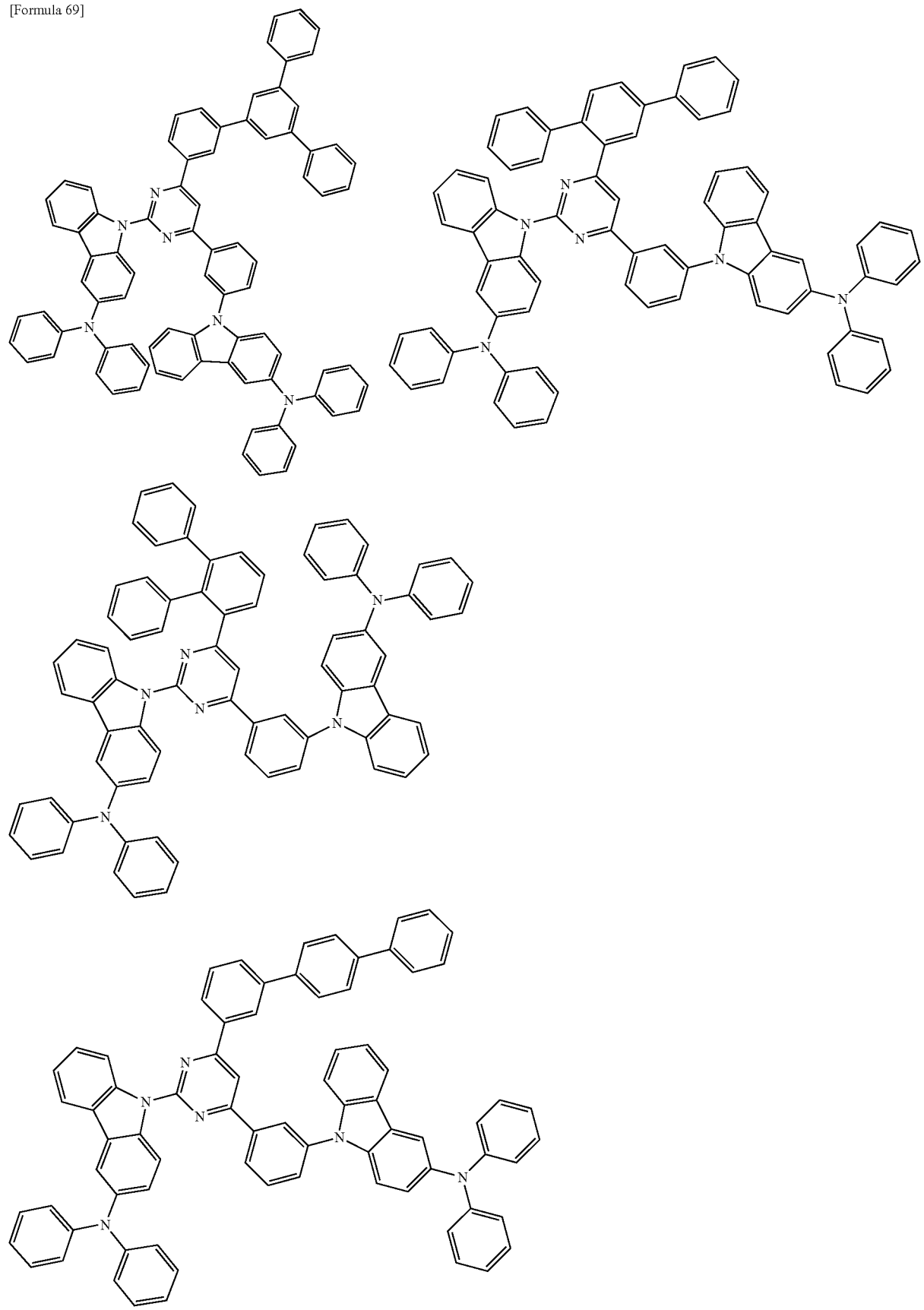

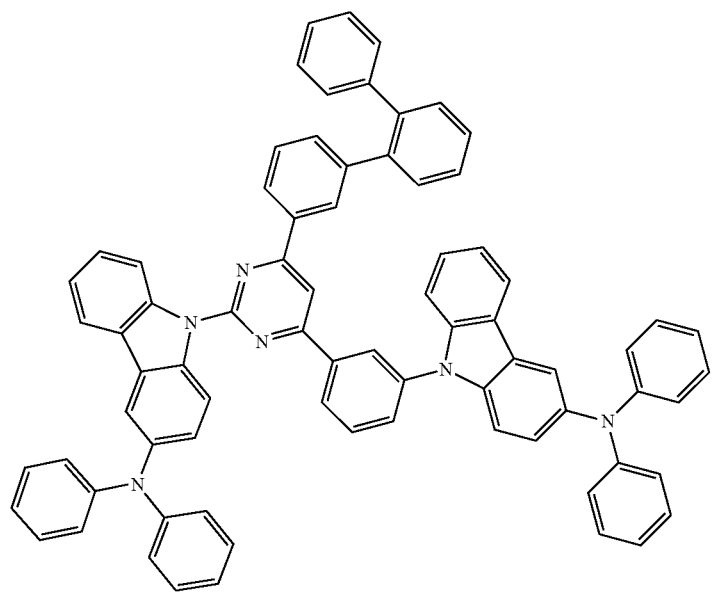
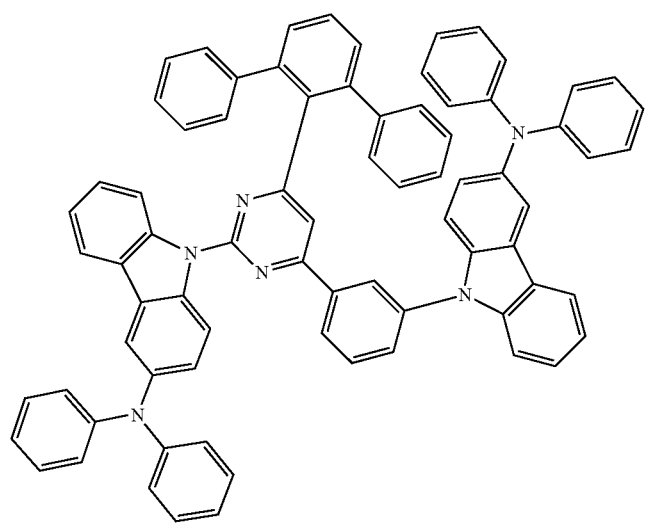

207 208
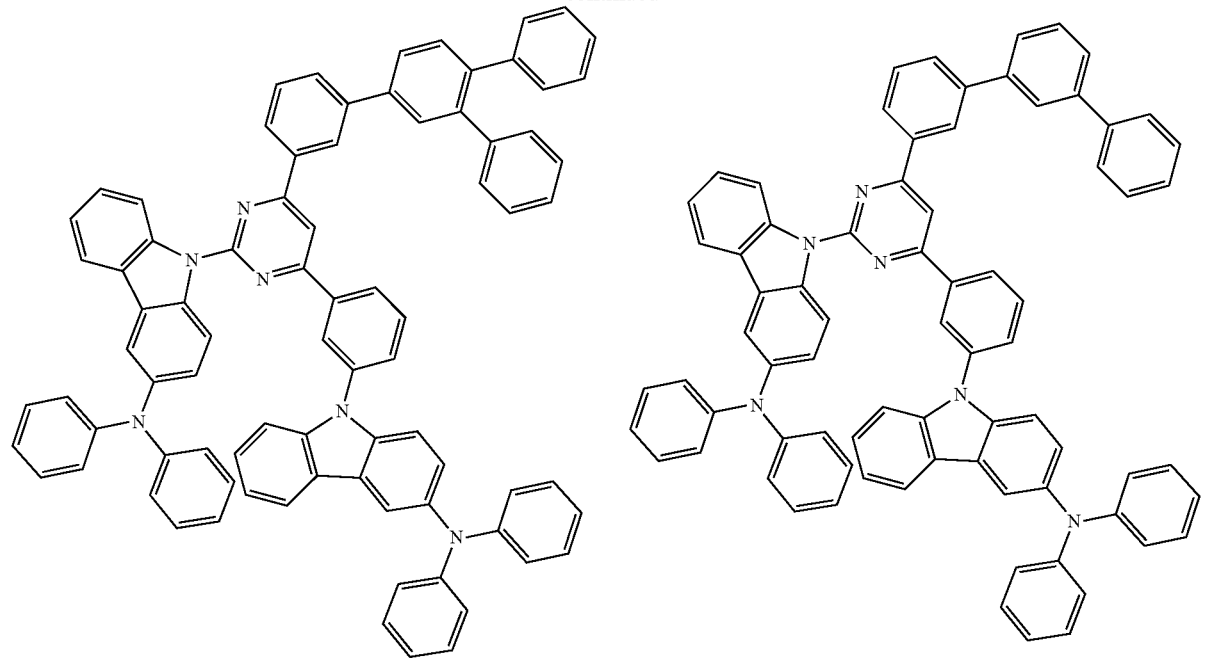
[Formula 70]
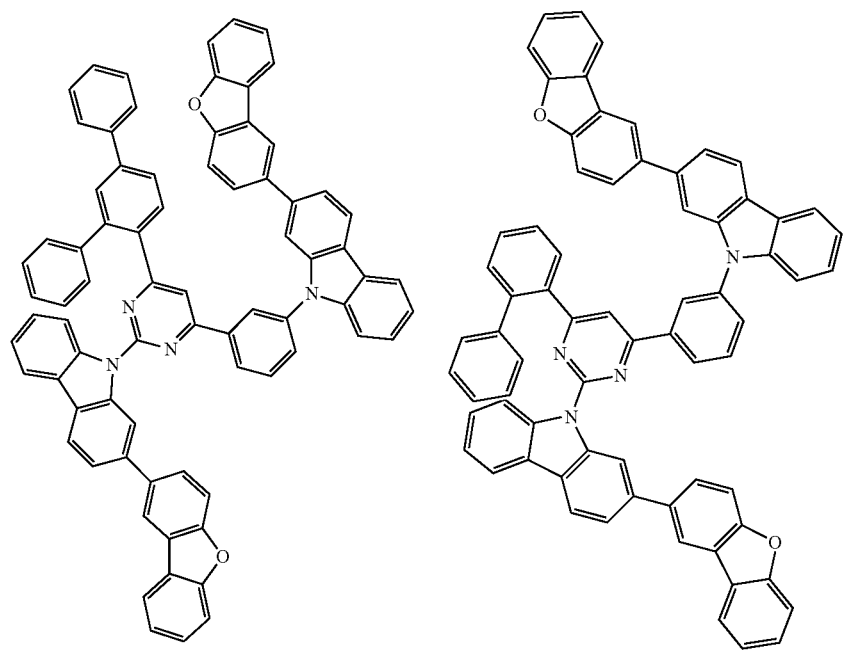

209
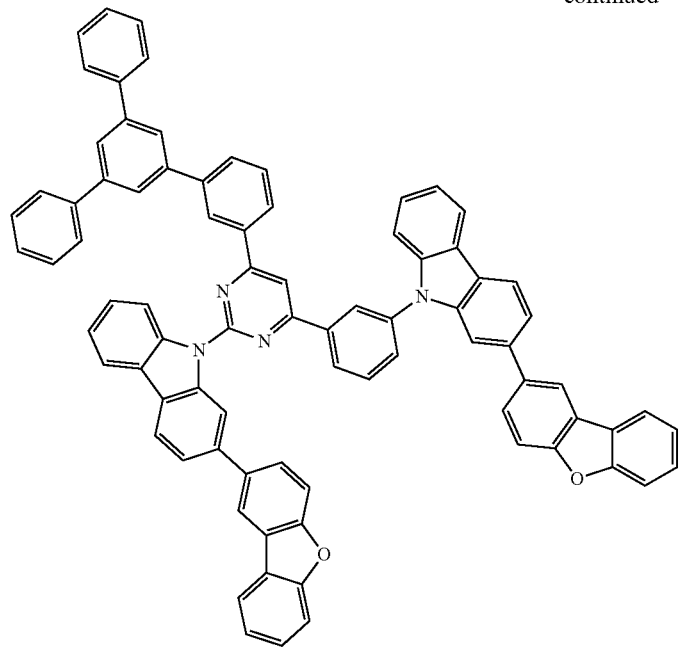
210
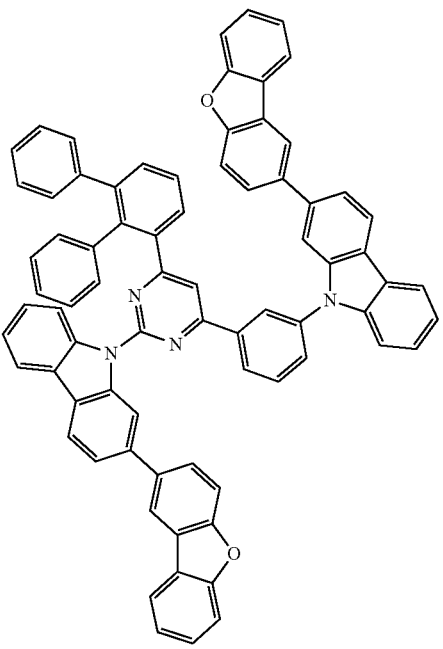
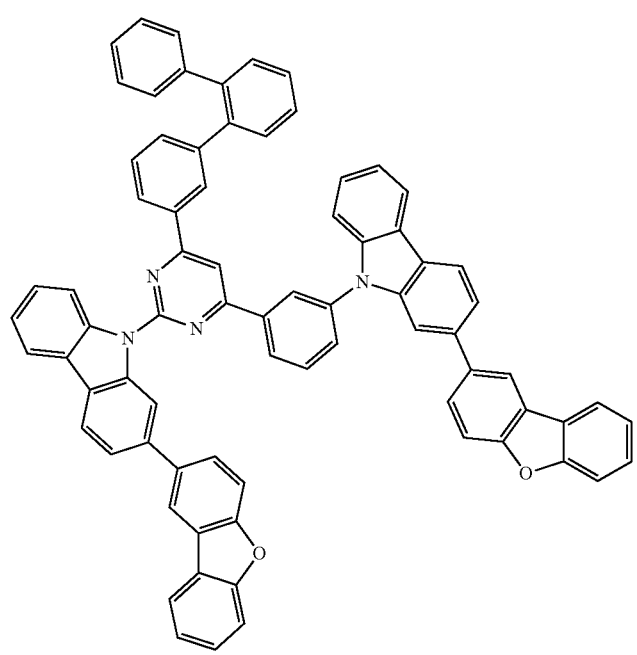

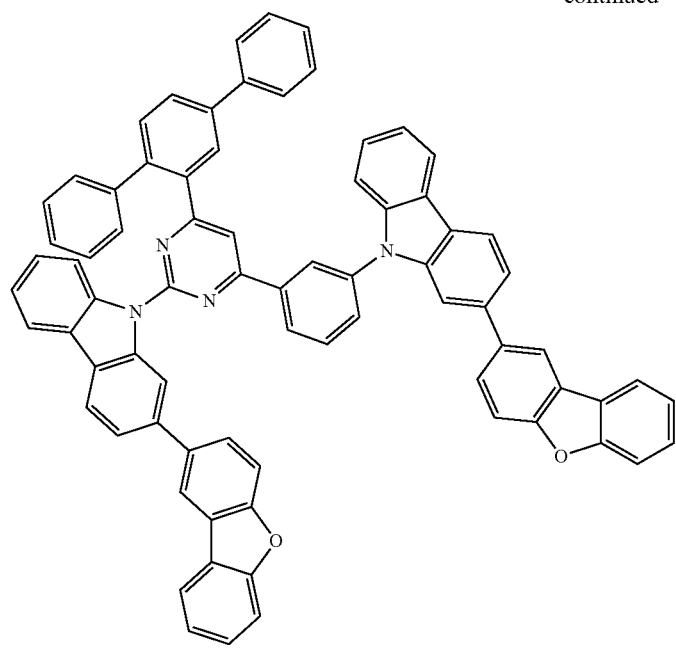
[Formula 71]
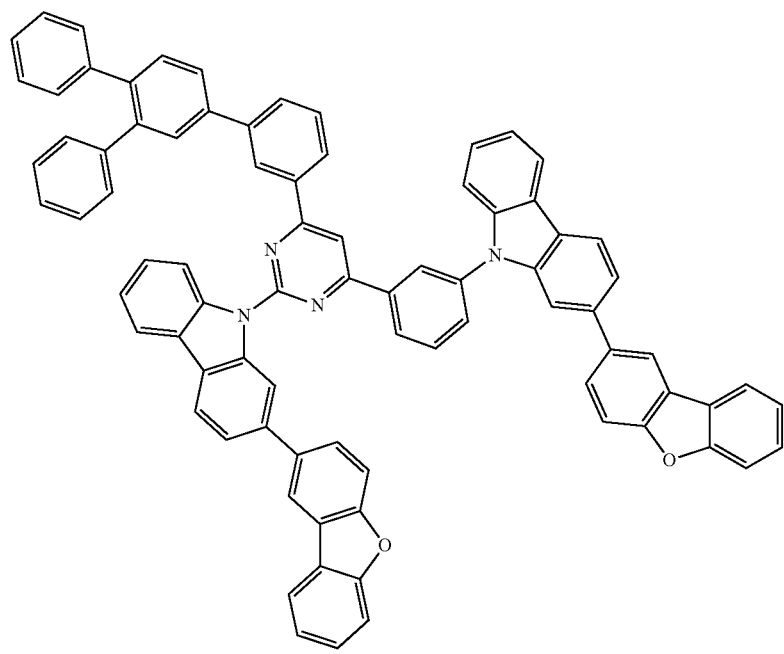

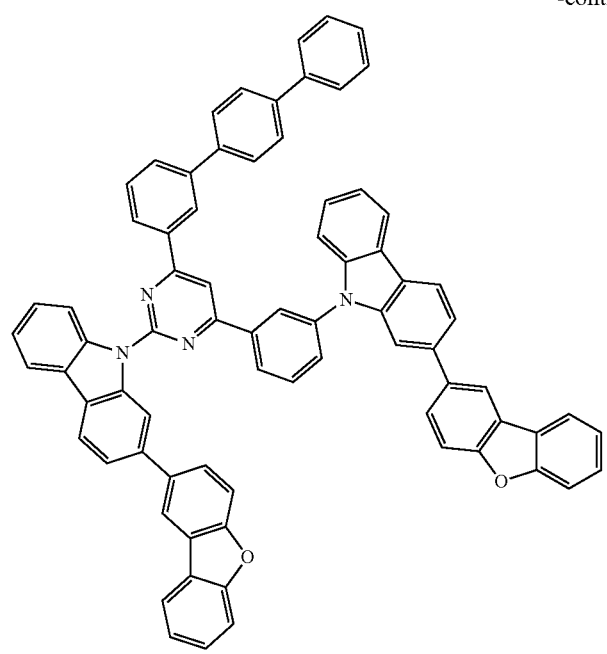
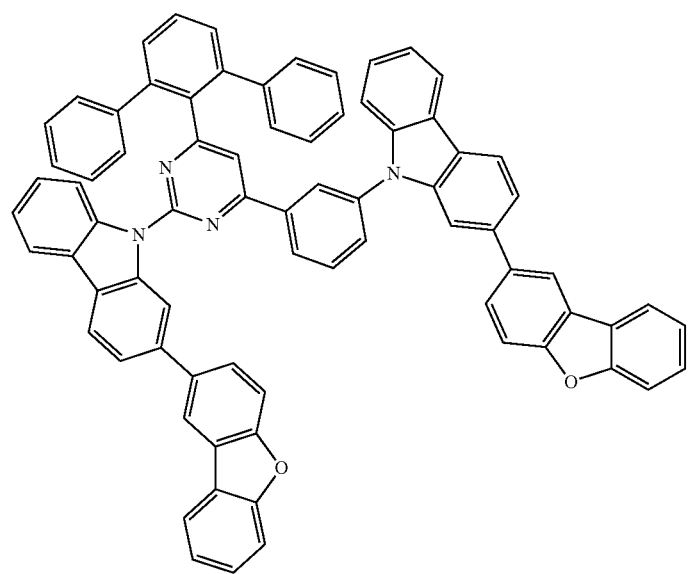

-continued
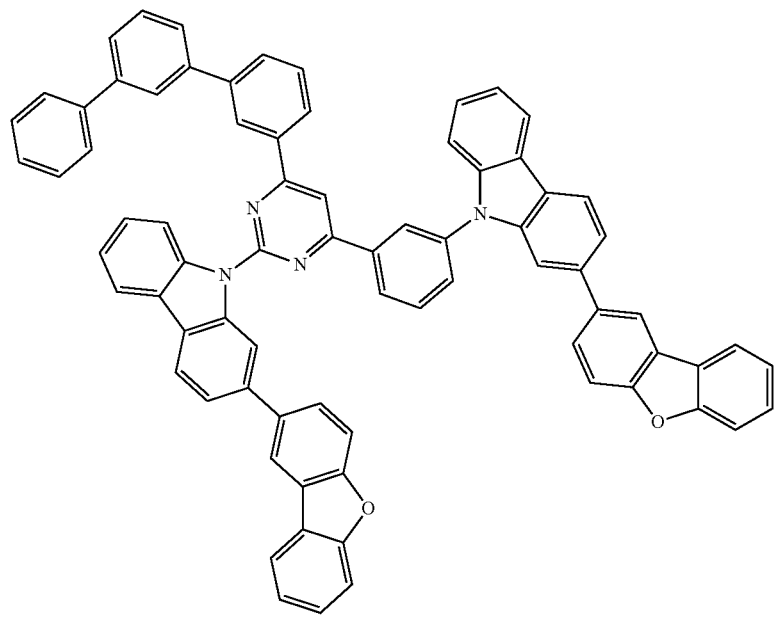
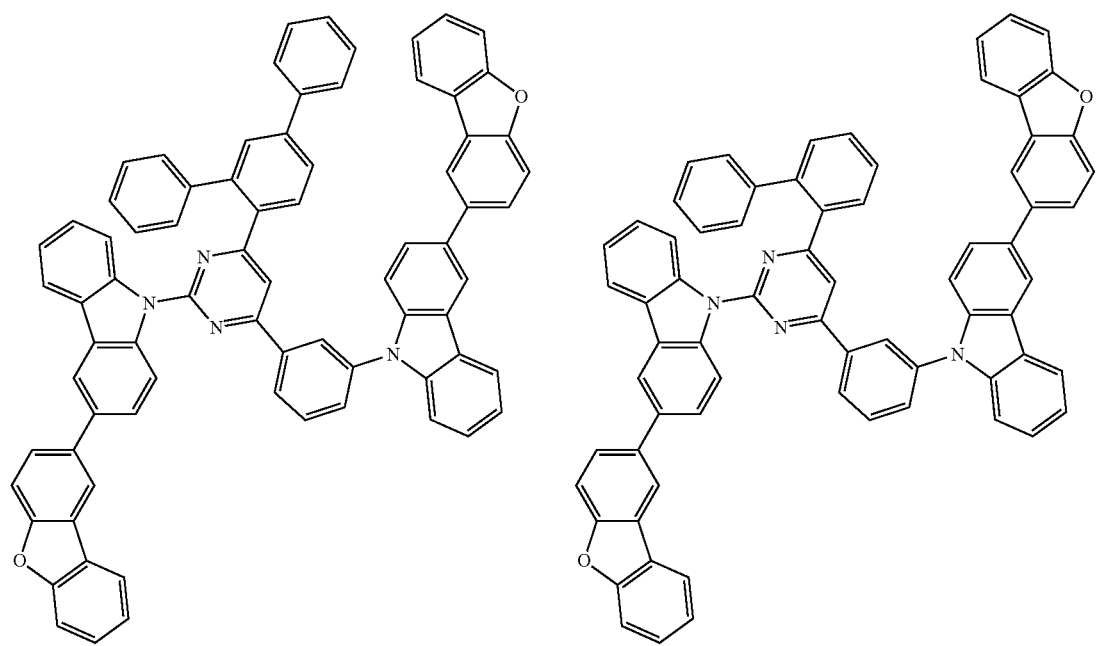

[Formula 72]
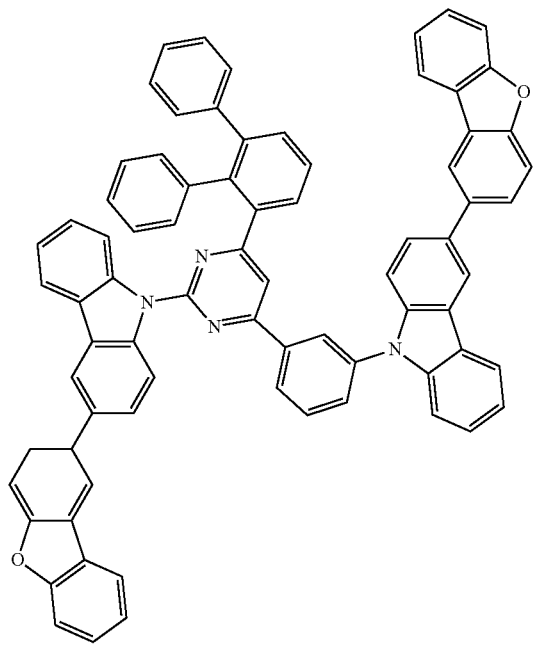
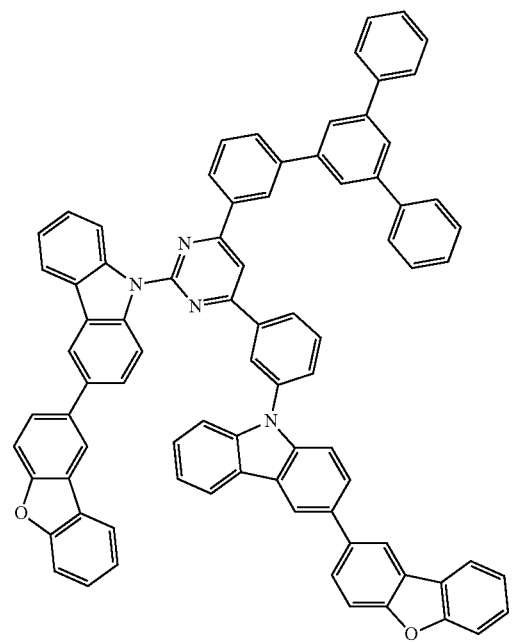
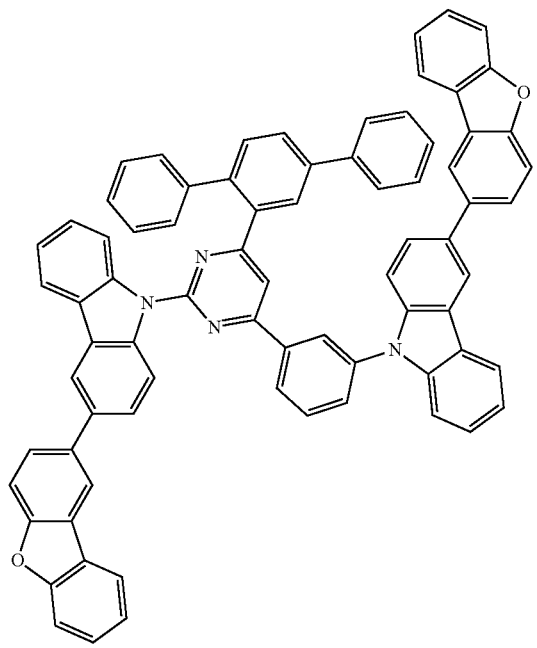
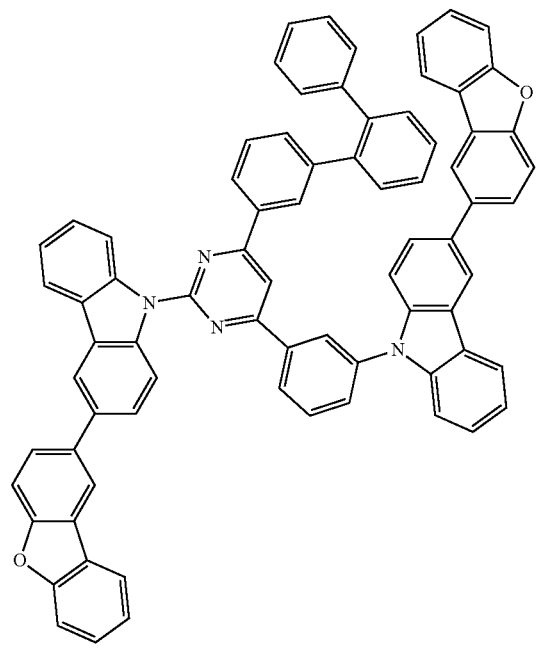

219 220
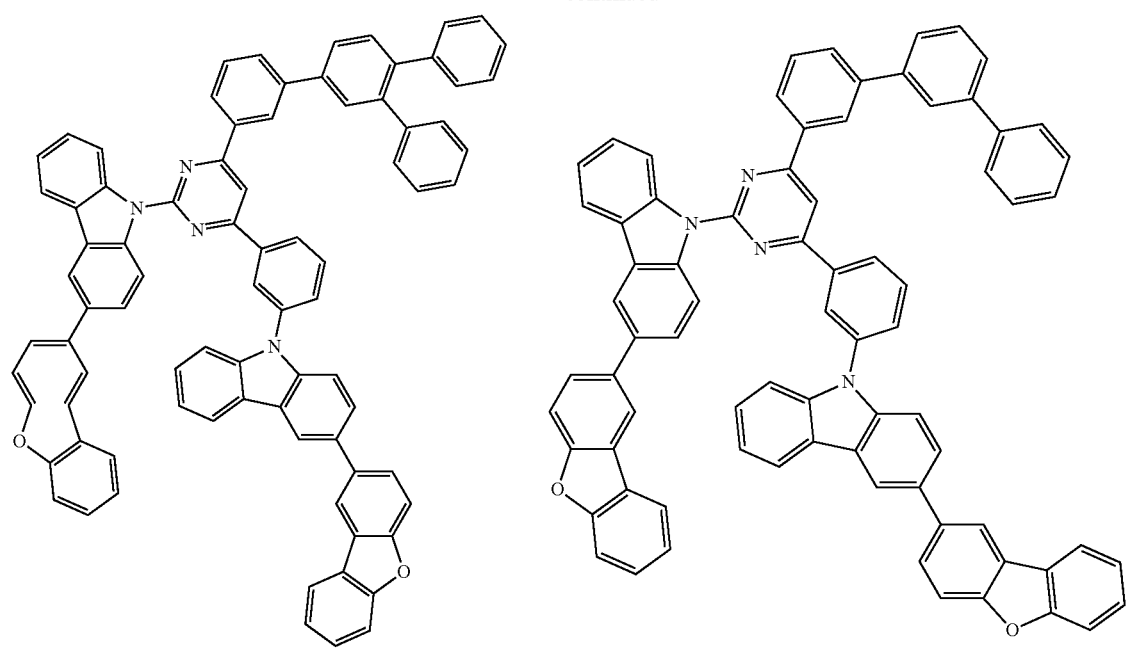
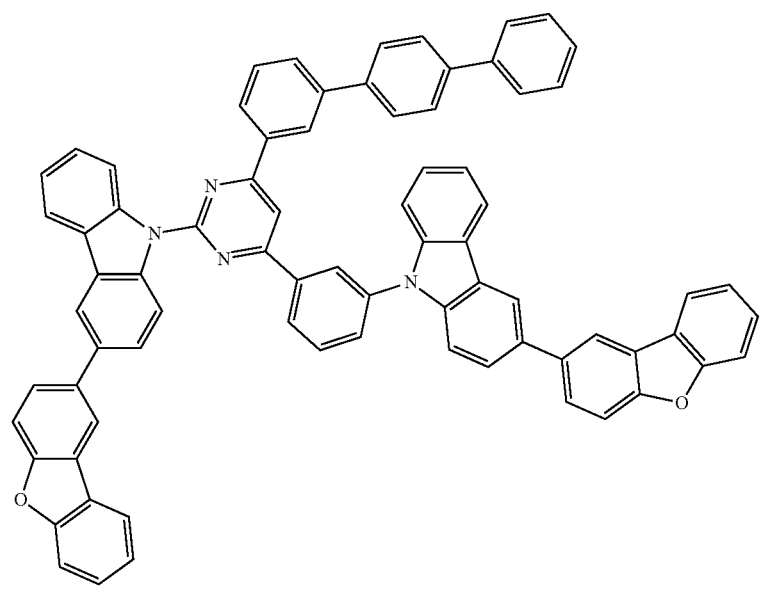

221 222
-continued
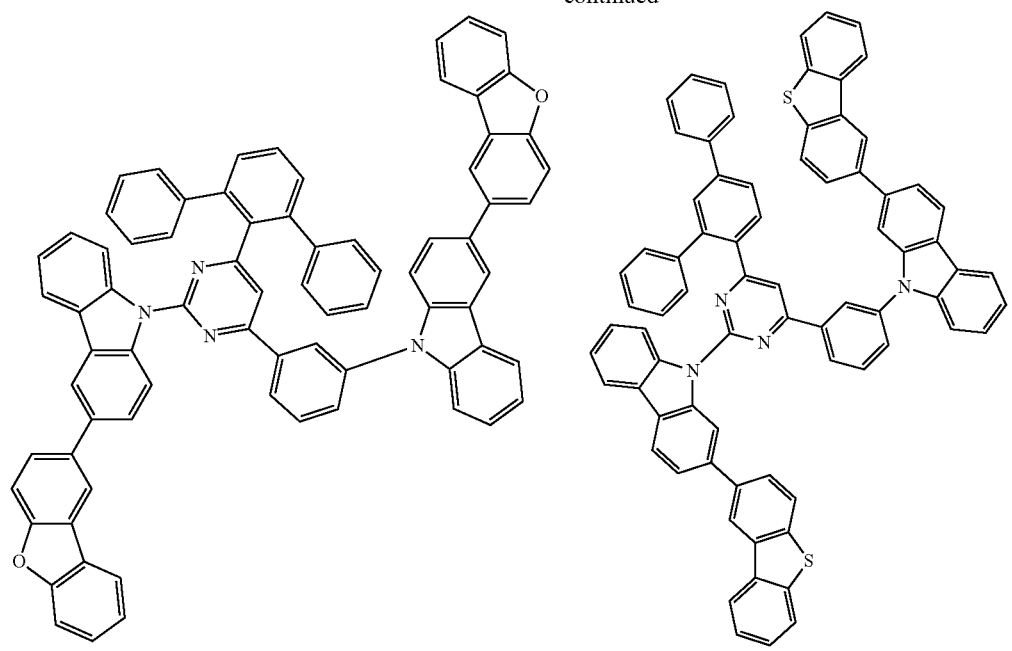
[Formula 73]
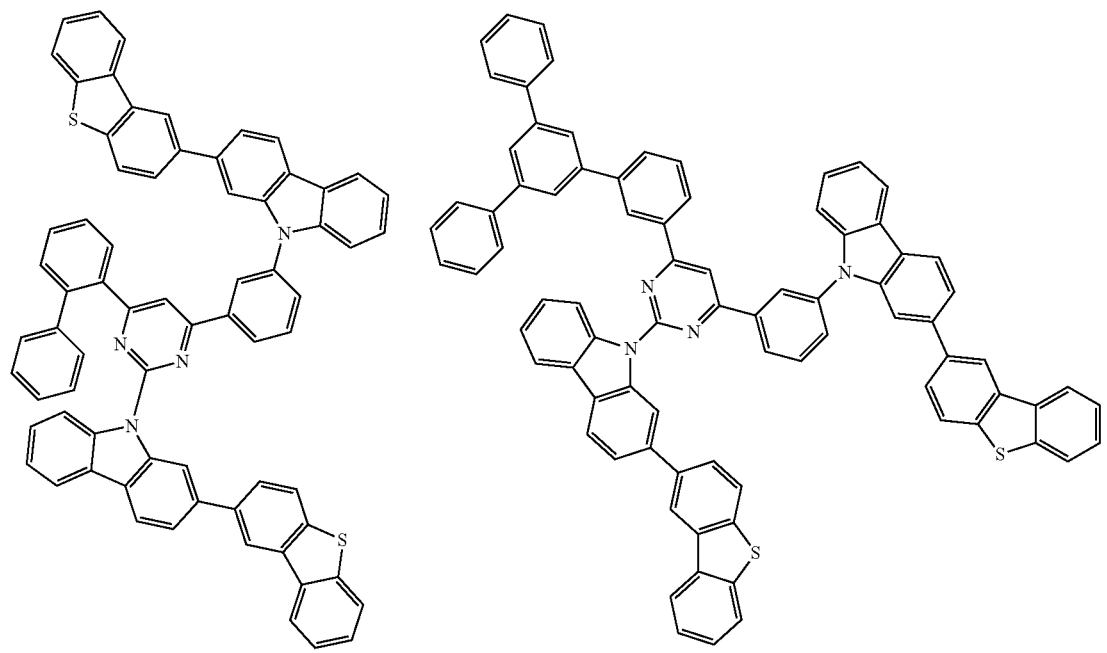

-continued
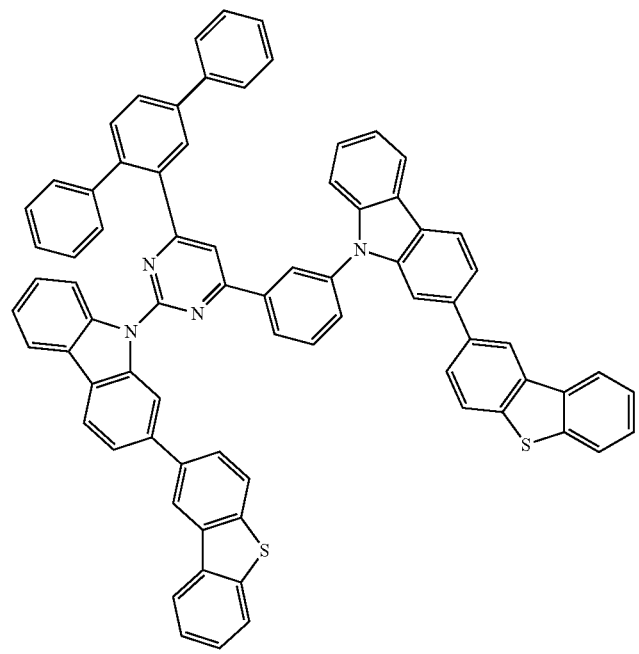
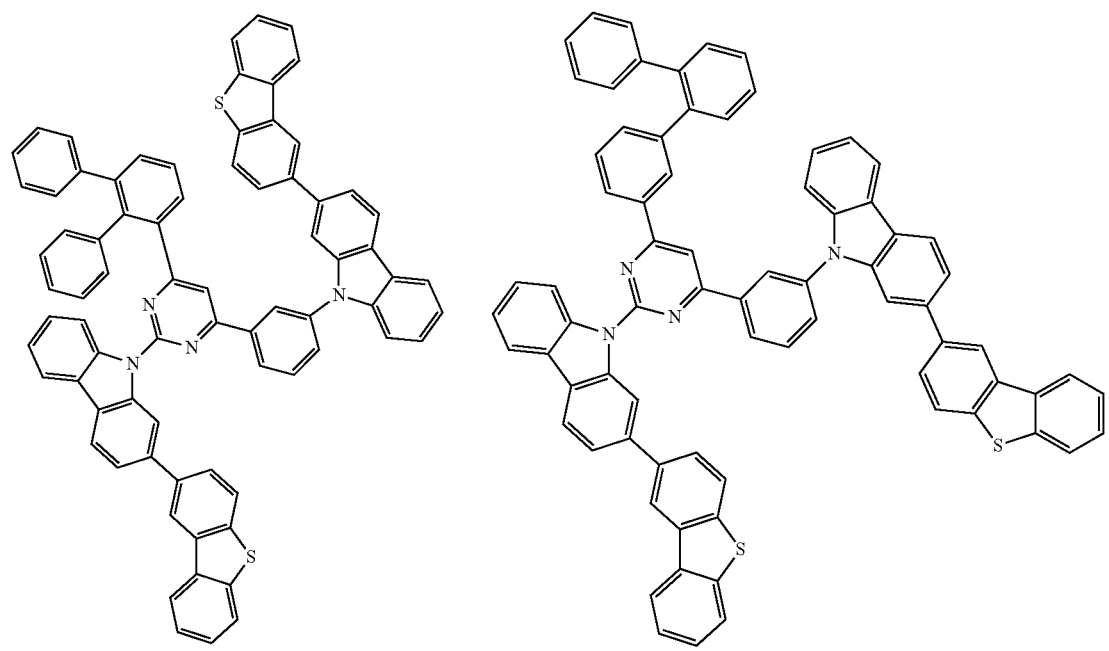

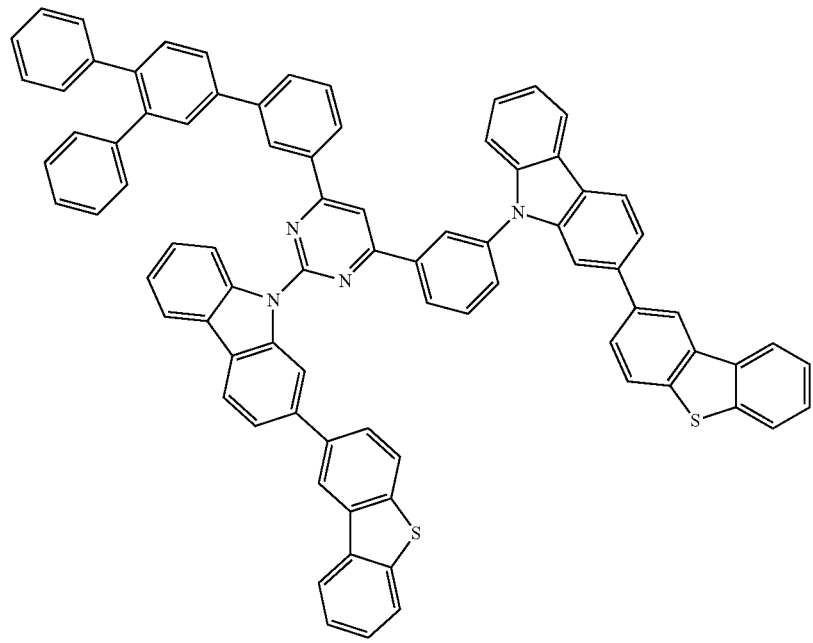
[Formula 74]
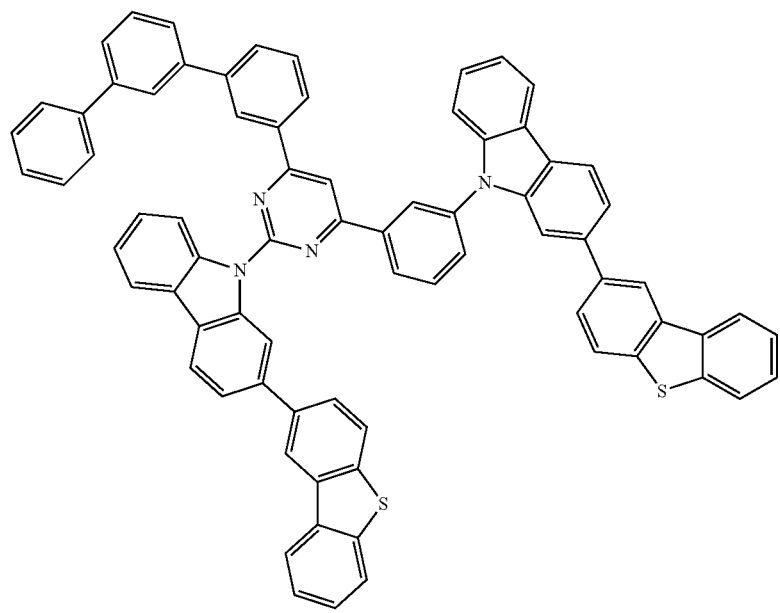

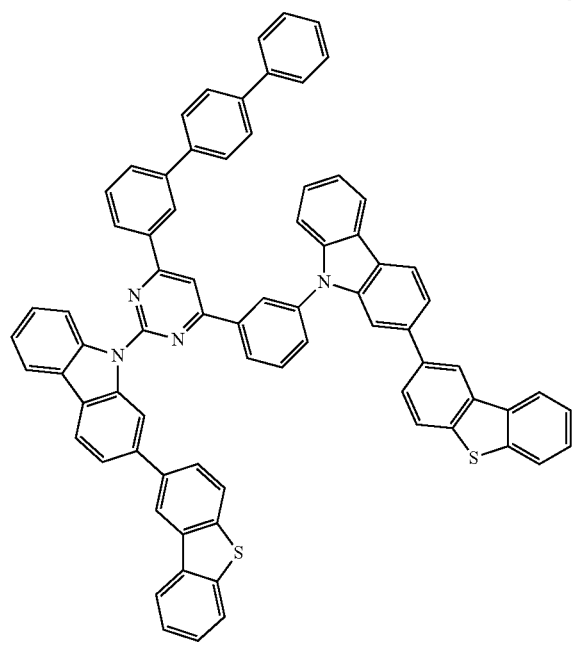
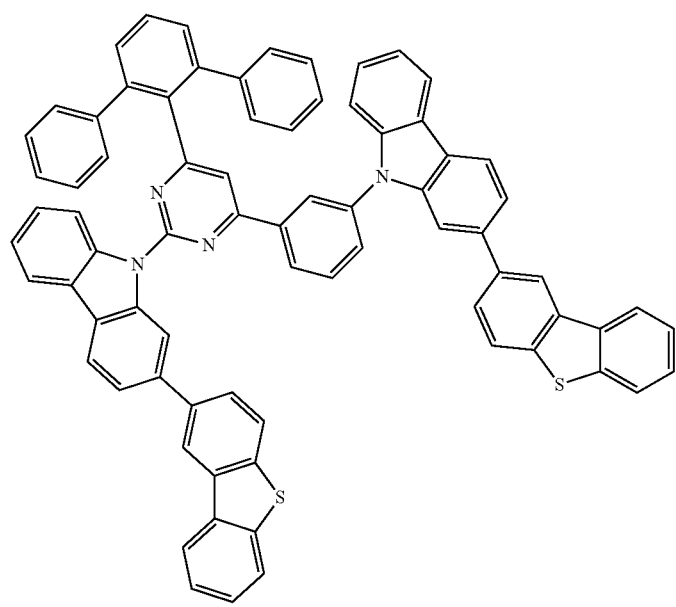

229 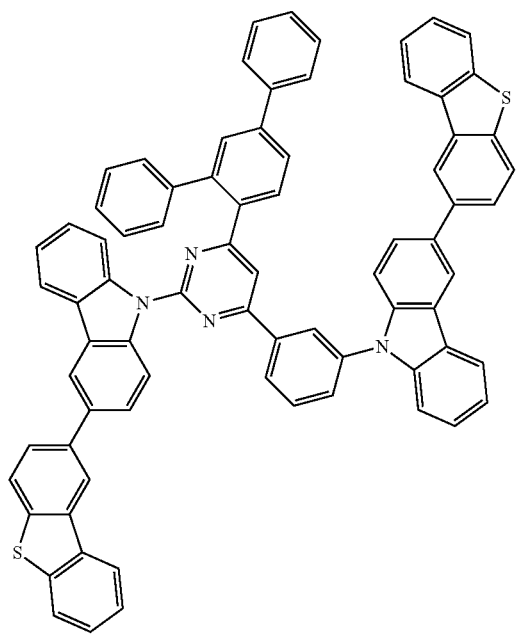
230 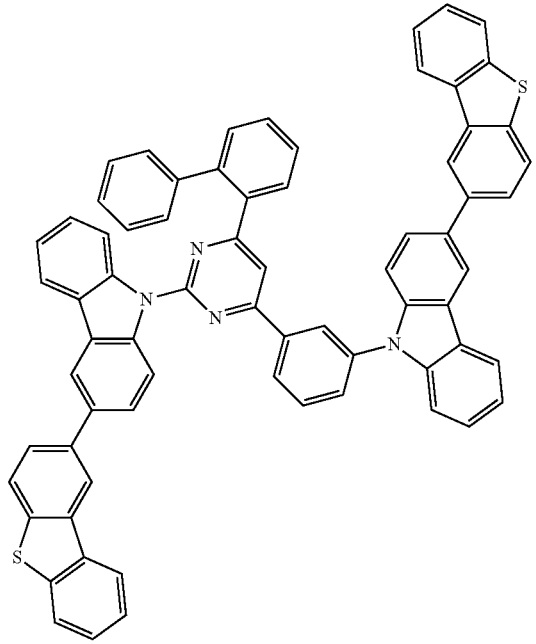
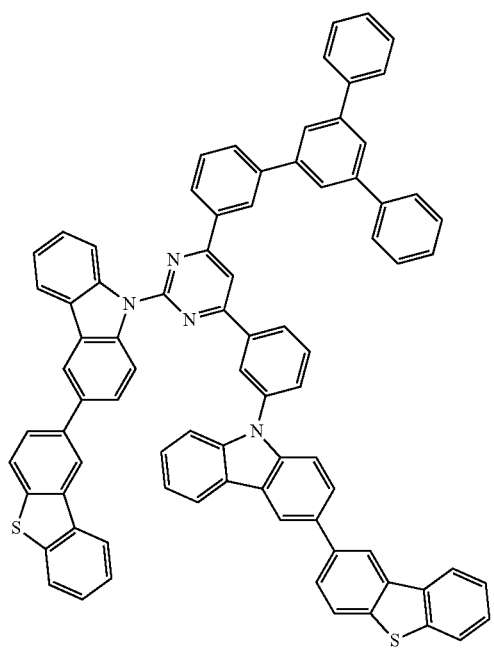

[Formula 75]
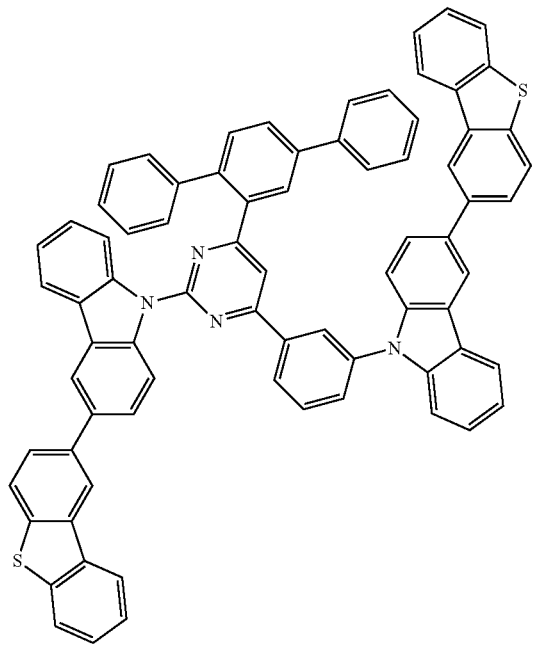 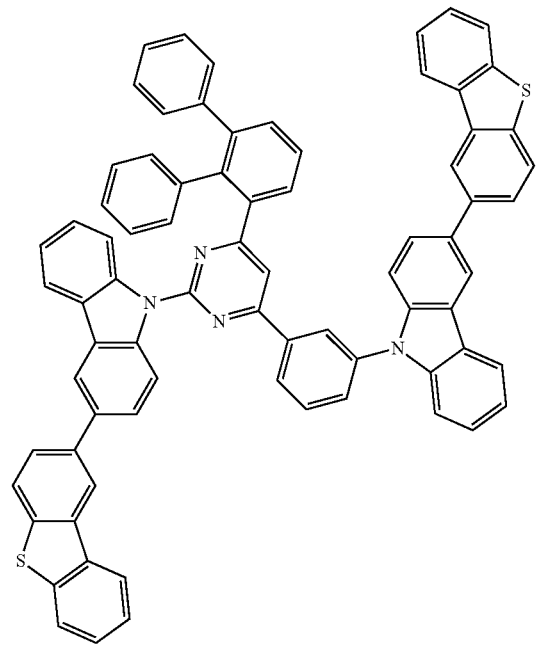
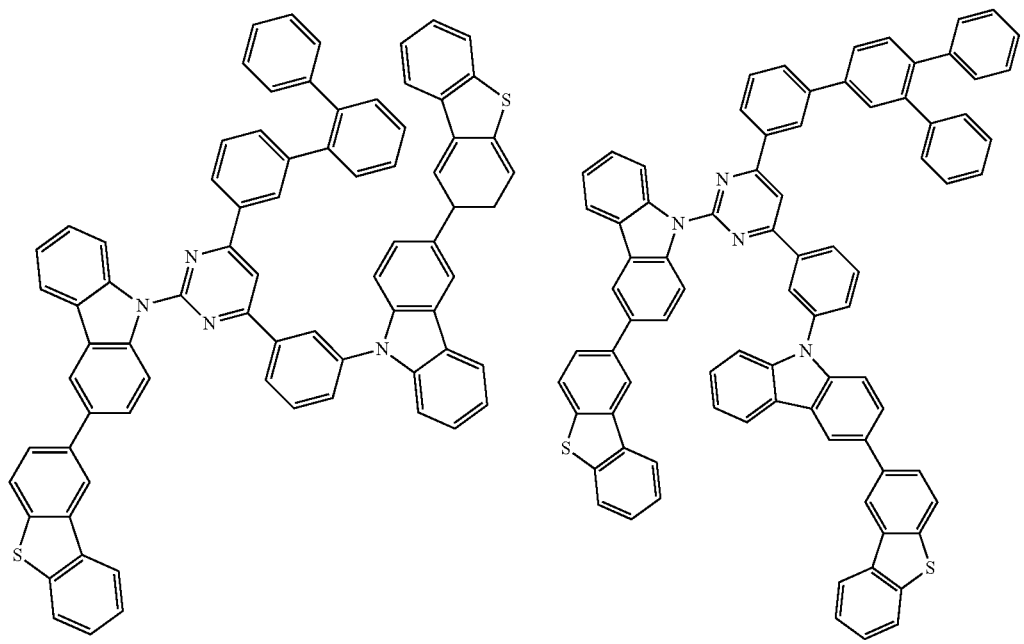

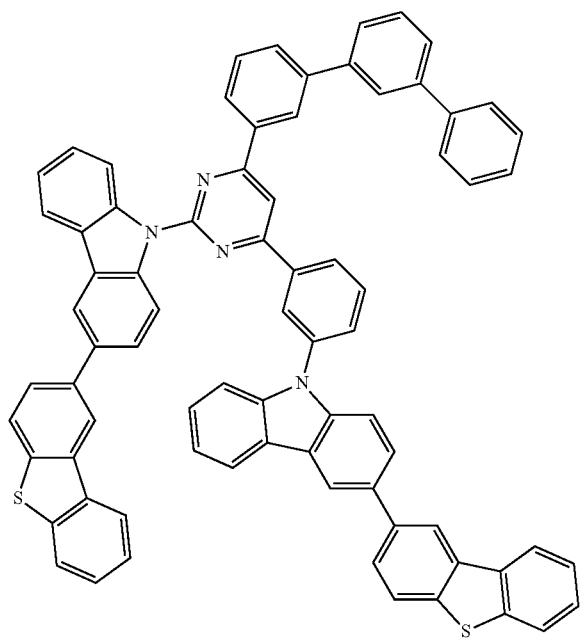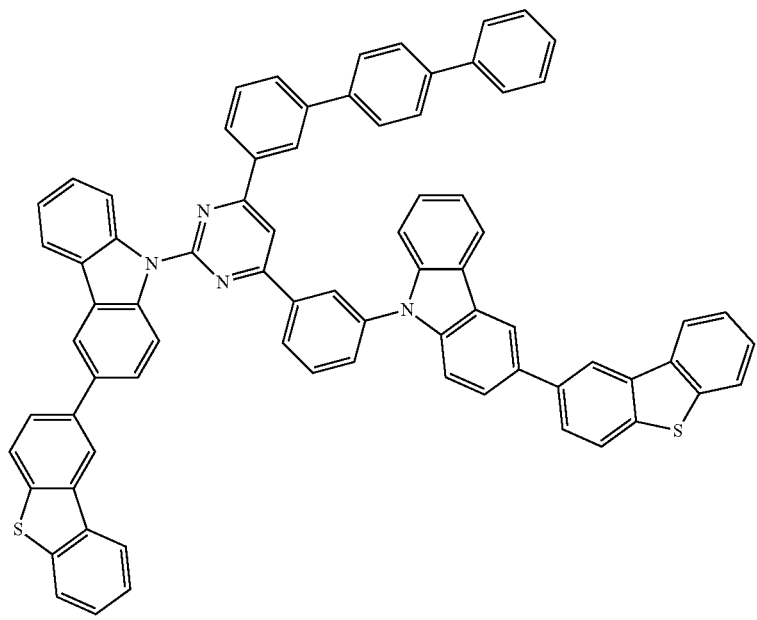

-continued
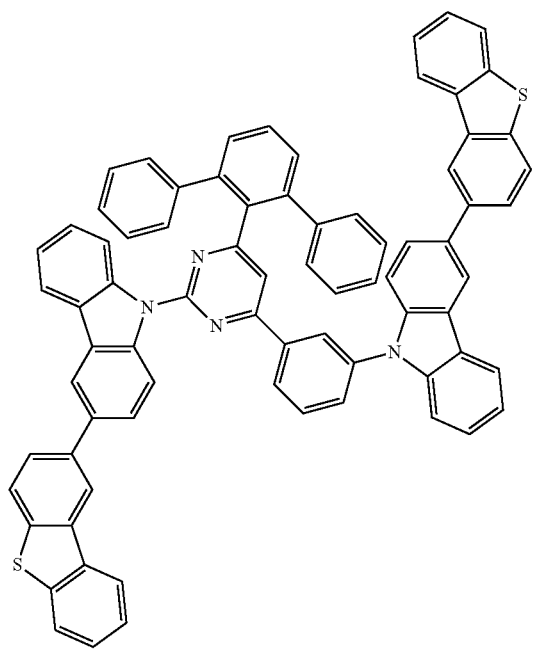
[Formula 76]
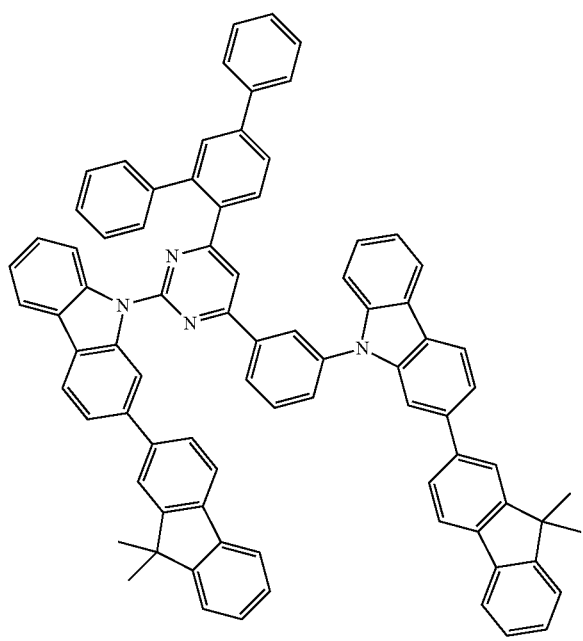
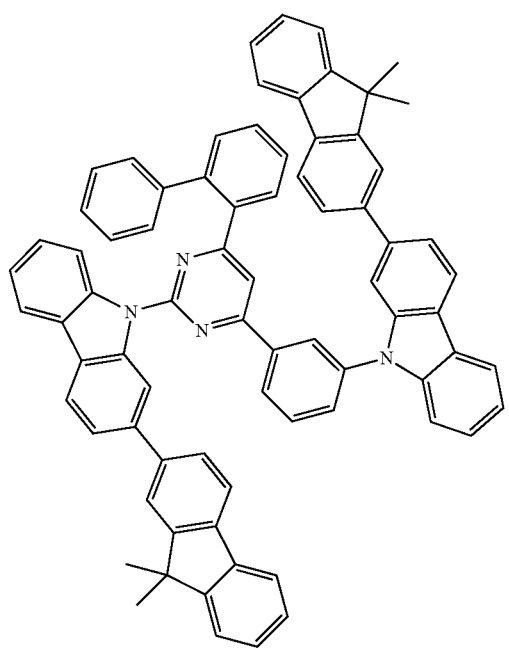

-continued
237
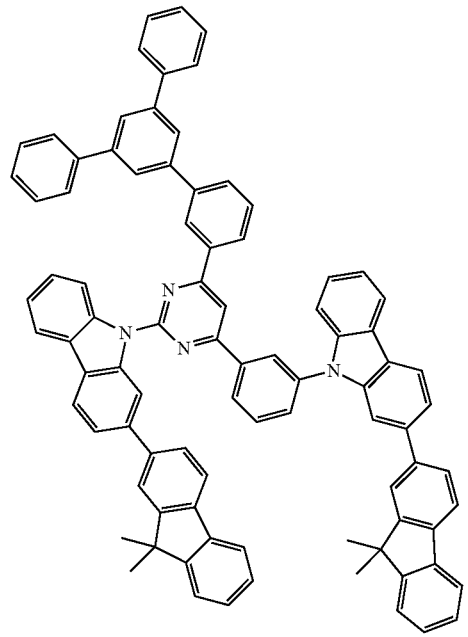
238
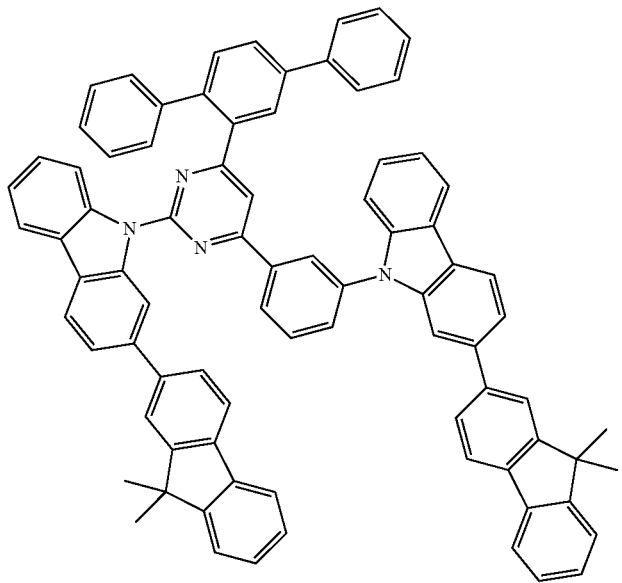
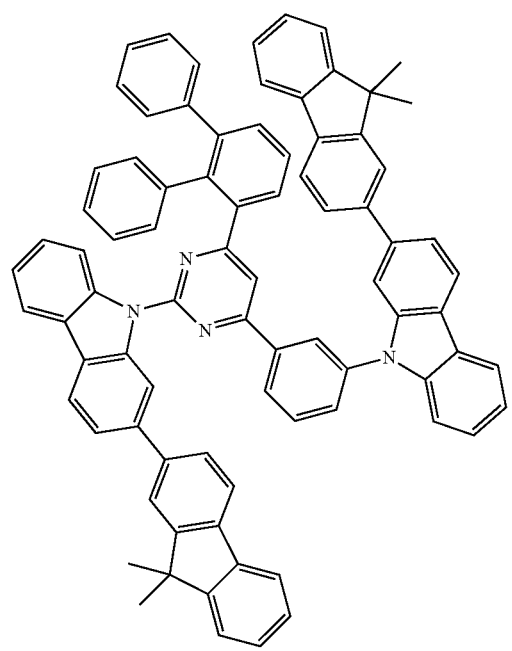
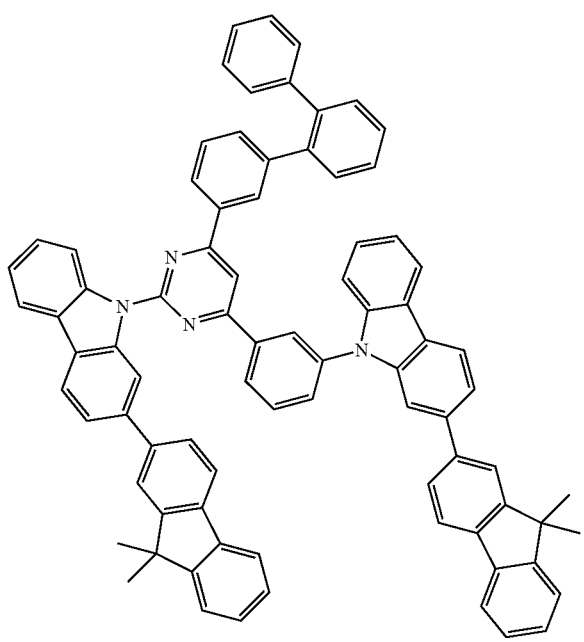

[Formula 77]
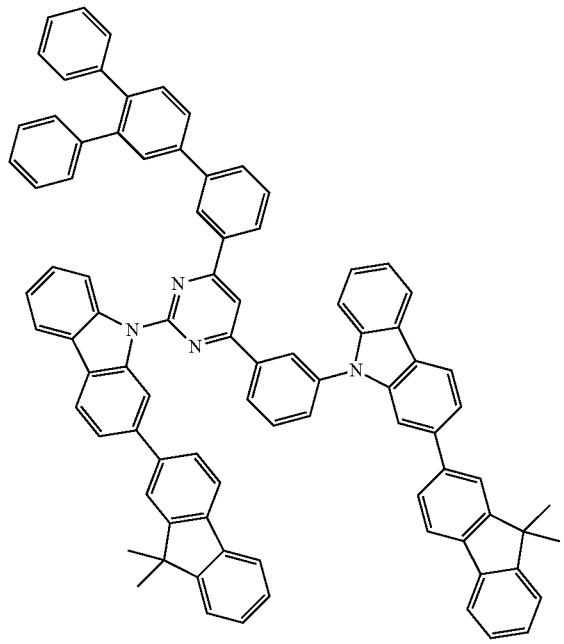 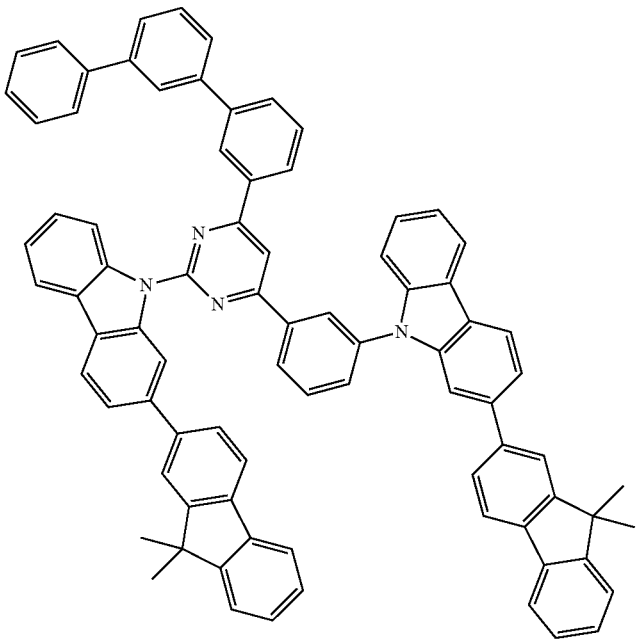
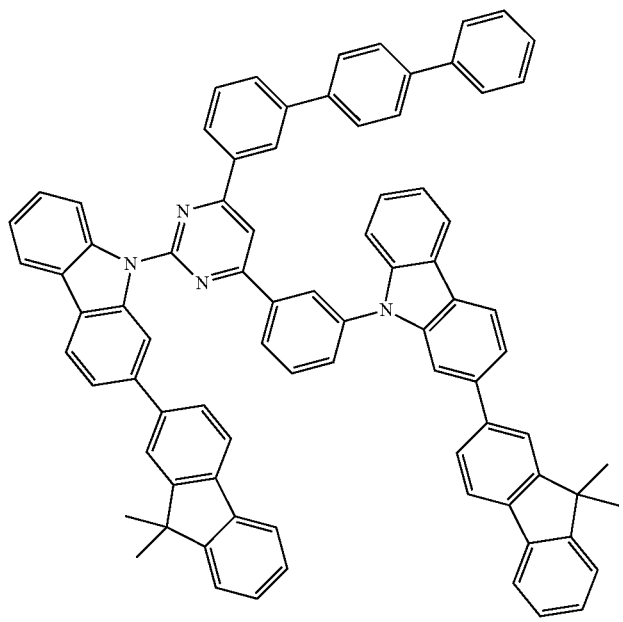

241
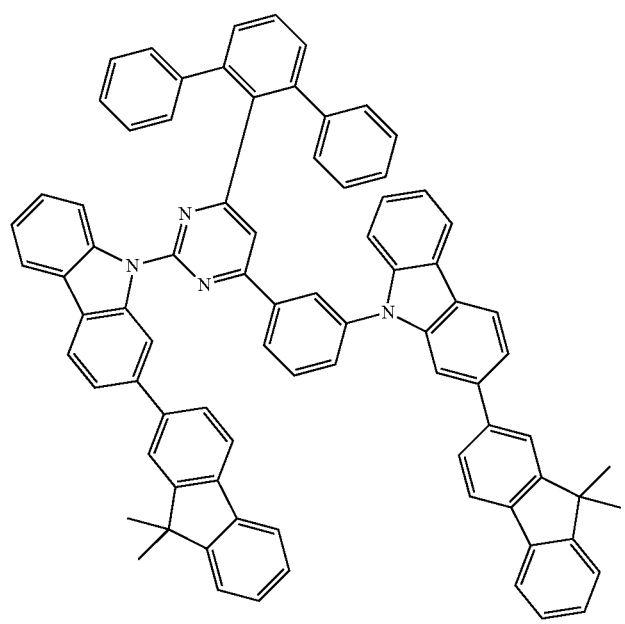
242
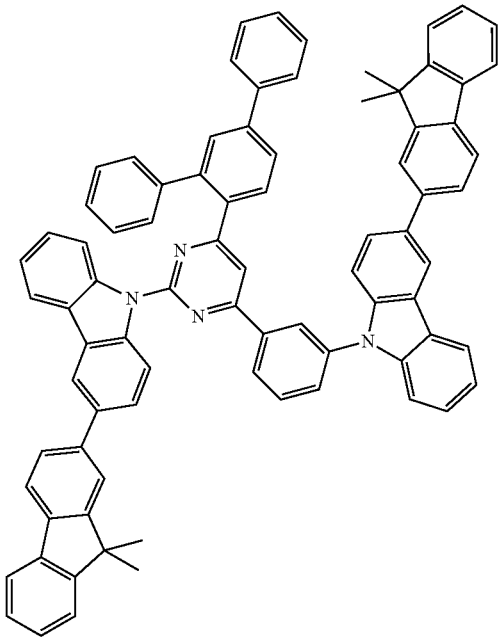
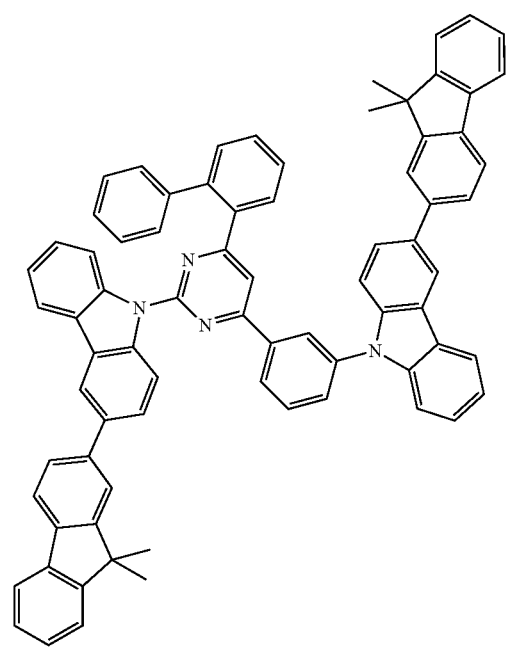

[Formula 78]
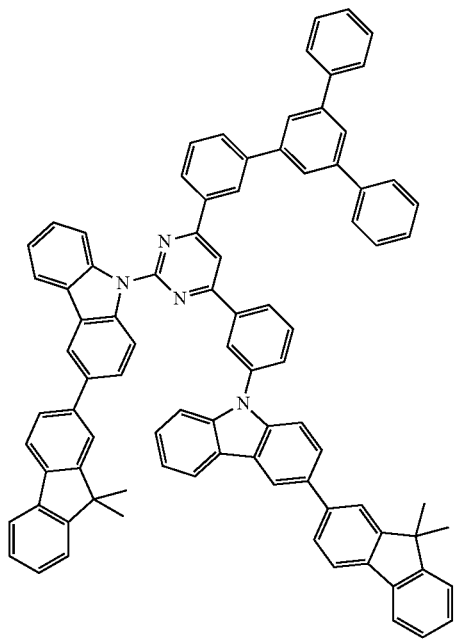
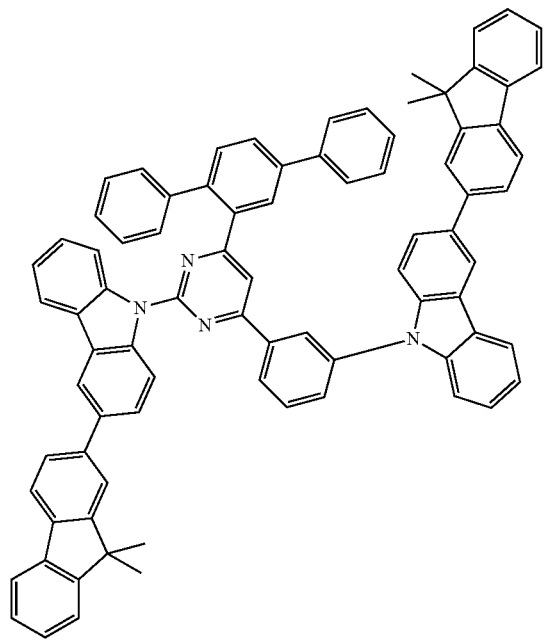
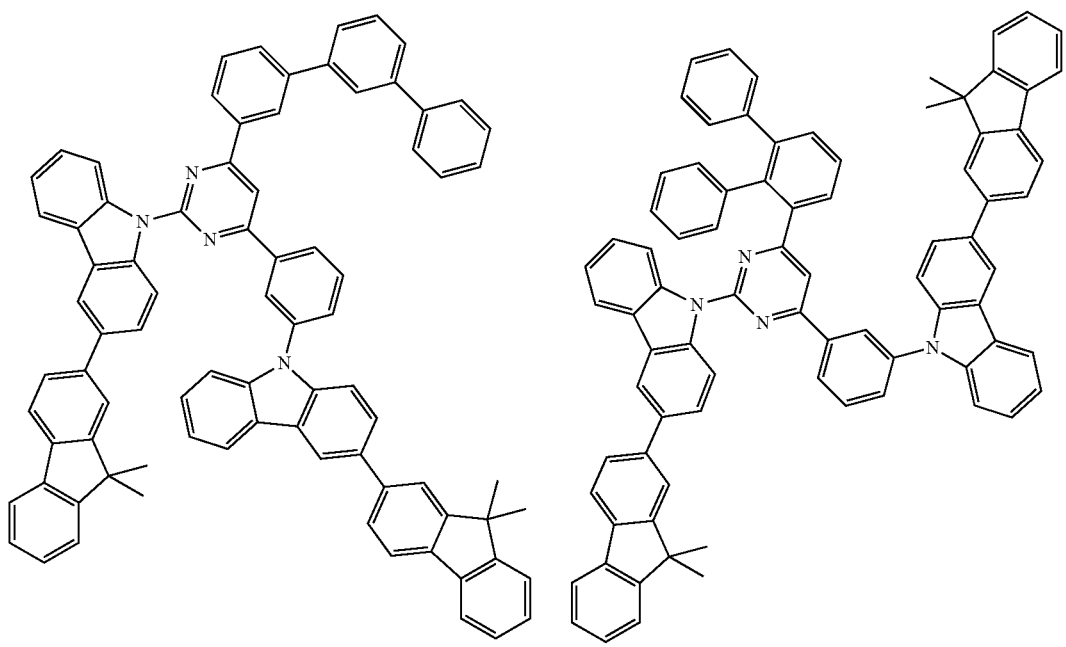

245 246
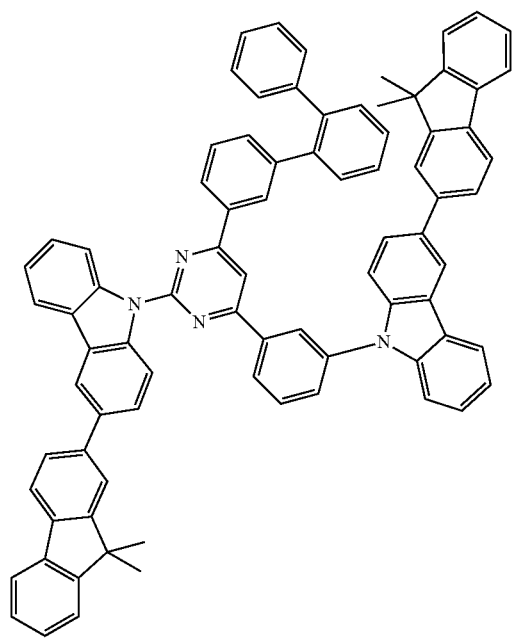 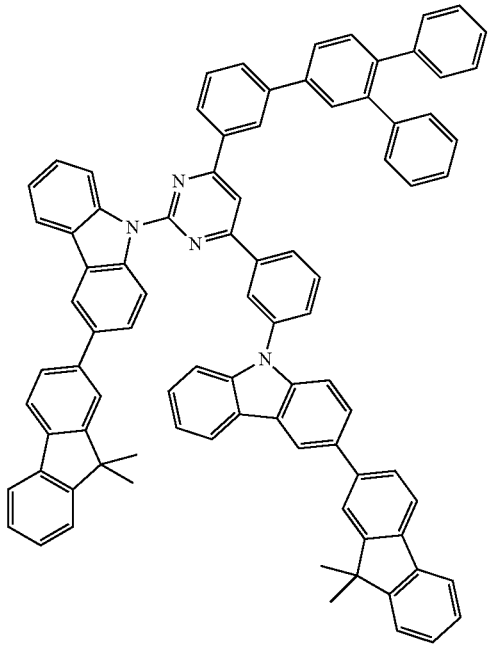
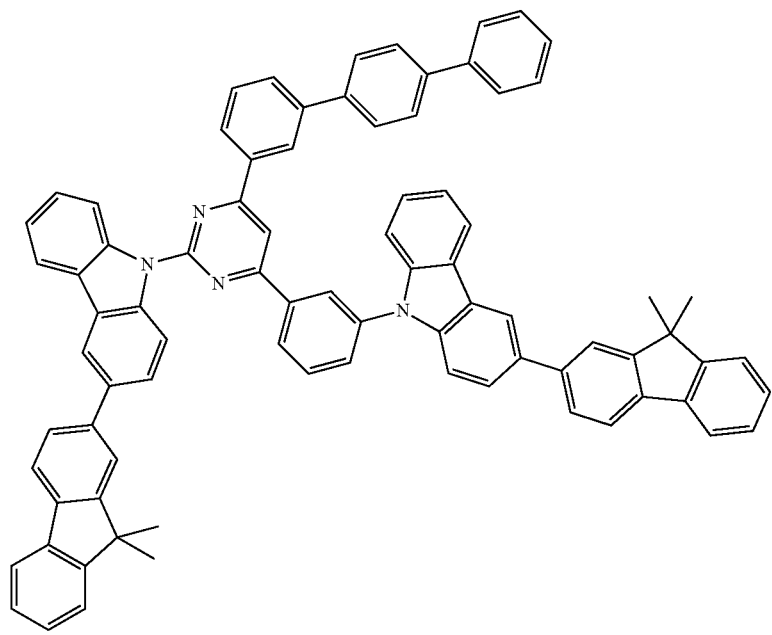

-continued
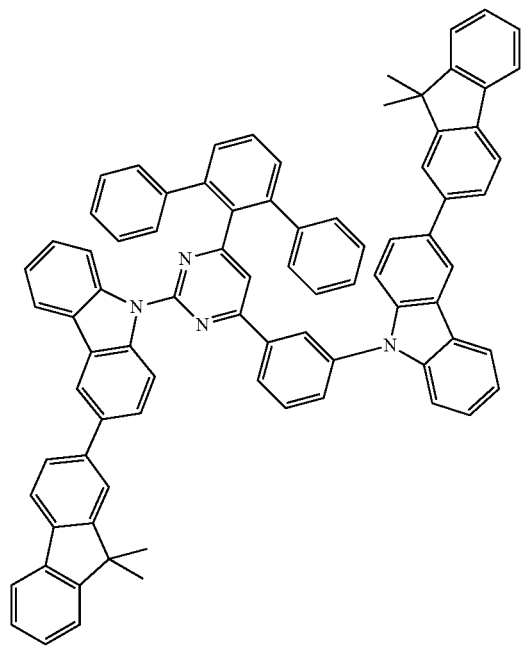
[Formula 79]
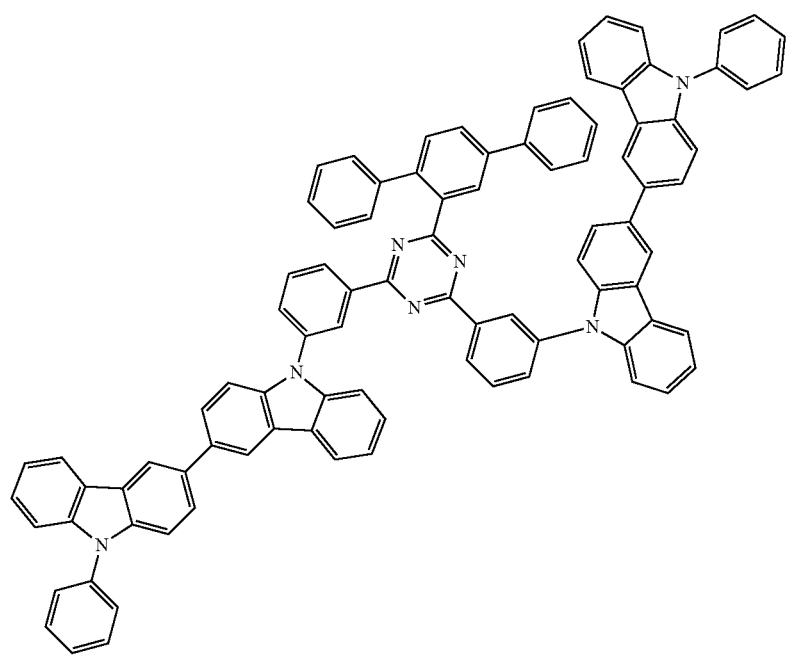

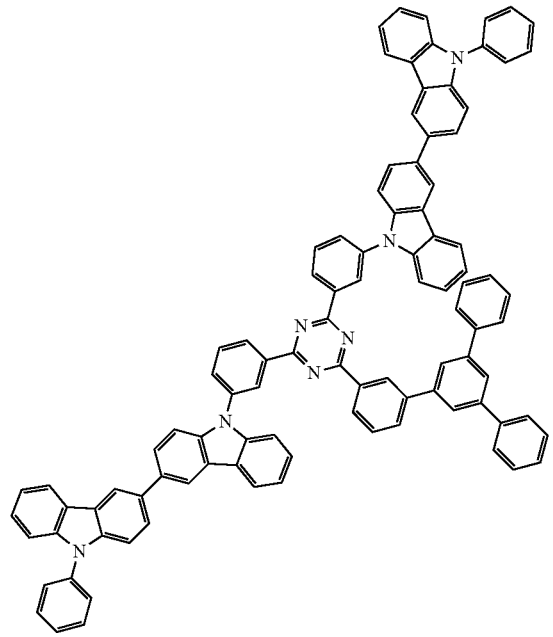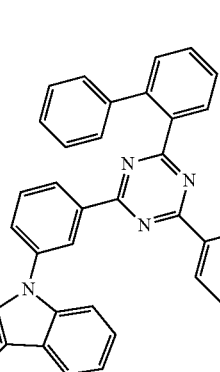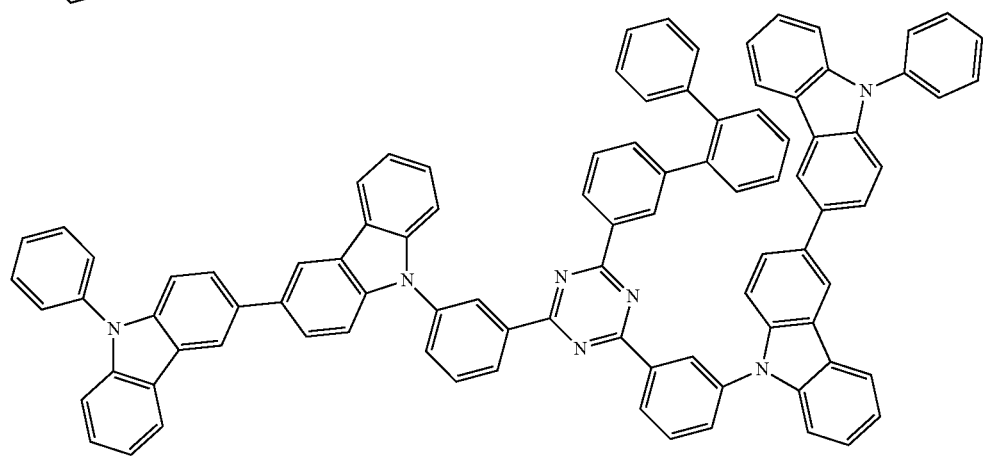

-continued
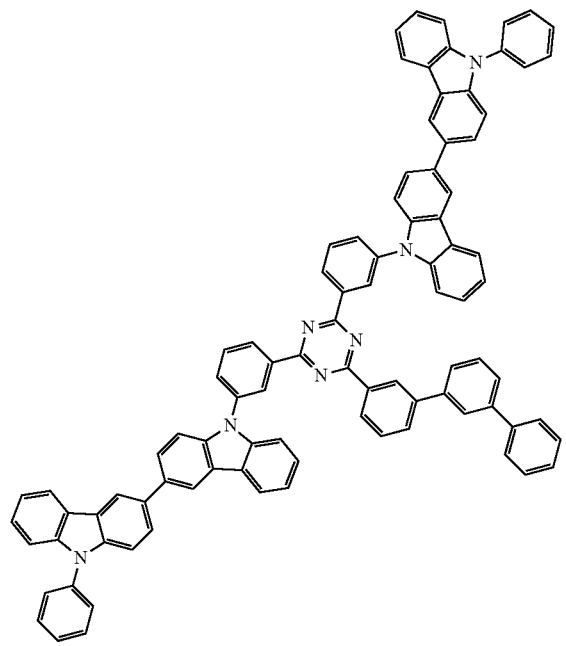
[Formula 80]
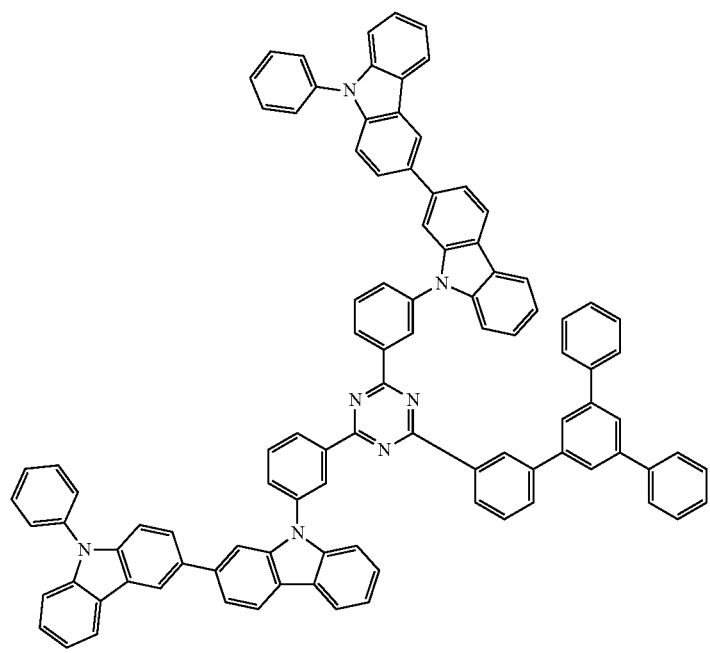

-continued
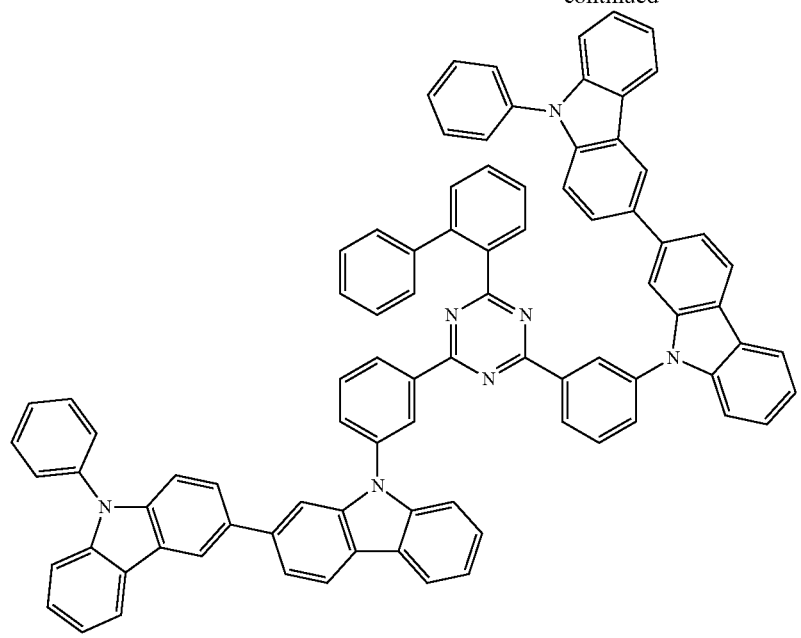
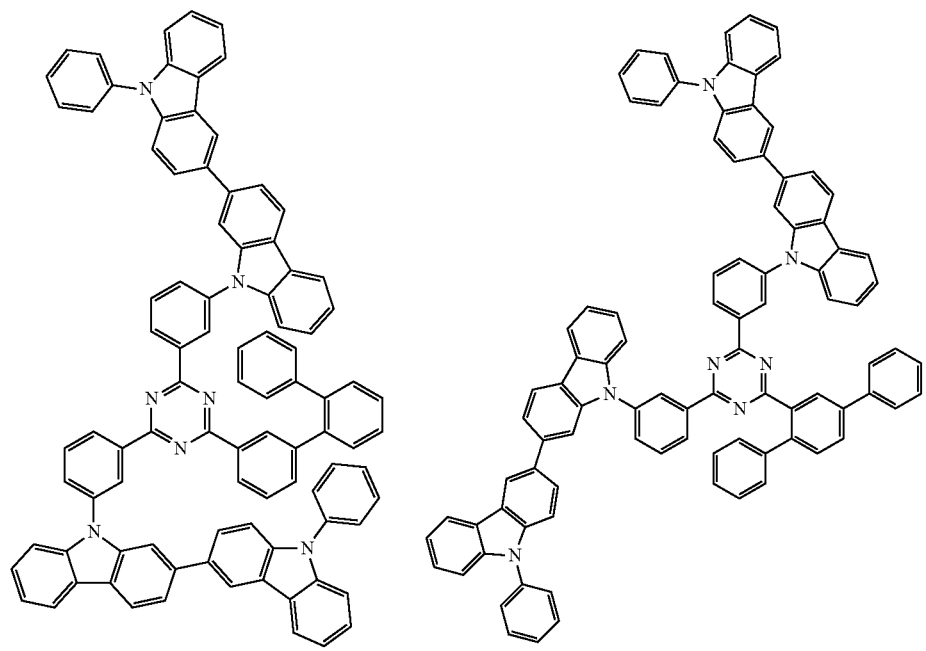

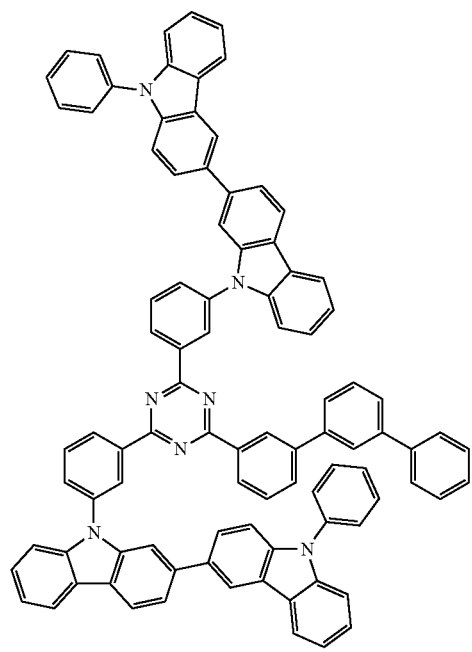
[Formula 81]
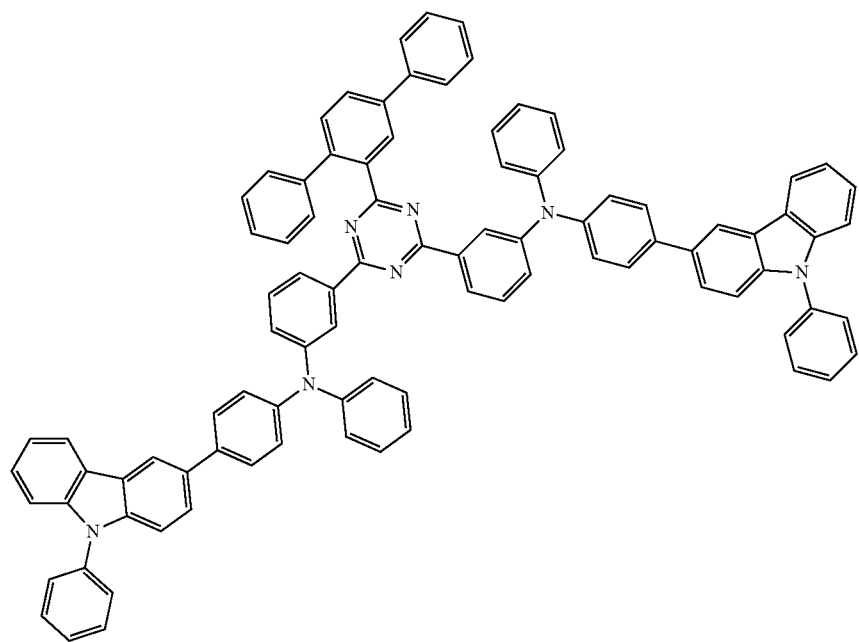

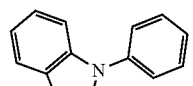
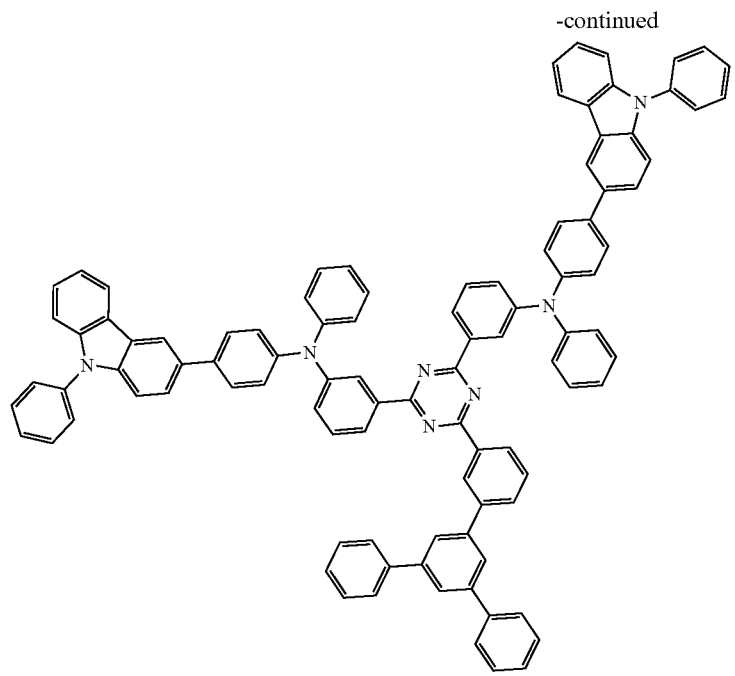
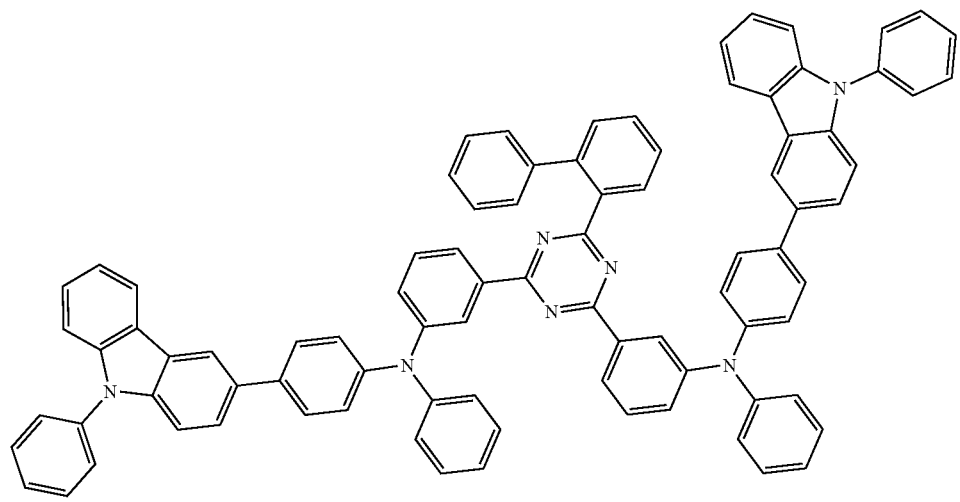

-continued
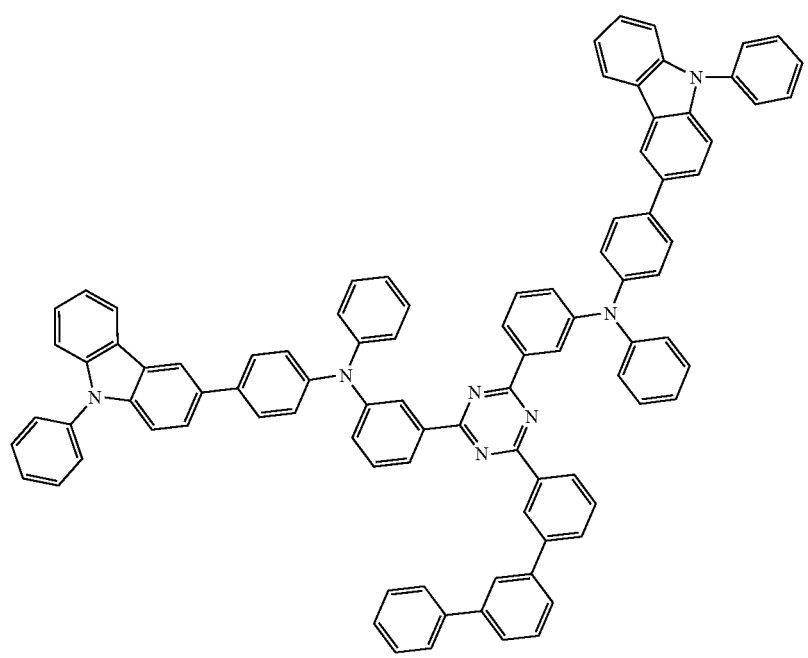
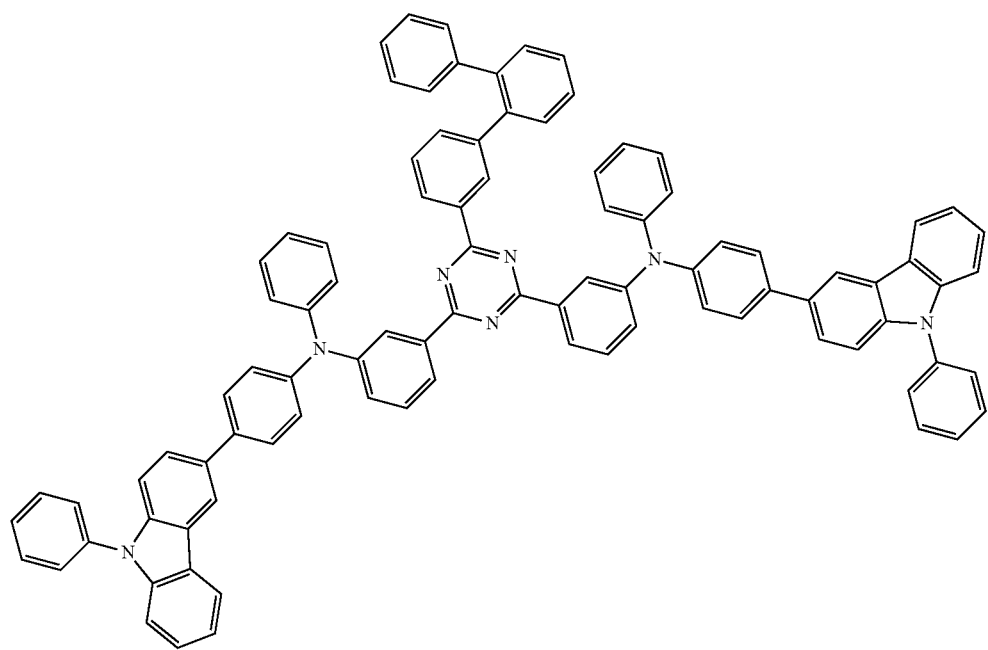

[Formula 82]
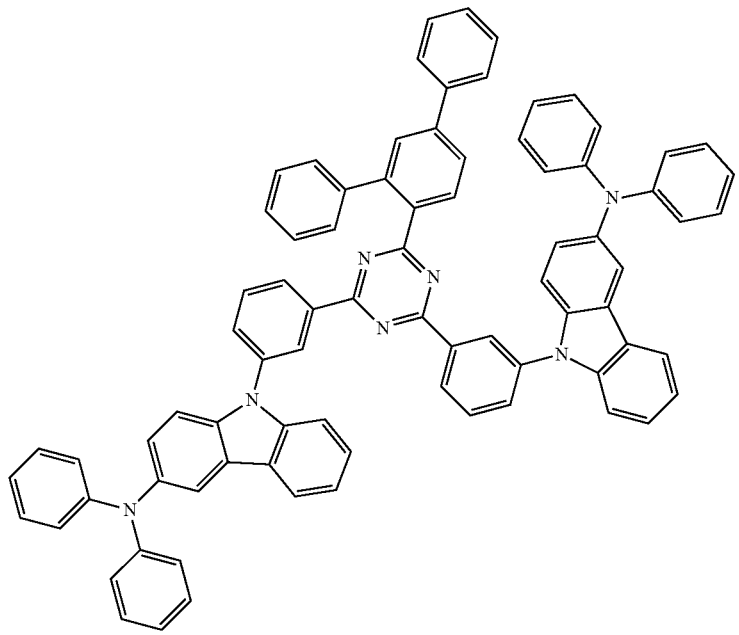
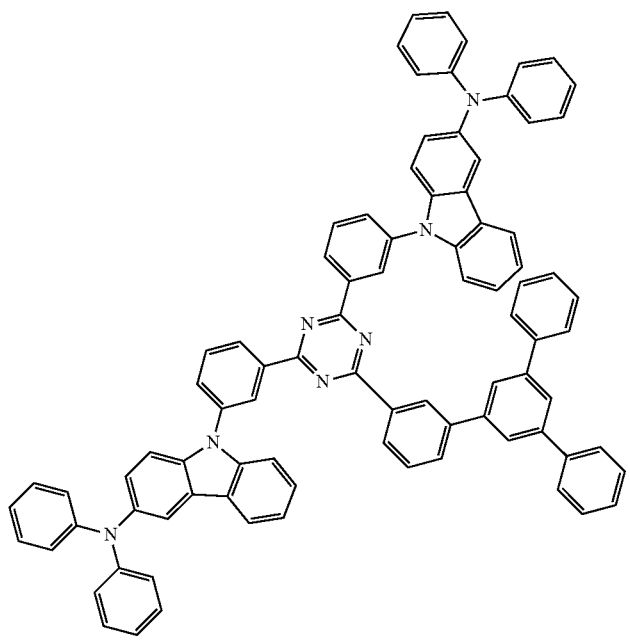

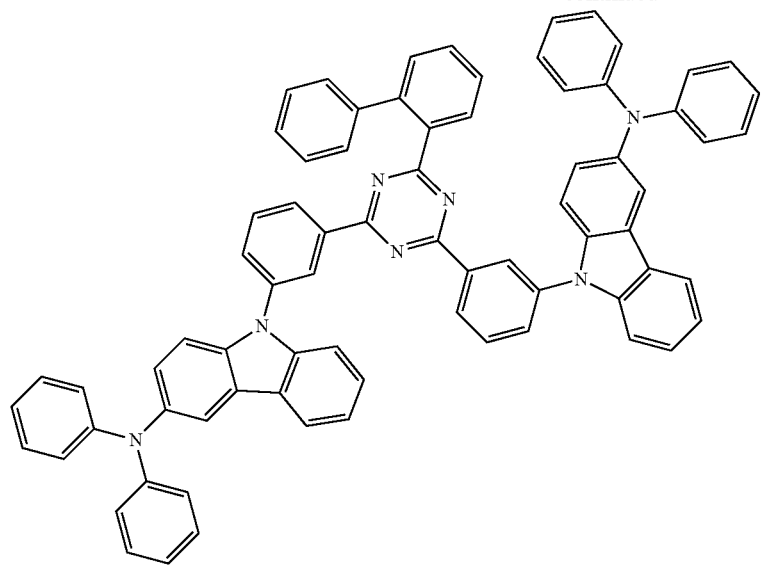
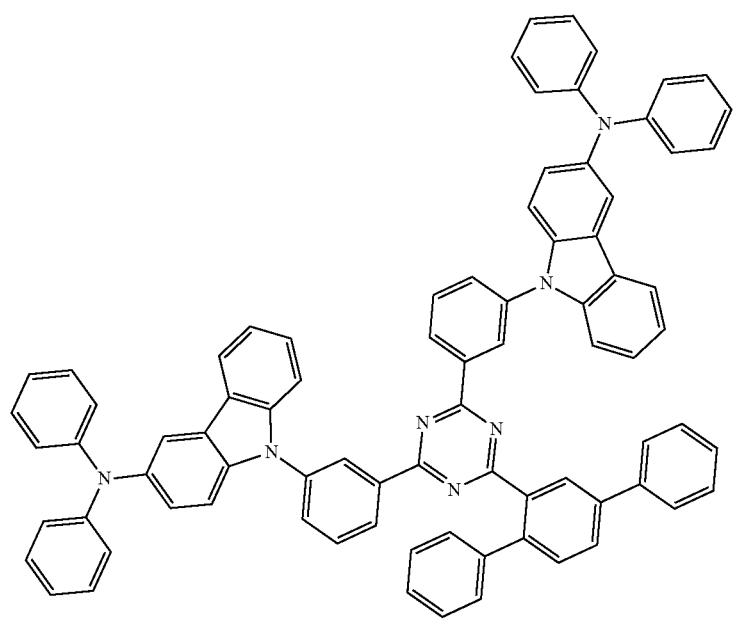

265 266
-continued
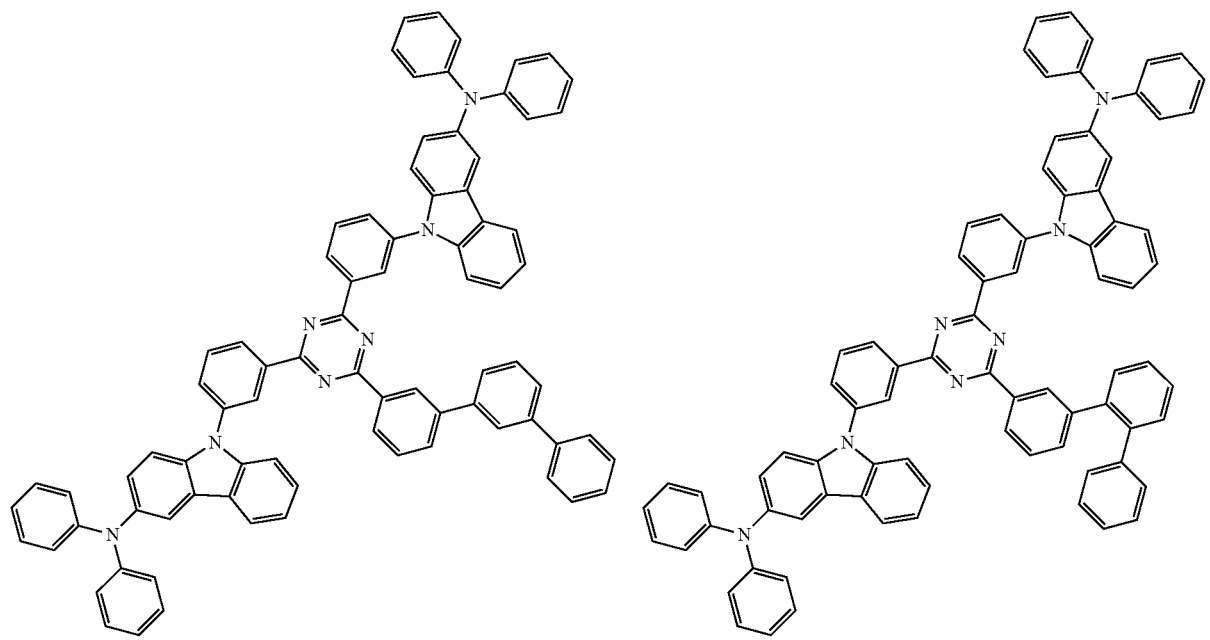
[Formula 83]
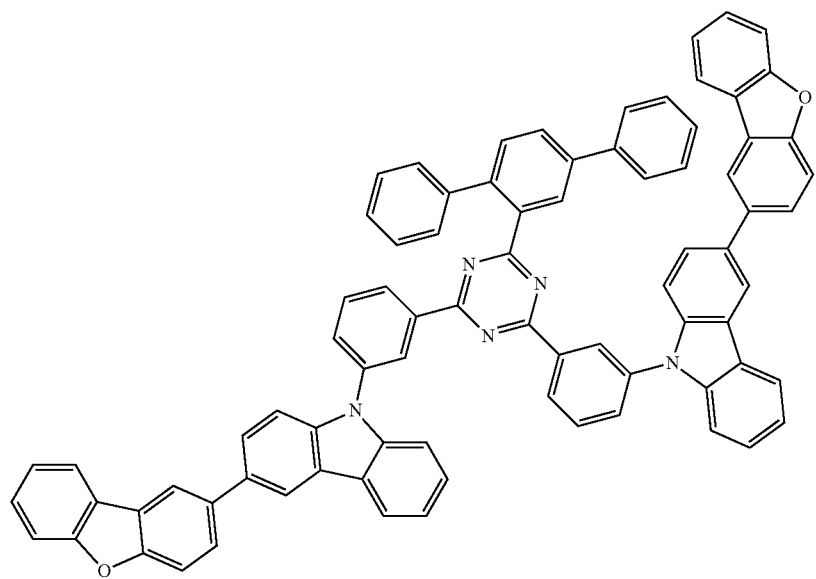

-continued
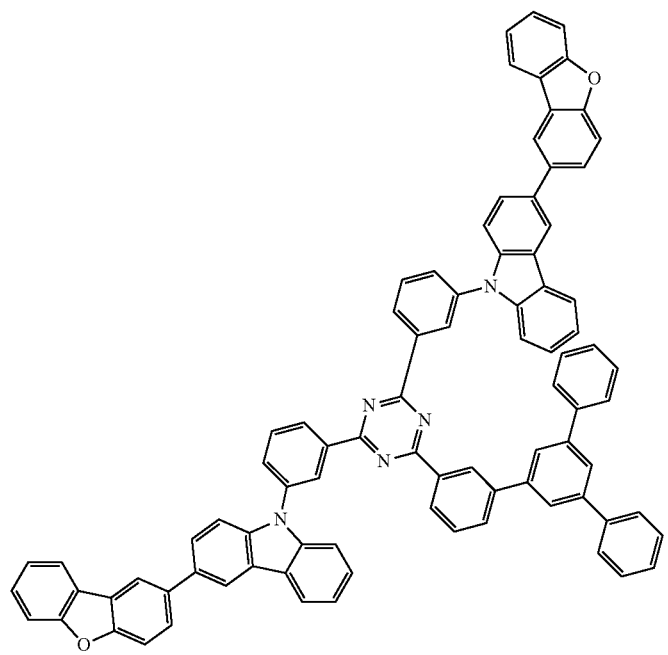
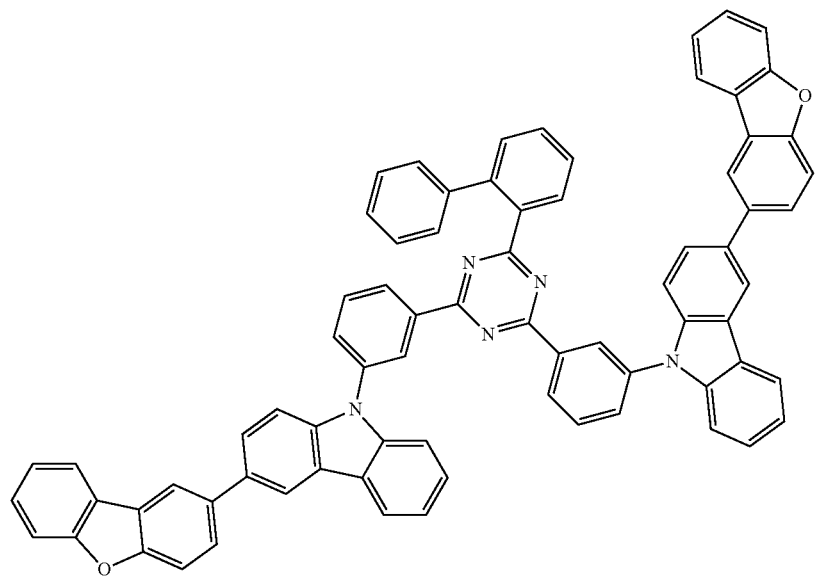
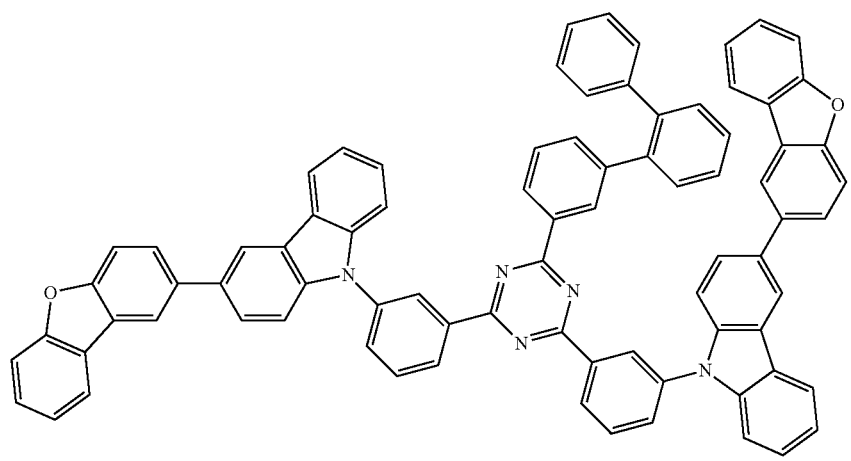

-continued
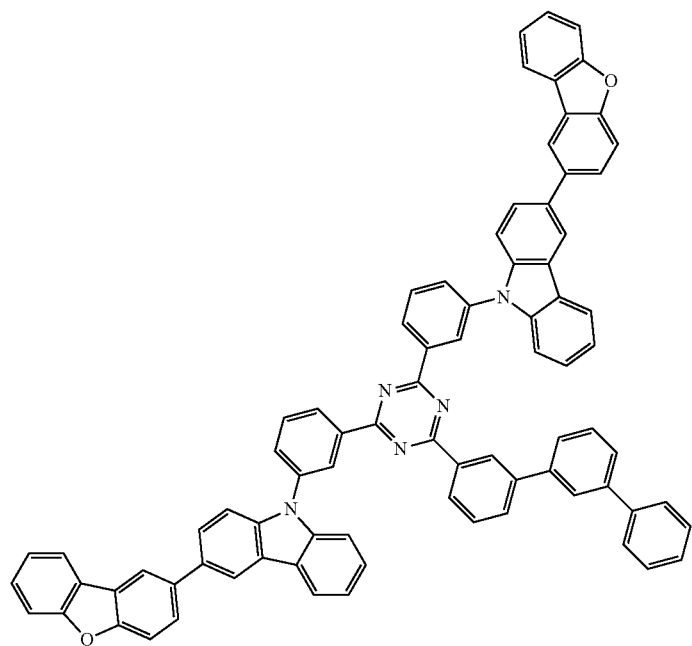
[Formula 84]
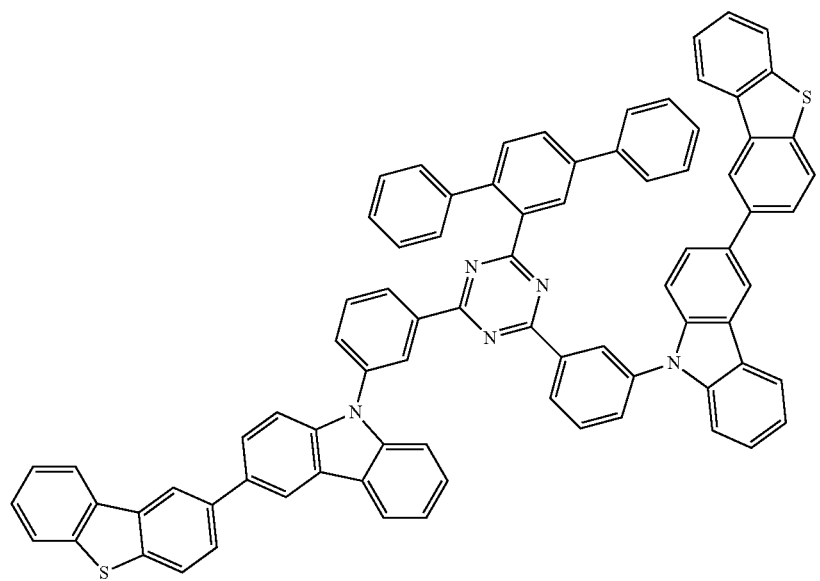

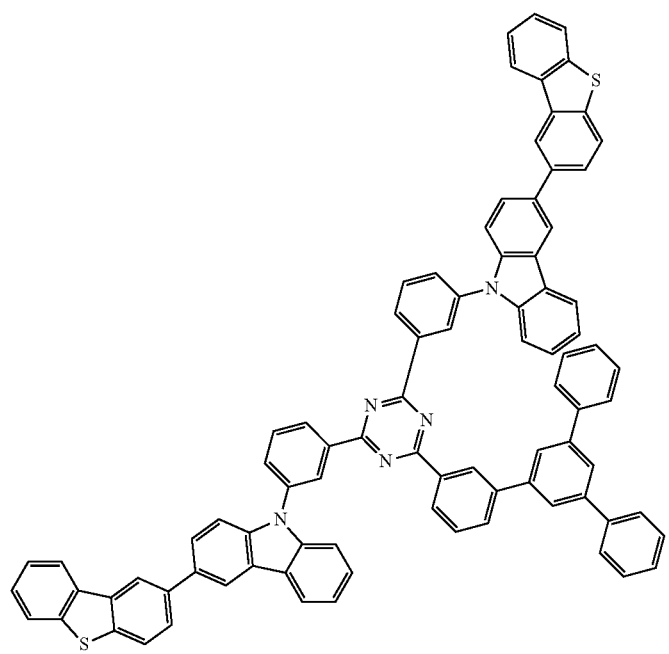
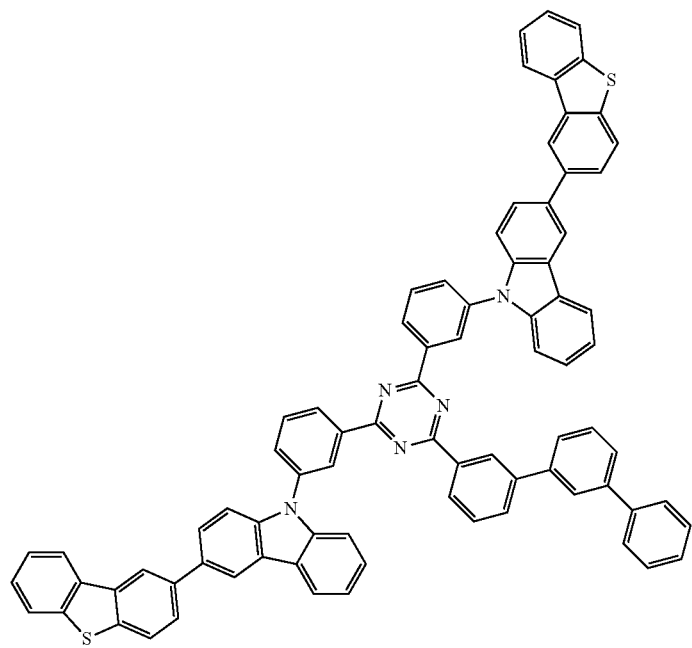

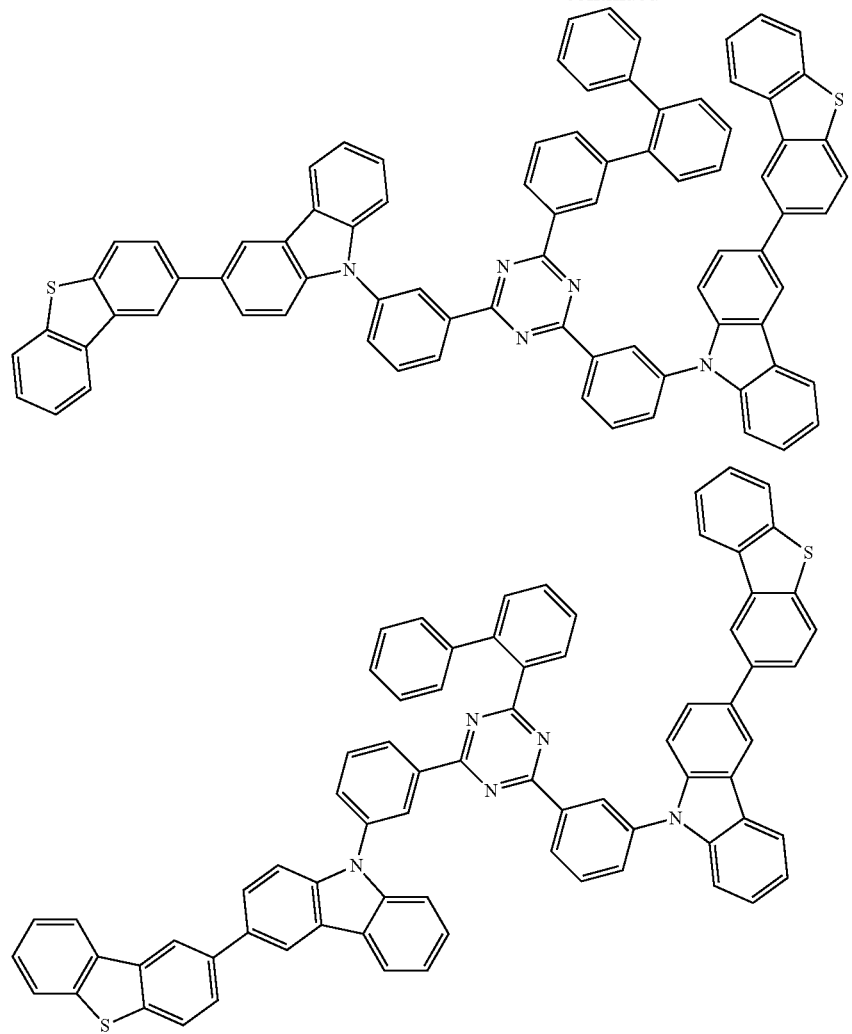
[Formula 85]
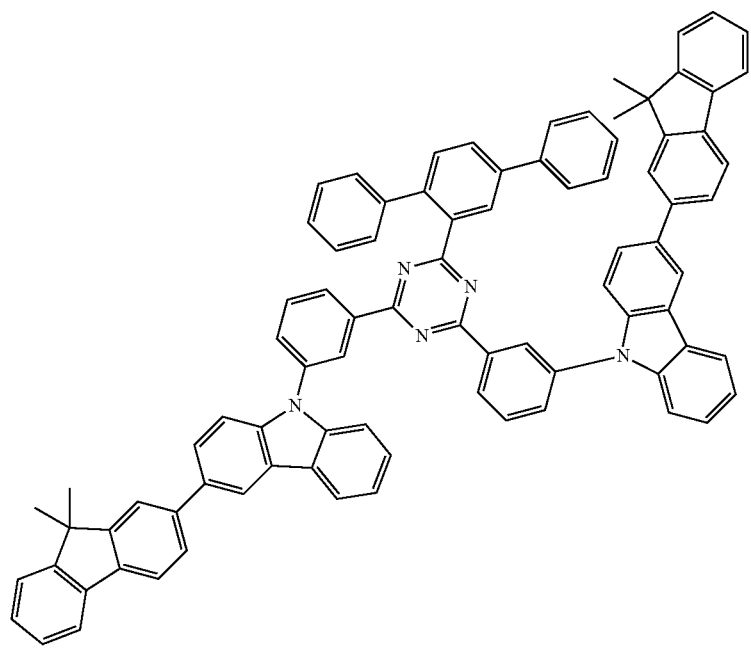

-continued
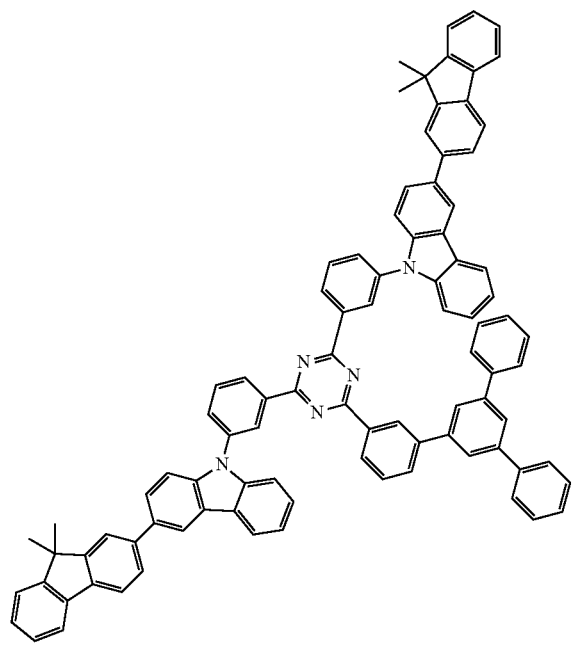
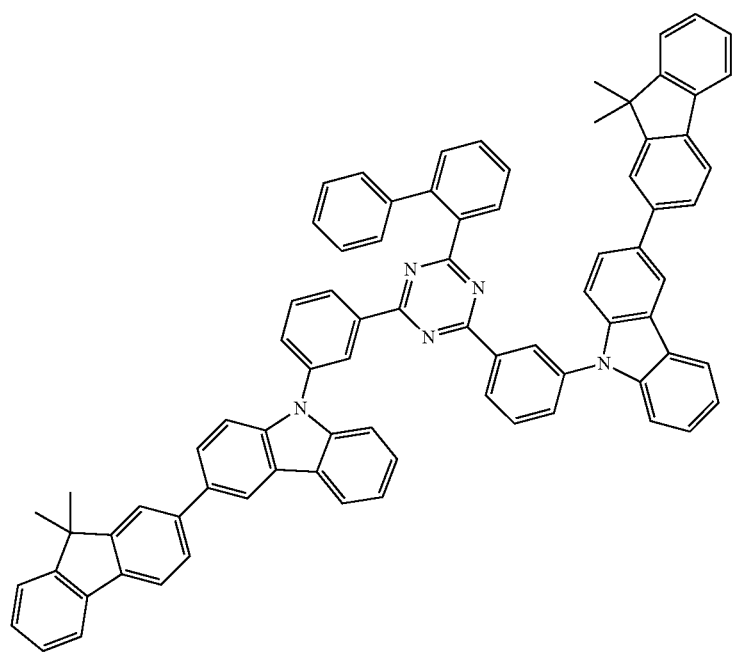

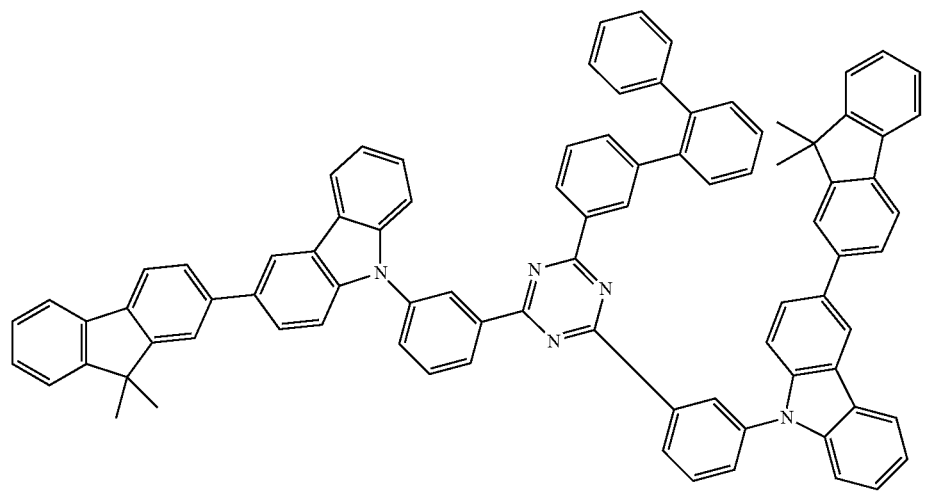
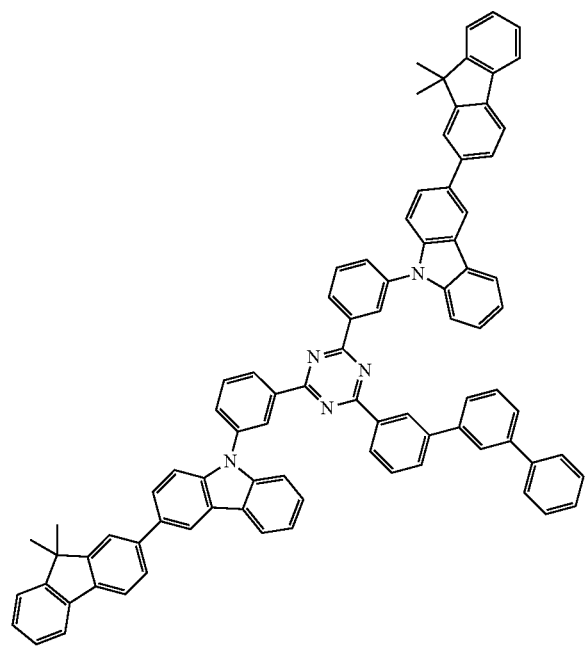

[Formula 86]
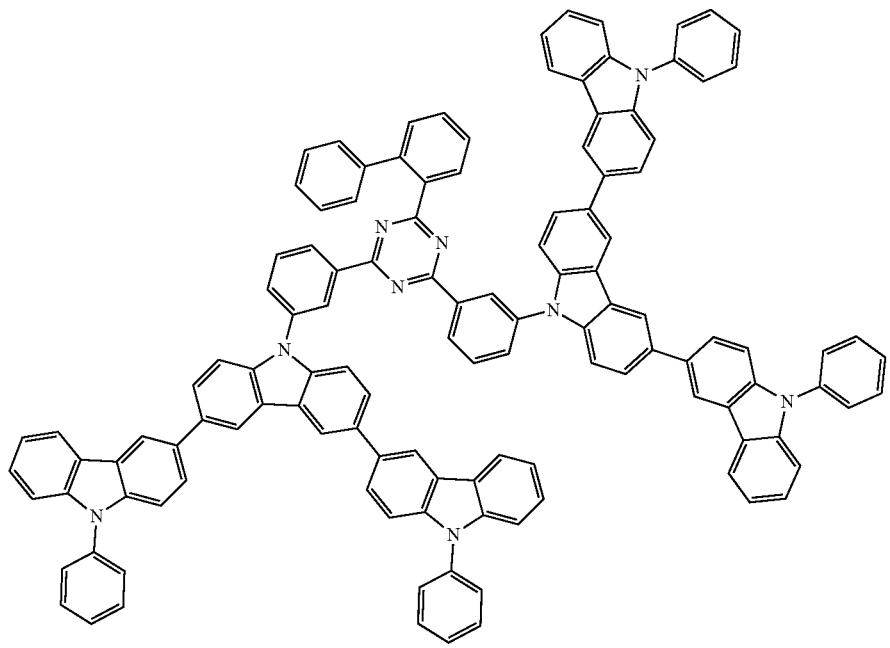
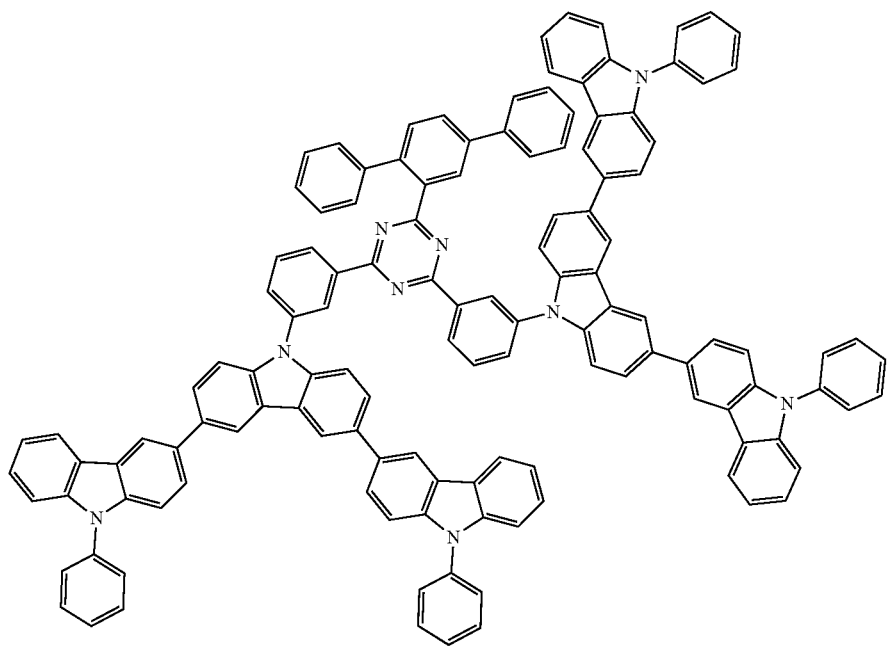

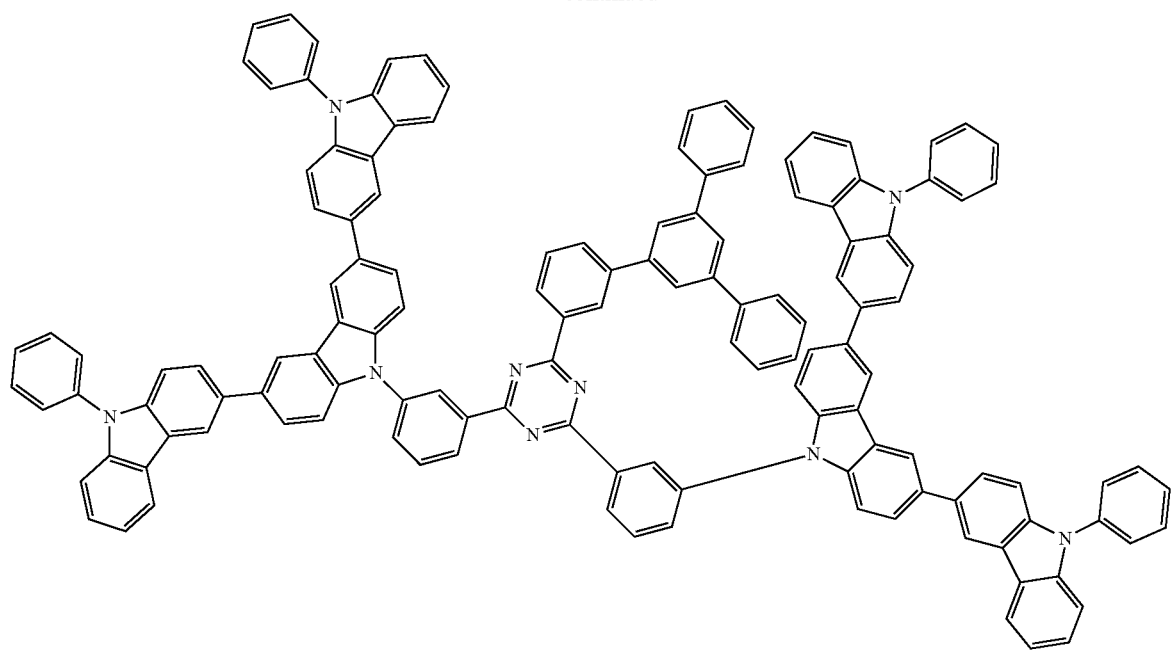
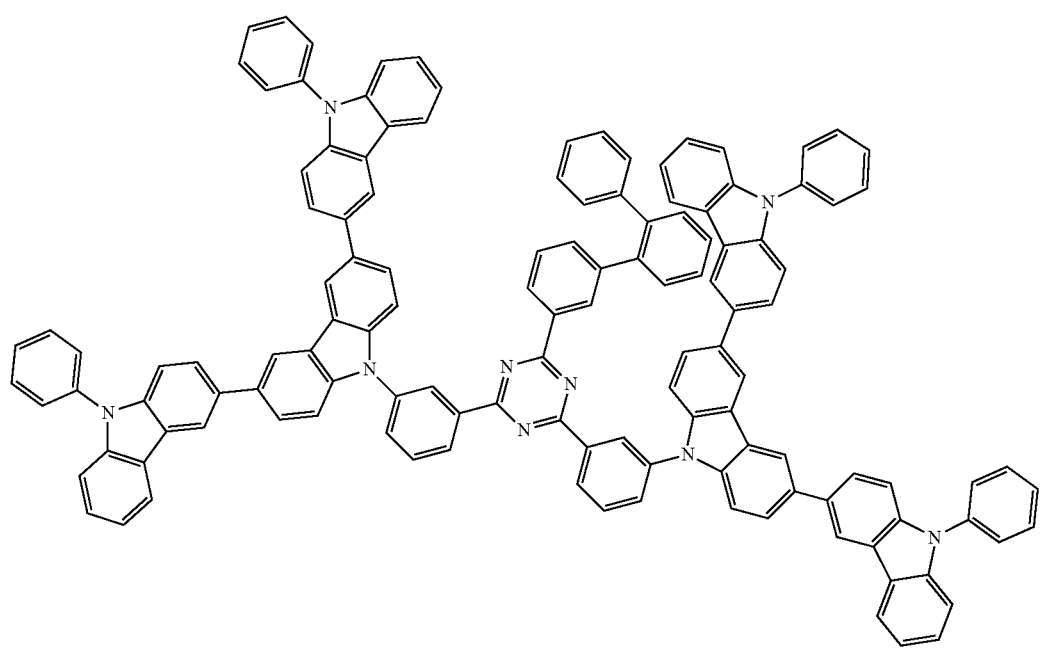

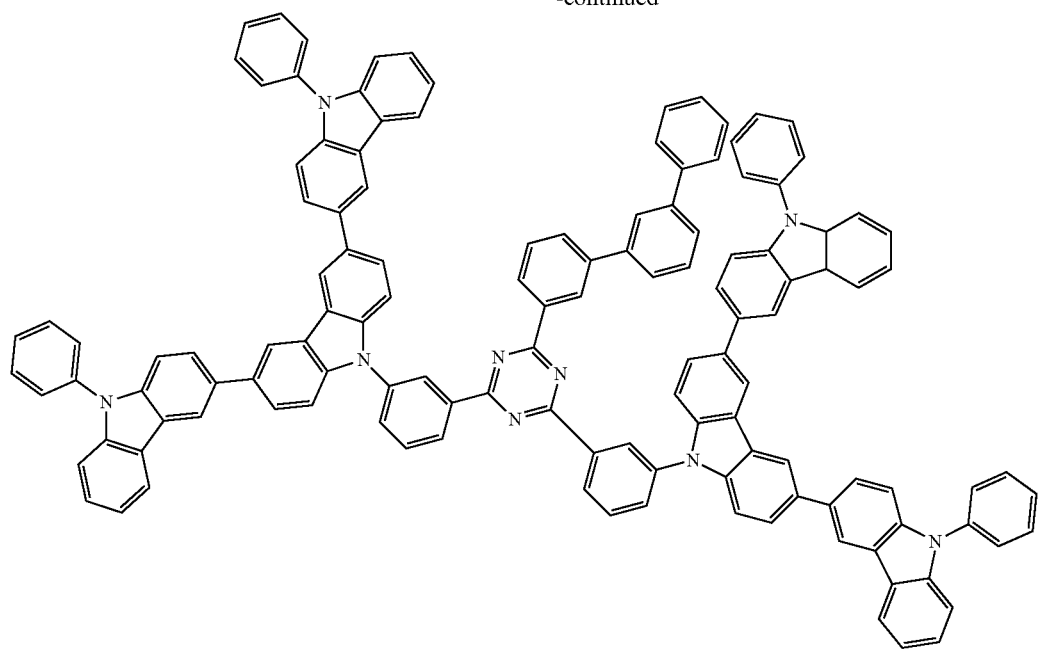
[Formula 87]
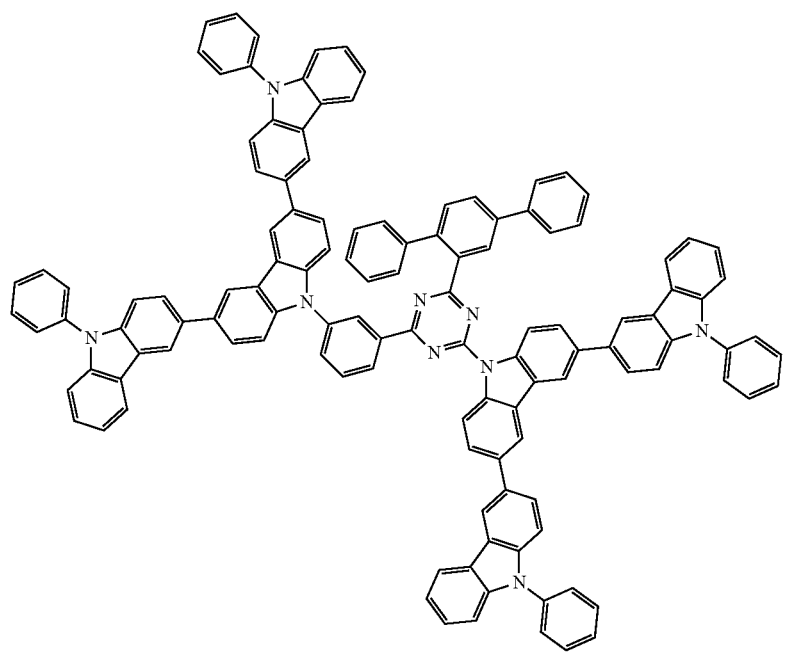

-continued
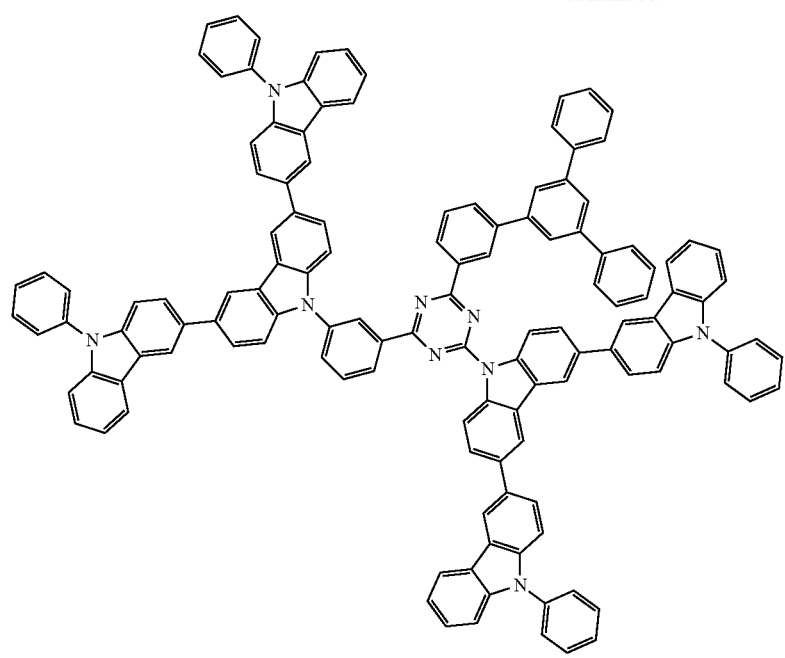
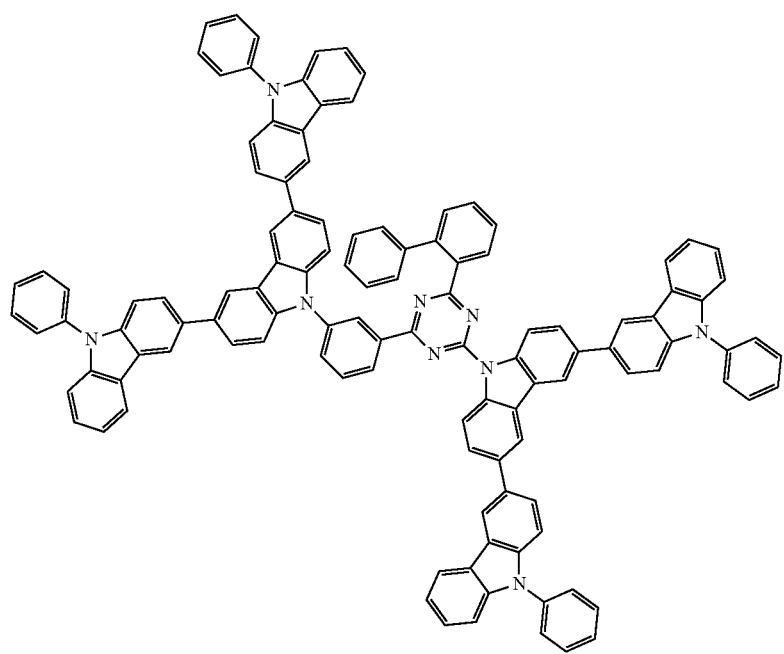

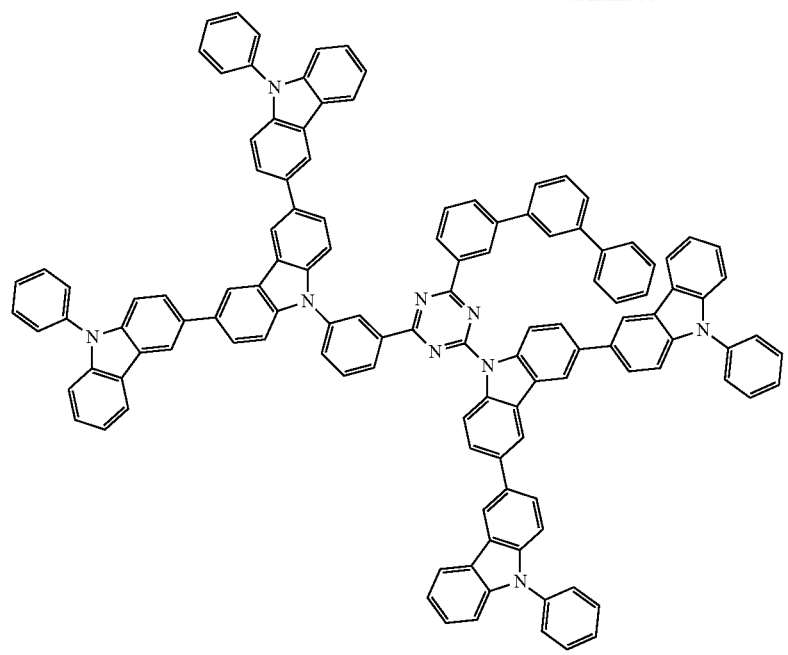
[Formula 88]
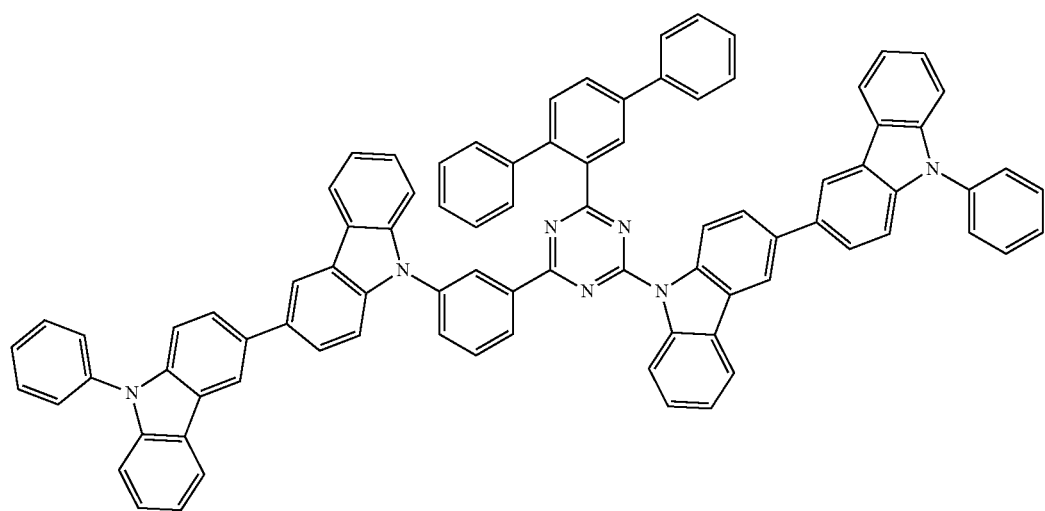

-continued
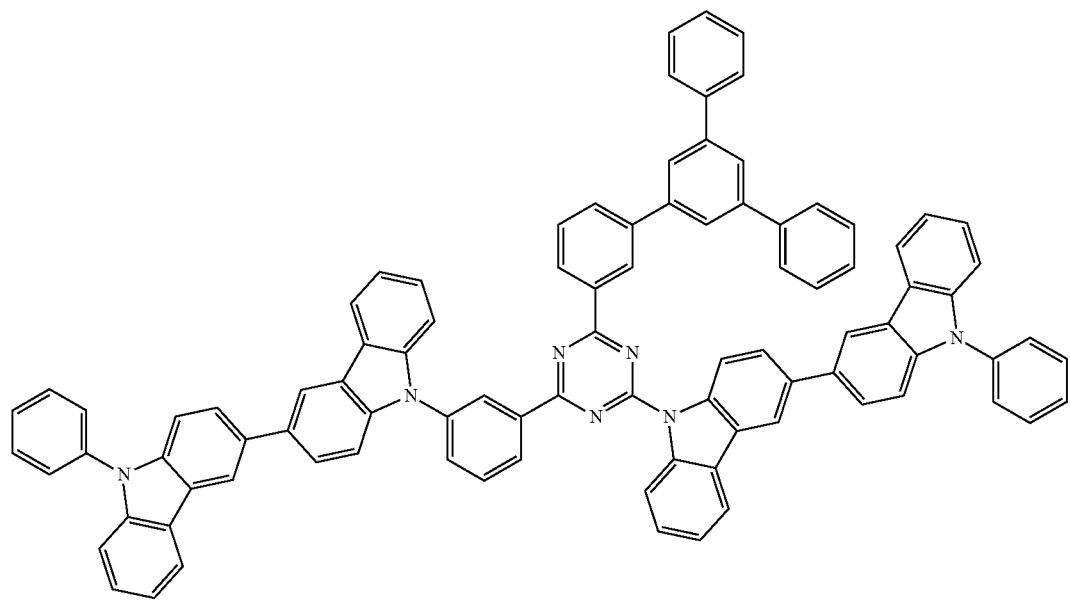
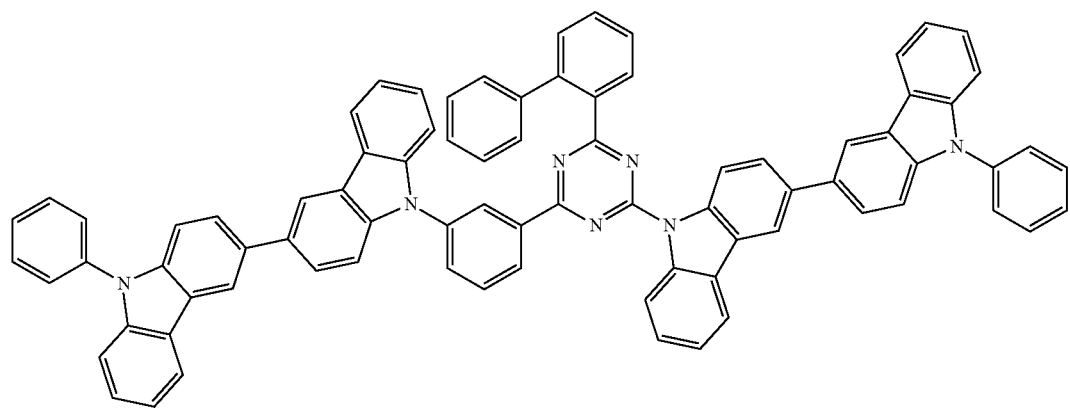
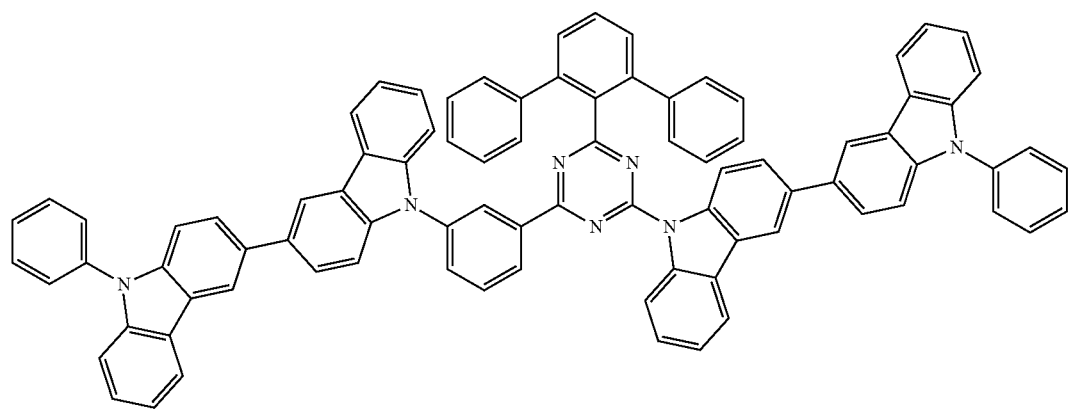

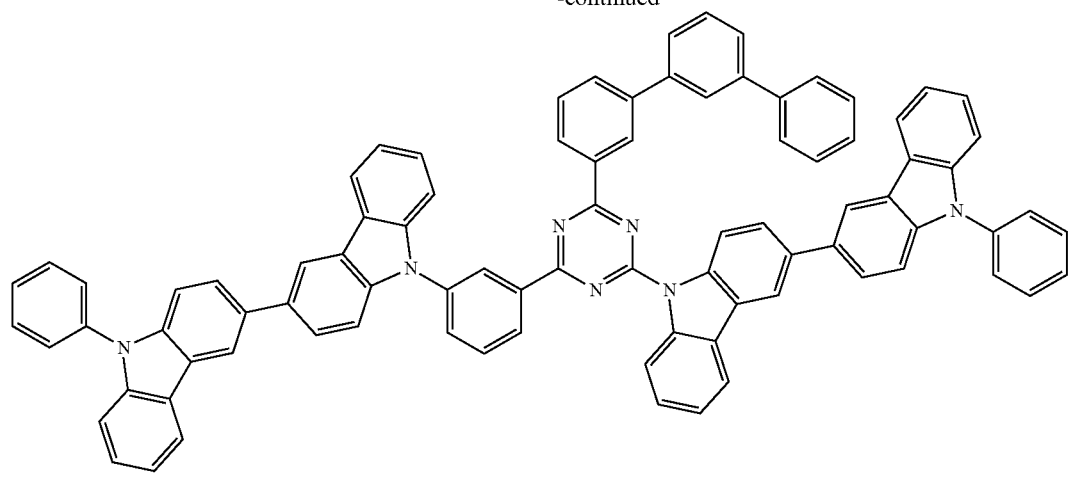
[Formula 89]
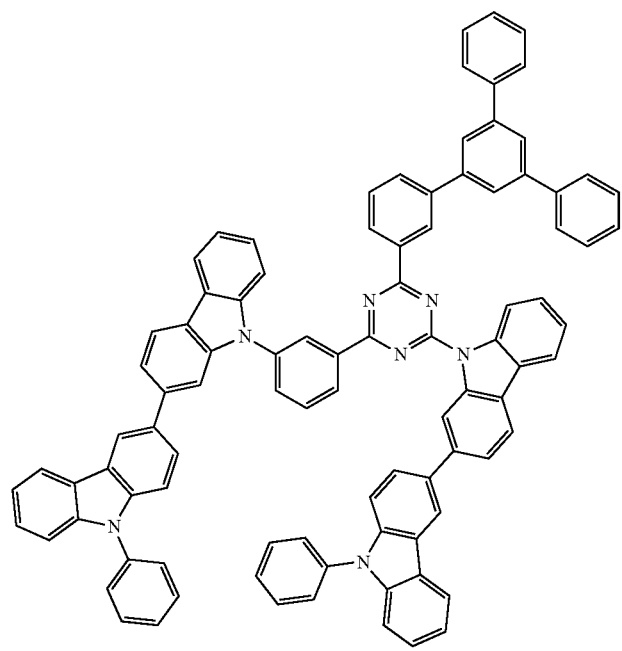

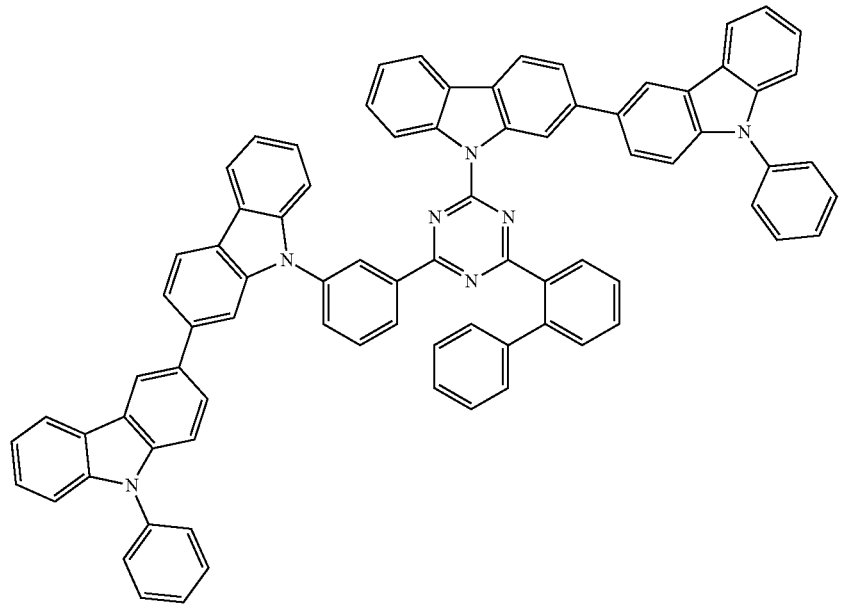
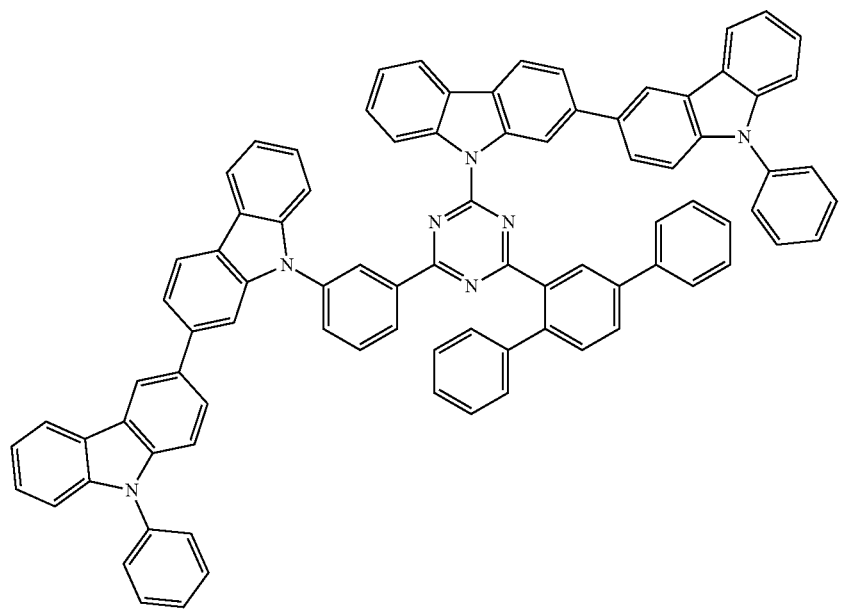

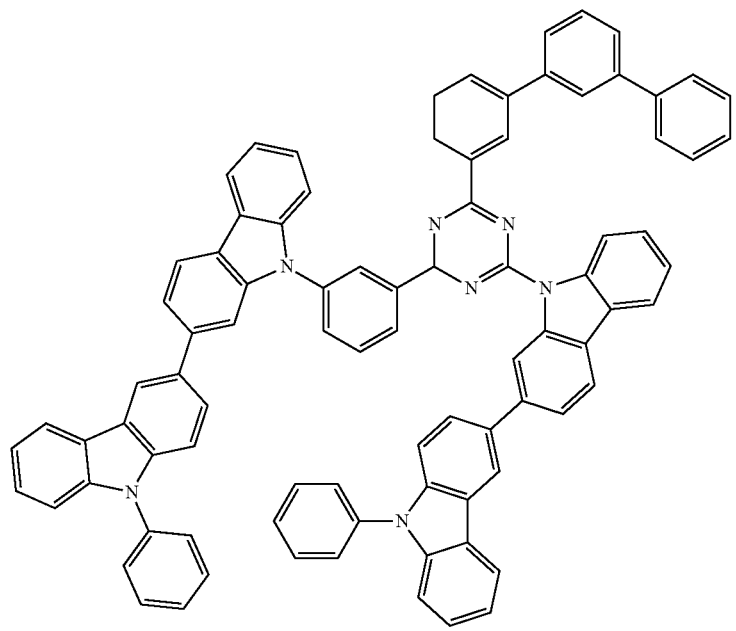
[Formula 90]
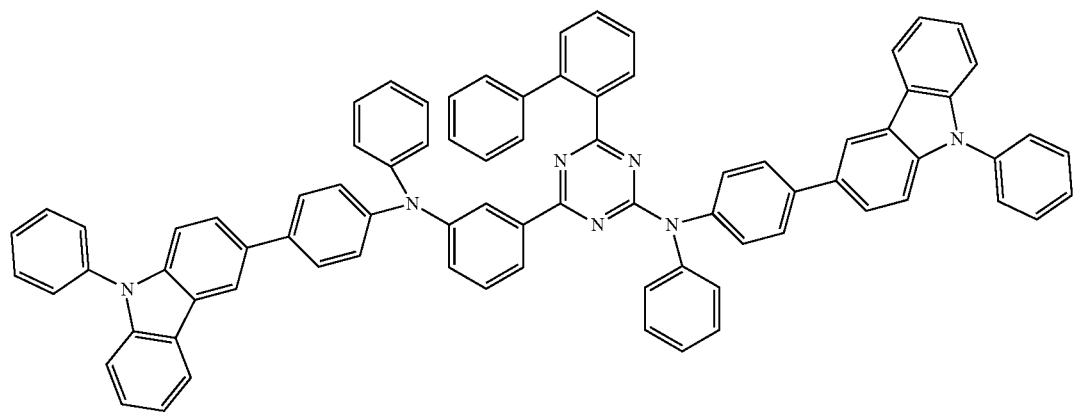
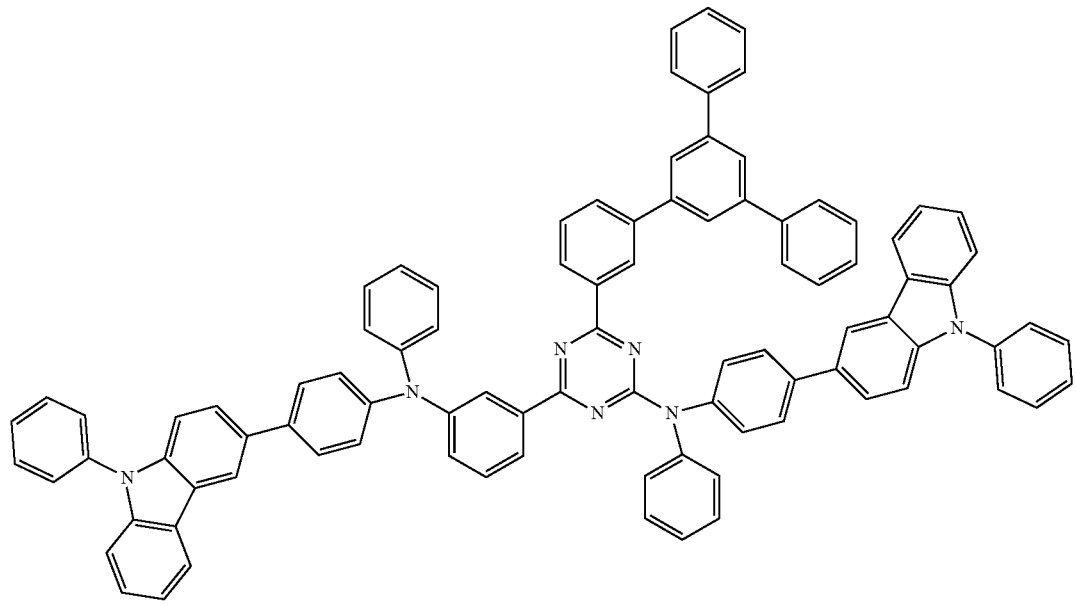

-continued
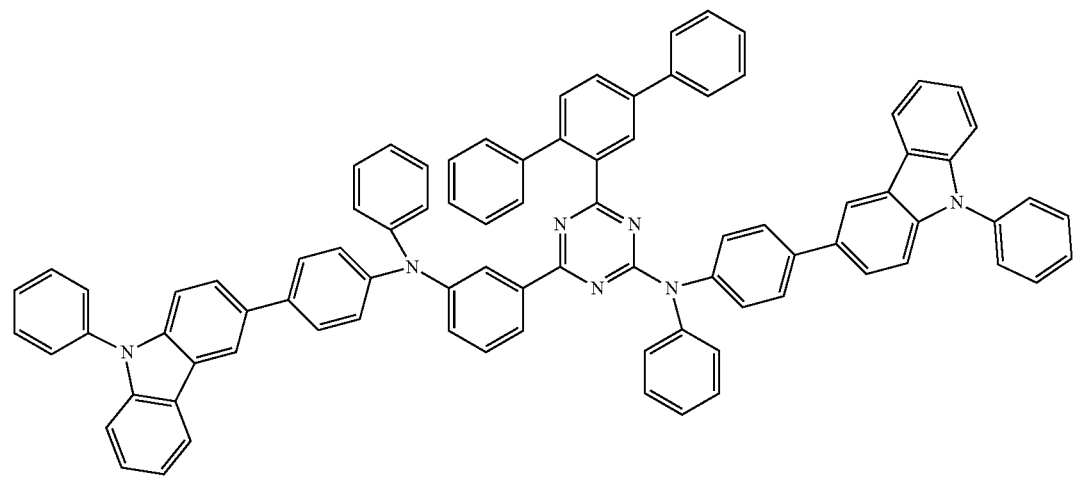
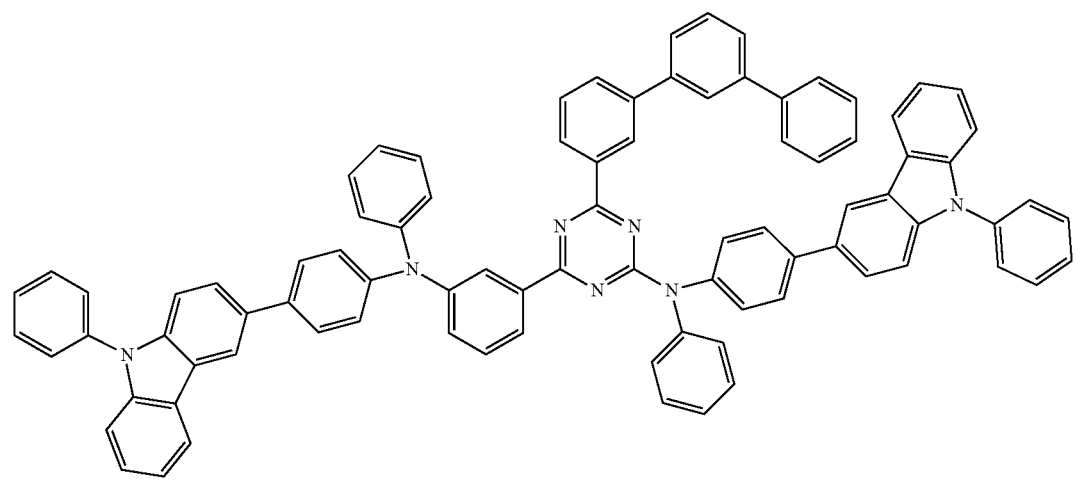

[Formula 91]
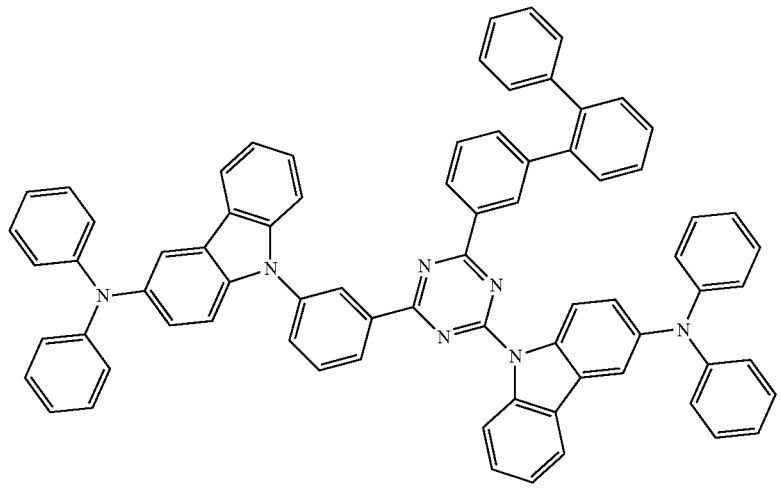
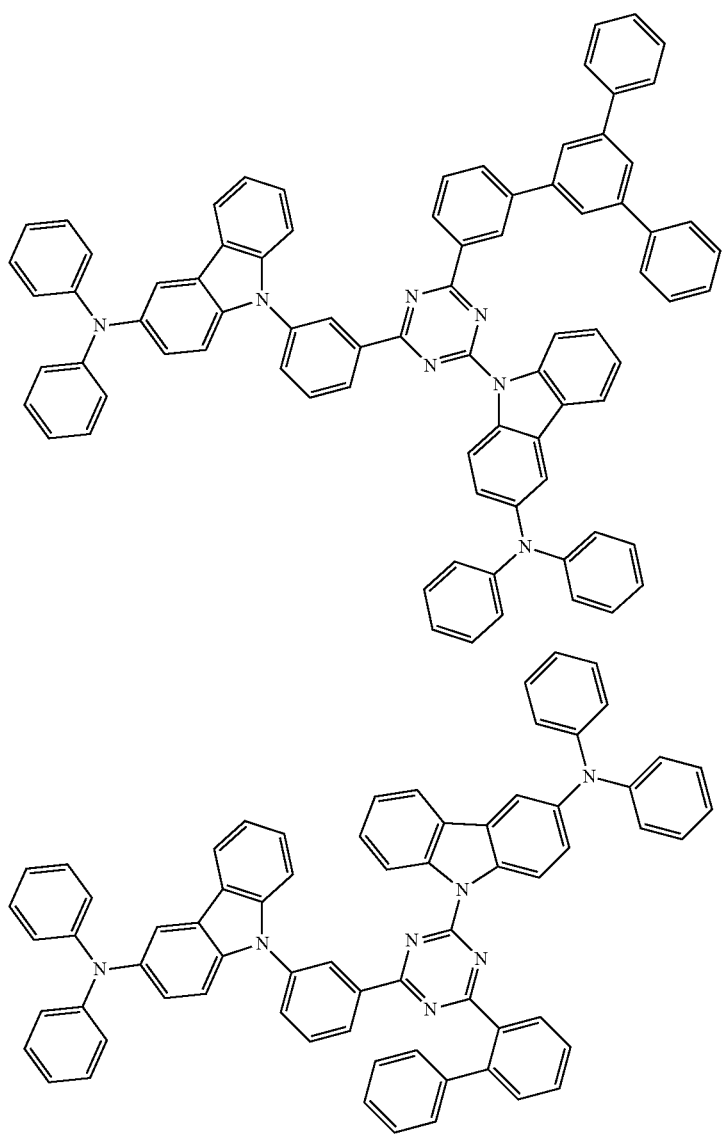

-continued
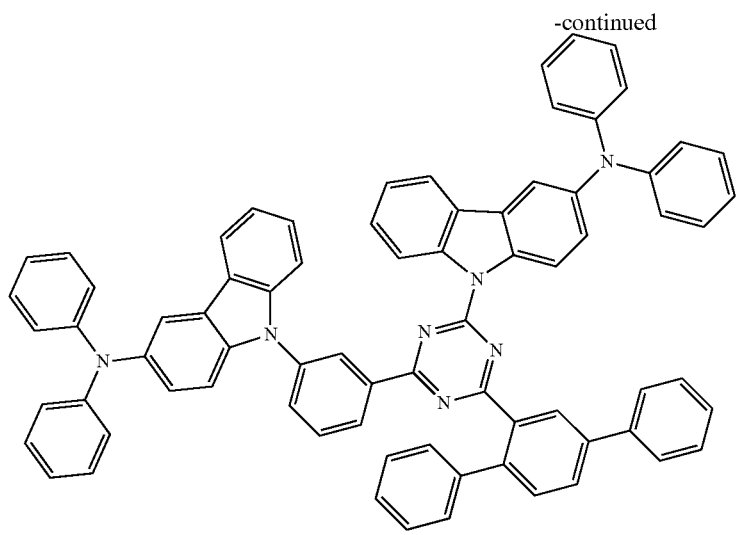
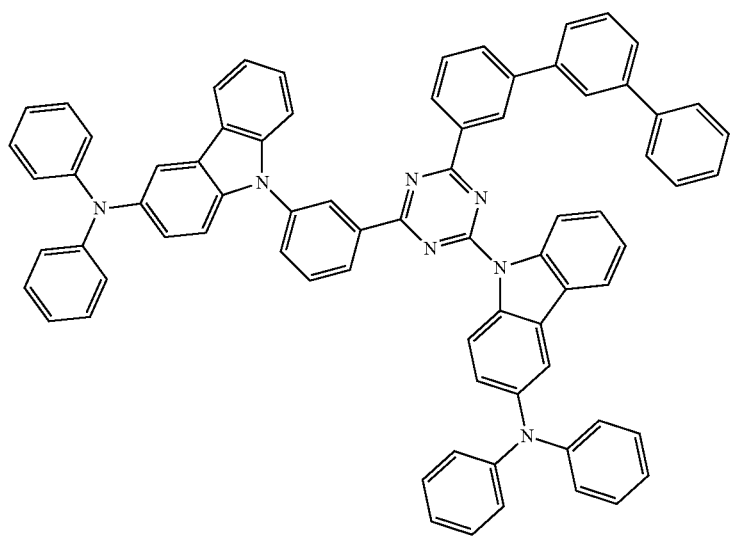
[Formula 92]
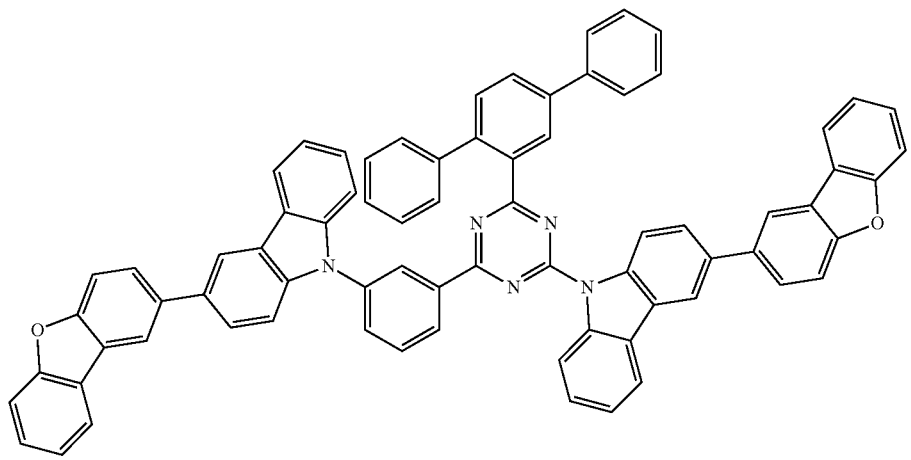

-continued
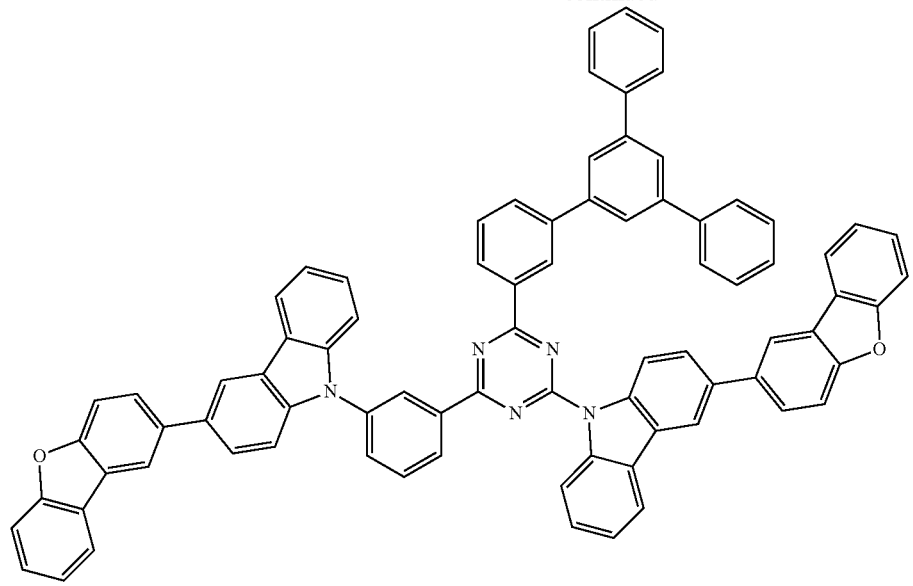
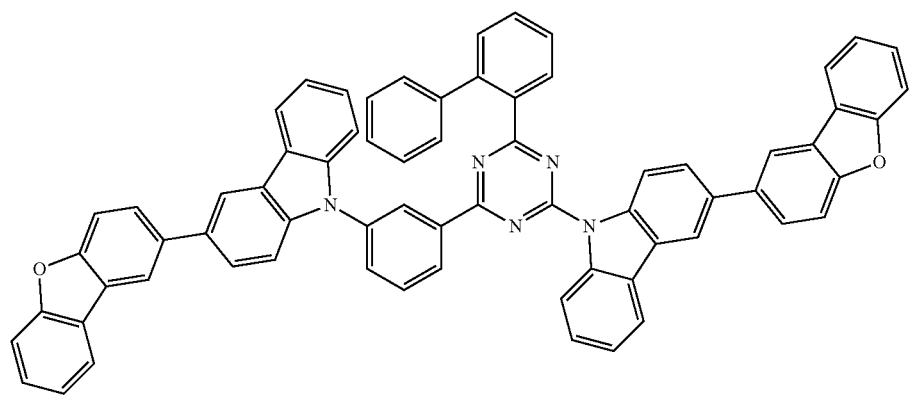
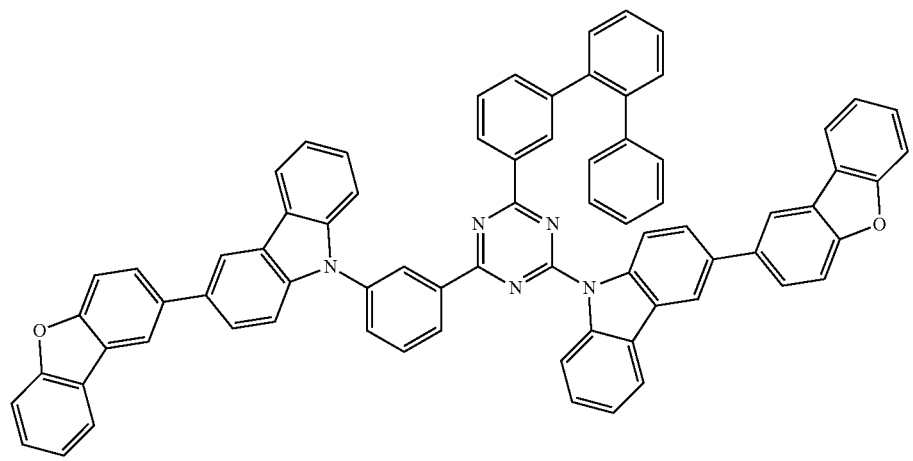

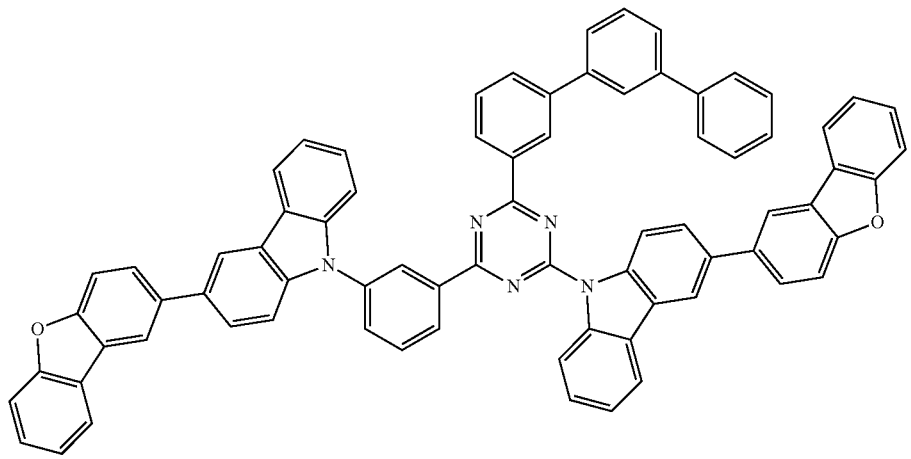
[Formula 93]
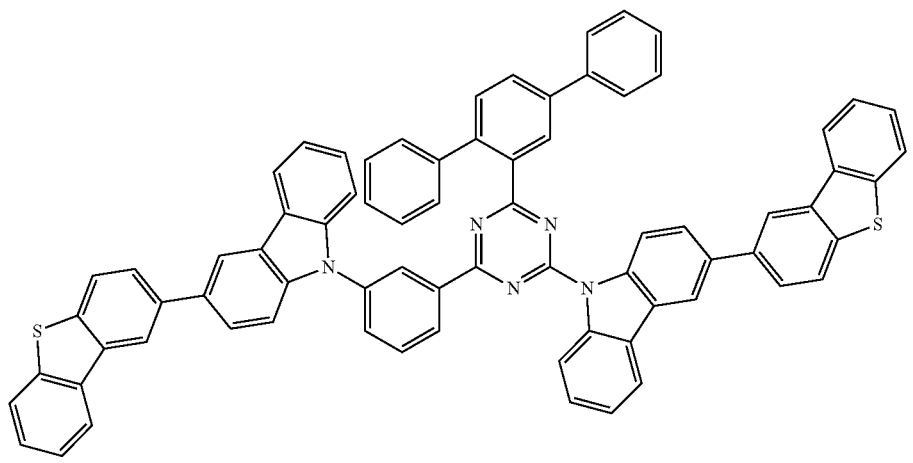
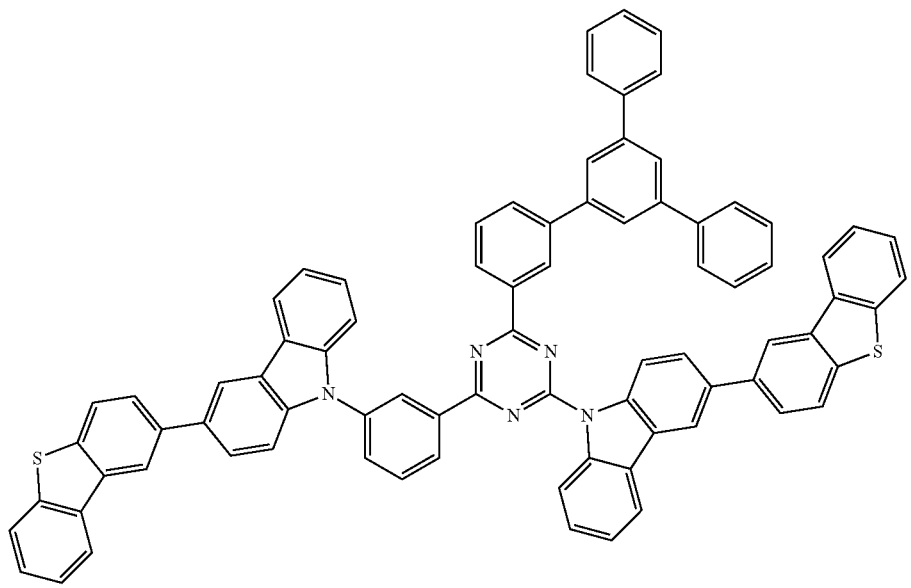

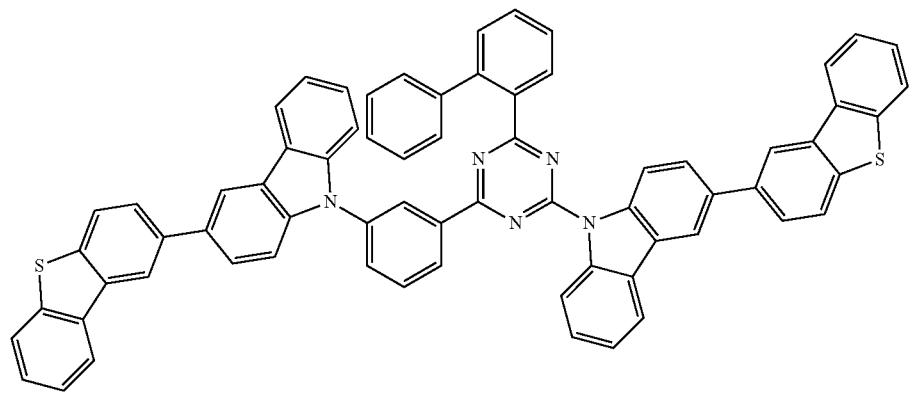
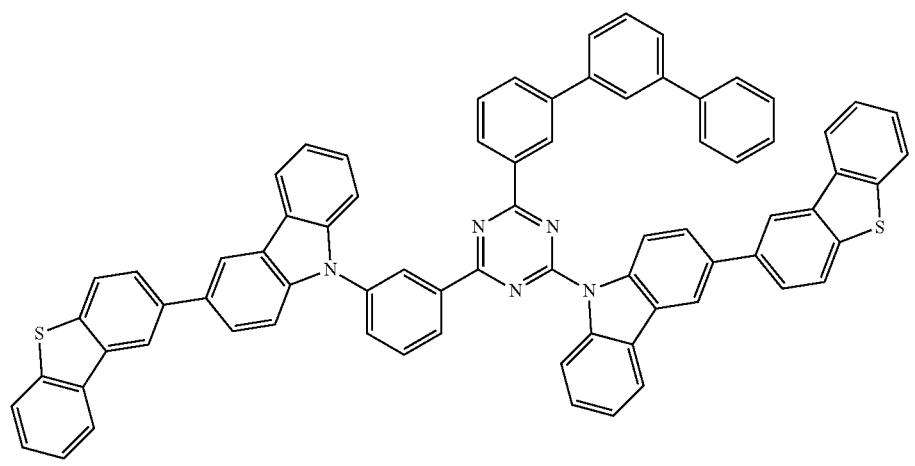
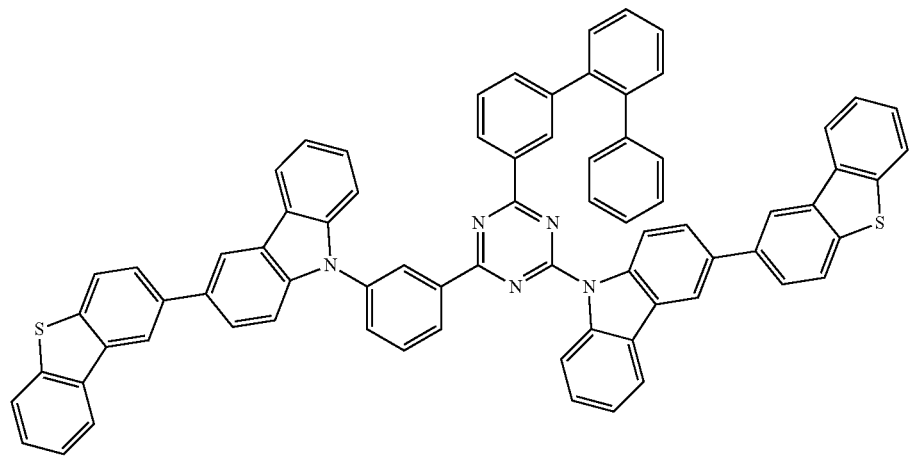

[Formula 94]
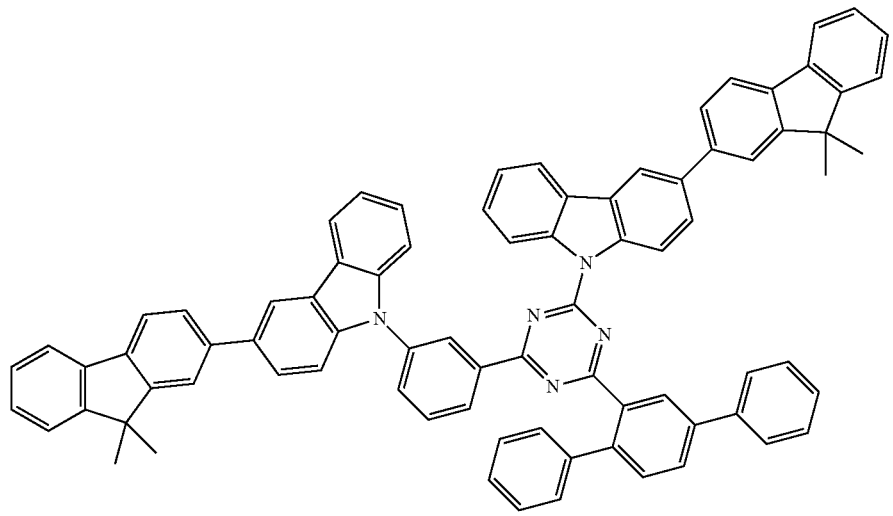
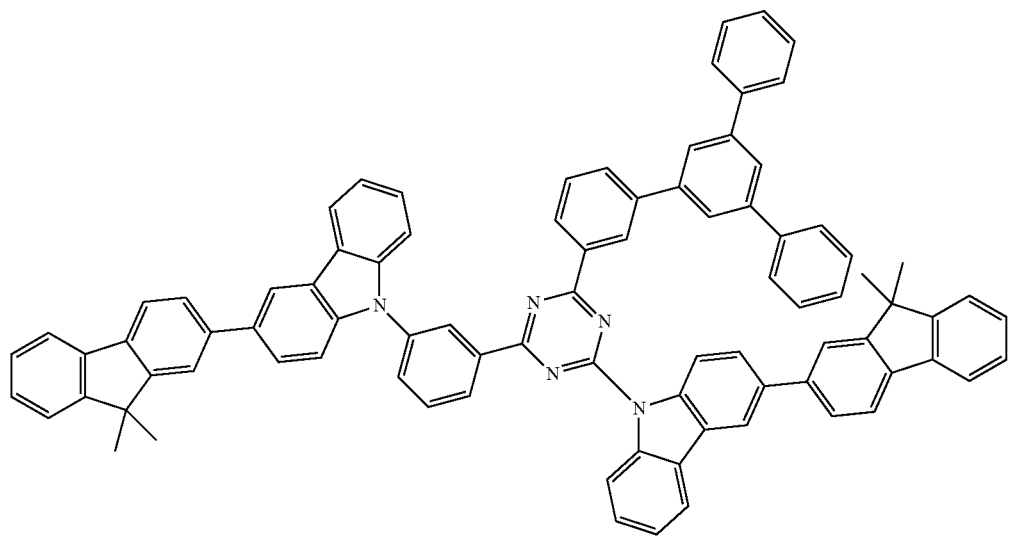
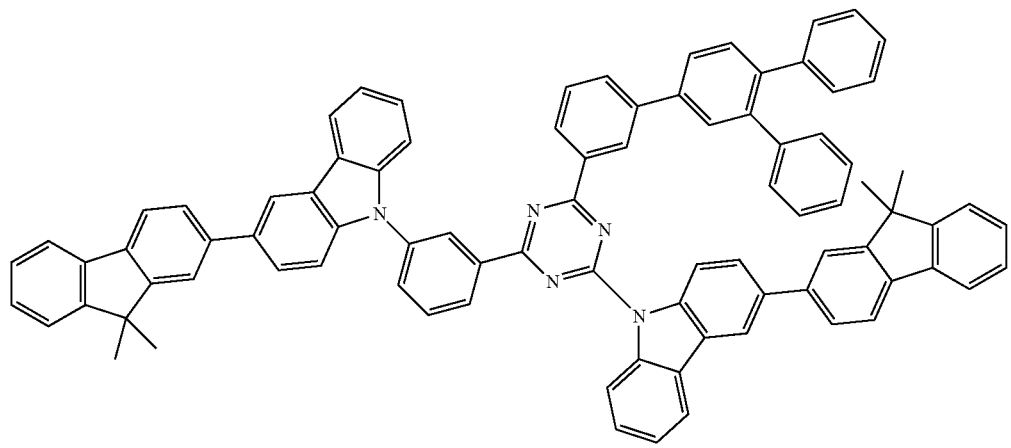

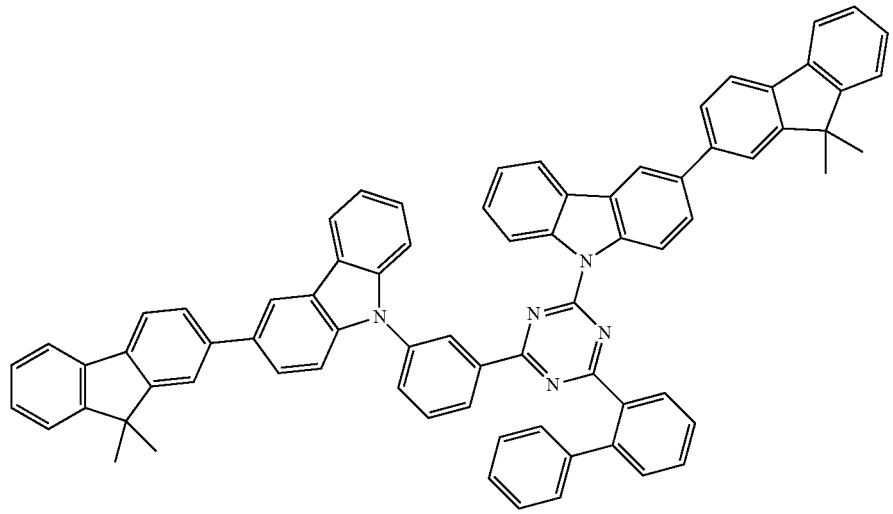
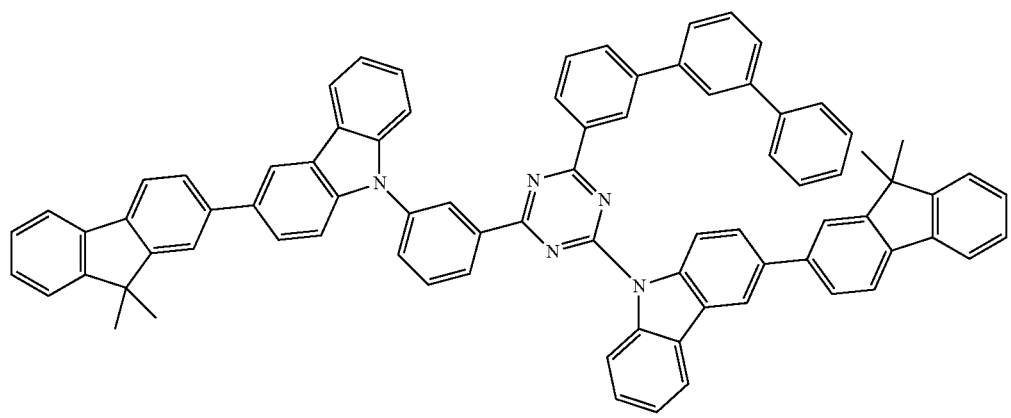
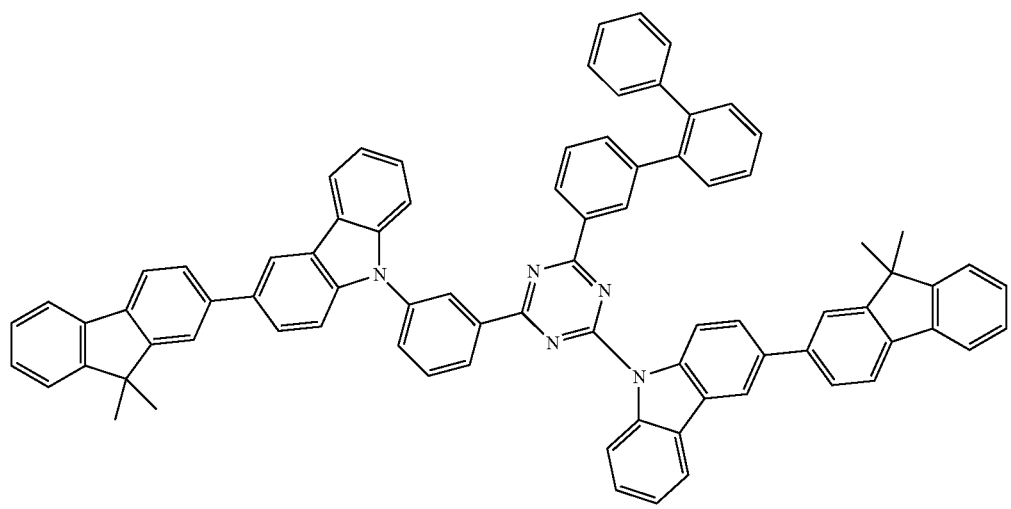

[Formula 95]
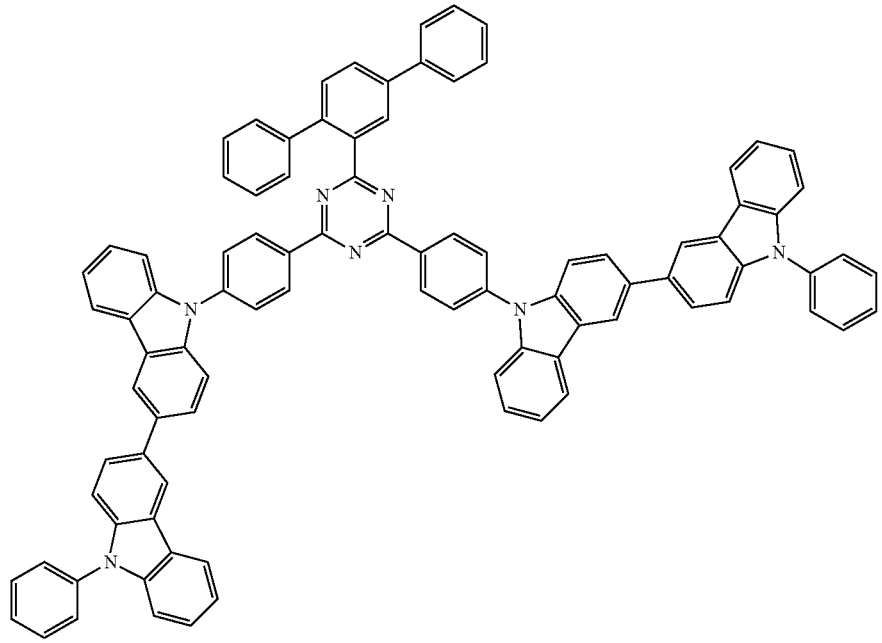
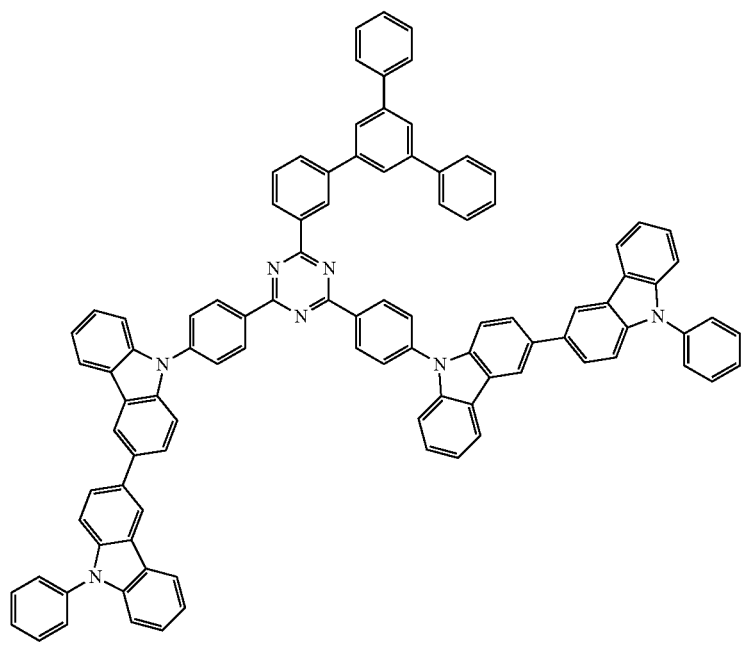

-continued
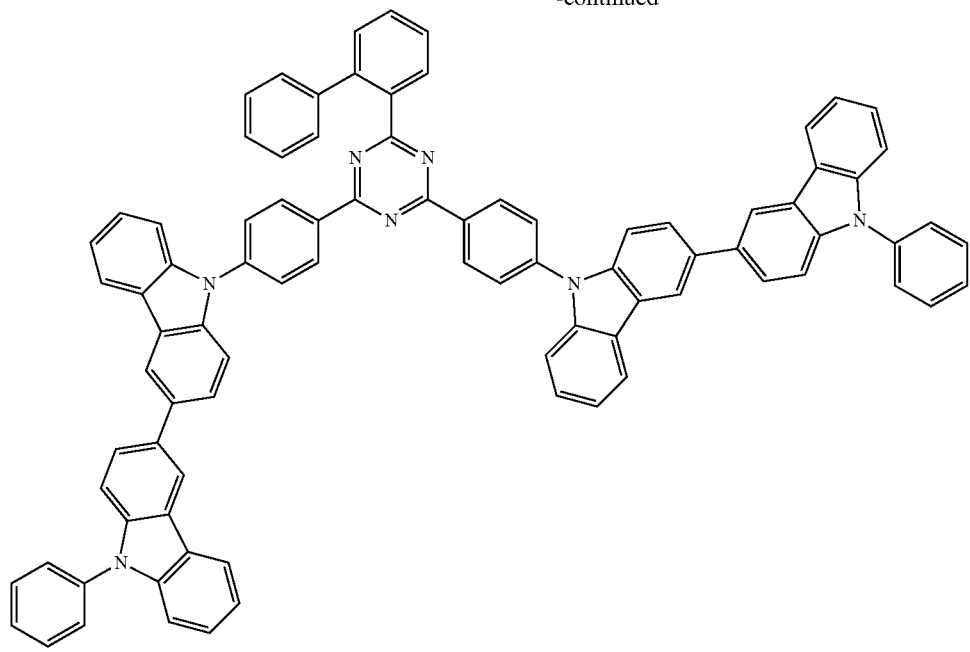
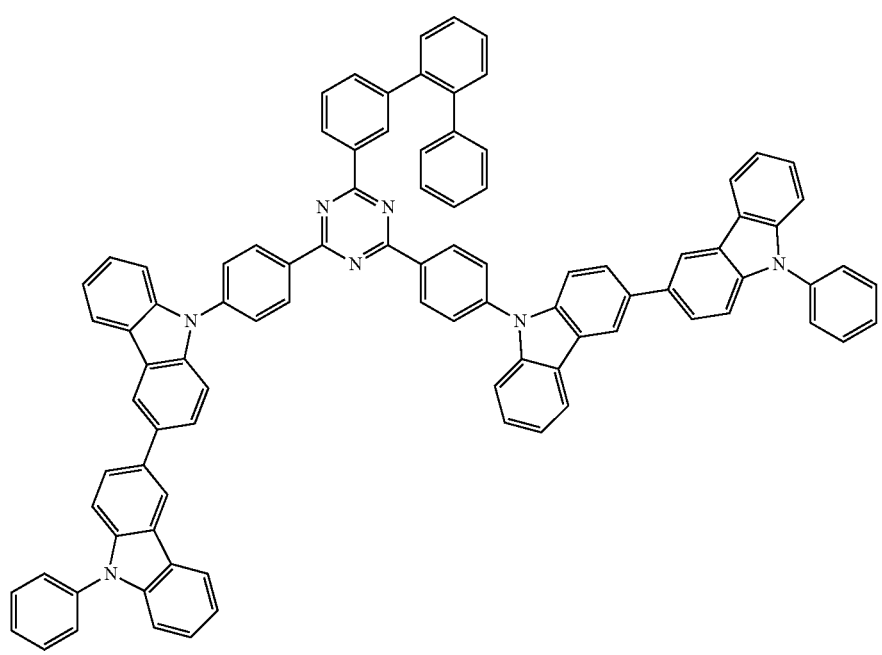

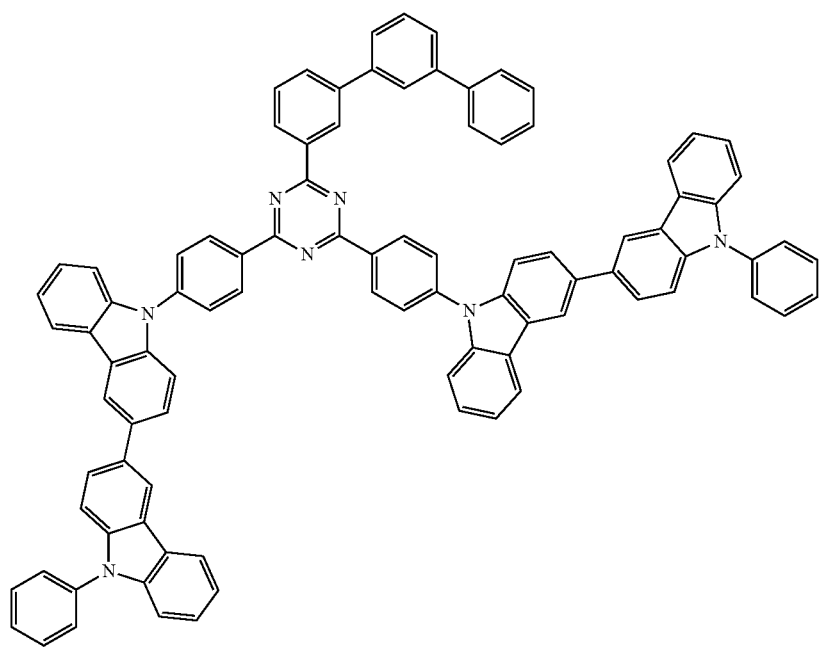
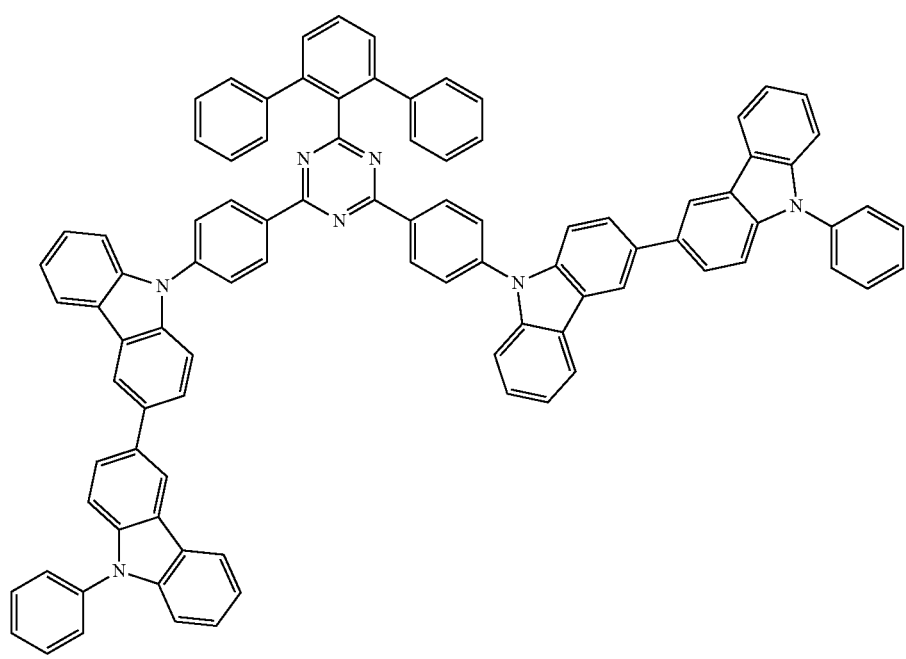

[Formula 96]
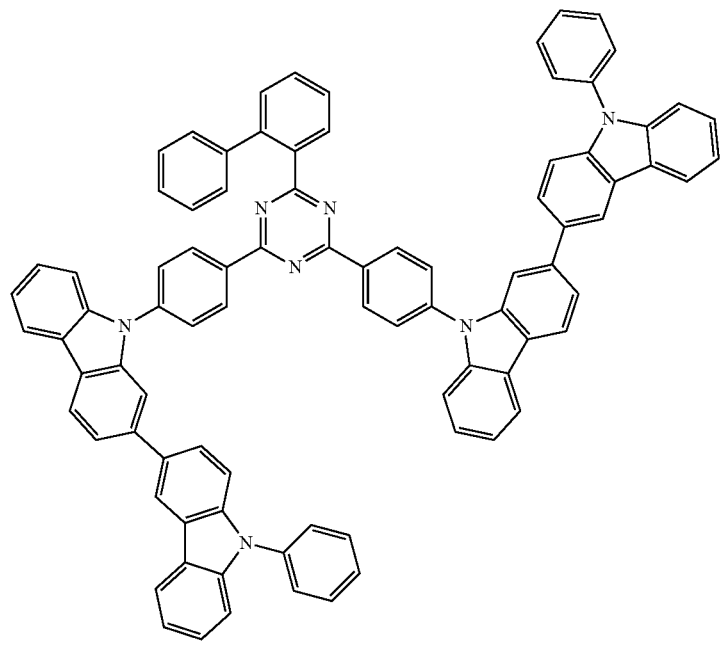
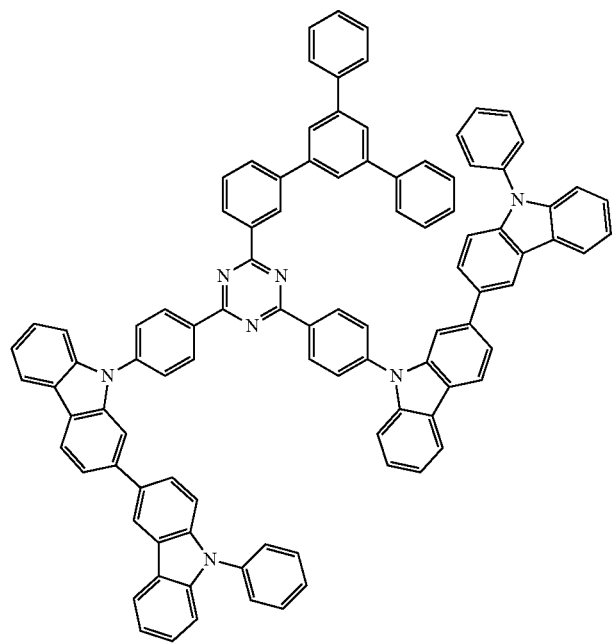

321
-continued
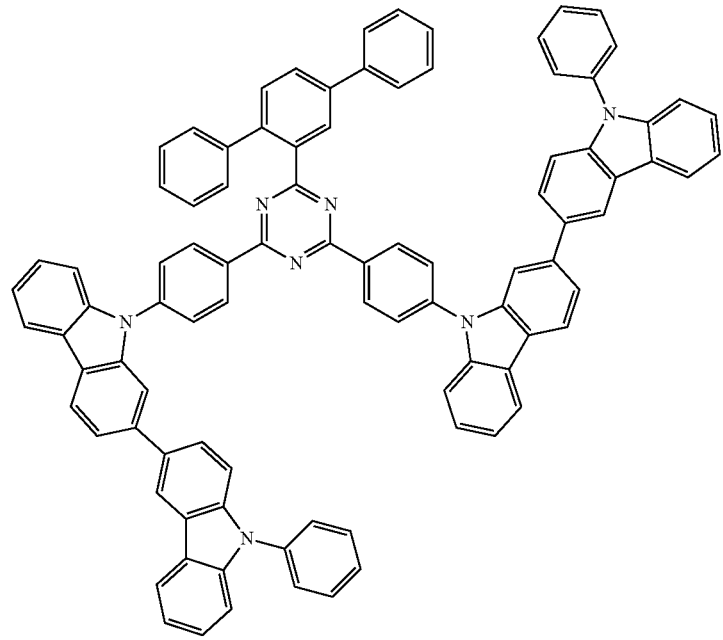
322
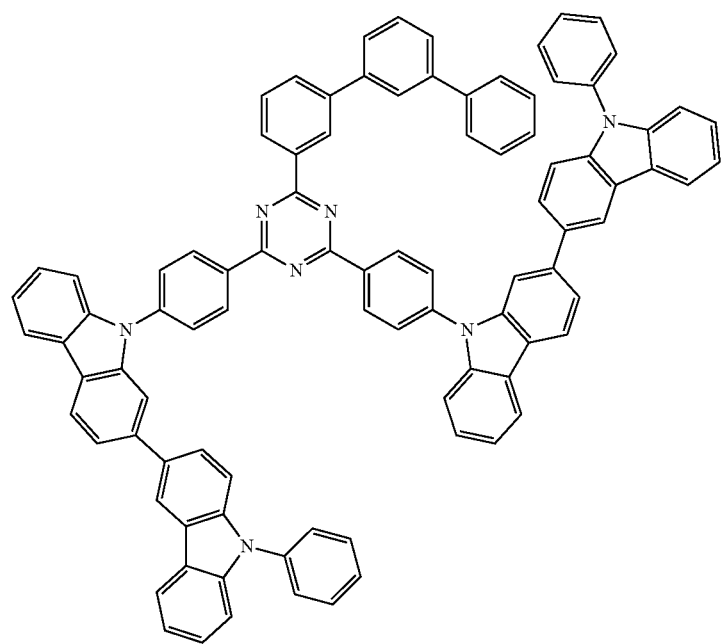

323                                   324
           -continued
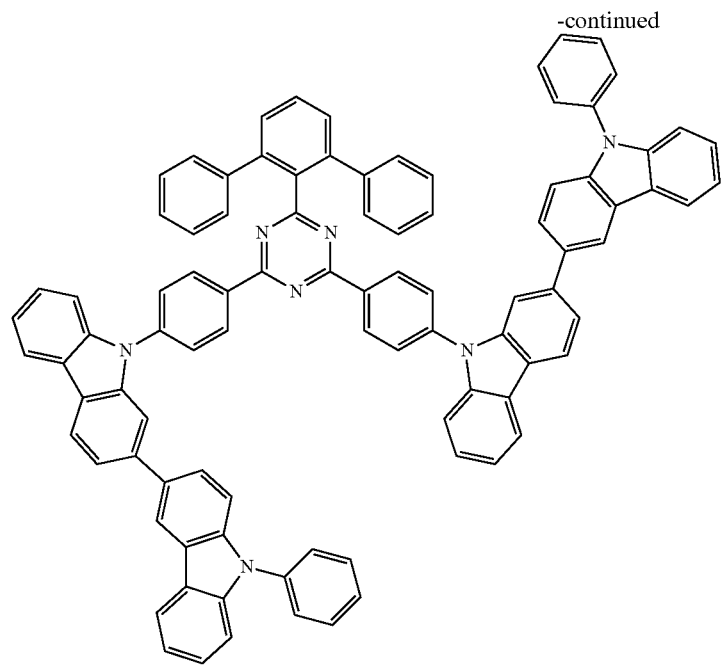
[Formula 97]
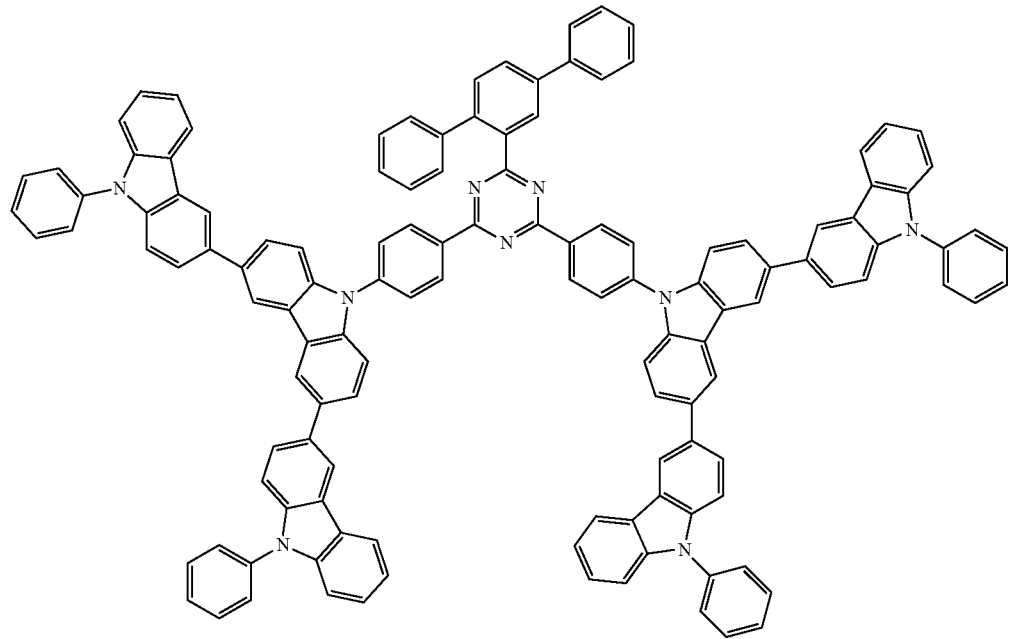

-continued
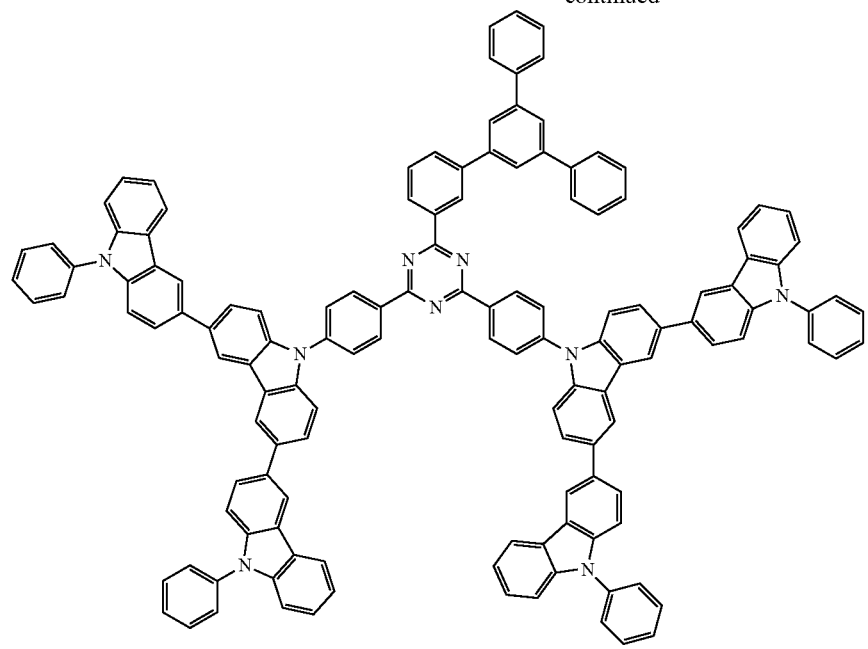
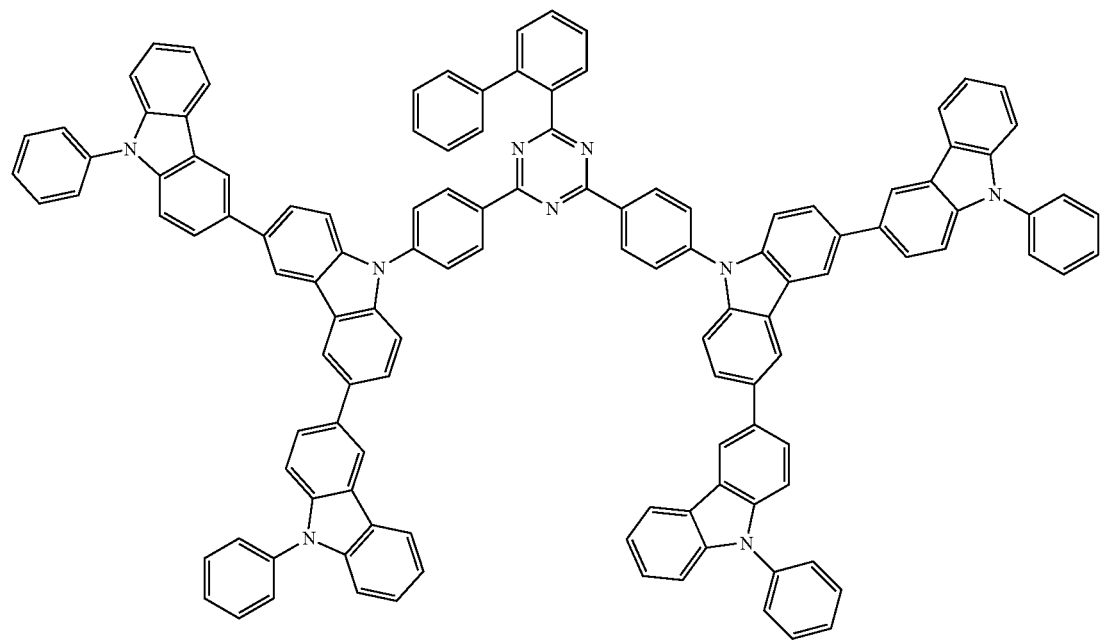

-continued
327
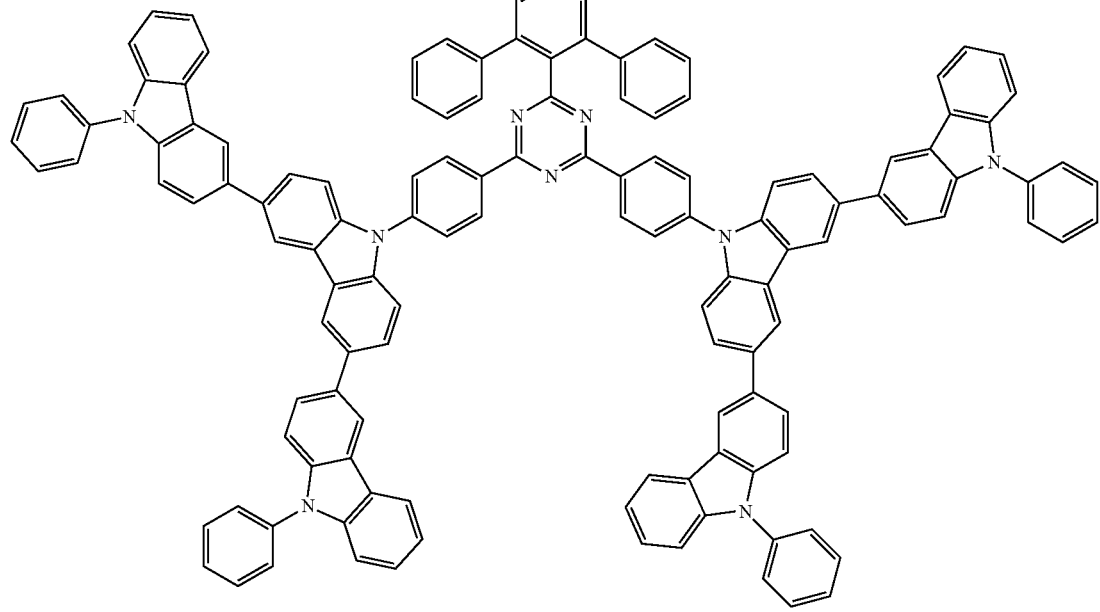
328
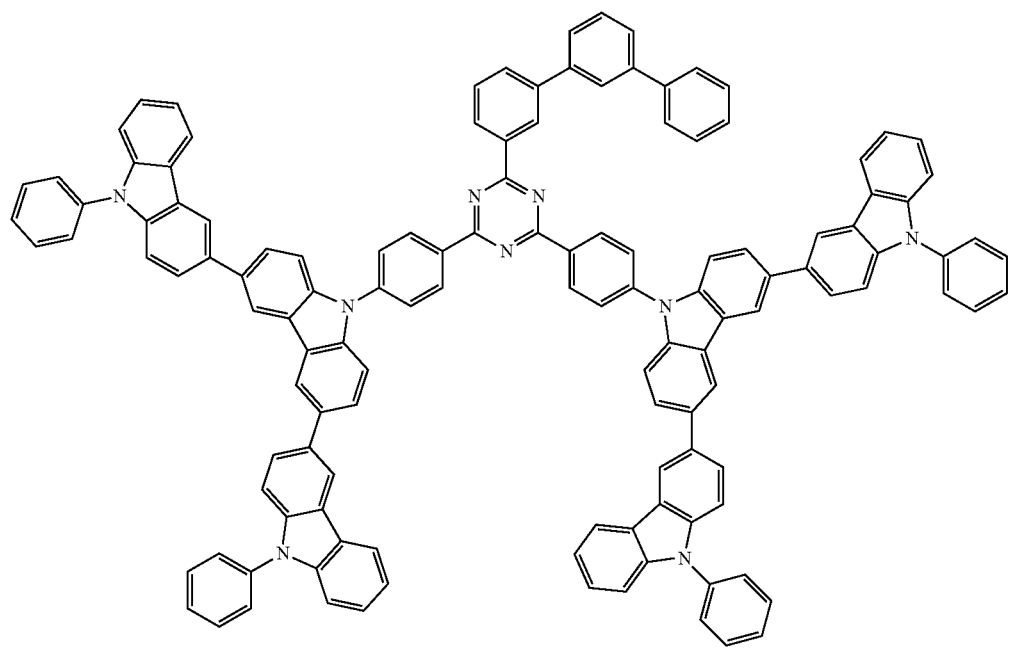

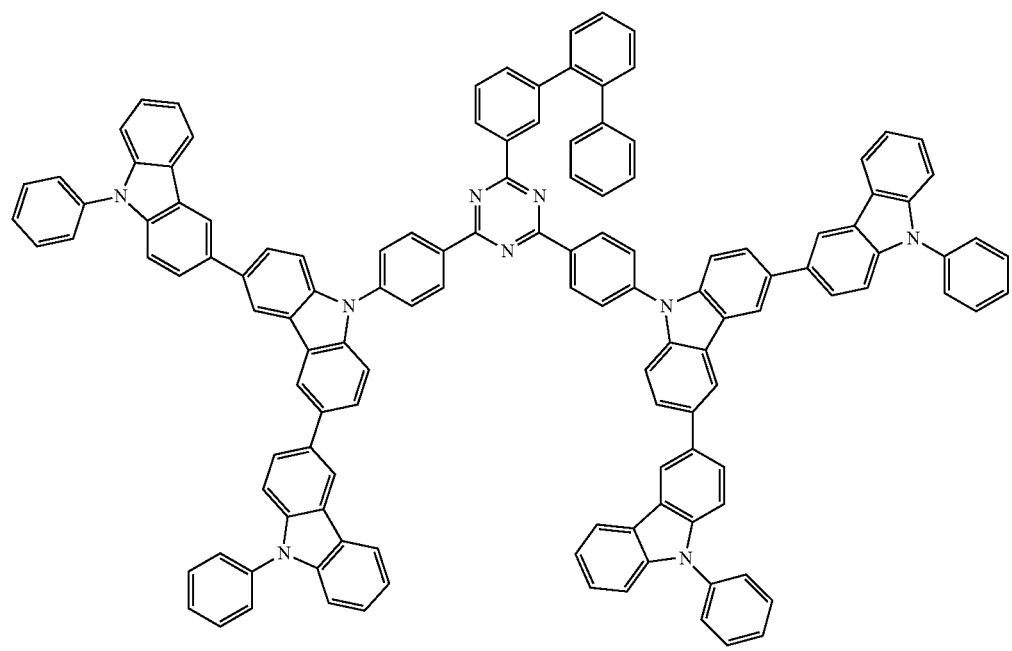
[Formula 98]
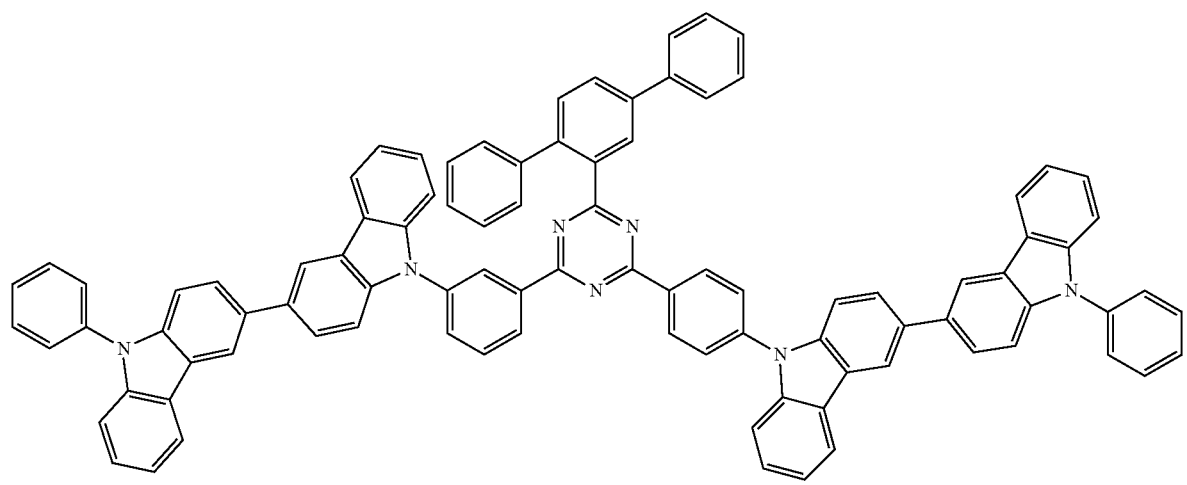

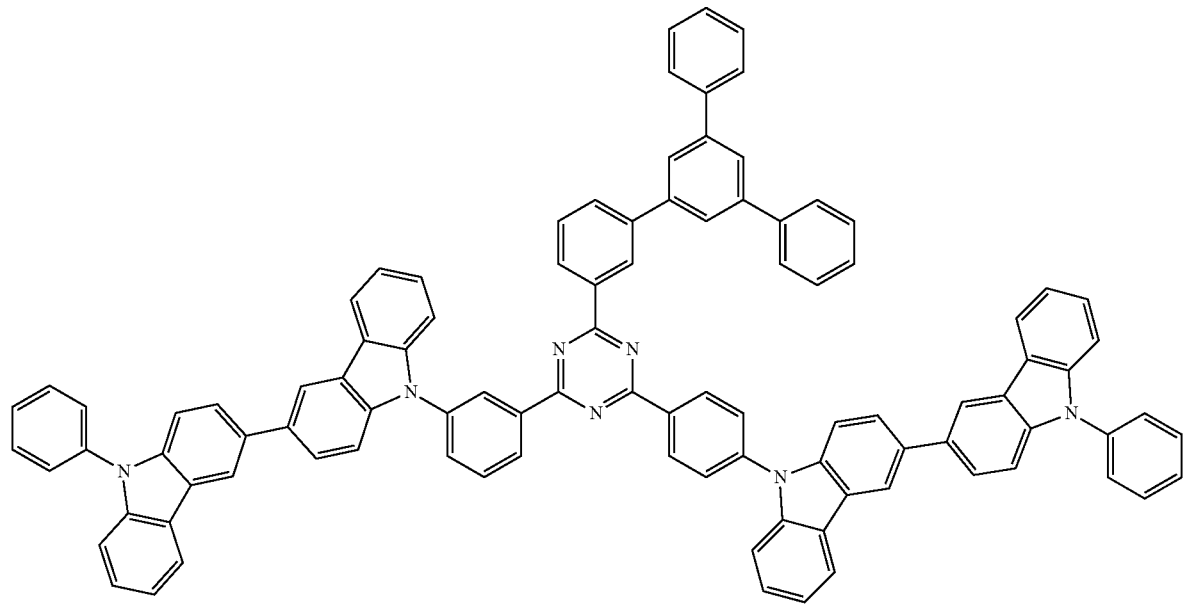
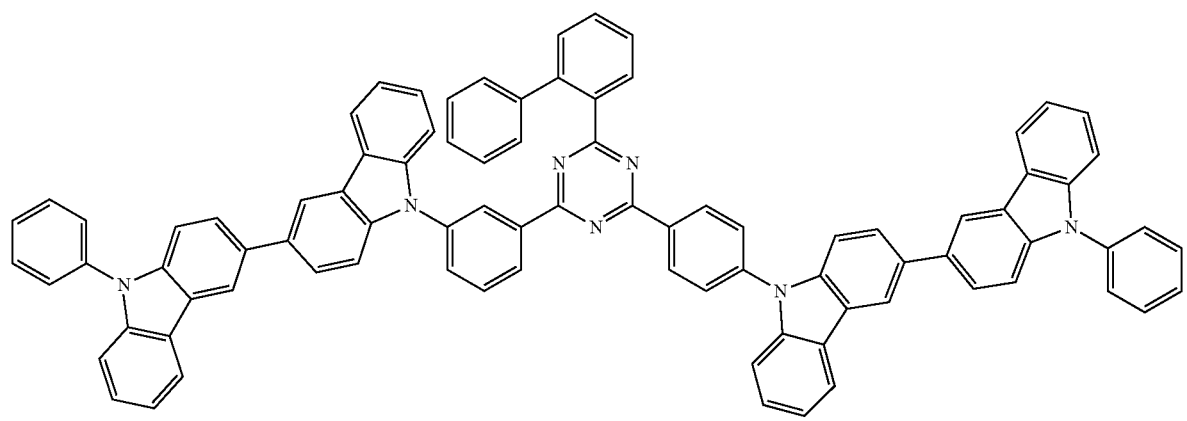
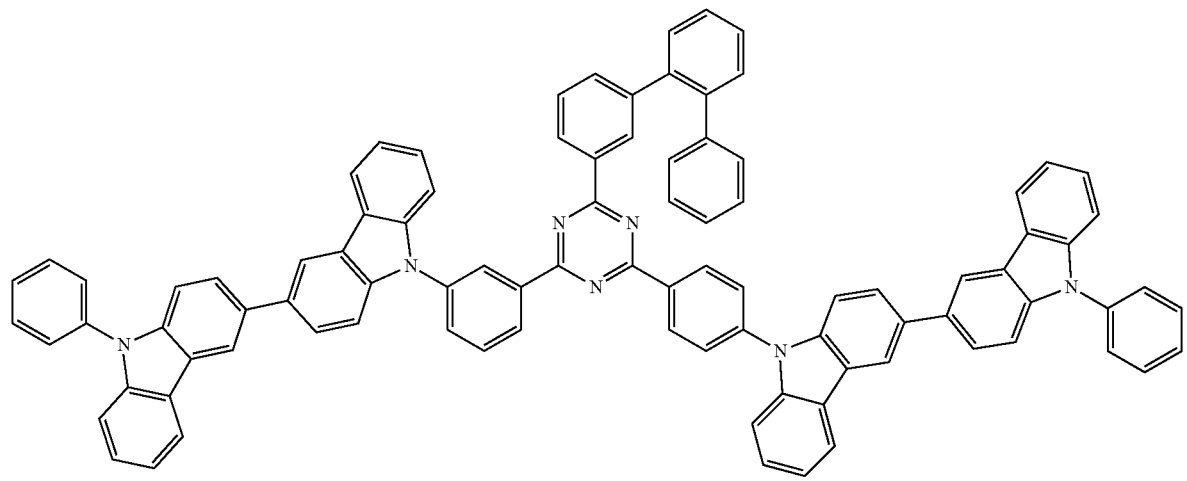

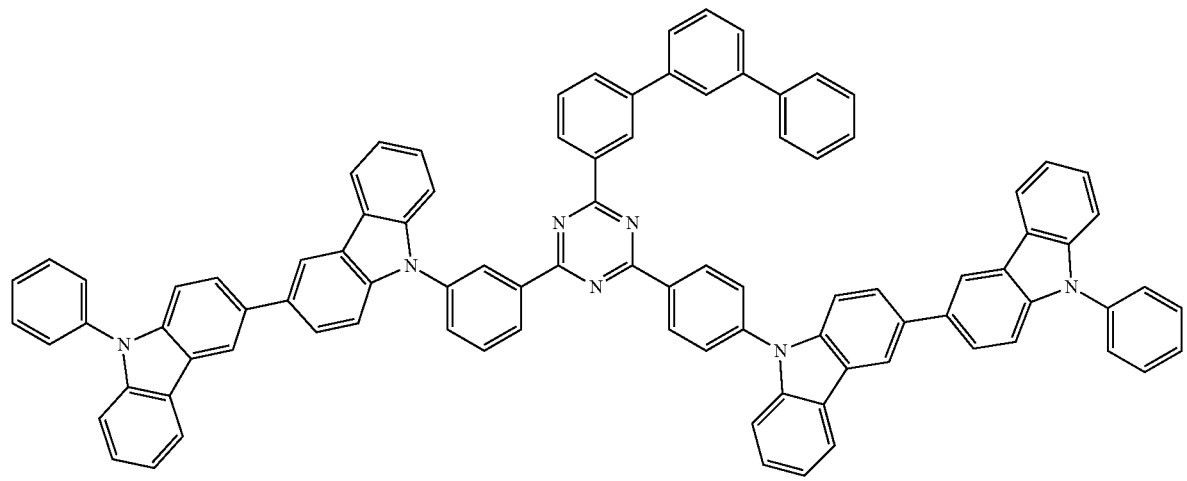
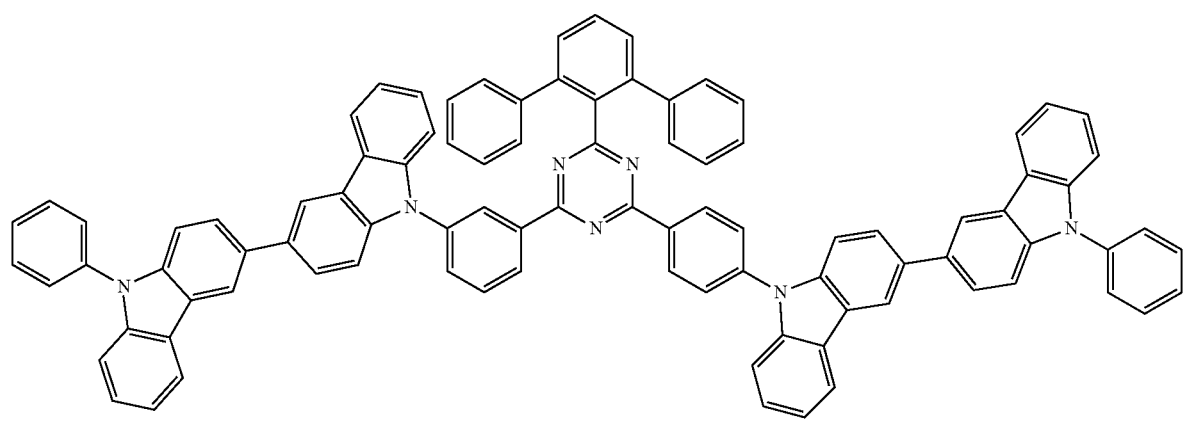
[Formula 99]
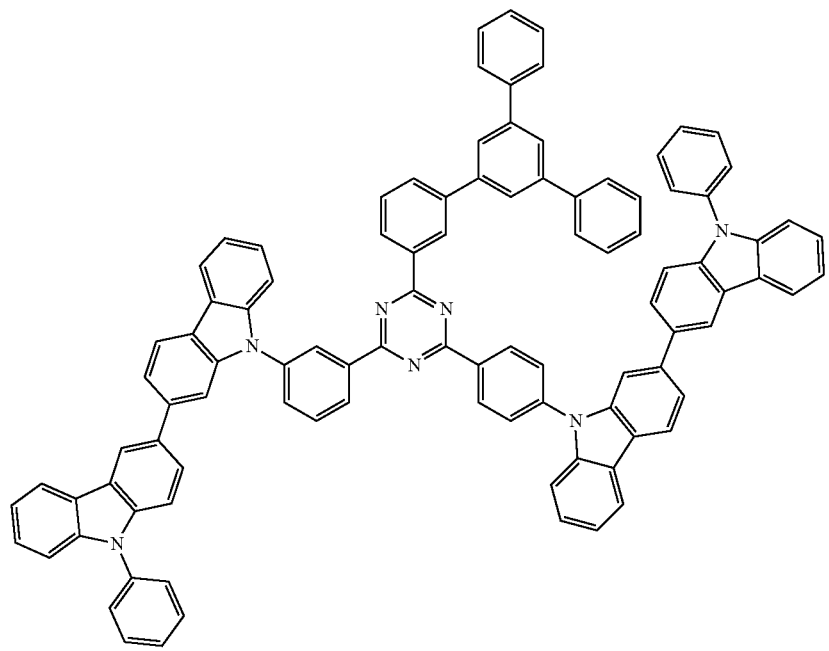

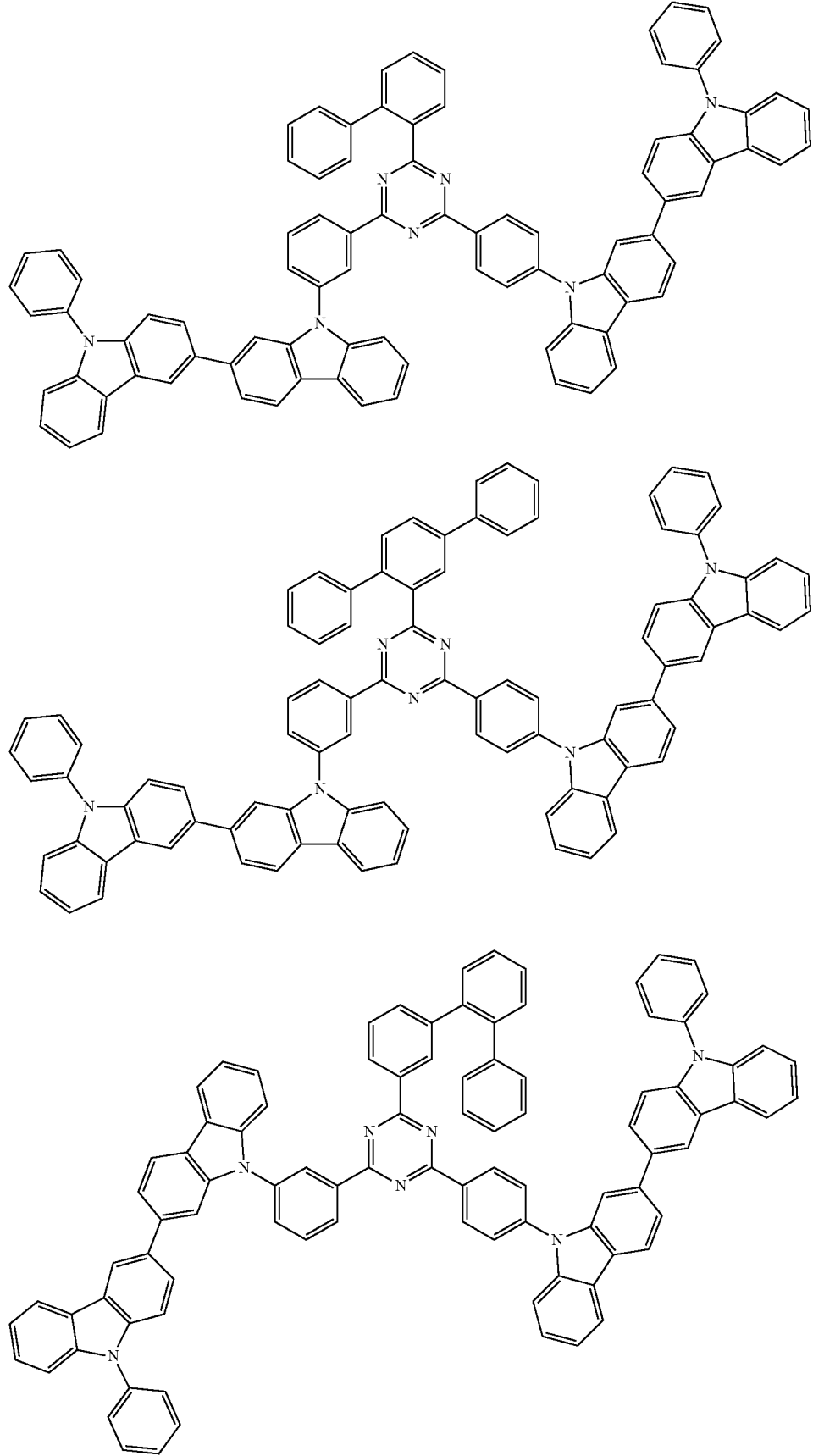

-continued
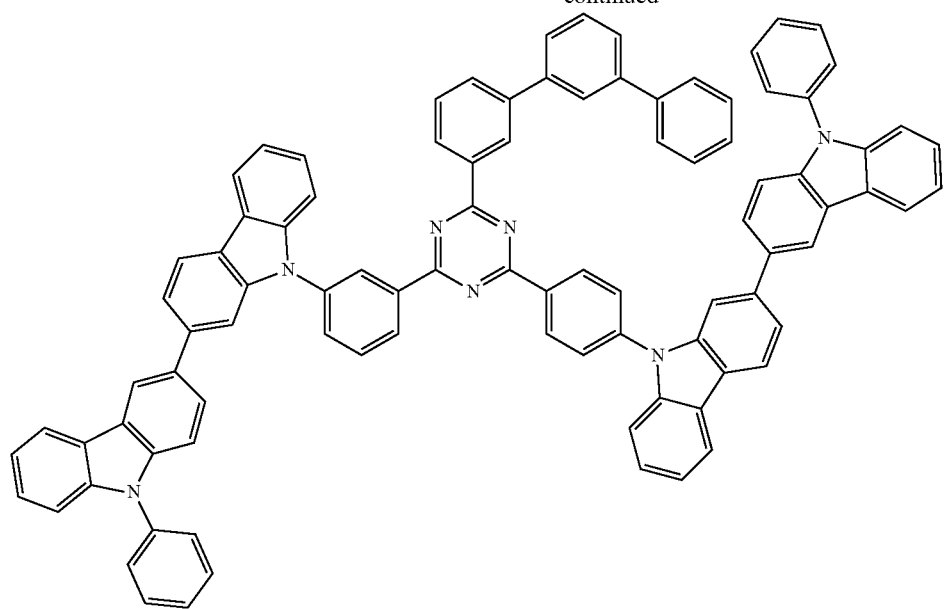
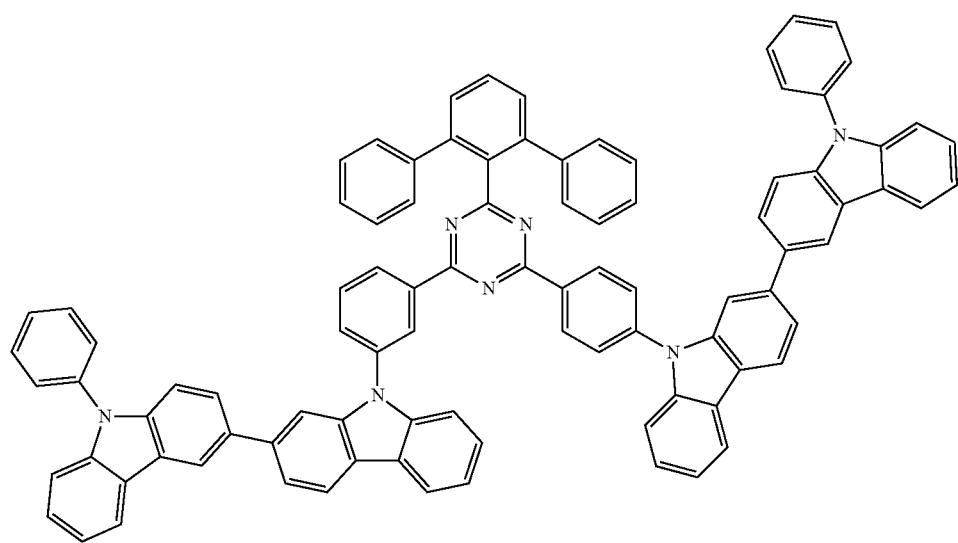

[Formula 100]
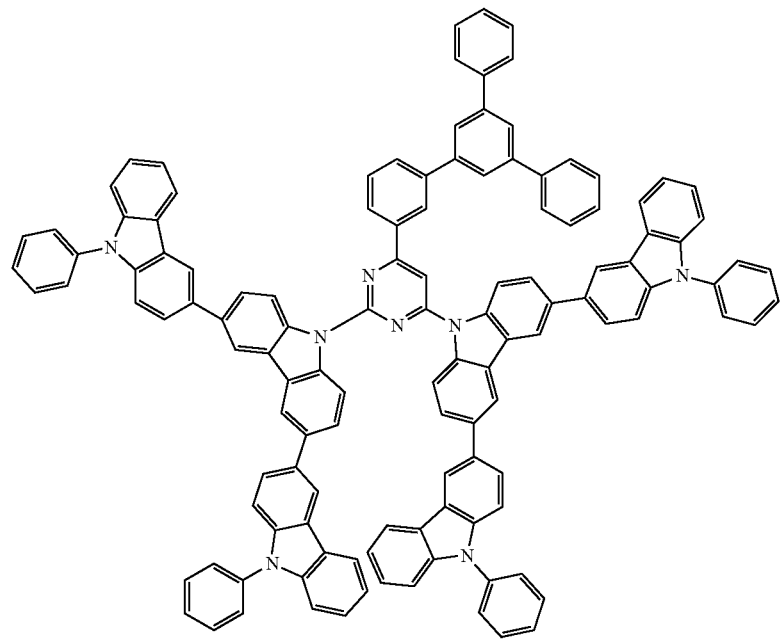
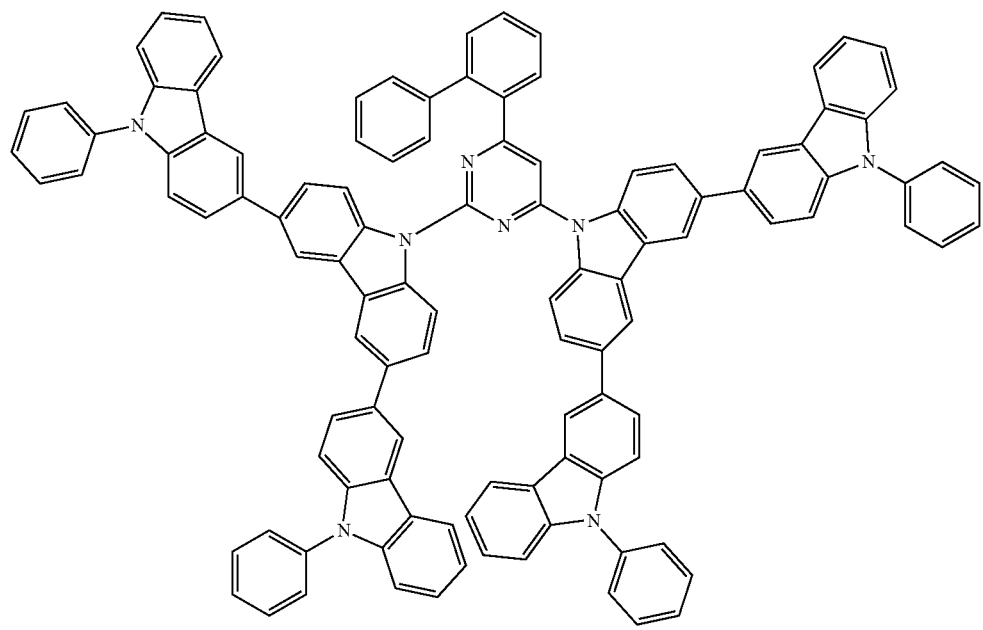

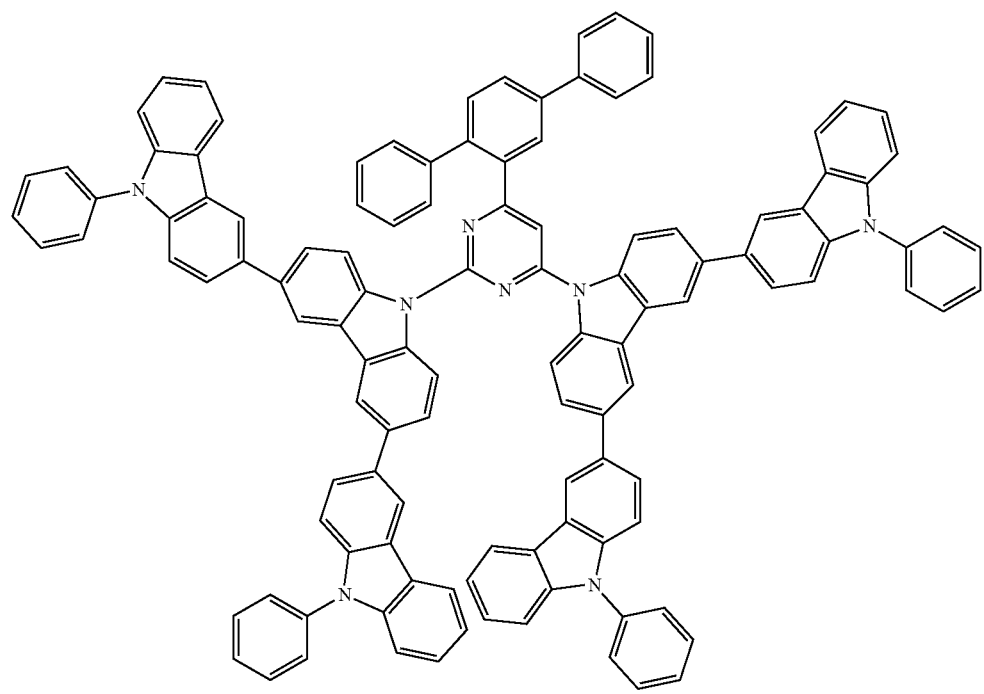
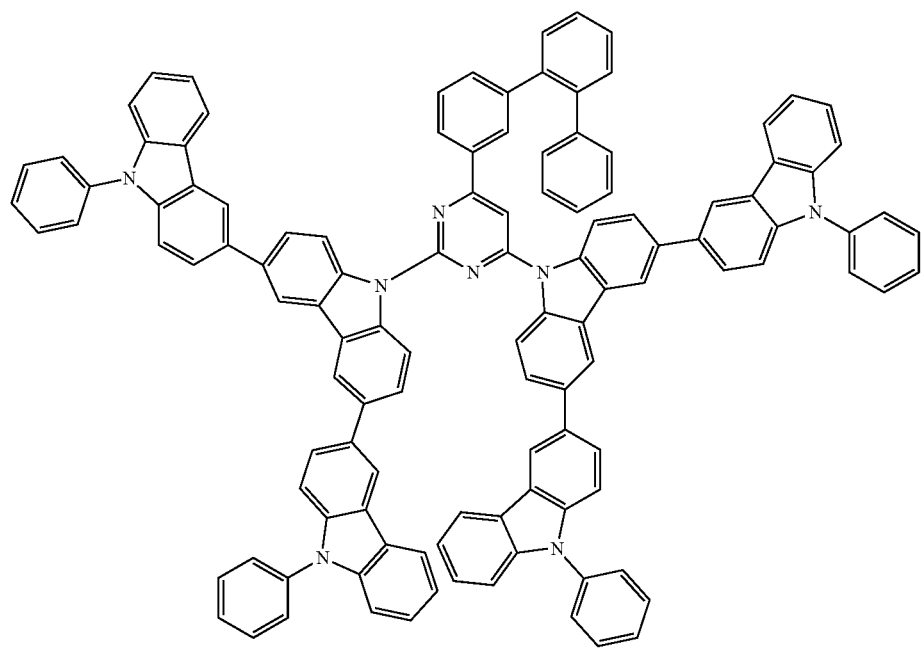

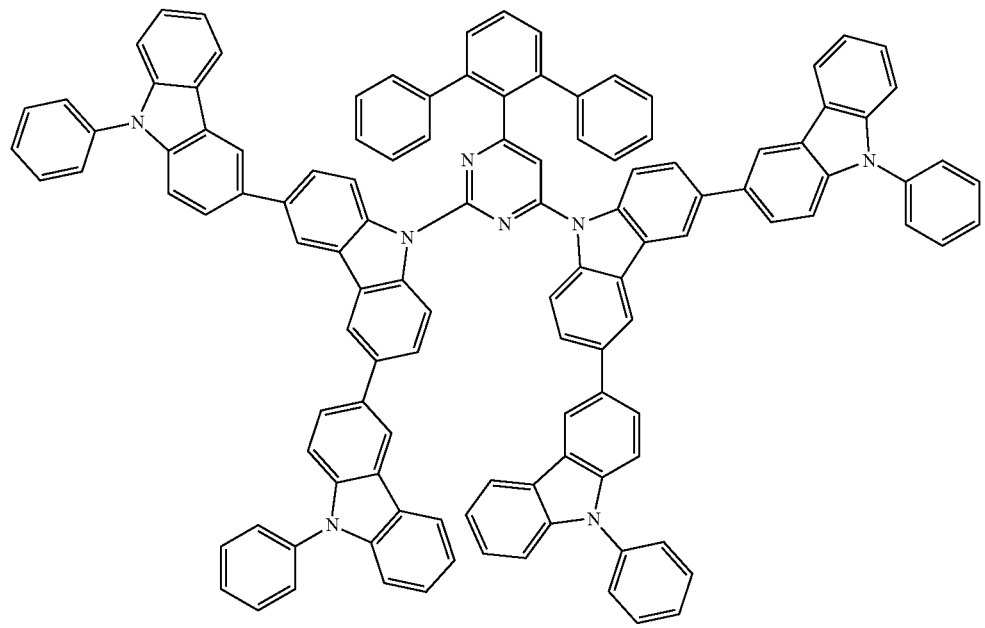
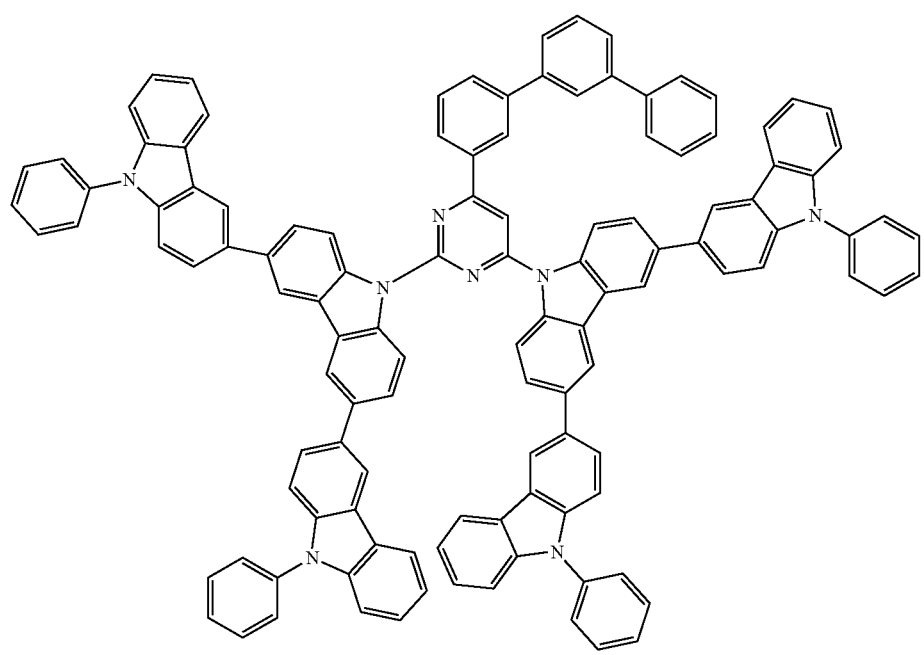

[Formula 101]
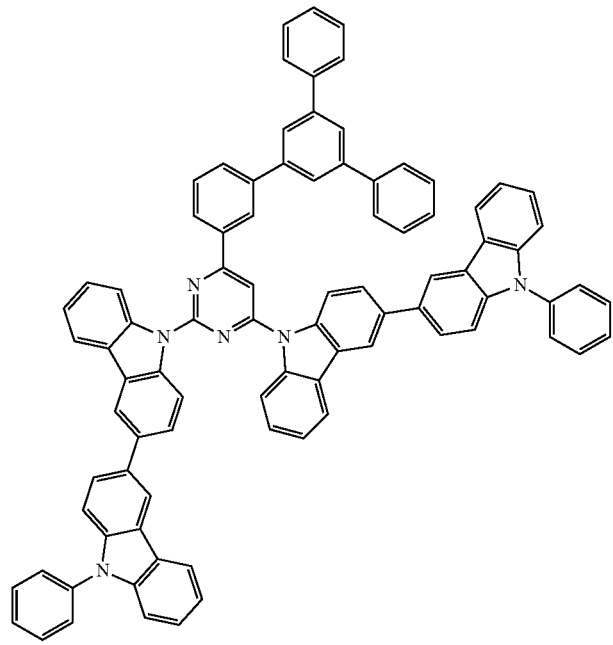
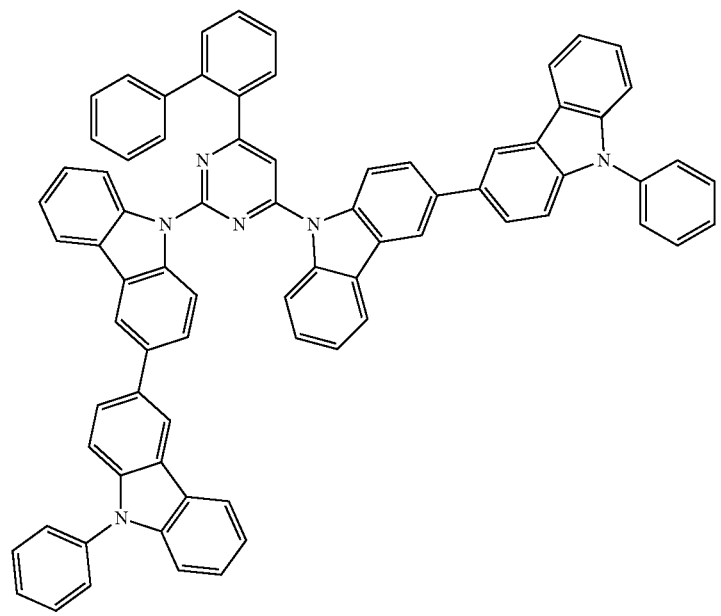

-continued
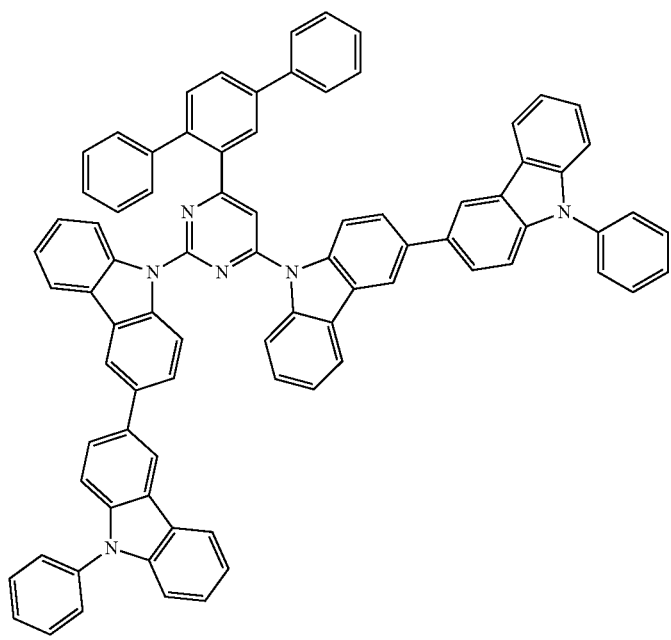
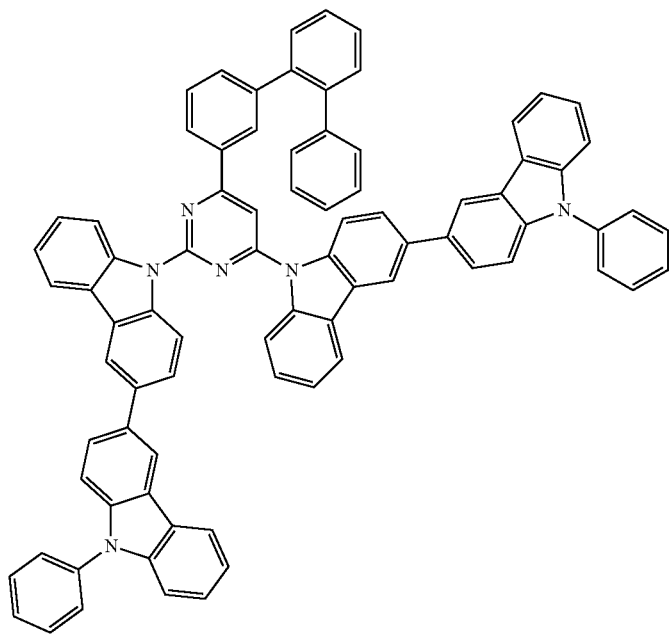

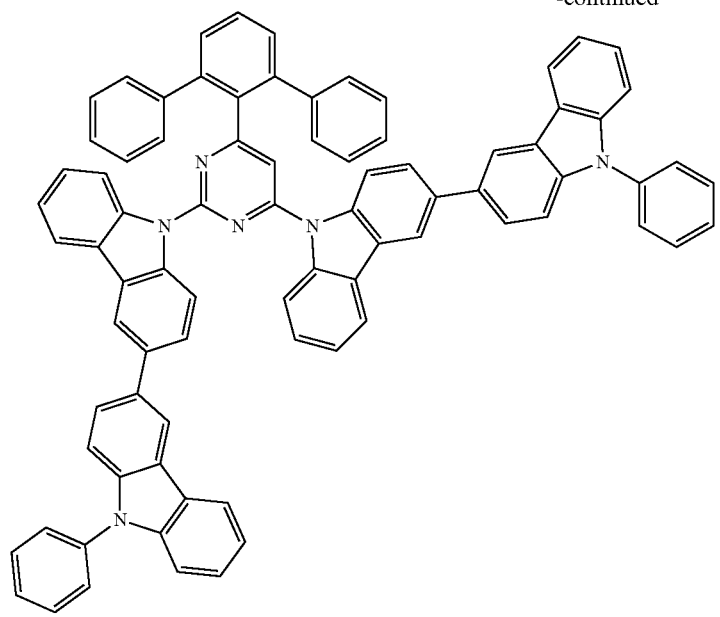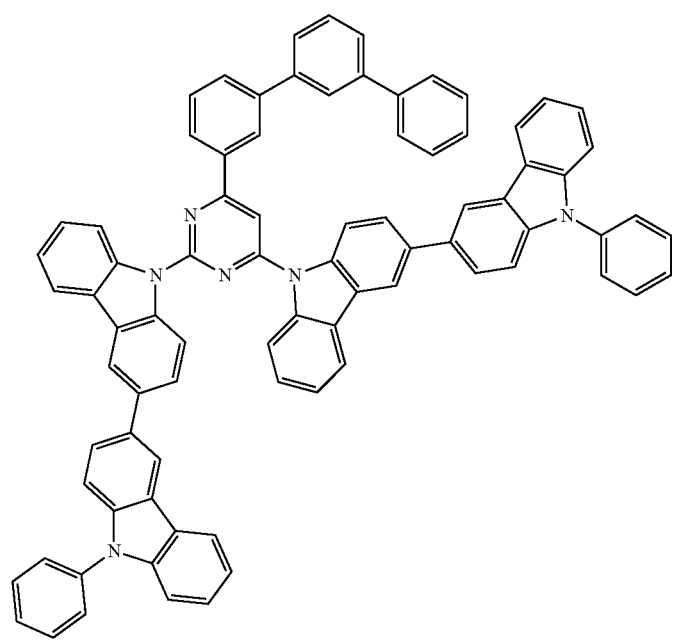

[Formula 102]
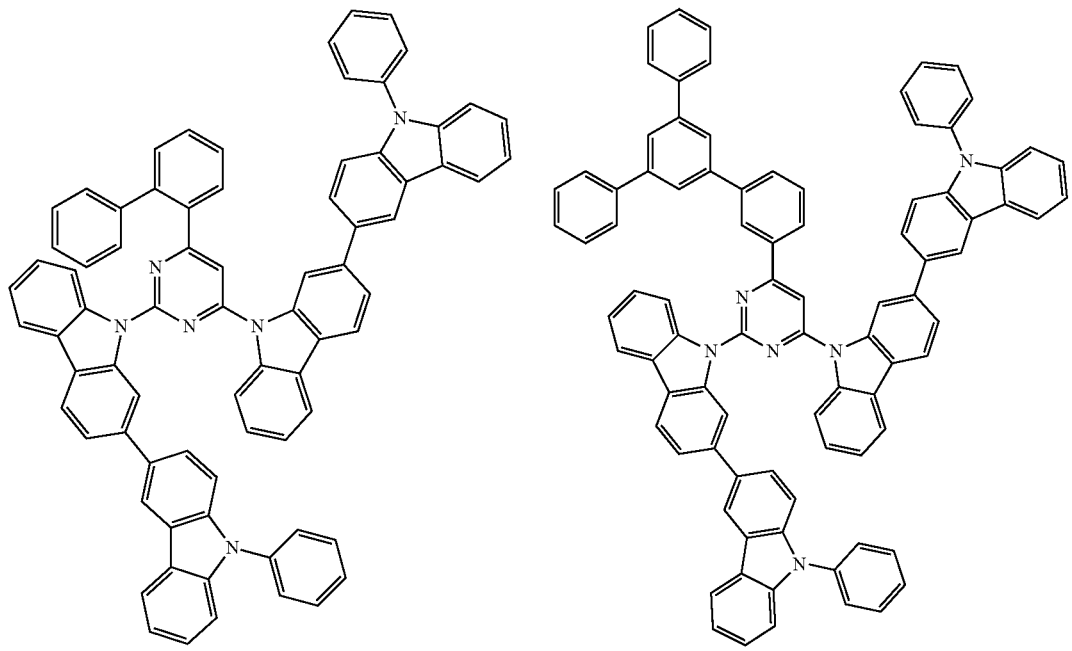
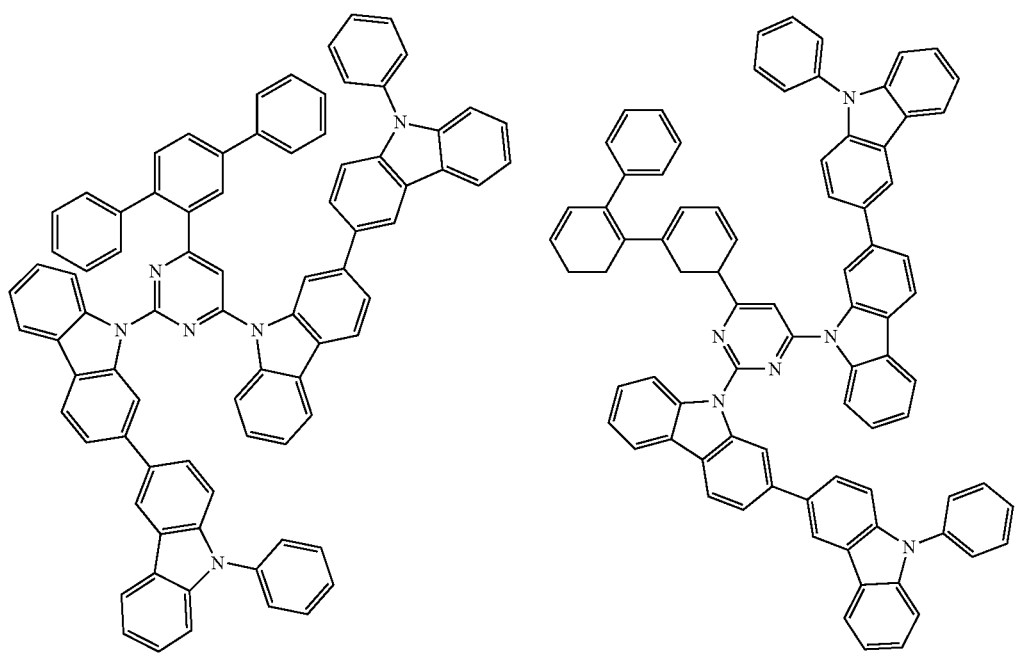

-continued
353
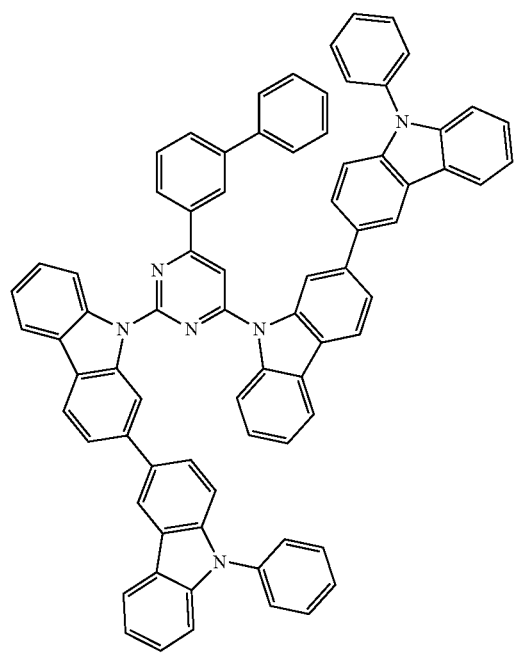
354
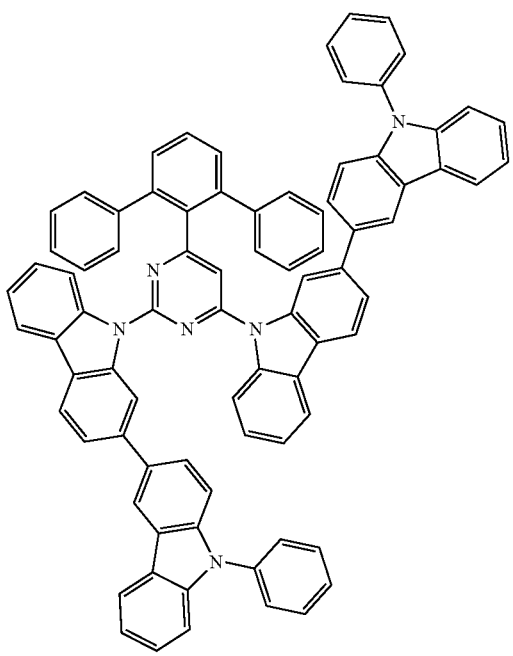
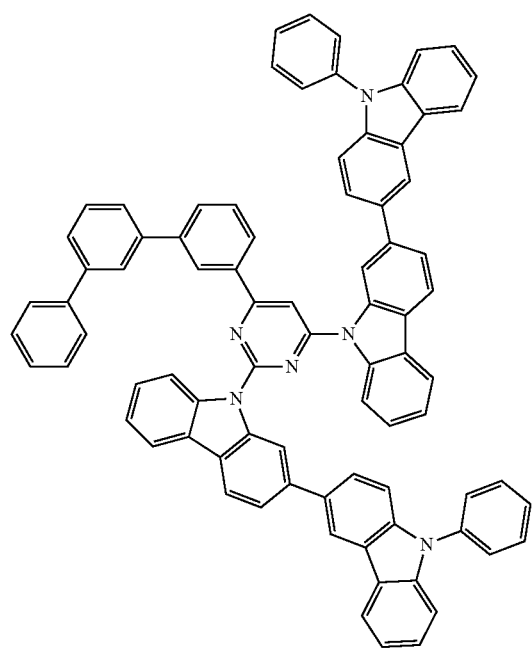

[Formula 103]
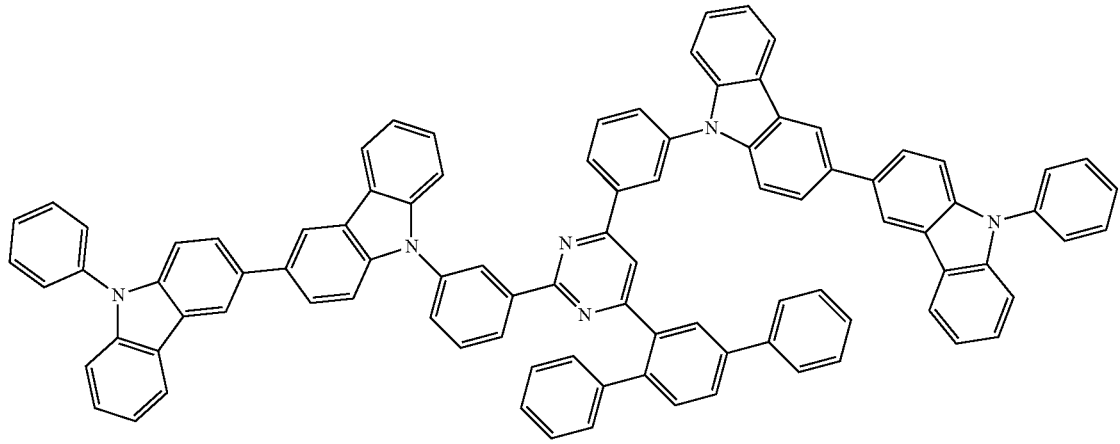
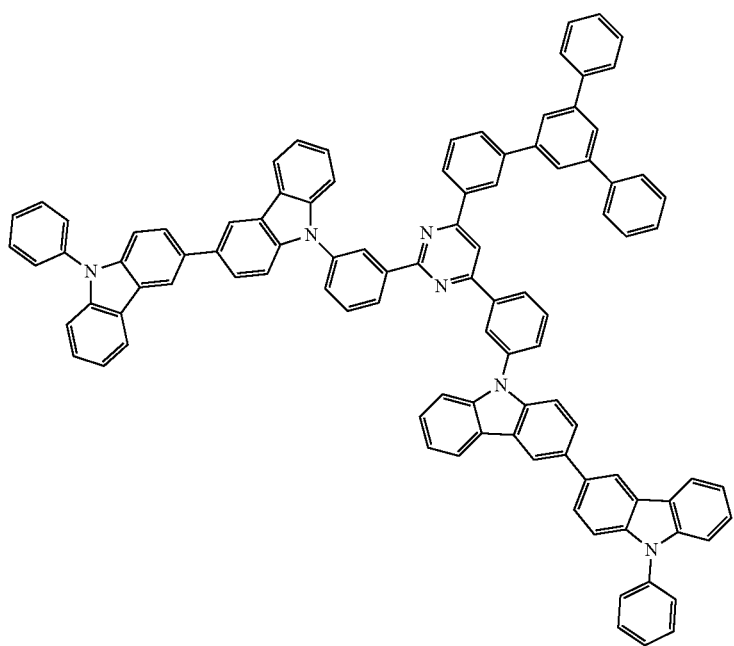
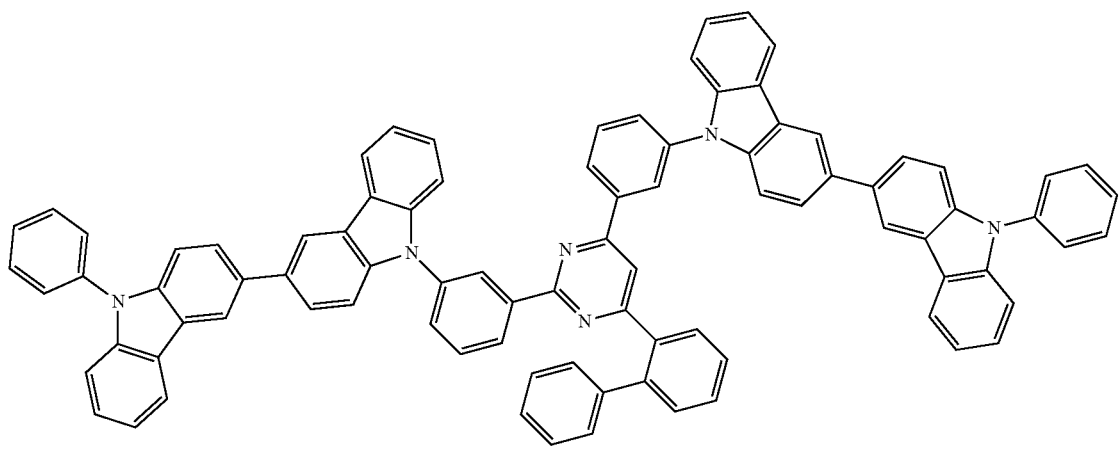

-continued
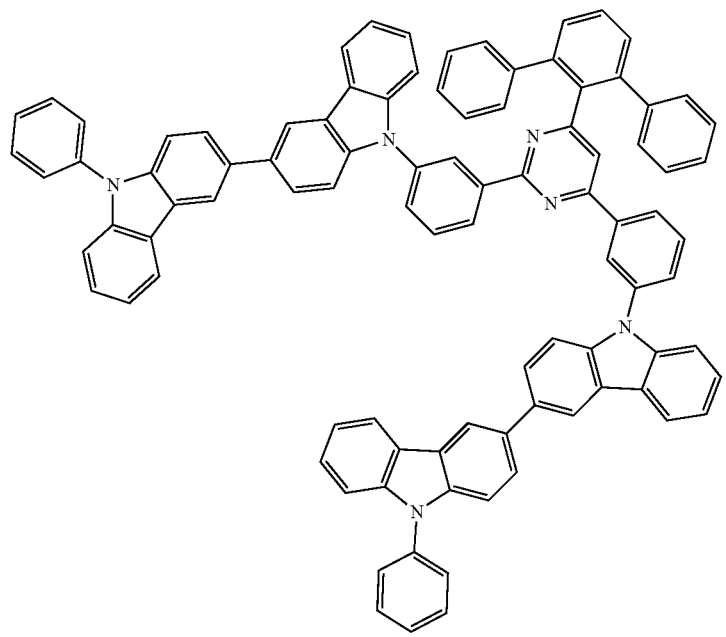
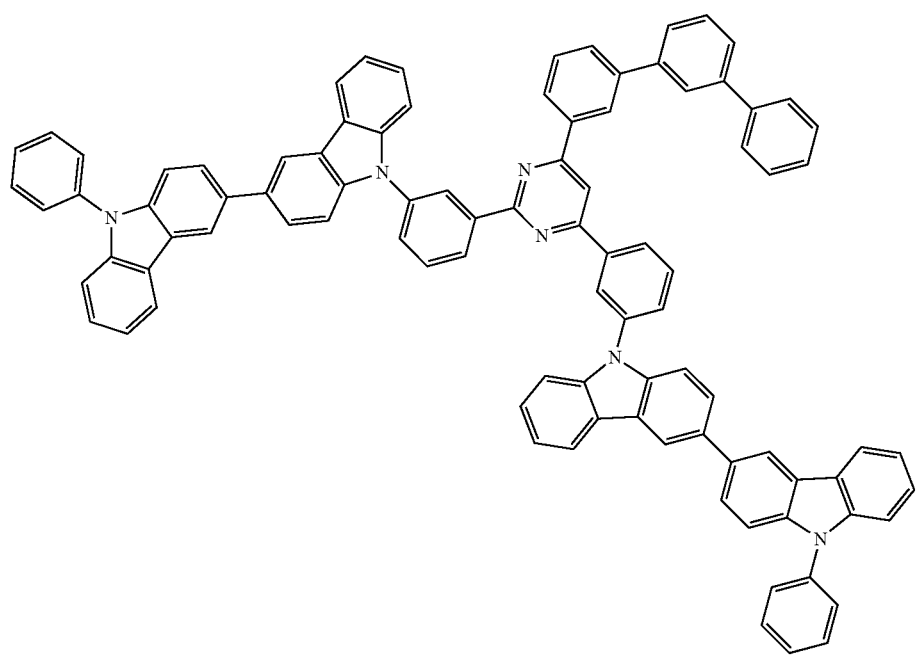

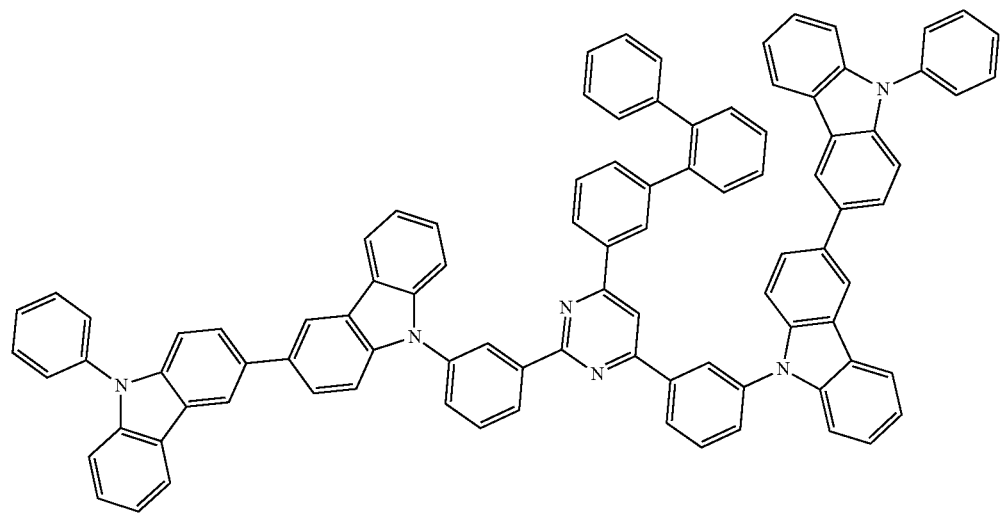
[Formula 104]
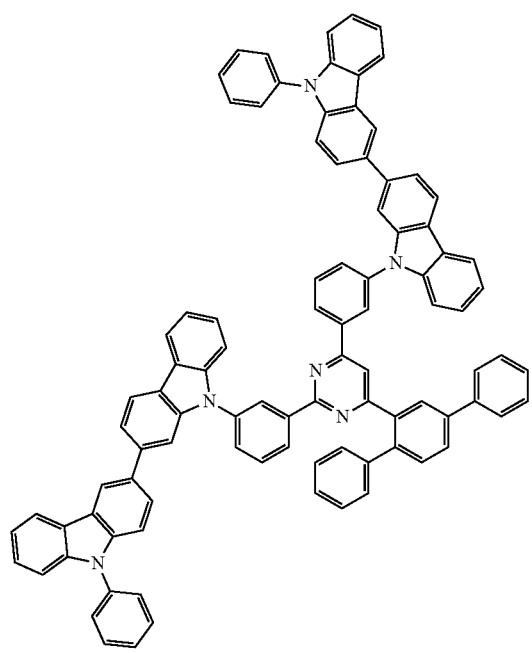

-continued
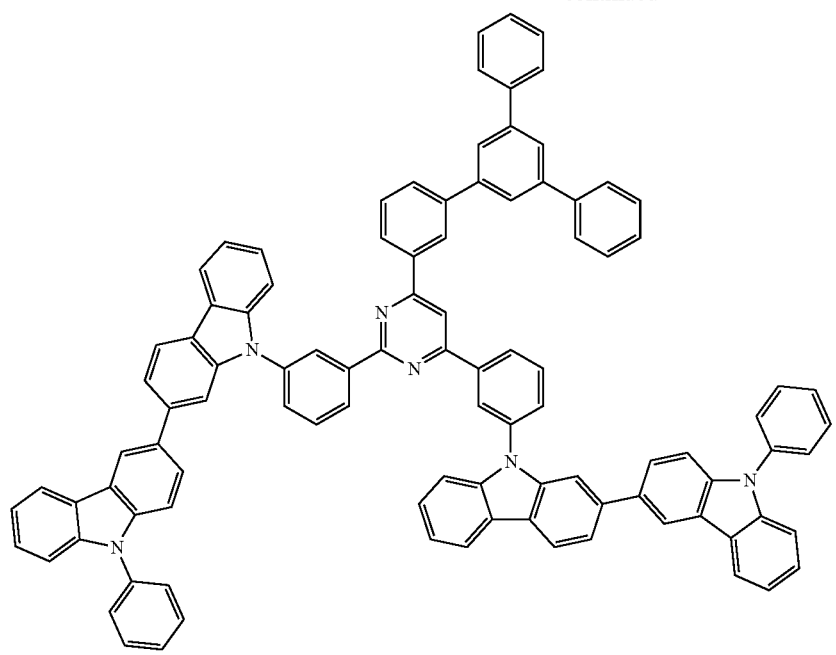
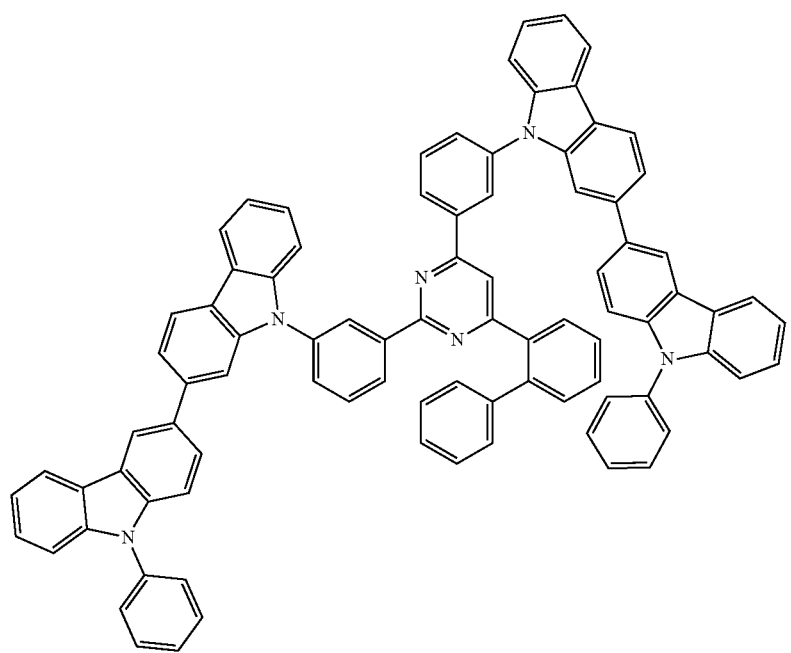

-continued
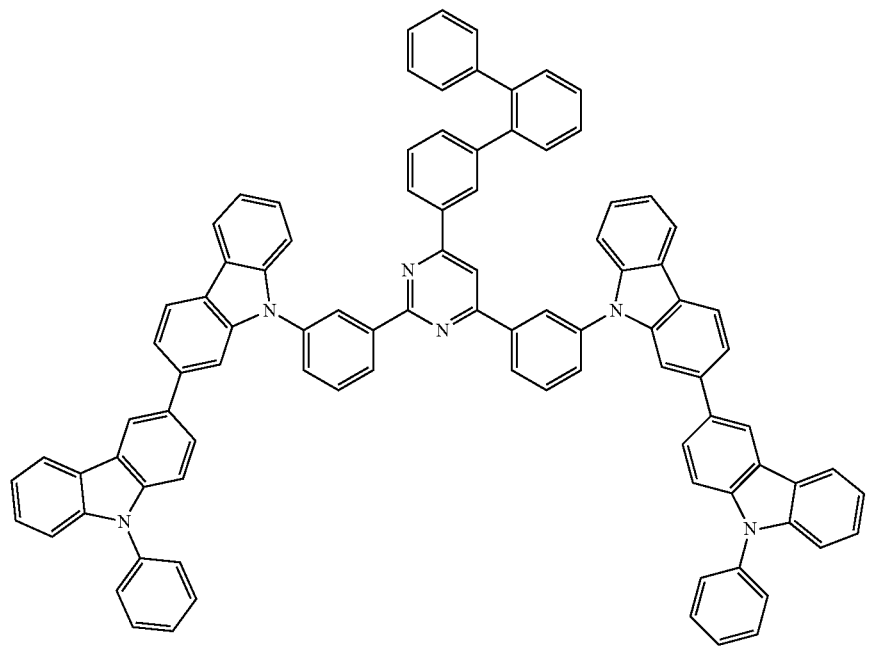
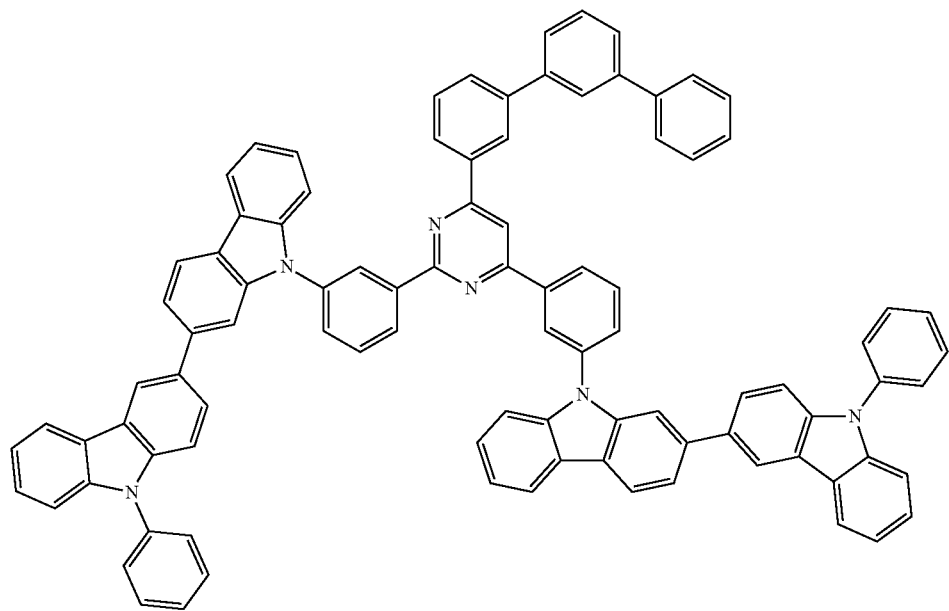

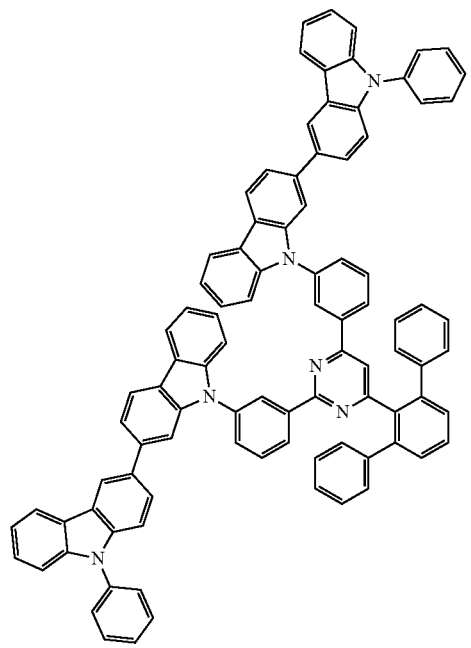
[Formula 105]
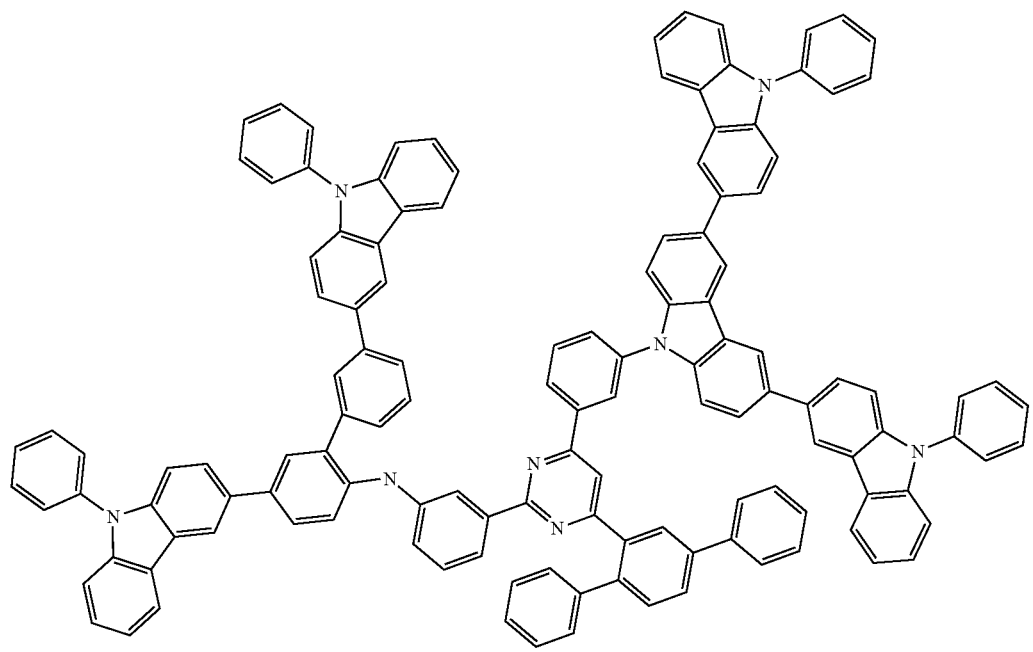

-continued
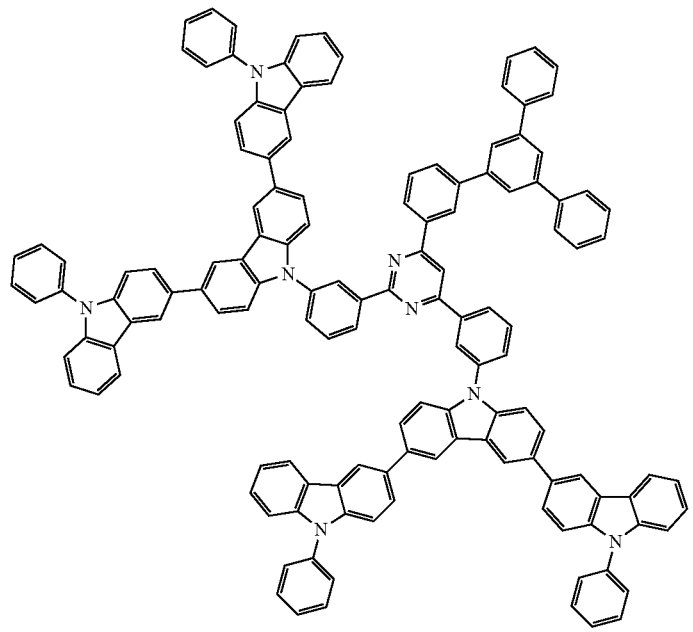
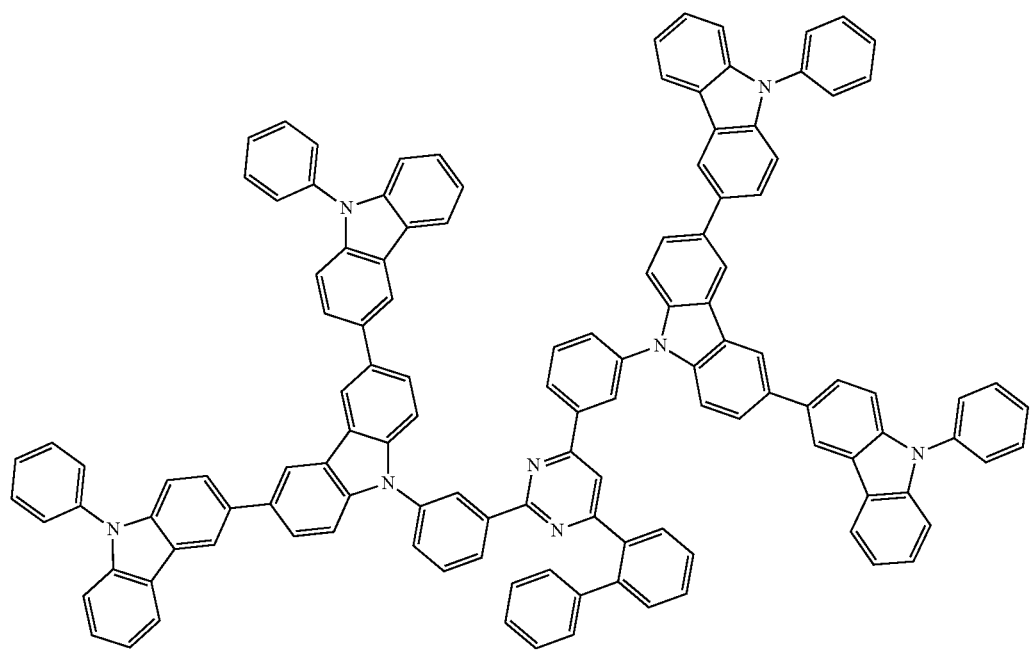

369
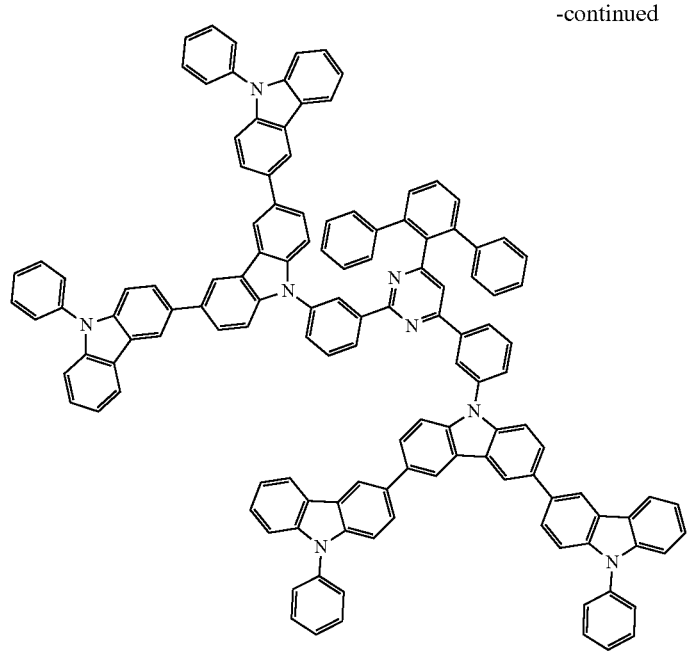
370
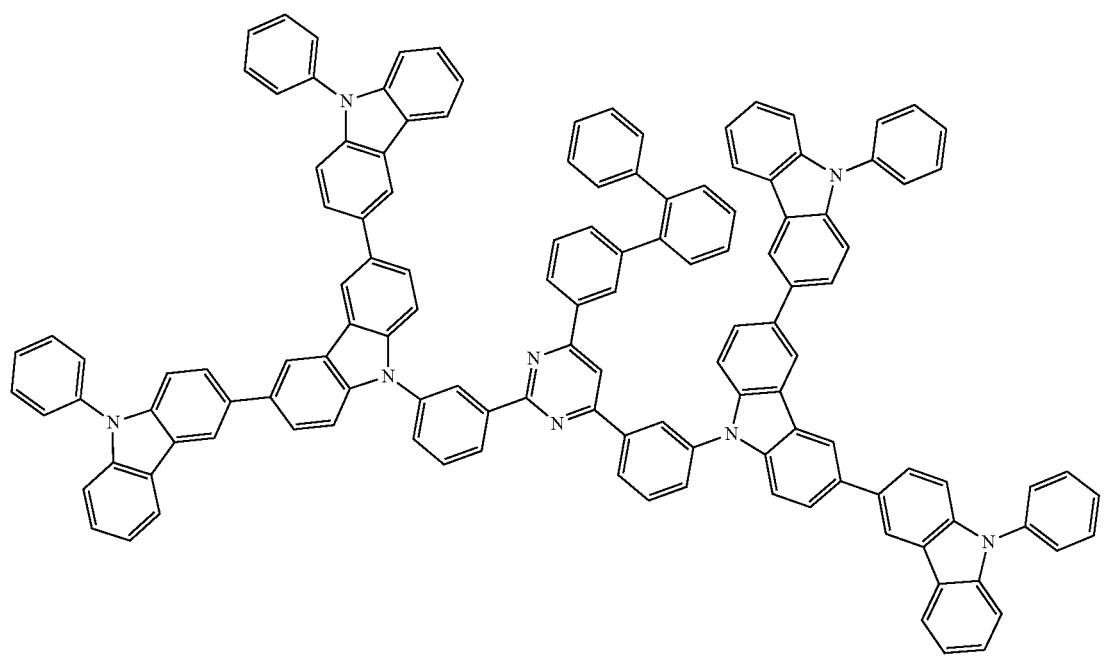

371 372
-continued
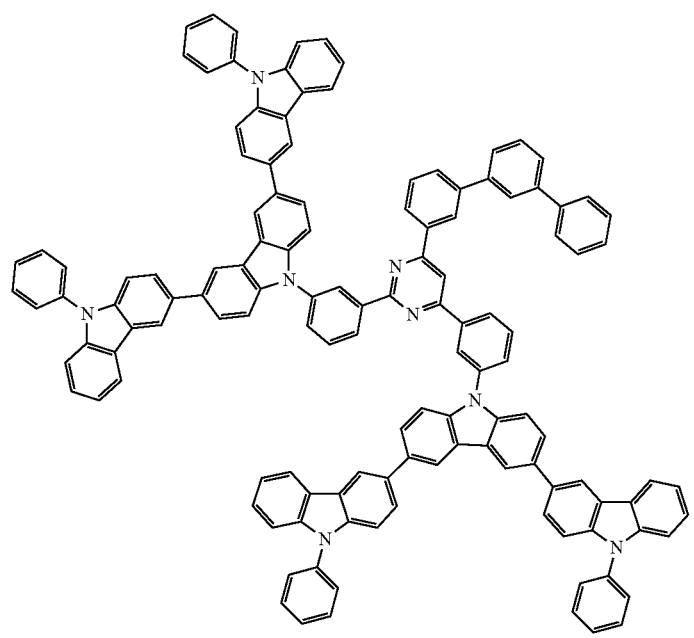
[Formula 106]
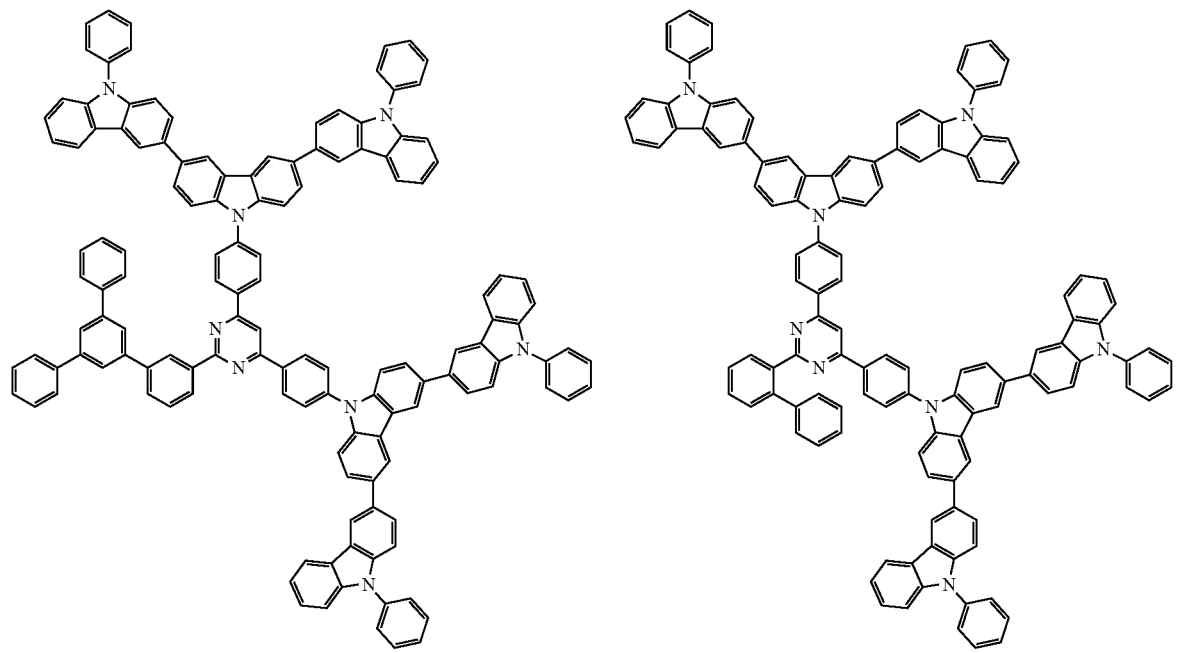

-continued
373
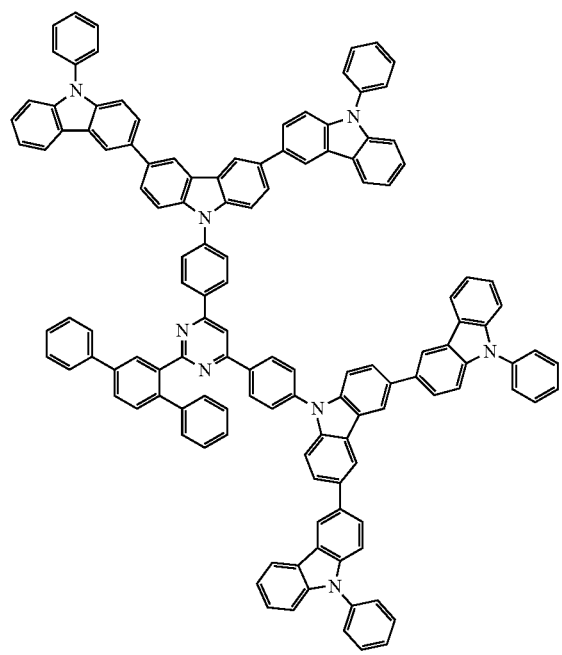
374
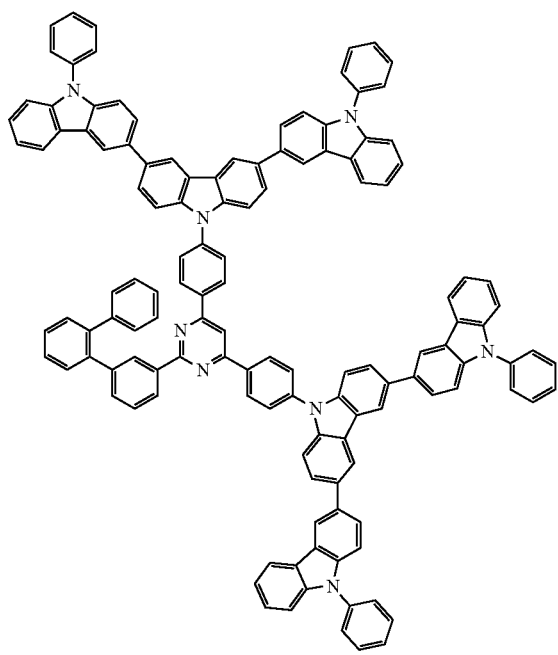
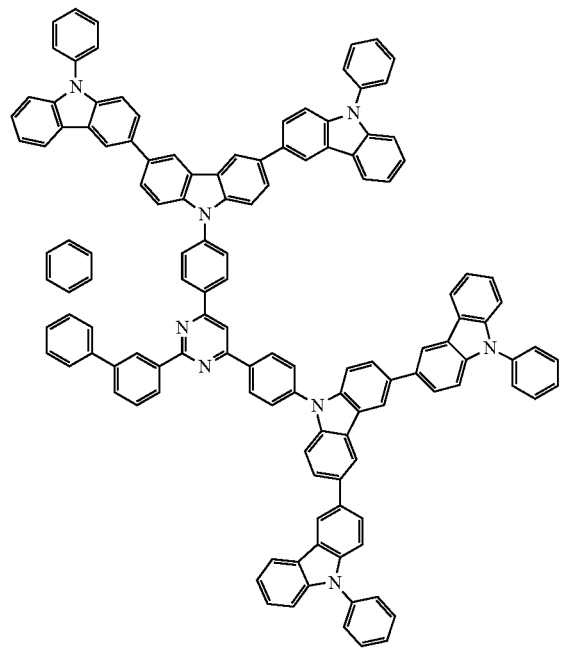
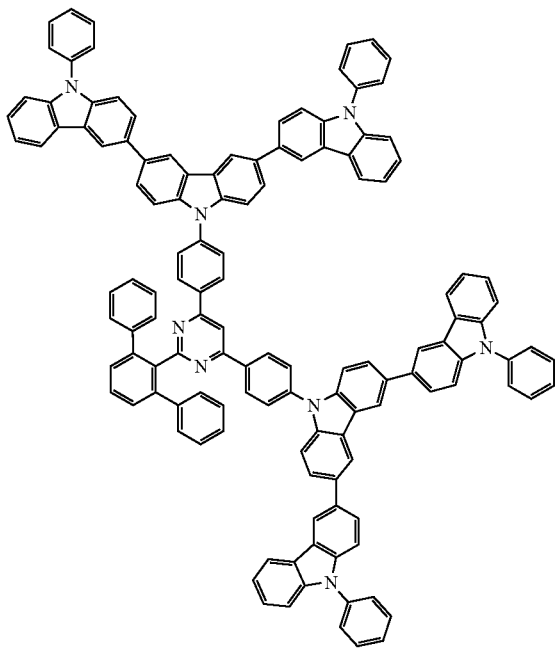

[Formula 107]
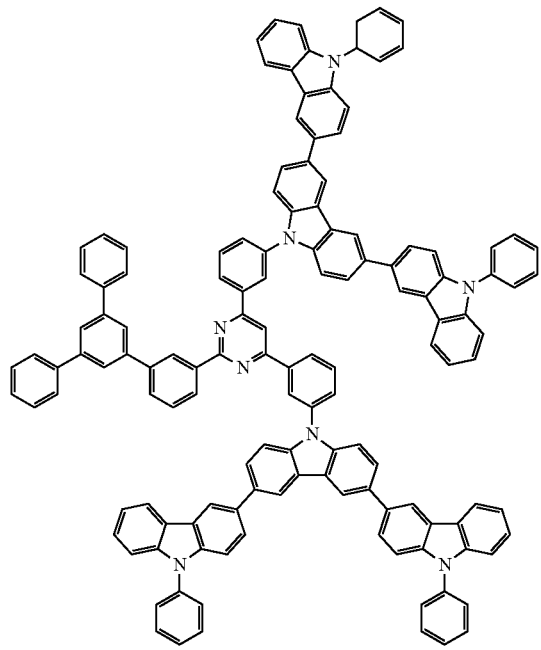
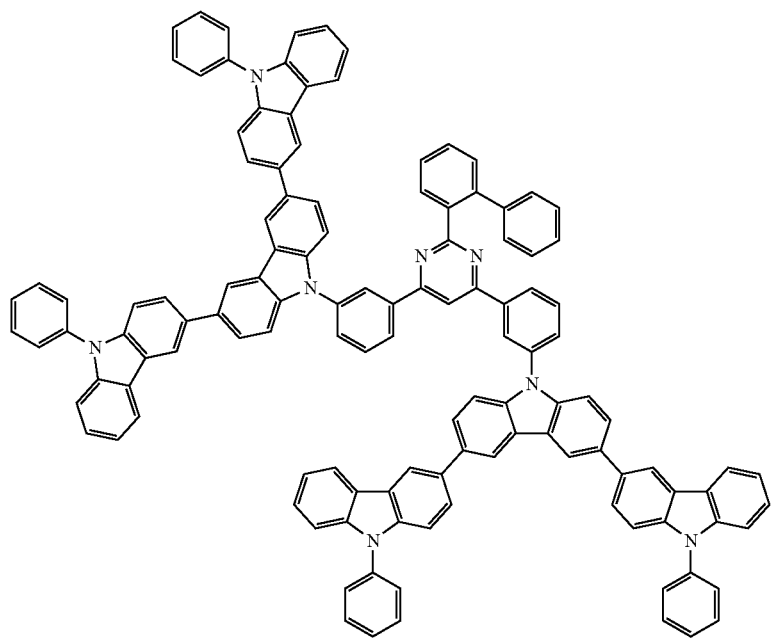

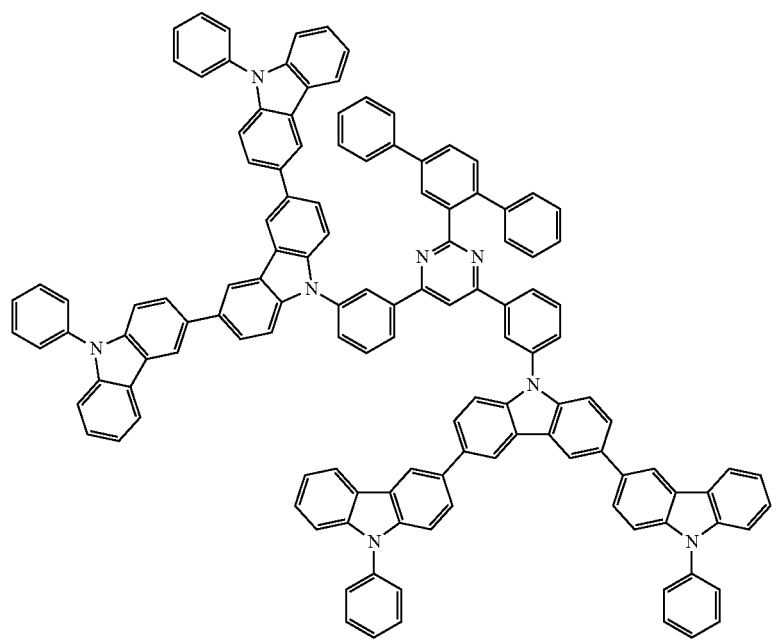
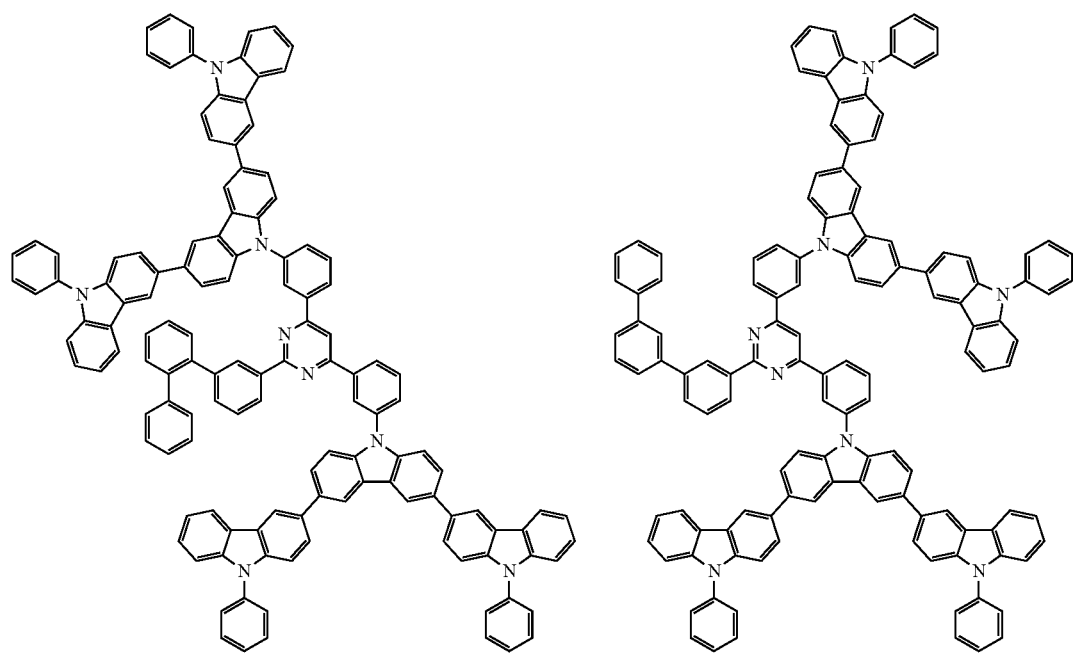

[Formula 108]
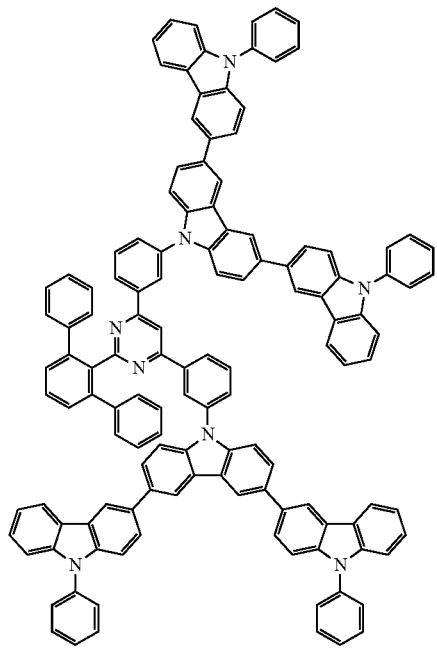
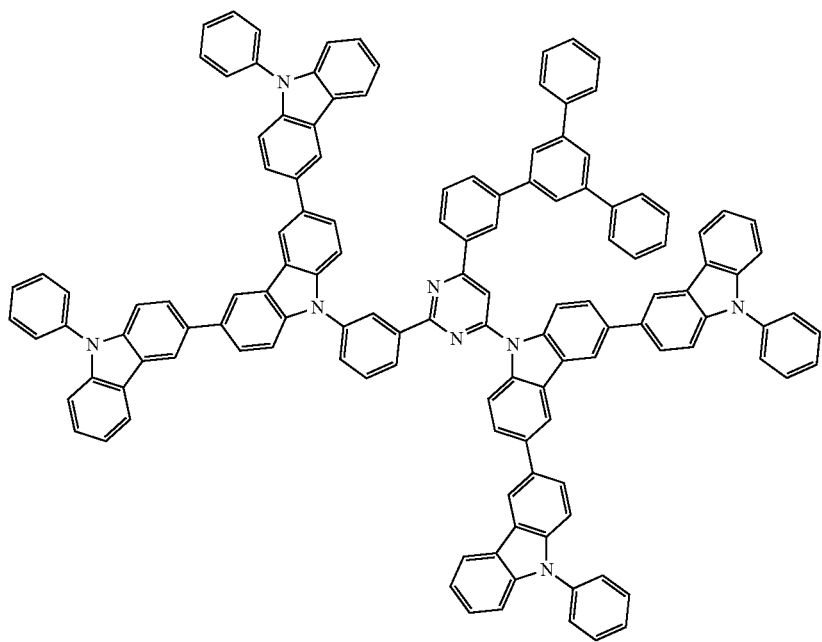

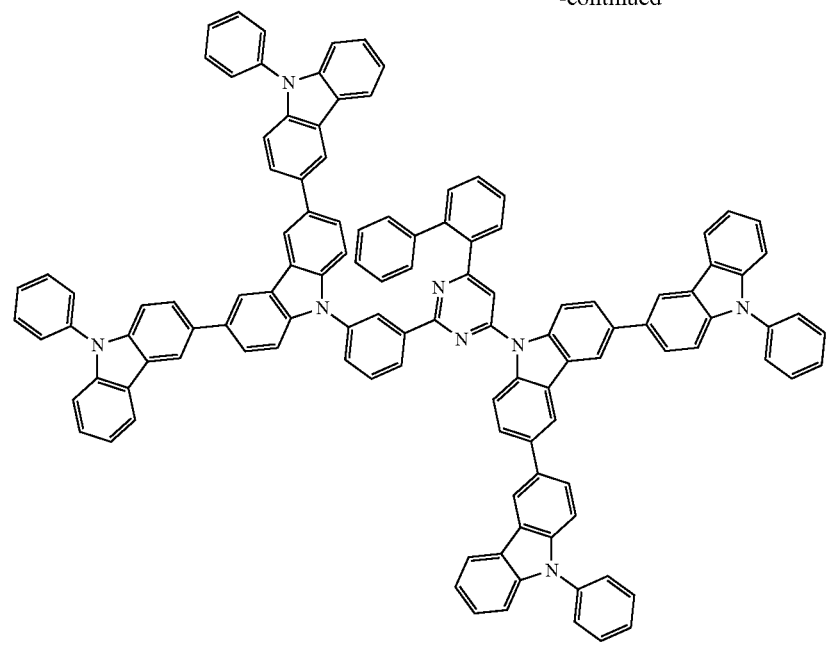
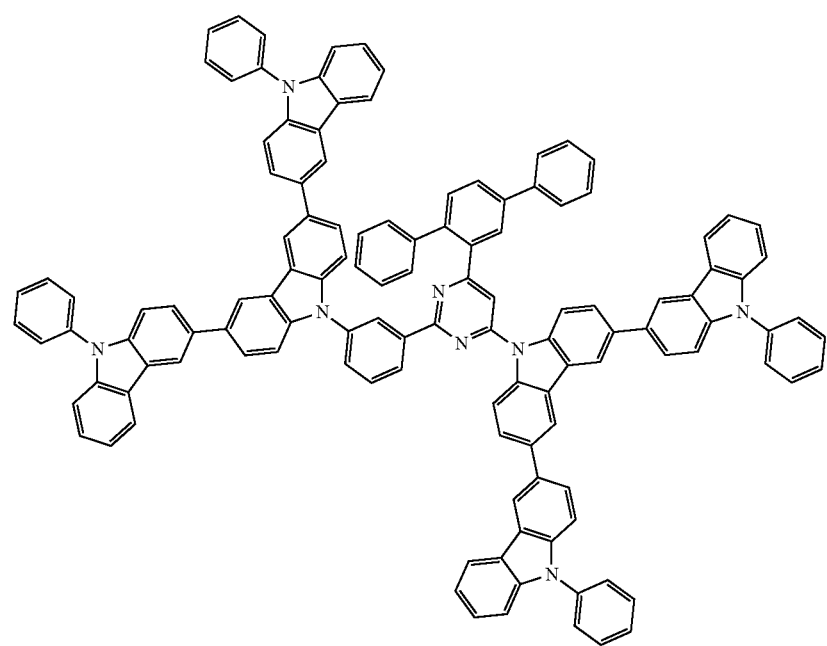

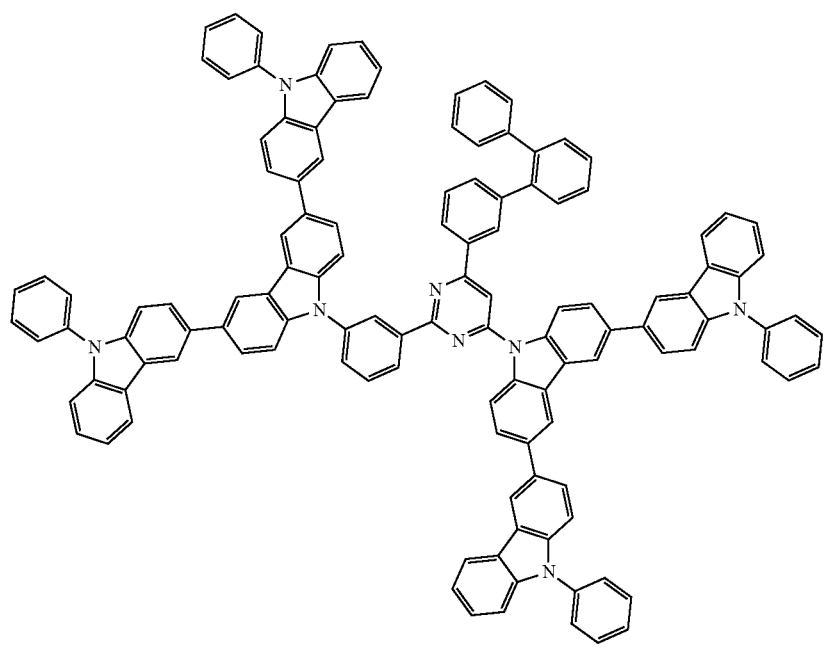
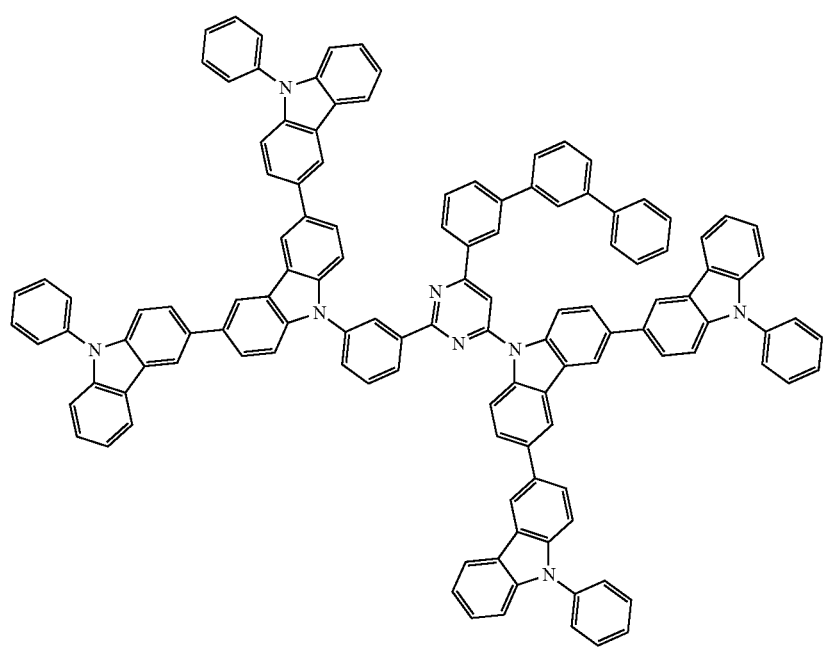

[Formula 109]
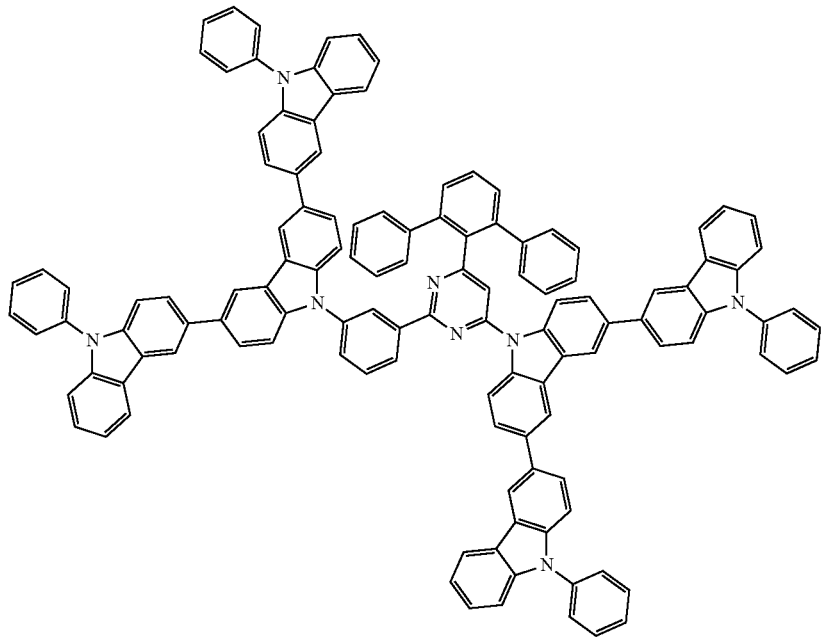
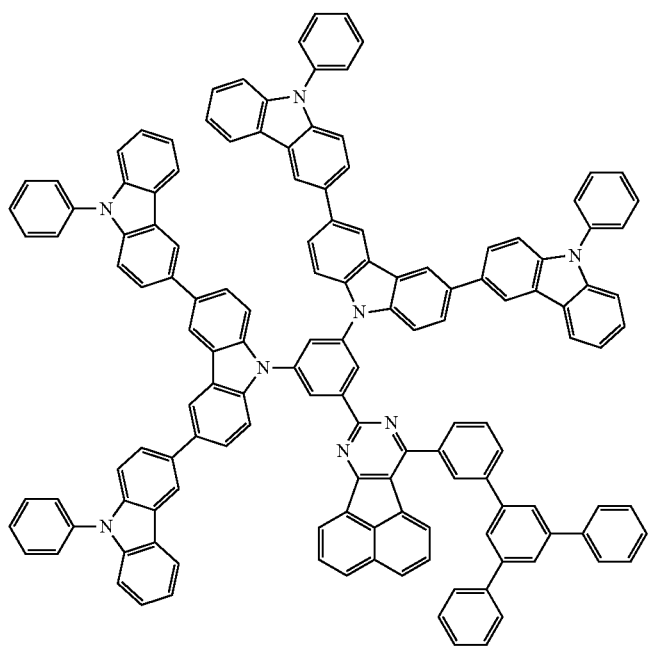

-continued
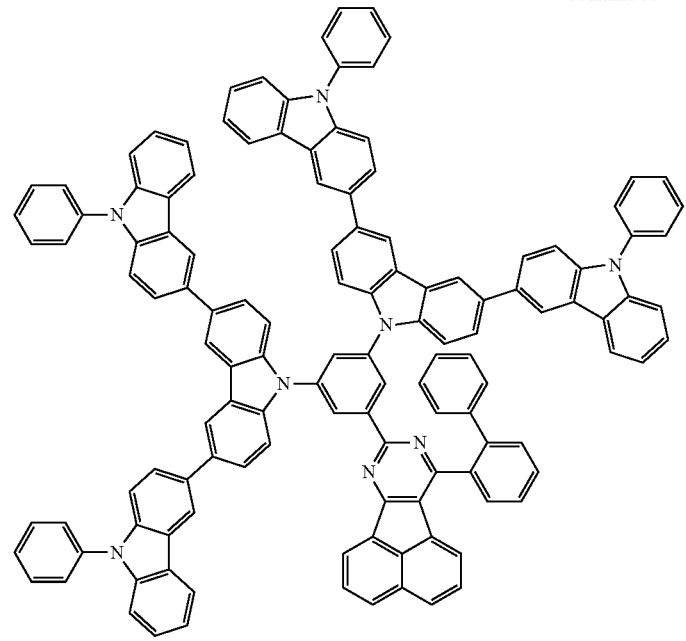
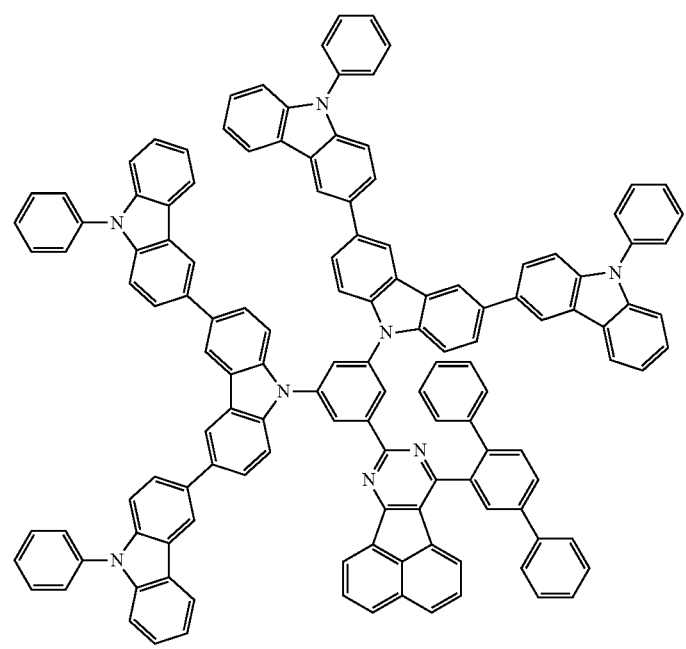

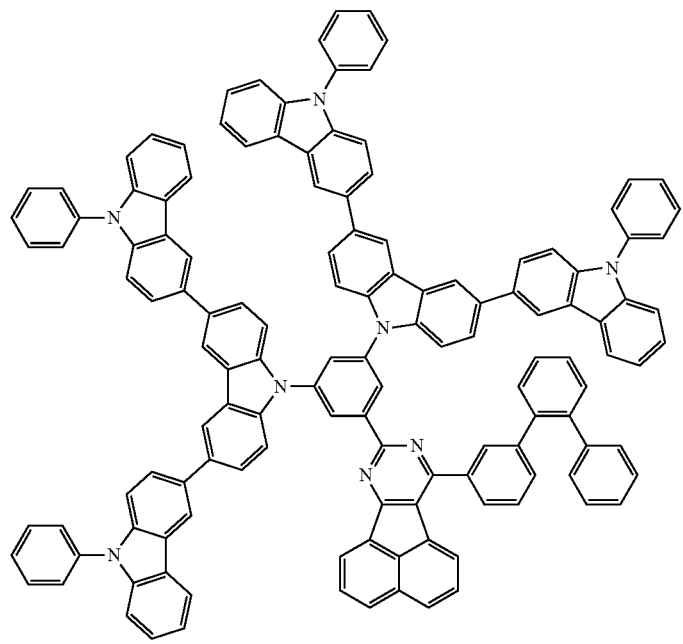
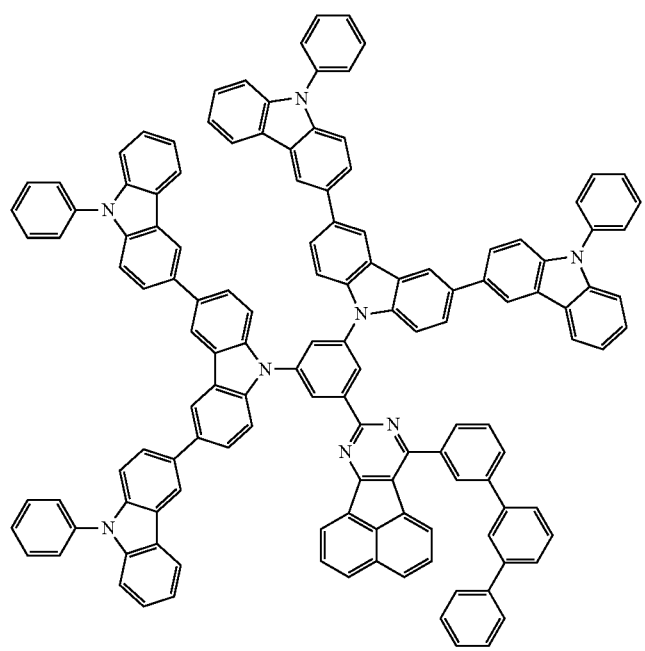

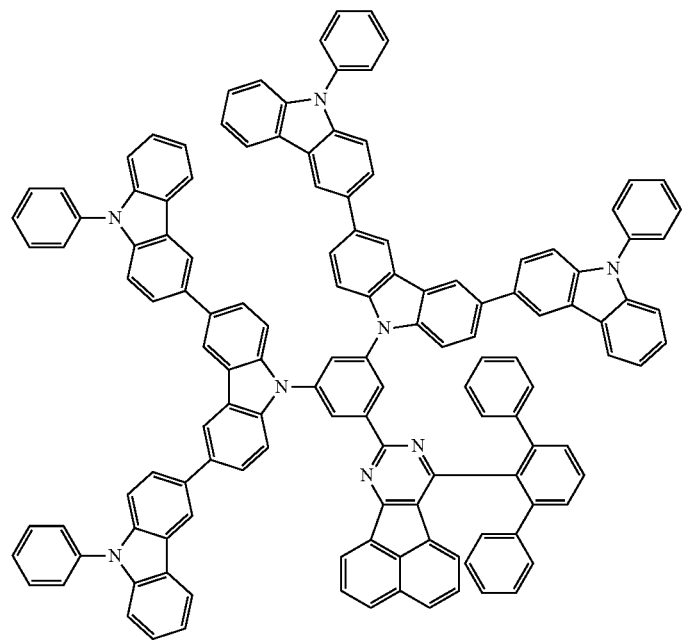
[Formula 110]
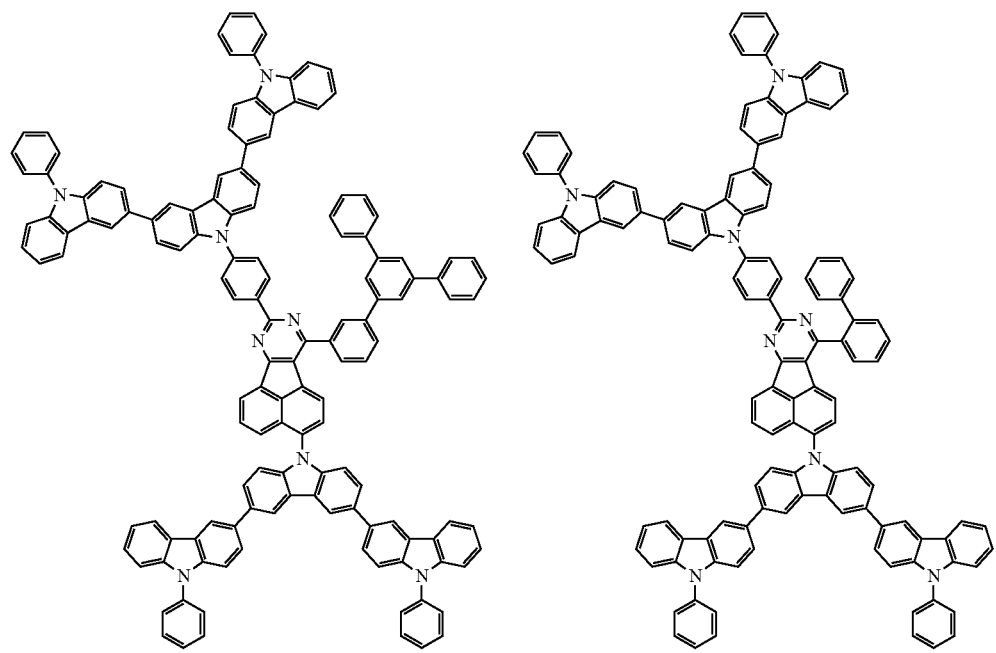

-continued
393
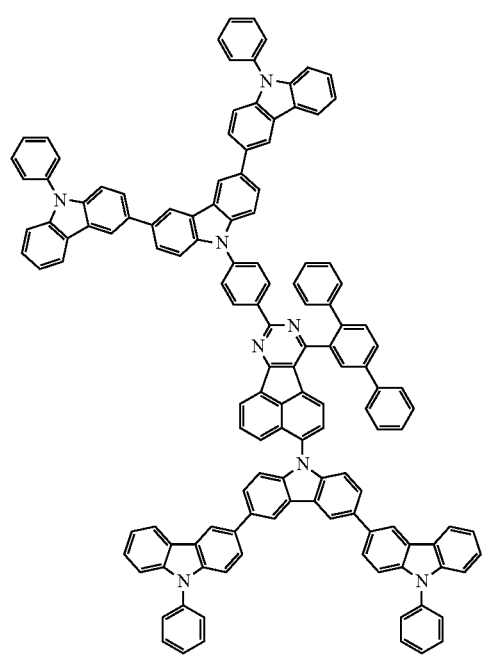
394
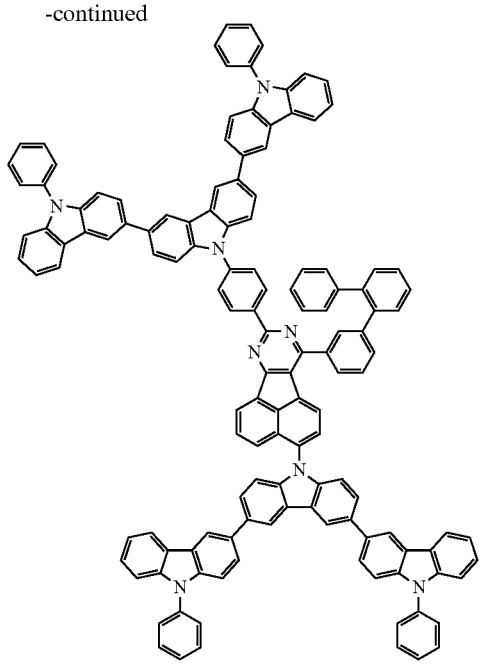
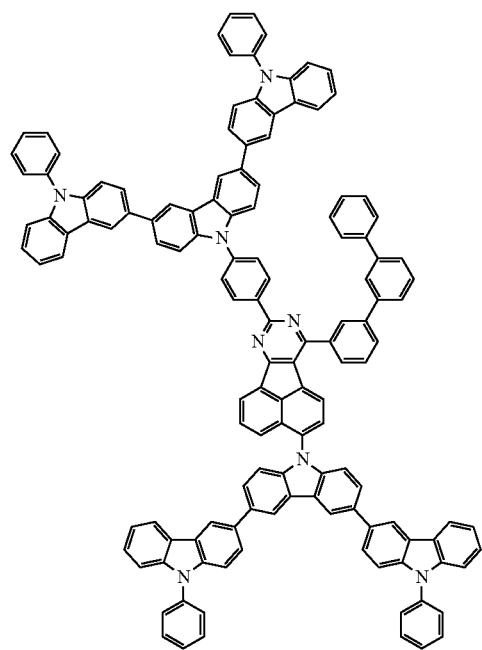
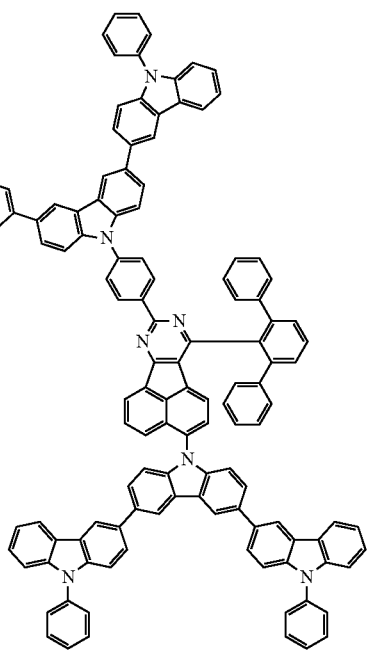

-continued
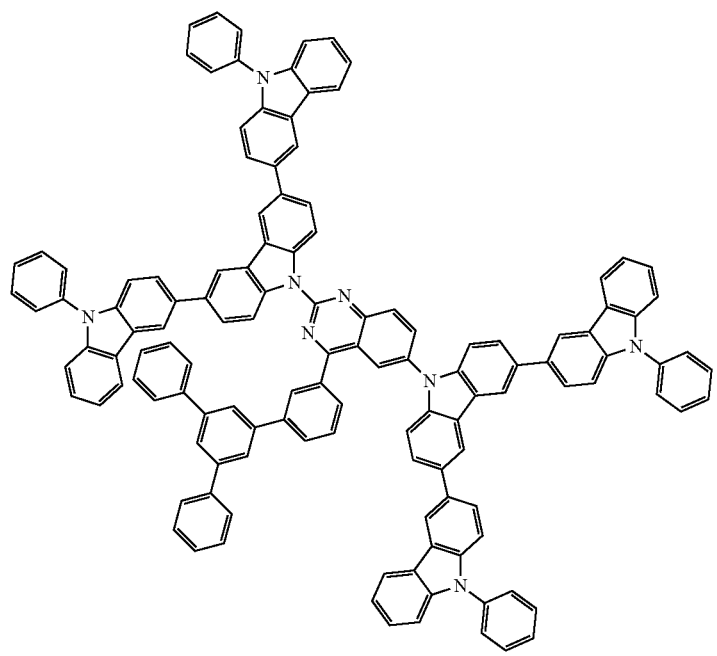
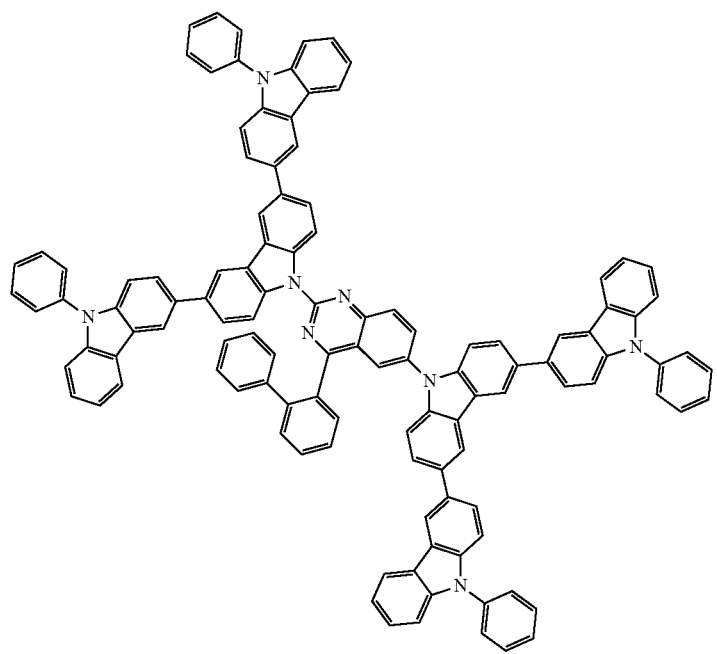

-continued
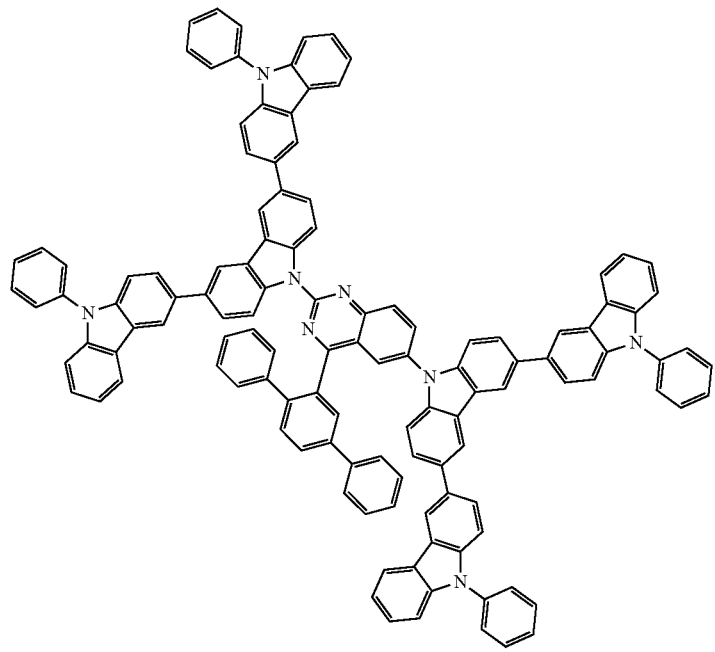
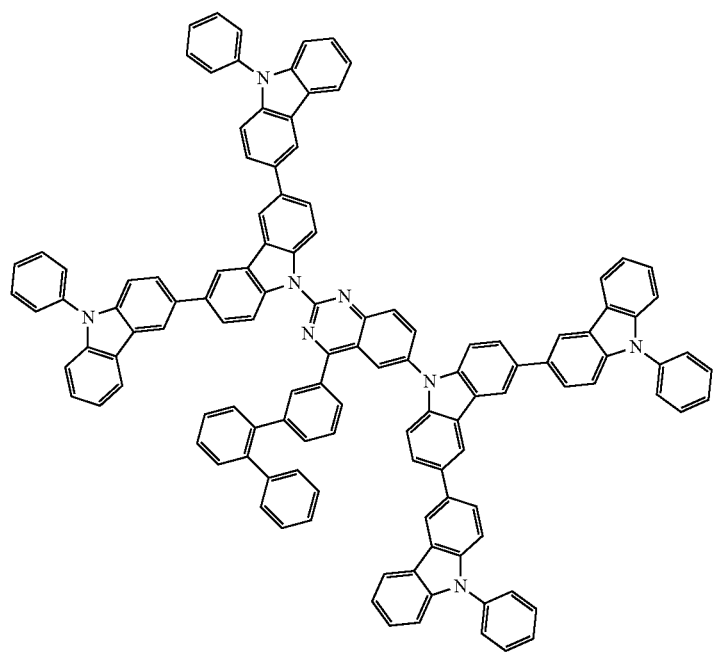

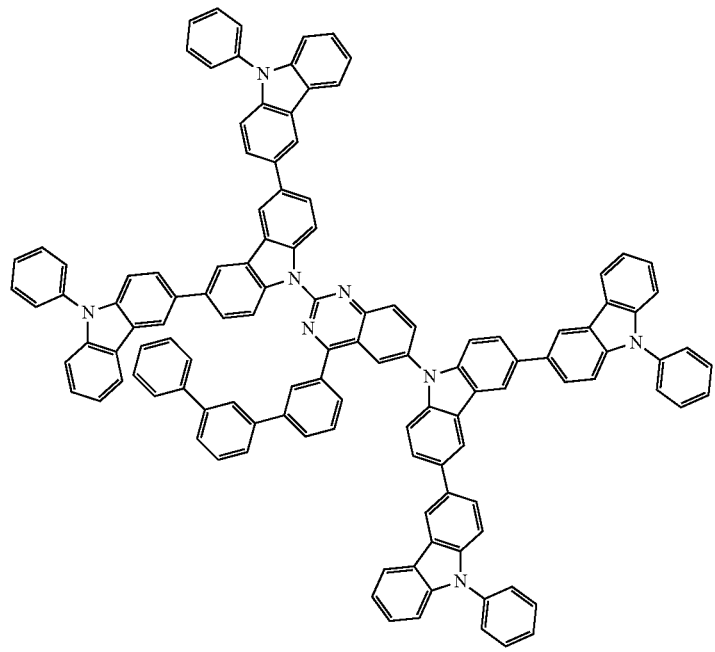
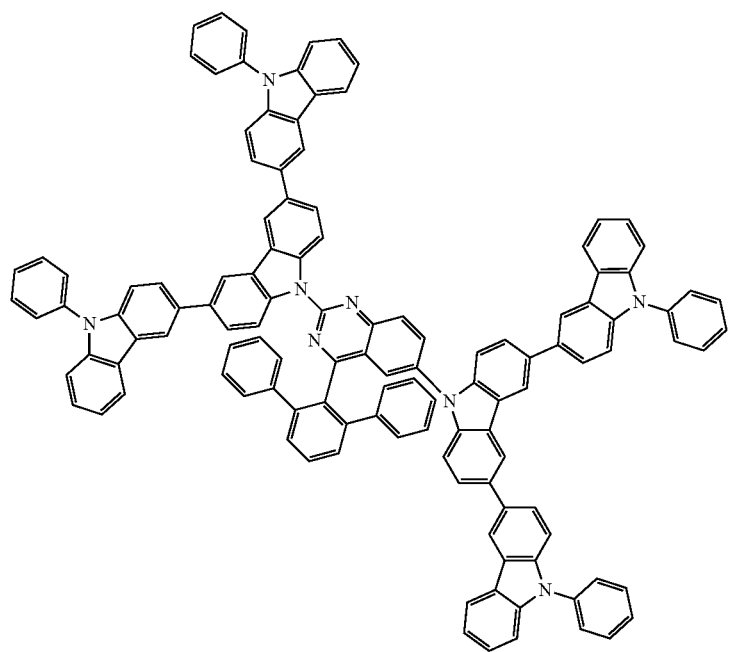

[Formula 111]
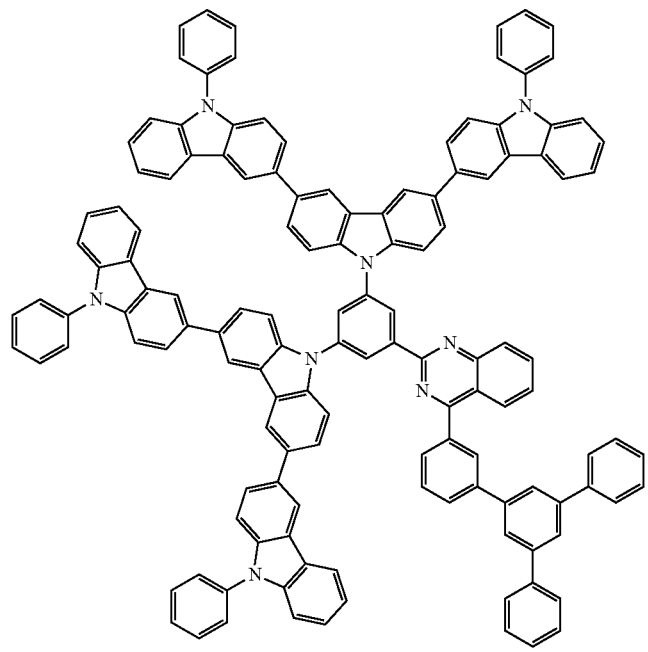
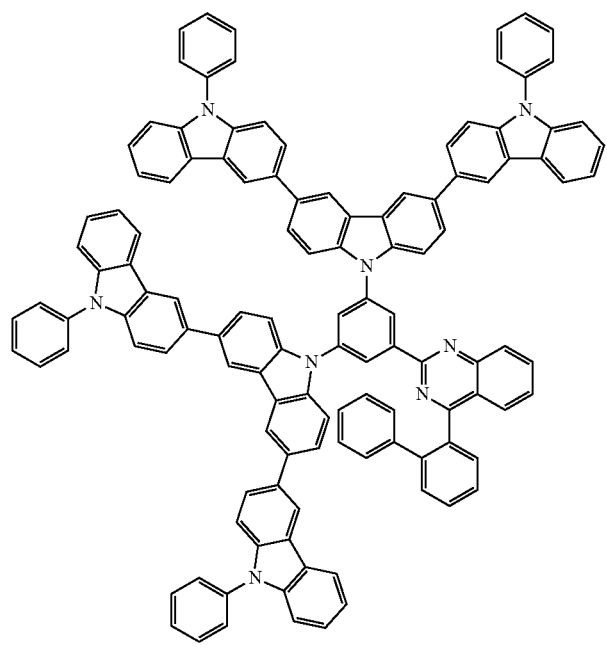

-continued
403
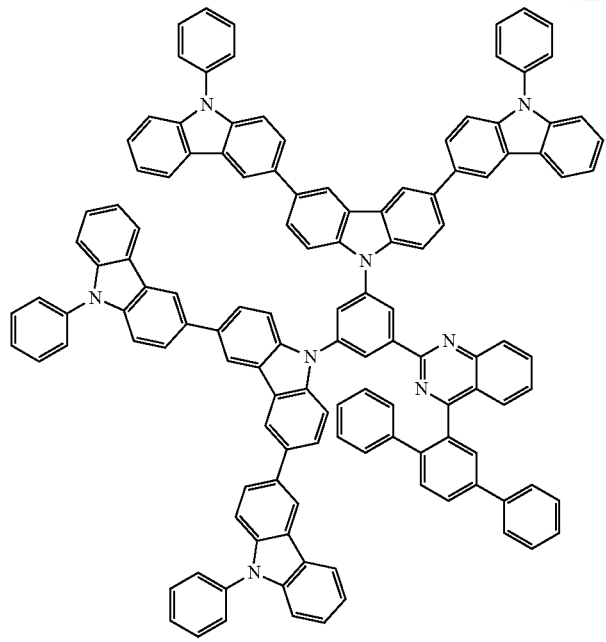
404
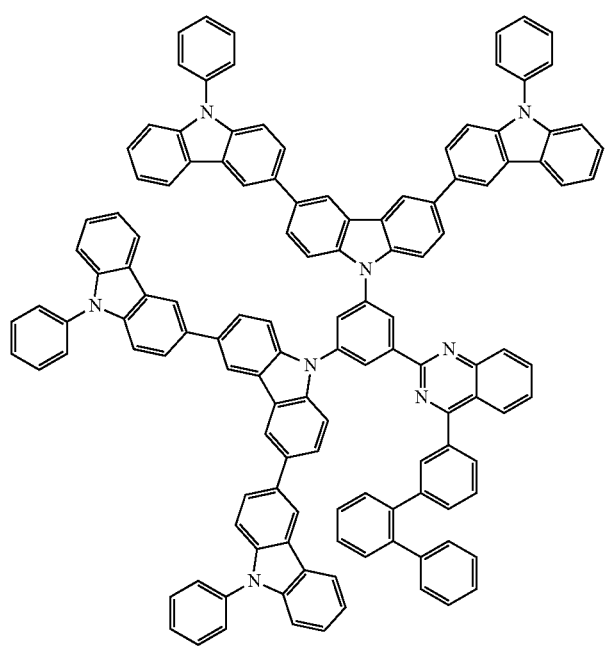

405
406
-continued
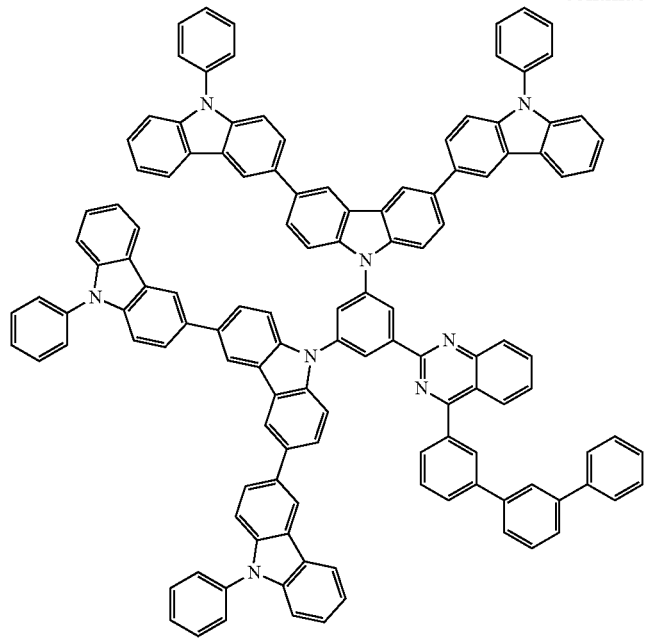
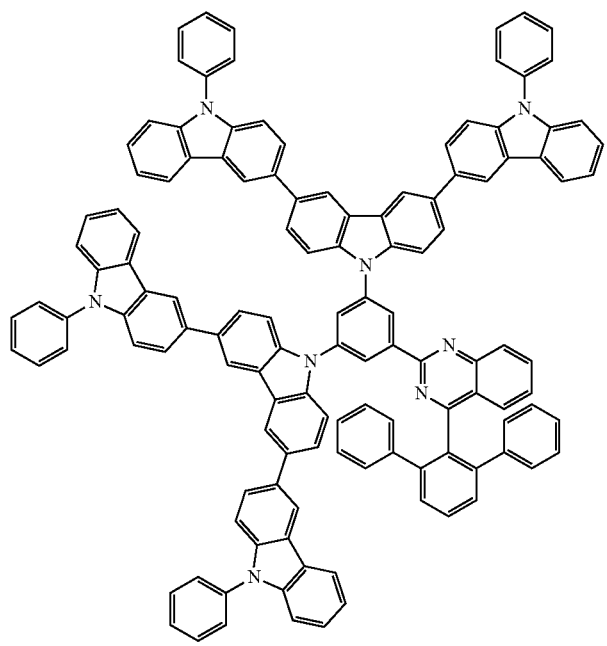

[Formula 112]
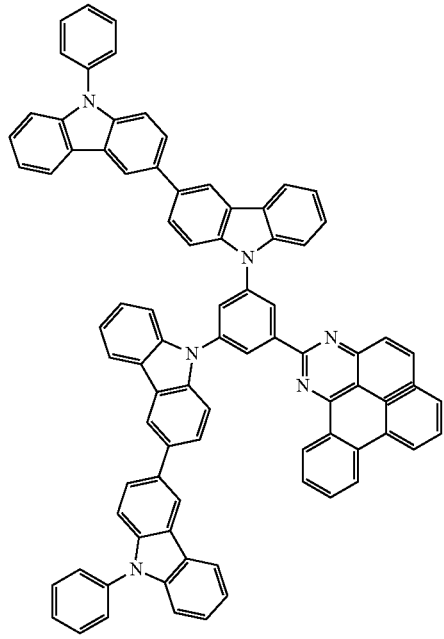
-continued
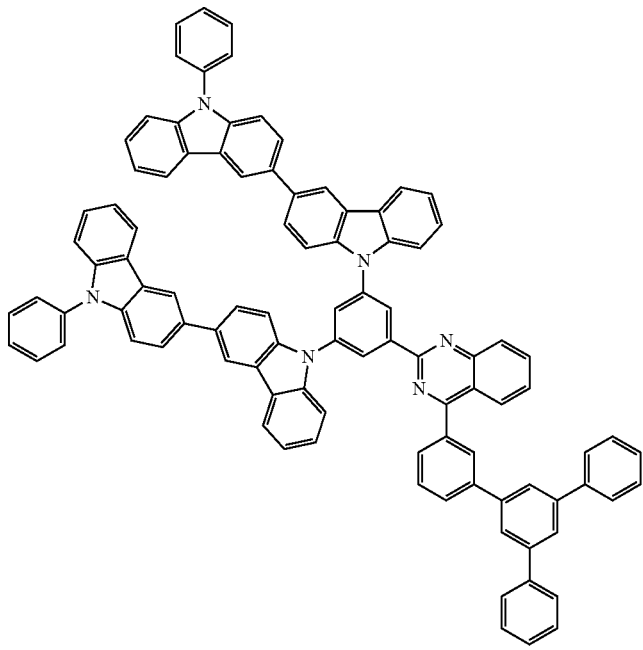
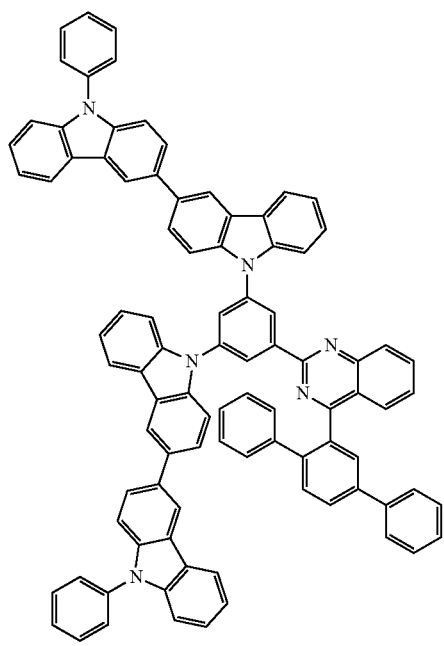
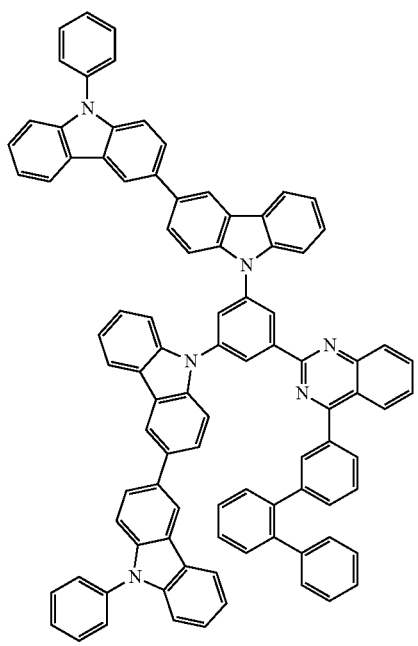

409    410
-continued
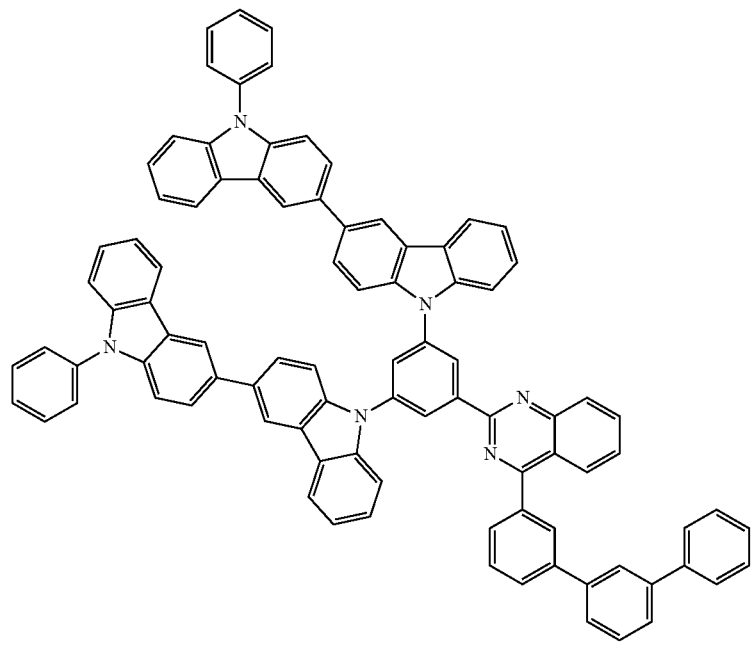
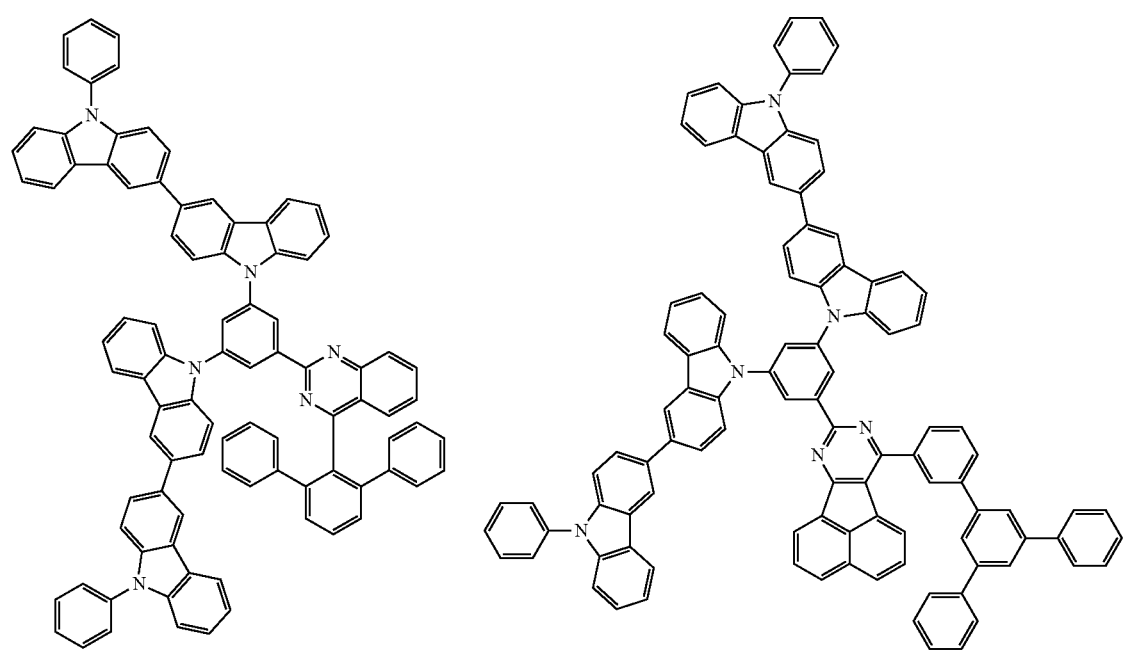

[Formula 113]
411
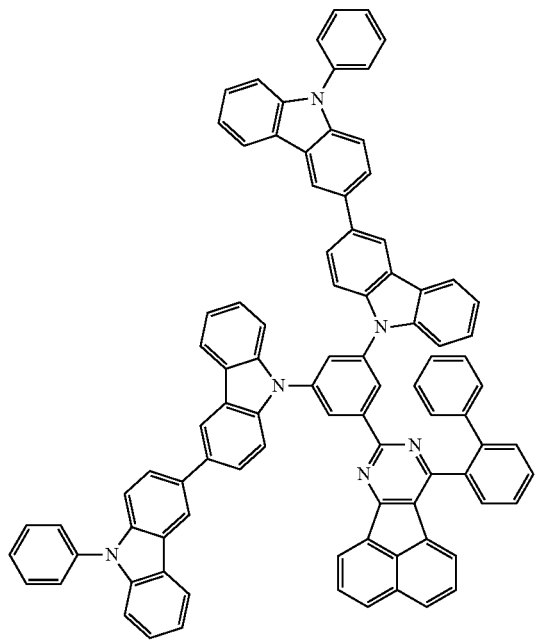
412
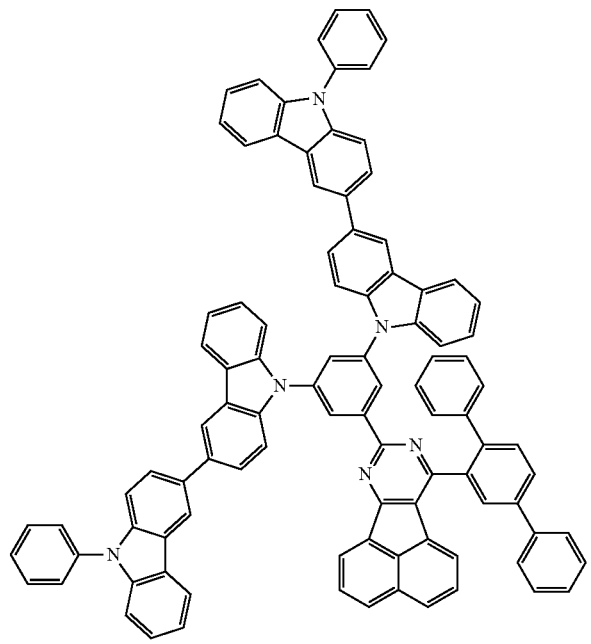
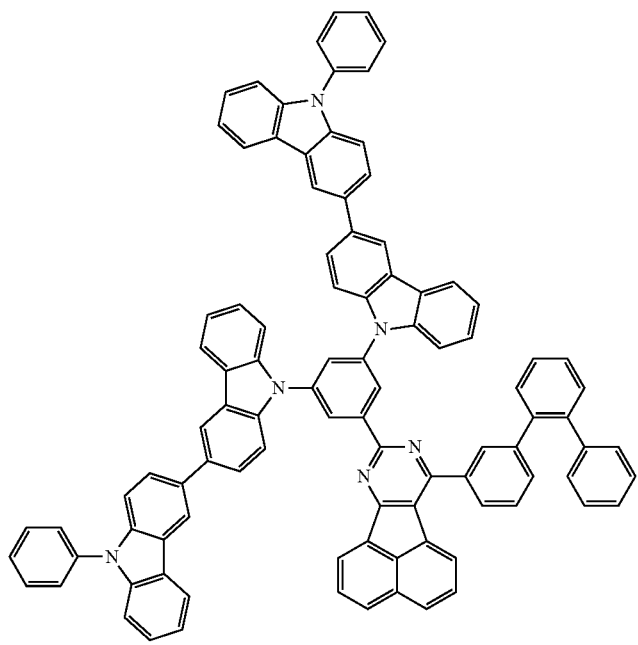

413
414
-continued
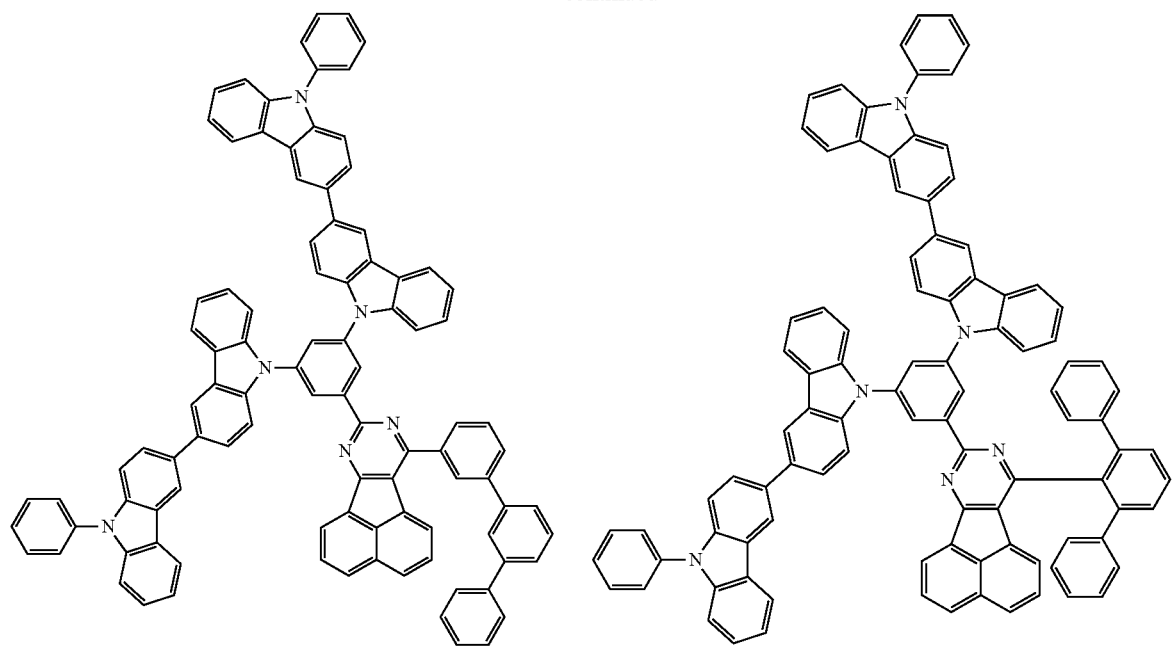
[Formula 114]
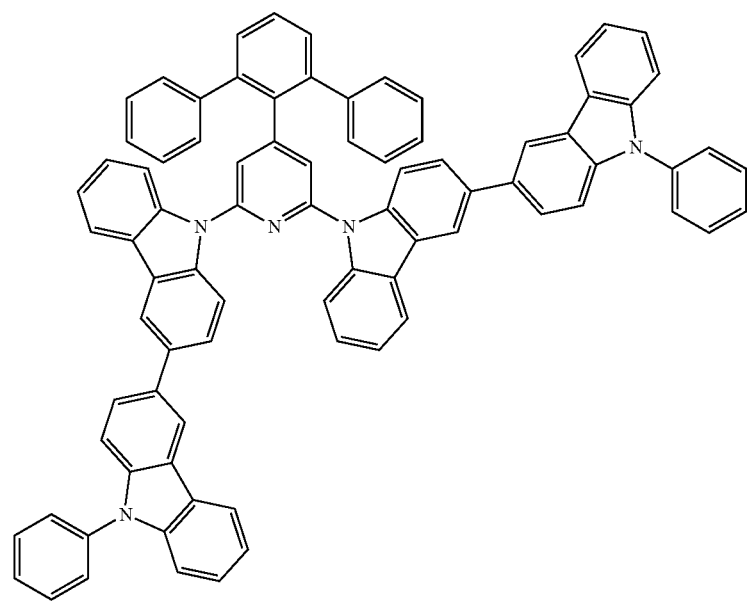

-continued
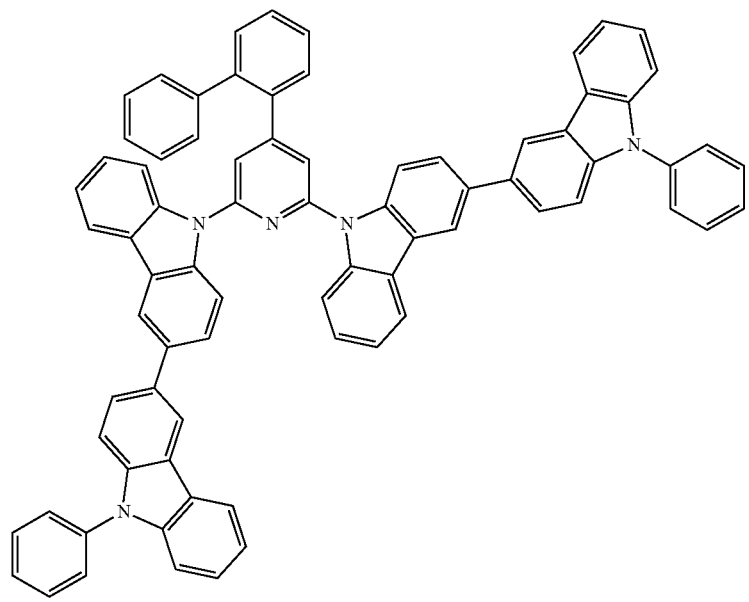
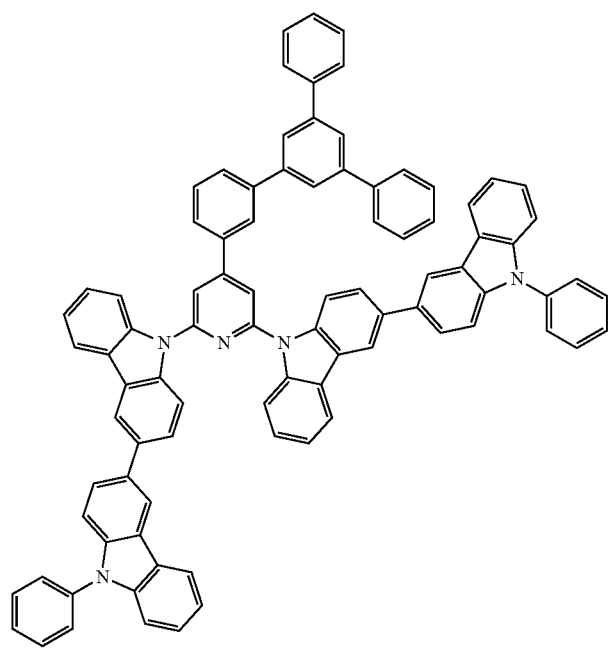

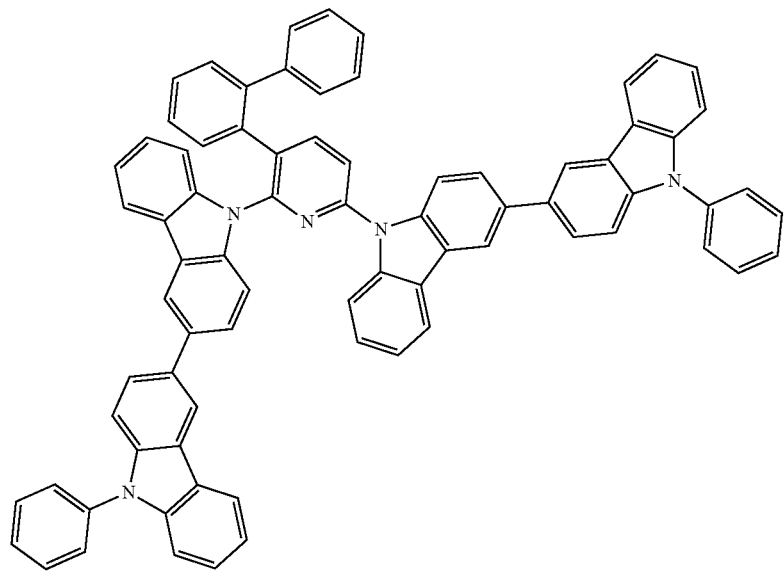
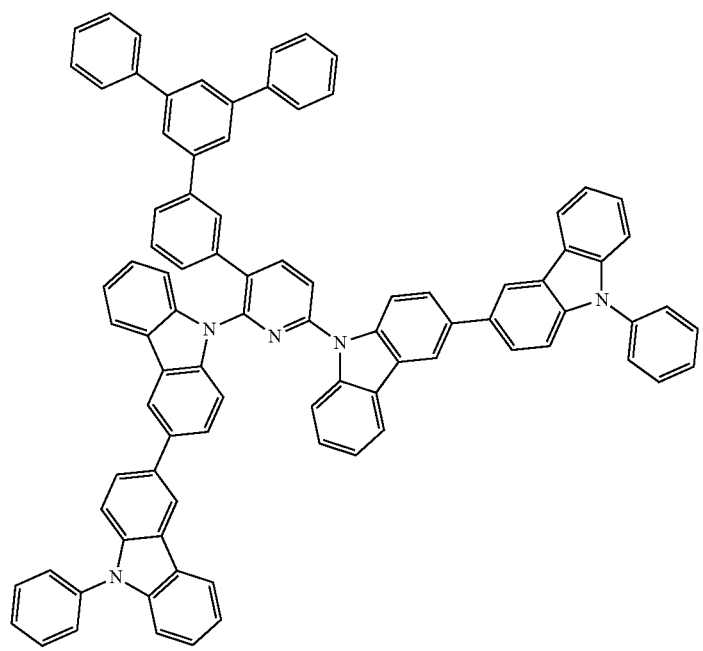

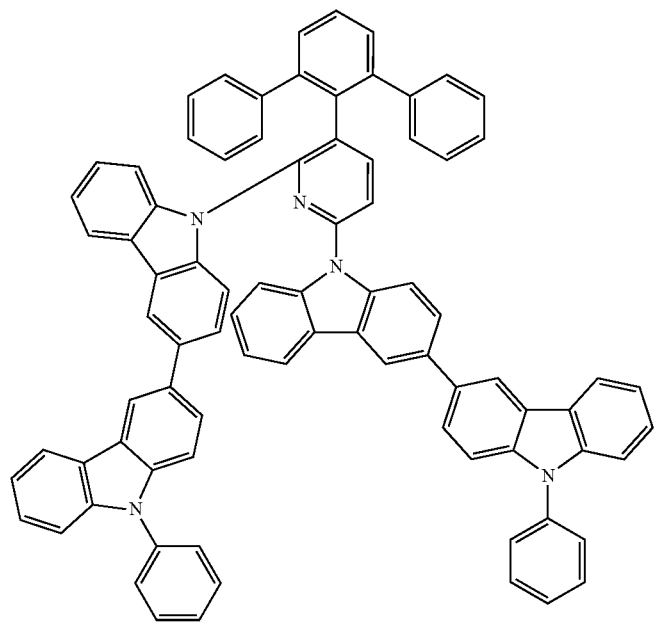
[Formula 115]
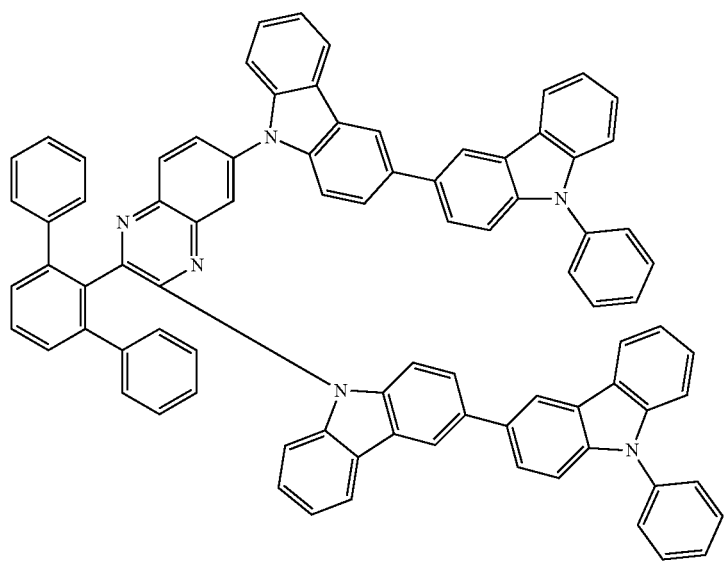

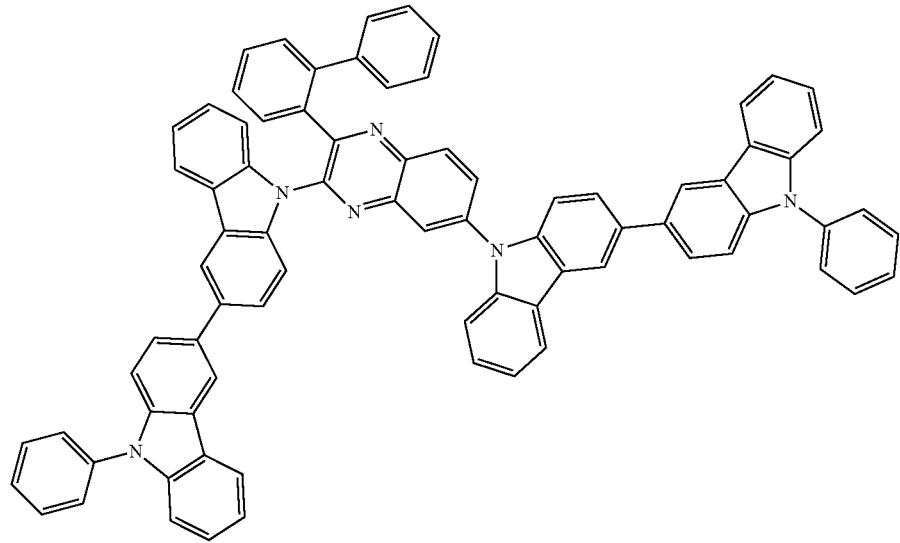
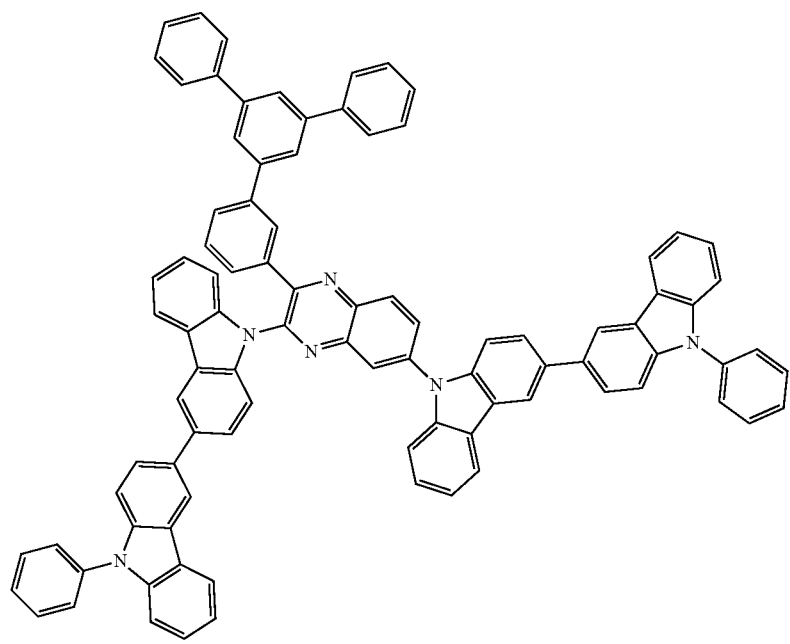

-continued
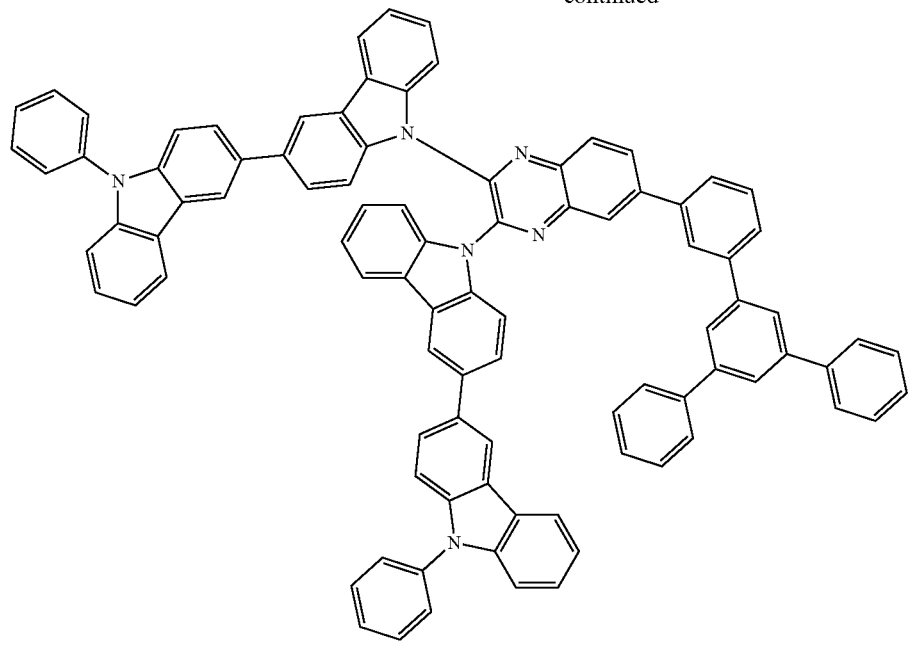
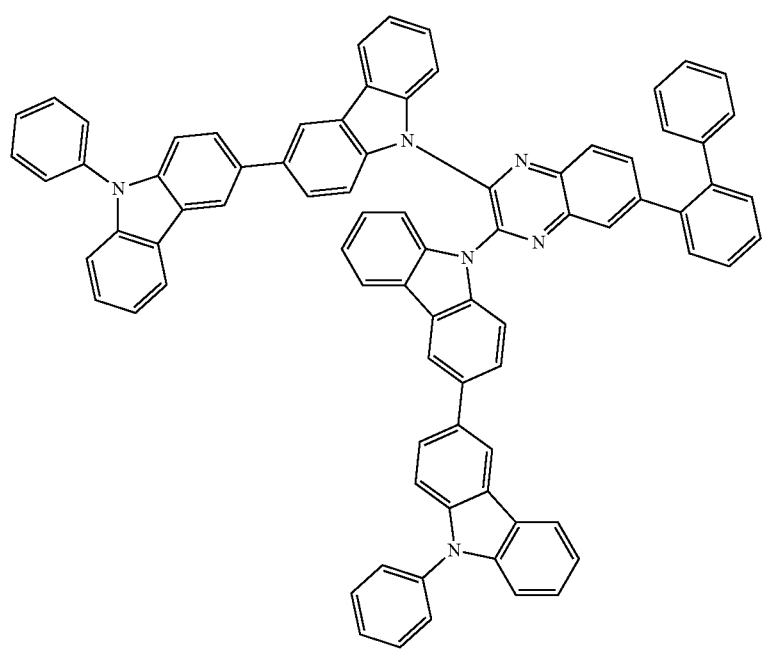

425
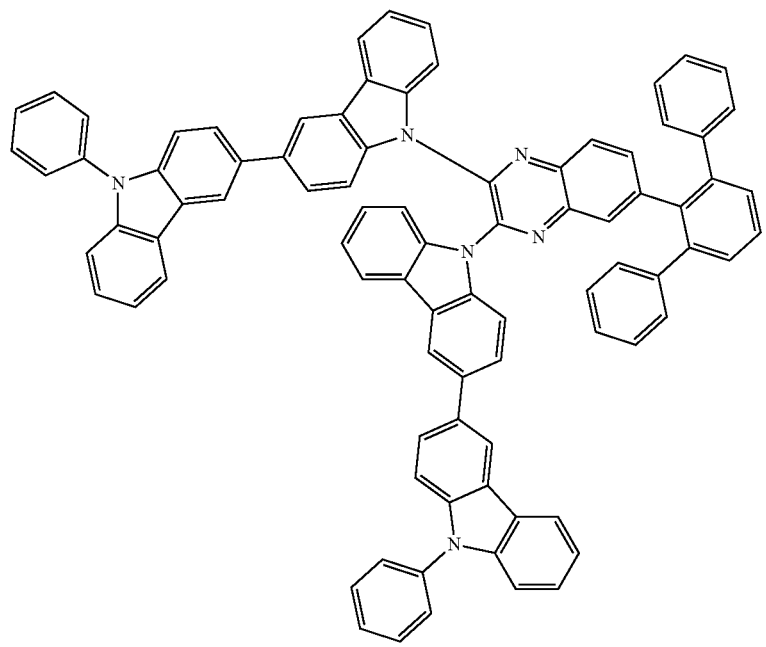
426
[Formula 116]
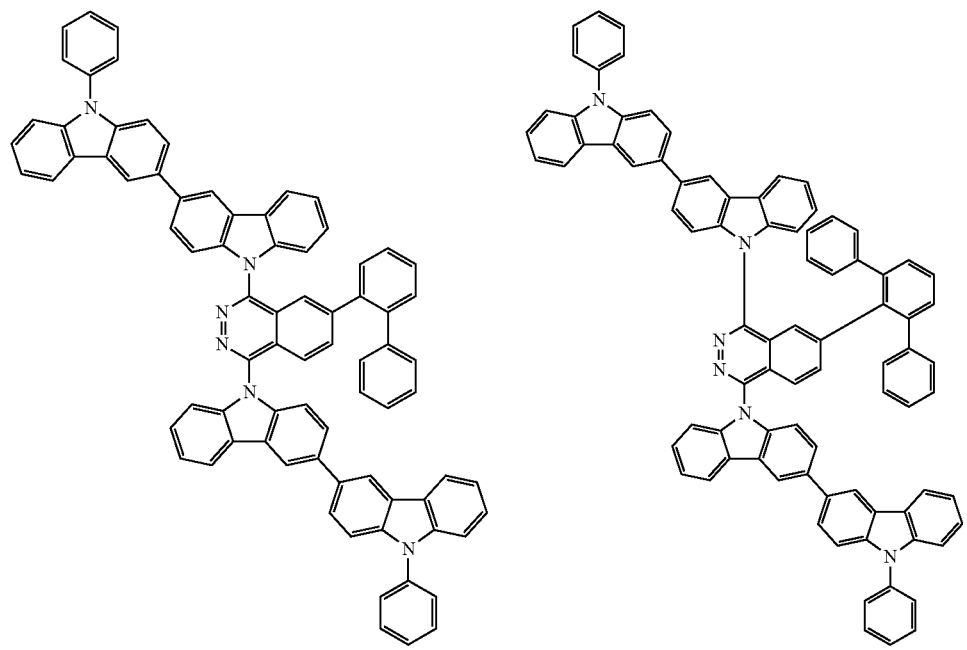

-continued
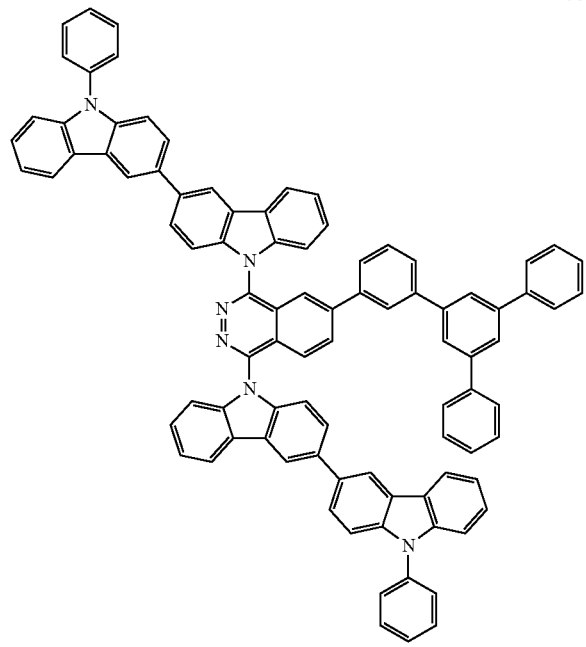
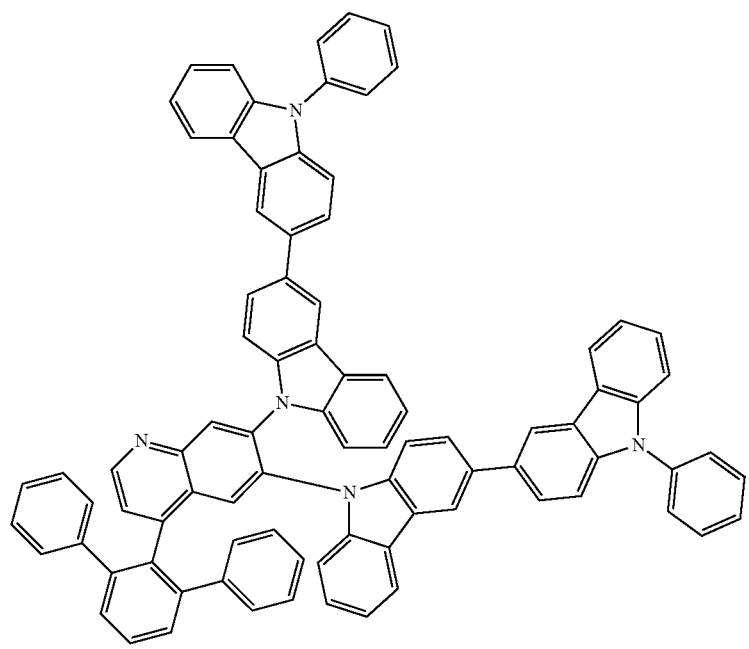

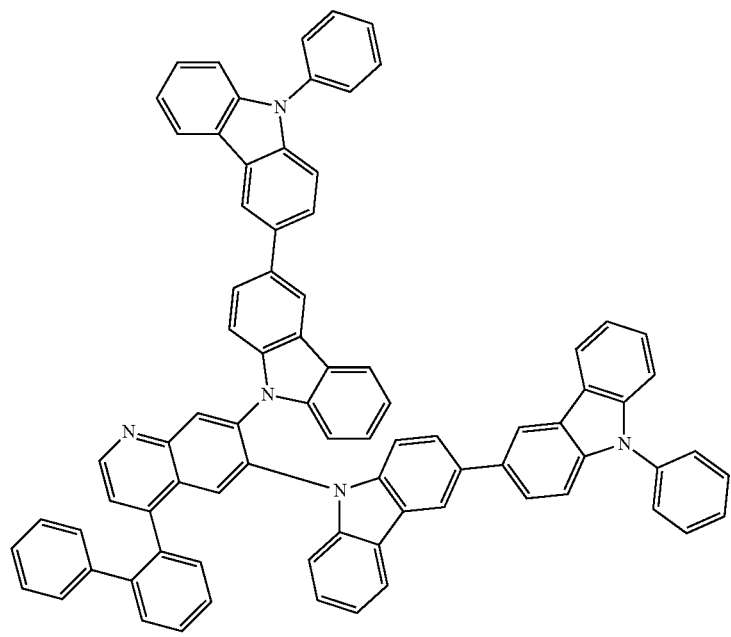

[Formula 117]
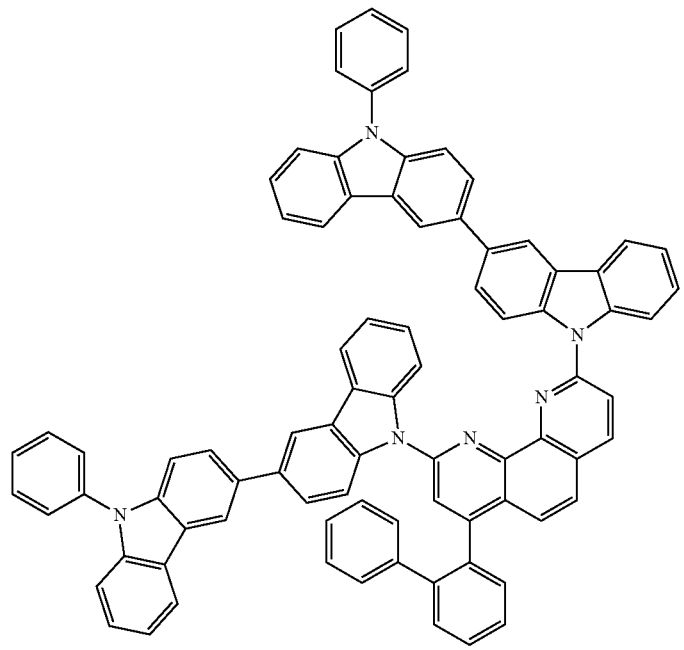
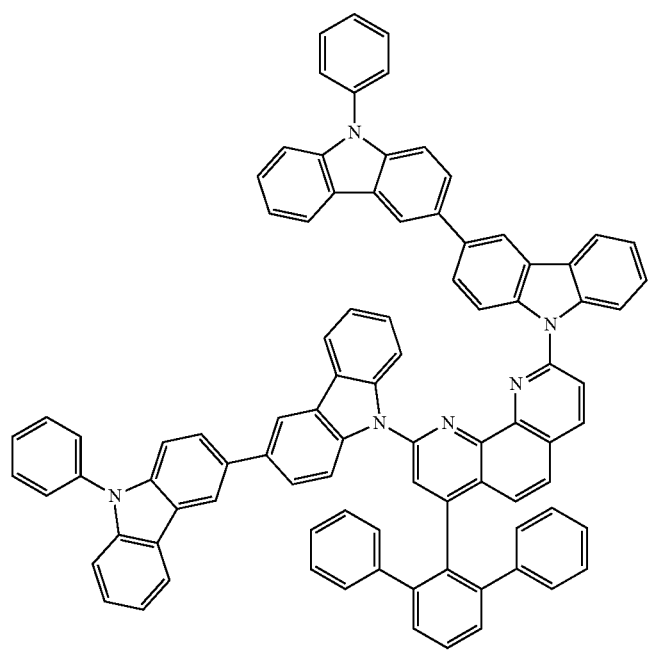

433
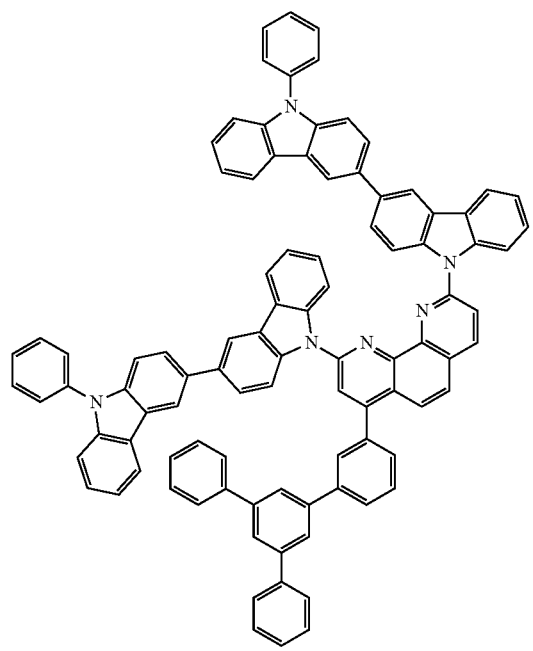
-continued
434
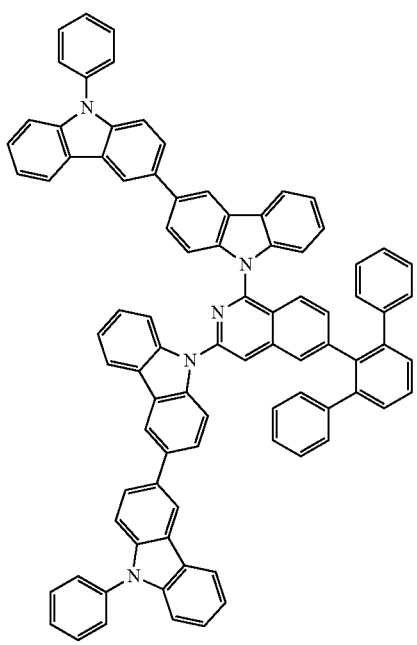
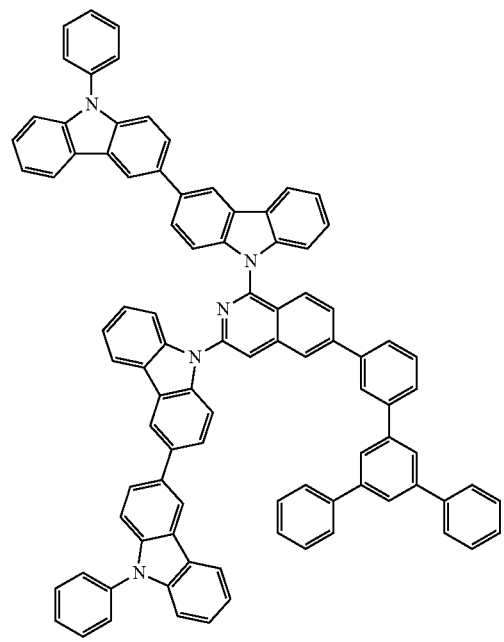
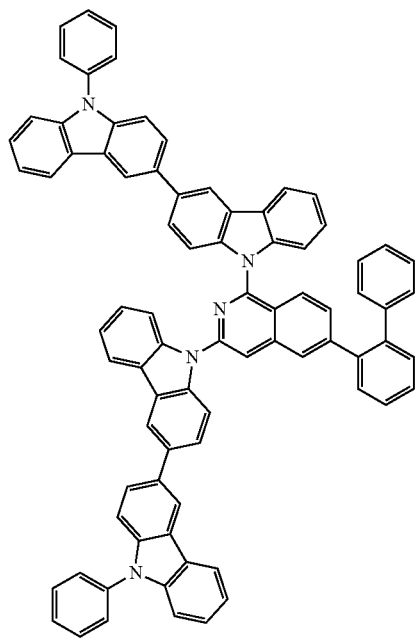

[Formula 118]
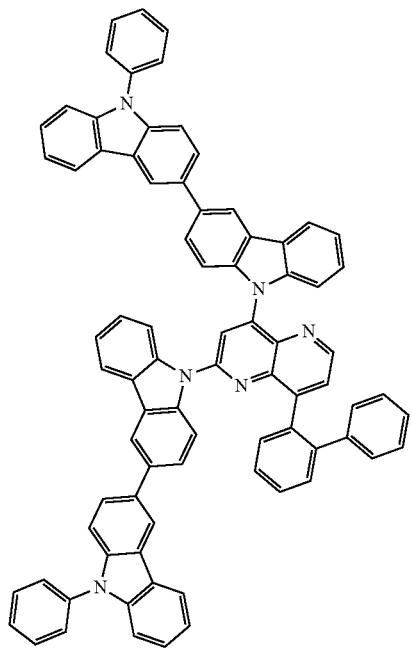
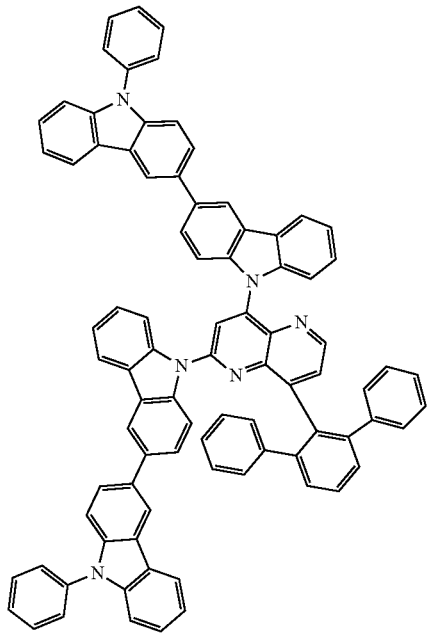
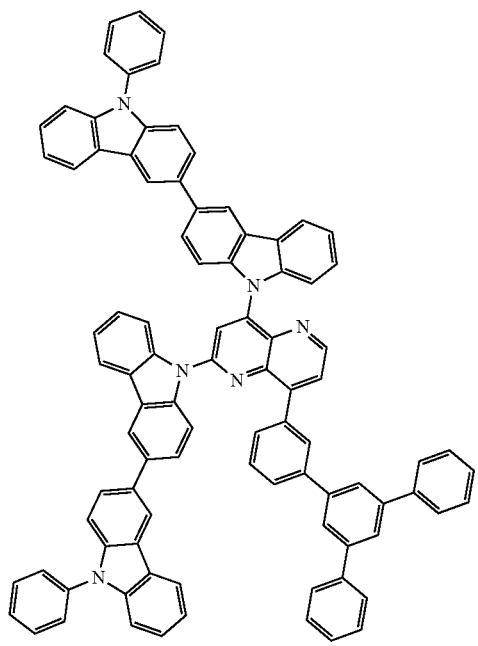
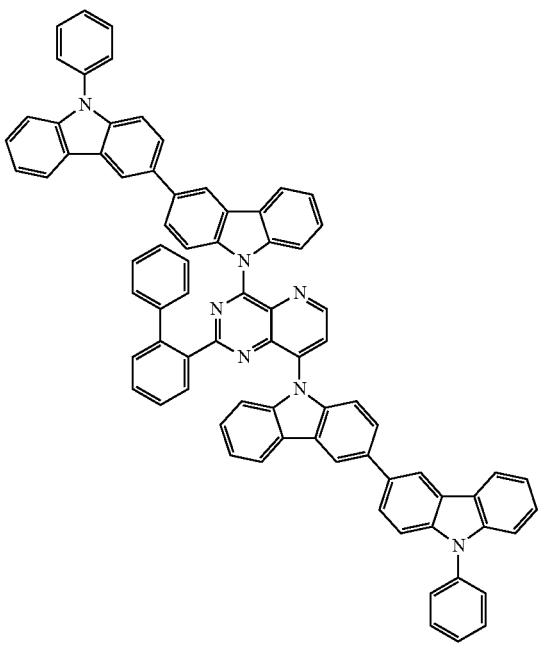

437
438
-continued
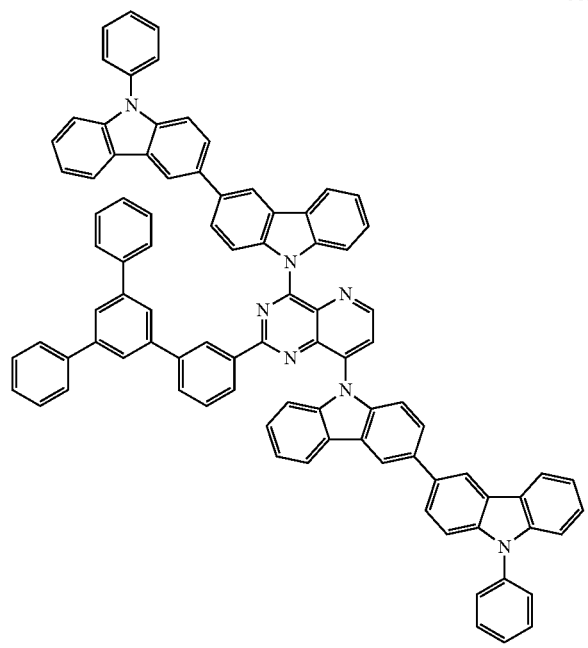
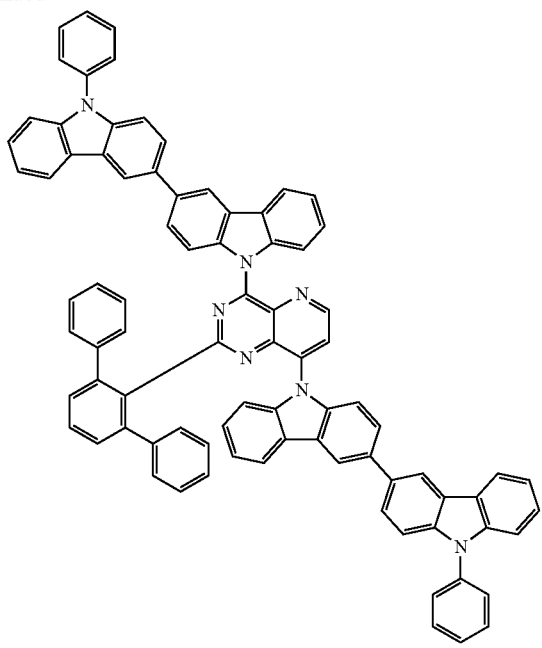
[Formula 119]
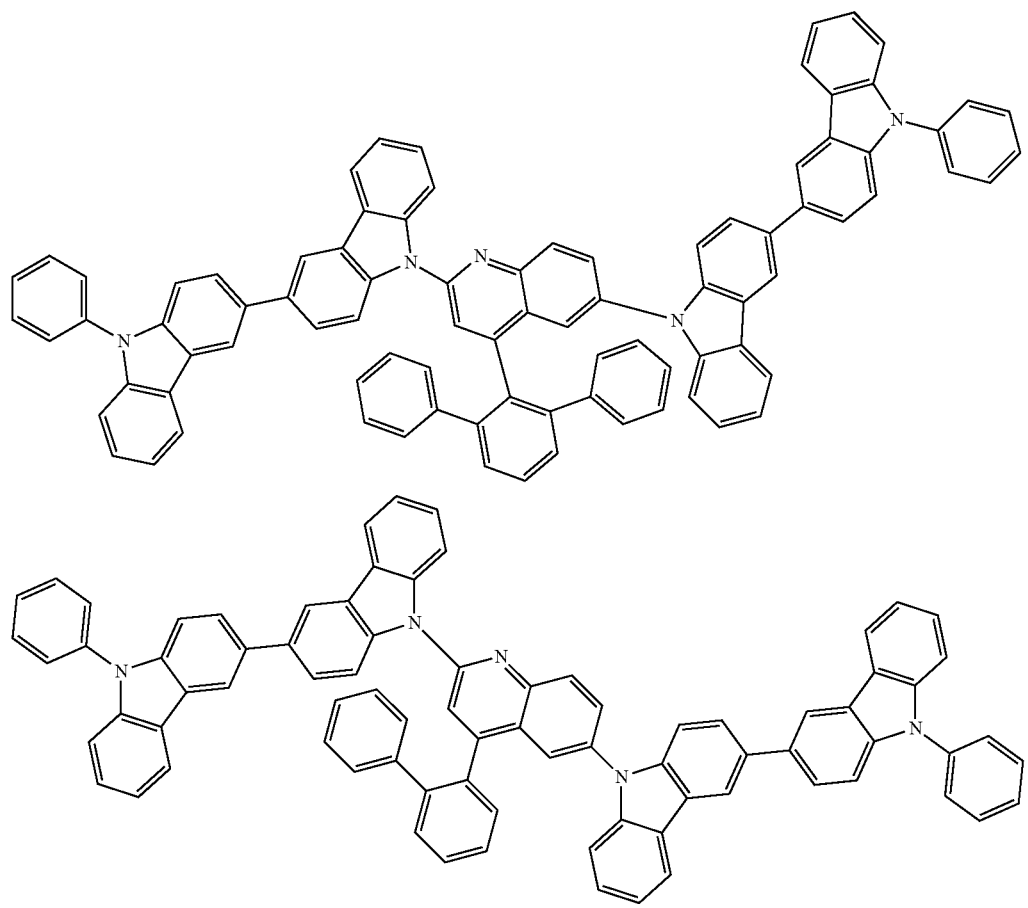

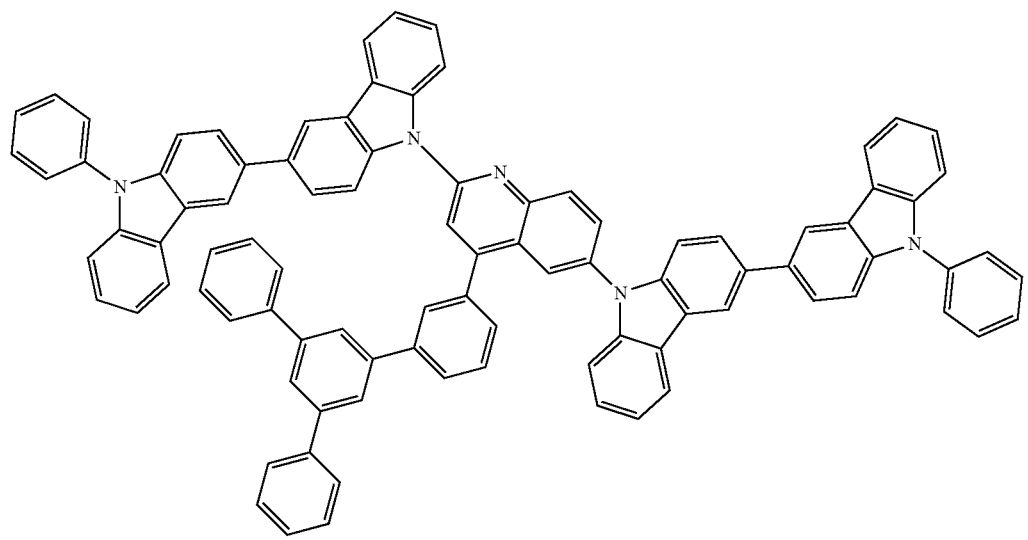
[Formula 120]
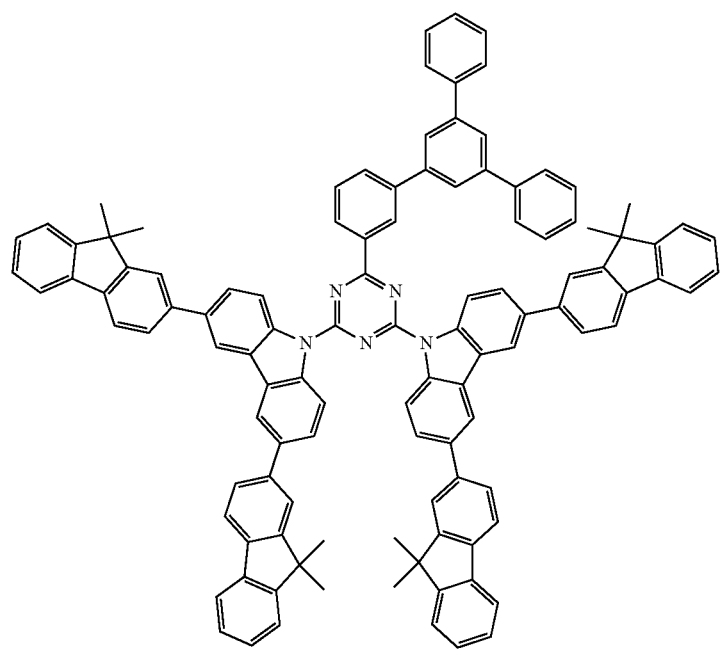

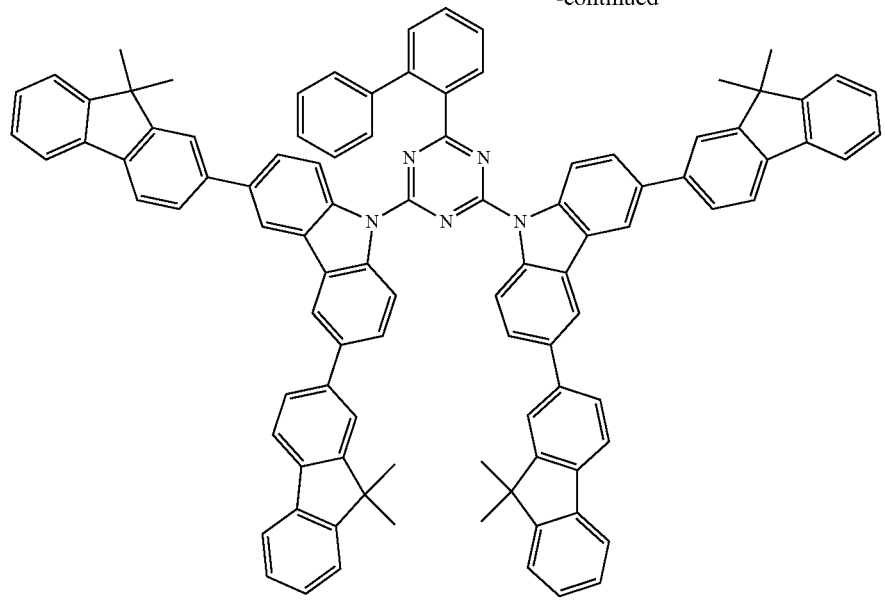
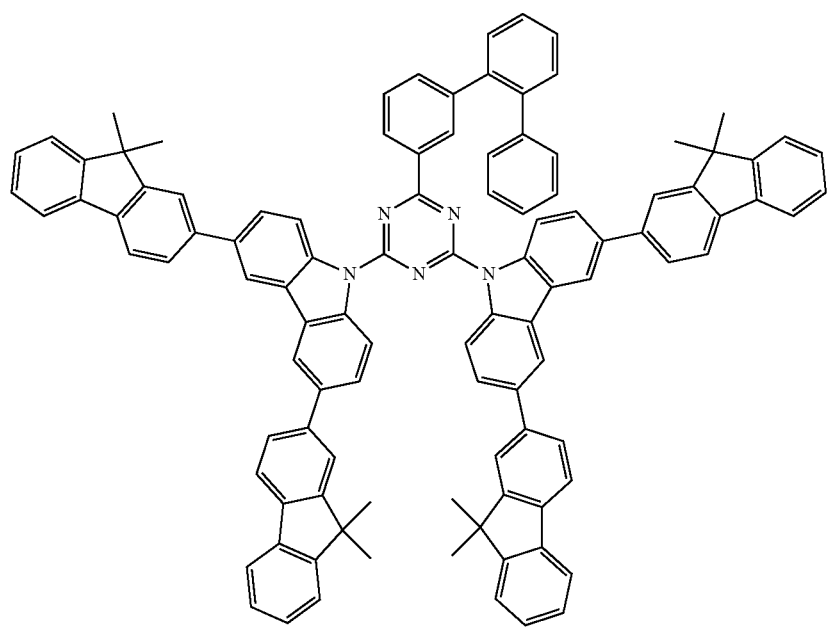

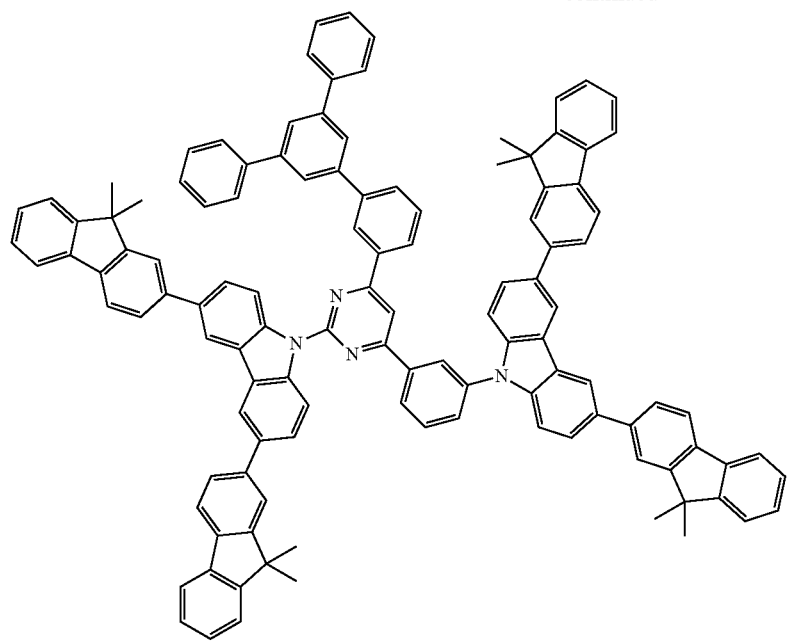
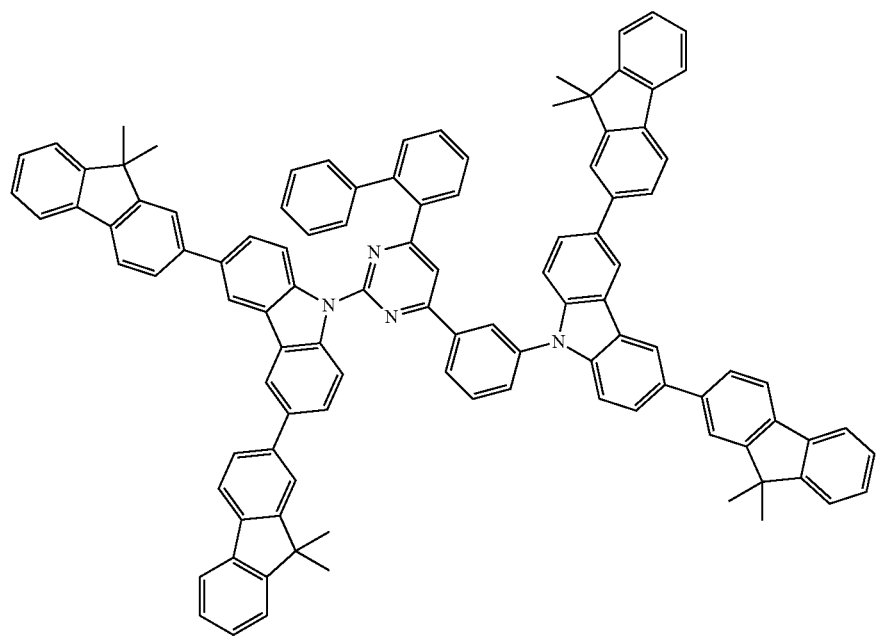

-continued
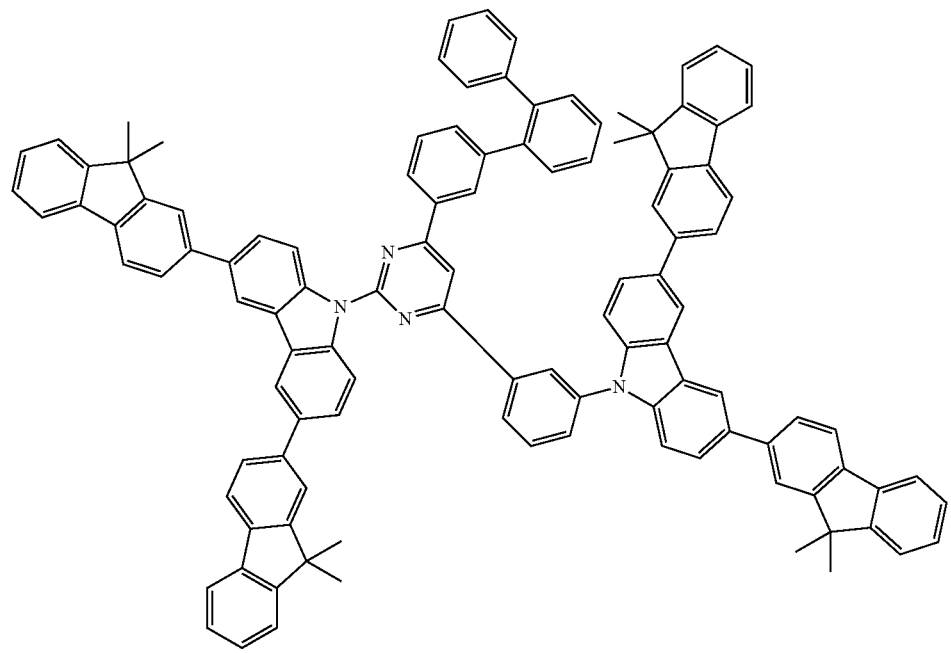
[Formula 121]
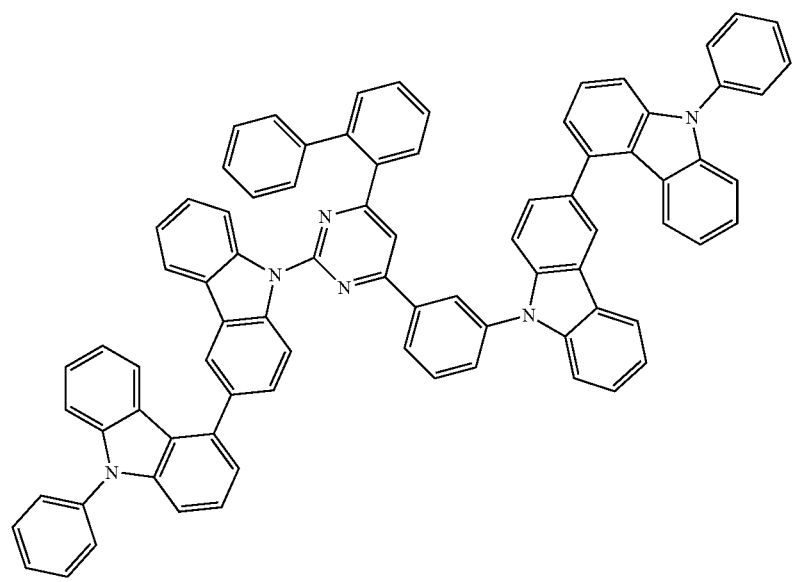

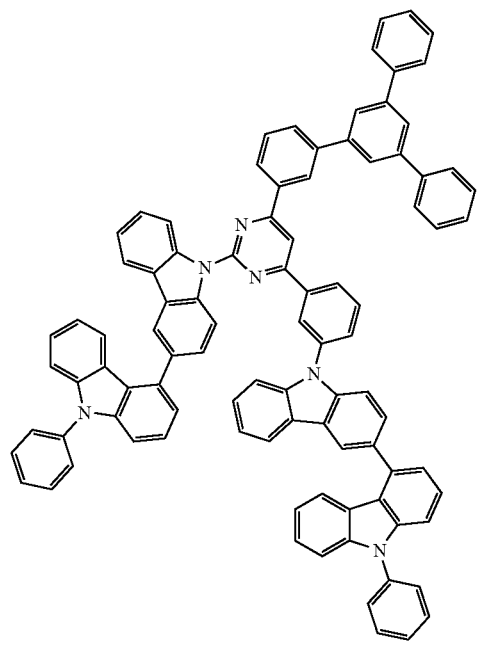
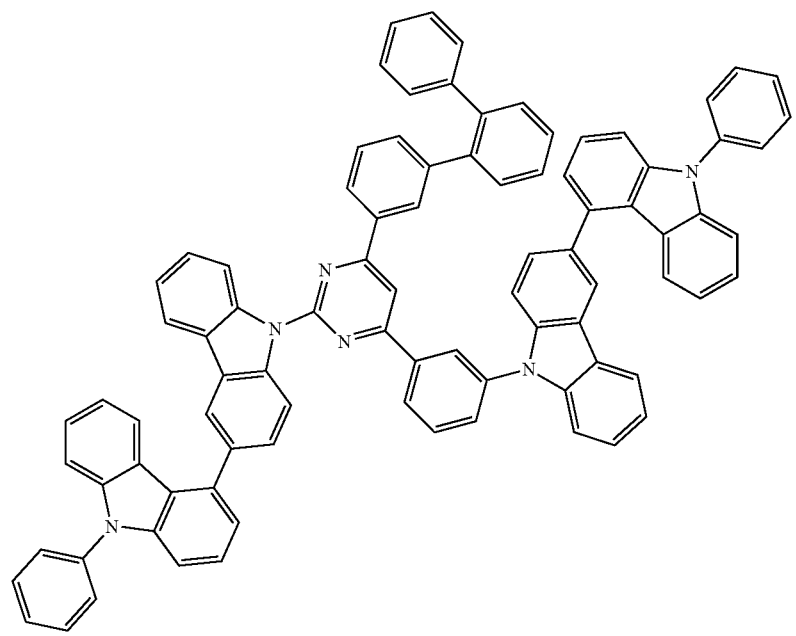

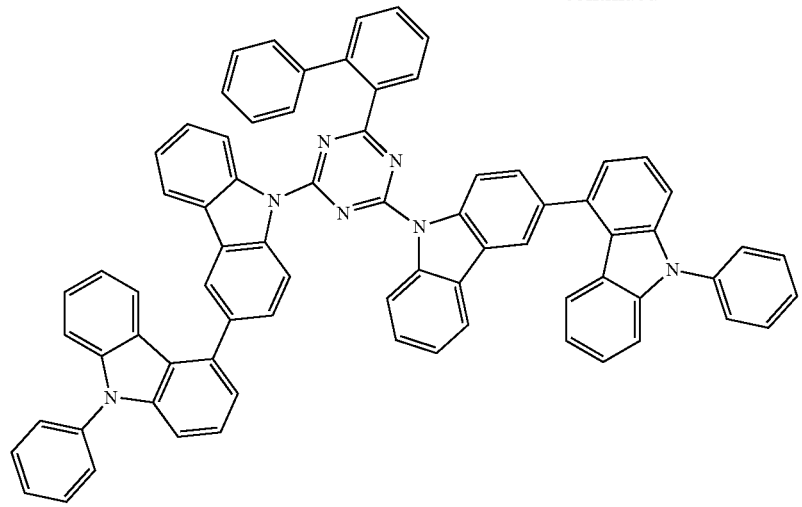
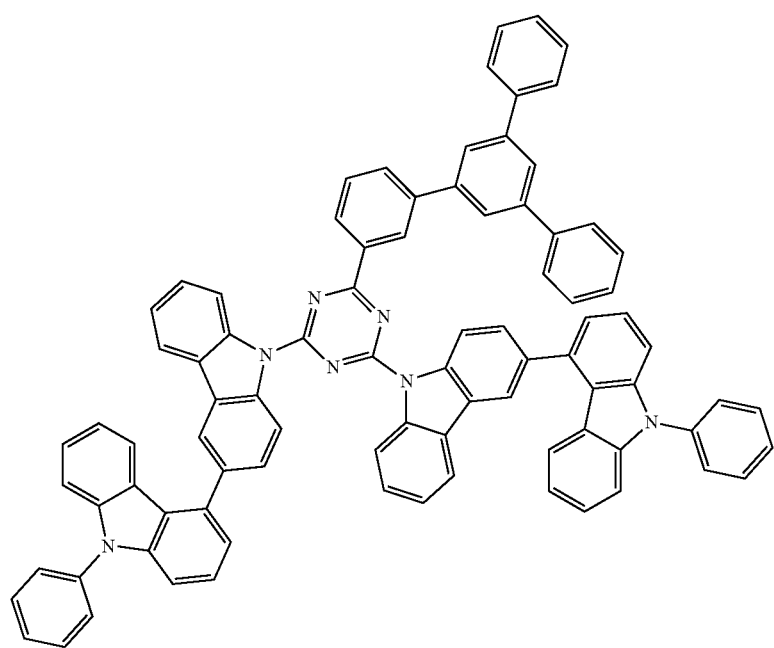

-continued
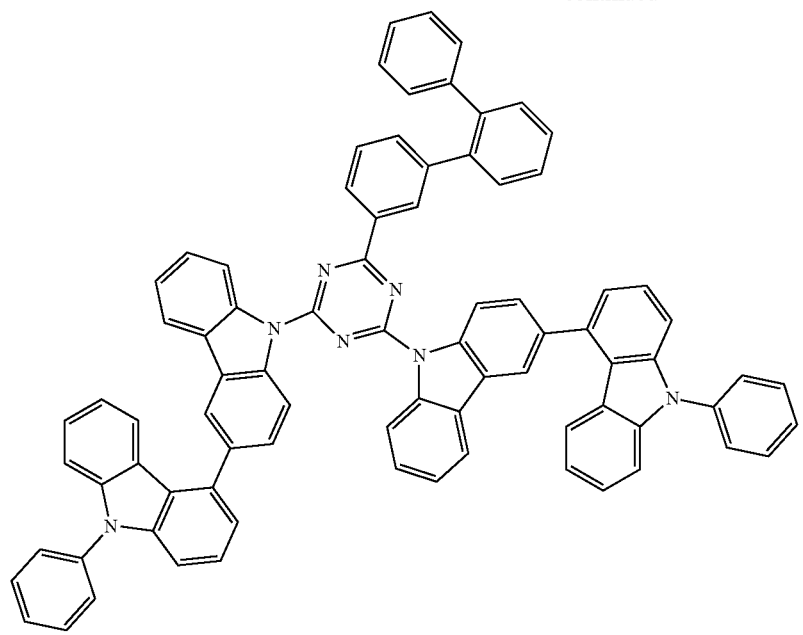
[Formula 122]
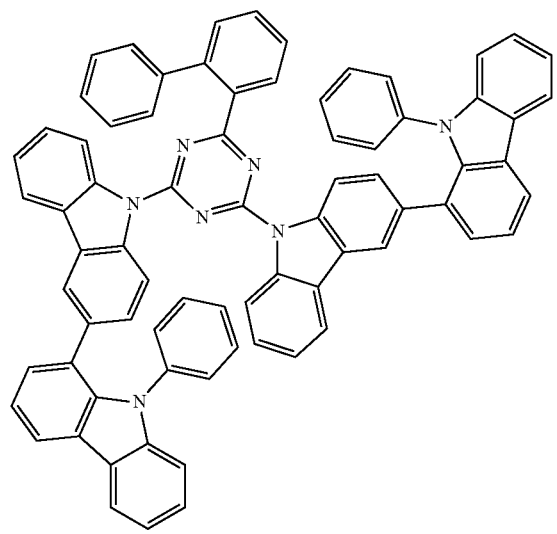

453
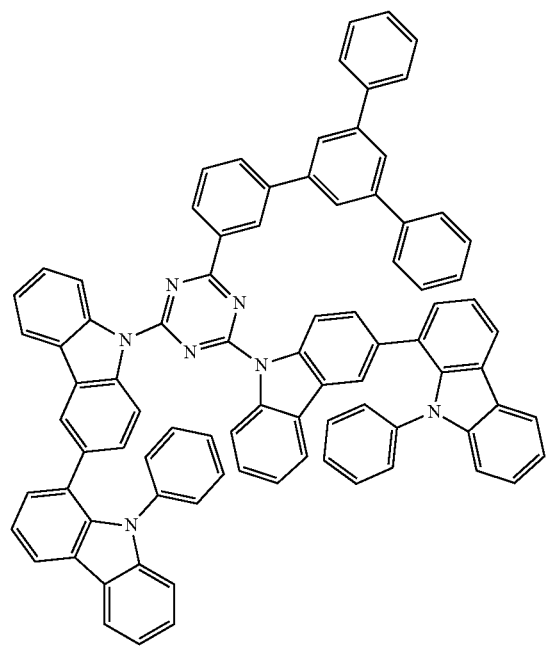
454
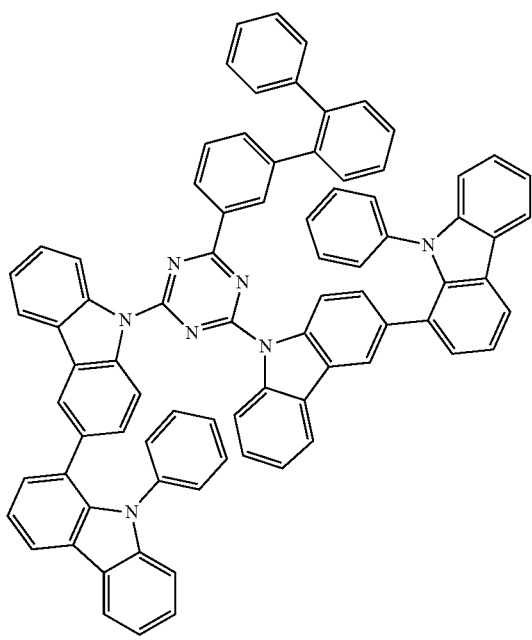
-continued
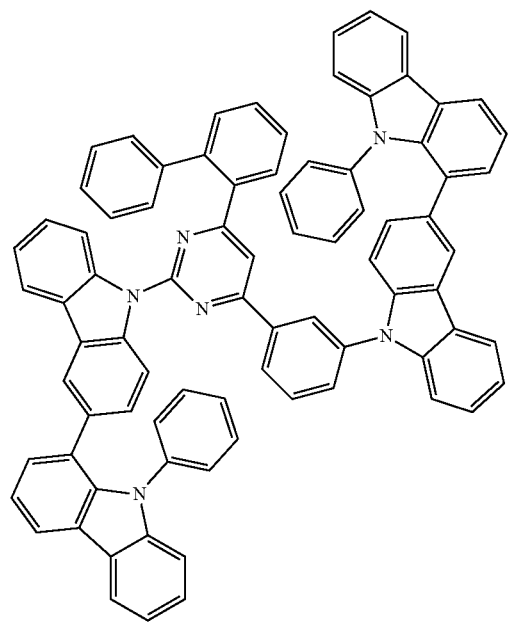
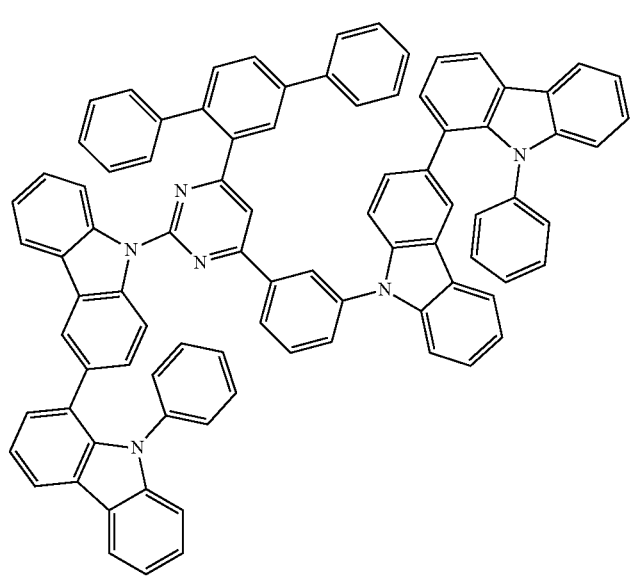

-continued
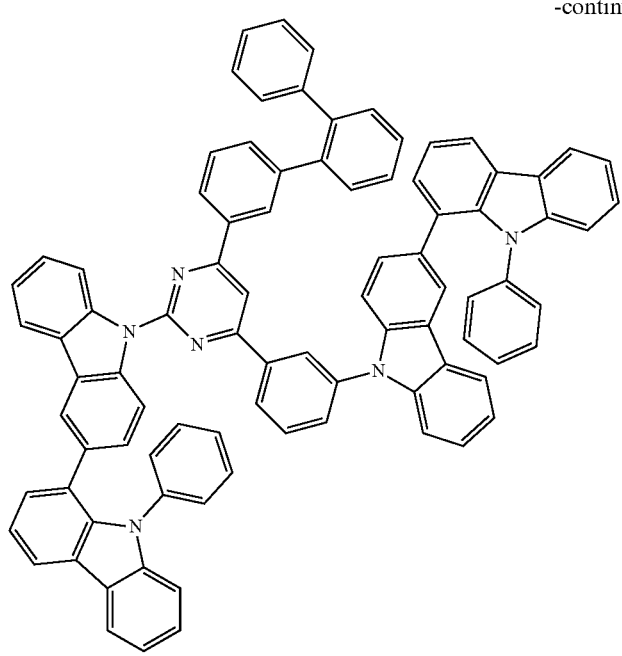
[Formula 123]
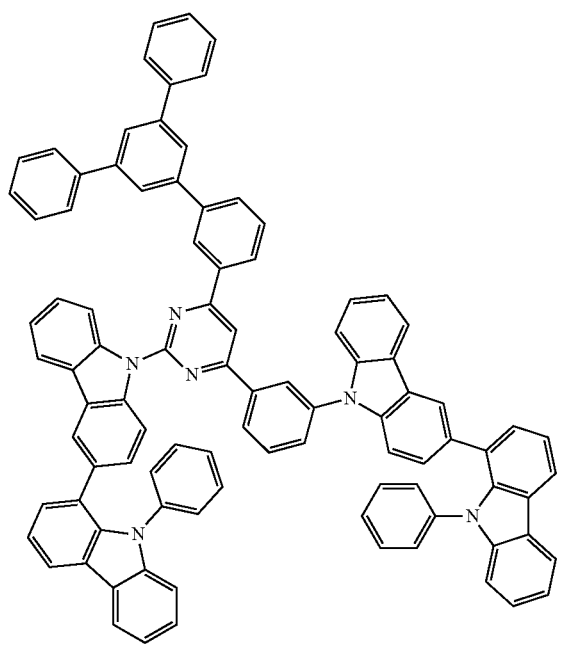

-continued
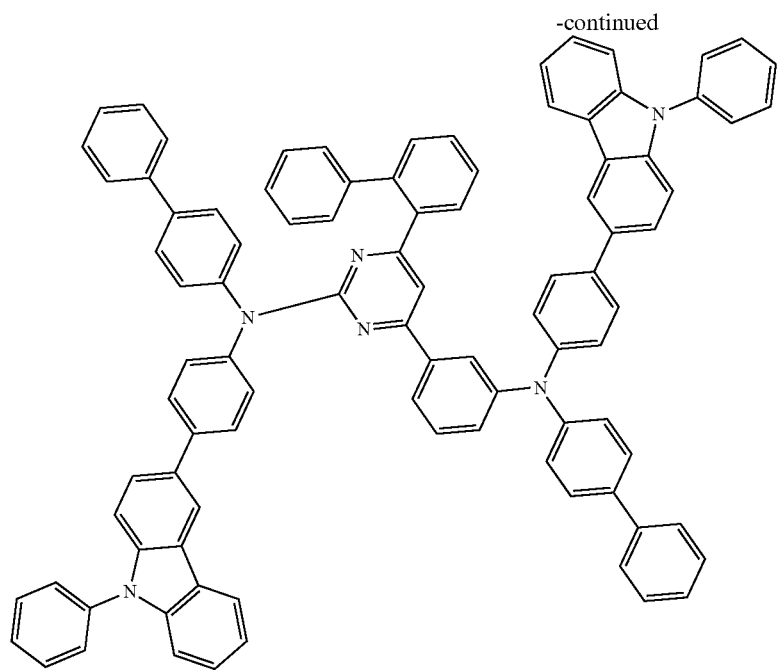
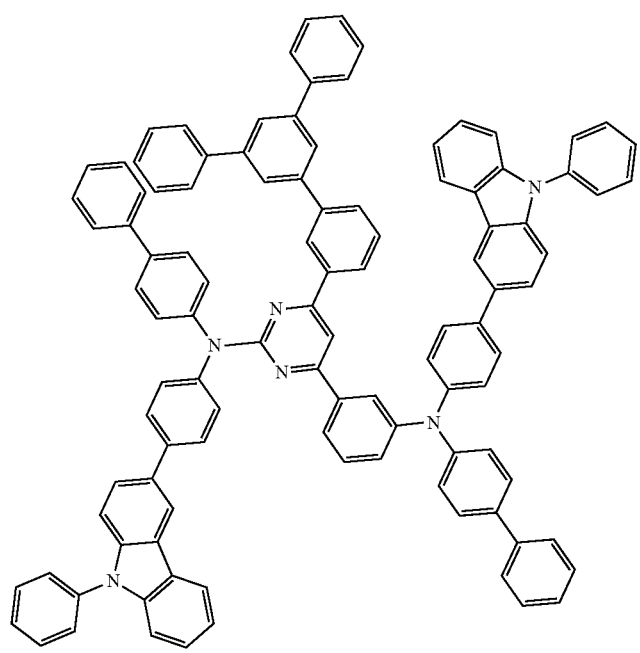

459
-continued
460
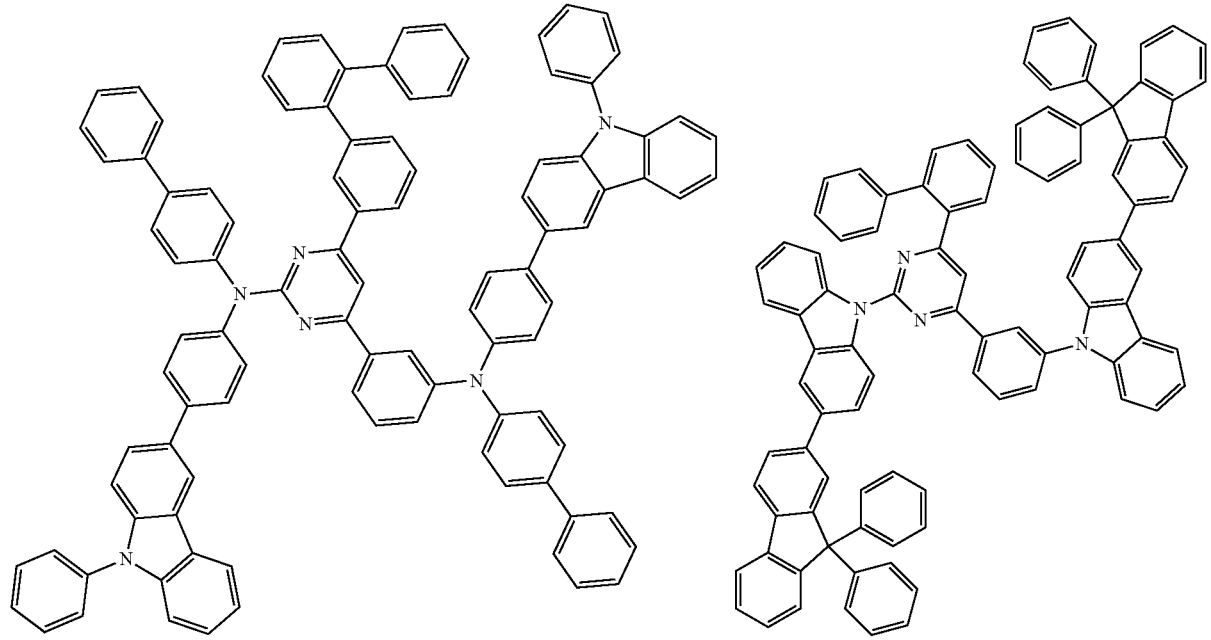
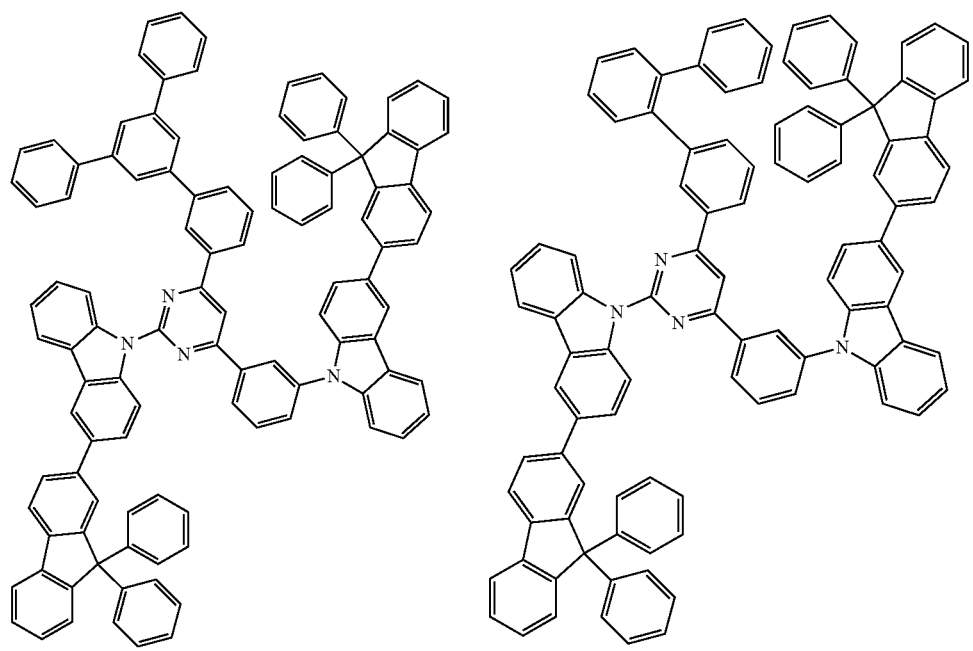

[Formula 124]
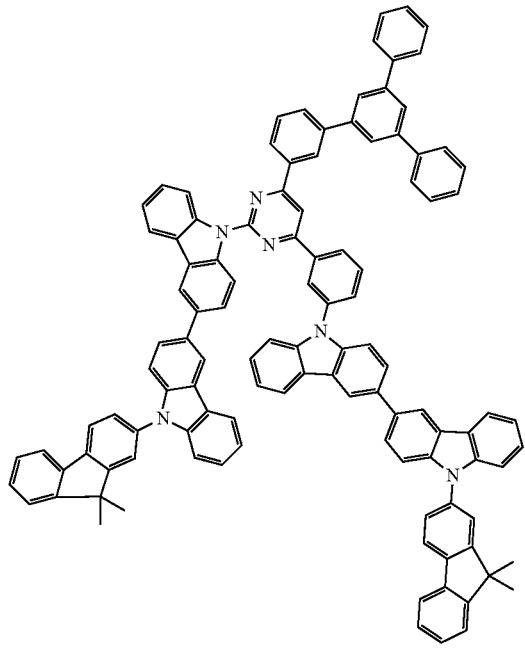
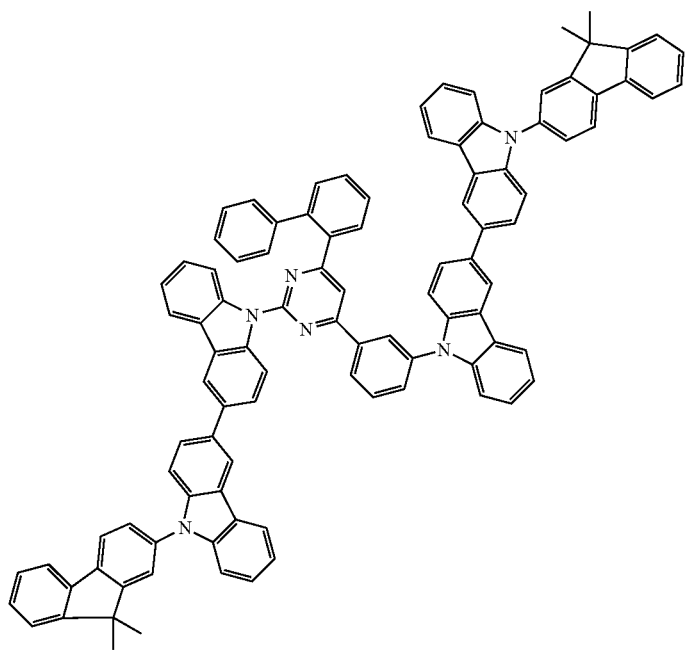

-continued
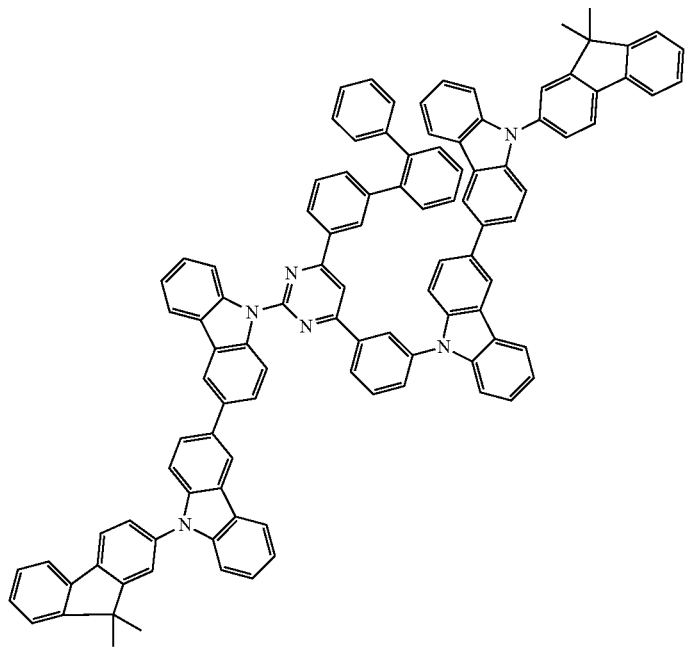
463
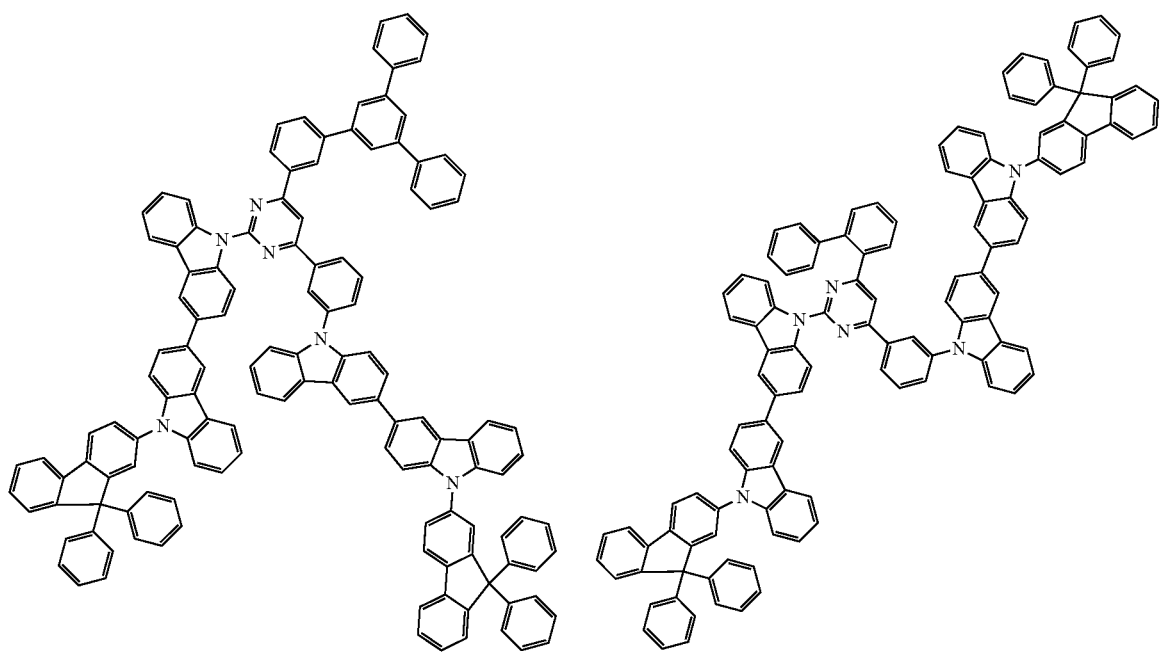
464

465 466
-continued
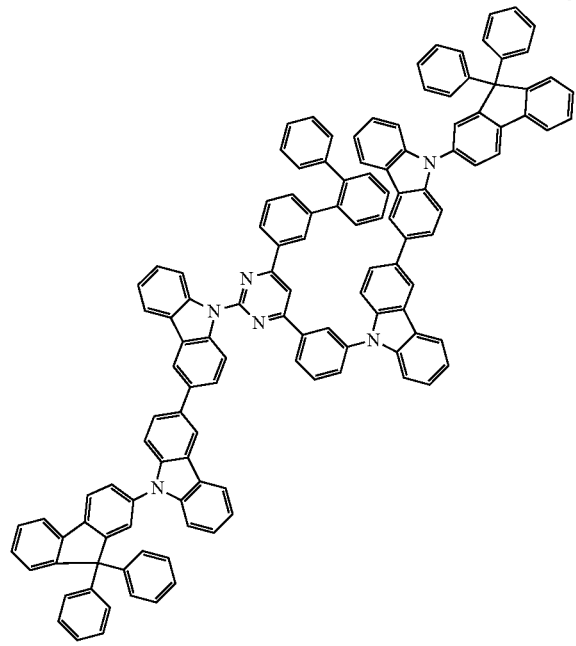
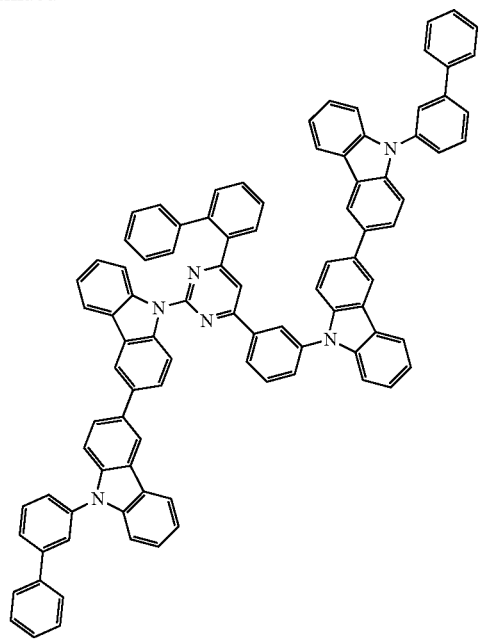
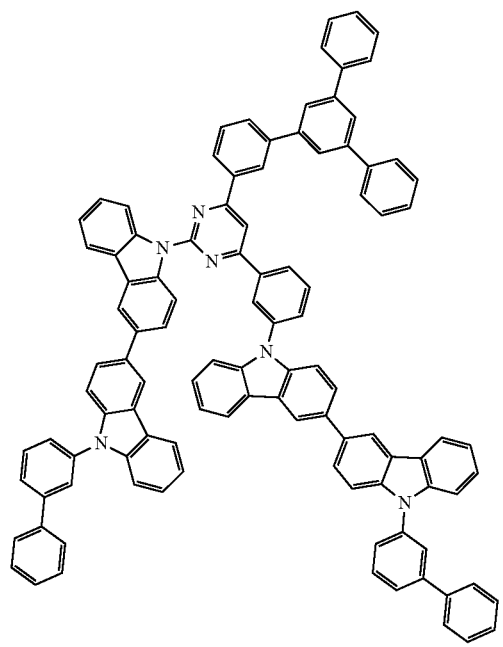
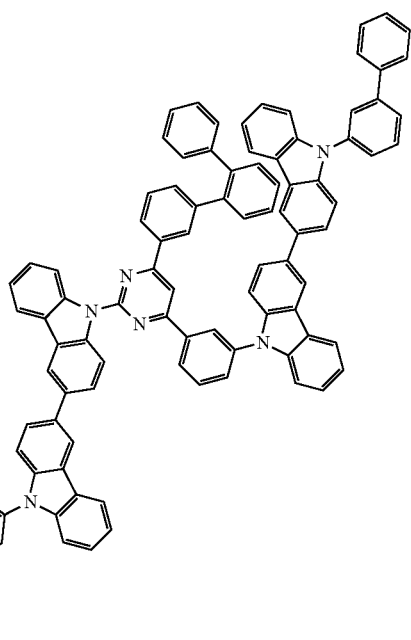

[Formula 125]
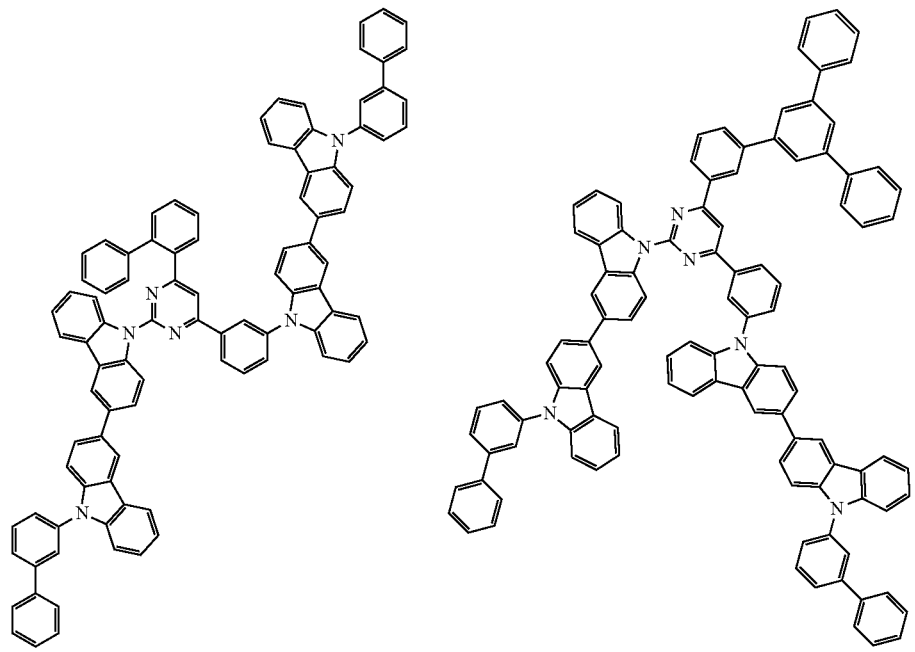
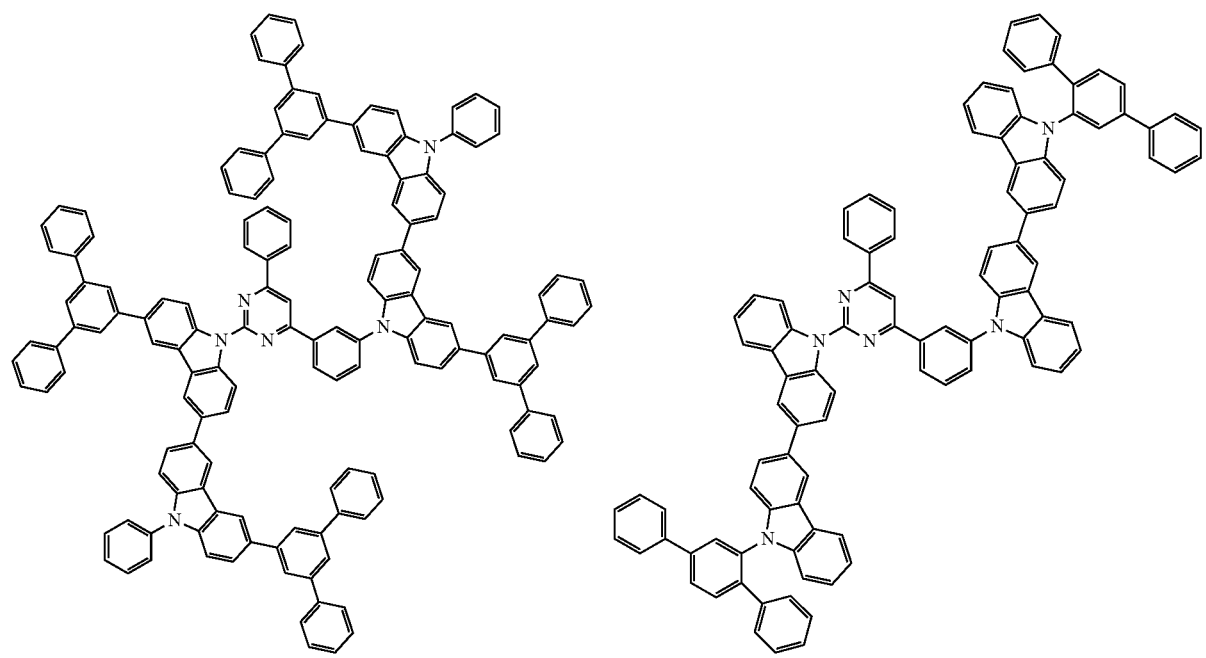

-continued
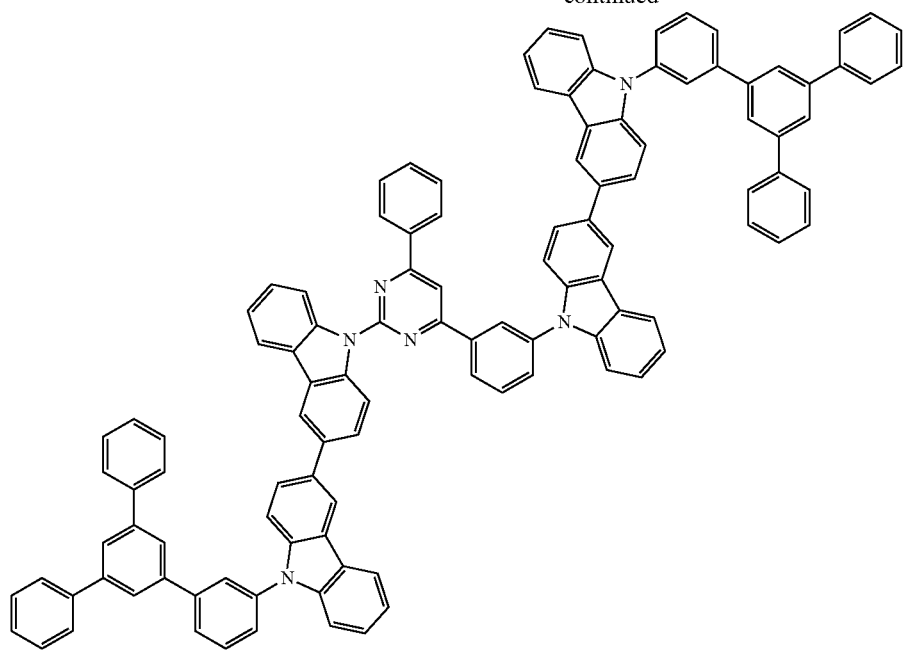
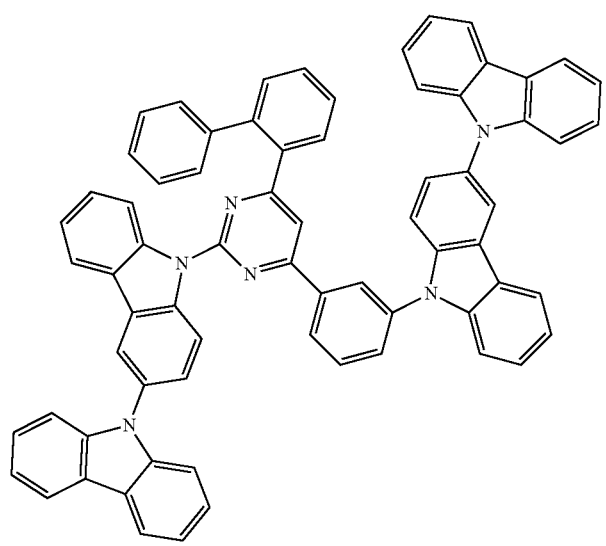

[Formula 126]
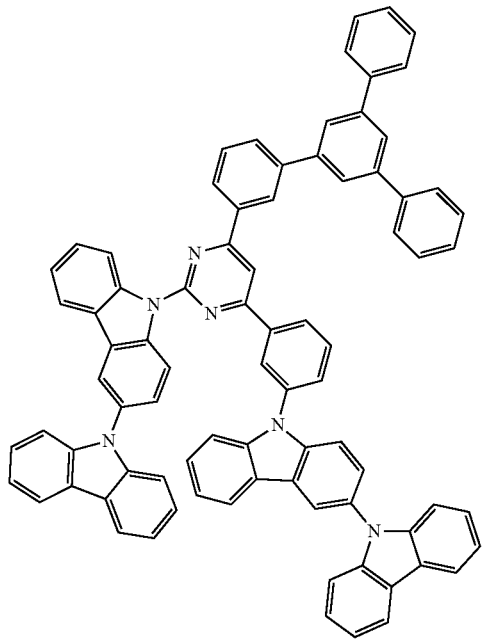
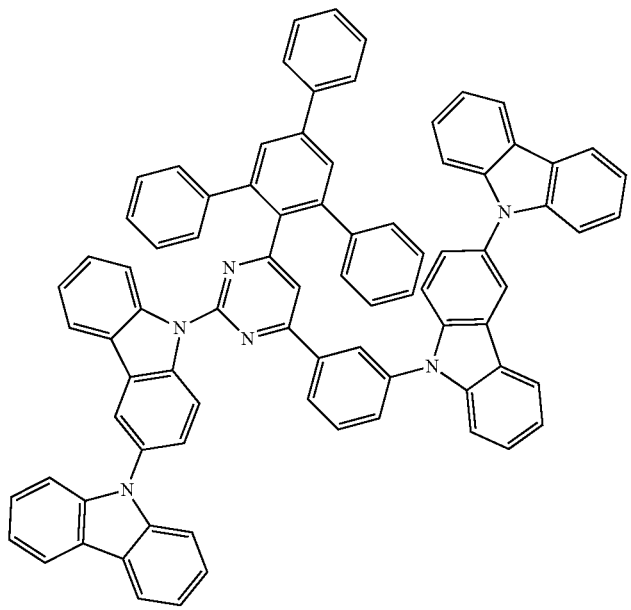
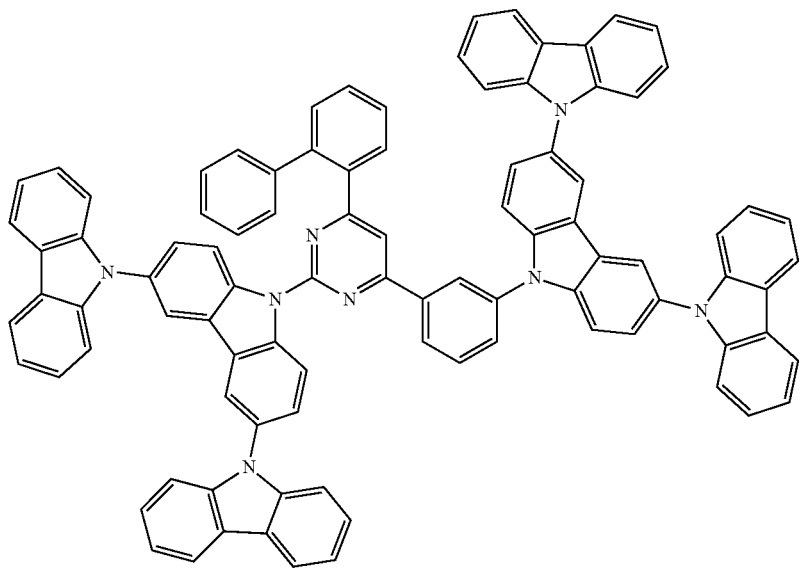

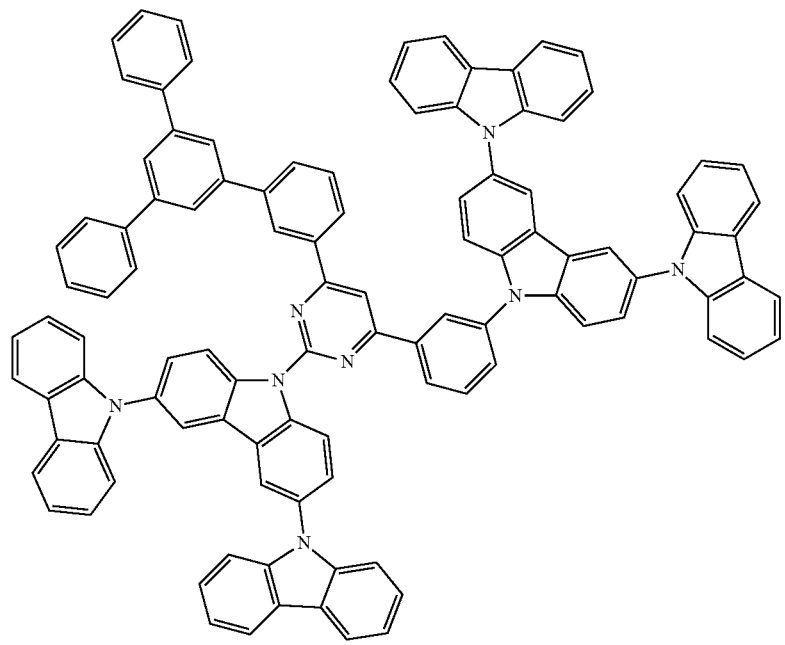
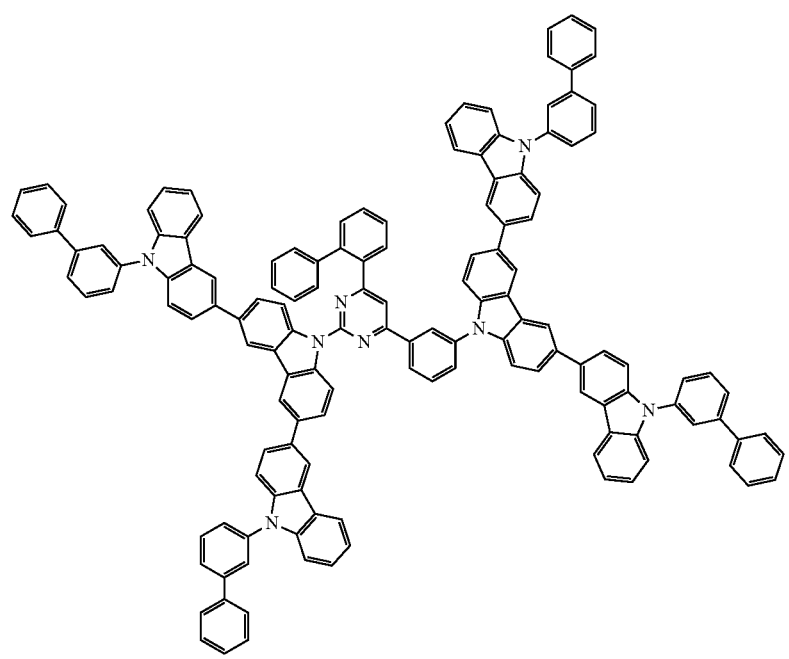

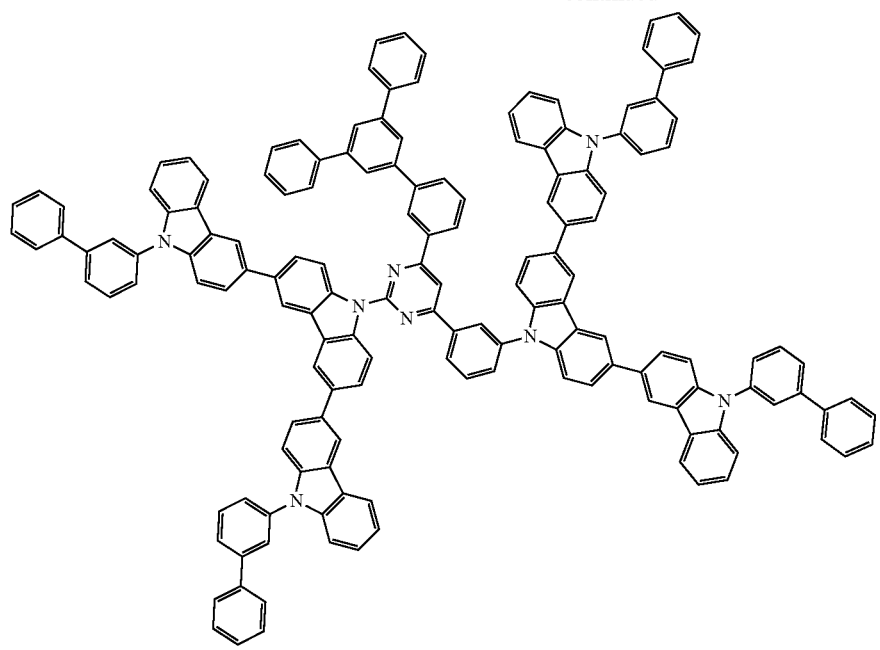
[Formula 127]
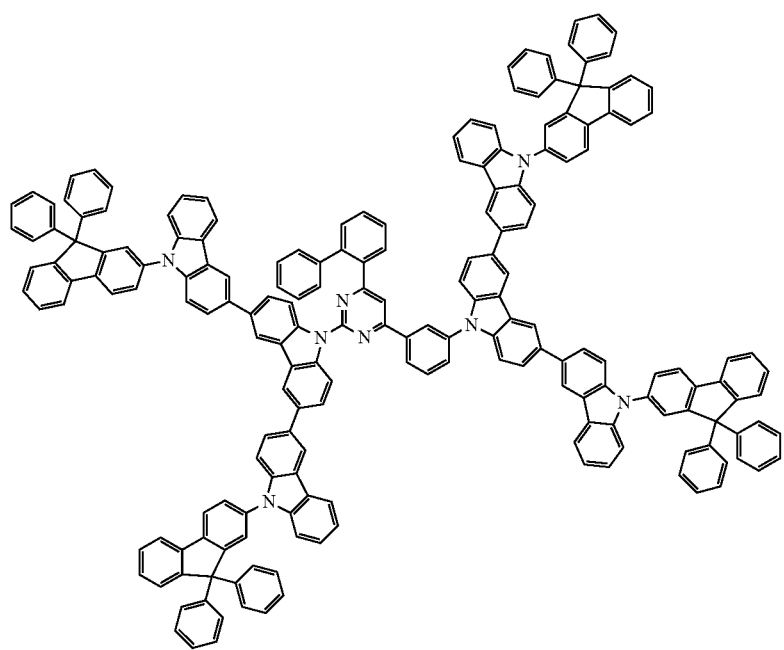

-continued
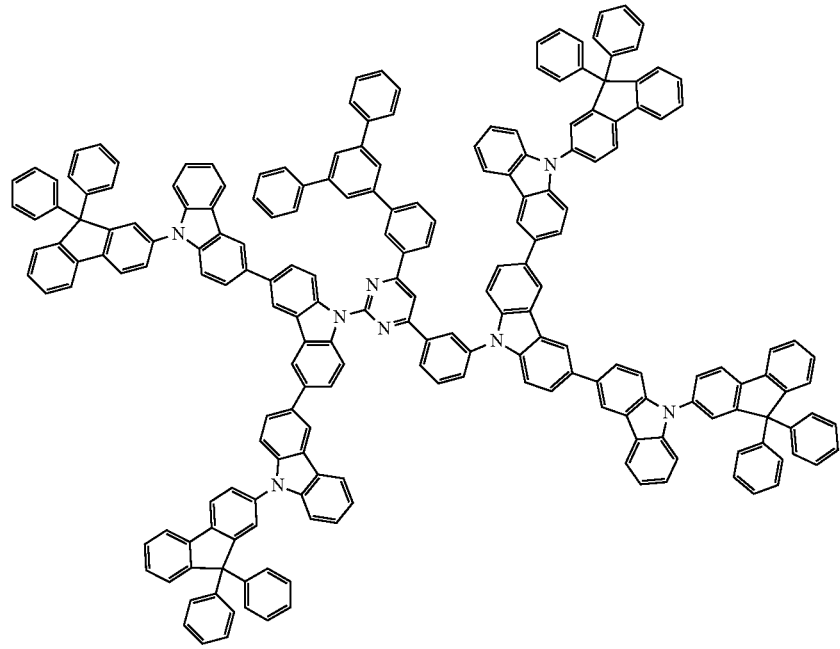
[Formula 128]
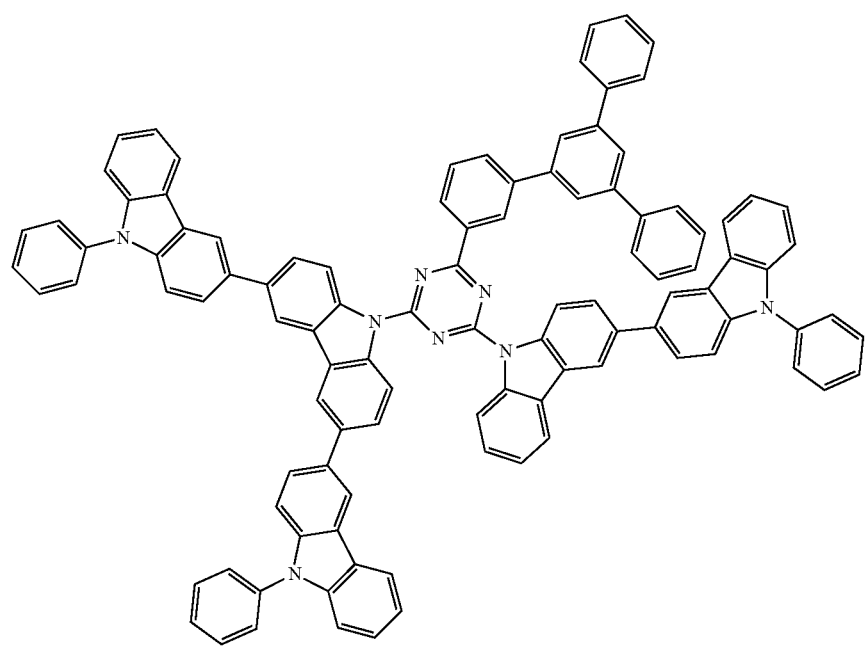

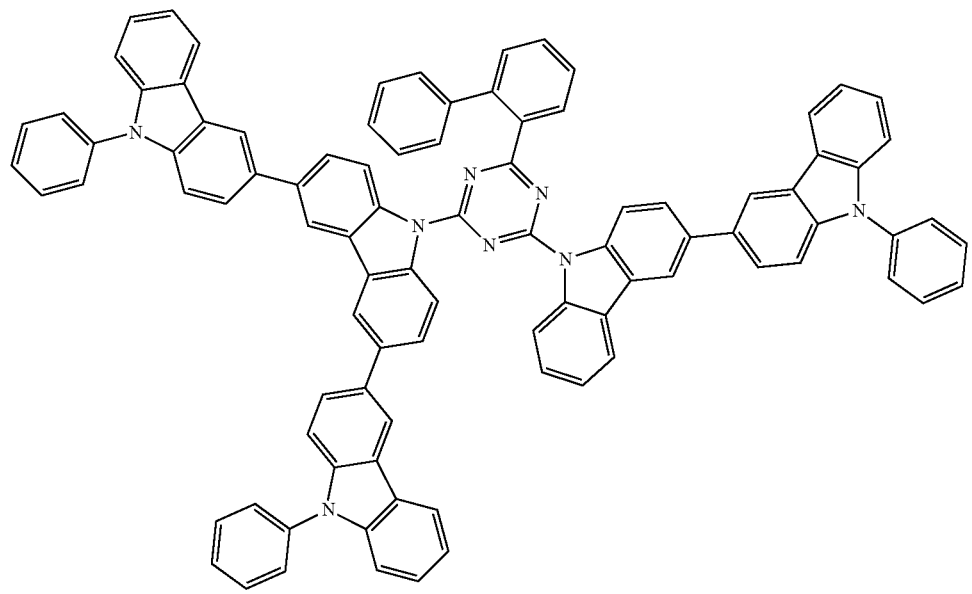
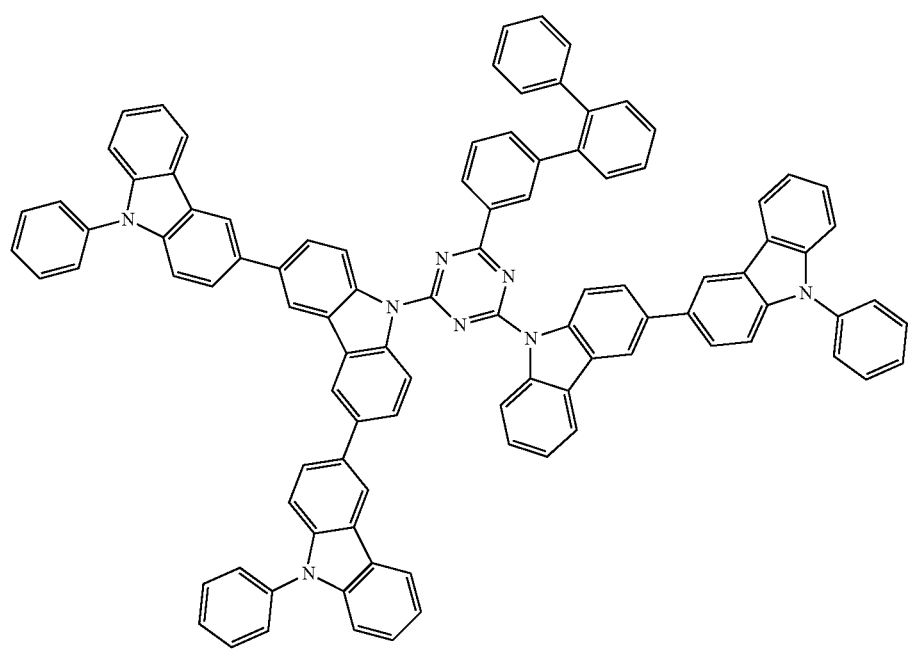

-continued
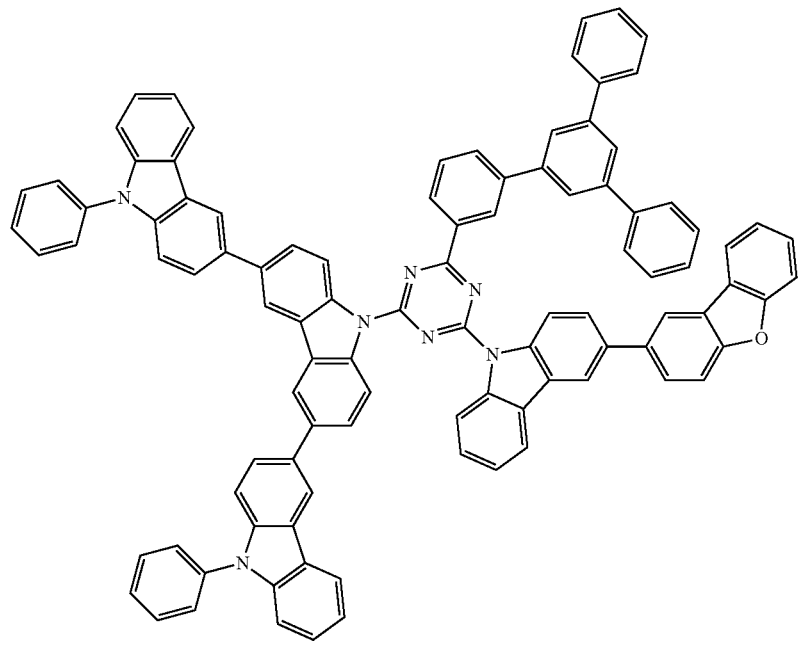

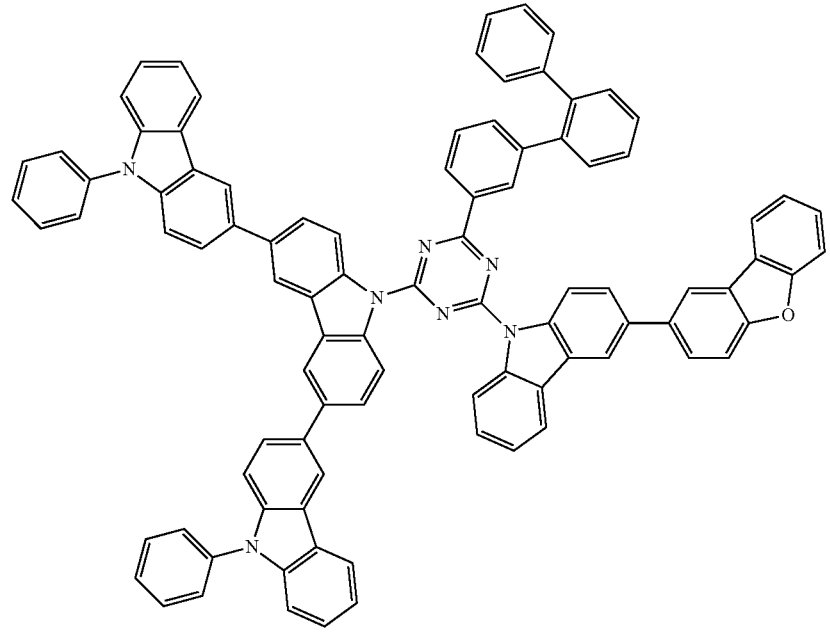
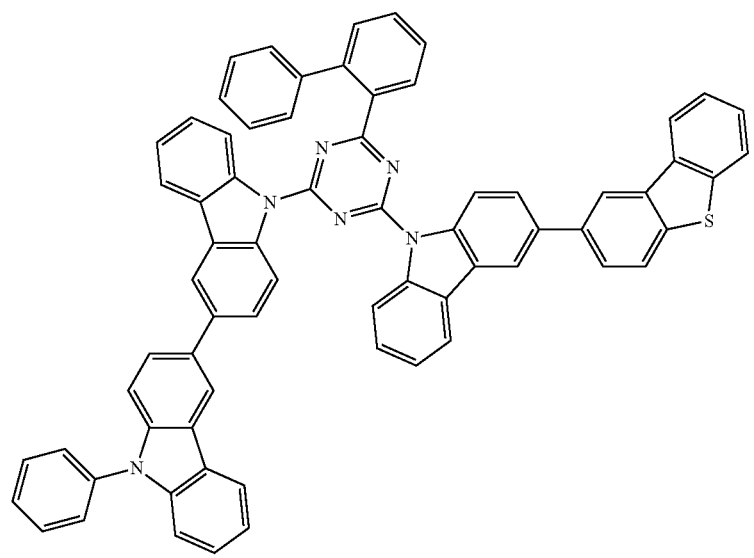

-continued
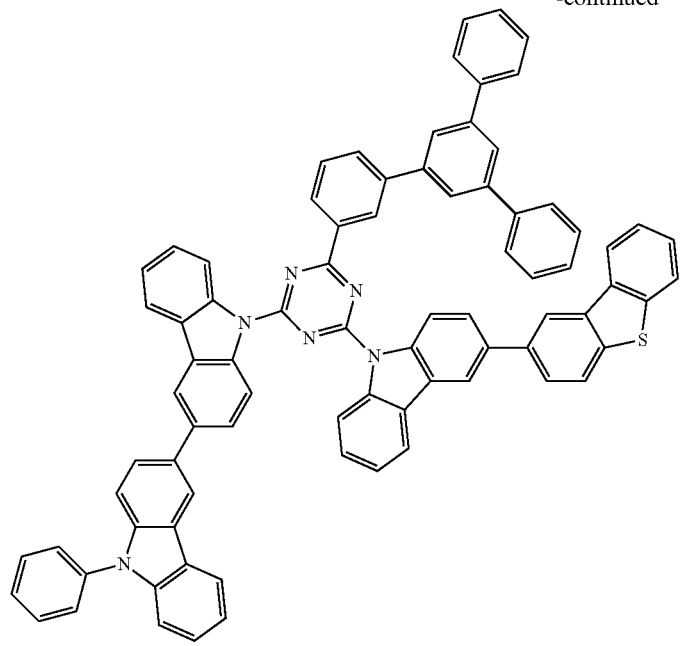
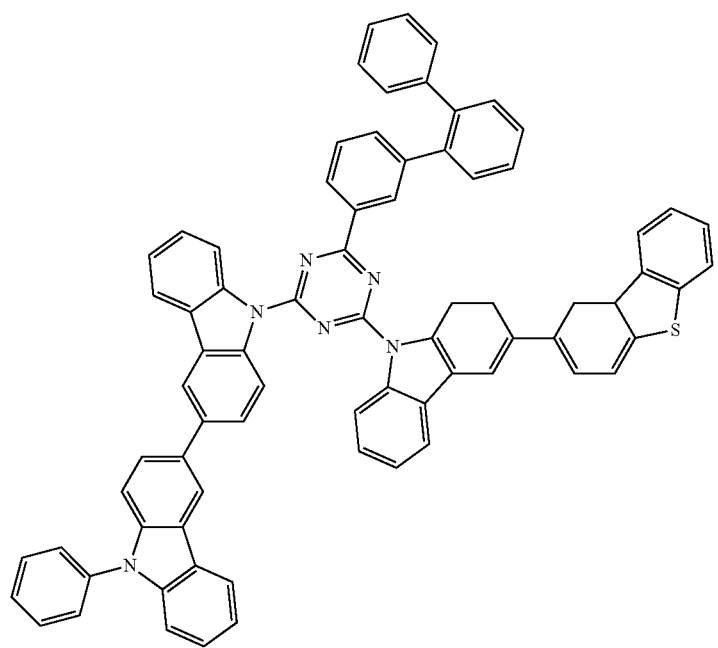

[Formula 129]
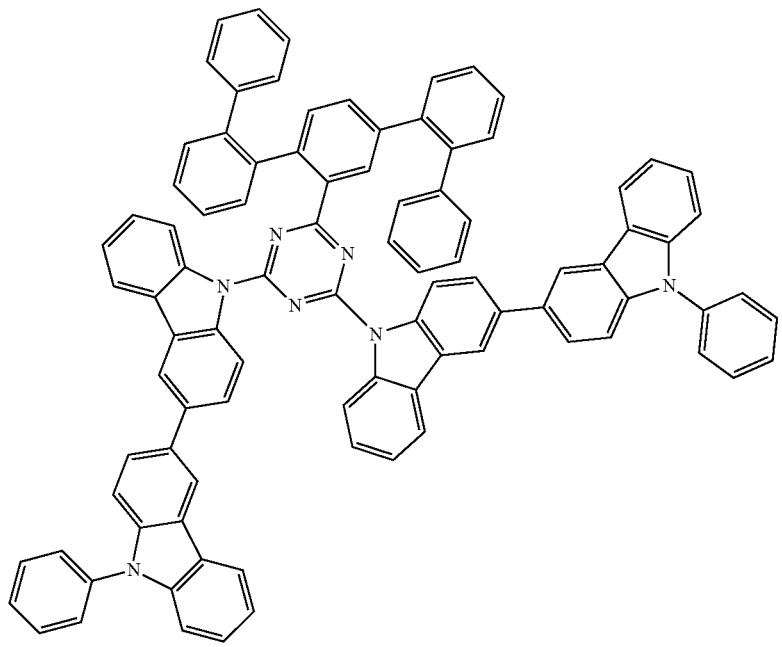
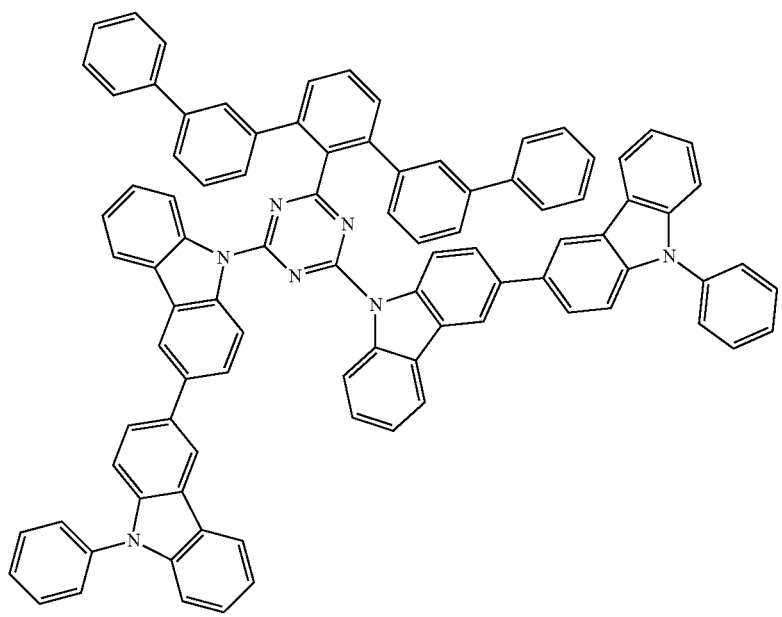

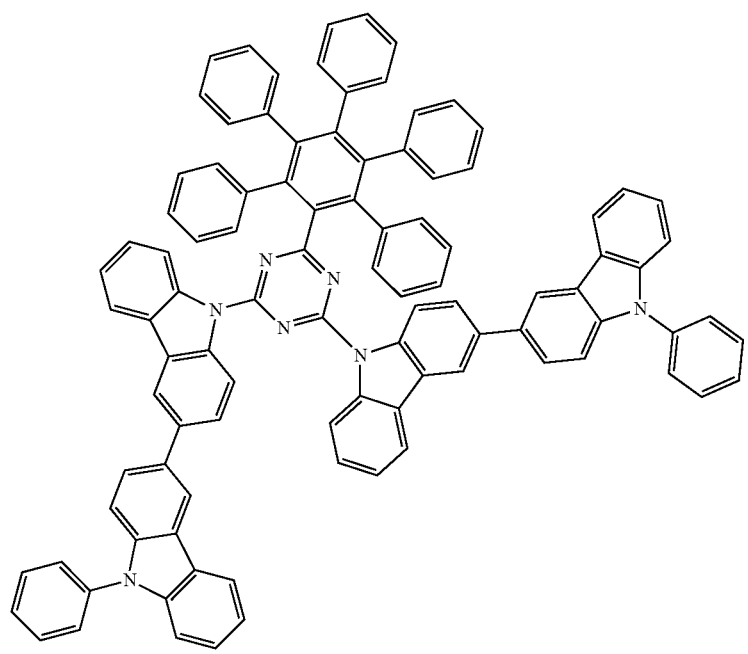
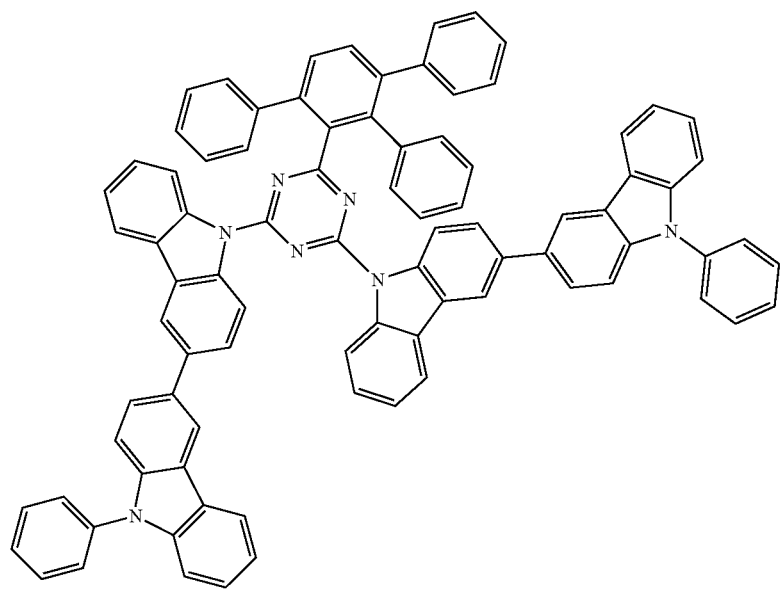

-continued
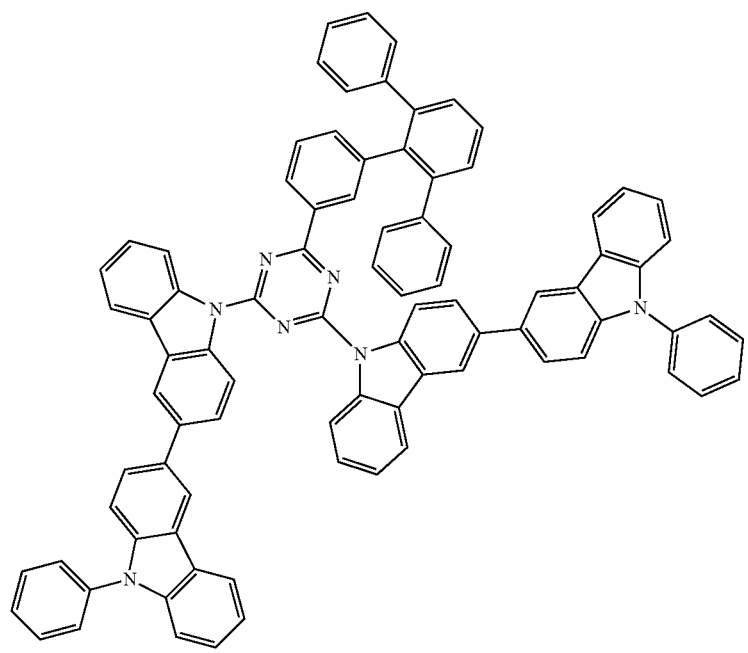
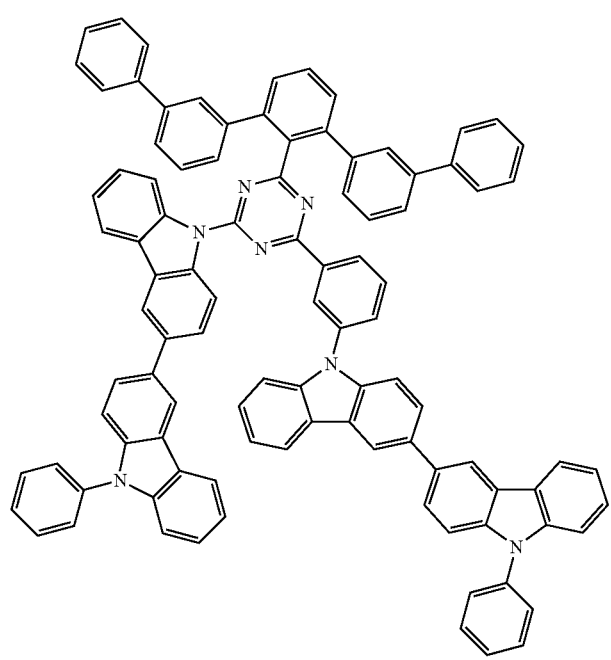

[Formula 130]
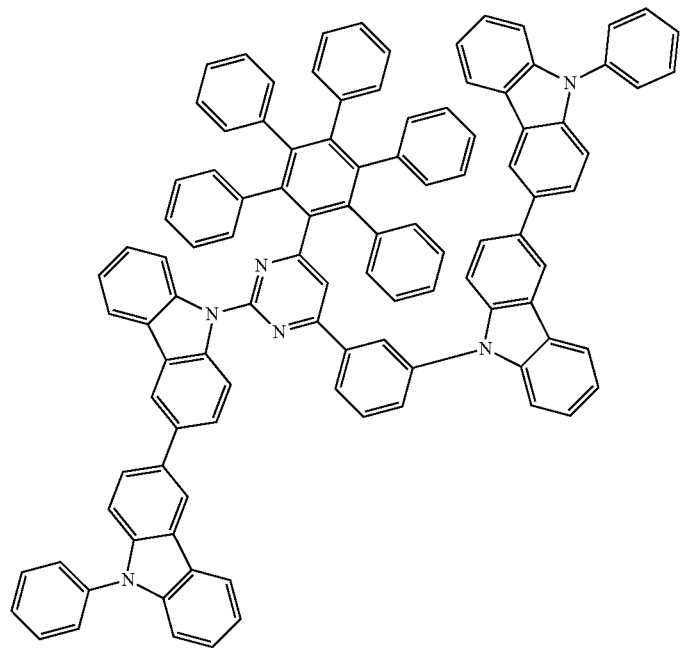
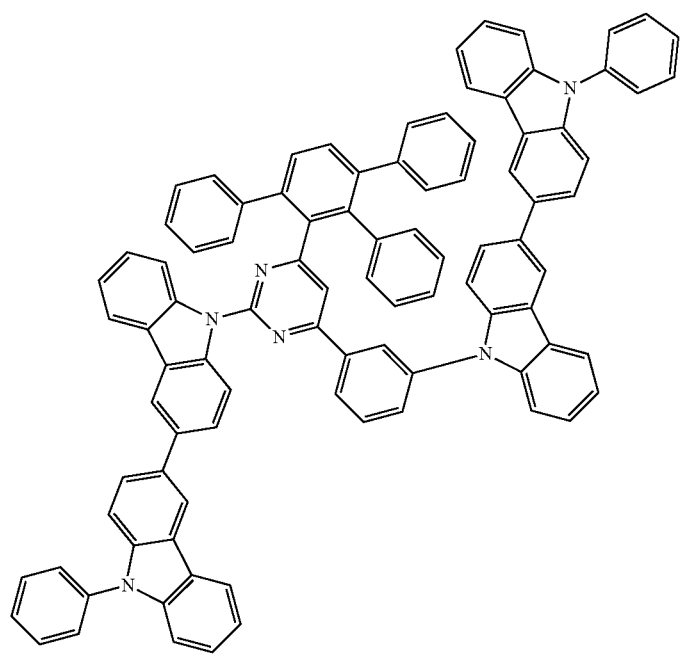

-continued
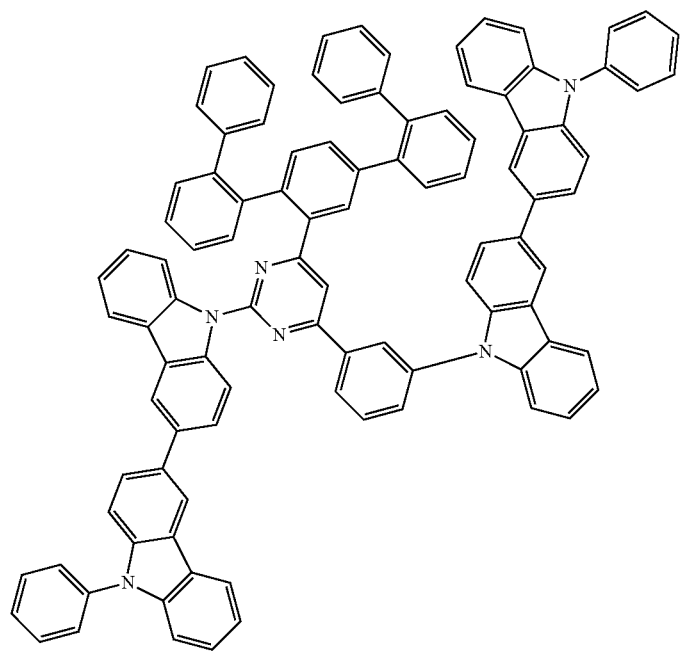
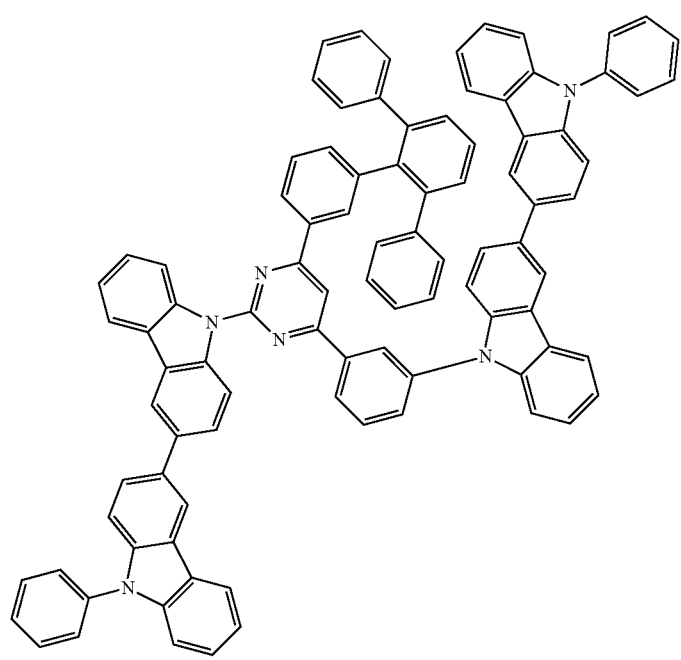

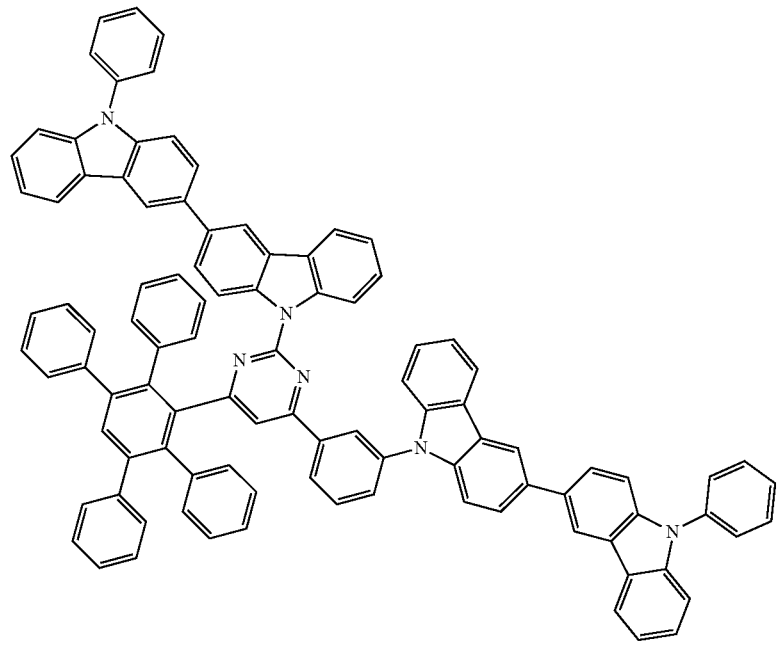
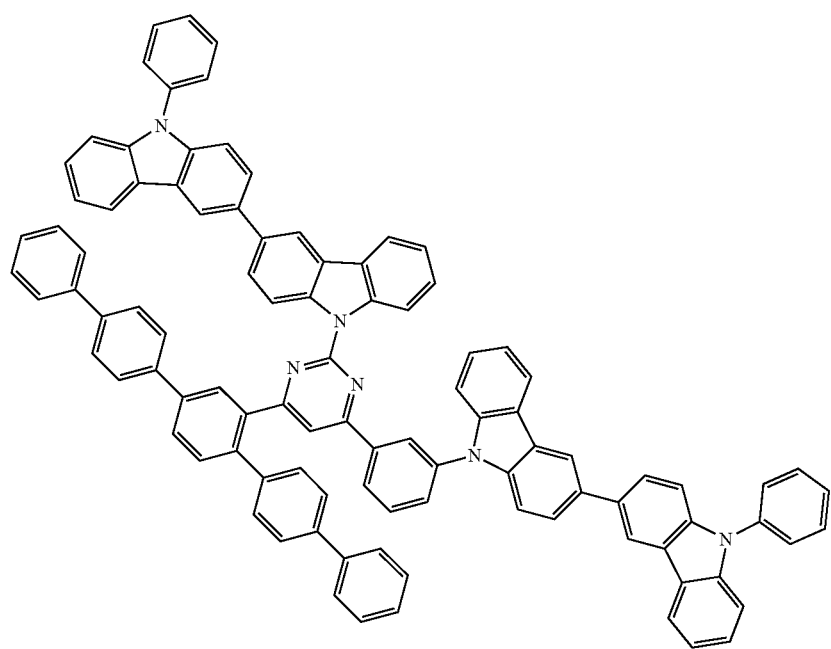

[Formula 131]
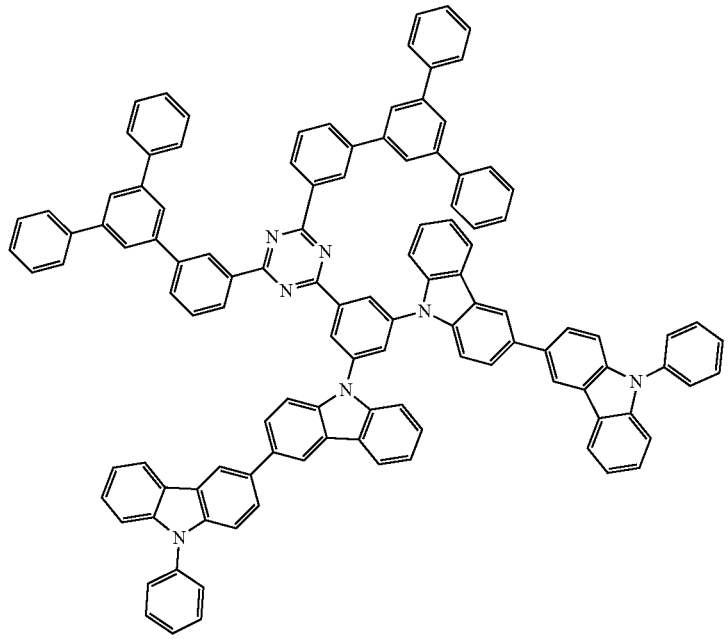
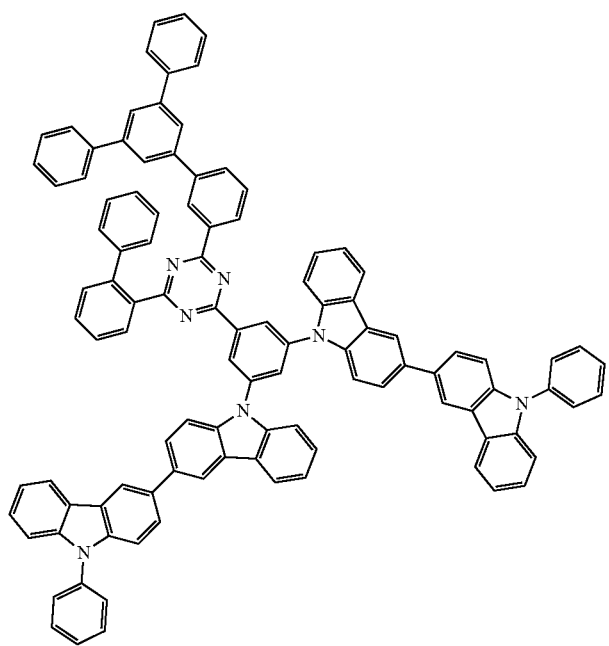

-continued
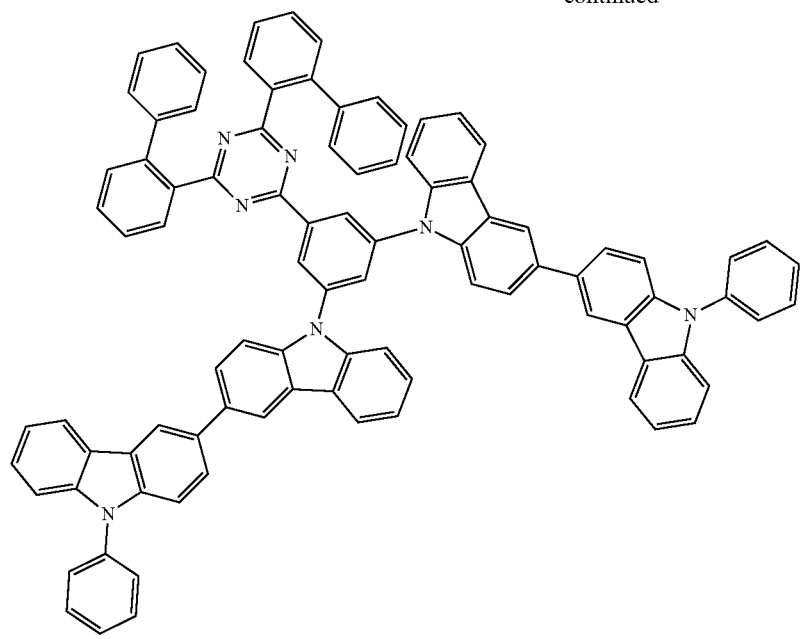
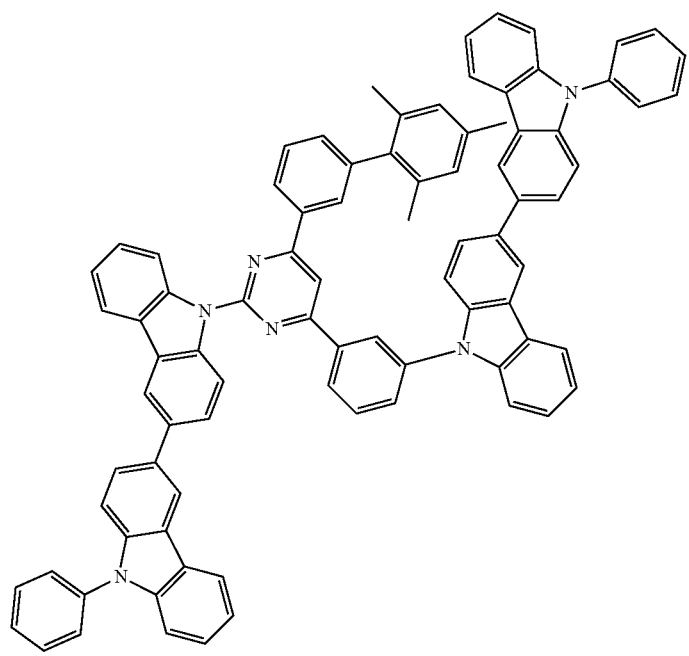

-continued
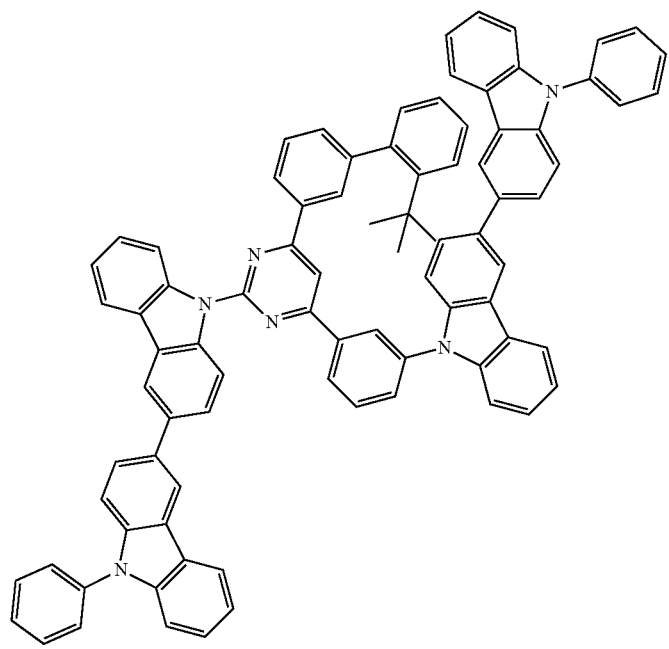
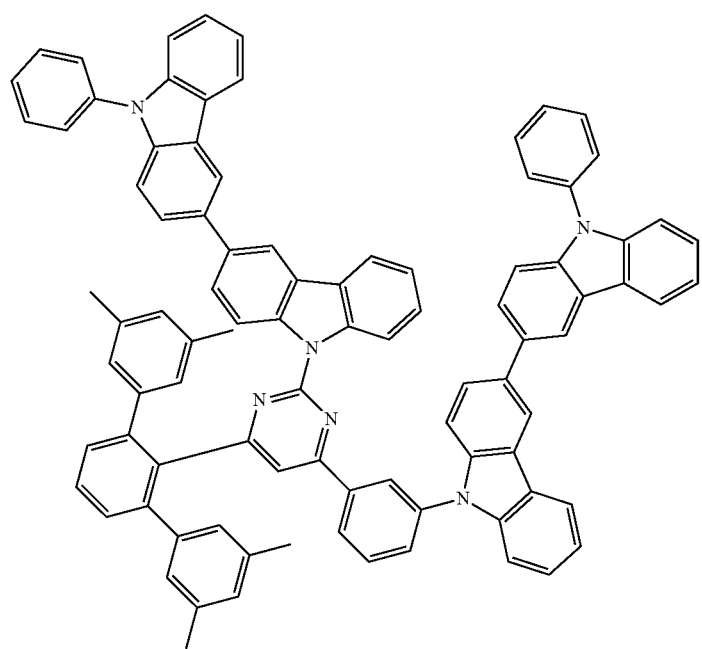

[Formula 132]
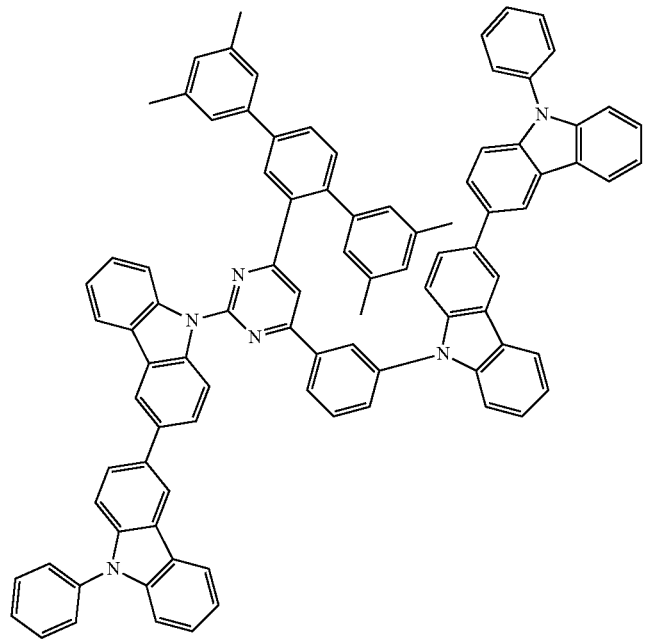
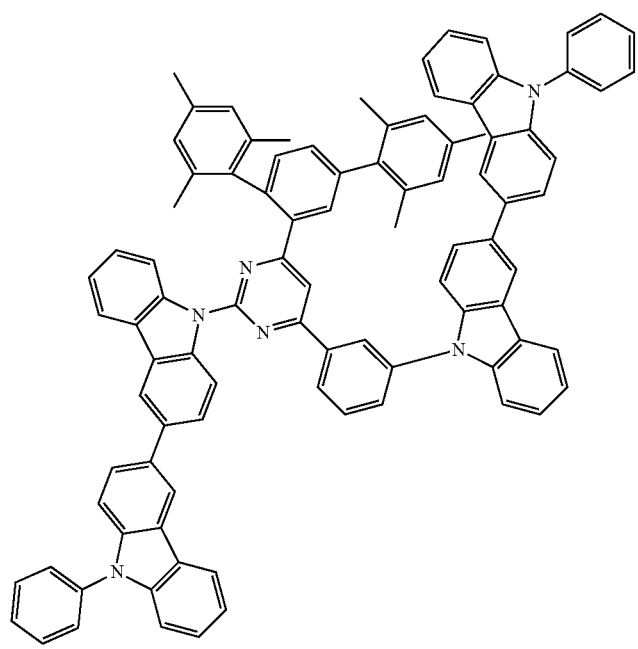

507
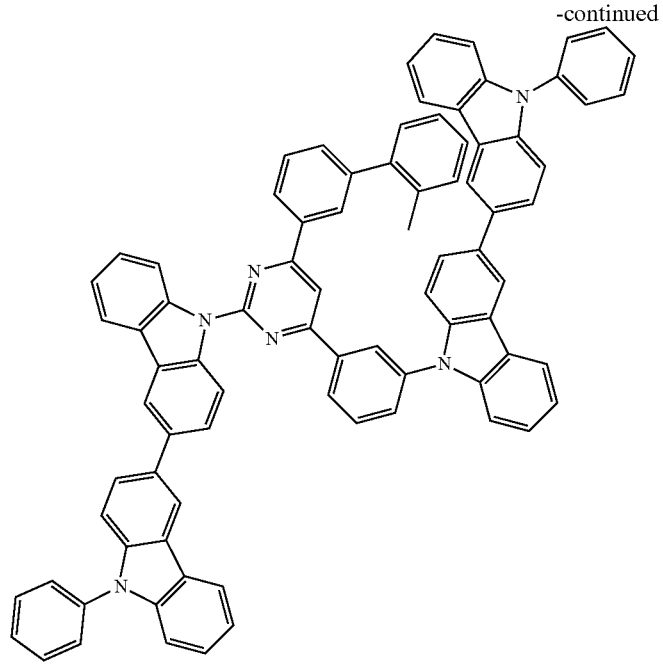
-continued
508
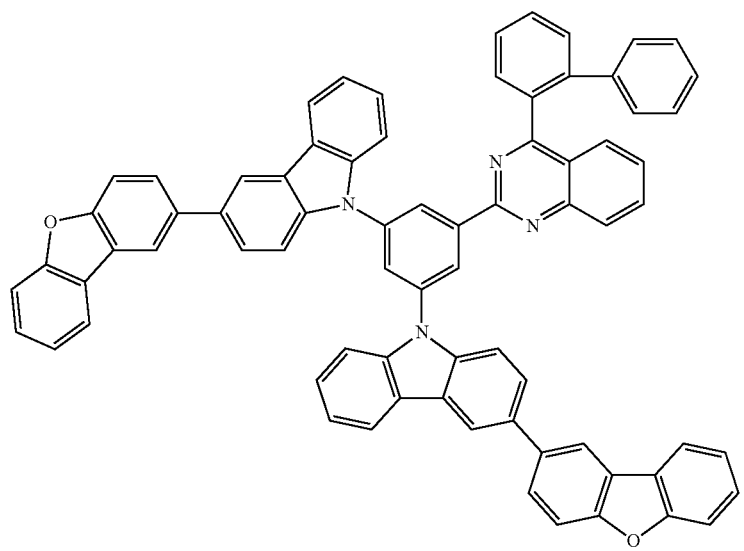

509 510
-continued
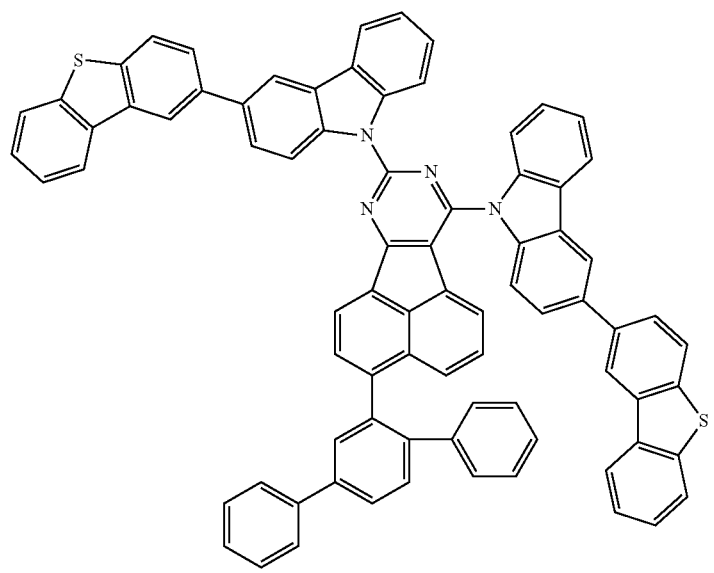
[Formula 133]
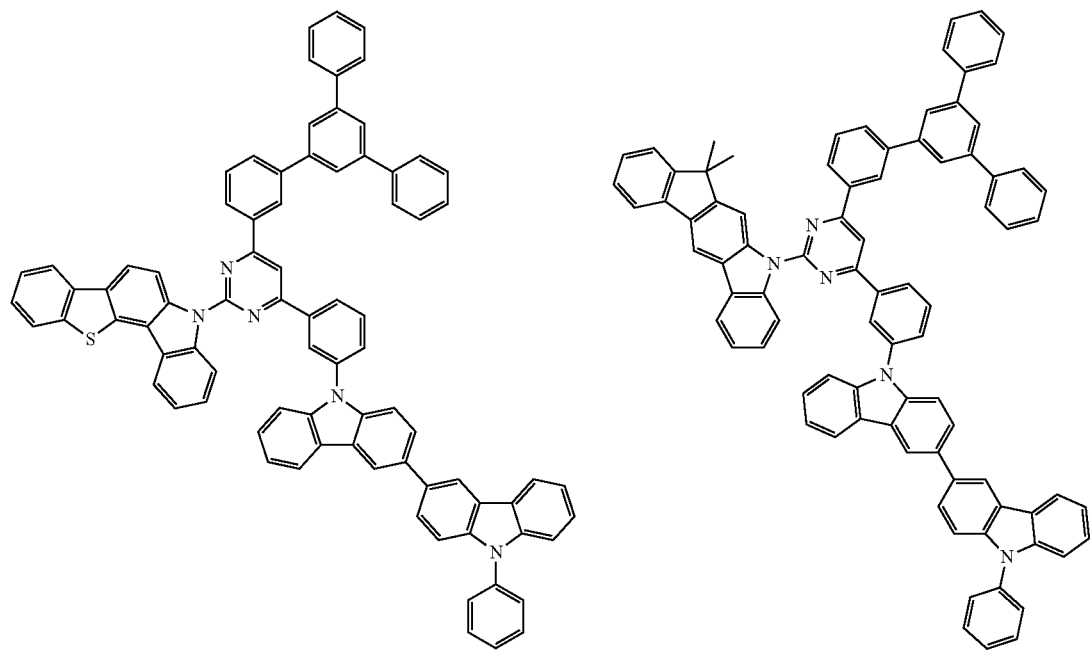

-continued
511
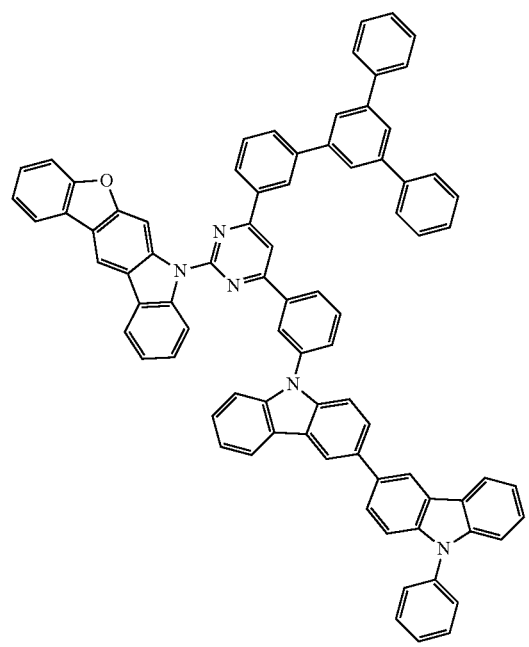
512
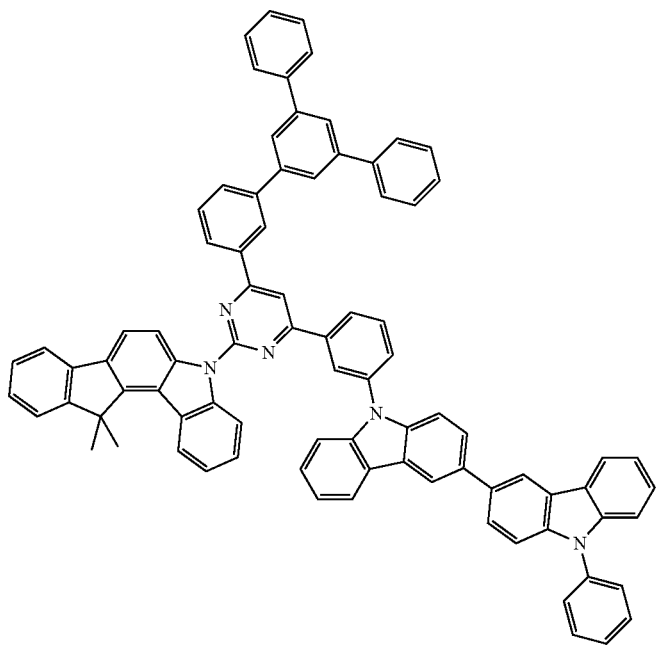
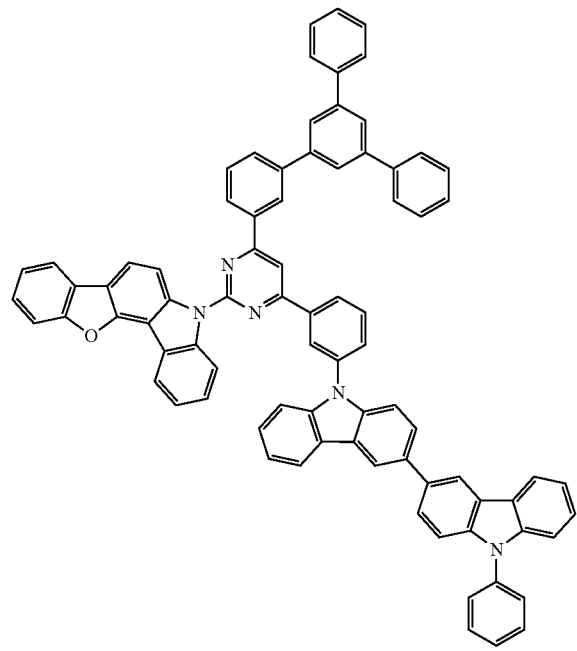
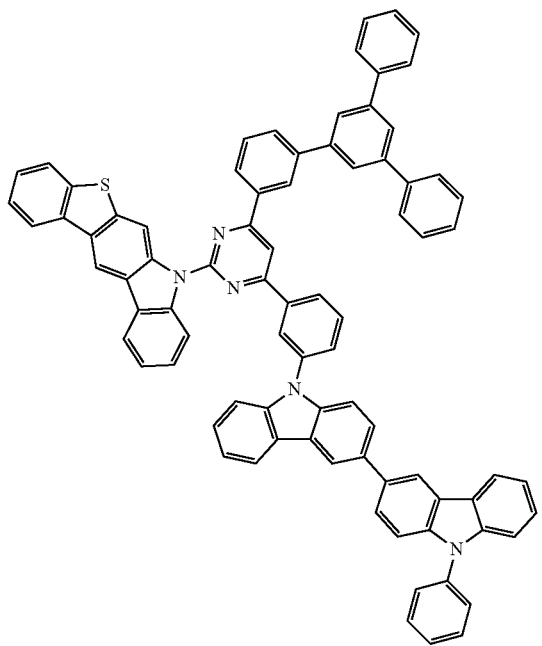

[Formula 134]
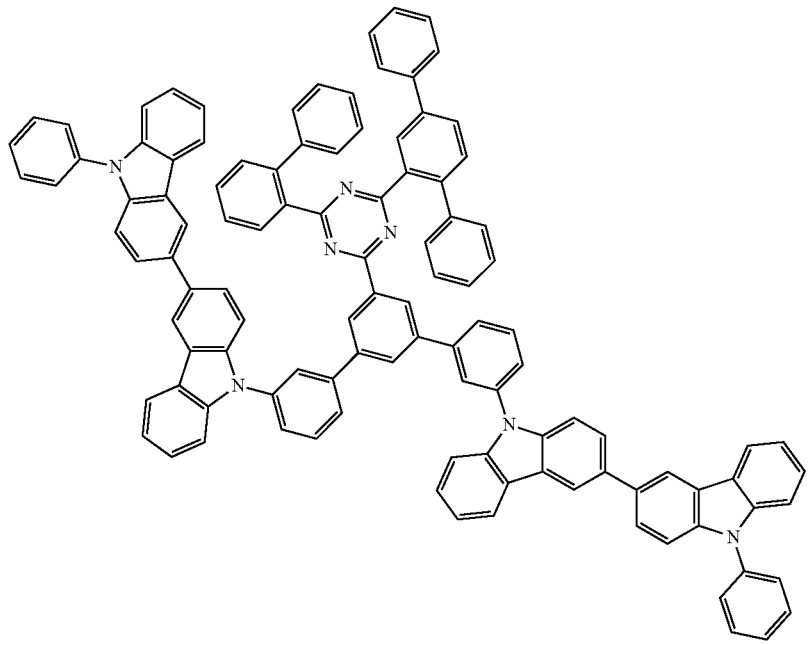
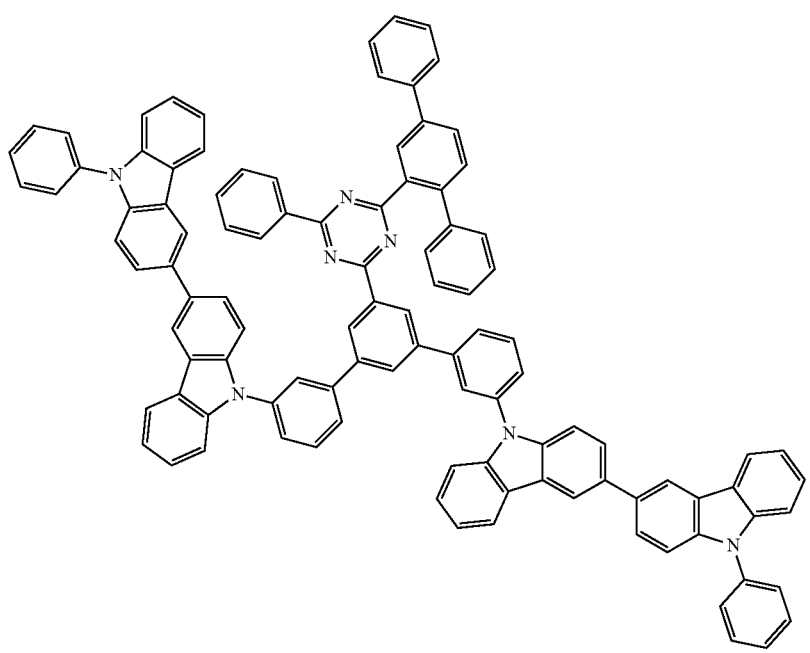

[Formula 135]
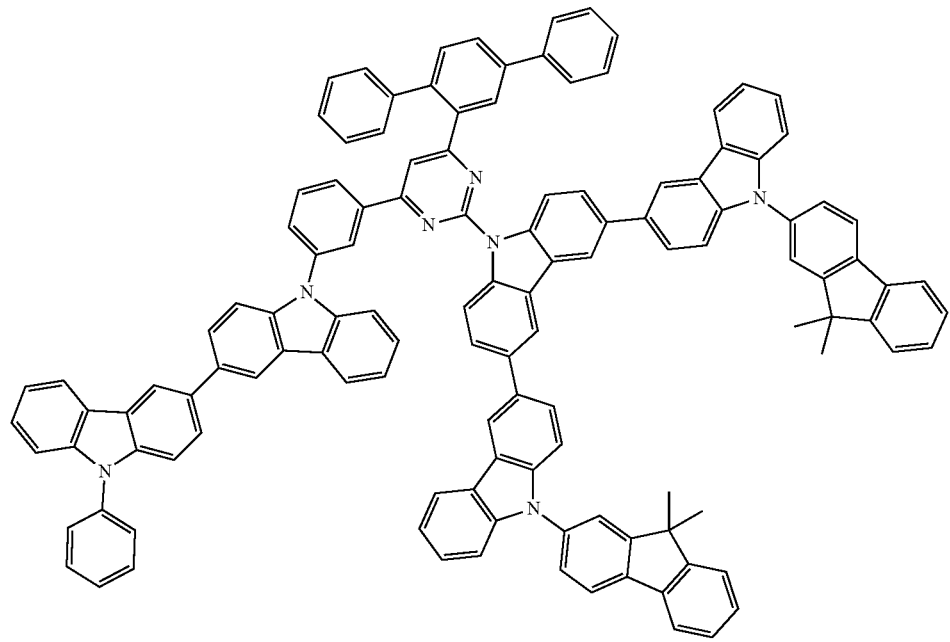
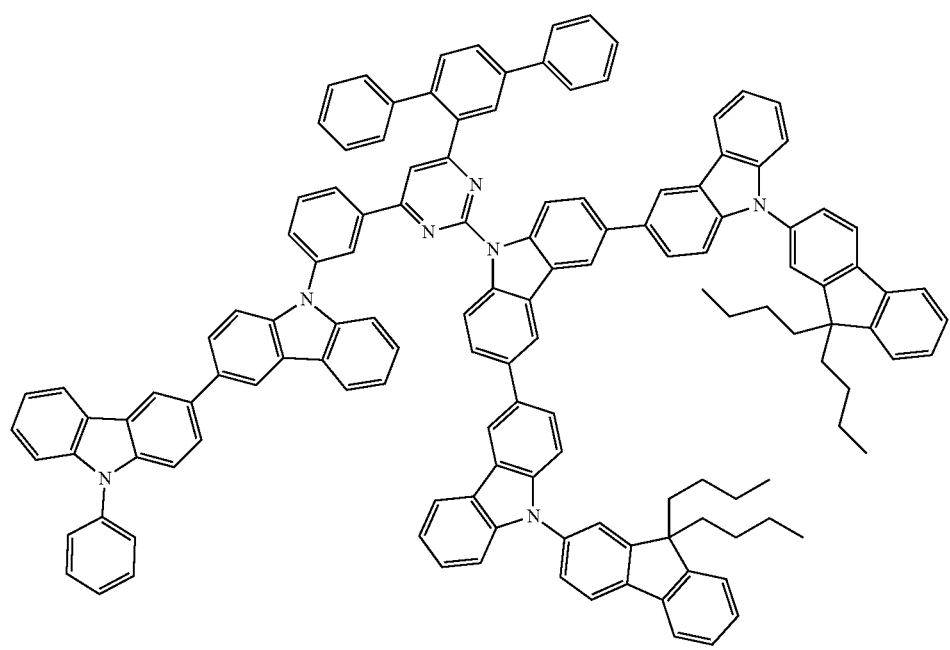

-continued
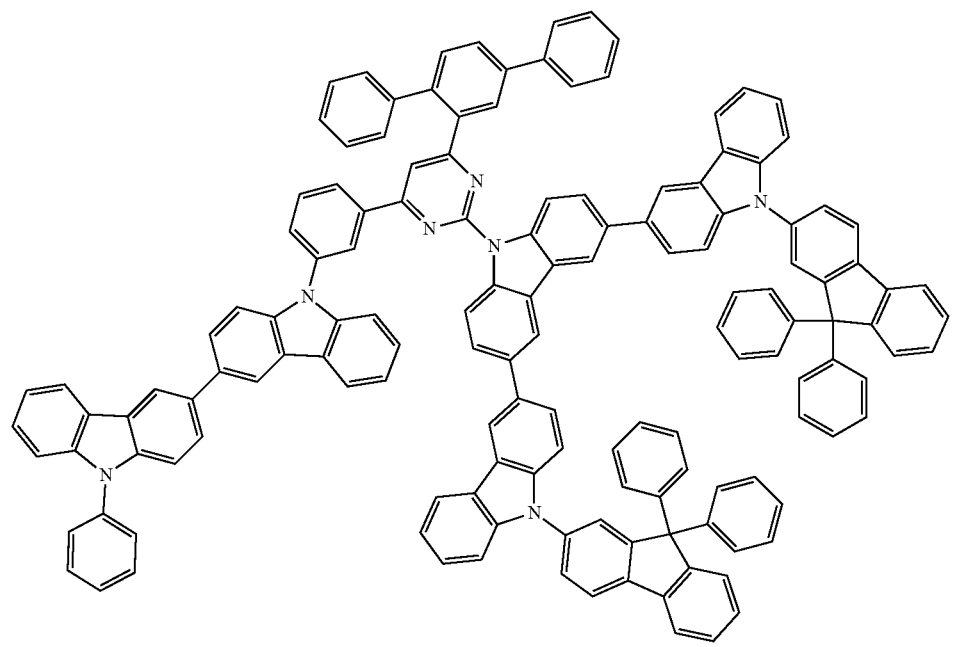
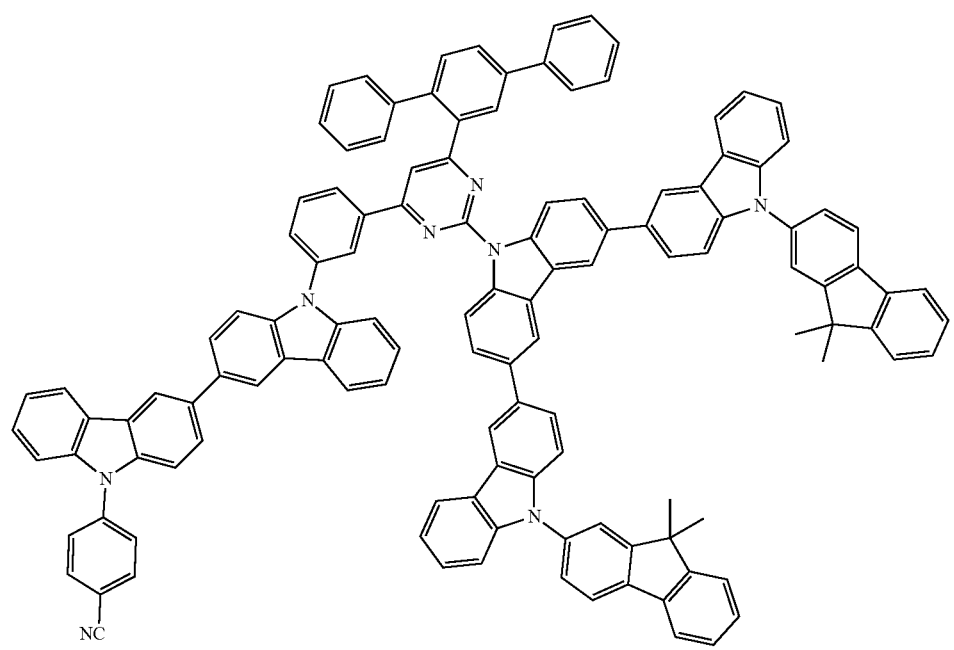

-continued

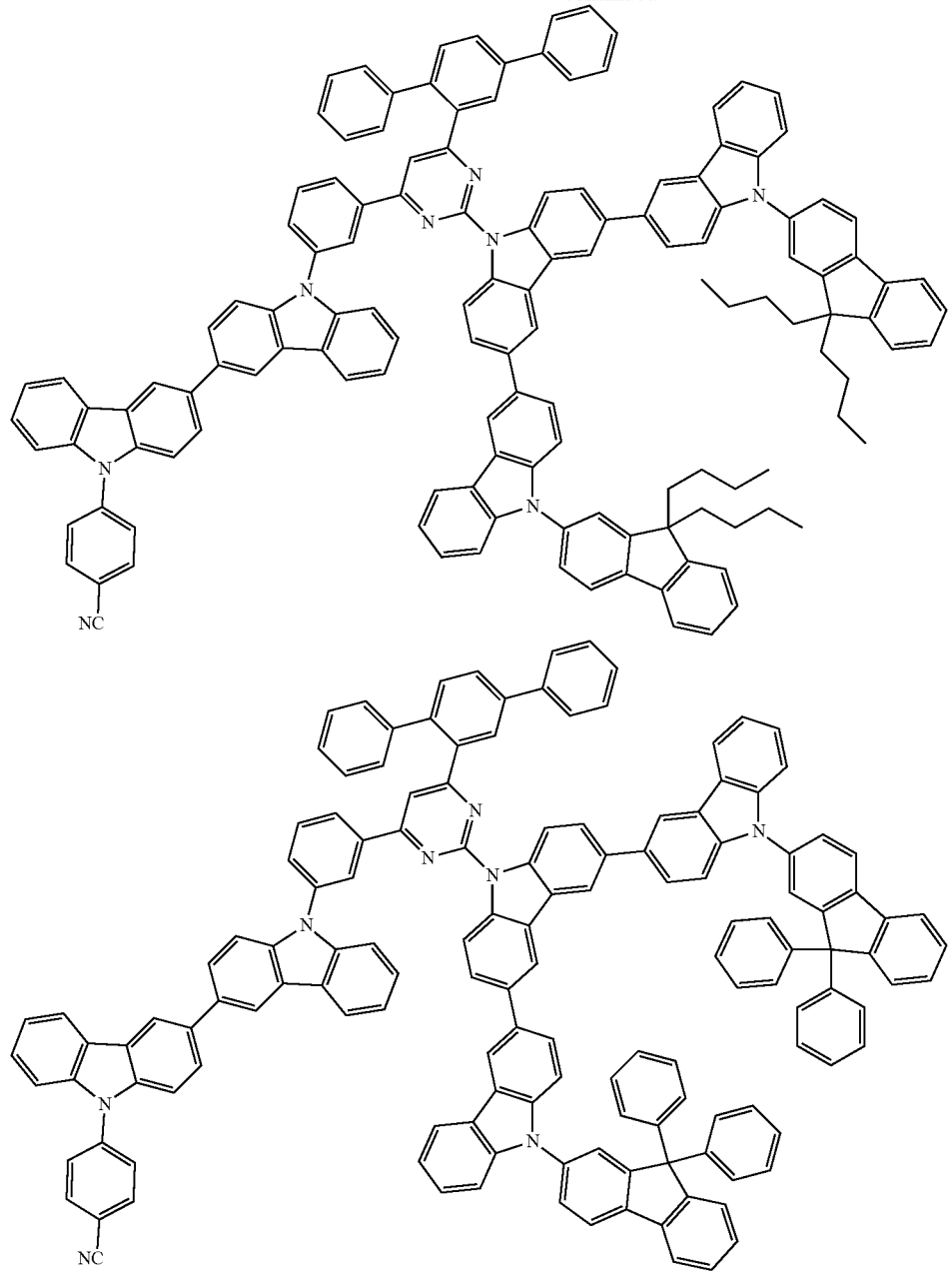

The compound according to the exemplary embodiment exhibits an excellent solubility.

Composition

A composition according to the exemplary embodiment contains: the compound of the exemplary embodiment of the invention; and a solvent.

The solvent is preferably an organic solvent. Examples of the organic solvent include: a chlorinated solvent (e.g., chloroform, chlorobenzene, chlorotoluene, chloroxylene, chloroanisole, dichloromethane, dichlorobenzene, di chlorotoluene, dichloroethane, trichloroethane, trichlorobenzene, trichloromethylbenzene, bromobenzene, dibromobenzene, and bromoanisole); an ether solvent (e.g., tetrahydrofuran, dioxane, dioxolane, oxazole, methylbenzoxazole, benzoisooxazole, furan, furazan, benzofuran, and dihydrobenzofuran); an aromatic hydrocarbon solvent (e.g., ethylbenzene, diethylbenzene, triethylbenzene, trimethylbenzene, trimethoxybenzene, propylbenzene, isopropylbenzene, diisopropylbenzene, dibutylbenzene, amylbenzene, dihexylbenzene, cyclohexylbenzene, tetramethylbenzene, dodecylbenzene, benzonitrile, acetophenone, methylacetophenone, methoxyacetophenone, toluic acid ethyl ester, toluene, ethyltoluene, methoxytoluene, dim ethoxytoluene, trimethoxytoluene, isopropyltoluene, xylene, butylxylene, isopropylxylene, anisole, ethylanisole, dimethylanisole, trimethylanisole, propylanisole, isopropylanisole, butylanisole, methyl ethylanisole, anethole anisyl alcohol, methyl benzoate, ethyl benzoate, propyl benzoate, butyl benzoate, diphenylether, butylphenyl ether, benzylmethylether, benzyl ethyl ether, methylene di oxybenzene, methylnaphthalene, tetrahydronaphthalene, aniline, methyl aniline, ethyl aniline, butyl aniline, biphenyl, methylbiphenyl, and isopropylbiphenyl); an aliphatic hydrocarbon solvent (e.g., cyclohexane, methylcyclohexane, n-pentane, n-hexane, n-heptane, n-octane, n-nonane, n-decane, tetradecane, decalin, and isopropyl cyclohexane); a ketone solvent (e.g., acetone, methyl ethyl ketone, cyclohexanone, and acetophenone); an ester solvent (e.g., acetic ether, butyl acetate, ethyl cellosolve acetate, methyl benzoate, and phenyl acetate); a polyhydric alcohol and a derivative thereof (e.g., ethylene glycol, ethylene glycol monobutylether, ethylene glycol monoethylether, ethylene glycol monomethylether, dimethoxyethane, propylene glycol, diethoxymethane, triethylene glycol monoethylether, glycerin, and 1,2-hexane diol); an alcohol solvent (e.g., methanol, ethanol, propanol, isopropanol, and cyclohexanol); and a sulfoxide solvent (e.g., dimethylsulfoxide); and amide solvent (e.g., N-methyl-2-pyrolidone, and N,N-dimethylformamide).

One type of the organic solvents as described above may be used alone or two or more types thereof may be used in combination.

The composition according to the exemplary embodiment may further contain other material(s) in addition to the compound according to the exemplary embodiment and a solvent.

The composition of the exemplary embodiment of the invention is suitably usable as a material for an organic EL device.

Organic EL Device

Arrangement(s) of an organic EL device according to the exemplary embodiment will be described below.

The organic EL device includes an anode, an organic layer and a cathode. The organic layer has at least one layer formed of an organic compound. The organic layer may further include an inorganic compound. In the organic EL device according to the exemplary embodiment, at least one layer of the organic layer includes the compound according to the exemplary embodiment.

Typical device arrangements of the organic EL device include the following arrangements (a) to (e) and the like:
(a) anode/emitting layer/cathode;
(b) anode/hole injecting-transporting layer/emitting layer/cathode;
(c) anode/emitting layer/electron injecting-transporting layer/cathode;
(d) anode/hole injecting•transporting layer/emitting layer/electron injecting transporting layer/cathode; and
(e) anode/hole injecting transporting layer/emitting layer/blocking layer/electron injecting transporting layer/cathode.

Among the above arrangements, the arrangements (b), (c) and (d) are preferably used. However, the arrangement of the organic EL device according to the exemplary embodiment is not limited to the above typical arrangements. It should be noted that the "emitting layer" is the organic layer having an emission function. The "hole injecting•transporting layer" means "at least one of the hole injecting layer and the hole transporting layer." The "electron injecting•transporting layer" means "at least one of the electron injecting layer and the electron transporting layer." When the organic EL device includes the hole injecting layer and the hole transporting layer, the hole injecting layer is preferably interposed between the hole transporting layer and the anode. When the organic EL device includes the electron injecting layer and the electron transporting layer, the electron injecting layer is preferably interposed between the electron transporting layer and the cathode. Moreover, each of the hole injecting layer, the hole transporting layer, the electron transporting layer and the electron injecting layer may be formed in a single layer or in a plurality of layers.

In the organic EL device according to this exemplary embodiment, the organic layer preferably includes the emitting layer and the emitting layer preferably includes the compound according to this exemplary embodiment.

The FIGURE schematically shows an exemplary arrangement of the organic EL device according to the exemplary embodiment.

An organic EL device 1 includes a light-transmissive substrate 2, an anode 3, a cathode 4 and an organic layer 10 disposed between the anode 3 and the cathode 4.

The organic layer 10 includes an emitting layer 7, a hole injecting layer 5 interposed between the anode 3 and the emitting layer 7, a hole transporting layer 6 interposed between the hole injecting layer 5 and the emitting layer 7, and an electron transporting zone 11 interposed between the emitting layer 7 and the cathode 4.

The electron transporting zone 11 includes an electron transporting layer 8 and an electron injecting layer 9.

In the exemplary embodiment, the emitting layer 7 includes the compound of the exemplary embodiment of the invention.

Emitting Layer

The emitting layer 7 of the organic EL device 1 at least includes the compound of the exemplary embodiment of the invention.

A content ratio of the compound of the exemplary embodiment in the emitting layer 7 of the organic EL device 1 is preferably 0.1 mass % or more, more preferably in a range from 1 mass % to 99.9 mass %, further preferably in a range from 5 mass % to 95 mass %.

The emitting layer 7 of the organic EL device 1 may include a material other than the compound of the exemplary embodiment of the invention.

For instance, the emitting layer 7 may include a luminescent material in a form of a fluorescent compound that emits fluorescence or a phosphorescent compound that emits phosphorescence. The fluorescent compound is a compound capable of emitting in a singlet state. The phosphorescent compound is a compound capable of emitting in a triplet state.

Examples of a blue fluorescent material usable for the emitting layer 7 include a pyrene derivative, styrylamine derivative, chrysene derivative, fluoranthene derivative, fluorene derivative, diamine derivative, and triarylamine derivative. Specific examples of the blue fluorescent material include N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenyl amine (abbreviation: PCBAPA).

As a green fluorescent material usable for the emitting layer 7, for instance, an aromatic amine derivative is usable. Specific examples of the green fluorescent material include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9, 10-diphenyl-2-anthryl)-N,N',N'-triphenyl-1,4-phenylene diamine (abbreviation: 2DPAPA), N-[9,10-bis(1,1'-biphenyl-2-yl)-2-anthryl]-N,N',N'-triphenyl-1,4-phenylene diamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), and N,N,9-triphenyl anthracene-9-amine (abbreviation: DPhAPhA).

As a red fluorescent material usable for the emitting layer 7, for instance, a tetracene derivative and a diamine derivative are usable. Specific examples of the red fluorescent material include N,N,N',N'-tetrakis(4-methylphenyl)tetracene-5,11-diamine (abbreviation: p-mPhTD), and 7,14-diphenyl-N,N,N',N'-tetrakis(4-methylphenyl)acenaphtho[1,2-a]fluoranthene-3,10-diamine (abbreviation: p-mPhAFD).

As a blue phosphorescent material usable for the emitting layer 7, for instance, metal complexes such as an iridium complex, an osmium complex and a platinum complex are usable. Specific examples of the blue phosphorescent material include bis[2-(4',6'-difluorophenyl)pyridinato-N, C2'] iridium(III) tetrakis(1-pyrazolyl)borate (abbreviation: FIr6), bis[2-(4',6'-difluorophenyl)pyridinato-N,C2]iridium(III) picolinate (abbreviation: FIr(pic)), bis[2-(3',5'bistrifluoromethylphenyl)pyridinato-N,C2']iridium(III) picolinate (abbreviation: Ir(CF$_3$ppy)$_2$(pic)), and bis[2-(4',6'-difluorophenyl)pyridinato-N,C2']iridium(III) acetyl acetonato (abbreviation: FIr(acac)).

As a green phosphorescent material usable for the emitting layer 7, for instance, an iridium complex is usable. Specific examples of the green phosphorescent material include tris(2-phenylpyridinato-N,C2') iridium(III) (abbreviation: Ir(ppy)$_3$), bis(2-phenylpyridinato-N, C2') iridium (III) acetylacetonato (abbreviation: Ir(ppy)$_2$(acac)), bis(1,2-diphenyl-1H-benzimidazolato)iridium (III) acetyl acetonato (abbreviation: Ir(pbi)$_2$(acac)), and bis(benzo[h]quinolinato)iridium(III) acetylacetonato (abbreviation: Ir(bzq)$_2$(acac)).

As a red phosphorescent material usable for the emitting layer 7, for instance, metal complexes such as an iridium complex, a platinum complex, a terbium complex and a europium complex are usable. Specifically, the metal complexes are organic metal complexes such as bis[2-(2'-benzo[4,5-α]thienyl)pyridinato-N,C3']iridium(III) acetylacetonato (abbreviation: Ir(btp)$_2$(acac)), bis(1-phenylisoquinolinato-N,C2') iridium(III) acetylacetonato (abbreviation: Ir(piq)$_2$(acac)), (acetylacetonato)bis[2,3-bis(4-fluorophenyl)quinoxalinate]iridium (III) (abbreviation: Tr(Fdpq)$_2$(acac)), and 2,3,7,8,12,13,17,18-octaethyl-21H, 23H-porphyrinplatinum(II) (abbreviation: PtOEP).

Moreover, since rare-earth metal complexes such as tris(acetylacetonato)(monophenanthroline)terbium(III) (abbreviation: Tb(acac)$_3$(Phen)), tris(1,3-diphenyl-propanedionate)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)) emit light from rare-earth metal ions (electron transition between different levels of multiplicity), the rare-earth metal complexes are usable as a phosphorescent compound.

Film Thickness of Emitting Layer

A film thickness of the emitting layer 7 in the exemplary embodiment is preferably in a range of 5 nm to 50 nm, more preferably in a range of 7 nm to 50 nm, further preferably in a range of 10 nm to 50 nm. At the film thickness of 5 nm or more, the emitting layer 7 can be easily formed and chromaticity thereof can be easily adjusted. At the film thickness of 50 nm or less, increase in the drive voltage is suppressible.

Substrate

The substrate 2 is used as a support for the organic EL device 1. Glass, quartz, plastic and the like are usable for the substrate 2. Moreover, a flexible substrate may be used. The flexible substrate means a bendable substrate such as a plastic substrate made of polycarbonate, polyarylate, polyether sulfone, polypropylene, polyester, polyvinyl fluoride, polyvinyl chloride, polyimide, and polyethylene naphthalate. Moreover, an inorganic deposition film is also usable.

Anode

Metal, alloy, an electrically conductive compound and a mixture thereof, which have a large work function, specifically, of 4.0 eV or more, is preferably usable as the anode 3 formed on the substrate 2. Specific examples of the material include indium oxide-tin oxide (ITO: Indium Tin Oxide), indium oxide-tin oxide including silicon or silicon oxide, indium oxide-zinc oxide, indium oxide including tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), nitrides of a metal material (e.g., titanium nitride) and the like are usable. The above materials are typically formed into a film by sputtering. For instance, a target of the indium zinc oxide which is prepared by adding zinc oxide in a range from 1 mass % to 10 mass % relative to indium oxide is used for forming a film by sputtering. Moreover, for instance, as for the indium oxide containing tungsten oxide and zinc oxide, a target thereof prepared by adding tungsten oxide in a range from 0.5 mass % to 5 mass % and zinc oxide in a range from 0.1 mass % to 1 mass % relative to indium oxide is usable for forming a film by sputtering. In addition, a vacuum deposition, a coating, ink-jet printing, a spin coating or the like may be used for manufacturing the anode.

Among the organic layers formed on the anode 3, since the hole injecting layer 5 formed adjacent to the anode 3 is formed of a composite material in which holes are easily injectable irrespective of the work function of the anode 3, other materials usable as an electrode material (e.g., a metal, alloy, electrically conductive compound, mixture thereof, and elements belonging to Group 1 or 2 in the periodic table of the elements) are also usable for the anode 3.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode 3. When the cathode 3 is formed of the alkali metal, alkaline earth metal and alloys thereof, vapor deposition and sputtering are usable. Moreover, when the cathode 4 is formed of silver paste and the like, coating, ink jet printing and the like are usable.

Hole Injecting Layer

The hole injecting layer 5 is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. In addition, the examples of the highly hole-injectable substance further include:

an aromatic amine compound, which is a low-molecule compound, such that 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenyl carbazole-3-yl)-N-phenylamino]-9-phenyl carb azole (abbreviation: PCzPCA1), 3,6-bis[N-(9-phenylcarbazole-3-yl)-N-phenyl amino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino [2,3-f:20,30-h]quinoxaline-2,3,6,7,10,11-hexacarbonitrile (HAT-CN).

Moreover, a high-molecule compound (e.g., an oligomer, dendrimer and polymer) is also usable as the highly hole-injectable substance. Specific examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamido] (abbreviation: PTPDMA), and poly[N,N'-bis(4-butylphenyl)-N,N'-bis(phenyl)benzidine] (abbreviation: Poly-TPD). Furthermore, the examples of the high-molecule compound include a high-molecule compound added with an acid such as poly (3,4-ethylene dioxythiophene)/poly(styrene sulfonic acid) (PEDOT/PSS), and polyaniline/poly(styrene sulfonic acid) (PAni/PSS).

Hole Transporting Layer

The hole transporting layer 6 is a layer containing a highly hole-transporting substance. An aromatic amine compound, carbazole derivative, anthracene derivative and the like are usable for the hole transporting layer 6. Specifically, for instance, an aromatic amine compound is usable for the hole transporting layer. Examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenyl amine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

A carbazole derivative such as CBP, 9-[4-(N-carbazolyl)] phenyl-10-phenylanthracene (CzPA) and 9-phenyl-3-[4-(10-phenyl-9-anthryl)phenyl]-9H-carbazole (PCzPA), and an anthracene derivative such as t-BuDNA, DNA, and DPAnth may also be used for the hole transporting layer 6. Moreover, a high-molecule compound such as poly(N-vinylcarbazole) (abbreviation: PVK) and poly(-vinyltriphenylamine) (abbreviation: PVTPA) is also usable for the hole transporting layer 6.

However, any substance having a hole transporting performance higher than an electron transporting performance may be used in addition to the above substances. A layer including the highly hole-transporting substance may be provided in the form of a single layer or a laminate of two or more layers.

When the hole transporting layer includes two or more layers, one of the layers with a larger energy gap is preferably provided closer to the emitting layer 7.

In the exemplary embodiment, the hole transporting layer 6 preferably has a function of preventing triplet excitons generated in the emitting layer 7 from being diffused into the hole transporting layer and confining the triplet excitons in the emitting layer 7.

Electron Transporting Layer

The electron transporting layer 8 is a layer containing a highly electron-transporting substance. For the electron transporting layer 8, 1) a metal complex such as an aluminum complex, beryllium complex and zinc complex, 2) heteroaromatic compound such as an imidazole derivative, benzimidazole derivative, azine derivative, carbazole derivative, and phenanthroline derivative, and 3) a high-molecule compound are usable. Specifically, as a low-molecule organic compound, a metal complex such as Alq, tris(4-methyl-8-quinolinato)aluminum (abbreviation: Almq$_3$), bis(10-hydroxybenzo[h]quinolinato)beryllium (abbreviation: BeBq$_2$), BAlq, Znq, ZnPBO and ZnBTZ are usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methyl-benzoxazole-2-yl)stilbene (abbreviation: BzOs) are usable. In the above exemplary embodiments, a benzimidazole compound is suitably usable. The above-described substances mostly have an electron mobility of $10^{-6}$ cm$^2$/(V·s) or more. However, any substance having an electron transporting performance higher than a hole transporting performance may be used for the electron transporting layer 7 in addition to the above substances. The electron transporting layer 8 may be provided in the form of a single layer or a laminate of two or more layers of the above substance(s).

Moreover, a high-molecule compound is also usable for the electron transporting layer 8. For instance, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)](abbreviation: PF-BPy) and the like are usable.

In the exemplary embodiment, the electron transporting layer 8 preferably has a function of preventing triplet excitons generated in the emitting layer 7 from being diffused into the electron transporting layer 8 and the electron injecting layer 9 and confining the triplet excitons in the emitting layer 7.

Electron Injecting Layer

The electron injecting layer 9 is a layer containing a highly electron-injectable substance. Examples of a material for the electron injecting layer 9 include an alkali metal, alkaline earth metal and a compound thereof, examples of which include lithium (Li), cesium (Cs), calcium (Ca), lithium fluoride (LiF), cesium fluoride (CsF), calcium fluoride (CaF$_2$), and lithium oxide (LiOx). In addition, a substance containing an alkali metal, alkaline earth metal and a compound thereof in the electron-transporting substance, specifically, a substance containing magnesium (Mg) in Alq may be used. In this case, electrons can be more efficiently injected from the cathode 4.

Alternatively, a composite material provided by mixing an organic compound with an electron donor may be used for the electron injecting layer 9. The composite material exhibits excellent electron injecting performance and electron transporting performance since the electron donor generates electron in the organic compound. In this arrangement, the organic compound is preferably a material exhibiting an excellent transforming performance of the generated electrons. Specifically, for instance, the above-described substance for the electron transporting layer 8 (e.g., the metal complex and heteroaromatic compound) is usable.

The electron donor may be any substance exhibiting an electron donating performance to the organic compound. Specifically, an alkali metal, an alkaline earth metal or a rare earth metal is preferable, examples of which include lithium, cesium, magnesium, calcium, erbium and ytterbium. Moreover, an alkali metal oxide and alkaline earth metal oxide are preferably used, examples of which include lithium oxide, calcium oxide, and barium oxide. Further, Lewis base such as magnesium oxide is also usable. Furthermore, tetrathiafulvalene (abbreviation: TTF) is also usable.

Cathode

Metal, alloy, an electrically conductive compound, a mixture thereof and the like, which have a small work function, specifically, of 3.8 eV or less, is preferably usable as a material for the cathode 4. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

When the cathode 4 is formed of the alkali metal, alkaline earth metal and alloy thereof, vapor deposition and sputtering are usable. Moreover, when the cathode 4 is formed of silver paste and the like, coating, ink jet printing and the like are usable.

By providing the electron injecting layer 9, various conductive materials such as Al, Ag, ITO, graphene and indium oxide-tin oxide containing silicon or silicon oxide are usable for forming the cathode 4 irrespective of the magnitude of the work function. The conductive materials can be formed into a film by sputtering, ink jet printing, spin coating and the like.

Layer Formation Method(s)

A formation method of each layer of the organic EL device 1 according to the exemplary embodiment is not limited except for the above particular description. For instance, known methods of dry film-forming and wet film-forming are applicable. Examples of the dry film-forming include vacuum deposition, molecular beam epitaxy (MBE method), sputtering, plasma deposition method and ion plating. Examples of the wet film-forming include spin coating, dipping, flow coating, casting, bar coating, roll coating, ink-jet, printing (e.g., letterpress printing, intaglio printing, lithographic printing, screen printing, and a combination of the above printing with offset printing), ink-jet printing, spray coating, slit coating, cap coating, gravure coating and meniscus coating.

In the organic EL device 1 according to the exemplary embodiment, the emitting layer including the compound of the exemplary embodiment of the invention is preferably formed by a coating method using a solution containing a solvent and the compound of the exemplary embodiment of the invention (hereinafter also referred to as a "coating liquid"). The coating liquid may further contain another material such as a luminescent material as needed.

The wet film-forming is preferably used as the coating method. Particularly, when a minute patterning is required, for instance, printing, ink-jet printing and dispenser coating are preferable. Moreover, a method including: forming a film of the compound of the exemplary embodiment of the invention on a transfer precursor substrate by the aforementioned wet film-forming; and subsequently, transfer the film onto a wire substrate having a target electrode using a laser beam, a hot pressing or the like can also be used. Since the film formation by these methods can be conducted by those skilled in the art under known conditions, the description of the method details is omitted.

The coating liquid used in the coating method only needs to include at least one of the compound of the exemplary embodiment of the invention, in which the compound may be dissolved or dispersed in the solvent. A content of the compound of the exemplary embodiment of the invention in the coating liquid is preferably in a range from 0.1 mass % to 15 mass %, more preferably in a range from 0.5 mass % to 10 mass % relative to the entire solution for forming the film.

The solvent is exemplified by the same organic solvent as the solvent for the composition of the exemplary embodiment of the invention.

Among the aforementioned organic solvents, in terms of solubility, uniformity of the film and viscosity characteristics, it is preferable that the coating liquid include at least one of toluene, xylene, ethylbenzene, amyl benzene, anisole, 4-methoxytoluene, 2-methoxytoluene, 1,2-dimethoxybenzene, mesitylene, tetrahydronaphthalene, cyclohexylbenzene, 2,3-dihydrobenzofuran, cyclohexanone, and methyl cyclohexanone.

The organic solvent used for the coating liquid preferably has a boiling point of 110 degrees C. or more and solubility of 1 mass % or less in water at 20 degrees C. The organic solvent is more preferably a compound represented by a formula (5).

[Formula 136]

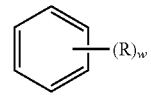

(5)

In the formula (5), R is a substituent having 1 to 20 carbon atoms and w is an integer of 0 to 6. A plurality of R may be mutually the same or different.

The coating liquid for the film formation preferably contains: the compound of the exemplary embodiment of the invention; and the compound represented by the formula (5) and having a boiling point of 110 degrees C. or more and solubility of 1 mass % or less in water at 20 degrees C. Moreover, an additive may be added as needed to the coating liquid for the film formation. Examples of the additive include a viscosity modifier, a surface tension modifier, a cross-linking initiator and a cross-linking catalyst. It should be noted that the additive desirably have no influence on device characteristics even when the additive remains in a film, or the additive is desirably removable from a film during the film formation process.

Film Thickness

A film thickness of each of the organic layers of the organic EL device 1 according to the exemplary embodiment is subject to no limitation except for the above particular description. The film thickness is generally preferably in the range from several nanometers to 1 μm, where defects such as a pin hole are unlikely to be caused and efficiency is improved at a low applied voltage.

In the exemplary embodiment, the number of carbon atoms forming a ring (also referred to as ring carbon atoms)

means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, carbon atom(s) included in the substituent is not counted as the ring carbon atoms. The same applies to the "ring carbon atoms" described below, unless particularly noted. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring or a naphthalene ring is substituted, for instance, by an alkyl group, the carbon atoms of the alkyl group are not counted as the ring carbon atoms. For instance, when a fluorene ring (inclusive of a spirofluorene ring) is bonded as a substituent to a fluorene ring, the carbon atoms of the fluorene ring as a substituent are not counted as the ring carbon atoms.

In the exemplary embodiment, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., hydrogen atom(s) for saturating the valence of the atom which forms the ring) and atom(s) in a substituent by which the ring is substituted are not counted as the ring atoms. The same applies to the "ring atoms" described below, unless particularly noted. For instance, a pyridine ring has 6 ring atoms, a quinazoline ring has 10 ring atoms, and a furan ring has 5 ring atoms. Hydrogen atoms respectively bonded to carbon atoms of the pyridine ring or the quinazoline ring and atoms forming a substituent are not counted as the ring atoms. For instance, when a fluorene ring (inclusive of a spirofluorene ring) is bonded as a substituent to a fluorene ring, the atoms of the fluorene ring as a substituent are not included in the ring atoms.

Next, each of substituents described in the above formulae will be described.

Examples of the aromatic hydrocarbon group having 6 to 30 ring carbon atoms (occasionally referred to as an aryl group) in the exemplary embodiment are a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, more preferably 6 to 14 ring carbon atoms, further preferably 6 to 12 ring carbon atoms. Among the aryl group, a phenyl group, biphenyl group, naphthyl group, phenanthryl group, terphenyl group and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aryl group having 6 to 18 ring carbon atoms later described in the exemplary embodiment.

In the exemplary embodiment, the heterocyclic group (occasionally referred to as heteroaryl group, heteroaromatic ring group or aromatic heterocyclic group) having 5 to 30 ring atoms preferably contains at least one atom selected from the group consisting of a nitrogen atom, sulfur atom, oxygen atom, silicon atom, selenium atom and germanium atom, and more preferably contains at least one atom selected from the group consisting of nitrogen, sulfur and oxygen.

Examples of the heterocyclic group having 5 to 30 ring atoms in the exemplary embodiment are a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthirdinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4-carbazolyl group is preferably substituted by a substituted or unsubstituted aryl group having 6 to 30 ring carbon atoms or a substituted or unsubstituted heterocyclic group having 5 to 30 ring atoms in the exemplary embodiment.

In the exemplary embodiment, the heterocyclic group may be a group derived from any one of partial structures represented by formulae (XY-1) to (XY-18).

[Formula 137]

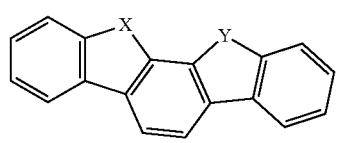

(XY-1)

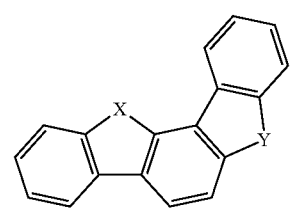

(XY-2)

-continued
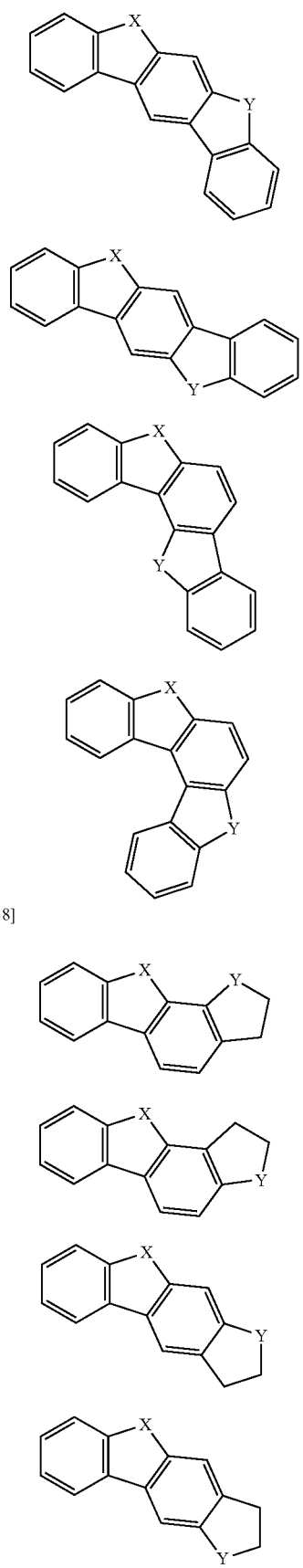
(XY-3)
(XY-4)
(XY-5)
(XY-6)
[Formula 138]
(XY-7)
(XY-8)
(XY-9)
(XY-10)
-continued
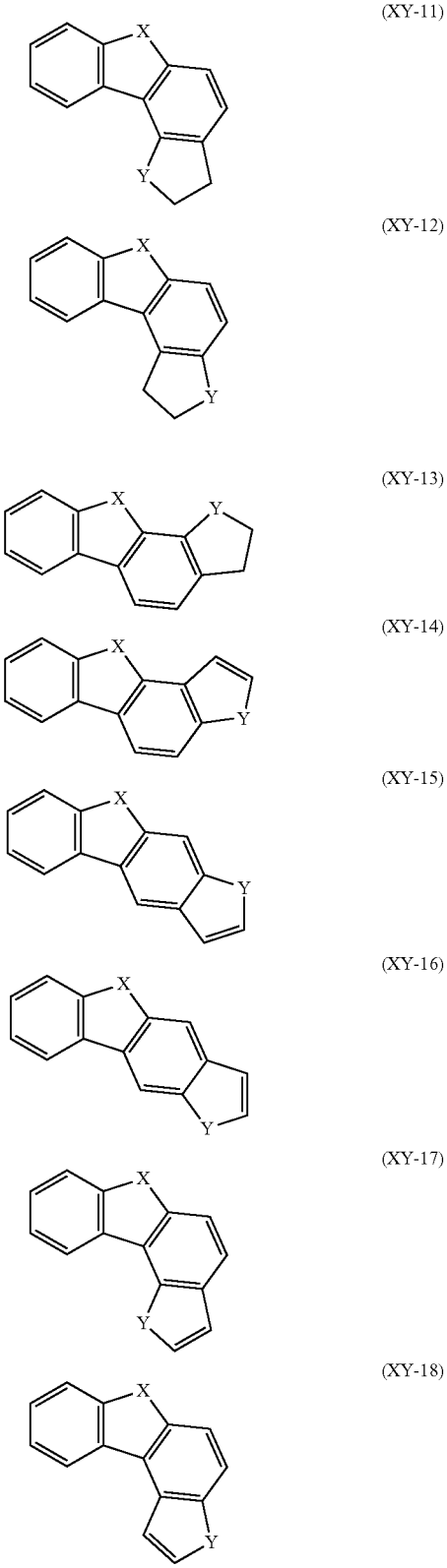
(XY-11)
(XY-12)
[Formula 139]
(XY-13)
(XY-14)
(XY-15)
(XY-16)
(XY-17)
(XY-18)
In the formulae (XY-1) to (XY-18), X and Y are each independently a hetero atom, and are preferably an oxygen atom, sulfur atom, selenium atom, silicon atom or germanium atom. The partial structures represented by the formulae (XY-1) to (XY-18) may each be bonded in any position to be a heterocyclic group, which may be substituted.

In the exemplary embodiment, examples of the carbazolyl group may include a group in which a carbazole ring is further fused with a ring(s) as shown in the following formulae. Such a group may be substituted. The group may be bonded in any position (a wavy line) as desired.

[Formula 140]

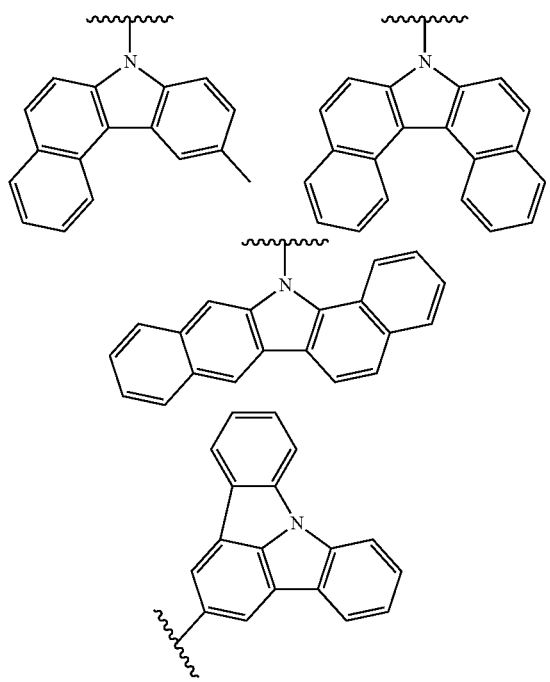

[Formula 141]

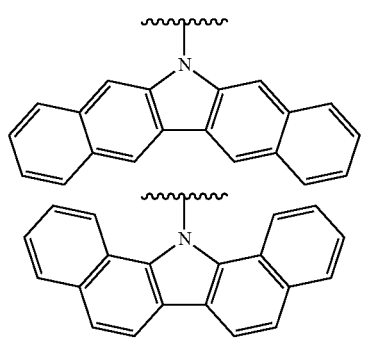

The alkyl group having 1 to 30 carbon atoms in the exemplary embodiment may be linear, branched or cyclic. Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are particularly preferable.

Examples of the cycloalkyl group having 3 to 30 in the exemplary embodiment are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are particularly preferable.

A halogenated alkyl group provided by substituting an alkyl group with a halogen atom is exemplified by a fluoroalkyl group provided by substituting an alkyl group having 1 to 30 carbon atoms with one or more halogen atoms. Specific examples of the above halogenated alkyl group are a fluoromethyl group, difluoromethyl group, trifluoromethyl group, fluoroethyl group, trifluoromethylmethyl group, trifluoroethyl group and pentafluoroethyl group.

The aralkyl group is preferably an aralkyl group having 6 to 30 ring carbon atoms and is represented by $-Z_3-Z_4$. $Z_3$ is exemplified by an alkylene group corresponding to the above alkyl group having 1 to 30 carbon atoms. $Z_4$ is exemplified by the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, 3-naphthylmethyl group, 1-β-naphthylethyl group, 2-β-naphthylethyl group, 1-β-naphthylisopropyl group, and 2-β-naphthylisopropyl group.

Examples of the substituted silyl group in the exemplary embodiment are an alkylsilyl group having 3 to 30 carbon atoms and an arylsilyl group having 6 to 30 ring carbon atoms.

The alkylsilyl group having 3 to 30 carbon atoms in the exemplary embodiment is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be the same or different.

Examples of the arylsilyl group having 6 to 30 ring carbon atoms in the exemplary embodiment are a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms.

The triarylsilyl group is exemplified by a triarylsilyl group including three of the aryl group listed as the examples of the aryl group having 6 to 30 ring carbon atoms. The triarylsilyl group preferably has 18 to 30 carbon atoms.

In the exemplary embodiment, the substituted germanium group is preferably represented by —Ge($R_{101}$)$_3$. $R_{101}$ is each independently a substituent. The substituent $R_{101}$ is preferably a substituted or unsubstituted alkyl group having 1 to 30 carbon atoms or a substituted or unsubstituted aromatic hydrocarbon group having 6 to 30 ring carbon atoms. A plurality of $R_{101}$ are optionally mutually the same or different.

In the exemplary embodiment, a substituted phosphine oxide group is preferably represented by a formula (200) below.

[Formula 142]

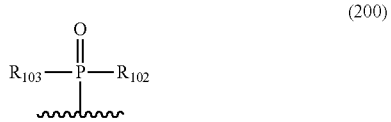

(200)

In the formula (200), $R_{102}$ and $R_{103}$ are each independently substituents. The substituents $R_{102}$ and $R_{103}$ are preferably a substituted or unsubstituted alkyl group having 1 to 30 carbon atoms or a substituted or unsubstituted aromatic hydrocarbon group having 6 to 30 ring carbon atoms. A wavy line represents a bonding position.

Examples of the halogen atom are a fluorine atom, a chlorine atom, a bromine atom and an iodine atom, among which a fluorine atom is preferable.

In the exemplary embodiment, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

In the exemplary embodiment, a hydrogen atom includes isotope having different numbers of neutrons, specifically, protium, deuterium and tritium.

Examples of the substituent meant by "substituted or unsubstituted" are an alkenyl group, alkynyl group, alkoxy group, aryloxy group, alkylthio group, arylthio group, siloxanyl group, alkylamino group arylamino group, amino group, aldehyde group, carbonyl group, ester group, carbamoyl group, hydroxyl group, nitro group and carboxy group, in addition to the above-described aryl group, heterocyclic group, alkyl group (linear or branched alkyl group, cycloalkyl group and haloalkyl group), aralkyl group, alkylsilyl group, arylsilyl group, halogen atom and cyano group.

Among the above substituents, an aryl group, heterocyclic group, alkyl group, halogen atom, alkylsilyl group, arylsilyl group and cyano group are preferable. More preferable substituents are one listed as the preferable substituents described for each substituent.

These substituents may be further substituted by an alkenyl group, alkynyl group, alkoxy group, aryloxy group, alkylthio group, arylthio group, siloxanyl group, alkylamino group, arylamino group, amino group, aldehyde group, carbonyl group, ester group, carbamoyl group, hydroxyl group, nitro group, and carboxy group, in addition to the above-described aryl group, heterocyclic group, alkyl group, aralkyl group, alkylsilyl group, arylsilyl group, halogen atom, and cyano group. In addition, plural ones of these substituents may be mutually bonded to form a ring.

The alkenyl group having 2 to 30 carbon atoms may be linear, branched or cyclic. Examples of the alkenyl group are a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group and cyclohexadienyl group.

The alkynyl group having 2 to 30 carbon atoms may be linear, branched or cyclic. Examples of the alkynyl group having 2 to 30 carbon atoms are an ethynyl group, a propynyl group and a 2-phenylethynyl group.

The alkoxy group having 1 to 30 carbon atoms is represented by —O$Z_a$. $Z_a$ is exemplified by the alkyl group having 1 to 30 carbon atoms. Examples of the alkoxy group are a methoxy group, ethoxy group, propoxy group, butoxy group, pentyloxy group and hexyloxy group. The alkoxy group preferably has 1 to 20 carbon atoms.

A halogenated alkoxy group provided by substituting an alkoxy group with a halogen atom is exemplified by one provided by substituting an alkoxy group having 1 to 30 carbon atoms with one or more fluorine atoms.

The aryloxy group having 6 to 30 ring carbon atoms is represented by —O$Z_b$. $Z_b$ is exemplified by the above aryl group having 6 to 30 ring carbon atoms. The aryloxy group preferably has 6 to 20 ring carbon atoms. The aryloxy group is exemplified by a phenoxy group.

The alkylthio group having 1 to 30 carbon atoms is represented by —S$R_v$. $R_v$ is exemplified by the alkyl group having 1 to 30 carbon atoms. The alkylthio group preferably has 1 to 20 carbon atoms.

The arylthio group having 6 to 30 ring carbon atoms is represented by —S$R_w$. $R_w$ is exemplified by the above aryl group having 6 to 30 ring carbon atoms. The arylthio group preferably has 6 to 20 ring carbon atoms.

A siloxanyl group is a silicon compound group with an ether bond and exemplified by trimethylsiloxanyl group.

The alkylamino group having 2 to 30 carbon atoms is represented by —NH$R_v$ or —N($R_v$)$_2$. $R_v$ is exemplified by the alkyl group having 1 to 30 carbon atoms.

The arylamino group having 6 to 60 ring carbon atoms is represented by —NH$R_w$ or —N($R_w$)$_2$. $R_w$ is exemplified by the above aryl group having 6 to 30 ring carbon atoms.

An aldehyde group, carbonyl group, ester group, carbamoyl group, and amino group may be substituted by aliphatic hydrocarbon, alicyclic hydrocarbon, aromatic hydrocarbon, or hetero ring. The aliphatic hydrocarbon, alicyclic hydrocarbon, aromatic hydrocarbon, and hetero ring may further have a substituent.

"Unsubstituted" in "substituted or unsubstituted" means that a group is not substituted by the above-described substituents but bonded with a hydrogen atom.

In the exemplary embodiment, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. "YY" is larger than "XX" and each of "XX" and "YY" represents an integer of 1 or more.

In the exemplary embodiment, "XX to YY atoms" in the description of "substituted or unsubstituted ZZ group having XX to YY atoms" represent atoms of an unsubstituted ZZ group and does not include atoms of a substituent(s) of a substituted ZZ group. "YY" is larger than "XX" and each of "XX" and "YY" represents an integer of 1 or more.

In the exemplary embodiment, when substituents are mutually bonded to form a cyclic structure, the cyclic structure is a saturated ring, unsaturated ring, aromatic hydrocarbon ring, or a heterocyclic ring. Moreover, in the exemplary embodiment, examples of the aromatic hydrocarbon group and the heterocyclic group include a cyclic structure from which the above-described monovalent groups are derived.

In the exemplary embodiment, examples of the aromatic hydrocarbon group and the heterocyclic group in the linking group include a divalent or multivalent group obtained by eliminating one or more atoms from the above monovalent groups. Examples of the "substituted or unsubstituted, linear or branched hydrocarbon group having a carbon-carbon double bond and 2 to 30 carbon atoms" in the linking group include a divalent or multivalent group obtained by eliminating one or more atoms from the above alkenyl group. Examples of the "substituted or unsubstituted, linear or branched hydrocarbon group having a carbon-carbon triple bond and 2 to 30 carbon atoms" in the linking group include a divalent or multivalent group obtained by eliminating one or more atoms from the above alkynyl group.

Electronic Device

The organic EL device 1 of the exemplary embodiment of the invention is usable in an electronic device such as a display device and a light-emitting device. Examples of the display unit include display components such as en organic EL panel module, TV, mobile phone, tablet, and personal computer. Examples of the light-emitting unit include an illuminator and a vehicle light.

Modification of Embodiments

It should be noted that the invention is not limited to the above exemplary embodiments but may include any modification and improvement as long as such modification and improvement are compatible with the invention.

An arrangement of the organic EL device of the invention is not particularly limited to the arrangement described in the above exemplary embodiment.

For instance, a blocking layer may be provided adjacent to an anode-side or a cathode-side of the emitting layer. It is preferable that the blocking layer is adjacent to the emitting layer and blocks at least one of holes, electrons and excitons.

For instance, when the blocking layer is provided in contact with the cathode-side of the emitting layer, the blocking layer permits transport of electrons, but prevents holes from reaching a layer provided near the cathode (e.g., the electron transporting layer) beyond the blocking layer. When the organic EL device includes an electron transporting layer, the blocking layer is preferably interposed between the emitting layer and the electron transporting layer.

When the blocking layer is provided in contact with the emitting layer near the anode, the blocking layer permits transport of holes, but prevents electrons from reaching a layer provided near the anode (e.g., the hole transporting layer) beyond the blocking layer. When the organic EL device includes a hole transporting layer, the blocking layer is preferably interposed between the emitting layer and the hole transporting layer.

Further, a blocking layer may be provided in contact with the emitting layer to prevent an excitation energy from leaking from the emitting layer into a layer in the vicinity thereof. Excitons generated in the emitting layer are prevented from moving into a layer provided near the electrode (e.g., an electron transporting layer and a hole transporting layer) beyond the blocking layer.

The emitting layer and the blocking layer are preferably bonded to each other.

The compound of the exemplary embodiment of the invention may be contained in the hole transporting layer or the electron transporting layer, or may be contained in both of the hole transporting layer and the electron transporting layer.

When the hole transporting layer and/or the electron transporting layer contain the compound of the exemplary embodiment of the invention, the hole transporting layer and/or the electron transporting layer are preferably formed by the above coating method using the solution containing the solvent and the compound of the exemplary embodiment of the invention.

Specific structure and shape of the components of the invention may be designed in any manner as long as the object of the invention can be achieved.

EXAMPLES

Examples of the invention will be described below. However, the invention is not limited to Examples.

Synthesis Example 1: Synthesis of Compound H-1

(1) Synthesis of Compound B1

[Formula 143]

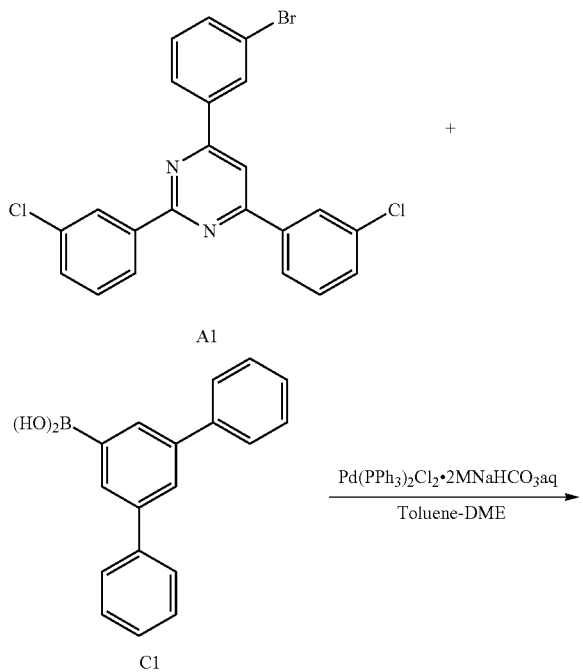

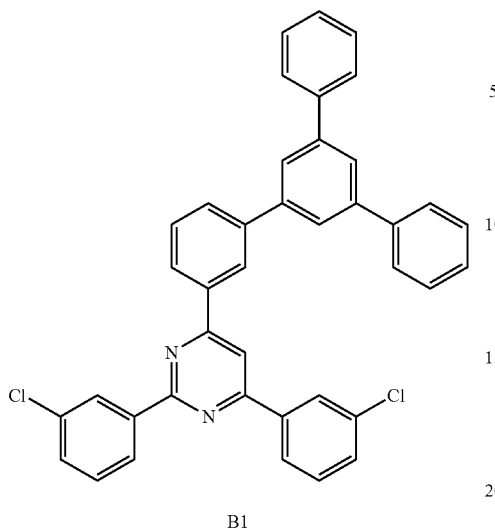

B1

Under an argon atmosphere, a compound A1 (a pyrimidine intermediate) (5.47 g, 12.0 mmol), boronic acid C1 (3.62 g, 13.2 mmol), dichloro(bistriphenylphosphine)palladium complex (210 mg, 48.0 mmol), 2M-sodium carbonate solution (24 mL), toluene (24 mL), and DME (24 mL) were sequentially mixed and heated with stirring at 100 degrees C. for eight hours.

After the reaction solution was cooled down to the room temperature, the reaction solution was separated into an aqueous layer and an organic layer. An organic solvent of the organic layer was distilled away under reduced pressure. The obtained solid was refined by recrystallization, so that a compound B1 (3.63 g, a yield of 50%) that is a pyrimidine intermediate was obtained.

(2) Synthesis of Compound H-1

[Formula 144]

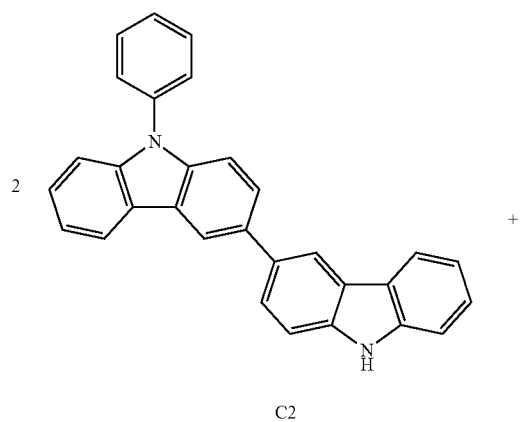

C2

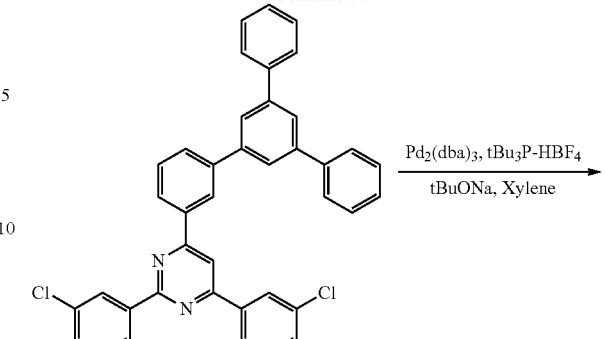

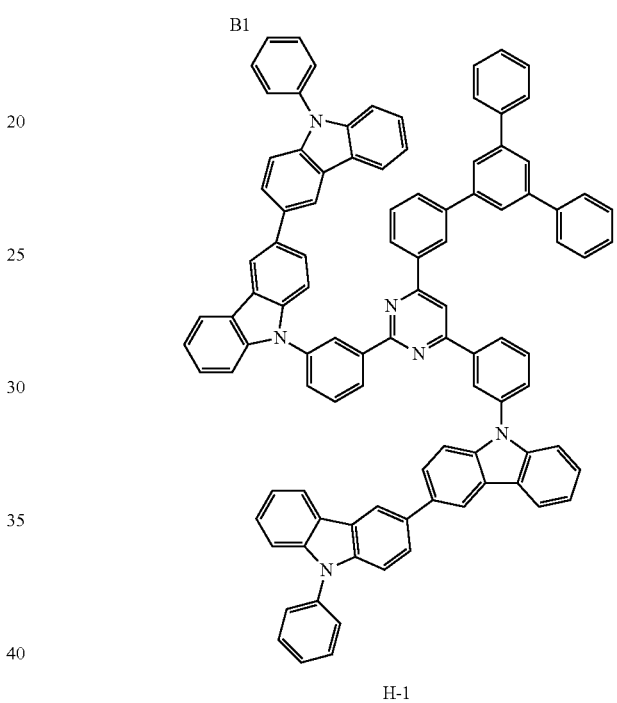

H-1

Under an argon atmosphere, biscarbazolyl body C2 (4.90 g, 12.0 mmol), the compound B1 3.63 g, 6.00 mmol), tris(dibenzylideneacetone)dipalladium (110 mg, 0.120 mmol), tri-t-butylphosphonium tetrafluoroborate (70.0 mg, 0.240 mmol), t-butoxy sodium (1.73 g, 18.0 mmol), and anhydrous xylene (80 mL) were sequentially mixed, and heated to reflux for eight hours.

After the reaction solution was cooled down to the room temperature, an undissolved substance was removed by filtration and the organic solvent was distilled away under reduced pressure. The obtained residue was refined by silica-gel column chromatography, so that a compound H-1 (5.68 g, a yield of 70%) was obtained.

Analysis results of the compound H-1 by HPLC (High Performance Liquid Chromatography) and LC-MS (Liquid Chromatography-Mass Spectrometry) are shown below.

HPLC: purity of 98.6%

LC-MS: calcd for $C_{100}H_{64}N_6$=1348, found m/z=1348 (M+, 100).

Synthesis Example 2: Synthesis of Compound H-2

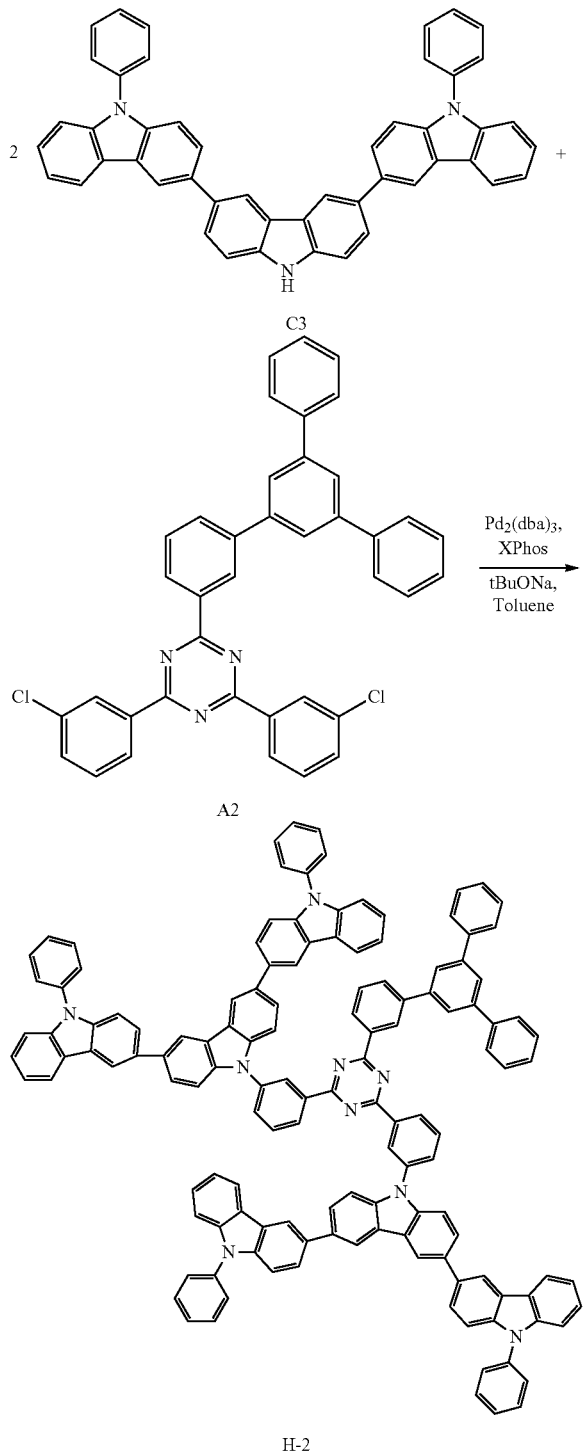

Under an argon atmosphere, tricarbazolyl body C3 (2.73 g, 4.20 mmol), a compound A2 (1.21 g, 2.00 mmol) that is a triazine intermediate, tris(dibenzylideneacetone)dipalladium (73.0 mg, 0.0800 mmol), 2-dicyclohexylphosphino-2',4',6'-triisopropylbiphenyl (150 mg, 0.320 mmol), t-butoxy sodium (1.15 g, 12.0 mmol), and anhydrous toluene (40 mL) were sequentially mixed, and heated to reflux for seven hours.

After the reaction solution was cooled down to the room temperature, an undissolved substance was removed by filtration and the organic solvent was distilled away under reduced pressure. The obtained residue was refined by silica-gel column chromatography, so that a compound H-2 (1.94 g, a yield of 53%) was obtained.

Analysis results of the compound H-2 by HPLC and LC-MS are shown below.

HPLC: purity of 98.9%

LC-MS: calcd for $C_{135}H_{85}N_9$=1833.

found m/z=1833 (M+,100).

Example 1

Cleaning of Substrate

A glass substrate (size: 25 mm×0.98 in×1.1 mm thick) having an ITO transparent electrode (manufactured by GEOMATEC Co., Ltd.) was ultrasonic-cleaned in isopropyl alcohol for five minutes, and then UV/ozone-cleaned for 5 minutes.

Formation of Base Layer

CLEVIOUS AI4083 (product name) manufactured by HERAEUS was used as a hole transporting material to form a 30-nm thick film on the ITO substrate by spin coating. After the film formation, an unnecessary portion was removed with acetone from the film. Subsequently, the film was burned on a hot plate heated at 200 degrees C. in the atmosphere for ten minutes to manufacture a base substrate formed with a base layer.

Formation of Emitting Layer

The compound H-1 obtained in Synthesis Example 1 was used as a host material and the compound D-1 was used as a dopant material at a mixture ratio by mass of the compound H-1:the compound D-1 being 90:10 to prepare a 1.6-mass % toluene solution. The materials were dissolved using ultrasonic waves. The toluene solution was visually checked to confirm that all the compounds were completely dissolved to be transparent. The toluene solution was coated on the base substrate by spin coating to form a 50-nm thick film. After the film formation, an unnecessary portion was removed with toluene from the film. Subsequently, the film was heated and dried on a hot plate heated at 150 degrees C. to manufacture a coated laminate substrate on which an emitting layer was formed. It should be noted that all the operations for forming the emitting layer were conducted in a nitrogen-atmosphere glove box.

Deposition and Sealing

The coated laminate substrate was delivered into a deposition chamber. A compound ET-1 was deposited at 50-nm thickness on the substrate as the electron transporting layer. Further, lithium fluoride was deposited at 1-nm thickness on the electron transporting layer. Furthermore, aluminium was deposited at 80-nm thickness on the deposited lithium fluoride. After all the deposition processes were completed, the obtained laminate was sealed with a counter-bored glass in the nitrogen-atmosphere glove box, so that an organic EL device was manufactured. The obtained organic EL device was driven to emit light with direct current, and an external quantum efficiency (EQE) at an electric density of 10 mA/cm² was measured. Measurement results are shown in Table 1.

[Formula 146]

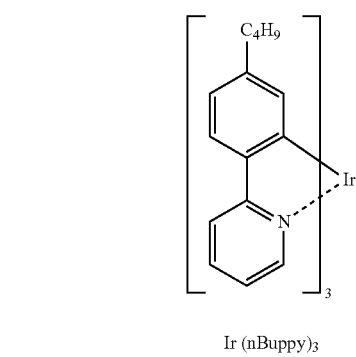

Ir (nBuppy)₃

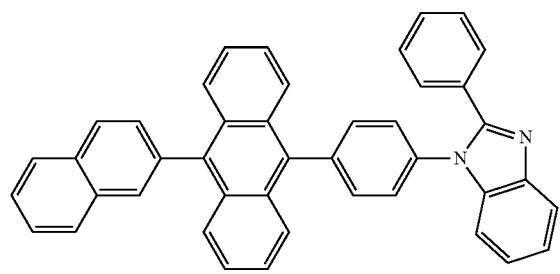

Example 2

An organic EL device was manufactured in the same manner as in Example 1 except that the compound H-2 was used in place of the compound H-1. The obtained organic EL device was driven to emit light with direct current, and an external quantum efficiency (EQE) at an electric density of 10 mA/cm² was measured. Measurement results are shown in Table 1.

Comparative 1

In Comparative 1, manufacturing of an organic EL device was attempted in the same manner as in Example 1 except that a comparative compound H-a was used in place of the compound H-1 as the host material. However, the materials were not dissolved in the toluene solution but whitened to be unable to prepare a solution, so that an organic EL device was not manufactured.

[Formula 147]

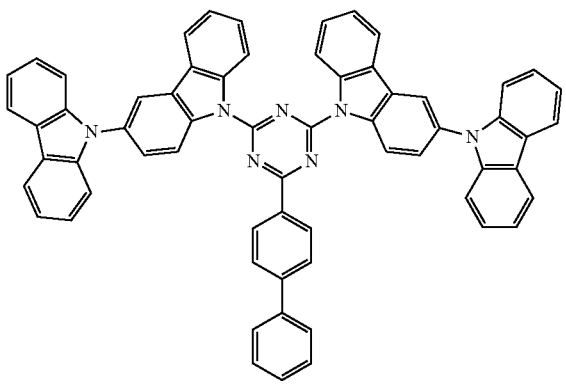

TABLE 1

| | Host Material | Dopant Material | External Quantum Efficiency (%) |
|---|---|---|---|
| Example 1 | H-1 | D-1 | 11.0 |
| Example 2 | H-2 | D-1 | 9.2 |

As described above, it was confirmed that the compound of the exemplary embodiment of the invention used in Examples 1 and 2 exhibit an excellent solubility.

As is shown in the Table 1, it was confirmed that the organic EL devices in Examples 1 and 2 exhibit a high external quantum efficiency EQE.

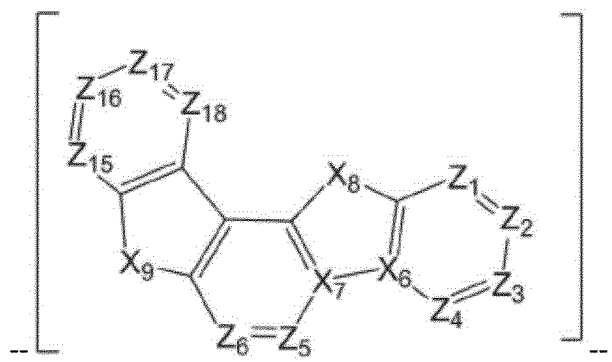

The invention claimed is:
1. A compound comprising:
a first structure represented by a formula (1);
a second structure represented by a formula (2);
a third structure represented by a formula (3); and
a fourth structure represented by a formula (4),
the first structure, the second structure, the third structure and the fourth structure being mutually independently present in a molecule, wherein
the first structure is bonded to the second structure,
the first structure is bonded to the third structure, and
the first structure is bonded to the fourth structure,

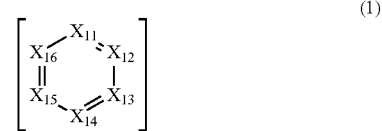
(1)

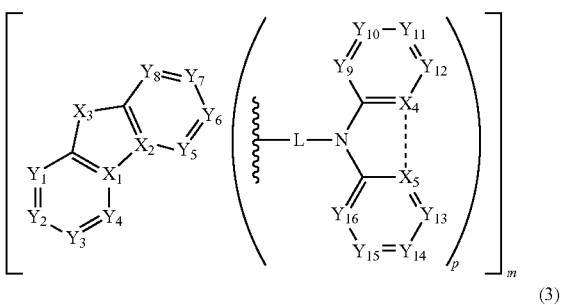
(2)

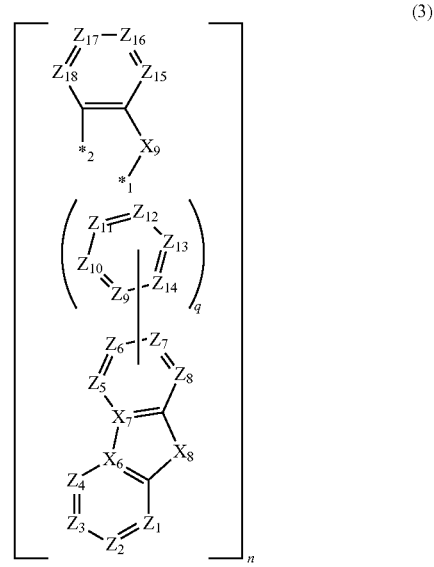
(3)

-continued

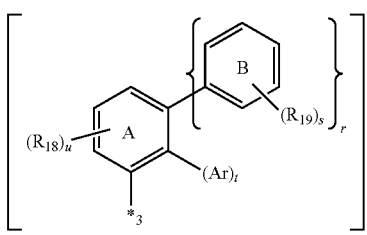

(4)

wherein in the formula (1):
X$_{11}$ to X$_{16}$ are each independently a carbon atom bonded to R$_1$, a nitrogen atom, or a carbon atom bonded to an atom contained in at least one of the second structure, the third structure and the fourth structure in a molecule;
at least one of X$_{11}$ to X$_{16}$ is a nitrogen atom;
R$_1$ is a hydrogen atom or a substituent;
a plurality of R$_1$ are optionally mutually the same or different; and
the plurality of R$_1$ are not bonded to each other,
wherein in the formula (2):
X$_1$ is a carbon atom bonded to R$_2$, or a carbon atom bonded to X$_2$;
X$_2$ is a carbon atom bonded to R$_3$, or a carbon atom bonded to X$_1$;
X$_3$ is an oxygen atom, a sulfur atom, a nitrogen atom, or a carbon atom bonded to R$_a$ and R$_b$;
R$_a$ and R$_b$ are each independently a hydrogen atom or a substituent;
the nitrogen atom in X$_3$ is bonded to R$_4$, bonded to L, or bonded to an atom contained in at least one of the first structure, the third structure and the fourth structure in a molecule;
X$_4$ is a carbon atom bonded to R$_5$, or a carbon atom bonded to X$_5$;
X$_5$ is a carbon atom bonded to R$_6$, or a carbon atom bonded to X$_4$;
at least one of a combination of X$_1$ and X$_2$ and a combination of X$_4$ and X$_5$ is a combination of mutually bonded carbon atoms;
L is a single bond or a substituted or unsubstituted aromatic hydrocarbon group;
L is bonded to one of Y$_1$ to Y$_8$, bonded to X$_3$, bonded to R$_5$ or R$_6$, bonded to an atom contained in at least one of the first structure, the third structure and the fourth structure, or bonded to a substituent;
L as a substituted or unsubstituted aromatic hydrocarbon group is optionally bonded to Y$_9$ or Y$_{16}$ to form a cyclic structure;
Y$_1$ to Y$_8$ are each independently a carbon atom bonded to R$_7$, a carbon atom bonded to L, a carbon atom bonded to one of Y$_9$ to Y$_{16}$, or a carbon atom bonded to an atom contained in at least one of the first structure, the third structure and the fourth structure in a molecule;
Y$_9$ to Y$_{16}$ are each independently a carbon atom bonded to R$_8$, a carbon atom bonded to one of Y$_1$ to Y$_8$, or a carbon atom bonded to an atom contained in at least one of the first structure, the third structure and the fourth structure in a molecule;
Y$_9$ or Y$_{16}$ are optionally bonded to L as a substituted or unsubstituted aromatic hydrocarbon group to form a cyclic structure;

when L is bonded to one of Y$_1$ to Y$_8$, Y$_9$ and Y$_{16}$ are not bonded to Y$_1$ to Y$_8$;
R$_2$ to R$_8$ are each independently a hydrogen atom or a substituent;
a plurality of R$_7$ are optionally mutually the same or different;
a plurality of R$_8$ are optionally mutually the same or different;
m represents the number of the second structure in a molecule and is an integer of 1 or more; and
p is an integer of 1 to 3,
wherein in the formula (3):
X$_6$ is a carbon atom bonded to R$_9$, or a carbon atom bonded to X$_7$;
X$_7$ is a carbon atom bonded to R$_{10}$, or a carbon atom bonded to X$_6$;
R$_9$ and R$_{10}$ are each independently a hydrogen atom or a substituent;
X$_8$ is a nitrogen atom bonded to a substituted or unsubstituted aromatic hydrocarbon group, or a nitrogen atom bonded to an atom contained in at least one of the first structure, the second structure and the fourth structure in a molecule;
Z$_1$ to Z$_4$ are each independently a carbon atom bonded to R$_{11}$, a carbon atom bonded to an atom contained in at least one of the first structure, the second structure and the fourth structure in a molecule, or a carbon atom bonded at a position represented by *1 or *2;
Z$_5$ to Z$_8$ are each independently a carbon atom bonded to R$_{12}$, a carbon atom bonded to one of Z$_9$ to Z$_{14}$, a carbon atom bonded to an atom contained in at least one of the first structure, the second structure and the fourth structure in a molecule, or a carbon atom bonded at a position represented by *1 or *2;
R$_{11}$ and R$_{12}$ are each independently a hydrogen atom or a substituent;
a plurality of R$_{11}$ are optionally mutually the same or different;
the plurality of R$_{11}$ are optionally bonded to each other to form a cyclic structure;
a plurality of R$_{12}$ are optionally mutually the same or different;
the plurality of R$_{12}$ are optionally bonded to each other to form a cyclic structure;
Z$_9$ to Z$_{14}$ are each independently a carbon atom bonded to R$_{13}$, a carbon atom bonded to one of Z$_5$ to Z$_8$, a carbon atom bonded to an atom contained in at least one of the first structure, the second structure and the fourth structure in a molecule; or a carbon atom bonded at a position represented by *1 or *2;
R$_{13}$ is a hydrogen atom or a substituent;
a plurality of R$_{13}$ are optionally mutually the same or different;
the plurality of R$_{13}$ are optionally bonded to each other to form a cyclic structure;
q is 0 or an integer of 1 to 4;
X$_9$ is an oxygen atom, a sulfur atom, a nitrogen atom, or a carbon atom bonded to R$_{14}$ and R$_{15}$;
R$_{14}$ and R$_{15}$ are each independently a hydrogen atom or a substituent;
the nitrogen atom in X$_9$ is bonded to R$_{16}$, or bonded to an atom contained in at least one of the first structure, the second structure and the fourth structure in a molecule;
R$_{16}$ is a hydrogen atom or a substituent;

$Z_{15}$ to $Z_{18}$ are each independently a carbon atom bonded to $R_{17}$, or a carbon atom bonded to an atom contained in at least one of the first structure, the second structure and the fourth structure in a molecule;

$R_{17}$ is a hydrogen atom or a substituent;

a plurality of $R_{17}$ are optionally mutually the same or different;

the plurality of $R_{17}$ are optionally bonded to each other to form a cyclic structure;

*1 and *2 each independently represent a bonding position to a carbon atom in $Z_1$ to $Z_{14}$, or a bonding position to a substituted or unsubstituted aromatic hydrocarbon group bonded to the nitrogen atom in $X_8$; and n represents the number of the third structure in a molecule and is an integer of 1 or more, wherein in the formula (4):

$R_{18}$ is a hydrogen atom or a substituent;

a plurality of $R_{18}$ are optionally mutually the same or different;

the plurality of $R_{18}$ are optionally bonded to each other to form a cyclic structure;

Ar is a substituted or unsubstituted aromatic hydrocarbon group;

$R_{19}$ is a substituent;

s is an integer of 1 to 5;

a plurality of $R_{19}$ are optionally mutually the same or different;

the plurality of $R_{19}$ are not bonded to each other;

u is 3 or 4;

t is 0 or 1;

r is 0 or 1;

t+r is 1 or 2;

when r=0, t=1, u=4 and $R_{18}$ in place of the ring B is bonded to the ring A;

when t=0, r=1, u=4 and $R_{18}$ in place of Ar is bonded to the ring A; and

*3 is a bonding position bonded to an atom contained in at least one of the first structure, the second structure and the third structure.

2. The compound according to claim 1, wherein the fourth structure is represented by a formula (41), wherein u is 3,

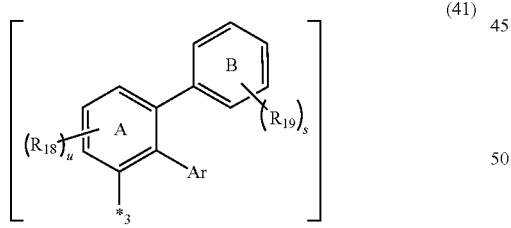

(41)

3. The compound according to claim 1, wherein the fourth structure is represented by a formula (42), wherein u is 4,

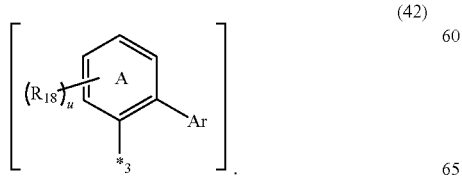

(42)

4. The compound according to claim 1, wherein the fourth structure is represented by a formula (43), wherein u is 4,

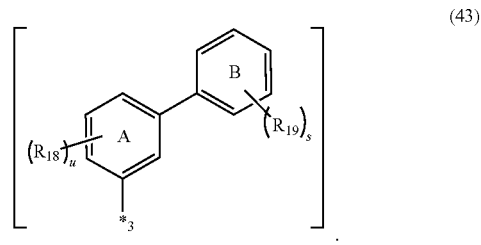

(43)

5. The compound according to claim 1, wherein

*3 in the formula (4) represents a bonding position to $X_{11}$, $X_{11}$ is a carbon atom bonded to the fourth structure; and the first structure bonded to the fourth structure provides a structure represented by a formula (1-4),

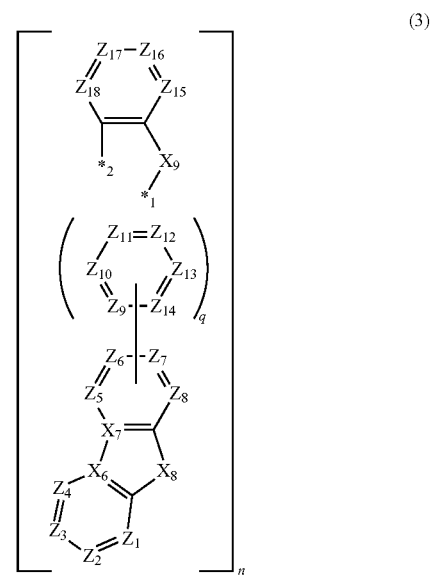

(3)

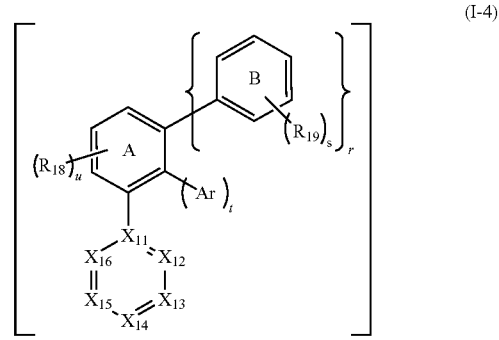

(I-4)

(2)

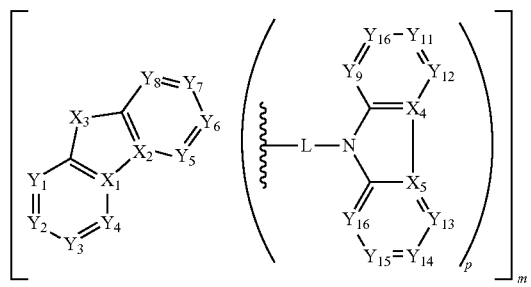

6. The compound according to claim 5, wherein one to three of $X_{12}$ to $X_{16}$ are nitrogen atoms.

7. The compound according to claim 5, wherein $X_{12}$ and $X_{14}$ are each a nitrogen atom, $X_{13}$ and $X_{15}$ are each a carbon atom bonded to the second structure or third structure, and $X_{16}$ is a carbon atom to be bonded to $R_1$.

8. The compound according to claim 5, wherein $X_{12}$, $X_{14}$ and $X_{16}$ are nitrogen atoms, and $X_{13}$ and $X_{15}$ are each a carbon atom bonded to the second structure or third structure.

9. The compound according to claim 1, wherein at least one of the second structure and the third structure is bonded to $R_1$ of the first structure.

10. The compound according to claim 1, wherein m+n is an integer in a range of 2 to 4.

11. The compound according to claim 1, wherein the second structure represented by the formula (2) is represented by a formula (20), wherein in the formula (20):
$X_1$ and $X_2$ are carbon atoms bonded to each other;
$X_4$ and $X_5$ are carbon atoms bonded to each other;
p is 1;
one of $Y_1$ to $Y_8$ is a carbon atom bonded to one of $Y_{13}$ to $Y_{16}$, and
one of $Y_{13}$ to $Y_{16}$ is a carbon atom bonded to one of $Y_1$ to $Y_8$, (20)

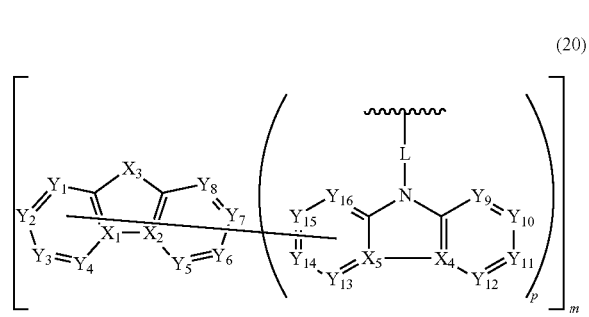

12. The compound according to claim 1, wherein L is a substituted or unsubstituted aromatic hydrocarbon group having 6 ring carbon atoms,
$Y_{16}$ is a carbon atom bonded to L, and L and $Y_{16}$ are bonded to each other to form a cyclic structure, and
the second structure represented by the formula (2) is represented by a formula (21), wherein in the formula (21):

$X_1$ and $X_2$ are carbon atoms bonded to each other;
$R_{20}$ is a hydrogen atom or a substituent;
v is 3 and a plurality of $R_{20}$ are optionally mutually the same or different; and
p is an integer of 1 to 3, (21)

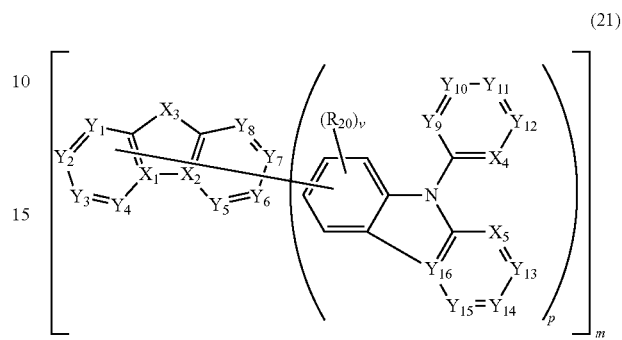

13. The compound according to claim 1, wherein the second structure represented by the formula (2) is represented by a formula (22), wherein in the formula (22):
$X_1$ and $X_2$ are carbon atoms bonded to each other;
$X_4$ and $X_5$ are carbon atoms bonded to each other;
p is 2;
$X_3$ is a nitrogen atom bonded to $R_4$, or a nitrogen atom bonded to an atom contained in at least one of the first structure, the third structure and the fourth structure in a molecule;
$Y_1$ to $Y_8$ are each independently a carbon atom bonded to $R_7$, a carbon atom bonded to L, or a carbon atom bonded to an atom contained in at least one of the first structure, the third structure and the fourth structure in a molecule;
$Y_9$ to $Y_{16}$ are each independently a carbon atom bonded to $R_8$, or a carbon atom bonded to an atom contained in at least one of the first structure, the third structure and the fourth structure in a molecule, (22)

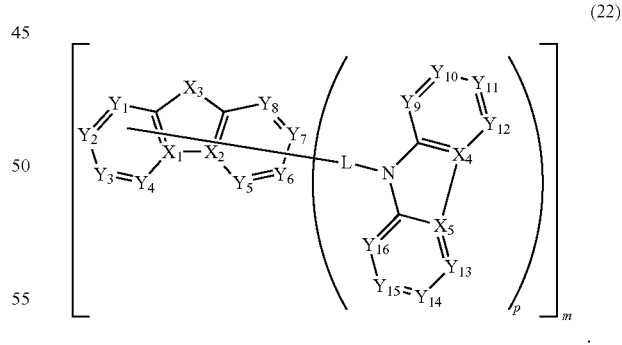

14. The compound according to claim 1, wherein the second structure represented by the formula (2) is represented by a formula (23), wherein in the formula (23):
$X_1$ and $X_2$ are carbon atoms bonded to each other;
$X_3$ is a nitrogen atom bonded to $R_4$, or a nitrogen atom bonded to an atom contained in at least one of the first structure, the third structure and the fourth structure in a molecule;

$X_4$ is a carbon atom to be bonded to $R_5$;
$X_5$ is a carbon atom to be bonded to $R_6$; and
one of $Y_1$ to $Y_8$ is a carbon atom bonded to L,

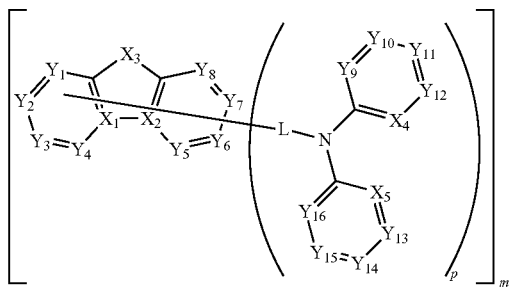 (23)

15. The compound according to claim 1, wherein
the second structure represented by the formula (2) is represented by a formula (24), wherein in the formula (24):

$X_1$ and $X_2$ are carbon atoms bonded to each other;

$X_3$ is a nitrogen atom bonded to $R_4$, or a nitrogen atom bonded to an atom contained in at least one of the first structure, the third structure and the fourth structure in a molecule;

$X_4$ is a carbon atom to be bonded to $R_5$;

$X_5$ is a carbon atom to be bonded to $R_6$;

$X_a$ is a carbon atom to be bonded to $X_b$;

$X_b$ is a carbon atom to be bonded to $X_a$;

$L_{21}$ and $L_{22}$ each independently represent the same as L in the formula (2);

$Y_a$ to $Y_d$ are each independently a carbon atom bonded to $R_8$, a carbon atom bonded to $L_{21}$, or a carbon atom bonded to an atom contained in at least one of the first structure, the third structure and the fourth structure in a molecule;

$Y_e$ to $Y_h$ are each independently a carbon atom bonded to $R_8$, a carbon atom bonded to one of $Y_5$ to $Y_8$, or a carbon atom bonded to an atom contained in at least one of the first structure, the third structure and the fourth structure in a molecule;

$Y_1$ to $Y_4$ are each independently a carbon atom bonded to $R_7$, or a carbon atom bonded to an atom contained in at least one of the first structure, the third structure and the fourth structure in a molecule;

$Y_5$ to $Y_8$ are each independently a carbon atom bonded to $R_7$, a carbon atom bonded to one of $Y_e$ to $Y_h$, or a carbon atom bonded to an atom contained in at least one of the first structure, the third structure and the fourth structure in a molecule,

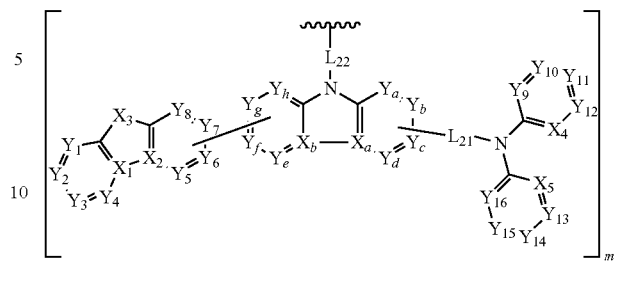 (24)

16. The compound according to claim 1, wherein
q=0 and the third structure is represented by a formula (31);
*1 and *2 each independently represent a bonding position to a carbon atom of $Z_1$ to $Z_8$;
$Z_1$ to $Z_4$ are each independently a carbon atom bonded to $R_{11}$, a carbon atom bonded to an atom contained in at least one of the first structure, the second structure and the fourth structure in a molecule, or a carbon atom bonded at a position represented by *1 or *2;
$Z_5$ to $Z_8$ are each independently a carbon atom bonded to $R_{12}$, a carbon atom bonded to an atom contained in at least one of the first structure, the second structure and the fourth structure in a molecule, or a carbon atom bonded at a position represented by *1 or *2; and
at least two of $Z_1$ to $Z_8$ each are a carbon atom bonded at a position represented by *1 or *2,

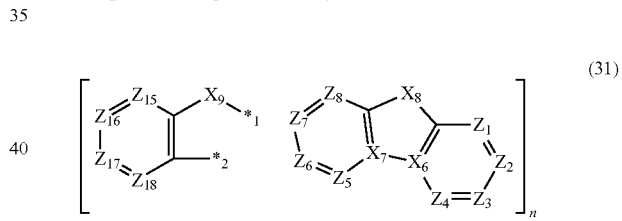 (31)

17. The compound according to claim 1, wherein the third structure is a structure selected from the group consisting of structures represented by formulae (31a), (31b), (31c), (31d), (31e) and (31f),

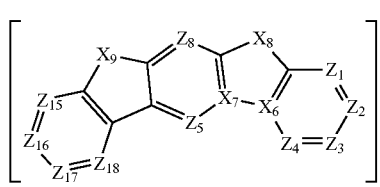 (31a)

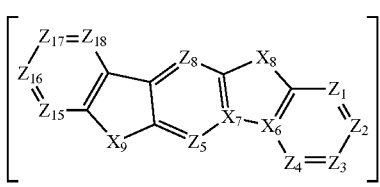 (31b)

(31c) 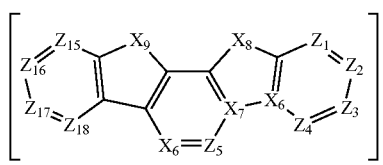

(31d) 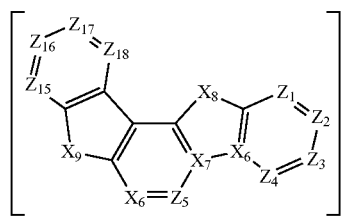

(31e) 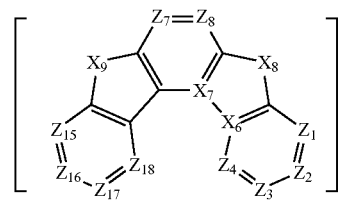

(31f) 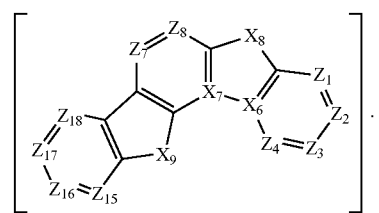

18. The compound according to claim 1, wherein $R_1$ to $R_{20}$, $R_a$ and $R_b$ as a substituent are each independently selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a halogen atom, a cyano group, a nitro group, and a carboxy group.

19. A composition comprising:
the compound according to claim 1; and
a solvent.

20. An organic electroluminescence device comprising:
an anode;
an organic layer; and
a cathode, wherein
the organic compound layer comprises the compound according to claim 1.

21. The organic electroluminescence device according to claim 20, comprising an emitting layer, wherein
the emitting layer comprises the compound.

22. The organic electroluminescence device according to claim 21, wherein the emitting layer further comprises a luminescent material.

23. The organic electroluminescence device according to claim 21, further comprising a hole transporting layer interposed between the anode and the emitting layer.

24. The organic electroluminescence device according to claim 21, further comprising an electron transporting layer interposed between the emitting layer and the cathode.

25. An electronic device comprising the organic electroluminescence device according to claim 20.

26. The compound according to claim 1, wherein n is 1 and m is 1.

* * * * *

UNITED STATES PATENT AND TRADEMARK OFFICE
CERTIFICATE OF CORRECTION

PATENT NO. : 10,538,514 B2
APPLICATION NO. : 15/549212
DATED : January 21, 2020
INVENTOR(S) : Taro Yamaki et al.

It is certified that error appears in the above-identified patent and that said Letters Patent is hereby corrected as shown below:

Column 545, Lines 2-10, Chemical Formula (4):

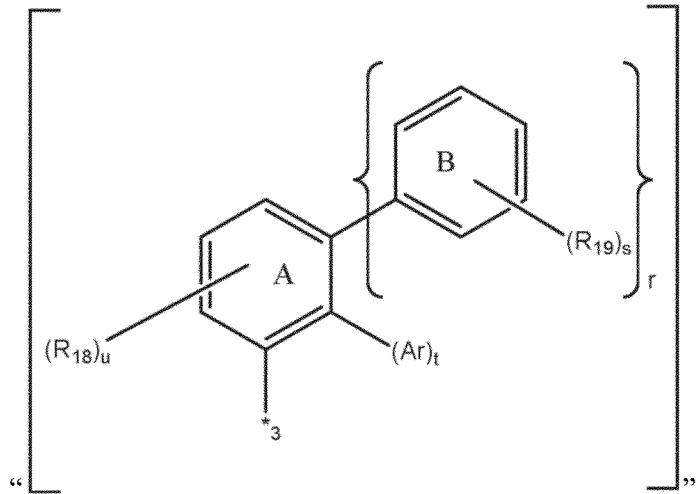

Should read:

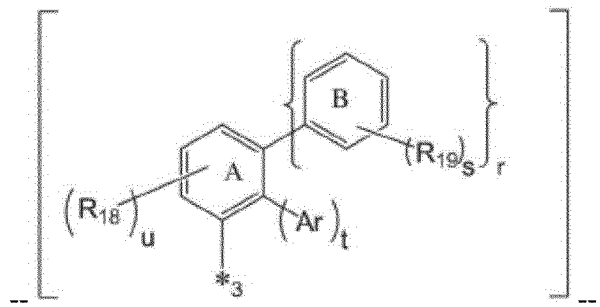

Signed and Sealed this
Seventh Day of July, 2020

Andrei Iancu
*Director of the United States Patent and Trademark Office*

CERTIFICATE OF CORRECTION (continued)  Page 2 of 2
U.S. Pat. No. 10,538,514 B2

Column 553, Lines 3-7, Chemical Formula (31C):

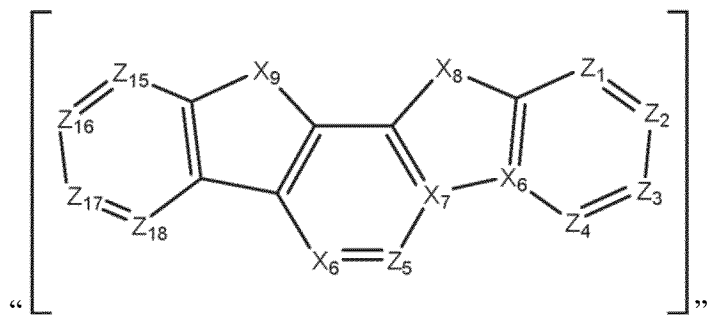

"

Should read:

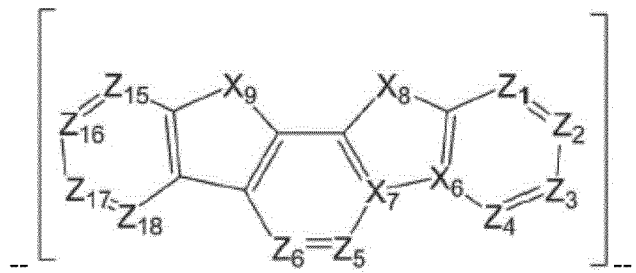

Column 553, Lines 9-17, Chemical Formula (31d):

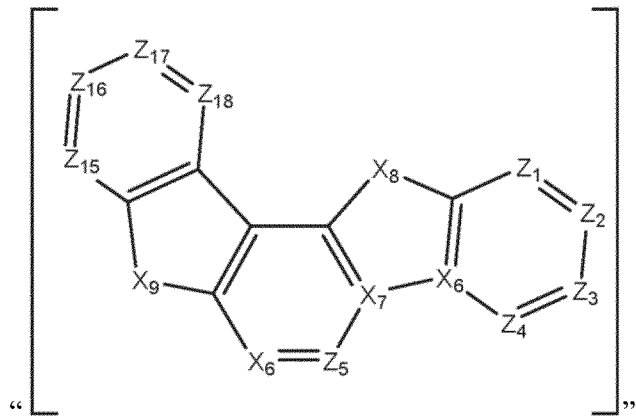

"

Should read: